(12) United States Patent
Rohlfs et al.

(10) Patent No.: US 9,234,243 B2
(45) Date of Patent: Jan. 12, 2016

(54) MUTATIONS ASSOCIATED WITH CYSTIC FIBROSIS

(71) Applicant: Laboratory Corporation of America Holdings, Burlington, NC (US)

(72) Inventors: Elizabeth Rohlfs, Hopkinton, MA (US); Deborah Alexa Sirko-Osadsa, North Grafton, MA (US); Lynne Rosenblum, Hopkinton, MA (US); Narasimhan Nagan, South Grafton, MA (US); Zhaoqing Zhou, Natick, MA (US); Ruth Heim, Shrewsbury, MA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 0 days.

(21) Appl. No.: 14/271,106

(22) Filed: May 6, 2014

(65) Prior Publication Data

US 2014/0234842 A1   Aug. 21, 2014

Related U.S. Application Data

(63) Continuation of application No. 13/053,626, filed on Mar. 22, 2011, now Pat. No. 8,728,731.

(60) Provisional application No. 61/316,321, filed on Mar. 22, 2010, provisional application No. 61/359,029, filed on Jun. 28, 2010.

(51) Int. Cl.
   *C07H 21/04* (2006.01)
   *C12Q 1/68* (2006.01)
   *G01N 33/68* (2006.01)

(52) U.S. Cl.
   CPC ............ *C12Q 1/6883* (2013.01); *C12Q 1/6816* (2013.01); *G01N 33/6872* (2013.01); *C12Q 2600/156* (2013.01); *C12Q 2600/16* (2013.01); *G01N 2800/382* (2013.01)

(58) Field of Classification Search
   None
   See application file for complete search history.

(56) References Cited

U.S. PATENT DOCUMENTS

| | | |
|---|---|---|
| 4,956,778 A | 9/1990 | Naito |
| 4,996,617 A | 2/1991 | Yaeger et al. |
| 5,019,513 A | 5/1991 | Kasper et al. |
| 5,132,405 A | 7/1992 | Huston et al. |
| 5,543,399 A | 8/1996 | Riordan et al. |
| 5,776,677 A | 7/1998 | Tsui et al. |
| 5,846,710 A | 12/1998 | Bajaj |
| 5,885,775 A | 3/1999 | Haff et al. |
| 5,888,819 A | 3/1999 | Goelet et al. |
| 5,945,526 A | 8/1999 | Lee et al. |
| 6,117,986 A * | 9/2000 | Nardone et al. ............ 534/727 |
| 6,201,107 B1 | 3/2001 | Lap Chee et al. |
| 6,280,947 B1 | 8/2001 | Shuber et al. |
| 6,482,595 B2 | 11/2002 | Shuber et al. |
| 6,503,718 B2 | 1/2003 | Shuber et al. |
| 6,919,174 B1 | 7/2005 | Shuber |
| 7,501,251 B2 | 3/2009 | Koster et al. |
| 2001/0053519 A1* | 12/2001 | Fodor et al. ....................... 435/6 |
| 2002/0150894 A1 | 10/2002 | Batra et al. |
| 2003/0235834 A1 | 12/2003 | Dunlap et al. |
| 2004/0110138 A1 | 6/2004 | Lem et al. |
| 2004/0166760 A1 | 8/2004 | Kikuchi et al. |
| 2004/0253636 A1 | 12/2004 | Soloviev et al. |
| 2005/0048544 A1* | 3/2005 | Gardner et al. ................... 435/6 |
| 2006/0024692 A1 | 2/2006 | Nakamura et al. |
| 2007/0254289 A1 | 11/2007 | Li et al. |
| 2008/0153088 A1 | 6/2008 | Sun et al. |
| 2009/0317797 A1 | 12/2009 | Paterlini et al. |

FOREIGN PATENT DOCUMENTS

| | | |
|---|---|---|
| WO | WO 91/02796 | 3/1991 |
| WO | WO 2004/040013 | 5/2004 |
| WO | WO 2005/006951 | 1/2005 |

OTHER PUBLICATIONS

NEB catalog (1998/1999 pp. 121, 284).*
Rothstein (PNAS 1994 vol. 91 pp. 4155-4159).*
Ahern (The Scientist vol. 9 No. 15 p. 20 Jul. 24, 1995).*
Audrezet, M. et al., "Genomic rearrangements in the CFTR gene: extensive allelic heterogeneity and diverse mutational mechanisms," Hum Mutat. 2004: 23(4):343-57.
Ausubel, F. M. et al. 1994, Current Protocols in Molecular Biology, John Wiley & Sons, Secaucus, NJ.
Boat et al., "The Metabolic Basis of Inherited Disease," 1989, 6$^{th}$ ed., pp. 2649-2680, McGraw Hill, NY.
Castellani, C. et al., Consensus on the use and interpretation of cystic fibrosis mutation analysis in clinical practice, Journal of Cystic Fibrosis, 2008, 7:179-196.
Chu, et al., "Immunohistochemical Staining in the Diagnosis of Pancreatobiliary and Ampulla of Vater Adenocarcinoma," Am J. Surg Pathol., 2005, 29(3):359-367.
Huston, J. et al., "Protein engineering of antibody binding sites: recovery of specific activity in an anti-digoxin single-chain Fv analogue produced in *Escherichia coli*," Proc Natl Acad Sci U S A. Aug. 1988;85(16):5879-83.
Kerem, B. et al "Identification of the cystic fibrosis gene: genetic analysis," Science. Sep. 8, 1989;245(4922):1073-80.
Lemna, W. et al., "Mutation analysis for heterozygote detection and the prenatal diagnosis of cystic fibrosis," N Engl J Med. Feb. 1, 1990;322(5):291-6.
Noone, P. et al., "'CFTR-opathies': disease phenotypes associated with cystic fibrosis transmembrane regulator gene mutations," Respir Res., 2001;2(6):328-32. Epub Aug. 9, 2001.
Okayama, H. et al., "Rapid, nonradioactive detection of mutations in the human genome by allele-specific amplification," J Lab Clin Med. Aug. 1989;114(2):105-13.

(Continued)

*Primary Examiner* — Amanda Haney
(74) *Attorney, Agent, or Firm* — Kilpatrick Townsend & Stockton LLP

(57) ABSTRACT

The present invention provides novel mutations identified in the cystic fibrosis transmembrane conductance regulator (CFTR) gene that can be used for a more accurate diagnosis of cystic fibrosis (CF) and CF related disorders. Methods for testing a sample obtained from a subject to determine the presence of one or more mutations in the CFTR gene are provided wherein the presence of one or more mutations indicates that the subject has CF or a CF related disorder, or is a carrier of a CFTR mutation.

10 Claims, 61 Drawing Sheets

(56) References Cited

OTHER PUBLICATIONS

Poddar, S., "Symmetric vs asymmetric PCR and molecular beacon probe in the detection of a target gene of adenovirus," Mol Cell Probes. Feb. 2000;14(1):25-32.

Richards, C. et al., "ACMG recommendations for standards for interpretation and reporting of sequence variations: Revisions 2007," Genet Med. Apr. 2008;10(4):294-300.

Rowntree, R. et al., The phenotypic consequences of CFTR mutations, Annuals of Human Genetics, 2003, 67:471-485.

Sarkar, G. et al., "Characterization of polymerase chain reaction amplification of specific alleles," Anal Biochem. Apr. 1990;186(1):64-8.

Southern, K. "Cystic fibrosis and formes frustes of CFTR-related disease," Respiration, 2007;74(3):241-51.

Handbook of Fluorescent Probes and Research Products, 9$^{th}$ Ed., Molecular Probes, Inc., Eugene, OR, 2002.

Hoogendoorn, B. et al., "Genotyping single nucleotide polymorphisms by primer extension and high performance liquid chromatography," Hum Genet. Jan. 1999;104(1):89-93.

Ju, J et al., "Fluorescence energy transfer dye-labeled primers for DNA sequencing and analysis," Proc Natl Acad Sci U S A. May 9, 1995;92(10):4347-51.

Landegren, U. et al., "A ligase-mediated gene detection technique," Science. Aug. 26, 1998;241(4869):1077-80.

Mann, D. et al., "Elevated tumour marker CA19-9: clinical interpretation and influence of obstructive jaundice," Eur J Surg Oncol. Aug. 2000;26(5):474-9.

Newton, C. et al., "Analysis of any point mutation in DNA. The amplification refractory mutation system (ARMS)," Nucleic Acids Res. Apr. 11, 1989;17(7):2503-16.

Nickerson, D. et al., "Automated DNA diagnostics using an ELISA-based oligonucleotide ligation assay," Proc Natl Acad Sci U S A. Nov. 1990;87(22):8923-7.

Patent Cooperation Treaty, International Search and Written Opinion, International Application No. PCT/US11/32702, mailed Jun. 14, 2011.

Paul, W. E., Fundamental Immunology, 1993, Raven Press, NY.

Piggee, C. et al., "Capillary electrophoresis for the detection of known point mutations by single-nucleotide primer extension and laser-induced fluorescence detection," J Chromatogr A. Sep. 26, 1997;781(1-2):367-75.

Sambrook et al., Molecular Cloning: A Laboratory Manual, 2$^{nd}$ Edition, 1989, Cold Springs Harbor Press, Plainview, NY.

Stears, R. et al., "A novel, sensitive detection system for high-density microarrays using dendrimer technology," Physiol Genomics. Aug. 9, 2000;3(2):93-9.

Wall, J. et al., "A 31-mutation assay for cystic fibrosis testing in the clinical molecular diagnostics laboratory," Hum Mutat. 1995;5(4):333-8.

Weiss, F. et al., Complete cystic fibrosis transmembrane conductance regulator gene sequencing in patients with idiopathic chronic pancreatitis and controls, Gut, 2005, 54:1456-1460.

Wu, D. et al., "Allele-specific enzymatic amplification of beta-globin genomic DNA for diagnosis of sickle cell anemia," Proc Natl Acad Sci U S A. Apr. 1989;86(8):2757-60.

Doucet et al., "Applicability of Different Antibodies for the Immunohistochemical Localization of CFTR in Respiratory and Intestinal Tissues of Human and Murine Origin", J. Histochem Cytochem, 51(9):1191-1199, 2003, XP055073665.

Database Geneseq (Online), "Human CFTR probe SEQ ID NO 245", XP002708092, Database accession No. ADW15425, dated Apr. 7, 2005, web page at http://ibis.internal.epo.org/exam/dbfetch.jsp?id+GSN:ADW15425, as available via the internet and printed Jul. 31, 2013.

Kerem et al., "Identification of the Cystic Fibrosis Gene: Genetic Analysis", Trends in Genetics, Elsevier Science Publishers B.V. Amsterdam, NL, vol. 5, p. 363, 1989, XP025207998.

Anonymous: "Mutation Details for c.1692delA" Cystic Fibrosis Mutation Database XP882788893, web page at http://www.genet.sickkids.on.cajMutationDetailPage.external?sp=1831, as available via the Internet and printed Jul. 30, 2013.

European Patent Office Extended European Search Report, Application No. E26577EP, mailed Sep. 10, 2013.

State Intellectual Property Office of the People's Republic of China, Notification of the First Office Action, Application No. 201180022402, mailed Oct. 25, 2013.

European Patent Office, Communication pursuant to Rules 161 (2) and 162 EPC, Application No. 11760022, dated Nov. 23, 2012.

European Patent Office, Communication pursuant to Article 94(3) EPC, European Application No. 11760022, dated Jun. 26, 2014.

State Intellectual Property Office of the People's Republic of China, Second Office Action, Application No. 201180022402, dated Sep. 2, 2014.

Japanese Patent Office, Notice of Reasons for Rejection, Application No. 2013-501365, dated Apr. 21, 2015.

European Patent Office, Communication pursuant to Article 94(3) EPC, European Application No. 11760022, dated Mar. 23, 2015.

* cited by examiner

```
   1 aattggaagc aaatgacatc acagcaggtc agagaaaaag ggttgagcgg caggcaccca
  61 gagtagtagg tctttggcat taggagcttg agcccagacg gccctagcag ggaccccagc
 121 gcccgagaga ccatgcagag gtcgcctctg gaaaaggcca gcgttgtctc caaactttt
 181 ttcaggtgag aaggtggcca accgagcttc ggaaagacac gtgcccacga agaggaggg
 241 cgtgtgtatg ggttgggttt gggtaaagg aataagcagt ttttaaaaag atgcgctatc
 301 attcattgtt ttgaaagaaa atgtgggtat tgtagaataa aacagaaagc attaagaaga
 361 gatggaagaa tgaactgaag ctgattgaat agagagccac atctacttgc aactgaaaag
 421 ttagaatctc aagactcaag tacgctacta tgcacttgtt ttatttcatt tttctaagaa
 481 actaaaaata cttgttaata agtacctaag tatggtttat tggttttccc ccttcatgcc
 541 ttggcacttt gattgtcttc ttggcacata caggtgccat gcctgcatat agtaagtgct
 601 cagaaaacat ttcttgactg aattcagcca acaaaaattt gggggtaggt agaaaatata
 661 tgcttaaagt atttattgtt atgagactgg atatatctag tatttgtcac aggtaaatga
 721 ttcttcaaaa attgaaagca aatttgttga aatatttatt tgaaaaaag ttacttcaca
 781 agctataaat tttaaaagcc ataggaatag ataccgaagt tatatccaac tgacatttaa
 841 taaattgtat tcatagccta atgtgatgag ccacagaagc ttgcaaactt taatgagatt
 901 ttttaaaata gcatctaagt tcggaatctt aggcaaagtg ttgttagatg tagcacttca
 961 tatttgaagt gttctttgga tattgcatct actttgttcc tgttattata ctggtgtgaa
1021 tgaatgaata ggtactgctc tctcttggga cattacttga cacataatta cccaatgaat
1081 aagcatactg aggtatcaaa aaagtcaaat atgttataaa tagctcatat atgtgtgtag
1141 gggggaagga atttagcttt cacatctctc ttatgtttag ttctctgcat gtgcagttaa
1201 tcctggaact ccggtgctaa ggagagactg ttggcccttg aaggagagct cctccctgtg
1261 gatgagagag aaggactta ctctttggaa ttatcttttt gtgttgatgt tatccacctt
1321 ttgttactcc acctataaaa tcggcttatc tattgatctg ttttcctagt ccttataaag
1381 tcaaaatgtt aattggcata aattatagac tttttttagc agagaactt gaggaaccta
1441 aatgccaacc agtctaaaaa tgcagttttc agaagaatga atatttcatg gatagttcta
1501 aatactaatg aacttaaaa tagcttacta ttgatctgtc aaagtgggtt tttatataat
1561 tttctttta caaatcacct gacacattta atataggtta aaaaatgcta tcaggctggt
1621 ttgcaaagaa aatgtattac aaaggctgct aagtgtgtta agagcatact catttctgtt
1681 ctccaaaata tttcataagg tgctttaaga ataggtatgt ttttaaagt taagttccta
1741 ctatttatag gaactgacaa tcacctaaaa taccaatgat tacaaacttc cttctggcct
1801 tctggactgc aattctaaaa gtgtaaaaaa catattttct gcattaagtt aggcagtatt
1861 gcttagtttt caaagtggta ggctttggag tcagattatt ttgattcaga tcctacatct
1921 actgtttagt agctctgttg cctgaggcag gtcccttaac atctctgtgt gtgacttgac
1981 ctttaaaatt tggagactgt cataggggtt aatcccttga gaaatgaat gtgaaaagtt
2041 agcctaatgt taactgctat tattatggat taccatattt tcacattcat cacagtacat
2101 gcaccttgtt aatataagat gctcaattca tctttgagta aatttttgtg actctcaatc
2161 tggatatgca atgagtgggc ctgtatgaga atttaattta tgaaaaattg tgtttcacat
2221 ggccttacca gatatacagg aaacacgtca catgtttcta ttgtatgttg ttaaatgcct
2281 tagaatttaa ctttctgaat aggatccctt cagtttgaga gtcataaaag agtaaaatta
2341 ttatggtatg agttatagat tgtattgaat atctctttat atgtctaggt tttgtcattg
2401 gaaaaccaaa aagtttggaa aaaaaatcta agttatttct tactttctta attttgtgtg
2461 gatttcacat caagtataaa atttgaagaa catctgaact atcataatcc atatatatat
2521 ataaaataaa cataatctaa gagagaattt caccatgaaa aattcaggta gttcatgact
2581 atcagagcaa acaagtacat taaattgaaa cttttatgaa aataacattt atgaaatagg
2641 aagctatttt taaactagaa gtgatatatt agcatataat ttataattca tatacaagtg
2701 ggattgattt ataaatggtc accaacagag attgtgctat ttaatttggg aaaattttt
2761 aaatttacat tttctcacaa cttttaaggt agttattcag tttgttcctc tctgtctctt
2821 ctctcatgcc ctgaattttt catatttcgt ttagttgtaa gagtgtatat caaccgtgt
2881 gtcacatgac ataacttgaa ttttcgtcgt gatatctgtg ctatgtctag gtctatactg
2941 aggaactgtg ggaacccac agaatccaag tatacagtgc cactgatttc ttacaaggga
3001 tgtggggtct cctgtaaact ctgcagttag tctcaagtaa gaccaaagag taaaatattg
3061 ttaggatcta aggtggaaat tcagcaaaga atcacatagt ctaagtctcg agtttaacag
3121 taagataatt tgagatactt ttgtaattat taaacacaaa gtaatgagag attttaaaac
3181 aaacaaatac acctgaattt atatatcaga ataggtatgg tggttcaaaa tagctatcta
3241 ataaaaacca cactcctatt ctaaacattt gcctttgatc aaaataattt tgggtctctt
3301 attatgaaat tgcctttcta aataatacat aaatttcttc tcataagtat atattagcca
```

FIG. 1 (SEQ ID NO: 1)

```
3361 cattatttta ttgttattgt tttatattca tagcttgctt tagattaaaa attatattac
3421 ccagactggt ctcttggact tgcttccaag tgacttttga ctgtatcaca aaatcaaatt
3481 cactctgaaa atataaagat ttttcatcat aatttccttt gttaacagcc aagtgctacc
3541 taattttagg tgttttcatt aaaaaaaaat gcattgcaaa ctttaaagac aattcttttg
3601 tttgtttgtt tttaaaagac agagtctcac tctgttgccc aggctagagt gcagtgacac
3661 aatcataact cactgcaacc tccacctcct gggctcaagt gagccttcca tcttgcctca
3721 cgagtagctg ggtcttcagg tgtacaggtg tgtaccacca tgcctggcta actttttttt
3781 tttttaagtt atatagagac agtatctcac tatgttgccc aggctgctct ggagctcct
3841 ggcctcaagt tatcctccca ctcagtctcc caaagtgctg gattacagg cgtaagccac
3901 ctcacctgt cagcctaaag acagtgctta atgaagagaa atataagtgc tttgagcaat
3961 ggaagtataa ttaaaattat actatgaaag atttataaag atgaccattt tgaatgggac
4021 cacacttatt tggttatata aattatgata cactattaaa aattcatcat gatgattttg
4081 tatttacatt ttatttacat gtttgcaatt tgtgaggaaa gctaaaatta tggctaagcc
4141 ataaatattt ttgcagtttg ttgagggtgt ttgtaaaagt gttgccaagg aagaccagtt
4201 ggctacccaa acaagggttt agtctaggtc tgatcaatac atacacatta tctcaggttt
4261 gtctatcaga aaaaccttag gttatccaaa tcaaataaaa atagatgcat aaaacaaagg
4321 ccaatatgtg ttgaacaatt atattgtgat atacaactgc caagcattcc cgattaccat
4381 gactccattt agtcagtcca tggcaaatg ccatcaatga ggacagccca gggtttccat
4441 attctctctt ggctttacat cctataggaa ttggaggggc ccacctctgg gataggagcc
4501 cttctgtctt gaacaatgtt gtctgaacac taacaaatgt tgactttcta caccagtccc
4561 tcaatagtct tttctattta tccttttgct gaccatgttt tgttattaca cagttgagat
4621 ttttcagctg ggaatctgtg ttaattttgt attaattttg attagcttaa ctctcagagt
4681 tctaaaagta cctcctgtac ctgatatatg acaaaatta taattacatt tatttatata
4741 taaaatatct ttgtatatgt aaaatatctt tgtatatata attatataat tgtttctttt
4801 aattttgcaa attttaaaaa gttctccttt gttttgaagt ttattcctat agtttttat
4861 atgctagtta aattattaat cacttgattc aagtaatatt cttatatact tataaggaat
4921 agtgtagttt taatatttaa ttccttgcta aagagagaag tggaatctat ttttcttagc
4981 tacttcatca atatttatg tttgatgtga cagtcaaaat atccctcaga gctaactgtt
5041 acactaggga aatcacggtt ttccagtttt ccatttatgt gttatgggag ggagtggaac
5101 ttagtgtaat aatattcaat acataaatgt taacacttgt ttaaaggtcc ttgagtgagt
5161 actgctataa aatgcattat tattgctagt gtcattcac aagagcctat aatttcagtg
5221 tgatagagct acaatataag tatagtattg caaaaccatc aggaagggtg ttaactattt
5281 agcatgcagt tatgtgttgg ttgtcaaaac gttaaaaaca tctctgactc agcagcaatt
5341 ttggcaattt tgatcctgag gcatctgtgt agggcatctt cctggagaaa aacctctgag
5401 atgcaatgag gtcaaaaggg gaaaacagac tatgataaag atcaagttgt ttggagatct
5461 tgtagaaaga ttaatttaca aatatgtcaa gtgcattatc atggaggaaa acattgctat
5521 ttctgttggt tctcttcaga gctctagaat caatttacca catagttgtt tcagtgtgaa
5581 attagcatta cagagtggct ttacggcttt actgtagggc attgtgtcag caaagagctt
5641 aggcttcttt tagcaagaag cttgtaaaaa tttaatttac tcttagattg cttgatgtag
5701 agaattacat tcctacagag ctctgaaaaa tcttttttca gagtttttca cagctgtatt
5761 caagttgcaa ggcttgtcaa cttttgctatt tttctgtgca gctctgttaa cttattatta
5821 tcttttgaca taaattatga ttccaaattg taaagctctg gatgtcaggg ccttttctaa
5881 tttgtttagt atgatattca gaccatttca agactcttcc gtggaacaat ttaataaaga
5941 ttttttttgtg atgttaatga gttcatggtg atcaaccta gagacctgtg tctattgtag
6001 atcgatgaca ttcaacagtc ctgcagtgct ggcatcattt tgataaaaag gggtcaaagc
6061 aagtgggact gtgggcagat ttttaatgct tagaacaatt attccatcga agttttcttg
6121 tgtcccttct gccttagcct ttgtaggata gcatgcttgc taattcttg ctcatggggt
6181 aaggaaatga agatttttgc taggtccgta ggattattag gactactcag gcctgaagct
6241 atgcctggat atagccagaa aactctccca tagcttgctc caaggagctg agatacagca
6301 gtacttcctt tgtaggtcat gattctgggt aacctggaag atgacctcat tcatattctg
6361 tattctatgt gagacgttaa gaaggtagag gtggccaaga aggaaattgt tgctgccttt
6421 atggaacaaa ttatctgaaa cccagctttc tcgagggctt cattgaagta ctcaactggg
6481 gcacttaacc cagtctaagg ctggtcaagg aaggcttgct ggggaagtg tcttttgtat
6541 tcacacctaa aggaggttat tcaattagaa ttatccaaag agggtaggga tgggctagga
6601 aaaatttaaa caggtagtgt ggaggactga caggataagt aagcatggca ccttcaaaat
6661 atcctgagaa gttccctatg acgggaacat aaaatatgtg acagagattt gtgggagatg
6721 ggtctggaaa ctctagcagg ggccagatcg taaggggggct ttgtaggctt tgtaggcttt
6781 gtttgggctt tatcatactg gaagtgaaaa gccatggctt taaacagga gagggacata
6841 atcagttcat atactgttgc agttttgtaa aagaaaagat gagctgaaag agtggccatg
```

FIG. 1 (cont.) (SEQ ID NO: 1)

```
 6901 gtggaggtgg gtggggtggg ggggaggggg cggggagaga gagagagaga gagagatttg
 6961 aaagacattt aggaggtaaa atcaactggt ttggtaatca attagtagtt gaaggtgaag
 7021 gaaagagaag agttaaggat aacatctata tttgttgatt tggataatag aggggacagt
 7081 ggtgctgctt attgaatgag aaaatttaat cggagaagaa ggcatggagc aggagtgcag
 7141 acctatgtga ctctacttct ctcaaaacca gaaacggaaa tgatgtatat ggctcaggt
 7201 taggtaatat ggttatttga aaatgtatta aagtgattta gagcttagtc ttaggtaaga
 7261 gatataagat gtctgaggtg acagttttat aaatatgtag agtgcccact tgtttggcct
 7321 tattgtggca tagtgtgacc tgagtgtgtt aggaagaagc agctgagttc tagggacagt
 7381 actggttaaa ttctacttag aaattatact tagaactctc ctatataacc tgctaactga
 7441 tgtctgaacc tcctgataac ttcactcctt taggcagtgc ttttcacatc acgggacaca
 7501 acatatgaga gatcatagaa attcaatgtg gtatgaaaat ctgcttggga cttcagatat
 7561 tgtctccagt gattgaataa aataggagc tcacctacta tgatgaggtt tctgtgtgtg
 7621 ttaaaagaag gttttcatta cttttgaaaa ggttatgtat ccttgtttta tgttaaaact
 7681 ttgagctttg ttaaatatgc agagttctct ttcttagcat ggactacaga ggtgcaacta
 7741 cctcctacct gacttcacat ctactcccaa atgcctagtg aaggcttaat aatttcaaaa
 7801 agggactcta gaatttcatt tgataccagt cagacaaatg tgtgaaaatt aagcataata
 7861 ggcagaatcc caggggtact gacagctgta ttaagaggtg attcaagggc taaaccttag
 7921 agtccagcat tggttatggg tgtgacaaga aaatgaagcc tatgttggct gggattagca
 7981 accacagttc tagaggaagc aaggtggaga aactatatag ggggctccct ttgtacgttt
 8041 tatttatttt aaacatctct ataaactcta gaaattaaaa caacaatacc aacacaaaag
 8101 catcactttt tcgaccaaag accattgcta tactttttg tgtaaagggc tagatagtaa
 8161 atattttcag ctttgtgggc cacataagtc tctgcaatag acaatatgca aacaaataag
 8221 catggctgtg tttcaattaa actttattat gaacattaaa atttgaattt catataactt
 8281 ttacatgttg caaaatattc tttatttaaa ttctattgca atatgcttta aagatacag
 8341 tttttagtct ttcttagttt aaaataaaat ctagaaaaaa ttttaagtct tctataactt
 8401 tttttcggta actgaataat tttaaagta agtgaaacat ttagacatgc aaaatggact
 8461 tttcagaaga agaaaatggt agcttaacag ttattagatt attgtccaga ataattttg
 8521 acttataagt ctctgttgac catttcattg cctcttttt tggaatatgc atcttttaat
 8581 gtgtccttca aggcaaaggc tctatcttat ctatcttgtg tcttgcattt tcccagggca
 8641 atgtttttca caattttttt aaaaaacaat actgtaatca attttcaaat aaaattttcc
 8701 atgggaccgc agtgtataca aatagcagtg acaataaaag ataataactc tcccataaat
 8761 acaaagaaac agttaaccta gtgctctaaa gtaaaggcta cagtgatttt gtataacatt
 8821 tatatgtaat ttcttgatc ctacatggtt gtgttttca cagtgttatg tttctgaaat
 8881 cgagatgcct tttataattg atgtcaaaag aaacttgtca gccacaaggc ccaggaataa
 8941 gttgtaatat gggaacttag caatacataa aggtatatat actcctgtga cctcagctga
 9001 attatttgca ttggttgcat cccacaaggt tgactcttaa ataaatttag tttgttgctt
 9061 gaaatttctt gggataaatt actttgtgat gtagttttga aaaaaaaaca ggtaatattt
 9121 agtctgaagt ttgtctgaca tactaagcaa tgtaattaaa gtagaagtcg cctaagctca
 9181 gcactttatt atgccttgaa attatactgc ctgtcctaca ggtgaaggtg ttatgaatgc
 9241 agtttgtcac tgtaactcta ttcatagctc tgaaaggctg agagtgactc agaagaatat
 9301 ttttgctctg aatatgaaga acgcttagac taaaacttta attacgatgc tgaagaagaa
 9361 agtggtaggt gattgcatga ataagtatgt aatattgtta atttctaaaa actgtgtata
 9421 gttaatgtag tgcttctttt tggaaaggct attgttaaat tgatggtaaa ttctataacc
 9481 aatatcacct taaagcaagt acgcatgata agtattata aaccatgat aatatcatat
 9541 gtggcttatt attgttccct gagtgttgta caactctgtt atgctgtgat gaaacctcat
 9601 gcaaacaggt atgtcaaaga tatgatgggc tgttaactga gcttggccca catatggtgt
 9661 agtgacatgc tcactaatgc agtgcagaga taaccaataa cagatcataa caggtttaaa
 9721 tatgtgcaag gagatgtcag cagaagcttt cctacatagt gaatactaaa caagcctgac
 9781 agcccaggat catgttcgga tcaatctagt gtgctaaaat taacatatag tcctacattt
 9841 gagaatgtgt gattttcttg gttcctgtct ataaaataat attttaaaat acatacattt
 9901 caaatcagaa gttggtgaat tcactgaaat atttctagag aacactaggt attgggctc
 9961 atagtgtgaa aaccactgac ttaattcttc ccccatcttg gttgttcctg atcttccctt
10021 gtgtccccat tccagccatt tgtatcctta gaaaatgatc tcatattcta cttcatcttt
10081 atcttcattg tcaactgtca ggtagcaata tatgatggaa gaagcatgta ctttggaatc
10141 agacagacct ggctggaatc ctaactctgt cacttattaa caatgtgatc ttaggcaatt
10201 tacttaatct ctctgaacct cagctactct cgtcagtaca atgagttatc cttatcttta
10261 catggcacag tattattatg atatcaaaaa ttcattgagt atttactctg catattagtc
10321 aaggttctcc agagaagtag aaccaatgat acacacacac acacacacac acacacacac
10381 acacacacac acaatttatt ataaggaatt gacttacatg attatgatgg ctaacaagtc
```

FIG. 1 (cont.) (SEQ ID NO: 1)

```
10441 caaaatctgc agtatgggtc agctggcagg aaacccagga gagtcaatgt tccagtttga
10501 gtctgaaggc agtctgttgg ggaatttcgt ccttctctgg gaggccagcc tttttgttct
10561 atacaggcct tcaaccgatt ggatgaagtt cacctttatt agtgagggca atctgcttta
10621 accaaagttt actgatttaa atgttaatct catccaaaaa cacccaccca gttgacacat
10681 aaaattaacc atcactctct gtaagcactt tctatgcatt aagtgatagc aaataatgcc
10741 agacataggg cgtctttaat aaatggtaag cactgttatc agcaacaaca ggattattat
10801 aattagcacc ttttcatctt tctgtctggg ctctgagaaa gtacctctct tctctaaatt
10861 tatccctcct ttcctatgaa ttagacccag tgctttctct gaattatgaa ggtcacactc
10921 ctacaaatgc cccttcccaa ttgcacatct gtcggctttc tttgccattg acttttatct
10981 ctagctttta aatttacagg catatgtcag ttaacaatgg gaatgcgttc tgggtaatat
11041 gtccttaggc aattttatcg ttgtgagaat actatagagt ataccacac aagcctagat
11101 gtcgtatagc ctactacaca cctaggcaat atgacatagt cttttgcttc taggctacaa
11161 acctgtacgg cttgttacta tactgaatac tgcaggcagt tgtgacacag tggtatttgc
11221 atatcggaac atgtctaaac acagaaaagg tgcactaaaa atactatgta gtgatctcat
11281 gggaccacca ttgtatatgc agtctgctgt agactgaaat gtcatgcagt gcataactgt
11341 atcttaaata ctcaaagtat cacctttgtt tgtttgtccc cttgtgtgca tcatcctaac
11401 gtggaatttc tctgttgatt agggccagcg tattagtttg ctagggctac cataacaaaa
11461 taccacaaat ttggtggctt aaataacagg aatttattat cttatggttt tgaagactag
11521 aagtacaaga tcaaggtgtt ggcaggtttt tcttctaagg gccatgagga agagtctatt
11581 ccatgccttt cccctacctt ctggtggttt gctagaaatc cttggcattc cttgacttac
11641 agaggcatca ccctgatctc tgttttcatc ttcacatggc attctccctg tgagcctgtc
11701 tctgtgtcca aacttcttta ctattaatat aaggacacca gtcatattgg attagggtct
11761 actttagtga cctcattgga atgttattac ctctgtaaag atcctatctc taaataaggt
11821 cacatcctta ggtaccgggg gttaggactc aaacatacct ttttttgggg aaacacaatt
11881 caacctataa caattgataa cactctttag gagcagaatg cgatatgaa gtaatttgag
11941 accataaagt atatacatgt agggagttaa tctatgaaac ctattgaaag ccatatatac
12001 ctcatgtata gtggtccata aatagcatgg agacattgca gaggatgtta agtgatatga
12061 tacaggaaca atccaagaag gtcataagaa aaaggaccctt ttgctcttga gaggactgaa
12121 gaatgacttt ccatttatga aatttttggta catgtccact aaaaatagga tgaaggccaa
12181 acttaggaag aatattttga taatggagaa ggttgcatat aaaaacattt tattgaggac
12241 aattaaataa tgttggctgg aagtttagg atgatcatct ttaggactca gaaaagaga
12301 agaaacatta ttaaagaatt gtccctgaac aagtataggc accctcacat ttgcattgca
12361 tttactatag aattgaaaaa tgttttgacc tttttttttt ggcttttaat atatttgacc
12421 aagagtaaca gctaagcaat acctatttgc aatcagtgtc atcatgtggg ctccaaacat
12481 atcatgtttg tgtaattaat tgattgaccc attaatttgt tcaatttctg ctctgttcca
12541 ggcactgaac aacatgatgg agataaaaga taaatattac acctgccttg tcctcaagaa
12601 gttagtcttc tgagggaaag aaattagcaa acaaattgta atctcagtta tgtgccatgt
12661 tccatgctgg gcacagggga tacagtagtt taaaaaaaac acaagatcta taaggtgttt
12721 cttcttgtgg accttacagt ctagggtgct tggaaacatg gggcgttggc agacaagtaa
12781 atacacattt tgtggtaaag gctcaggtag aagaagtaca ggatagaata gagcacacca
12841 tggggaatta atctagactt cagagaggct cacacataca taatttatgt gtgactattt
12901 caatgcattt gaggtttctt ggaaatagag gttaggtttt attttaagga agttaccatt
12961 ttttttttca gtgtgatgtg gttgaaccaa agaatgccat gcccagtgat ggtaatagga
13021 taatctttt aaaaattaag agccacctaa taaatcaata gtttcattca gcgggagctc
13081 ctgcagagtt caaaagaag agaatctggc acagcgtttc ctttaaagtt cattttccta
13141 gagtgtgaat ggaagcaaga gattataaca ttttgaggtc aaaaaaattc tgaaatgcct
13201 ataaaaatta ttttctccaa attatcatca tttgtgcttt taatgacctg attgcaaaga
13261 tgaacatttt gaattcttaa attgcttatt aggattggtt aatgaatcaa ttatctatta
13321 ctgtatgttt tgctattgga aaaaatagca acttaagtgt tttgcagacc tttacttagg
13381 tatatgttgc ttttatgaaa aaaagatgt aaatattaag taaagggat ttaaagcaag
13441 gcttttgagg tagagtctta ttaattcctt ggtaaacctt gagccaattg ttgtctatgt
13501 tctctgcctc tgtcttgctc cttccttctg ggattcactg tgggaatgcg ggattgttaa
13561 tctggggatg ctgtccaatc ctgcctctct caagctttgc tattgatctc cctcccagtg
13621 ataataaagc ttgaagaaaa tgaaagtagc gttagtattg gtcctcaaac tcaagaacag
13681 gatgaaactt aaatcttgag tcatacaatt gtgtctacat actgctcccc aaaaagagaa
13741 gtaaagaaga tgctaacttt ccctttaat ttgcagtact tagcaatttg ttttcttgag
13801 ggttaagtaa taacagtgga agaaaaaagg gttaaaatgc caccaagaac ccaattccat
13861 gtttagtttg aaagtgggaa atcagctgcc actgggaagt ctgaatccaa tgccatgatg
13921 ttctttgaat ccttctgaga aataatcatg tgtagccata acatacctgt ataacagagc
```

FIG. 1 (cont.) (SEQ ID NO: 1)

```
13981 agagaacata aacaaatgaa ggtgaaggga agattaagac agaagagaaa aattccagaa
14041 tcgactgatc attttatct gtttagatga tttcaggcag aatcctagag accaacttta
14101 tcacaactga attttaaaaa tcaccagctt tgtcattgtg atgcagcatc agtttcagta
14161 ttatccttgg agtattaatt cttaatcatc ttcatcttag aacattttg aggtcacttc
14221 tagtctctat ttcaccagtg aagaaacaaa aatcccaaa ctatatcagg tggaattaca
14281 cagtatttt tttttaattt tggggaaagt cgattcaagg cagtaacttg caagctagtg
14341 ttagaaagga tttaataaat agtggttttt ctgtacacat agtgagaggt cattacatca
14401 tttggttgtt gaaagtcata aggatgtcta gcatgcgctt tgcctgtagt ggttcatgcc
14461 aggcagattc ctgactccta taccccagag cttatcagag catttatgtc cccaaagaga
14521 aatgtcacct ccatctttca ataacactt tagcaaagaa aatcaagta ctttaattcc
14581 aaatcttgag ttaattccag aataacaatg atggctcgga aaatatggg tatttctgtc
14641 aaaggacaga gaacctagt agagagtatt tactttgggt cctagtgatg gtatctgaac
14701 aagctaggtg aacaagagc ctcaataagg gattttgagg tctagaaaa gagaggaaat
14761 accaaataaa tggaataatt ataaaataaa taccagcaaa gttaaatcaa tatatcatgt
14821 gggagatatc cttatatcac tcatgtgatt tctatttgt tcctatatta ggccaaggag
14881 aggtggaact tgttttcctt tttccctctc agctacgaat ggacatactt aaaactgttt
14941 ctctgcttct gttctctaaa atgtgattgt ctaacagtaa ccgtgatgac gttttgacag
15001 ttgcacaagt ttctttcttt aagctttaaa aatgccagcc agtaacccag tggcatttct
15061 actataaaat cttaaggcca atccatttcc ccttttcctt attttcttgg tttcaaatat
15121 atttttattg ccaatggaaa taaaaatcct aaattagaga gcaatggcat cccttgtctt
15181 gtgaataaag agctcctaaa tgtgaactta tacaggatgc agcaatttat agggtagtta
15241 atcattcttc tttctagcca gttgttccag ctacagtttt gtggctcttg ttagtggctt
15301 cattcccaga tagaataaaa atcaaaccaa aatcctggaa aggcactctg aggatgcttc
15361 tctaaagtag atgggcatca actataaatc acaatgcttt gtttcctctg ttatgtttca
15421 agatgggtgg gattttttt gtagcattac ttattattgc ctctcaagtg cttgagtctt
15481 tgaaatccaa gtcatgtgag tgaattagat acagctgtta gaagtggcct ttcaatgcca
15541 atggtacaca ttccttggtt tctttacgat actattgctc ttacaacttt tatctgaagt
15601 cataaattca tagttgtccc agaagttaag ttccttgctt ctagaggaca gaaaacaaac
15661 aatttacaca actcatggtg catgtcacca gtccttagat ctcatgaaat atgcatgaaa
15721 tcttaaatca cttgctgtag ccacccagcc attgacatat ttgaaagact ttagtgtatc
15781 aaagtcacta taatgaaaat tttgatttca ccagttctag gagtgaaaaa tcaaatgttt
15841 agtaaaactt tctaaaatta acactgacag ttgatttctg tatactgttg ttcttaataa
15901 tagctttatt gagatataat tcatattcaa aacaacttac ccattaaag catacaatcc
15961 aatgattttt tagtatcttc aaagagttgc ctatccaccat aaccaatttt agaacacttt
16021 catcactgta aaaagaaact ccattcctat tagcagtcat tccttattcc aaatccccct
16081 gctcgcccta gacaactaca aatgtacttt ccatctctat agatttgcct gttctggaaa
16141 ttttatgtaa atagaacaaa gtgttctttt gtgactggct tatttcactt agcattttt
16201 ttcaaagatt catccctgtt gtagcgtgta tcagtgcatc attctttttt attttttag
16261 agacagggcc ttgctctgtt gcccaggttg gaatgtgcag tggcatgatc atgggtcact
16321 atagctttga agtcataggc gaaagcggtc ctcccacctc agtctccga gtagctgaga
16381 ctacaggctt gcaccacatg actgtctaat ttataatttt ctttagagac agggtcttgt
16441 tatgttgtct aggctgctct caaactccag ggctcaagtg gtcctcctcc cacagcatcc
16501 taaagtgctg ggattatagg tgtgagccac agcacctggc ttgcatcatt cttttattg
16561 ttgaataata tcccacttgt aagaatatgt attttattta tccttcccc agttaataga
16621 tatttcgatt gttcctaatt cttgtctatt ataaataatg gtgctatgaa catttgtgta
16681 caagtttttg tgcagacatc catttccctt tcttttgggc atataccctac gagtgtaatg
16741 gatgggccat atagtaactt tatgtttaat atttgagga ttttcaaac tgtttccaa
16801 agtggctgca tcattttaaa ttccttccac cattgtgtga gtgtttcaat ttctccacat
16861 atttgcaaca cttactatta tctactctta aaattacag ccatcctact gggcatgaag
16921 tggtatttca ttgtgagttt tttttttctt tttcttttt tcttttttg ctaatgtttg
16981 tggattttct tttcattttc ttgatggtgt cctttgaagc acaaaagtat ttaatttga
17041 taatttccaa tttattttt gttattgctg tttgtgcttc tggtgttgta tctaagtgta
17101 tgctacttta aaaattagt tgtaatatgg caaattggat acatgtgtag gctttggtgt
17161 cacaatccta attttaaaat tctgactctg cccttgacaa attaactaat taagcttcct
17221 tagcctcagt ttctcaactg taagttggag atattaccaa gacctacctc ttgaattgtt
17281 gtgggatca gatgaaataa tgtatgtgaa atatttagaa ttatgcaagt ctgtggtaat
17341 gaatactaat gttagctatc attattgtta taatcccaat aataaattct ggtgctttga
17401 aaattaaacc aaagccaagc agttgatatg aagaagcatg taataatgta cagacataat
17461 gctttataga caacattgaa tttggctctc atgaacatca ggaatagtgg tcatggtagt
```

FIG. 1 (cont.) (SEQ ID NO: 1)

```
17521 tattatctcc agcaggaact gtagctgaga gatcttcaga gcttttccca aggcgatatc
17581 actgggaaat aatagagaca aggttacaag ctagggctgt gttttcttct taaaatcttt
17641 agttcagttt ttttcaataa cagatttgta gtaggcatca ggtgactggg gattcgtatt
17701 cttcaagttg aaatattacc ttgttgagaa agaaaccatg tgtgagacaa ccatgttgag
17761 aaagaaaaag tgattttata gaaaattaat attgatagtg agcattatat gaaaatcatg
17821 aagttagaac atatttggcc agaaaattta cattaatagt tacccatagc aattaatgca
17881 ttataattac acatacottt tctttaatga aaaagaattc tttccttcca aagttatgca
17941 tgctattgtt aaacattaga gaatatagag aagcaaaaaa gaaaatatct tttttgatat
18001 tttcttaaca tacgtctgtt cctaataatg tttatagttt agaagcattg catgaaatgg
18061 gtagatcaat tttctattta atgtttggat tcattaggta cgaagttagc aaattaattt
18121 ccattagggt gcctgtatgg ttgtaaatcc tggacctgca gaagattttt cagtattggt
18181 ttgtagtctt ttgtttagca gcaaataatt agttctccag agcttctgaa attaattgac
18241 cactttaatg gtgtttacct acctagagaa agaaaagaa cttctccaag tcccttggta
18301 aaattaagcc tcatgaacaa ttaactcaaa tatacacaag gcttgtcttt agcgagcata
18361 tactccctaa agttgattaa gctgaccaag tgattactgc ttataaattc accattttat
18421 ggagaagaag caaacactgc taaataccTt gtggaatcag aggagggaa attagtaact
18481 tgacccccaat actgcgattt taaattgaat tcttgaagcc tacaagtttt acacaggact
18541 ttagagagct ggatagtatc actttgtcaa gtcctacttt tactatgatt ctttgagaaa
18601 aatacatctg actaaataac tctgaatcta aattggataa aataaatgtg acattcaaaa
18661 tgttatttat gatttttagaa aaatatcctt atagcacacta gatgagtttt agtctcaaat
18721 caatcctccc tatcatagtc acttatcaaa ataactaaag caaagtggta gagctgtgct
18781 ctagaagttt gggatttatg atcacaatct tttccaatga gtccctctt tcctctgcct
18841 gtcttcaaca tttgttttttt ttttttttg gttaggacta tccagattgt gtggcctatt
18901 tcaaactcat ggcaaataca ttggatgatc agaaatttc taatgtattt gaatttgtct
18961 acacaaacta gagtaattgc tattaattcc tcaagtgtta attatttcat gcaaaaagga
19021 aaaaggctat tagtctttaa gtgtattagt atgtcaatat ttgggagaag tgtcatgcaa
19081 ttagtggttt gaatttccta tttattttta ttgcattttta ttttatttgc ctagtcaaat
19141 aaaagtaat gttaaataca tggaagcatg attgttttct acactaaaaa tcattttgac
19201 ttgaaaagat ctgatatcca tgaccttcat ctgaagtttt ggcagatgaa aatgtcagat
19261 gcgtcttttg gattaataaa aggcaaaagt cagatcgaaa aatgagtata agctttaatt
19321 atatgacttt aggaggatat gttatgaaaa tcaaagcttt aatagtgatt ataattggca
19381 agttcttttt ttataaggaa ttacaagtca ctctatacaa aaattggaat ttttgtccta
19441 agaaatgaaa tttactatag tttcatctgt gtgtgtgtgt gtgtgtgt gtgtgtgt
19501 ttaaaaaatc aagtgatagg gcttttcctc aataaaatct gaaatctctt atagttaagt
19561 gaacagaaca gtgtatctag gatgctagac tttttttca aagttagttt aaaacttata
19621 catagtaaaa tctgtatgcc ttagggatct ctgtttgcta tcccatagtg aatgattaat
19681 tagtttctgt tagaaatagt cagaactagg ctgggtgtgg tggtggctca tgcctgtaat
19741 tccaggactt tgggaggcca aggcaggagg atctcttaag cccaggaatt tgcaaccagc
19801 ttgggcaggc tggtgagatc ctatctctac aaaaacaaac aaacaaacaa aggacaataa
19861 gaaagaaaga aatagccaga gctttgaaca aaatttctaa gtagaccaat gtaaaagtct
19921 gtcgtcaata tgtagtggct atgaatggag gttatgaatg aaagagaagg ataagatgaa
19981 ctagaggtga gagggaaga cagcaggccc aagtgaaagg cagagccgag tttattgctt
20041 tttggttatt ccaggtgtgt ctgctttgtc tcatgaaaca cctggatgat cactgatttc
20101 tagtggaaga aatgctgaaa agtccttact gtgcatttaa acattctagg tttaatatac
20161 tcagggtttt tcaaaagaaa gggtggctgg agtttgcac taactaatat ttcataaagt
20221 gtctaagtat agatgtctgg ttttttttg tatttctaag actggcttga ggtaggcatg
20281 gagaattctt tgatgggaca taattttctt cctttctttt tttttttttt tttttttttt
20341 tgagacggag ttttgctctt gttgcccagg ctggagtgca atggcacaat ctcggctcac
20401 tgcaacctcc gcctcccagg ttcaagcaat tctcccacct cagcctcccg cgtagctggg
20461 attacaggca tgtgccccca tgcctggcta atttttttg tattttagt agagatgggg
20521 tttctccatg ttggtcaggc tggtctcgaa ctccttacct caggtgatcc acccacctcg
20581 gcctcccaaa gtgctggat acaggcgtg agccaccgcg cctggcctga tgggacatat
20641 ttttcattca atttattga tttaacctca caaaataaaa tattttccta agatgactct
20701 gtggtcattg ttgggcagca taagcttaat ggattttagt tatcataatt taccttaaac
20761 ccaatttgta tttcaggata taaatagagg tttattgtag tgaatcttcc aggaaatact
20821 aagtgatact aataattata gatggtgaac ttaagtcttt atattactga atttgtttgg
20881 tttgatgatg ctaggctatg gcattcttgc taatcaaaac gatgtgtcat ggtgtaacat
20941 aacttattaa aatgggcaca gataacacag gaagcttttt ataaaagcag ctcacaaatt
21001 gtgttacttt gaactgaact ggccatttat gggaaaggtc actgggttgt aaataaggac
```

FIG. 1 (cont.) (SEQ ID NO: 1)

```
21061 caaaagagtt acgtttatat ttttaaaag agattgagga gatttatttt tacatttctt
21121 gaaaatgcct tattttggta tggtattgac agatagtgaa attctgctca tttgtaaata
21181 tagtgtcata ttttaataat ttcaaacata ttgaaaatgc agaatttatt aatagtggga
21241 gcacattttc cttttacta aatgttctac aggttctttt ctttccatcc acacacagtg
21301 ccattaccct cattctaagc ctttcaaaca tctggcagta agtgatctgc tgcacttagc
21361 tctttccagc tgagctgatt tttaaatttt cagaaaattt gtgagctaat tgttaaacat
21421 ggccattatt aaaaattaaa ttatttcaac ttataattaa ataaattata ttaaaacaaa
21481 agtattaaaa actcaaaagt tggctgggcg cactggctca cgtctgtaat cccagcactt
21541 tgggagaccg aggcaggtgg attgcctgaa gtcagggtt cgagaccaac ctgaccaaca
21601 tggagaaacc ctgtctctac taaaaatata aaaaatagc cgggcatggt ggtgcatgcc
21661 tgtaatccca gctactcagg aggctgaggc aggagaattg cttgaaccca ggaggtggag
21721 gttgtggtga gctgagattg cgccattgcg ctccagcctg gcaacaaga gtgaaactct
21781 gtctcaaaaa aaaaaaaaa aaaaaaaag aaacaaaaaa aaaaaaaaa caaaaagcaa
21841 acaaacaaaa aaacaaaaat tatcacttcc taattatttt gcattttact attatctatg
21901 ctattaacgt tatttgcctt cattgtattt gaaaggtgga ctatattcta ttgcactttc
21961 attgtactat attctaatat gcaactgtgt atcccttccc aactctgtgt tcaatgactt
22021 tatatttggt tgctttaaaa tgatgacgat gagagtattt atatcataga aattggcaaa
22081 tgccgtaagt cagtttttgt ttttgttttt gttttccgga gagggattg ttaaatattt
22141 gcctgcatgc aacaccacta catgcagtct gctatctttt gttcttcctg ctttcaggct
22201 cctctcccag ctgtctgtct agcacaaccc agcataccaa atttcttaa atagggaaag
22261 ttgaacatgg taaagaatg aatgaagtca aaagaatgtg gaaagaccta ggctttgcca
22321 tttagtaaag tttagcatct ctaagcctcc atctcttat caataaaatt gagcaatgat
22381 cccttttagt tctacccatt taagaagatt ttcaaatgaa accacaacc tgctcatgtt
22441 tatgaaggca ctttggaaag cgctaaatac acgggttttt attagtagta aacacttact
22501 tcacctttt cacttcttga ctttagttta caagggctca taatctaaat tatatcataa
22561 attgctgtcc cagattttt tacagcctaa ttgccacctg tatgttcgac tttccttctg
22621 ttctttatgt tagatactgg gatagtatgc accaggtggg tgtgccatca ctttctcaga
22681 tgatgtccac tgaagacctt gcatgatcat ggcattcatt tcctgctgt attcagactg
22741 gcctcaacta ttttctttat tgctctccag gaaaaattac aaatgaatca gactgggcaa
22801 tgaagggtaa acctaattat cgctctttgt taaagacagc tcttgttaaa atgcggatat
22861 tgcaaattaa tggaaaaaat atgacatagt aaaccatact cacttattaa tatcttagta
22921 aggaataatt gatgaagtta cttaaccta gagcctaat tcagttaagt tttaatgaag
22981 gacaagttgt agagatatcg agaacccagg gcaggtgcct actgaagaag ttccagacca
23041 aggaagtata aagaaggacc tgggtgggag cagtgagatt ggatatgagg gccactggca
23101 aagttttgcc ccagaacagt gtcaaaatgt ttgcatttgg catagccctt tctctttttg
23161 ttctgaatgg ctttgctaga atatctttc tataatgaat ttatcctgct tctcagatat
23221 tgctaaagca ctcccttttg aattttggtg ctttaacatg cattttgata cattaccaaa
23281 taaggtctga atgacacaaa ttttagaact ctccagagaa aagaaagatg ctgagggaaa
23341 aagcataggt ttgggactca ctaaatccca gttcaattcc tttctttaat aaatatattc
23401 aattttacct gagaaagctc tcgtgctctc gaatttatt tagaaatttc tctttgtaca
23461 tgattgattt cacaatcctt cttctgcctc ctcttctact ttcttctttc tagattttcc
23521 tatctttatg aagattattc tgccttatcc tcaacagtta gaaacaatat ttttgaaaat
23581 cactacggta tcctgcatag tgatttccca tgccaacttt actaatttcc attataaatt
23641 attatttatt gatgcctaga gggcagatga gtgtagctgc tatggagtga ggagacaaaa
23701 cataagaaag ttatgatcct accctcaggt aatgattcag acatgataat taagtcaaca
23761 aattgataga aactaatcac taactctctg gctatagtca ttctttcaat gaatagctca
23821 ttactgagta tgcatgctac agtaacaaaa ttatataagg ctgttgatta aatgttgatt
23881 aagtgcatgt cttattcaga gttttttat atttgaaatg gaagaggctg gacttcagta
23941 atttgctata aactgctagt atgattat tggggggcag ttattttta aagaataatt
24001 taaatatgga atgtttagca gtttgttttt tccctgggaa aaccatact attattccct
24061 cccatccct ttgacaaagt gacagtcaca ttagttcaga gatattgatg ttttatacag
24121 gtgtagcctg taagagatga agcctggtat ttatagaaat tgacttattt tattctcata
24181 tttacatgtg cataattttc catatgccag aaaagttgaa tagtatcaga ttccaaatct
24241 gtatggagac caaatcaagt gaatatctgt tcctcctctc tttattag ctggaccaga
24301 ccaattttga ggaaaggata cagacagcgc ctggaattgt cagacatata ccaaatccct
24361 tctgttgatt ctgctgacaa tctatctgaa aaattggaaa ggtatgttca tgtacattgt
24421 ttagttgaag agagaaattc atattattaa ttatttagag aagagaaagc aaacatatta
24481 taagtttaat tcttatattt aaaaatagga gccaagtatg gtggctaatg cctgtaatcc
24541 caactatttg ggaggccaag atgagaggat tgcttgagac caggagtttg ataccagcct
```

FIG. 1 (cont.) (SEQ ID NO: 1)

```
24601 gggcaacata gcaagatgtt atctctacac aaaataaaaa agttagctgg gaatggtagt
24661 gcatgcttgt attcccagct actcaggagg ctgaagcagg agggttactt gagcccagga
24721 gtttgaggtt gcagtgagct atgattgtgc cactgcactc cagcttgggt gacacagcaa
24781 aaccctctct ctctaaaaaa aaaaaaaaaa aggaacatct cattttcaca ctgaaatgtt
24841 gactgaaatc attaaacaat aaaatcataa aagaaaaata atcagtttcc taagaaatga
24901 tttttttcc tgaaaaatac acatttggtt tcagagaatt tgtcttatta gagaccatga
24961 gatggatttt gtgaaaacta aagtaacacc attatgaagt aaatcgtgta tatttgcttt
25021 caaaacctt atatttgaat acaaatgtac tccctgggaa gtcttaaggt aatggctact
25081 ggttatcaaa caaatgtaaa aattgtatat tttgagtac ctgttacatg ccaggtagaa
25141 tatctcctct cagccactct gagtggaaag catcattatc tctattttac agaaaagcaa
25201 actgaggctc agagagataa tatactttgc cagttaatga atgatggagc catgattcca
25261 gctgaggtct gtattgcctt gctctctagg aatggtagtc ccccccataa agaatctctc
25321 agtttccttt ccaatcaaaa ggttaggatc cttttgattg ccagtgacag aaacccaatt
25381 tactagctta agtaaataaa aggaacgaat ttattggctc atgaagcctg aactatgtga
25441 agacctaggt ggagaactgg ccttaggaac tcaatgggac caaggactca aatgccacct
25501 ggtggcatt gccttatgct ggttttattt tctcagaccg gaccagcttt ctacataaag
25561 tgggtccctg gttagaactc tttgctccta tctttaagga ccacgaaaga aggagcccctt
25621 tgtccttggc taaatgtgaa aaatcccaga gactcttgag tcatagtgct tacccccttgg
25681 gccactcata gtctagaatg aactaggctg agtctcgtgc caacagcaca ggcctgatgc
25741 cagataaag ggtgagtgaa ggggataaa aaataagaca tagctactaa attattgcac
25801 caaagtaaaa acattgagtt gacttgcaat ttgtttcttt taattaaatt catttccttt
25861 ttttggcatt ttgaaggcaa agtaagatat taaactttat ttttattgat tttattcaaa
25921 gaattaagct agtgggagta gcagattcac acttctaaga tcaagggcca gcttctatta
25981 ttgaacactt ggtgtgtgca aatgccatga ggtagggata ctttgttttg ttttttattt
26041 tttattgggt tcgatctctt ttgtttatga tgtatcccca agtgcctaga atagggcctg
26101 gcatatgtca tatactcaat aaatatttgt tgaatgaatc catgatggaa tgtgaaatgg
26161 ctagcattac atagaaacct gtagcattgc tggaagatga aaatatataa acataatcca
26221 ttgcaggtat attgacaagt tcaaaataat ataatgggta ttgaatatct aaatgtttgt
26281 tgttgttgtt gctgttgttt ttgagacaga gtcttgctct gttgcccagg ctggagtgta
26341 atggtgcaat tttggctcac tgcaaacttc gtctcctggg ttcaagtgat tctcctgcct
26401 cagcctctcg agtagctggg tttacaggca ctcgccacaa tgcctggcta atttttgtat
26461 tttagtagat gtggagtttc gccatgttgg ccaggctggt cttgaactcc tgacctcaag
26521 tgatctgccc accttggcct cccaaaatgc tgggattata ggtgtgagcc actatgccca
26581 gctttgaata tctaagtttt aattggatgc tgagggaatg attaatcaga gtagggctgg
26641 gttaattgaa aaatgtgata catttgtatt tatggccaga tagagaacat gaatctgaat
26701 ttgcagaatt atctggctta acattttttt cttttccagtt ttcactgtat ccccccatgtt
26761 gattcaattt aaaaaatata cctatttac ttcaattcaa caatgctatg ccagtacaaa
26821 cccatacgtt ctattatttt tgttttgttt tgttttgta tctccaccct gttacttctt
26881 ttcttataaa attggtattt gaaatttatt gaaatatttt ggaagagtga cataccattt
26941 ttggtacttt gtacctctgc acccttggga agtgaccctg gcttcacatt tcataactgc
27001 cttgtgacca tggccctcaa gtggttgcca gatggttgaa gaacattaac ctatctggct
27061 caattttgtg accatggatt gaatcctcta cataactgca gtgtgcaaac cacacatccg
27121 ttccaagatt gtagtcagga tatgaacttt ttaagaataa aacttcttcc cttctgatct
27181 gggcctggta tgtggcccta ctagaaccac atcacctact cttggtgcta caatttgtg
27241 gcaccaagtt gttcaagttt cacccattaa agaaattccc cgaccttgcc ttctcctcag
27301 gtaactaccc cattctattt tttcttcat agctaacatt ctctgctctc ctggtctctc
27361 tacttcactt tcatttacat ctcagctcct gaagtatggt ttccaccatg ttcctaaaac
27421 tacattgccc agggtcacta gagacctctt atgaaatata acaacacctt tctacattac
27481 ttccgtgtgg accacttttt cacattgaac ccatttgtt ggtttatgta cacacccctt
27541 ccttggcttt cccatctgat ccatttctcc tttgatggag aaggtgagtc tgctccatat
27601 ttagcttctt actctgagta accaaatgtt atggatggga ggttagctct gtgtgtgaga
27661 gaaaggtgga gaagcatgtg gggagggaaa tagatgggaa aaggtaatta ggctttatag
27721 aagggctctc attagcaagc ttctagggga tgccaagatc catgcttaga gattgccagg
27781 cttgtcttca aatctcagct gtgtattact cctttatgtt ttttgtttgt ttgtgttgtt
27841 tgtttttgag acagagtctc gctgtgtcac ccaggctgga gtgtagtggt gtgatctcag
27901 ctcactgcaa actctgcctc ctgggtcaa gcgaatctca gtctcctgag tagctgggac
27961 tacaggcatg caccaccagg cctggctaat ttttgtagag acggggtttt gctatgctgg
28021 ccaggctggt cttgaactcc tgacctcaag tgatctgccc gccttggcct cccaaagtgt
28081 tgggattagt ggcgtgagcc actgccccgg cctattactc ctttagagtg atttagagcc
```

FIG. 1 (cont.) (SEQ ID NO: 1)

```
28141 atgtttactt atggtaactt gacagtaatg ggaataacca ctgatgaaac gtaaagcctt
28201 tgtctaattg tttacctagt tcttccttgt ggttcatgaa attttcatc tctgtacagt
28261 ttgaaaatta agatgataat atttagagat attttattcc tttgtgaaga gaaaaaaggc
28321 tttcattaac agaaatcagt ggcaataact taataaatac aatcagctgg tgttcctata
28381 gtatttaaaa gaaaacagaa agtttactag atttcagcca gttttcagac tatttaatgt
28441 ctattcttac tataatagaa aatatataat ttgatcttgt tctcattttt caaagacctt
28501 taatacatga ttttagtagt tgaaaatgaa gtttaatgat agtttatgcc tctactttta
28561 aaaacaaagt ctaacagatt tttctcatgt taaatcacag aaaaagccac ctgacatttt
28621 aacttgtttt tgatttgaca gtgaaatctt ataaatctgc cacagttcta aaccaataaa
28681 gatcaaggta taagggaaaa atgtagaatg tttgtgtgtt tattttttcc accttgttct
28741 aagcacagca atgagcattc gtaaaagcct tactttattt gtccaccctt ttcattgttt
28801 tttagaagcc caacactttt cttaacaca tacaatgtgg cctttcatg aaatcaattc
28861 cctgcacagt gatatatggc agagcattga attctgccaa atatctggct gagtgtttgg
28921 tgttgtatgg tctccatgag attttgtctc tataatactt gggttaatct ccttggatat
28981 acttgtgtga atcaaactat gttaagggaa ataggacaac taaatatttt gcacatgcaa
29041 cttattggtc ccacttttta ttcttttgca gagaatggga tagagagctg gcttcaaaga
29101 aaaatcctaa actcattaat gcccttcggc gatgttttt ctggagattt atgttctatg
29161 gaatcttttt atatttaggg gtaaggatct catttgtaca ttcattatgt atcacataac
29221 tatattcatt tttgtgatta tgaaaagact acgaaatctg tgaataggt gtaaaaatat
29281 aaaggatgaa tccaactcca aacactaaga aaccacctaa aactctagta aggataagta
29341 aaaatccttt ggaactaaaa tgtcctggaa cacgggtggc aatttacaat ctcaatgggc
29401 tcagcaaaat aaattgcttg cttaaaaaat tattttctgt tatgattcca aatcacatta
29461 tcttactagt acatgagatt actggtgcct ttattttgct gtattcaaca ggagagtgtc
29521 aggagacaat gtcagcagaa ttaggtcaaa tgcagctaat tacatatatg aatgtttgta
29581 atattttgaa atcatatctg catggtgaat tgtttcaaag aaaaacacta aaaatttaaa
29641 gtatagcagc tttaaatact aaataaataa tactaaaaat ttaaagttct cttgcaatat
29701 attttcttaa tatcttacat ctcatcagtg tgaaaagttg cacatctgaa aatccaggct
29761 ttgtggtgtt taagtgcctt gtatgttccc cagttgctgt ccaatgtgac tctgatttat
29821 tattttctac atcatgaaag cattatttga atccttggtt gtaacctata aaaggagaca
29881 gattcaagac ttgtttaatc ttcttgttaa agctgtgcac aatatttgct ttggggcgtt
29941 tacttatcat atggattgac ttgtgtttat attggtcttt atgcctcagg gagttaaaca
30001 gtgtctccca gagaaatgcc atttgtgtta cattgcttga aaaatttcag ttcatacacc
30061 cccatgaaaa atacatttaa aacttatctt aacaaagatg agtacactta ggcccagaat
30121 gttctctaat gctcttgata atttcctaga agaaattttt ctgactttttg aaataataga
30181 tccataatat atattcttat ggaaatctga aaccatttgg gcatttgggg gtaaaaagta
30241 ttttattagt aaatttaaat gaggtagctg ataattaaa ttacttttaa gttaccttttg
30301 agatgattt tctcaatcag agcaccaccc agagctttga gaaacaattt tattcacagc
30361 ttctgattct atttgatgta attttttagaa aataagttttt gctggttgct ttgaatcagg
30421 gtatgagta cagttcactc tgatcctatc atataaatca tgtaagtata taacattttc
30481 aataagtgat tgttggattg aagtgaatga tatttcaagt aattgttatg tcatggccaa
30541 gatttcagtg aaactcaaaa tttctcctgg ttgtgttctc cattgcatgc tgcttctatt
30601 gattaaccta agcactactg agtagaagct ggaagagggg tctaattaga aggccccttt
30661 ctatgctctg cttggcttgt aaaataattt atttctctag atcccaccaa catagtagtt
30721 tcatgtatgc aaaaacaccc acctaaatgt caaagtttgt atgatacatg acatatcta
30781 tagaatttt tttggtctgg tgcatgccaa aaaataaaca tgatatagaa gaattttaata
30841 ttattgagt acctaatctg ttccagttca atatgaaggt ctttatgcag attatttttac
30901 ttaattttcc tagtaactcc atggagcaaa aattatctct aatttatata acaggaagtt
30961 gagcgtgagg caaattaagt aactttccca aagttacaca tatggtaagt ttgagagata
31021 tcccagtctc tttagctcca aagcctttga ccctttcacc ataccagatt atgattgcta
31081 ttaatatata attataatta taatgattgt atttaggtac tcaacagaat ggtgactcta
31141 gtaaccagcc ttggttctgc tgagcttctc tgcgtcttct caggagacac aggctacaga
31201 gcttgaaggc tgaggattct ccagggtca cttcaggggc aaatctgaaa cttttcttcag
31261 gacaggaatc aacgagatct tctcacttac ttatacctgg gggaggaact gtatgaaatc
31321 cacccaagaa ccagtcatgc taagggccaa acctatagac aaaaaaaggg ataggagaat
31381 ggagtatgta tggagaaaga ctaaattgtt cttaaacttc tcaagcttaa aaatatccca
31441 gcaaaagaga tcgtaaaagc ccttcatggc gtattaatta tccatgcatg ggggtgagtg
31501 gaaaggtact cctgagcccg aggctacagc tttggaacta gcagcaccct tgaaggggaa
31561 agcgtgtttc catcatctca actcctactg ataaccaatg gaatattggt gagtaaagga
31621 tcctggggga agaagcagct gaaatgtgta ggtgagaagg cagagagaag aatatttata
```

FIG. 1 (cont.) (SEQ ID NO: 1)

```
31681 ttgggaatgg cacaagtgtg atgaggctgc aggttttttca cccttgtcat agagaaaaaa
31741 ccacgctgac accatgcagt tttaaatagt gagaaatttg caaattgtta gatcttaaat
31801 aatttagata aacatagtgg ccatttagat tattgcagtt ttttcaggat atctgatctc
31861 ttgatttcat tcttttgtc tcttataaga ataaaagggg gggagaaaat ttagccatta
31921 tagtatttct ctacattttc tctgtccttt tacataactt acaccagtgc cttcctattt
31981 atggtattat ttatgggtat ttcttctttt ctttcactga gcaaggataa atgagccagg
32041 gattcttgaa actactgtaa cacttctctt agaaatagat ggtcatactt tcagaatctc
32101 tacacattct tagtccctct aaacaatgat agttgtggca taaaaatatt tgcttggttt
32161 caggactgat agagaaaagt actataaaat ttgctgttaa ctgtgaaagg ttaaaaaaaa
32221 ggaggtgcca tcatgaagga gctaatcttt ctgaagtact gctgtagttt aaatattat
32281 tagctatgac ttctcaccat taactatgca cttgctttt cttcatctga ctcagcagcc
32341 agatagatgc aacattgtct ttaacattta agactcctag caagtccggg cacggggggct
32401 cacacctgta atcccagcac tttgggaggc cgaggtgggc aaatcacaag gtcaggagtt
32461 tgagaccagc ctggccaata tggtgaaacc ctgtctctac taaaagtaca aaaatcagcc
32521 aggtgtggtg gcgtggtggc gggcacctgt ggtcccagct acttgggagg ctgaggcagg
32581 agaatagctt gaacctggga ggcagaggtt gcagtgagct gagatcgcac cactgcactc
32641 cagcctgggt gacagagcga gactccatct caaaaaaaaa aaaaaaaaaa aagactccta
32701 gcatggaaga gaaactggct gttgaaaacc tgaatgtgag agtcagtcaa ggatagtttg
32761 agggaagcca agtagaggaa gctctcacaa gcagattggt gagagaatat gattatacaa
32821 tgcatttatt atgataagaa attcacaagc attcattcaa atactcttg attcctaggc
32881 agctctgggc atatttccac caacaaattg aggcatatgt cagtgcagcc taggtcagac
32941 tacctttttt cattaaacct cacaaaatta aggacatac aggagaagtc ctggtactca
33001 tgttgcagac tacagtctat atggcaaagg aggatctctg tcccttatgt ttggatgaaa
33061 acattgggta ggcatttgaa tacaagccta ctgctaatat ggggctaagg tcttttggccc
33121 cctaaaggtt tgctgaaata ttactgacag gaggcagatt gataagagga aaagcacata
33181 aatgtatttg acatgtatac atgggagcct tcaggatgaa gacctaccct ctcagtgcag
33241 tatggaagct tgtataccat cttgaggtta cagaaagaat gggggtttgg atcttttgtaa
33301 aacaggtttc agtggcaaga caggttatga gaaggagaaa ggaagagact tgggtagcaa
33361 aggggtgtctt gttttgtagg taaatcgttg gcagcccaca gagaaaatag atggagaatg
33421 tttctttca gaccttggca ggtgtcagat tctcagttaa tctctcctag atttgaaaaa
33481 aaaaaaaaag gtctagaaag ggagagcctg gctgcactaa cacattttct acagatgcaa
33541 atttctccca caaaatacag ctttgcaggt ccacttctat ctgctgggcc tgtggcaacc
33601 atttcaaaat atgtgaatga atatatgtg ggggtaaact attttattt acttccctaa
33661 agaagggatg gtgttctctc gggaattctg tgcatagaga gcctgtggct taggcacttt
33721 gatttatgta tatctcttcc tgtgattggc tatctaggga ctgctatctc cagcaaatct
33781 tctaaatgtc tgccatgtag aattccttc tcatctttct gtctcacccc cttatctagc
33841 tgcttctcta accctagagt gacactgcac tccccacaat ctcctatgtc ctgaatattt
33901 tacccccatcc taaactccat ctctaacaca gatgcacttt cttgtgctgc ctactgcatt
33961 gtacatcttc cccttagttc ccatgatgca actctgccct accccagaaa atgtaattta
34021 attggtctgg gataaaacct gggacactat cattcttgaa atattcccca agcgattcta
34081 attatatagc caaagttgag aactatttgt agacaggcat cagcatgatc acttaatgat
34141 ttgacttttg ctagatctaa ggtgaggaaa ttggagagtg gtatccatag gaagaactgt
34201 ttagtttaat tttttttta ttttttcttc taaaaaaaaa tccaacaacg agatacatgt
34261 gcggaacatg caggtttgtt acataggtat aatgtgccat ggtagtttgt tgcacctatt
34321 gacccatcct ctaagttccc tcccctactc cttacttccc aacaggccct ggtgtatgtt
34381 gttccctct ctgggtccac ctgttctcaa tgttcaactc ccttttacga gtgagaacac
34441 atggtgtttg attttctgtt cctgtgttaa tttgctgagg atgatagttt ccagcttcat
34501 ccacgtccct gcaaaggaca tgatctcatt ccttttatg gctgcatagt attccatgat
34561 gtatatgtac cacattttct ttatccagtc tgtcattgat gggcatttgg ttggttcca
34621 tgtctttgct attgtaaata gttctgcagt aaacatatat gtccatgtgt ctttatagta
34681 gaatgattta tattactttg ggtatatacc cagtaatgag attgctgggt caaatggcat
34741 ttctggttct agatacttga ggaatcgcca cactgtcttc cacaatggtt gaactaattt
34801 acactcccac taacagtgta aaagcgttcc tatttctcca cagcctcacc agcatctatt
34861 gttcctaac attttaataa ctgctattct gactggcatg agatggtatc tcattgtggt
34921 tttgatttgc atttatctga tgatcagtga tgctgagatt tttaaaatat gtttgttggc
34981 catgtaaatg tcttttgtga agtgtctgtt catatccttt gcccacctta atagggtttt
35041 ttttttcttg tgaatttgtt taagtgcctt gtaaattctg gaaattagat ctttgtcaga
35101 tggatagatt gcaaaaattt tctcccattt tgtaggttgc ctgttcactc tgatgatagg
35161 ttcttttgct gtgcagaagc tctttagttt aattagatcc aatttgtcaa ttttggcttt
```

FIG. 1 (cont.) (SEQ ID NO: 1)

```
35221 ttttgcaatt gcttttggca ttttcctcgt gaagtctttg cccgtgccta tgtcctgaat
35281 ggtattgcgt aggttttctt ctagggtttt tatagttttg ggttttacat ttaagtcttt
35341 aatacatctt gagttaattt ttgtataagg tataaggaag gggtccagtt tcagttttat
35401 gcataatggc taggcagttt tcccaccacc atttactgaa taggagatct tttcctcatt
35461 gcttgttttt gtcagatttg tcgaagatca gatggttgta gatgtgtggt gttatttctg
35521 aggtctctgt tctgcaccat tggtctatat gtctgttatc gtaccagtcc catgctgttt
35581 tggttaccgt agccttgtag tatattttga agtctggtag cgtgatgcct ccagctttgt
35641 tcttttttgct taggattgtc ttggctatat ggagtcttct ttgattccat atgaaattta
35701 aaataatttt tttttattct gtgaagaatg tcaatggtag tttgatggga atagcattga
35761 aattataaat tactttgggc agtatagcca tgttcacaat attgattctt tctatccgta
35821 aggacgacac ttttccatt tgtttgtgtt ctctcttatt tccttgagca gtggtttgta
35881 gttctcctta aagaggtctt tcacatcctt tgttagctgt gttcctaggt attttgttct
35941 ctttgtagtg attgtgaatg ggaattcatt cttgatttgc ctctctgctg cctgttgttg
36001 gtgtaaacaa aattcatttc ttgttcttat ttgtgaaatt ttggaaccaa atctattttc
36061 aaattagaaa ttgcttgtga taatggtttt gcaacttaga ctggatatga gacgatgaga
36121 tattagttct ttcattcctt tgtaggaata tggtgcatct tgcattattt tagctaacta
36181 gtgtccttta atgactaatg aaatatgacat ggtgaaacaa agtaaaatat atatgatgca
36241 ctaagtatgc attgttcca aaggttcagc atttttttt tgttaactct gctgggatct
36301 gctttatgca ctgataacat aacttatttt atgatcttaa gcaaataaaa acacttatct
36361 ggacctcagt ttccttaact gtacaactga gggaaactgt atagtatagc tatagtacag
36421 tataccatct ttaccgtcac ttccatcttt taaattatgt gtatataaga tagggcctag
36481 ataaatggta tttatcttaa attacagtga tactagctta taacttaatt tgctaggtca
36541 tgttgaactg ataacaatgt gtgaactgat gagcaactga gaagtaacca ggttgtgtta
36601 taacagtttg ttttttgattt agggttatca gtgagggtgg cggtggggag gggactttgg
36661 agtctaactg tctagttcaa atattagttt ttgtttattt ttatttttaa ttttttgtggg
36721 tacatagtag atgtatatat ttatggggta catgtgatgt tttcatatag gcatgcaatg
36781 tgaaataagc acatcataga gaatggggta tccatcccct caaacactta tcttttgagt
36841 taccaacaat ccaatgacac tctttaagtt atcaaatcac agttttgcca gctactagcc
36901 atgtgatttt gggtaggtta cttaaattct cttcatctca atttcattat tgtaaagtgg
36961 agataatgat agcacatttt ttcttttttct ttttttcttt attttttatt attatacttt
37021 aagttgtgtg atacatgtgc agaatgtgca ggtttgttac ataggtatca acaactctat
37081 aaaacatgtt ctatccagga aaagaaacta tcatcagagt gaacaggcaa cttacggaat
37141 gggagaaaat gtttgcaatc tagatggcga ttgcaatggc ggttcgctgc atccatcagc
37201 ccatcatcta cattaggtat ttctcctaat gctatccctc ccctttgctcc ccaccccctc
37261 acaggcccct gtgtgtgatg ttccccctccc tgtgtccatg tgttctcatt gttcaactcc
37321 cacttatgag tgagaacatg tggtgtttgg ttttctgttc ttgtgttagt ttgctgagaa
37381 tgatggtttc cagcttcatc catgttcctg caaggacatg aactcatcct tttttatggc
37441 tgtatagtat tccatggtat atatgtgcca catttttcttt atccagtcta tcattggtgg
37501 acatttgggt tggttccaag tctttgctat tgtgaacgct gcagcaatga acatacataa
37561 gcatatgtct ttctagtcaa ataagttata atcctttggg tatgtaccca gtaatgggat
37621 tgctgggtca aatggtattt ctggttctag attcttgagg aatcgccaca ctgtcttcca
37681 caatggttga attaattttac actcccacca acagtgtaga agcattccta tttctccaca
37741 tccgctccag catctgttgt ttcctgactt tttaatgatc accattctaa ctggtgtgag
37801 atggtatctc attgtggttt tgatttgcat ttctctaatg actagtgatg atgagcttct
37861 tttcatgttt gttggctgca taaatgtctt cttttgagaa gtgtctgttc atatcctttc
37921 cccactttttt gatggggttg tttttttccct gtaaatttgt ttaagttcct tgtagatttt
37981 ggatattagc cctttgtcag gtggatagat tgcaaacatt ttctcccatt ctgtaagttg
38041 cctgttcact ctgatgatag tttcttttgc tggatagaac atgtttttata gagttgttgt
38101 gagaattaaa tgcattaagc acatagaata gattctggta catagcaagt gctctctcta
38161 tatatggaac tctatatgta gttggtgcaa aagtaattgt ggttttcacc attgaaagta
38221 atggcaaaga ccatcattac cttttcacca atttaaaatat atggaaggaa tatatatata
38281 aaacctatat atatatgtca catatatgtc tctaacccat tattaaata tataatacaa
38341 tatatattat aattataatt gtatataaca tatgttatat aataatatag taatatttat
38401 tctaaataaa tatataatac tataaataat ataataattt atatatatga ttaatatata
38461 taataggcta tattatatat tattaacata tacatatgtg tatatatatg tctttcatag
38521 acttaaatat atagagcaat aataggttag aaaatagcaa acatgtatat ataaacatat
38581 atacatatag aaaacatata taaaaacata tatatatata tatatatgtg tgttttctgc
38641 ctttcatttt tagagacagg gtctcatcat gttgcccagg ctggtctcaa actcctgggc
38701 tcaagtgatc ctactgcttt ggactcccga agtgctggga tttcagacat gagacactgc
```

FIG. 1 (cont.) (SEQ ID NO: 1)

```
38761 acccagtcca gtccctgtct ttttaaatag actctctacc taagtgcaca aatactcatt
38821 atttacattt agttatttct gtatatatgc tataagcaaa tcttgtagca ccagtttgat
38881 ttttataagg cacaagaata tattttacta atgctttaaa atggcagcta gattctagta
38941 ttactttaga aattaaaatt aatattttaa cacatctttc attattgtgt tatctgaacc
39001 aaacctatta ttgctgctat ttcagcaaat ccaggggctt tttcttataa aatatgaaga
39061 atatagctta gatttctagt gaagatgtta ccagtaataa ttaataaaat cagtaagcac
39121 taaaaggaaa ataccaaaac taaagcattt tgaattagtc attgaatcta aaagaaaggt
39181 agatttttt ctgagattct gttctaggtg tggtatatgt gtattttgc aaaaactata
39241 aacaattgtg gcaaatgaa ggaaatattt aaaacaaac ctcttaattc ttcagtggat
39301 taagcgtgaa tatgttttta ttttctatga tgaatatgga aaaattcatt tccttagcaa
39361 tttgtatgag cccaaaaact attgtcagac tctgctgtat caaaatagac aaaaattga
39421 cactcacttt taccctgcca aaagcaaaat cttaaacttt tgctttagta tataagccag
39481 cattcattgt atcctatgat gggttctgag tgtaggtgta tttgctttct tccattttt
39541 gtatgcatgt tttcttttta tttattattg taagttgtat gaaattttta tccaattttt
39601 tattttcttc tgattaataa tcagaataat cagataatta ctggtaaatt tgatgttaat
39661 ccttccagct ttttcccatg gaatttata cttaataaag gggagaagtc atcattacat
39721 aatgtgcata ttaatctgct tctcccttta atgtgttgtg aatgcctttc catgtcatta
39781 gatgttttc tacctagtta ctttcatgaa tcatatggct gtaccatgat ttatttaatc
39841 agttcctcat cattgagtat gtaaattgcc tccattttt tattactata aaggtcctt
39901 cagtacacac ccctttaaaa gctgactctt agaaggtgtt cttgactctc tacctaagtg
39961 taaaaataca aataaattgc tttccagaaa aggtgcacta ctatttact ttcctgatac
40021 taaactatga aaattcagtc ctaacaatag atatttaaat aaagttttaa aaatgccaag
40081 tgaaaagag catattatta ttttcatttg cattactttt ggttcctggt gagtttaatc
40141 tgtttttgta tattaattat gcatttatat ttctttttgt gtgtgtgaat tgcctttcat
40201 gttctttgtg tgtttttatt ttgttgtatt tgtctctttc ttgatatatg agagaatatt
40261 ttccctagcc tgtcaattgc cttgtaattt tgtttctagt gagttttttt tttttttttt
40321 acaattaaaa gctttaattt ttgaaaattt tgctggcaaa tctatatatc tttttctttg
40381 ttttctgctt tgacattatt cttttataaa ggcccatgcc acccaaatat tatgtaagca
40441 tgcatctatg tttttattac ttcatctttt acatttaaat atctactcta tttagaattc
40501 attgtgatgc atgtatgagg tagaaatcta atttcaaaaa gatgagtatc cagtttgtcc
40561 atcatttatt gcatgatctc tttctccact gaattaaaat gccgtatttt ataatatatt
40621 aaagtattac atgtgcttgg acatgttcct ggactttga gataaatcag tctatttctt
40681 tgtcatgtca catattatta tggctttatg atttaatatc cagtaatgta aaccctctga
40741 cacattattc ttattcctca aatgttttg atgagttttc ttccaaatga aatttataat
40801 catttattc attgattcaa caaatatttg ttgaatggat attctgtgct tggtattgtg
40861 catggtatta ggattgttgc aaaaatttga actgacagtc cctactctta cggtgctaaa
40921 aattcacttc caaaaaaatc tttaaatttt gatgaagatt gcactaatct tataaaataa
40981 cttggagggg aatgtaatct ttgcaacatt aagttcttca ttttagaaag ttttaagact
41041 ctccattat ttgagacttt taaaatatgt cccaataatg ttttgtgaga tgtatatttt
41101 aagatatata tcttattgct attacattgt atcttttgtt atattgttac tatgaatggg
41161 atactcattt aattagatgt catttttggt atatagaaat ctatttctt agcatagtca
41221 ttttttaaac ctcgatctat taaattcttg attcatttac atttgttaca caatcatatt
41281 ctatgctgat aatacttctt gcttcttcc aatatttgta cctcgatcat ttttcttgtt
41341 gagttgtatt agctagaagt tctagaaaaa tgttaaatgg tagtaatagc tagtattctg
41401 ttttttcctg actctaaatg taatgcatct agactttat aattatggca ttgattgtaa
41461 catttgagg aagaaatcct ttttcaggtt aataatgtat ctttatattc aagtttatta
41521 agaacattta ttggaaacat attgaaattt tatcagattc cttttcagtt gttactgaga
41581 taatcatagg ttcttctgta ttctttaat taatttctca aaattaaact gtcctattat
41641 tcttggaata acgacatata aagtactgta tatttaaaag aagttaaaat gataatggtg
41701 attttattaa gtgacctcac acaatagaaa acagtgtagc cttagaagtt ttccaagtga
41761 ccattctact tagaaacaac cctgctttgg gatcagaact gtaatttta aagtaaagtt
41821 ttctgggttt aattcattta gtgtaattac aagcatgagt tcaggttct attttttca
41881 cctgaacttt ccttcatggt ttgaatatct agaaaagca gactttccta tctctagact
41941 aaacatttga tcctatctta ggtatgcatt acaattttt aaccataaat ggttaaagaa
42001 tttagactca tctacaataa ctttgaagct ctggtcttga agaacatgtg agaaatgaga
42061 tataactcct agaagatata ggagacattt ttagtcttcc aaattttccc tgggaggctg
42121 atctaaattg agtcacaaaa ttgttcccac caggaatgca atcacttgag ctgttttcta
42181 atctgagccc ctctacccag atgatcttct gaactcatac tgttcagact ttcatccttc
42241 tgagtagaaa acagccatag tcatggcagg atgagggcta ggacaattac ccaaggaatt
```

FIG. 1 (cont.) (SEQ ID NO: 1)

```
42301 cttggcctct gccatgggac tctgcagact cagatcatat aatcagagat gttagcactg
42361 gagggacat cacaattagc tttctccacc tcttagttta tcagtgagga aaactgtcca
42421 gagcgcggaa gagactaaaa taacacagcc aatgtaggta atgtgctgga taagaatttg
42481 gaattcacga ttttgaattc agtgtttatt tcaccatcac gctggcttac acgttggtat
42541 caggcttctt ctattattga agtgagccat taagtgaatt ccatcttgat ttgtgtctga
42601 tacagagtaa taaactattt tattaaatat ccaaataatt atacattcct ccttcttaca
42661 tgcaagccta agtttgcttg tactatttca tgtggtagca aatcaggacg cttcttgtgt
42721 ctctgaaaat actctgagta atggagtaca gtcagctttc ttgtaccaag aatatangga
42781 ctatgtttct cccagtcatt ctgggataa ttttgtgaa ggattgcact tcataggtta
42841 agctaggtat cagttaccag tgttttttcc aaataaaaaa aaaatcaggt gatatctgta
42901 aatggttcca ttgtaaatat taagaacat gatgcttaaa acagattagg gaaaactata
42961 gaaggggtgg ggtttcggag tgctaatttt gtccttgaat ggtaacagct ccatgtggtg
43021 gtgaggttta tgttggtttg ctgtttgcag atgatcttat tattagaatt tttcataccg
43081 aaaataaact gcatttagt ttgtaaacat gcccttccag agtaatgcta ccagttcttt
43141 gtgaaatagc tactgttgtt caaggatga ctatgtcctc ttcggttgag gaaagatgac
43201 aacaaactca gtaatgacat gtaaatagg tattacaaac caggtatggt ggcatgagcc
43261 tgtaatccca gctacttgag aggctaaagc aggaggatct gttgatctat ggatttgagg
43321 ctgtagtgtg ttgtgatggc acctatgaat agcccttgca ctccagccca agcaacaaag
43381 caagactgtc tctgaatttt tgtttgttt tgttttttgt ttttttttt ttgagacaga
43441 gtcttgctct gtcacccagg ctgaagtgca gtggcgcgat ctccactcac tgcaagctcc
43501 gcctcctggg ttcacgccat tctcctgcct cagcctcccg agtagctagg actacaggcg
43561 cccgcctcca cgccagcta aattttttgt attttagta gagacgaggt ttcactgtgt
43621 tagccaggac ggtcttgatc tcctgacctt gtgatcctcc tgcctcggcc tcccaaagtg
43681 ctgggattac aggcgtgagc caccgcgccc ggccctgtc tctgaatttt ttaaaaaggc
43741 attccactca aattaataca catttaatt gtgtttgtt gtaaattaca actgaataaa
43801 aattcagcaa ataagtctgt tgtggtaggg aaaagtctat tgtgatctgg aaaatataat
43861 ggagaaatcc agtggaagag atttatttc acattactca aaataaaaaa atcttataca
43921 agtctttaca cttgtaacttt gaaaattct gtgctaaaat ttagcttggt tgctaaaata
43981 tttctctttt tttctcagaa gcttcttttt agcatcctat agacacaagt tacttttaa
44041 aatatttgca tacttgcttt gcaatgtatt gtttatcagt agttctatat tcttgagat
44101 agtctatcca gtctttctgt atttatcgta tgtctgtata gatatatatt agcagataaa
44161 tgagttctga aaggggagaa atgtgattat gctaatcatg atataaagaa ttgactttat
44221 aagcagtgtt cacaggtcat acctttcccg ttactgtctt acagtgaaca agaaatgatg
44281 ctttgtctgg tatgcatggt aaataatgcc ccttgctctc tgcttcatga tcacatgtga
44341 tacttctaac atagatagca catgtaaatc cagtggcctt gactgcaact caagagagca
44401 ttttggccaa gtacaaaccc actagtcatg aaaaaaaaa aaaaaccaaa tcaaagtaaa
44461 ttgatggtat tgacatttgt ctatgaaaaa caacataata tagaacaatt ctggggtaaa
44521 atattgatct aaaataattt taaggattaa atattgccat tgtaagcata ctatgagcaa
44581 ttatgtttgt aatgcagata tatttataat tttaaatcca agatttacct taattgtaca
44641 ttttcctaat ttaaaaagt tattttgaaa aaaaaatcct cgaatctaga gaaaggttgg
44701 caaatacata tggaactttg taaaaaacat ccagggcagc actttcactg attgcagtag
44761 cttaggagtg aaaaacaaca caactgctcc aatgtatggc aatgggcaaa tatcccgatt
44821 tattcacagg gtggcatgtt aggcagtgct tagaataaat gagttggtta tacaagtatc
44881 aatagggata aatgtgaaaa acacagtgtt aagttttaa aaagttgtaa aaagcacagt
44941 aggatgttat ttatataaaa tttaaaaacc tcaaaaacca ttcttctttg atatatattc
45001 taaagatgaa catatatgta atagaagtac aaaacataca taaaataata tacactatgc
45061 agtcatttgt gtacttactt ttcaaaaata tttcagtaga tatagcaaac agttaacatg
45121 taatatttgg ataggaggtt ggcaattttc tttttagcac ctgcctgtct gctatcattc
45181 aaactcacat ttaaaatgtg gctatgtgag atgagagaac tataatattc caggttgtgt
45241 attagtttgg aaacttttta aaagtttgaa tgtggtctga gagatagttt gttataattt
45301 ctgttctttt acatttgctg aggagagctt tacttccaac tatgtggtca attttggaat
45361 aggtgtggtg tggtgctgaa aaaaatgtat attctgttga tttggggtgg agagttctgt
45421 agatgtctat taggtctgct tggtgcagag ctgagttcaa ttcctgggta tccttgttga
45481 ctttctgtct cgttgatctg tctaatgttg acagtggggt gttaaagtct cccattatta
45541 atgtgtggga gtctaagtct ctttgtaggt cactcaggac ttgctttatg aatctgggtg
45601 ctcctgtatt gggtgcataa atatttagga tagttagctc ctcttgttga attgatccct
45661 ttaccattat gtaatggcct tctttgtctc ttttgatctt tgttggttta aagtctgttt
45721 tatcagagac taggattgca accctgcct ttttttgttt tccattggct tggtagatct
45781 tcctccatcc ttttatttg agcctatgtg tgtctctgca cgtgagatgg gtttcctgaa
```

FIG. 1 (cont.) (SEQ ID NO: 1)

```
45841 tacagcacac tgatgggtct tgactcttta tccaatttgc cagtctgtgt cttttaattg
45901 gagcatttag tccatttata tttaaagtta atattgttat gtgtgaattt gatcctgtca
45961 ttatgatgtt agctggtgat tttgctcatt agttgatgca gtttcttcct agtctcgatg
46021 gtctttacat tttggcatga ttttgcagtg gctggtactg gttgttcctt tccaggttta
46081 gcgcttcctt caggagctct tttagggcag gcctggtggt gacaaaatct ctcagcattt
46141 gcttgtctat aaagtatttt atttctcctt cacttatgaa gcttagtttg gctggatatc
46201 tctcagacca cagtgcaatc aaactagaac tcaggattaa gaatctcact caaagccgct
46261 caactacatg gaaactgaac aacctgctcc tgaatgacta ctgggtacat aacgaaatga
46321 agacagaaat aaagatgttc tttgaaacca cgagaacaa agacaccaca taccagaatc
46381 tctgggatgc attcaaagca gtgtgtagag ggaaatttat agcactaaat gcctacaaga
46441 gaaagcagga aagatccaaa attgacaccc taacatcaca attaaaagaa ctagaaaagc
46501 aagagcaaac acattcaaaa gctagcagaa ggcaagaaat aactaaaatc agagcagaac
46561 tgaaggaaat agagacacaa aaaccctte aaaaaatcaa tgaatccagg agctggtttt
46621 ttgaaaggat caacaaaatt gatagaccgc tagcaagact aataaagaaa aaagagaga
46681 agaatcaaat agacacaata aaaatgata aagggatat caccaccaat cccacagaaa
46741 tacaaactac catcagagaa tactacaaac acctctacgc aaataaacta gaaaatctag
46801 aagaaatgga tacattcctc gacacataca ctctcccaag actaaaccag gaagaagttg
46861 aatctctgaa tagaccaata acaggctctg aaattgtggc aataatcaat agtttaccaa
46921 ccaaaaagag tccaggacca gatggattca cagccgaatt ctaccagagg tacaaggagg
46981 aactggtacc attccttctg aaactattcc aatcaataga aaaagaggga atcctcccta
47041 actcattta tgaggccagc atcattctga taccaaagcc gggcagagac acaaccaaaa
47101 aagagaattt tagaccaata tccttgatga acattgatgc aaaaatcctc aataaaatac
47161 tggcaaaccg aatccagcag cacatcaaaa agcttatcca ccatgatcaa gtgggcttca
47221 tccctgggat gcaaggctgg ttcaatatac gcaaatcaat aaatgtaatc cagcatataa
47281 acagagccaa agacaaaaac cacatgatta tctcaataga tgcagaaaaa gcctttgaca
47341 aaattcaaca accttcatg ctaaaaactc tcaataaatt aggtattgat gggacgtatt
47401 tcaaaataat aagagctatc tatgacaaac ccacagccaa tatcatactg aatgggcaaa
47461 aactggaagc attccctttg aaaactggca caagacaggg atgccctctc tcaccgctcc
47521 tattcaacat agtgttggaa gttctggcca gggcaatcag gcaggagaag gaaataaagg
47581 gtattcaatt aggaaaagag gagtcaaat tgtccctgtt tgcagacgac atgattgttt
47641 atctagaaaa ccccatcgtc tcagcccaaa atctccttaa gctgataagc aacttcagca
47701 aagtctcagg atacaaaatc aatgtacaaa atcacaagc attcttatac accaacaaca
47761 gacaaacaga gagccaaatc atgagtgaac tccattcac aattgcttca aagagaataa
47821 aatacctagg aatccaactt acaagggatg tgaaggacct cttcaaggag aactacaaac
47881 cactgctcaa ggaaataaaa gaggacacaa acaaatggaa gaacattcca tgctcatggg
47941 taggaagaat caatatcgtg aaaatggcca tactgcccaa ggtaatttac agattcaatg
48001 ccatcccat caagctacca atgactttct tcatagaatt ggaaaaaact acttaaagt
48061 tcatatggaa ccaaaaaaga gcccgcatcg ccaagtcaat cgtaagccaa aagaacaaag
48121 ctggaggcat cacgctacct gacttcaaac tatactacaa ggctacagta accaaaacag
48181 catggtactg gtaccaaaac agagatatag atcaatggaa cagaacagag ccctcagaaa
48241 taacgccgca tatctacaac tatctgatct ttgacaaacc tgagaaaaac aagcaatggg
48301 gaaaggattc cctatttaat aaatggtgct gggaaaactg gctagccata tgtagaaagc
48361 tgaaactgga tcccttcctt acaccttata caaaaatcaa ttcaagatgg attaaagatt
48421 taaacgttag acctaaaacc ataaaaaccc tagaagaaaa cctaggtatt accattcagg
48481 acataggcgt gggcaaggac ttcatgtcca aacaccaaa agcaatggca acaaaagcca
48541 aaattgacaa atgggatcta attaaactaa agagcttctg caaagcaaaa gaaactacca
48601 tcagagtgaa caggcaacct acaacatggg agaaaatttt cgcaacctac tcatctgaca
48661 aagggctaat atccagaatc tacaatgaac tcaaacaaat ttacaagaaa aaacaaaca
48721 accccatcaa aaagtgggcg aaggacatga acagacacta ctcaaaagaa gacatttatg
48781 cagccaaaaa acacatgaag aaatgctcat catcactggc catcagagaa atgcaaatca
48841 aaaccactat gagatatcat ctcacaccag ttagaatggc aatcattaaa aagtcaggaa
48901 acaacaggtg ctggagagga tgtggagaaa taggaacact tttacactgt tggtgggact
48961 gtaaactagt tcaaccattg tggaagtcag tgtggcgatt cctcagggat ctagaactag
49021 aaataccatt tgacccagcc atcccattac tgggtatata cccaaaggac tataaatcat
49081 gctgctataa agacacatgc acacgtatgt ttattgcggc actattcaca ataggaaaga
49141 cttggaacca acccaaatgt ccaacaatga tagactggat taagaaaatg tggcacatat
49201 acaccatgga atactataca gccataaaaa atgatgagtt catgtccttt gtagagacat
49261 ggatgaaatt ggaaaccatc attctcagta aactatcgca agaacaaaaa accaaacacc
49321 gcatattctc actcataggt gggaattgaa caatgagatc acatggacac aggaagggga
```

FIG. 1 (cont.) (SEQ ID NO: 1)

```
49381 atatcacact ctggggactg tggtggggtc ggggagggg ggagggatag cattgggaga
49441 tataccdaat gctagatgac acgttagtgg gtgcagcgca ccagcatggc acatgtatac
49501 atatgtaact aacctgcaca atgtgcacat gtaccctaaa acttagagta aaaaaaaaa
49561 aaaaaaaaaa gtttgaatgt tttcttgcat tcagagcctt ggttgacata gttaattaaa
49621 aataaaacat tgtatataaa gcacagaatg agcagctaca caaagctgct caatcaatga
49681 cagctctata tgggttaggg tttcttgtgg ggatgacatt gatgtagaaa gcatggtcat
49741 ctattgagaa tgatggggct ggaggtattg gatacttgag gtttagaaaa tacattgtag
49801 aaaatggaca aaaaccctc aaattaggg atgaggcaga ataatgcttg gcaataccag
49861 gggtaggctg cagtctttct tggaaatata tattttaaat ggaaccaatt atcatagcat
49921 catttcctct cagggttacc ctctgatccc tattttacta aatcgttata aaacaaaatg
49981 aggaattatg tgtccttccc tttgaagcc aatgtaacaa gatgggtaag aattagacct
50041 cctgagttca aaatccctgg attcagatct attcctgtat attcaggaga agtggtaata
50101 aattcgatgg acaatttggt ttagtagtcg attgaggacc ctgatgaggt atatttggga
50161 aaacataact tccgctctct ctcattgact cacgggcctt tgaggagtcc aggagtcatt
50221 ggaatctggc ctgaggttga ggctgctggc aaaactcctt ccccaaagtc cattcctatt
50281 gctgactgag aagggactag cattggaagt ggctgatttt aaataccgct agtgctggtg
50341 tgctcctccc tcccattccc agctctgctt tgtgtagttg ccttgagaag ctaagttcat
50401 tctgaaaata atgccattgc acaaaacact tttgaaagtt ctagtttgaa attcatcag
50461 gtcacttggt ctgtgtggcc tcagtttctt catctgccat gtgaaaataa taatgcctac
50521 tctgtagcaa agaaagtctc tatagtaaac aaaaaaaaag cctactctga tactgaaagt
50581 tgttatgaaa aataaaaaag ggaaatgctt tagaaactgt taagtgctat gtagatgtta
50641 ctaattaaca aaccatttca gaaactatac tttttatttt atggccacta ttcactgttt
50701 aacttaaaat acctcatatg taaacttgtc tcccactgtt gctataacaa atcccaagtc
50761 ttatttcaaa gtaccaagat attgaaaata gtgctaagag tttcacatat ggtatgaccc
50821 tctatataaa ctcatttta gtctcctcta aagatgaaaa gtcttgtgtt gaaattctca
50881 gggtattta tgagaaataa atgaaattta atttctctgt ttttcccctt ttgtaggaag
50941 tcaccaaagc agtacagcct ctcttactgg gaagaatcat agcttcctat gacccggata
51001 acaaggagga acgctctatc gcgatttatc taggcatagg cttatgcctt ctctttattg
51061 tgaggacact gctcctacac ccagccattt tggccttca tcacattgga atgcagatga
51121 gaatagctat gtttagtttg attataaga aggtaatact tccttgcaca ggccccatgg
51181 cacatatatt ctgtatcgta catgttttaa tgtcataaat taggtagtga gctggtacaa
51241 gtaagggata aatgctgaaa ttaatttaat atgctatta aataatggc aggaataatt
51301 aatgctctta attatccttg ataatttaat tgacttaaac tgataattat tgagtatctt
51361 ctgtaaactg cctctgttgt agttttttt ttctcctaat catgttatca ttttttttgga
51421 atccatggtt tcctgttaag atgactcaca cagcctacat aaaagtaatt gacaaaatat
51481 catcttatag taaaatgcca catatcttta tgttcagcaa gaagagtata atatatgatt
51541 gttaatgata acccaaacaa caaaagattt caccttaact ggttgtcata agtagtagta
51601 tccacgcct tattttgagt tggattttta tcatcctatg agccctacaa atttaaagtt
51661 tttggaacag cacgtgcatt gaacccataa gaacctactc tgcttttctg catgtattgt
51721 ccagacaaga gaccaaattg ccgaggcatc atttaggtga attctaatta acatttagct
51781 accttacaac cacaattcaa ggttgtttca aaggcatgtg cttgcatcat cctgattcac
51841 taccatgtgt tactaacttg gatctgcaaa gtcattataa aaagctgttt tgatggactt
51901 atttggatat tgctttaccc ttcttctctc ttttcttta tcaatgtaaa aacattatat
51961 gttaaatact tggcttttaa gagcatagat ctgaaatctg cctctagcaa ataacccata
52021 acacttctaa gatatacctg caaggtcaat tgtgttgtaa aaccttgata accatacttt
52081 attgttcaaa aaagcctttt atgaaggcag aagttaaaaa aaaaaaacaa aaaaacaga
52141 gtccacagtt atcacctcag ctacaatctc atcagttcac aagtaccagc aaaacatgtg
52201 ataagtcaac aaatgtttta tttcaatctg aacatttac gtaagtgaag actttgttag
52261 atatcatttg gaatgtggaa tctacacagt tggcatatca gagaaggttg aattcagttt
52321 aataaatgtt tatagaaagt gcttgttatc ataatgataa tagctcagga tgtgcatgac
52381 aagcttttaa gcgattgggt acactatctc atttgatctt ctgcacaact attaatggta
52441 ggtactatta tccctatctt atggataagt aaactaagat ttaaaagta cagaacatgg
52501 tgtgaacact gcttcaaaat ttctaaaata ggtaaatcac gatctctaaa ctggagggtt
52561 gtccaaccac tagggacaat agagtactga tatttagtgg tcagactgta atgcgggaag
52621 agacaggcat gggctaaacg ggtgtagaga tcaaataagg ggcaggttag tttgtaaaca
52681 tgtccatatg taacatttag cacaaataca ggatataggt gctttcagac ccagctgcat
52741 tgataaaaag ttaggtggta ttgtatctgt cttcctttct caatgttgca tatctgtgtt
52801 cttgcccagt tgcttcatc tctcagcca cacttattgg cctacaatgg catcatcacc
52861 aaagaaggca atcccatctc cgtgtggctt tggtttgctc cctaaagtaa accttgtgtt
```

FIG. 1 (cont.) (SEQ ID NO: 1)

```
52921  tacttttccc aggtctcatg ctttcccata tctgacctgt tttgtcctca tggccaggat
52981  atgtgggacc tttcctacaa tgttccaaag tttgtaatag agctcttctc tgctttgttc
53041  caaattctgc aacattttac tttaaataat gaatttaaat acaaacaaac ttgagctttg
53101  cctatacttt tcaagaatgc agagataact aaattaataa aatattcat tgagtcctta
53161  ctgtgcacac agctctatgt taagccttgt gcagaactca aagtcactcg agattaagcc
53221  tgttactaag ttatgtgcaa tttagctcag tggatttccc ccacttcata ttgctctgat
53281  aatgttttgg aattaactgc cttgattcct tcttttctct gcttgtctat acactattta
53341  ttattctaca ccatctcaaa ttctaactcc tcaagaaaat ccttccagat gattttcta
53401  accaggagtt ttaacttcct tttaactacc ctattacttt ctacttcctt aactcatcta
53461  tcatattata tttagttatt tatatactag gtcgccttga agaagggatt gtgttttcat
53521  aaatcttaat aatccctgag gcatcaagta cagtgatttg catttactaa atgctcaaca
53581  aatatgtgag ggattcactt gaaactaata ttagataatt cccagtcaaa gtgatctaat
53641  agcaaatcaa ttcttcagtt ttataggcaa agtatgactc tggttttcca taatcataat
53701  taatttgtca actttataat tttaattaag taaatttaat tggtagataa ataagtagat
53761  aaaaaataat ttacctgctt aactacgttt catatagcat tgcatttttc tttgtaaaat
53821  ttaagaattt tgtattaata aacttttta caaagtatt aattattcag ttattcatca
53881  tatacttttta ttgacttaaa agtaattta ttcaaagag ttagtatagg actacatgaa
53941  aaattcaagg ccaaggctta atttcaaatt tcactgcctt tggctctatc ttttaaaaca
54001  aaacaaaaaa ctcccgcaca atatcaatgg gtatttaagt ataatatcat tctcattgtg
54061  aggagaaaaa ataattattt ctgcctagat gctgggaaat aaaacaacta gaagcatgcc
54121  agtataatat tgactgttga aagaaacatt tatgaacctg agaagatagt aagctagatg
54181  aatagaatat aattttcatt acctttactt aataatgaat gcataataac tgaattagtc
54241  atattataat tttacttata atatatttgt attttgtttg ttgaaattat ctaactttcc
54301  attttctttt tagactttaa agctgtcaag ccgtgttcta gataaaataa gtattggaca
54361  acttgttagt ctccttcca acaacctgaa caaatttgat gaagtatgta cctattgatt
54421  taatctttta ggcactattg ttataaatta tacaactgga aaggcggagt tttcctgggt
54481  cagataatag taattagtgg ttaagtcttg ctcagctcta gcttcctat tctggaaact
54541  aagaaaggtc aattgtatag cagagcacca ttctgggtc tggtagaacc acccaactca
54601  aaggcacctt agcctgttgt taataagatt tttcaaaact taattcttat cagaccttgc
54661  ttctttttaa aactttaaat ctgttatgta ctttggccag atatgatacc tgagcaattc
54721  ttgttctggg ttgtcttatg tgaaaaataa attcaaggtc cttgggacag ataatgtgtt
54781  ttatttatct ttgcatatcc attacttaaa acagcattgg acccacagct ggtacaaaat
54841  taattactgt tgaattgagc aaatatttat tctaaatgtc tctgtcaaat gacagagtgt
54901  ggttgtgtgg attaagtccc tggagagagt tctttgttct ctcatgttct atgctgtggt
54961  tcttgcttta tgcaaaaaga agtaagttac ttaaaacctg gacatgatac ttaagatgtc
55021  caatcttgat tccactgaat aaaaatatgc ttaaaaatgc actgacttga aatttgtttt
55081  ttgggaaaac cgattctatg tgtagaatgt ttaagcacat tgctatgtgc tccatgtaat
55141  gattacctag attttagtgt gctcagaacc acgaagtgtt tgatcatata agctccttt
55201  acttgctttc tttcatatat gattgttagt ttctaggggt ggaagataca atgacacctg
55261  ttttgctgt gcttttattt tccagggact tgcattggca catttcgtgt ggatcgctcc
55321  tttgcaagtg gcactcctca tggggctaat ctgggagttg ttacaggcgt ctgccttctg
55381  tggacttggt ttcctgatag tccttgccct tttcaggct gggctaggga gaatgatgat
55441  gaagtacagg tagcaaccta ttttcataac ttgaaagttt taaaaattat gtttcaaaa
55501  agcccacttt agtaaaacca ggactgctct atgcatagaa cagtgatctt cagtgtcatt
55561  aaattttttt ttttttttt ttttgagac agagtctaga tctgtcaccc aggctggagt
55621  gcagtggcac gatcttggct cactgcactg caacttctgc ctcccaggct caagcaattc
55681  tcctgcctca gcctccggag tagctgggat tagaggcgca tgccaccaca cccagctaat
55741  ttttgtattt tagtagagac agggtttcac caggttgccc aggctggtct cgaatgcctg
55801  acctcaggtg atccgcccac ctcggcctcc caaagtactg atattacagg catgagctac
55861  cgcgcccggc ctaaaaaata cttttaaga tggtgtaaat attactttct gtatcaatgg
55921  tacatttttt acttgtcagt ctctagaatt tctttataaa tatgttgatt cagttcattt
55981  ttgtagatta taaacaggt aaaaaaggat aaaacattta tgtgaattaa agggaatacc
56041  taattttttgt gtagagttta ttagctttta ctactctggt ttatggatca tcacaccaga
56101  gccttagtta ctttgtgtta cagaataact aatatgagtg aatgaatgac ttacacaagt
56161  cactgcttag gataaagggc ttgagtttgt cagctagagt atgacagaaa gtatctaagt
56221  tttggagtca aatagcactt tgtttgaatc ccagattgca tgcttactag ttatgtgacc
56281  ttagtcaagc cacttcacct cactgagtct ttgctttttt catctctaaa atagagatac
56341  ccaccgctca taggctgtca taagggatag agatagcata tggaatgagt ctgtacagcg
56401  tctggcacat aggaggcatt taccaaacag tagttattat ttttgttacc atctatttga
```

FIG. 1 (cont.) (SEQ ID NO: 1)

```
56461 taataaaata atgcccatct gttgaataaa agaaatatga cttaaaacct tgagcagttc
56521 ttaatagata atttgacttg tttttactat tagattgatt gattgattga ttgattgatt
56581 tacagagatc agagagctgg gaagatcagt gaaagacttg tgattacctc agaaatgatt
56641 gaaaatatcc aatctgttaa ggcatactgc tgggaagaag caatggaaaa aatgattgaa
56701 aacttaagac agtaagttgt tccaataatt tcaatattgt tagtaattct gtccttaatt
56761 ttttaaaaat atgtttatca tggtagactt ccacctcata tttgatgttt gtgacaatca
56821 aatgattgca tttaagttct gtcaatattc atgcattagt tgcacaaatt cactttcatg
56881 ggctgtagtt ttatgtagtt ggtccagggt gttatttat gctgcaagta tattatactg
56941 atacgttatt aaagaatttc ctacatatgt tcactgctgc tcaatacatt tatttcgtta
57001 aaacaattat caagatactg aaggctgatt ggtaactcac atggaactgg gagagtatac
57061 aattctgaac caaatagatg attctctatt attatatctt aatttatgtg ttatggtata
57121 ttaaacatga aaaaattgt atttggttag aatatgtttg ctcttcctta actcgggaat
57181 gacatagggt aatattcaca gattgggttc ctataaatcc tccacttgaa gtgaagtcag
57241 ttcaagtaat gaaagctacc tcctgagata gaatcagtac ttggcaccta tctctagtgt
57301 tctttcacct catataacct ttcactgatt agtaaagatt atatccaaca aagaaagtac
57361 agcacagact gagatatgat tactgagata aatttgggca aaatataaac tacagcattt
57421 ctgtagcaat gagaccattt ttcttcagtt gagctccatg ttctacaaac ttcaatcaaa
57481 aaaggttcta ggagactcag tgaaagttga tacactgttc aaggaacaaa taatttcagc
57541 acatgggaat ttcacaggga aaaatatact aaaagagag gtaccatttt ggatggtgtc
57601 aatatggtt atgaggaatt caggctgctg agtccagtgt acaatggaaa ctgagctgca
57661 ggtgtgtgat tgtaacaaca aaagaaatgc tgaaatatta agtcctttgc catgtaaata
57721 gaaaagagt atttatttcc caaacattat tgctcacctg ttttgttat gcctttcaag
57781 ataaatccag gaaggaatt gcatttctt tccagaaaac aagttcttgg gggaattgtt
57841 caattggtag atgttgtttt tctcattaac aagtgagtgc tccatcacac ttgctgagtg
57901 ctccatcaca cttgctctct gcattactcc tctgcctgca aacacatata tagcaagggt
57961 gatgacaagg atatcagagg gtctggtttt ctcaaactca tgataaactc atggctgggt
58021 cattcttggt gctgatttta ctttgttttt tgttgttatt gttccctctt cctcaaaaga
58081 tgaaatctat ccctcttact tggaatttct ctttgatata tagcgaatgt ttggttgtaa
58141 cctgtataat ctggcatgaa attgtcactc gaaaggcta gaagtgttga cataaatatg
58201 ggacagcaag agttgctcct actcaagaga gcaaatataa tgttctggaa gagattggca
58261 gaattcacat caaaggagtg attacttcag cctgggccac tgttgtactg gtcaaaggc
58321 tgtgcaaagc tctctgaaaa tccactcttt tattgctctt tagtaataaa gtcactttca
58381 attttaaaaa taacaaactg atatatttt atgactcata aaatgttagc aattatatta
58441 tggagaatct actttctggg tgattcttac aaatgttctt ggatctatt ttttttctta
58501 tagtacctat tcttcccatt tttctcagct ctagttaata tatttcaaca acagttcaac
58561 aaatttaaca tttttataaa aagtgttcc tatcatttta taaataccag cctagtccat
58621 gttattcctt ttcttgttga ggagaaagga cacacattgt aaattcaaat atagacctct
58681 actgtgctat ttaatcttgg taacaactcc acaaggaga tgacatgttt tccttctata
58741 gaggtagatt ctgtaaagtt agagggaaga gtgacttgct taagatggca taagctgtaa
58801 ctggcagaac caggattcaa agccaggtgg gatgccaaaa tcataatctg tcttcagtgt
58861 caagttactg aaattggtaa acattagacc taaatagacg gaattgcaat ccgggttggg
58921 cacattaaac tccatttct tcatcaatgt gctcagatta cattttactt tcaggctaa
58981 aaatggaaaa aaagagtccc tcttagttct gcacttgaga atgagaatag cttttctgaa
59041 ttatacaagg aagaagaact aatgcccaaa tgccaggtac ccacatgcac tatgccatgg
59101 cacagctgtt gccccttc accagagccc tctctctgta tcctggttga cctttccttg
59161 ggcaagagct gggtggggag gatcacaagt gactccaatt tggatggctt cgggaagact
59221 gggaccgagc tgaaggcagt gttgtcctct gcactccctg ttttctgtct gctggagcac
59281 tgaagcctca catatgtatt aaaaaaataa tttccatttg catttcagac tagaagattg
59341 aacgtatagt gtaatgtgat tgcaaataat tatattgaaa tgagacagag aggatgtagt
59401 atctactgtc ataattttc aaacccacc tgcaacttga attaaaagaa ccacttgggt
59461 ttttttttt gtttcaaacg caatcctgg aaacctactg agactcattc agtcagtatc
59521 tctaagaggc aagcttgaga ctgtatattt aaaagcatc tcaggtgatt tttacacatg
59581 ctaaggctta agaaccactt ctctgtagct tatatgttat tttcaatgtt cctcaaagcc
59641 aagttagaat tccaaagtg ttaagaatcc attagacaat cacagaattg tctttttcct
59701 ttataaatct tgcaatgtta ttctcatttc catacttaat tacttaaaac accaaccaac
59761 caacaagcaa aaaatgatta gtctaactaa tattacaagt taataatgaa gtaaaggttt
59821 aaaaataatg tcataataat gttaataaca aattattaat tataatttaa aaataatatt
59881 tataattaa aaataatatt tacaagtact acaagcaaaa cactggtact ttcattgtta
59941 tcttttcata taaggtaact gagcccaga gagattaaat aacatgccca aggtcacaca
```

FIG. 1 (cont.) (SEQ ID NO: 1)

```
60001 ggtcatatga tgtggagcca ggttaaaaat ataggcagaa agactctaga gaccatgctc
60061 agatcttcca ttccaagatc cctgatattt gaaaaataaa ataacatcct gaattttatt
60121 gttattgttt tttatagaac agaactgaaa ctgactcgga aggcagccta tgtgagatac
60181 ttcaatagct cagccttctt cttctcaggg ttctttgtgg tgtttttatc tgtgcttccc
60241 tatgcactaa tcaaaggaat catcctccgg aaaatattca ccaccatctc attctgcatt
60301 gttctgcgca tggcggtcac tcggcaattt ccctgggctg tacaaacatg gtatgactct
60361 cttggagcaa taaacaaaat acaggtaatg taccataatg ctgcattata tactatgatt
60421 taaataatca gtcaatagat cagttctaat gaactttgca aaaatgtgcg aaaagataga
60481 aaaagaaatt tccttcacta ggaagtttata aagttgcca gctaatacta ggaatgttca
60541 ccttaaactt ttcctagcat ttctctggac agtatgatgg atgagagtgg cattttatgc
60601 caaattccct taaaatccca ataatactga tgtagctagc agctttgaga aattctaaag
60661 ttttcaagtg ataagactca atttatacaa agctaattgg ataaacttgt atatgattaa
60721 gaagcaaata aatacttatt atgctttttt gctgtttatt taaatattta acccagaaaa
60781 taagtcactg tgacagaaat aaaaatgaga gagaagggtg agccactctt aggtagttct
60841 ggcattattt aatctaggcc agaggttgca aatggtgtcc catagaacta attttggctc
60901 ctagacctgt cttatttaac ctttcattta aaaatttgt attggttgcc agcaattaaa
60961 aattgggaga tgtctcacac acacacacac ataaacacac acactcatgt gtgcagcctc
61021 ttttgaagaa ttggaataac tagtcaactg cgtcctcctt ttccacaagc tgtgacagct
61081 ccctgctcac agagcacctg ccctctcctg ttcatcatgc tctcttctca gtcccattcc
61141 ttcattatat cacctatttg gtcctgagac taagtgagtt tgagatctgt gatttagaca
61201 aagtggtgaa tctagctctg aatcatagta agtagctctg ggaatcatct tgtcttctgt
61261 tagcccattg agagagaaat agagagagag agagagagaa agaaagaaga agaaacagat
61321 ctggggagag tcactgaatg ggagcataga gacagagaaa cagatctaga aaaccaaact
61381 gggagaaaat gagagaaacc aaaagagagg tagagaggag cagagaagaa aatgaagaag
61441 caaggcaagg accaggcttt ttcattattt cttatgccca agacttcagt atgcgtggac
61501 ttaattcttc ccttatgctcc taccttccct agggaaactg atttggagtc tctaatagag
61561 cccttctttt agaatcacag tttgatgcct taaaactagt tatataccttc cacatgcttc
61621 cttaacccac agaagtgatg ctaatgaggc ccttaataag gagcgtgcta ttaagatgaa
61681 gacattcatt ttttttctcc gtccaatgtt ggattaaggc acattagtgg gtaattcagg
61741 gttgctttgt aaattcatca ctaaggttag catgtaatag tacaaggaag aatcagttgt
61801 atgttaaatc taatgtataa aaagttttat aaaatatcat atgtttagag agtatatttc
61861 aaatatgatg aatcctagtg cttggcaaat taactttaga acactaataa aattatttta
61921 ttaagaaata attactattt cattattaaa attcatatat aagatgtagc acaatgagag
61981 tataaagtag atgtaataat gcattaatgc tattctgatt ctataatatg ttttttgctct
62041 cttttataaa taggatttct tacaaaagca agaatataag acattggaat ataacttaac
62101 gactacagaa gtagtgatgg agaatgtaac agccttctgg gaggaggtca gaattttttaa
62161 aaaattgttt gctctaaaca cctaactgtt ttcttctttg tgaatatgga tttcatccta
62221 atggcgaata aaattagaat gatgatataa ctggtagaac tggaaggagg atcactcact
62281 tattttctag attaagaagt agaggaatgg ccaggtgctc atggttgtaa tcccagcact
62341 ttgggagacc aaggcgggtg gatcacctga ggtcaggagt tcaagaccag cctggccaac
62401 atggtaaaac ccggtctcta ctaaaaatac aaaaaattaa ctgggcatgg tggcagatgc
62461 tgtagtccca gctgctcggg aggctgaggc aggagaatca cttgaacctg ggaggcggag
62521 gttgcagtga gctaagatca cgccactgca ctccagcctg ggcaacaagg cgagactctg
62581 tctgaaaaag aaaaaaaaat aaaaataaaa ataaaagaa gtggaggaat attaaatgca
62641 atataaaagc ttttttttatt tttaagtcat acaatttgtt tcacataaca gatcaggaaa
62701 taatacagag atcataagtt ttggagctgg gtttgaatcc tggctctgcc atttactttc
62761 tgtgtaatct aagtcaagtt actgaacttt gtgggccctc tggctctcca tgtgtaaaat
62821 ggagaatatt aatatttacc ttgcaagttt gttgtgaaga ctgaaggaga gaatttaggt
62881 aaaacattca tcagagtacc atgcacacag ttgttcctca ataaacatta gcttctctga
62941 ttgcaagttc cagtctaaag tgctttatat ataccagcca ataaaggat gcgagagaga
63001 tataccagtg tattgttttc taccatttta aacctatttt catccactgt tacaaattct
63061 atcatactgc tccacataaa aatattatc aatgattttt agtctctgaa gtgcaatatt
63121 tgattattga gcacacctgt gaagttttta gtttcttctc acttacatgg gttgtgtaaa
63181 ggtaggaggt ataaaaccag tgtcctaggt ctaaatctttt cttaatgtca tactttggat
63241 tcattgatat aagtaacttg agcaccagcg cttcatttta cttcattttt taaagatata
63301 gtaagagtaa ttcccatctg cctagcaaaa ttgttttgta gaaagtttg tggatcagat
63361 ttattttact ttgatttttag gaatttcaag tgtcttcgtc ggcatgaagg aaaaatatgc
63421 agtttgacat tttctactac tttcaggtca ttattttcct actctggtgc aaaaaccctc
63481 aattcctgtc tcactccatc taatcaaata ggtagcatgc ttgagccctt actatgtgcc
```

FIG. 1 (cont.) (SEQ ID NO: 1)

```
63541 aggcactagg ataagcactt tatatgtttt gtcccaatta attctcacag catttctatg
63601 acctaaataa aattaatatt ttcatttcac caataataaa atggaggctt caaaaagttt
63661 agggacttgg ctcagctcac acaactggca aggactgaaa atggatttta gtcccaaatg
63721 tcataggcta gagccctttc actaaactgt tgtcttccat ctggtggcat cctcttcctc
63781 cagtctttgt cacctaaact ctgggcaccc cttgatggca tttacttatg atggtgatgc
63841 ttgttaaact tcctgtttgc gacttcaacg tccatataaa tgagtcttcc aatactgtac
63901 ttagaactta tattttgtag tgacttcttt aaaagctttc tctcttagtc atatcctgag
63961 ttttgttagc acctggactt accttacttt ggaaatgttg cactctgaaa tctctttctc
64021 agcttggaat ttcctaatct tccaactgtt tgagtctttt aattctacat ttactgcctt
64081 tccatttcat caggatttct agtctcttta attcttcctt ttgaactcct cctgatttaa
64141 cctctgctta ttcgaagaac aataatttta ttctctcagc tgcactctca attccctttt
64201 cctttggtg atttttcttt ttcctacaga acacttactt tatcagtttt ggagaaggaa
64261 gtgctatctg ggtaacagta gtgctatctg ttgactctag tcaactgtaa gttttataca
64321 tttattgttt aaaccttata tgggtctata atccttcttg ggaaatcctt tcatttgtct
64381 ttaatttcct ttaccatttc cctaaaggct attccagatt tttatcacat tcacaaaatt
64441 cccgtctttt ctcaggatct gttcaccccc agtagatagc cttgtctccc acaatacatg
64501 gagaaaatag aggccaccgt catatttgaa tgtttccaac ttctctcttc acctttggaa
64561 ttatctttt cttcttttgt gtctaagaga aagatgtata cttcttctta cccttgtctg
64621 aactactcta ttttgcttca tcttctcaga acaggggacc agcaattatt cttcctccag
64681 aagcttcaac atcttttgtc aactgactcc ttctcatgtt taaatatttt caagttaaac
64741 aatttctttc ctgactttcg ctcacgcaac ctcatgccca aaaccttatc actcttcttc
64801 cctttgctgt caaggctgtt ctcacttctt cactttttgt ggacttctcc ccactacaac
64861 atagattctg ctatcaccaa tctattaaaa ctgttatact cttgtggaat ttatcattta
64921 atttagcttc agtgaaccgt tctttccaga ttattttggc ctcagaccat gacttctaag
64981 tctgccgtgc ttgccactta agtgatgatg ggccagtggg tccccaccta ggcctctgtg
65041 ttagtctgtt ttcatgttgc tgataaagac atacccaaga atgggcaatt tacagaagaa
65101 aggggtttga gggactcaca gttccatgtg actggggagg cctcacaatc atggtggatg
65161 atgaaaggca tgtctcacat ggaggcagat aagagcatag aacttgtgca gggaaacttc
65221 cctttattaa accaccaggt cttgtgagac ttcttcacta tcacgagaat aggatgggca
65281 agaccctccc ccatgattca attatctccc actgggtccc tcccacaaca catgggaatt
65341 atgggagcta taattcaaga tgagatttgg gtgaggacat agccaaacca tatccagcctc
65401 cttctggctt tttatgttct ccgtgggtga cctctctcag gctcaagtga taaccaatgt
65461 gctgatgact ctcaaatgcg catctctggc ttcagtttct tccttgaact tcatacatat
65521 gtttccaaat ttcctgcgtg tacctcaagg ttcttgttca tcacttccca agcttcataa
65581 acgcactcat tttagtgtat tctctgtctc ctttgatagc atccctgaga ggcaagtccc
65641 tggtgagtta tatacaactc ctcccttgct ccaaacctga gagtaagtaa cattcctatt
65701 aacatattag gaagctgagg cttagacagt ttaagtaact caagcatggt tacacaacta
65761 gctagggcag agctaaaatg tcaggctagg cttctgtgac tccaaagccc tttctcactt
65821 agcatatcat cacttatttt tttttttaat cacatatatg attttttttt ctttaagaga
65881 tagaatcttg ctctatcacg tgggctggag tgcagtggca caatcatagc tcactgtaac
65941 cttgaacttg ggctcaagtg atcctcctgc cttagcctac tgagtagcta gggctacaga
66001 cacacaccac catgcctagc taatttttatt ttattttatt ttattttttg agacagagtc
66061 tcactctgtc acccaggctg gagtgcagtg gtgcgatctt ggctcactgg aacctctgct
66121 gcccgggttc aagcgattct cctgcctcag cctcctgagt agctgggatt acaggtgcct
66181 gccactgtgc ccagctaatt tttgtatttt tagtagagac ggggtttcac catcttggcc
66241 aggcttgtct tgaactcctg acctcgtgat ccactcgcct cggcctccca aagtgctggg
66301 attacaggtg tgagccacca cgcctggcca cctacctaat ttttaatttt tttgtagaga
66361 cagggtctca ctacgttgcc caggctggtc ttgaactcct gttctcaaac aatcctcctg
66421 cctcggacac cccaagtgca gggattacag gcatgagtca ttgcagctga cctgtatata
66481 tgattttttag tatatgtaaa tatacatatt tattaaatgt aaatataaat ataaatgtgt
66541 ggagtgatat ccattgaaat gttaaacata gttctcagtg gtacaactac aggtgatttc
66601 tcttttctta tttctggttt tctgtgtttt ccaaatttct tgaaatgtgt cttctgtaat
66661 cagaaataaa agttattagt aacaacagtc ttccactggt acaagtgctt attggataaa
66721 agtcccactt ctaagcatga tactcacaac tttaggttaa atagcctttg tcaccttgcc
66781 atatacatct gatccagcca ctcacaccat tcctgagata tattttgttc ctttgtgcct
66841 aaatcattgt gcatgcagat ccatcttcct ggaacaccta taaccatttc ttagtcctgt
66901 gaaatcctac ttacatcctt catagcctag catgtatgtc atttatttgg tcaagggtga
66961 gttggttgtt ctcttgaatg tactgccata tgacgtggtg tgatttcaat tgtagcacca
67021 agctcattgc aatattaatt cgtttgtcat tctcccatgt aggatgtttg aagtagtttc
```

FIG. 1 (cont.) (SEQ ID NO: 1)

```
67081 taacacagag attatactca ataaatattt attagataaa taaatgaata agggaataac
67141 aaatgccttt gtctcatttt aaaatacttt cattgttagc tacccatata ataaaaaact
67201 aaaagcagta gttttcaagc atgattgttt atgtatgcct taaaagaatt ttgaaaacct
67261 atgtacccct gacacacttt taagttaact tataaatttt tcaacatagt tttaagtggt
67321 ggcaaatgat gtagtttctt gtgtattta aactgcttaa gtatgctata catggatttc
67381 ttcaaaaccc tgaagctgca gtttcagtgc attcaattta tggaaaagaa attaatttat
67441 aaaattggtt cttattgtca agtcaatcag ctaaatataa cttgctttct gtcaggaaaa
67501 gtctgacttt aaaatacaga taagtaataa ctattattaa ttaattaaat tattaaaatt
67561 aaaataatta aataatttgt taattaaaat gccttattcc cctacttatt tctgcaattt
67621 gactctaaga atagatagga catgtagatt gccttaggtt tgaaatctgg gtgaaataag
67681 atactgcctc cttcagtatt tctgcctttg cttttatggg agcctctttc aagaaaaagt
67741 cattctctca tggtcccttt gtttgagtcc cagaggtttt cctactccag aaagtgcaac
67801 gtagtgagac tagtactata ctcccttgca tggtaagtga gaaggctgtc tgtataaaat
67861 gagggaagga ctcatgagag ggaagtaggt caggagaaat gataggttct caggcaggtt
67921 aattttagga aagagtgaat agagtccctt aaaacaaggt gcatctgctt cctcctgatc
67981 aatctttagg actgtttact ttgatttgaa gaccactatg ctaaagcttc cacggggc
68041 aatagtgagg caaggaattt taaaaggga attacttctt cgtagctact tttgtgaaat
68101 gaattcattt gaattatctg gcaatctctt catatttata ttcaacaata attacttaaa
68161 gaaatgcttt gagcttctca gaggagggtg ctaccagtgt gatggagtag aattcagatt
68221 tgggtagtga ctttaaagct gtgtgacttt agtcatttaa ctgctgagtc acagtctaca
68281 gctttgaaag aggaggatta taaaatctat ctcatgttaa tgctgaagat taaataatag
68341 tgtttatgta ccccgcttat aggagaagag ggtgtgtgtg tgtgtgtgtg tgtgtgtgtg
68401 tgtatgtgta tgtatacatg tatgtattca gtctttactg aaattaaaaa atctttaact
68461 tgataatggg caaatatctt agttttagat catgtcctct agaaaccgta tgctatataa
68521 ttatgtacta taaagtaata atgtatacag tgtaatggat catgggccat gtgcttttca
68581 aactaattgt acataaaaca agcatctatt gaaaatatct gacaaactca tcttttattt
68641 ttgatgtgtg tgtgtgtgtg tgtgtgtttt tttaacaggg atttggggaa ttatttgaga
68701 aagcaaaaca aaacaataac aatagaaaaa cttctaatgg tgatgacagc ctcttcttca
68761 gtaatttctc acttcttggt actcctgtcc tgaaagatat taatttcaag atagaaagag
68821 gacagttgtt ggcggttgct ggatccactg gagcaggcaa ggtagttctt ttgttcttca
68881 ctattaagaa cttaatttgg tgtccatgtc tctttttttt tctagtttgt agtgctggaa
68941 ggtattttg gagaaattct tacatgagca ttaggagaat gtatgggtgt agtgtcttgt
69001 ataatagaaa ttgttccact gataaattac tctagttttt tatttcctca tattattttc
69061 agtggctttt tcttccacat ctttatattt tgcaccacat tcaacactgt atcttgcaca
69121 tggcgagcat tcaataactt tattgaataa acaaatcatc cattttatcc attcttaacc
69181 agaacagaca ttttttcaga gctggtccag gaaaatcatg acttacattt gccttagta
69241 accacataaa caaaaggtct ccattttgt taacattaca attttcagaa tagatttaga
69301 tttgcttatg atatattata aggaaaaatt atttagtggg atagttttt gaggaaatac
69361 ataggaatgt taatttattc agtggtcatc ctcttctcca tatcccaccc taagaacaac
69421 ttaacctggc atatttggag atacatctga aaaaatagta gattagaaag aaaaaacagc
69481 aaaaggacca aaactttatt gtcaggagaa gactttgtag tgatcttcaa gaatataacc
69541 cattgtgtag ataatggtaa aaacttgctc tcttttaact attgaggaaa taaatttaaa
69601 gacatgaaag aatcaaatta gagatgaaaa agagcttct agtattagaa tgggctaaag
69661 ggcaataggt atttgcttca gaagtctata aaatggttcc ttgttcccat ttgattgtca
69721 ttttagctgt ggtactttgt agaaatgtga gaaaagtt agtggtctct tgaagctttt
69781 caaaatactt tctagaatta taccgaataa tctaagacaa acagaaaaag aaagagagga
69841 aggaagaaag aaggaaatga ggaagaaagg aagtaggagg aaggaaggaa ggaaagaagg
69901 aaggaagtaa gagggaagca gtgctgctgc tgtaggtaaa aatgttaatg aaaatagaaa
69961 ttaagaaaga ctcctgaaag gcaattattt atcaatatct aagatgagga gaaccatatt
70021 ttgaagaatt gaatatgaga cttgggaaac aaaatgccac aaaaaatttc cactcaataa
70081 atttggtgtc aggctgggtg cagtggctca cacttgtaat cctagcactt tggaggcag
70141 aggcaggtga attgcttgag tccaggagtt tgagaccagc gtgggcaaca tggcaaaccc
70201 cacctctaca aaaacacaa acaaagaaa atagctgggt gtggtggtgt gtgcctgtag
70261 tcccagctac ttgggaggct gaggtgggag gatcacctga gcctgagaag tggaggctgc
70321 agtgagccat gattgcacca ctgtacccta gcctaggtga taggctcaaa aaaaaaaaaa
70381 attggtgttt gcaatgctaa taatacaatt tggttgtttc tctctccagt tgttttccta
70441 catacgaaac agcttttaaa acaaaatagc tggaattgtg cattttttct tacaaaaaca
70501 ttttcttct taaaatgtta ttattttct tttatatctt gtatattatt actagcagtg
70561 ttcactatta aaaattata ctataggagg ggctgatact aaataagtta gcaatggtct
```

FIG. 1 (cont.) (SEQ ID NO: 1)

```
70621 aaacaaggat gtttatttat gaaaaggtag taattgtgtt tcatagaatt tttaaaatta
70681 attctgcgta tgtcttcaag atcaattcta tgatagatgt gcaaaaatag ctttggaatt
70741 acaaattcca agacttactg gcaattaaat ttcaggcagt tttattaaaa ttgatgagca
70801 gataattact ggctgacagt gcagttatag cttatgaaaa gcagctatga aggcagagtt
70861 agaggaaggc agtggtccct tgggaatatt taaacacttc tgagaaacgg agtttactaa
70921 ctcaatctag gaggctgcct tttagtagta ttaggaatgg aacactttat agttttttt
70981 ggacaaaaga tctagctaaa atataagatt gaataattga aatattaac atttttaagtt
71041 aaatcttacc cactcaatac aatttggtaa tttgtatcag aagcttaaaa gataacctaa
71101 tagttcttct acttctataa cttacccaaa tatgtttgca gagatcttat gtaaagctct
71161 tcattataac actgctttca ggagccaaaa attgggtggg ggagcccat aaatgttgaa
71221 taatagggt ttgattagat aaatttggt gtagttctat aatggcgtgt tattcagcca
71281 ataaaaggtt tgttaaagaa tgactgtgac ggatgtatat gatatactct taagtgaata
71341 aagagttaca aaatgttatg tacaagttac aaaatgtatg tacattatga tccatttttc
71401 ataaaatcat atgtatgtat atatgtgtgt ctggaaggat aaatttatca agttgttatc
71461 tctgaaattt tgggtatatt ttatatttct agattttctg ttactttgtt actttactga
71521 taaagtaata acgttgttga cttttgtcac tctccctat taataatcat ctaggctgca
71581 aaaggatcat gtcttcttta ttttatatt ccaaggactg tcaacaagtg cctagcactt
71641 gacaggtata ttatagaaat ttaactgaat atctttagga aatagatttt tgtttgtagt
71701 tgttctagtc tacattaaat gtcttgcgct tatgaaactt ccttgaatta ttttagtgaa
71761 gcaatattag tatagaattt tgcatcactg gatgcccttg actgaaagct ggcttatggc
71821 atctcaccag tgtgtgggga gtttcagtcc ttctgttgtc tgcatcacag ctgaagcagt
71881 gctgttgctg acaattcctg acaccaccttt gtctctatta ttgatcattg cctcactatg
71941 gtactgagtt ttagcttatt cttgtaataa ctgggactca tatgtataga ataagctatt
72001 agctcacgtt tttgcttgct ttttatacag aatacatgtc tgcaaatagt tttatcaata
72061 ttttggaatt ttgggagata tgaagttaaa aacatcattg aatatatata tatacacaca
72121 cacatatata tatgacacta tacatgattt atttttattta atttttaaaa tttttattctt
72181 tttagagatt aggtcttact ctgtcaccca ggctgaactt cagtggtgtg atcatagctc
72241 actgtaacct tgaactcctg ggctcaattg acctttccgc ttcagcctcc caaagtgctg
72301 ggtttatagg catgagccac tgtgtctggt ccaatatgca tatatatatt tttaacctgg
72361 attatcagag ctatattgtg tttaggttta taaagctgta ctatgtgaaa atatcacttc
72421 taggttttaat tttgtacaaa ggaattttat atagaaatga ggtaattcag atttttttccc
72481 atgtaataag aattgtaaaa tttactgaaa caaacatcaa aaagatatct gttacatgac
72541 cttcctttct tttgaatata tttcaggtga tattatttat taaaatttaa aaatgaaaat
72601 taaaatatat aaaaagttga aaattattcc tttctttact gtctctcatc tgtccatttt
72661 ccattctcct gcattccctc atccaaccaa ggtagccaat ccaggtaact tttttttagta
72721 tcttcccaga gatgtttctc tctatatata taatcaatat acattttta ttattcccca
72781 cctctctttt tatgtaacaa tatgcagagt tttgcttctt gcttttccca ctatcttgga
72841 caactttcca tattcaaagc acagaggact tgcacatatg ttcagactgc tgaatatttc
72901 tgtctctccc ctgccattca tatgttgaaa tcctaattcc caaggtgatg gtattgcagg
72961 gtggggcctt tgggaggtga ttagtccatg agggtgaagt ctttagtaaa tgagattagt
73021 gtctttataa aagaaacctt agagagaccc tcacacctta gagagaccct caccccttc
73081 tgccatgtga gaacacagca ggaagacagc tggctatcca ggattcagga gtctcttagc
73141 agacccaaat ctgctggcac cttgatcttg gacttcccag cctccagaac tgtgagaaat
73201 aaattcctgt tgtttataag ccacacagtt catggtattt tgttatagca gcctgaacaa
73261 ggacacacac acacacacac acacatgcac acacatttaa atagatgcat agtattctat
73321 catatggatg gatattctat gatataatga atcactattg attgacattt gggttgtttc
73381 caatattttg ttaacacaaa gaacaacact acaaataact ttatatacat atcatttagc
73441 acatctgcaa ttgtatcagt aggcttccta taagtggtca agcatttgtg tacttgtgat
73501 tttggtagat gttgtcaaat gtccttccct gaaatttgta ccaattcgta ctcatgccat
73561 acactctaaa tagagtgctg atttccccac agcattacta acagatgata ttatctaatt
73621 taaaaagttt ctcatcttat agggaaaata gtatgtcaat gtattcttaa cttgcatttc
73681 ttttattata agtagtgtaa aatatcattt caacttatac acaggaggaa tttctctcta
73741 tataaagtga tcctagaatc ataatgaaaa atatcaccaa ctcattagga aaatgtacaa
73801 aggattgaat agatatctca tcaaaaataa aaatataagt ggcctttaaa cattgaaagg
73861 taacatttga acaaagactt gcaggaggtg agggattagg gaatgcagac tctgggaaga
73921 gtcttccaag tagcaggtga agcaagtgca aagctttcag atgggactga ctatacctgt
73981 ctggtttgaa gaacagtaag gaggtcactg aggctggcat agagtaagac agggagggta
74041 gaatactgtc agagaagtaa tcggcggtgg aggtaggggg taaaccataa agtgctcgta
74101 aagactaagg cttatttctc tgggtgagat tagaggccac tggagagttt taaacagaag
```

FIG. 1 (cont.) (SEQ ID NO: 1)

```
74161 taacagggcc actttggcta atgtttttag gctattctgt agggagacaa gggaggaagc
74221 aaggagatga gttaggagtc tattgtgcca gttcaggcaa gtgatgatgg tggcttgatc
74281 caggtagtag tggaagtagt atagtaggaa gtgatcagat tcaggacatg ctttgaagga
74341 agatccaata ggattaatgg ataagttgaa caatggcata tgagaaaagt cacagaggag
74401 tcaaagatga ttccaagctt tctggactga gtaactggaa ggataaatgt gccgtttact
74461 agaaagataa tgggagaaac aggtttggga tggagcttgg tttgggaata ttaagtttga
74521 aatgcctatt tgacatccaa atagagatgt tagttggatg tacaagtcta gtttcaagga
74581 agaggggggct ggtagtgtga agatggggct ggataagatt ctaaaggaaa gagggttgat
74641 aagaagagaa agggggtgtag gggttagcct aagggcattc taagtattag aggttaagga
74701 ggtgggtgaa gaaaacccaa taaaataaaa gtctgagaag acaaagctag tgaatgaatg
74761 tggtatcccg gaacccaact gatgtcaagc agaagggtgt tatcaactag gtcaaatgct
74821 cattcatcaa gtaagatgaa actgttataa ttaaccggtg tcttctgaaa tacgagata
74881 actcgtgact taatgaaagc aatagtagag aaggtcaaac ttgaccagaa tgaaattaga
74941 aagaataaga ggaaagaaaa gaccaaatac agacaaccat tgatgcctta ttcttttgat
75001 atactcctgg agtccacttg ctaatacaat tgacccttaa acaatacagg cttgaactgc
75061 atgggtccac ttatttgtga attttttttc agttaataca ttggaaaatt tttggggttt
75121 tttgacaatt tgaaaaaact cacaaactgt ctagcctaga ataccgaga aaattaagaa
75181 aaagtaagat atgccatgaa tgcataaaat atatgtagac actagcctat tttatcattt
75241 gctactataa aatatacaca atctattata aaaagttaaa atttatcaaa acttaacaca
75301 cactaacacc taccctacct ggcaccattc acagtaaaga gaatgtaaa taaacataaa
75361 aatgtagtat taaaccataa tggcataaaa ctaattgtag tacatatggt actactgtaa
75421 taatttggaa gccacttcct gttgctatta cggtaagctc aagcattgtg gatagccatt
75481 taaaacacca cgtgatgcta atcatctccg tgtgagcagt tctctctcca gtaaattgca
75541 tattgcagta aaaagtgatc tctagtggtt ctcgcatatt tttcatcatg tttagtgcaa
75601 tgccataaac cttgaataac atcaagcaat ccatacaaag tgccactagt gatgcacgga
75661 aaagttgtaa cagtacaaga aaaagttga gttgcttggt atttaccata tattgaggtc
75721 tgcagctaca gttgcctgca atttcgagat aaatgaaccc agtataaaga ctgttgtaac
75781 aaaagaaaag aaaatgtgaa accatcagtg cagctatgcc agcaggtgtg aagtcttgca
75841 cttttttgcaa aatacaaaat atgaaatatg tgttaattga ctgtttatgt tatctgtaag
75901 gtttccactc aacaataggc tattagtagt taagttttttg tggagtcaaa aattatacgt
75961 ggattttttga ctatacagtg ggttggcacc cctaaccttc atgttgataa agggtcaatg
76021 gtatattatt taatttttt gtatttatat tcataaataa gattaaatct atatttccaa
76081 gtaatctcta taagattttg ttattaatat tactattatt tttgagacag agtcttactg
76141 tcaccaggct ggagcacagt ggtgcgatct cggctcactg caacctctgc ctcccgggct
76201 caagcaattc tcctgcctca ccctcccaag tagctgggac tacaggcacg cacaaccaca
76261 ctcagctaat ttttgtattt ttagtagaga cggggtttca ccatgttggc caggatggta
76321 ttgatctctt gacctcatga tctgcctgcc tcggcctccc aaagtgttgg gattacaggc
76381 atgagccact gtgcacagcc attaatatta ttgttaccca ataaaaaaaa tttggaaact
76441 tgtcttcttt tccctgatt ctgtttaaat agcactggag ttacctgttt tgaattttt
76501 ttccaagcgg tcccttatga gttttctcta tgttttattt gtttcatttc ttttttttt
76561 ttttttttt ttttgagac ggagtctcgc tctgtcgccc aggctggagt gcagtggcgg
76621 gatctcggct cactgcaagc tccgcctccc gggttcacgc cattctcctg cctcagcctc
76681 ccaagtagct gggactacag gcgccgcca ctacgcccgg ctaatttttt gtattttag
76741 tagagacggg gtttcaccgt tttagccggg atggtctcga tctcctgacc tcgtgatccg
76801 cccgcctcgg cctcccaaag tgctgggatt acaggcgtga gccaccgcgc ccggcctgtt
76861 tcatttctta tatcgtattt ttgcaactcc tttattgata cttttcttcc tgattaggtt
76921 tctactaaaa ccaaacaagc tttccatgaa ttagctttta gatttactta ttagtttaac
76981 tgttctgttg tattgtaact cattaattta taattttatc tttattaatt attctatttt
77041 tcttcgcttt tttgttgttt ttctagtttt tgagttagat gtttgacgct tttttaaaaa
77101 gctgtgcatt ttcctctggg taatacttta gctgtatatt atgtattctg atatatagtg
77161 tttccattac attgttttct agaaaatctg tagctttgat ttatatttgt ttcctctttg
77221 acctaagata tcctaaggga aaatttaaca ttttccagaa agaaaacaaa ttttctttgt
77281 tttccaagaa tgttgttcaa attattcta ctgcttggaa tttttatcat ttttgtgtat
77341 ccagtaaata gtcaatattt gtacttgctc tctgaccaca taaaagaata tattcgtgta
77401 gtttctatta atagattaga gttcaattca gatattaaat gtacatcatt attcatgata
77461 ttaggtcttt ctacatcttc acttatcttt tttctacttg ctttgccatt aacagataaa
77521 gttgaattaa aggcttctac tacatacatt tctccctgtt attccttata ggttctgtaa
77581 tttttgcttc aagaatattg ctttttaaat ttaatatata gatacttata attcactct
77641 agcattataa agagcctttt cttttttcatt gaatgtattt gggcctgcat atgtctaaca
```

FIG. 1 (cont.) (SEQ ID NO: 1)

```
77701 tgaaaattat agtcctttt ttgtttcttt gtttgtattt acagttttaa gttccatttt
77761 caacctttat gcactctttg ctttaggtgt gtctctttta gttagcataa agttaggttt
77821 gtctttaatt tcacctgaag tcttttcctc ttaatagatg ggttaagcca actgaaaaat
77881 aaaactgact tatatacttt tatttcaagt atgtcctcca caaatatttt ttgaatagat
77941 tagcttatat actttggaat ttgttaaaaa aagatttta taaaaataa ttgtggtgaa
78001 atgtacataa cataaaattt atcatttga ccatttaa gggcatagct ctgtggcata
78061 aagtatactc acatagttgt gcaactatca cctccttttg atttttttt actaattttg
78121 taaatttgtt tcatctgagc tgtcttatta tgttttgtt tatgttttc tttcctttat
78181 tatgaagtca ctgtattgtc tgtaggctat atgtatctgt gagtgtgtgt gtatatgtgt
78241 gtattatggt ttttaaaaaa gtctatattt gttttccagt ggctatactt aatactaata
78301 actttatgtt aaatttttca ttctatgtga ctctagttca ctaatatgag ctctgataaa
78361 atcagtgctt tttcgaggtt aggagatcaa gaccatcctg gctaacacag tgaaactccg
78421 tctctactaa aaatacaaaa aattagccag acgtgatggc gggtgcccgt agtcccagct
78481 actcgggagg ctgaggcagg agaatggcgt gaacccagga ggcagaactt gcagtgagcc
78541 gagatcgcgc cactgcactc tagcctgggt gacagagtga gactctgtct ctaaataaat
78601 aaataaataa ataaataaat aaataaaatc agtgctttt cttcctctgc tacctccttt
78661 ccttctactc agttttagtc agtagtatta tcttttttca gatttatctt tgtattgtta
78721 aatctgctta tgcttctatt actttattta ttagctttaa atgataccttt tgactttca
78781 gcttttctta ataaagcaat cagcaaattt cctttacact ccacacttat accccatttc
78841 ctttgtttgt ttatttggtt tttacttcta acttttctta ttgtcaggac ataacata
78901 tttaaacttt gttttcaac tcgaattctg ccattagttt taatttttgt tcacagttat
78961 ataaatcttt gttcactgat agtccttttg tactatcatc tcttaaatga ctttatactc
79021 caagaaaggc tcatgggaac aatattacct gaatatgtct ctattactta atctgtacct
79081 aataatatga aggtaatcta ctttgtagga tttctgtgaa gattaaataa attaatatag
79141 ttaaagcaca tagaacagca ctcgacacag agtgagcact tggcaactgt tagctgttac
79201 taaccttcc cattcttcct ccaaacctat tccaactatc tgaatcatgt gcccttctc
79261 tgtgaacctc tatcataata cttgtcacac tgtattgtaa ttgtctcttt tactttccct
79321 tgtatctttt gtgcatagca gagtacctga aacaggaagt attttaaata ttttgaatca
79381 aatgagttaa tagaatcttt acaaataaga atatacactt ctgcttagga tgataattgg
79441 aggcaagtga atcctgagcg tgatttgata atgacctaat aatgatgggt tttatttcca
79501 gacttcactt ctaatggtga ttatgggaga actggagcct tcagagggta aaattaagca
79561 cagtggaaga atttcattct gttctcagtt ttcctggatt atgcctggca ccattaaaga
79621 aaatatcatc tttggtgttt cctatgatga atatagatac agaagcgtca tcaaagcatg
79681 ccaactagaa gaggtaagaa actatgtgaa aactttttga ttatgcatat gaaccctca
79741 cactacccaa atatatatt tggctccata ttcaatcggt tagtctacat atatttatgt
79801 ttcctctatg ggtaagctac tgtgaatgga tcaattaata aaacacatga cctatgcttt
79861 aagaagcttg caaacacatg aaataaatgc aatttatttt ttaaataatg ggttcatttg
79921 atcacaataa atgcatttta tgaaatggtg agaattttgt tcactcatta gtgagacaaa
79981 cgtcctcaat ggttatttat atggcatgca tataagtgat atgtggtatc ttttttaaaag
80041 ataccacaaa atatgcatct ttaaaaatat actccaaaaa ttattaagat tatttaata
80101 attttaataa tactatagcc taatggaatg agcattgatc tgccagcaga gaattagagg
80161 ggtaaaattg tgaagatatt gtatccctgg ctttgaacaa atacatata acttctagtg
80221 actgcaattc tttgatgcag aggcaaaatg aagatgatgt cattactcat ttcacaacaa
80281 tattggagaa tgagctaatt atctgaaaat tacatgaagt attccaagag aaaccagtat
80341 atggatcttg tgctgttcac tatgtaaatt gtgtgatggt gggttcagta gttattgctg
80401 taaatgttag ggcagggaat atgttactat gaagtttatt gacagtatac tccaaatagt
80461 gtttgtgatt caaagcaat atctttgata gttggcattt gcaattcctt tatataatct
80521 tttatgaaaa aaattgcaga gaagtaaaa tgtagcttaa aatacagtat ccaaaaaaat
80581 ggaaaagggc aaaccgtgga ttagatagaa atggcaattc ttataaaaag ggttgcatgc
80641 ttacatgaat ggctttccat gtatatactc agtcattcaa cagttttttt tttagagccc
80701 cattcttatt ttttatacac tttgagagca taatgaaaag aaaagctacc tgcaaaagtt
80761 ttggacttac ctcaaagagg atatacttca ttcctcaaaa ggccttcttc caggaatagt
80821 atttcataac ctggaggttg gaaaaatctg gatttgttac aaaaaaatct gagtgtttct
80881 agcggacaca gatatttgtc taggagggga ctaggttgta gcagtggtag tgccttacaa
80941 gataaatcat gggctttatt tacttacgag tggaaaagtt gcggaaggtg ccttacagac
81001 ttttttttg cgttaagtat gtgttttccc ataggaatta atttataaat ggtggtttga
81061 tttcctcaag tcaaccttta aaagtatatt tagccaaaat atagcttaaa tatattacta
81121 gtaataaatt tagtactgtg ggtctctcat tctcaaaatg agcatttact aatttctgaa
81181 cactgtgcta ggtcctggga ataccaaatt gaataagaca tagtctatttt ttctgaaggg
```

FIG. 1 (cont.) (SEQ ID NO: 1)

```
81241 tttatagcag agtccctgt gttaataatg aaggagtgtg tggtatgtga atcatatatc
81301 aatagggttg ttaaaaataa tgaaaaaagg agaagaggaa gaacatcttt ttttttcctg
81361 attgcacggg cagccttaaa attattttg aagtgtacaa ttcagtgttt ttttagcata
81421 ttcacagggt tgtattatca tcaccatatt tttggcctct tgaaaagaaa tcctgtgcct
81481 attagcatcc aattaccgtt cctttgtagc taagtctccc ccattccagc tttaaacaat
81541 cacccatcta ctttctgtct ctataaattt gtctcttttg gacatttcac ataaatgaaa
81601 taatataata gggttttttg tgcctaaata agcttctaaa gaagaataag gtaaggaatc
81661 atcattcagc aaatatttat taagacttgc tttattttat acagtgtact aggagctgga
81721 gatgaaaata tgtgtagaac atgaatcata tacttcggga atttgtggac tagtgggaaa
81781 gattgacata tcaataacaa atcgaattag tgatgtaata gaggcatttt tacaggagta
81841 aaatgaggta gcatggactc tatctgggtc tgaataatgt gaggagtaac ctccttacac
81901 aaagaggcac aaggctaatg tcctctgatg gaatgattca ccatgcaatt ctaagggtga
81961 caagaatgaa agttagggcc ttgaagaaat attttgatta agagctgcca ataaagtaga
82021 gtaaagatta gattgatgtg aagaagtggg agattaatga gtaaatggtc actggcttgt
82081 tgagaagatt aaatgagatg tacatgtaat gtacctaaca caacgtcttg tacaaagtag
82141 ccattcagta gagactagct tgtattatct cccctttgagg taaagaaaac tgttagaaat
82201 agtatttcta ctactgatag tatttcttct acttatgcct ccctttgagg tgaagaatac
82261 tgttagaaaa catgacatag gagaaatacc cctgagagac agttcttatt agtgactact
82321 gtgcagaaaa gatggaggtt ggtgtaatta aggagaagga aagccatgaa gccaaagtat
82381 tatgaaaaag catcaatatg aatttccatg ttgacaaagt ggtataaaag ataattataa
82441 agatggtcac ttataaatac ggtagttctg tgtgacacaa tttacagaag ttggtatatc
82501 gtgtggaaga aaacagcata agatcctgaa ggtttgaact gtgggcacat tggctccatg
82561 ctcaggaaat ggcaatgggg ttgggaagtg attccacttt atgtcccttt cagacacata
82621 aaaattactt gtgtgagtat cttatgccag acactattca ctgtgtagtg agcatggtgg
82681 gtatgaaatg acaactttat tgtctttcct gtcaaagaac ttgtaggctg gttggggggaa
82741 agagaccatt tcaatatgaa gtgctgagct agaggtaccc ttagggcact acagaagcct
82801 agctgatggc ttttagcctg gctagacagt tcaggatctc taaaagcagg tgccttgaag
82861 gctgagtcaa atacaaaaat gtattttgga cagaggaaat tgtatgaaca gaaacacaga
82921 acatgaaact acttggttgg tgcagggtat catcagcata gaaccagaca gaaccagagt
82981 gtaaataagc cagaaggcca tgtcatggag gccttgtata ccagtctcag gaatttggtt
83041 gtggagagct ttcatcaggg gaatgatgta atcagcttgg aaatgtagat atatcactga
83101 ctgtgatagt gaggagcaga attaaggtgg acgtgattag aagctttgtg aatagcagaa
83161 agaacataga ttttgaaagc tggcagacgt aggttactga agaaagttac ttaaccttgc
83221 tatgtcttta gttttatcct ctgcaatatg gggataatac tgcctatttt gtagagtctt
83281 gtggattctt ctggcatata taatagaaaa taaaacagct attattatta ttgttgatgg
83341 tactatttgc tatatctgac tacaaggaga aagactaata ggaaaccatt tcaggaatcc
83401 agatatgtc atgatggaca ggaagagaca agagttacat agaggaattc tgggaagata
83461 agaaatgtca ttttttatgta ctgtttgcat ccatcagaca aggcatcagg aaaaatgatc
83521 cttcaggaaa gagtgatttt ttttcttcaa gaaattagaa gaggggagaa attggtttaa
83581 gattaaggac tccatgcata agagaaactg ggagggaaga caggtagaaa tgctatgggg
83641 ttaggaagga agaatgcaga ggtggattac ttagaattga gacatctgat caagacagag
83701 ggatcacagc ttttgctaac aaagtactag tggaggatgc cactaggtga ggtttaataa
83761 ataattgttg acaataagtt ccatttaaaa aataaacaat ttatgcttct tctttgccta
83821 agtgtcaaat aaaacattca gatttttatt tcaaagtatc cctgagtccc tgttcccttt
83881 tttgtcctgc tgacttttgg aactgattta ggcttcctta gtcatctcat aatagaaaaa
83941 atcagccagg tatttcctac atttcttgta tttttaaaaaa atgtaatgga tgtaatgaat
84001 tttaagcaaa tgtaatgaat acaataagta acttagtata tgctgttttc ttctctatgc
84061 tgaatgtttc atacatgtta ttttctatac aactacatgg tcaattcctt gaaaatatca
84121 actccaaaat ctttatttg gtatactcca cgtagcacat tgagagagtt ttaaactctt
84181 gttggatgac tgtttcaaaa gtgttttgaa gtaggcatgt cagttgcaaa aagtttgctc
84241 agcaaatgtt gttctgtctc acagtctcag acattgagca gatgattaca tgacagcacg
84301 tgattgctgg gagtaacaga caaagtaaac tgaaagtgct cggttatctt gacagtcaaa
84361 atcaaaagtg tccctatttt tcagtgacct aagagtttct ttttgtgttt ttggtattgt
84421 tgttaaataa gtgttctcac ctttgaaaag gtcaataaga attcaataca gtataatgtc
84481 tgtgtgccaa atgaaggtgc cccttatttt taagtgtgga ggagttttga tcataagaac
84541 ttgaaatacc tacagaatcc ttgatggtta agcagctggt gccagcacaa gaatccctca
84601 atatgttctc tatgaagccc cgatcaccaa atgcaaacat tcatgattca gtatattttc
84661 atcttgactg ccaaagttga tctgtttctt aatatattac atctagactt ggaactggag
84721 atgagaacag aatattatct tcctcatttt tgtgtttttg ttcaactcta atgtctgcaa
```

FIG. 1 (cont.) (SEQ ID NO: 1)

```
84781 agcacttgcg tatgtaatga tgctcagtgt cataggagca ggcaggtaag tgtaaatttg
84841 tctggatagg agaaagcatg cacaacatat ttcacatagt tttctgattt cagtttgttt
84901 ttgcaaatta ttcactcagt gagatagctt aaagacgtta tcacagggaa aggcatggag
84961 atagttctgt gttgatagaa aacttgtaat gtacagccat gagtgagaag tcaggttcag
85021 attcttcacc ttcagtcctc ctctttcata aacagctcca tgtcctattt tacatatcct
85081 actttaaaac gagattatag aagaatgaat ttctaggcaa agtgacactt attttaaaat
85141 actattacgt atccctgtgc ccattaactt atcctaccat ttttcttccc ctgtgtccaa
85201 accaccttta gaatctccta aatatttgta gctattgtaa acagcactgg agactttgct
85261 agtttaaaag gagaaatcaa cgcaattaag ccctagttaa tttacttatc ccttatgaga
85321 ttataattgt attttgttat taaaaggggg acagagtaca ctgttctctt gcctttttaa
85381 tttccagact accacttctc ctgcacttga caataccgca gtctaccacg tagtcccatg
85441 gctgacagga ggagaattct aggcaggcca gtgtttgagt agtgagtaat tggactgtct
85501 ttacccagca actcactgtt ttgtaaatgt acctgagttt ggagaagtaa ttggcttta
85561 taaggggtgc ggggtggagg gttggggtgg ggagagtgag aaggaggtca gagctttagg
85621 atatataatt ggtctccaca aagttgttgt gatacttttg gaaccacgta atggtcttca
85681 ttaactaagt gtctgtcatg acagccatta catatgcatt ataataaaaa tttatttaca
85741 gtgtaagttg aagaaggtaa aatctggatg tagtttctaa actctgcttg gcagttttca
85801 tatttaagcc actagaagaa aaaaattggg agggaagctg agaagaattt actgaaagaa
85861 aaaaatactt gggagggaaa ttggcaagaa gtatgaaaaa gcttgggagg aagtaagca
85921 aataaatgag ttaatgactg ttctggaaaa taaactctat catgcagata tcacatgact
85981 gattaaattt gaatttgacc tcctgctttc caggtctggt aaaaactaac ctgtaagaac
86041 ttgaaactta gcctttgaat ggtcaatcca ccactgtagg agaatttatg aatgttcagt
86101 tgagagaact gaaaataaag aagtaccata ggaattaaca tttgcattca gtagccaaga
86161 tataatggac atctgaaaca ggtatttgag gccaggcgtg gtgtctcatg cctgtaataa
86221 tagcactttg ggaggccgag gtgggtggat cacaggaggc caggagttca agaccagcct
86281 actaaaacac acacacacac acacacacac acacacacac acactagcca ggcgtggtgg
86341 tgcacgtttg tagtccaagc tacttgggag gctgaggcat gagaatagct tgaacccaga
86401 aggcggaggt tgctgtgagc tgagattgcg ccactgcact ctagcctggg tgacagagtg
86461 agactctgtc tcaaaaataa aataaaacat atatttgaaa cacattgaat tatgtccctt
86521 aaacaagaat aaacatcact aaatgactgt accttgaact acctgtaatt ttctcctgat
86581 aggtaattaa gcttcaaagt actgacactt atttactgta atatgaagca ataacttaaa
86641 aaaaaaaaaa aactattgaa ccagaaccaa acaggaatgc catagcattt tgtaaactaa
86701 actgctattt catttcattt gagccctgga acttgaaaat aaatgctagc taacatctgt
86761 gaacagaaca tacccatcag tactgtgcta agcaccttc atgaactggt cattaaatcc
86821 tcactttcca tttatttagt gacaacttca cccagagttt gcagtcaaag tgaaaatgtg
86881 ctgaattcca aaagtgtgag ctaggtttta gaagttaatc acaattctgg aacaaattac
86941 tagcttaaca aatgagagtt cttatgtctc taaaaccaaa atagccctaa gtctgtccct
87001 cccagtaaga tttgggccag tcaatggaac agtaatatac aaatataatt acagctgtct
87061 aggagcaaac tatcctatga atagataata aaattaagac acttaagcca tgttttcata
87121 ttaaaacaca aagtaaaaaa tcattgtttt ccaaagataa aagccatact gtatcatgac
87181 atatatatgc ccgatgtttc gaccctcttg aagaattgag attctcgact ctacactctt
87241 agcgttttct atattgaaca gatgtttaat ttaaggaggt caagagaaat cttacactta
87301 ttttttaatg gtaccttaga catagaagga acctcagaaa tctctggctg aatatttcca
87361 tctgcagatg atcatgtcat taggcttctg actctatagc catagaaaaa tattcatgaa
87421 gaccttcag gaagggaatg ttggtatttc taaaaattga gtacaagtat tctctagaca
87481 aaacagctct tgaaatggca gattgtattc ccattattat atttcagaat caagacatta
87541 atacctactt tttatttacc aggtttagtt atccttgaat tagattttat aaattaaaga
87601 aatagatttc aataaatatt tgttgagttc ctagtatgga aacatcgtgt ttggcaccag
87661 ggatgttgcc tgcaagtata acaggagttc gtatttgtaa tgagtttatg atttacagat
87721 atttgggggg caaagatatc attcggtaaa tacttatgag tgcaaacttt gaactaggga
87781 ctgggccaaa ctctaggaac atatttgatg acagagacac aatccctgtc ctcaaggagc
87841 tttcattcta gtagagaaga tgaaaaccag tacagtttgg taagttagat gatattggtt
87901 aatgtagggt tcttatgtaa gtctagaaa gtagcattta atctgttctt agaaggtcag
87961 gaaagatttc cctggaggaa gtgacattta agctgagaga ggatggataa acaggagtca
88021 tctgagtgaa caacagggag aacattccag aaagagaaca aaatgtacga ggcctgatgc
88081 caagagagaa cattcattgc attgggaac tatagtcact tctgtgtggc tgggatgtag
88141 aatgaaatga gcctggaccc aagagagcac tttgcccttt ggggaagctg taggtattac
88201 agtaaggttg gagtctggaa agaaaggggt atattgtgag atctgaattg ggagaggaca
88261 gttatatcca gacctttata tgctccagta agaagactga actttacact gggggccatg
```

```
88321 ggactcactg aatggcatta aatttgagag tggtcatatg accagatttg cattttacaa
88381 agattgtcat tgactgcaac atgaagtatg gagtattgga ggagcggtaa ggctggtggc
88441 agggagataa tttaggaggc tttaggtgag ggatgataat gacttgccag gtaggaagga
88501 gtaaatttct tctcagtgga taattagaag attgaatgga tggacttggt cactatttgg
88561 tatagaaggg gaaaaagat gtcaaagatg atgccaattt ttaaaaataa tttaacattt
88621 atttttaaat atttttttcag ccttattaag gtataatgga caacaattgt aggtatatgt
88681 catttacaac atgatgtttt gatttatgta tacattgtga aatgactgcc atagtcaagc
88741 tcattaacat atccatcact cacataatta acatttttgtg tgtatgcagt gagaacatca
88801 ggctctactc tcttagcaat tttcaagtat agattacatt tgttaccaac tatagtggcc
88861 acactataca atagagctcc aggacttatt catcctgcct aactaaaact ttgtactctt
88921 tgaccaacat cttcccattc gtctctcctc cccatgccaa gtttccatct tggtcagttg
88981 ggtggatagt agtactatct gccgaggcag gttggtaggg tgaaaacaat gtgttccctt
89041 ttggaaatgc tgaggtgacc agggaacttc caagggaatc tgtctggatc tagagcttag
89101 aagagatgtt tgggctggaa acagacatca ggtattcttc agtatatggg ttgtaaatga
89161 agtcacagga gtgggtgata tcaccaatgg tgagtgtagt ataagaagac tggactgagg
89221 acagatttcc aaggaatttc aatacttaag aggtacgcag agaaaagagg ggctgtgaag
89281 gacaccaagg aggagactaa gagccaggag ggaaaacttt caagagagta ttgcattatg
89341 gaagggaaga agagagaaca ttttaaatga tacgcaatgc tcaataatgg tatccgcttt
89401 ggagaggcca agtaagattc ctaagtaccc attggatcaa ggtccttaat cttacaaaaa
89461 cttatgcaaa tcaataataa agagatgata acccgataat caaaaataga caaggcatat
89521 aagaagaaaa tgaattaaaa atattcaaag cattcaacat atacaaatgc gctcaatctg
89581 atatataatg aaagaaaagt aaattaaaac aacaatgggc atgactaaat aacagtatga
89641 gggagcctga ggagaaggag catttgaaat ttcagtacag aagagaaaag gggtgactta
89701 tagaaaaagg agacagaaac catagaacat gtttggagga taagactcaa acaggtagtg
89761 gggacccttt tctagagtag gatgaaaaca ggtaatgtgt gtggatgcaa atatgaggta
89821 ggatgtaatg ggaagttgag cgaattcata tttagtcatt cattcaaaaa tacttaattg
89881 agttactgct gtgtggcaag catcattcta caaacagagg gcacagtgat aagcaagcca
89941 gtttgtactc tcgtgtaact tacattctac tttgagaaga cagattataa ataggttaaa
90001 aagtcaataa tatgatgttt cagcatcaac aataaaaaat tagggtgata tatagagtgc
90061 cagggaaagt gctttcatgg acctcttcat tctctcctct cctggtgtca taagctactc
90121 cttcatccat gctgccattt ctcttggttt acggttccag tatagtactc atcacattat
90181 tactatagag ccatccacct tatgaaggtg aaggtgtcca tctccttact taaaaaaaaa
90241 aaaacaaac aaaaaaacaa aaacccgaa aacaaaaaa agaggcagaa agacagaagg
90301 tcctccacta actttcacgt gccatgtaac cagcgaaatc caattatttt acagcattct
90361 agctatagaa gagtttggga agcgtagtgc ttagtgttct agcctttgta gcacaggaaa
90421 gggcctggaa ggaaaggaat tgtgtcttcc gcagttgctt ttctttatgg ggaagtgcta
90481 tagcccaaac aatatttttag gaatttttcat ctattgtcaa tatgcaaact ggaaggggat
90541 aatgaaaatg ttgtggttag aagtttatga aatattgtta ttcacatttt aaagtaaaaa
90601 gagggaatgt ttaagagact tgtttaagat cacatgtctc ataattggtg ggaccagcaa
90661 tacaatccaa atctaactac ttatctttttt gctatgccct attagtgttc atattagaaa
90721 agaaattcta tctcagacac taatgatttg ttctttggac accaatgact ttaagttaaa
90781 acttcatact agttaattta attatggtgt agcagtatta ttaaactatc aagactataa
90841 attttctatt tgtaaaggag attatgatac caaagattag tgaactaatg atattgagaa
90901 ttctatgaca taattttgaa aaatatttgc aggatatttta tttttgtgta aatgatgctt
90961 tcaagctacc ataatcctaa gtaagtgtat atttgggaaa accacctatt ctaacacact
91021 tgaaatttaa ataagtcagg aaattttttt ccagatcttc tcccaaatta tcttcatctt
91081 tttcctctcc ccttgggaaa gaatctcttc atgcctcata atatcaaatt taaactatgg
91141 aagtccaggt ggtggacagt cagcaaaggg gaagatgaga agcttgtgtt ataaagccag
91201 ctcttgtcag aataaggatc tggtaggaac ttcagaagtg atgggtaggt aagtatgaag
91261 gccaggtcct aagatctaaa ttacaaagca gaagacttac ttaccaggga gctggaaaac
91321 atgttaggaa atccagagca ggaacagatt tcaagatagc acaataatat agcagtgaag
91381 tactgagaaa agagtttttt tcacggttg gatttattct agcatttttag gcagcatttg
91441 ggcatttcta agtggtcaga cttagaggag atagttaagg aattagcagc tgctaaatgc
91501 caattcttag accagttgaa tcaaaatcat ctaaaaagct ttcagaaacc agacttttta
91561 agggccattt gagagactct caaatctgga atccagaaat ctatagctag atgagtttaa
91621 ggtagagcca gaataagaaa aataaaatag tttgtttgtt tcaggtatct tttccaatat
91681 tatttccgaa cctaccccaa acacctaaaa tcactgcatt ctatagccat tcttttaaaa
91741 atgcttgagt tattagtttt caaaacaaa tacaaatctg cacacataca gaaataaaca
91801 ttaaagagac ataagatat aaacagagt tacatatact tacaacttca tacatatata
```

FIG. 1 (cont.) (SEQ ID NO: 1)

```
91861 ttatatataa aactgaatat taagtgtttg atattagtga caaaatctgt aacatccatt
91921 atattagtgc ttttttgtact ttttgttggg tgtagtaaaa attgcattcg aatttgagtt
91981 ttctgctata tatttggtca gttcctatca gtgaaggaaa aaccttttt tattatttta
92041 ttgttttttt attttttgag acggagtcct gctctgttgt ccaggctgga gtgcagtggc
92101 atgatcttgg ctcactccaa cctctgcctc ccgggttcaa gcgattctcc tgcctcagcc
92161 tcctgagtag ctgggactac aggcacctgc caccaggtcc agctaatttt tgtattttta
92221 gtagaaatgg ggttttgcca tgttggccaa gttggtctgg aactcctgac ctcaggtgat
92281 ctgcctggct tggcctccca aagtgctgga attacaggtg taagtcacca cgcctggccc
92341 cttttattt tttaagctga ttgaagattc ttagttctca tgctttctag tggtgattaa
92401 tctttagcca atatttctat atacagttat tagtaatcat gtttgactta ggtcaacaaa
92461 caatctttcc taaaaaaaca gaacccccaat tttaattctt gaattatttta gtatctattt
92521 tctgctgtgg aagttgaatt atgttgatag atatcataca gggccatgta acactctcag
92581 atacacgttc acatgtatag tagctgtata caaaaatgtt acttcattct ctctctcttt
92641 ataatactct tggctctctt acgttctctc acacactcta ctcttccctt cctctgttct
92701 ttctacttgt tccctctgct cctaccacac ttattccccc cttgtccatt ttccttgtgc
92761 ataaagcaca agtgcttagt aattatcaaa tattaataac aatgacacta accacccaat
92821 gatttagtgt taatgacatg ctttattgaa tggcattacc tctaaagttc atgtttcctt
92881 tacccaacca agcttcttac cctcctccct taccacaagc atctatattg tcaaggttgt
92941 tataaagagt aataagccag ccattaaaaa agggtttatg gtatttcct atctacaaag
93001 tcacaggaag ctcaaatgta ctcagtaaat attgcaaaat tacacaggac cattaaatgt
93061 aacactccac cctttctctc tctctctctc tctcttgctc tctctctctc tttctgtcaa
93121 tatagcaaca ccctatatca ttgccctttg tatgtgcaaa tcagagttaa taagctttat
93181 attagcaatt actccttaac aacttctggt ttgtttggtc cagttgaata atgtaagcac
93241 ttaaaaaaat gaaattataa acatttatgt gaaaagtgca tatatcacat tggatatgtt
93301 gttatgcact ccttaataat aaagtaagtt aatctttatt gcacacttat tataatatta
93361 ctttgaccct ctctagtact ctttatctaa gtattctcaa gtgctttaca atctcaaaca
93421 gacccaatgt gttgtataca cagaatcctt tgaagctgac atttgccttt ctgaccagct
93481 tgttgtaaag gaaatcagcc aaaaaacaag tatctagatg agtagctcaa acattagtac
93541 acatagtaat cacaggtcaa aatgcagata gattaccctg tccaaattct cctgagtaag
93601 agtaggtgaa acattttaa ataagctccc caggtgattc tgaaattggt ccaaggacca
93661 catattaaga actaatgatc caaacaattt gactttttat tgtagattaa accatgctga
93721 gaaaattatt aaaaattgaa atggcagtgg aggatggttt gaaagaaagg tttttcaggg
93781 cccttttcaac aataaaatta attgaacaca atattaaaac tctatatttg atttaagact
93841 aaggttttca ttgttttaa atctcagtaa tttttatgta acaggtcaat tcatacccag
93901 catcttaatt ccaatgaatg atttcccaca acaattttg tggataactc caagggaact
93961 cgaaggaagt tgtagtatga acaaagagaa gtagaatttg tccctgtgtg taaggcttct
94021 ctgataagca gcacaggctc tcatactgct ttttaaaaaa attatgatag catcaagtgg
94081 aattaattttt ttttagatta tactttcatg gaagggaaga tctactgtga aggctggaaa
94141 accaacaccc ttaagataaa tatattacca gatttgagcg ctcttagtaa tcagcaaaga
94201 taaatgttta acagtgcata caaaatgaag tgttttatgt taaatcaaat agagaaagcc
94261 aaacactaat aatgtggtta caaatgaaca ataaattagg taatcagaac aggtacagac
94321 attaatagca ggatattggt attattaatg tattttgttt taaaataatg aacttaatta
94381 caattctcct catcctaccc cactatttta ttttattcca gattcagcag cttcatatta
94441 tgtctctgaa acacttatta ttaaagttat ccaaatgtac acatttctct ttatataaat
94501 gtttcagtcc agaaaaggag gccaaataca ttagctcaga acatcaaatc ttctcagatg
94561 tgggaatctt ttattttcac acttttaaag gtaatctgta tttctagcgt ctattataga
94621 cagaaaactt tcatatgaca acattcctat tttcttaact gccttgatag gggcgaagac
94681 aaattctaag taggactttt tacccccattc ttcttaccat cattctttca caaaccccc
94741 agctttagac aatcgctatt atgaatttga catgtactat tccaatccat tcccataaat
94801 ttacacccat atatacatat agttatctat gaacaatatt tagtagcttt tttgtgtgtg
94861 gctttaaaat ttacataaat tgtataattt gtgcacattc ttctttaatt tgccttcttg
94921 gctacggtta tcttttgag atctagctat gctgctggta tgtagaattc tatttcattc
94981 ttttttcatt gttgttttgt acccataacg tgtcacattt tatttatacc ttctgttcct
95041 gatggacatt tagattcttc caggatttta ctcaatactg caatgaaaat ctttgaattt
95101 ttctcttttg cacatattca agagactttt ctgacatata tctctatagg tgaattgtgt
95161 agtcatatga tacatacaca cattttaaat ttcactagat actgccaatt tgcccttttga
95221 aatagccata caatttatag taccaccagc cacttatgaa agttcccatt tcctcaaatc
95281 tttgaaagtt cttattataa acagacatat taattcttgc cattctgatt tgtaaatcag
95341 aatctctatt gttctacctc tagttctaat ttggaattcc ccaattactt gtaagatgct
```

FIG. 1 (cont.) (SEQ ID NO: 1)

```
95401 atatattttc atgtttgtta gtcattctga tttcatatcc tttaccaatt atcttttttgg
95461 taagttattg tggtggccat gagatgtgcc ttacagaggc cttgctagag ggaatgtgat
95521 tgaatgagag ccccagatgc tgtgtattaa aatcctgcac tgagtttgtc tcaagatttc
95581 ttgcacgtga atgaatgagt acagctggga tactaaagca gatgtgtatt tgggagatat
95641 gagacttctt tagtggctga tttttggctc ataaatgact ttgccaaacc ttccttagac
95701 tgctcagtgt tctaacatct tccatccagc cttctaccct tctttccttt actaggggat
95761 tgaatttaca ttgaggtctc atagccttct ctgcctctct ccttatttcc ttttatacaa
95821 atatttcccc taataaatcc atgcacattt aataccattt tgctatttgc aacctgcagg
95881 tcctggacta acacagttct atacattgca ttaccattct ctagagtggg atcttttgtt
95941 gtagagagtt ttaaaatttt tatgtagtca cttttatcca tattttttctt tatggtttat
96001 attttttgtgt cttctcttta acacatcttt tctagcagaa ttcataaata tattattcta
96061 tattgccaaa agtttgaaag ttgcaatcat tagaattaat ttttgtatat tgtgtaagtt
96121 aagaatctaa ttttattgtt tttcattgga aagccatttg tcccaagata attttttagt
96181 agtccctcct tcccctattg tcattctgac atattttttc taggttccga tctatgcatg
96241 tgtttcttta tggaagagtt ggcCCtttgt atctttgagt ttcaaatcca tggattcaat
96301 caaccacaga tagaaaatat ttagaaaagc gtcagaattg aacatgtaca tacattttgc
96361 ttgtcattat tccctaaaca atatagtata acaactattt atgtaggatt tacattgtat
96421 taggtattgt aagtaatcta gagatgattt aaagtataca ggaagatgtg catatgttac
96481 atgcaaatac taccccattt ataaagggt cttgagcatt catggatttt ggtatccaca
96541 gagagtcctg gaaccaattc cccacagatg ccaaggcaca actgtattta ttctatcatc
96601 tacttgttta atctcacatc agtatctact tttgaaataa caataacttt attatttaac
96661 tttttttatt acttaggatt agagaatttc ctctggtgag gcatcatagt gtctcaagct
96721 ggccataaag acaagtgagg gctaggatcg gtaagactgg gcagaggaag atacaacaga
96781 tctcctatgc atgaagcaaa agtgcagctc agaagccagc tcttcatta agttgtcctc
96841 tatccctca ctagattgta agctcttgaa atgagaggct ataccttaat tgtctctgtt
96901 atctaaaata cttccactca ctgcttggaa catattgcct gcaataatta agcttgccct
96961 ggctcccaaa gcatagagca aatcacactc ctcccccttgc ctttgagaag ctcacagtct
97021 tcgaaggtag agatatgtga acagataaga aaatggatga caggagaaca gaaacgcatg
97081 actgtcagag aagtcattgg agacttaca gaggaaatta aattttttatt gatcttgaaa
97141 gagtttgcca gatgaagtag aggacaggca ttttagacaa agggaacagg aaatgtgaaa
97201 acacaaagtg atggaagtca tggtgagttt ggagaactat aaaacttcaa tgtggctgaa
97261 gggtaaggtg gatatagagg agtgctggga ggtgaggctg aagaaataag ctaggaaatg
97321 tcttttatg ccattttta aagtttggac tttattctga agttcacatg gatccaatat
97381 ttttttgtttt gtgttgtttt aagcagaagc gtgacatgat cagcttgaat gatgaacaac
97441 ttgaattgtt taaagtggat cacacagtct actgttttac agttattctt tgaccaagat
97501 attctttatt aactgaggaa aaaagggct ttcctgaatt ttgcagtcat gggatatatg
97561 ataagcattc ttgatttatc atcttcaatc ctgttacata acataataac cattgttatt
97621 accttttagca atgctttcct cagtattatc taatggccta taaaatgtga cttttcatttg
97681 caaatacagt acatctaaca agaacttacc acagctgcta tgcaaaatac caatacaatt
97741 gacccttgga caatgtgggg gttaggggtg ctgattcccc atgcagttga acatgttaca
97801 taacataata cataaccatt gttattatgt aacaggattg aaaatgataa atctttggaa
97861 agtggggcaa atgaattctt atgaattcca tatcttccac atgtgttttta cttttttgat
97921 aagaagtagt aacctagttc agaaagaaaa taatcatccc cttttactta tgcaggatac
97981 caagtctatc ttagcaccat aatagtgaat gataggaatc aagctctatg aatacattca
98041 catgtacata tatatggcta tataggacac atgcatgcac atatacatat atacacttgc
98101 atatatgtgt atatacatgt acatatatgc atgtatattc aattgtatat gtgtatatag
98161 ccaagttatt gtacagttga cctttgaaca acacgggttt gaactatgca ggtccactta
98221 cacgtatttt ttttttccgt ttctgacacc cctaaggcaa caaggccaac tcctcccctt
98281 gctcttcctc ctcagctgac tcaacatgaa aactatgagg acgaagacct ttatgaagat
98341 tcacctccac ttaatgaata gtacatacat ttcttttttcc ccatggtttt cttaataaca
98401 ttttcttttc tctagcttgc tttattgtaa taatatagta tataatacat ataacatacc
98461 aagtatgtgt taattgactg cttatgttat cagtaaggct tctggtcaac agtagactat
98521 tgctagttaa gtttctggta gttacaagtt atatgtgggt gttcgactgc atggggagtc
98581 agcaccccaa ccctcatgtt gtccaaggc gttgtccaag ggtcagttgt aattggtatt
98641 ttggatagca gctgtggtaa attctggtta gatgtactat atttataaat gaaactcaca
98701 ttttataggc cattaaatat tattgaggag agcatttcta agggtaaaat cttgtctaat
98761 gcttgaaaca tcttcatttt cctgtcagtt tagatctttt tgaagtaatt ctgaaaatct
98821 ctcttttaag ctaaatttaa cacaaccaaa tagccaaata tttaagttcc actaatgaag
98881 atatctaaat ttctgttaaa aatttaagat atatgttaaa cccttctaat ataactcttc
```

FIG. 1 (cont.) (SEQ ID NO: 1)

```
 98941 tctcagtcaa acttttttttt ttaacagttg ctttgcttct tctttcaaag tcatacttca
 99001 acaaagttgc tattgaatat gtctgactaa acatgttagc tatatgataa gatggctgga
 99061 taagagataa atatagaaaa tgtagctttt tttctacttg caataaccct ttaggaatta
 99121 aaatggaaaa ctaataacta tttgattcat aatagtagca aaccgtaaaa tatttagaca
 99181 taaatctact aagaaattta taagacatat atggagaaaa ttcaattgaa taaaccgtta
 99241 ttgaagtata taaaataaga tctggatgaa tagaaagatc ataattttta ataaaatttt
 99301 gcatcttaaa aagtgaaccc tctccaaata tatgcacatt taataaaatt ataaatacat
 99361 cccaatgagg ttggttttga aattttgtta attggaactt aaatttcacc taagaagaaa
 99421 aaataaagaa tagttaagag tgcatgcttt gtagacaaat tgccttagtt agaatcctgg
 99481 ctctatcatc tattagctat gttatctttg gataacatt catctttct tatagatatg
 99541 cttaaaacag tgcctgacat atagtaagca caaatatcca ttagctattc ttcttattat
 99601 ttatgttatt agtattgtta atatttgtta ttatatggaa gactaaatga ccaaagagag
 99661 tcaagaaatt tatgaataag atttatgcgt tgttagatat tagagccatt aaaaaaaaaa
 99721 aaaccaaagt gccaaaaaac ctagcacagt gttaatacag gaataaaaaa atggatcaga
 99781 ggaaccaaac agaaaagcca gaatggatc ttaggaaaca tgagaatatg atatatgata
 99841 gatgctaaat gaattcagta taaaatatt aatgtaataa atcatgcttg ctattcaagt
 99901 aaaagaaaat gaggttagat tcatgtctca taccaaatat aaccataaat tataccttga
 99961 ttaaatttttt taattaaaaa gcaataatat ttgaaaagaa atataggata ctcaatgtat
100021 aacctgaagg ttgggtagta cttttcaaca aatataggaa tttttcactt gaaatactag
100081 aagaaaaaaa gatagcaaac aaatacagga attccaattt caagcagata taatgatttc
100141 atgaaatgtt aactgtgcac atgatagatg gtctatggat agtgcaaaag aaaaagagaa
100201 aagaaaaaat gttttttaac atatgcagca aaaaggttt ttaacatcta ttacatacaa
100261 ataaaaatga atgtataaca cagacttcaa taaaaatagg catttcacag gagaacaatt
100321 cagatggcca gtatttacaa tttcataagt attaaggaaa atacaaatta aaatggcaaa
100381 ttagcaaaaa ttgaggtgtg attatattaa tatctgttgg tggtggtgat tatgggggaaa
100441 agggtacttt caaaacttgc taatataaat ataattcttt tggttgtttt gtaaaggaac
100501 ctgacaatat cttttaaaaa taaagaaaac gcatactttt gacctagcca tcccattcat
100561 gagggtatgt cttagaaaaa taagatcaca aaatcataga gatttatgtg caatgatatt
100621 attggtaggt cattttatg aggaggggtg tggatagtaa atgccagggt aaatcacata
100681 gcatctaata aacgtattta tgaactacaa aagcttacac tttcagtcta gtctagtcca
100741 gactgcaaat aaatgtgagc aagtgaattc aagcacagaa gtgcttaag gcaggtttca
100801 taaatctact ttcttacagt atcctgatat tgacttatcg agacagttac tgtggggttg
100861 attattaaaa tatttatgta tctaggtatt tttcattcag tagtatgtta ttcaattagc
100921 aacaagtgtg gggatttaaa gatattcttg tttgttttta ctgctgaaac atattctagt
100981 ggaaatttcg aataaacgat tagtcatcct aaaagcaaga tacatttct cagaaaagac
101041 aaggtaaaga acttgtatat cctccctcaa ttcgtttata aggtaataag atgaataaaa
101101 atatcatagt acaatttagc attgtaaaat aaaattaatt ggtcatctct agtgtggtcg
101161 tgcttggaag gtgaaagaag ccaagatctt gtctgggaat atcatgtcta ccttgacctc
101221 acccttaaga atcctagcct ttagttaaa atcacatggc tacatacata ccaacttcaa
101281 caatagtaca tctggcaagg tcatgcaaac ctgggacttg agcttctgat tctaagtcca
101341 gtgcttttg tgtacatcat ctcttgtaca taccttatga tgatatgcta ataaaagcta
101401 cgtgatcagg ccttaaaaat ctgcttttttt tttgtaatgg tagaatgggg catattatca
101461 catcaggtaa acactctatt caaggataaa tggaaatgaa tgtcatatat agatcattga
101521 taaatatctc attacaaaat tatgagagtt accaatgttt gagtgtatat tatgggccag
101581 ccctttatat taaattactt caaatttta caactgttaa aggaagatat tattataccc
101641 atttttataga tggacaagtt agggccagaa aagacttcct caaagctgtt agtccagtaa
101701 tggagacagg gctagaaaac aggtcatttt gctctttgac taatgttact actcatgttt
101761 tgtattttgt ttaaagttttt atttattttt gctttattta tttttgaga caagatctta
101821 ctctgtcacc caggctggag tgcaatggag tgatcacggt tcattgcagc cttgacctcc
101881 tgggctcaag cgatcctccc acctctcaat ctccagagta gctaggacta ctacaggtgt
101941 gtgccaccat acctggctaa attttgcatt ttttgtgggg acagggtttc actatgttgc
102001 ccaggctggt cttgaactcc tgggctccag cgattcacct gccttgacct cccaaagtgc
102061 cagtatcaca ggcttgagcc accatgtcca gccaagtttt attttagaat aaaaaaaat
102121 tccacttgga ttgttacatt ttatctcatt gctttatatt tatagaatta ctttataaat
102181 gccactttct taattttcat agttagcact ctttatgaaa cataaactat tatttgaccc
102241 aggttttgt tagaggaatt gagtcagaga gctgttaagt aactgagatt tcacaataag
102301 ccagacagac cagggttcaa attctgggtc tcacattatc caattcaata ttccagcttt
102361 gttacttatt gagcaaccac tacaagcaca gttacatgaa catctgatag ctctcaaaat
102421 gaattttaca aacataattc agatttcaac tcagcagtga ctcaggagaa aggacacttg
```

FIG. 1 (cont.) (SEQ ID NO: 1)

```
102481 gatgcatttc tttatggcat ttttcccagg gtacacgcaa cctggaagat ctcccaagta
102541 tgggggaagg tttcaccctg aggaatccca ttccctctaa tctgggacaa gggggaggag
102601 agtactgtct cttatcagcc atctccccag ggaggcctgg gccctcctgg aatgcatacc
102661 atggcttact gactcaaagt gttgaaaaga ccaggcattg ggacacacaa cactactctt
102721 aaaataaaaa aagaatcaga gtagcttgtg gttataattg aaatggacag agtaacatgg
102781 taccaagaaa ctattagcaa ttccttccct aaatccctca ttttcttaaa gcattttctc
102841 cttttcctca acaagcttta agttggattt gaagaatgat aagactaaaa ggagggctgt
102901 ttctggtctt tggaggaatt tgatattcca ttcgatctga gtgtgcaaag cctgagttca
102961 catgaactct tctgatctct ttctctaata ttttttcacc ttattcatat gggaaagaag
103021 gaggggaata ctttagttcc attctccctc ctcctatttc cttgacttgt ttaaaatata
103081 aatgttatag acacctaaga tagaaatttg actgaaacag cctcttaatt attgtcttaa
103141 aaaattggta taatgaaatt gcatttgtag tctttggaca tttaaatcca gaagggatat
103201 tttctttttc ttttttaaaa atttaattca atagttttg ggctacaggt ggttttggt
103261 tacatggata agtgctttag tggtgatttc tgagattttg atatacccat cacctgagca
103321 gtgtgcactg tacccaatat gtagtctttt atccccccc cgctccaccc ttcctttatc
103381 gtccccaaag cacattatat aattattatg cctttgcagc ctcattggtt agctcccact
103441 tgtaagtgag aacatgcgat atttggtttt ccattcctga gttacttcat ttagaataaa
103501 ttgtctctag ctccattcaa gttgctgcaa aggccattat ttcattccgt ttttggctg
103561 aatagtattc catagtgtat atatgccaca ttttctttat ccacttgttg attgataggc
103621 atttaggttg gacccatatt ttcgcaatta tgaattgtac tgctgtaaac atgagtgtgc
103681 ttttttttttt tccatataat gacttctttt cctttgggta gatacccagc agtgggactg
103741 ctggatcgaa tggtagttct ccttttagtt ctttaaggaa tctccatact gttttccaca
103801 gtggttgtac tagtttacaa ccccaccagc agtgtaaaac tgttccattt tcagcacatc
103861 catgccaaca tctattattt tttgacttt taattgtggc tattcttgca ggagtaagat
103921 ggtatctcat tgtggtttta atttgcattt ccctgataat cagtgatgtt gagcattttt
103981 tcctgtgttt gttatttgtt tgtatatctt gagaattatc tattctgtcc tttgcccact
104041 ttttgatgga attatttgtt ttttttttctt gctgatttgt ttagttcct tgtagatcct
104101 ggatactagt cctttatcgg atgcatagtt tatgaatatt cttccccact ctgtaggttg
104161 tctgtttacc atgctaatta tttattttgc tgtgcaaaag cttttcagtt taattattc
104221 ccatctattt attttgttt ctgtttatt tgcttttggg atcttagtca tgaacttttt
104281 acctaaacca atgactataa gagtttttcc aatgttatct tctagaatgc ttatgttttc
104341 tggtcttaga tttaagtctt tgattcatct tgagttaatt tttgtataag gtgagcattg
104401 aggatccagt ttcattcttc tacgtgtggc ttgccagttt tcccagcacc atttattaga
104461 tagggtatcc tgtccccact ttatgttttt gtatgctttg tcaaagatca gttgactta
104521 agtatttggc tttatttctg ggttctctat tctgttccat tgtctacttg cctatttgtg
104581 taccagtacc aggctgtttt agtaactata gccttgtagt ataatttgaa gtcgggtaat
104641 atgatgcctc cagattttgtt ctttttgctt agtattcctt tagctatgtg ggctcttttt
104701 tagttcccta tgaatttttag gatttttttc tagttctgtg aagaattatg atgatatttt
104761 gatgggaatt gtattgaatt tgtagattgc ttttggcagt atggtcattt tcatagtatt
104821 gattctaccc atccatgagc atgggatgtg tttccatttg tttgtgtcac ctgtgatttc
104881 tttgagcagc attttgtagt tttccttgta gagatcttta acctccttgg ttaagtatat
104941 tttcatgtat tttagttttt tttttttgtt tgttttgttt tgttttgttt tgttttgca
105001 gctgttgtaa aagggattga gttcttgatt tgattctcag cttggttgtt gtcagcaggg
105061 acattttcta aagtatagac tgtagttcct tatcttctat ctgtttctta ctgtcccctt
105121 cagtattctt gtccttttt cccgctatta tcttttgac cttttaatat atagatatct
105181 acttctactt ctgacaattt ttgcttctcc aattttcttt cttttctcc tctgcacaca
105241 tttatttatt ttcttctatg tacttcttta tttttaactt aatatttgat taacttccct
105301 tccctgtctc ttttccttct ttccataaat cttcattaat tgcctgcact gagctaggat
105361 tctatactct ctaaatcaat aatctatttt ctatagtcaa ctgtgttata atcgtactgt
105421 caagataact acttatttt aatacttaaa aatattttga aattttaacc aatttaatta
105481 atacaatgtt gagttcaaat ttgaaaaaaa caatggaaaa ctgaataat tctagcaacc
105541 tcctgctttt taataatgta ttagaaaatt tgcctcttt tcaaaagcct acagtgaatc
105601 tattcataca aggcaaaagc aaaccattct cttcattctc tttttttctc caaaagattt
105661 aagtgttttt tgtttgtttg tttttgtttg ttttttagat attgagtctt gctctgtcat
105721 ccaggctgca gtgcagtggt gtgatcatag ctcgctatag cctcgaattc ctgggttcaa
105781 gcaatcctcc tccctcaccc tcctgagtag ctggggctac agtgcatgc taccatgccc
105841 agctaattta aaggaaaaa aattgtgtag agatgggtct tgctatgttg cccaggctgg
105901 tctcaaactt ccaatctcaa gcatttctcc cacccagcat cctgaagtgc tgagattata
105961 agtgagccac tatgcccaac cagatttagt ttttaaaaag agaatacgat ttgaaaaagg
```

FIG. 1 (cont.) (SEQ ID NO: 1)

```
106021  aaaaatgtga ggcaggagag aagaaataca cacacgagct gttttgtaat tgctgtaaaa
106081  ctgaaatctt cagcctcact aaaggagcac ttgcatgaac acctctaaat taccttatta
106141  ccttctaaat taggtgtgaa gtctaacttc taaattatga gtgaaatcca ctgcaattct
106201  tgttatttgg atggaatcct aggtatgtgg tccagttcat gagttgaaca aaagcatgct
106261  catttaggcc aggtagaaag aaataaagac ctatgtttta catgtctcat aaccactgaa
106321  ggtccttctc ataagcagtg cttatgggta ttaacgacct ctctatattt tacttctcca
106381  gtgcctaagt agccgagtcc actgagtcct gctacatctc ctccaacatg tcagcatttt
106441  tttcacaggc cttttgttac tctagatcag aaatgttgat agcaacagtt ccttgagggc
106501  agcagctagc atgatgccag ccaacaggaa ccaccaaatg gttcttaata taaattacta
106561  cttattaatc tatttacttt gtgcatttgg agttttgcat gtaaagtcct atttatgtcc
106621  atatggtaga taaatggaac aaatgaataa cagaagtaac cattttgata ctttagatat
106681  agataatatt ggattatttc tggattgtga aagaagaagg aagaagcata tggaagagaa
106741  gttttagtag aggggaggaa ggaggaggtg gaaacgaatg tacaaggatg ggaggagaaa
106801  agggagagag acttttttt ttttaaggcg agagtttact acctatctaa ctcttcgcat
106861  tcttgaagtc tcagaccaaa tcccatcggt ttgaaagcct ctagggtatt ctatctattg
106921  tatacttctg ttatgtacaa aattaatttg ccaattaatt gtgaactgtt ttataaacta
106981  tcttaaaatg gttagttaaa tctttgggat agtatttagc tttctccagg attatgactt
107041  accttctaaa ttagacatac aatgcctagg agtcaaggac tattttgcat aaattccagt
107101  cttcttttac aatgcctaga atgattgtta ccacagaaat attcattacc tgggagaaag
107161  gatgacagga ggggcagaat gaatggagag aggtcgtgag aatgaggtgc tgaggatgga
107221  cgaggaagaa agctgtttta gttgggagga taggtgacag aagcatggaa aggaattgcc
107281  ttggacccat ggaagcccag tgaagatact tagatcctgc aggggtgtga ataatgttct
107341  tttagtttct cttcttagga ggtttgttca ttttgggaga tttcttttga aagagtgaa
107401  cttaaattgg agaaaagtac attttagtat gttgataaca tttgaatttg taaaatggac
107461  ctatggatga tctacacata tttatatacc cataaatata cacatatttt aattttggt
107521  attttataat tattatttaa tgatcattca tgacatttta aaaattacag aaaaatttac
107581  atctaaaatt tcagcaatgt tgttttgac caactaaata aattgcattt gaaataatgg
107641  agatgcaatg ttcaaaattt caactgtggt taagcaata gtgtgatata tgattacatt
107701  agaaggaaga tgtgcctttc aaattcagat tgagcatact aaaagtgact ctctaatttt
107761  ctattttggg taataggaca tctccaagtt tgcagagaaa gacaatatag ttcttggaga
107821  aggtggaatc acactgagtg gaggtcaacg agcaagaatt tctttagcaa ggtgaataac
107881  taattattgg tctagcaagc atttgctgta aatgtcattc atgtaaaaaa attacagaca
107941  tttctctatt gctttatatt ctgtttctgg aattgaaaaa atcctgggt tttatggcta
108001  gtgggttaag aatcacattt aagaactata aataatggta tagtatccag atttggtaga
108061  gattatggtt actcagaatc tgtgcccgta tcttggtgtc agtgtatttg tttgcctcat
108121  agtatagttt actacaaatg gaaaactcta ggattctgca taatactgga cagagaagat
108181  gtaaatatct gttagttcca tcatagaccc tgccactcca atgtacacac cagctttagg
108241  cttcttggta tagataaaca tacattttca aaattttca tcataattt cataacaaaa
108301  taggaaggca aatgatgtca cttggcttaa aatctataat atttaaaata aacaggacaa
108361  atgcattaac attgttgggg gaggaggtcc cttagtagaa cactcttgg tccaagcatt
108421  ttaaagctgt caaagagatg taaatataga taatgtatgt caaggagaga gctttgtggt
108481  taaactgtaa ctttcagttt aaacaattat tggtgactct gatgtcaaat gtttctcaag
108541  ctttatctga acaaaattct tctcactttg ttgccaaagt cgttaacaag aaatcacatt
108601  gactcattga tgttttggct cctttccctt actttctgtt gctttccaaa agctgagaca
108661  ggaaactaac cctaactgag cacctgcaat tgcctggtag tattctagtc atgtgtgtac
108721  ttttgtgtgt atgtaatccc cttacagctc tgcaaagtaa gaattgttct ccctgcttta
108781  cagaagagat cataagataa ttgaggctgt tagatgttaa cttgccaaaa gccatacagg
108841  aaaatggtag agtcacagtt gaaccaggt ccttttgatt ctttacatta aaccatgctt
108901  tgatcttgga aatacactgt aaggcaataa atcaatagat acggataatt cacaggcttc
108961  taaataaatg gaagttgatt gttttatct gtgagccaaa gtaagactta ttctaagaat
109021  tccacaaatt tagataagat agagtatatg gcttctagac atccaacata gaactgagtt
109081  tgtgttatca gtttaagatt tggttttgct gtaaggtgca cacactttga ggaactaaaa
109141  ataattgtct gttcttattc tgatcagaat gtgtaatgtg ttgtccagtt ttggatgatg
109201  aatttcttat ttctaatctc ataagaaact tgtcatagat gtgagggaga gaattaagaa
109261  cagagtgtgg ggaagaaact tgtgtacattt tgatgggatc cattatgtag ctcttgcata
109321  ctgtcttcaa aaataagtta cactataaag gttgttttag acttttaaag ttttgccatt
109381  ggttttttaaa aaaatttta aattggcttt aaaaattct taattgtgtg ctgaatacaa
109441  ttttctttat tacagaagta ccaacaatta catgtataaa cagagaatcc tatgtacttg
109501  agatataagt aaggttacta tcaatcacac ctgaaaaatt taaatgttat gaagaaatta
```

FIG. 1 (cont.) (SEQ ID NO: 1)

```
109561 tctcatttct attaatatgg gaactgtgtc ttcatcttta ttactgttct aaggtcaact
109621 caatgtagat tttacttgct tatggtttca tattttagct aaatagtaaa ataatatgga
109681 tatacatttt gttgtgactt actcatactt tccttatttg aacttttat gaatatgata
109741 tagagactga aactacaagg aacaaaatgc aatatcaatt atacagttgt ggcagcactg
109801 ctatcaattt gttgatagtg gttaacactt agaaaaacat tttaaaaata atttcacata
109861 agtaatgtaa tttattagct gtctctgaca ttttacagtt tggaatagtt tattttcttt
109921 ttggtgtcct caccaaaacc caacatcttc aagggcagga actgtataat ttttgccatt
109981 gtattttgag cacatagcat ggtacttgcc tctaaataga tactattgtt aaaatatttt
110041 ttaaggtaat atttttaaagt gtatgctatg gtacagttca gtttgtgact tttgctagtt
110101 tatgccactt acagttagca aaatcacttc agcagttctt ggaatgttgt gaaaagtgat
110161 aaaaatcttc tgcaacttat tcctttattc ctcatttaaa ataatctacc atagtaaaaa
110221 catgtataaa agtgctactt ctgcaccact tttgagaata gtgttatttc agtgaatcga
110281 tgtggtgacc atattgtaat gcatgtagtg aactgtttaa ggcaaatcat ctacactaga
110341 tgaccaggaa atagagagga aatgaatttt aatttccatt ttcttttag agcagtatac
110401 aaagatgctg atttgtattt attagactct ccttttggat acctagatgt tttaacagaa
110461 aaagaaatat ttgaaaggta tgttctttga ataccttact tataatgctc atgctaaaat
110521 aaaagaaaga cagactgtcc catcatagat tgcattttac ctcttgagaa atatgttcac
110581 cattgttggt atggcagaat gtagcatggt attaactcaa atctgatctg ccctactggg
110641 ccaggattca agattacttc cattaaaacc ttttctcacc gcctcatgct aaaccagttt
110701 ctctcattgc tatactgtta tagcaattgc tatctatgta gttttgcag tatcattgcc
110761 ttgtgatata tattacttta attattatta tacttaacat ttttatttac ttttgtgtt
110821 agtattttat tctgtcttct ccttagatag taaccttctt aagaaaatat atatgctaag
110881 tgttttactg gtttaatatg cttagactac tcatctacct caatacttcc ttggagatct
110941 cctcctcagt cacacagagc tcaggactta tatttccttg gaactcctgt tagggtccaa
111001 tgtacatgaa attccctaga cagacagaca gtcagttata tggcttgatt tcaaagtttc
111061 aaaatgattt aatggactat caagtagttt attaggagaa cagttattat actcttctaa
111121 aaataaagac tttaagcaat aaagatgtat atgtatataa aatggctggg ttattcctag
111181 aagtaccttt cttagaattt agttaaattt aatatccaag atactatctt ttcaaccctg
111241 agattgtgaa aagtaacttc tatcaatata aacttactta catttgtatt gtgttagtgt
111301 gttacagtat aatctagaac aatgtgtctt tctatatgat atatgacatt ttaatgccta
111361 aaaaaactga tatgtcttag atgattctag tcaggattta cttctagaat agattaaaat
111421 tctatttgag gagagtcaaa ttaattatcg aattctcagt tgttattatt gctgttttat
111481 ttttagtgaa acagattagt cttaatgtaa acacttgaga aataaattga tggtcaacct
111541 aaaatgtaaa aaagaaatta atagaaaatt taaagagcaa caaagctctg acatttaaaa
111601 gaaatgaagt acaaatctct agggaccttaa aagatcatct aataatttcc tcatttcta
111661 gataaataaa ctgagagacc ccgaggataa atgatttgct caaagtcaaa tatctactta
111721 atataggaaa tttaatttca ttctcagtct gttaacatgc aacttttcaa tatagcatgt
111781 tatttcatgc tatcagaatt cacaaggtac caatttaatt actacagagt acttatagaa
111841 tcatttaaaa tataataaaa ttgtatgata gagattatat gcaataaaac attaacaaaa
111901 tgctaaaata cgagacatat tgcaataaag tatttataaa attgatattt atatgttttt
111961 atatcttaaa gctgtgtctg taaactgatg gctaacaaaa ctaggatttt ggtcacttct
112021 aaaatggaac atttaaagaa agctgacaaa atattaattt tgcatgaagg tagcagctat
112081 ttttatggga cattttcaga actccaaaat ctacagccag actttagctc aaaactcatg
112141 ggatgtgatt ctttcgacca atttagtgca gaagaagaa attcaatcct aactgagacc
112201 ttacaccgtt tctcattaga aggagatgct cctgtctcct ggacagaaac aaaaaaacaa
112261 tcttttaaac agactggaga gtttggggaa aaaaggaaga attctattct caatccaatc
112321 aactctatac gaaaattttc cattgtgcaa aagactccct tacaaatgaa tggcatcgaa
112381 gaggattctg atgagccttt agagagaagg ctgtccttag taccagattc tgagcaggga
112441 gaggcgatac tgcctcgcat cagcgtgatc agcactggcc ccacgcttca ggcacgaagg
112501 aggcagtctg tcctgaacct gatgacacac tcagttaacc aaggtcagaa cattcaccga
112561 aagacaacag catccacacg aaaagtgtca ctggcccctc aggcaaactt gactgaactg
112621 gatatatatt caagaaggtt atctcaagaa actggcttgg aaataagtga agaaattaac
112681 gaagaagact taaggtagg tatacatcgc ttgggggtat ttcaccccac agaatgcaat
112741 tgagtagaat gcaatatgta gcatgtaaca aaatttacta aaatcatagg attaggataa
112801 ggtgtatctt aaaactcaga aagtatgaag ttcattaatt atacaagcaa cgttaaaatg
112861 taaaataaca aatgatttct ttttgcaatg gacatatctc ttcccataaa atgggaaagg
112921 atttagtttt tggtcctcta ctaagccagt gataactgtg actataagtt agaaagcatt
112981 tgctttatta ccatcttgaa ccctctgtgg gaagaggtgc agtataaata actgtataaa
113041 taaatagtag cttcattat ttatagctcg caaaataatc tgtatggaag tagcatatat
```

FIG. 1 (cont.) (SEQ ID NO: 1)

```
113101  aaggtatata aacatttagc ctcttgatag gactaactca cattctggtt tgtatatcag
113161  tcttgcctga atttagctag tgtgggcttt tttttatctt gtgagtttgc tttatacatt
113221  gggtttctga aaagatttct tttagagaat gtatataagc ttaacatgta ctagtgccaa
113281  tcttcagaca gaaattttgt tctattaggt tttaagaata aaagcatttt attttttaaaa
113341  caggaaataa tataaaaagg agagttttg ttgttttagt agaaaactta atgccttgga
113401  tgaaatgagc catgggcagg gttgtaatga attgatatgt ttaatagtat agatcatttg
113461  tgaataatat gacctttgac aagacacaag ccattaacat ctgtaggcag aagtttcctt
113521  ctttgtaaaa tgagggaata aaatagatcc ctaaagtgtg taatttagt atttctaaac
113581  tttatgaagg tttcctaaat gataattcat ctatatagtg tttttttgtg tgtttgtttg
113641  tttgtttgtt tgagatggag tctcgctctg tcacctaggc tggagtgcaa tggtgcaacc
113701  tcggctcact gcaacctctg cctcctgggt tcaagctaat ctcctgcctc agcctcctga
113761  gtagctgaga ttacaggcat gcaccaccat gccgagctaa ttttgtatt tttagtagag
113821  aaggggtttc atcatgttga ccaggctggt cttgaactcc tgaccttgtg atccaccac
113881  ctcagcctcc caaagtgctg gtattacagg cgtgtgccac cacgtccagc ctgagccact
113941  gcgcccagcc catctatata gtttaatatc aatctaaatg aatttctcag tcctgagcct
114001  aaaaatttag ttgtaaagaa tgatatcctt gactaataat agtttctatt aatggattgc
114061  atctagtgct aggtggcata tatttagtcc ccacaactac cctggaaggt atttaaaatt
114121  tttcacattt gcagataagg aaactaaagt tcagagttcg gcaacatgct tgaattcaag
114181  cagctcctag gatgttaatg gtggaggttg ggttcaaatc cagatctgtc tgactcaaaa
114241  aatgcatact cctaaccagt gcactatatc ccaattccat aggagccctt ctttgtgatt
114301  catagcactt tcccatgagt tttgttgatt ttgtgagaaa caaaactctt tttcctttgg
114361  actgtctgga atctctcttt ttcaaatttt tgaaatgtat ttctatgcca aaagacaaag
114421  atttctagag gaatatgcct aggatgagaa ttatgtaatt taaatcacag ctggaaagag
114481  agaaagtcct aagttactaa gaatgttca aacacaaatg agctttcagt ctattggaag
114541  acctttatag ctagaagtat actgaactgt acttgtccat ggaccctga agaaacaggt
114601  taaatcaaag agagttctgg gaaacttcat ttagatggta tcattcattt gataaaaggt
114661  atgccactgt taagccttta atggtaaaat tgtccaataa taatacagtt atataatcag
114721  tgatacattt ttagaatttt gaaaattac gatgtttctc atttttaata aagctgtgtt
114781  gctccagtag acattattct ggctatagaa tgacatcata catggcattt ataatgattt
114841  atatttgtta aaatacactt agattcaagt aatactattc ttttatttc atatattaaa
114901  aataaaacca caatggtggc atgaaactgt actgtcttat tgtaatagcc ataattcttt
114961  tattcaggag tgctttttg atgatatgga gagcatacca gcagtgacta catggaacac
115021  ataccttcga tatattactg tccacaagag cttaattttt gtgctaattt ggtgcttagt
115081  aattttttctg gcagaggtaa gaatgttcta ttgtaaagta ttactggatt taaagttaaa
115141  ttaagatagt ttggggatgt atacatatat atgcacacac ataaatatgt atatatacac
115201  atgtatacat gtataagtat gcatatatac acacatatat cactatatgt atatatgtat
115261  atattacata tatttgtgat tttacagtat ataatggtat agattcatat agttcttagc
115321  ttctgaaaaa tcaacaagta gaaccactac tgatatttta ttatttcata ttacatataa
115381  aatatatttta aatacaaata taagaagagt ttttaataga ttttttaataa taaaggttaa
115441  gagattcgaa agctcaaagt agaaggcttt tatttggatt gaaattaaac aattagaatc
115501  actgttgata ttttattatt tcatattaca tataaaatat atttaaatat aaagataaga
115561  gttttttaata gattttataa taaatgttaa gagattaaaa aactgaaaat agaaggcttt
115621  tatttggatt gaaattaaag gccaggcatg gtggttcatg cctgtaatcc cagaatttta
115681  ggagactgag tggggaggat tgcttgagcc caggggtcaa gaccagcctg gcaacacag
115741  tgagacaccg tatctacaaa ataattaaaa aattagctgg catggtggt gtgtgcctgt
115801  atgctaccat taactaagga ggctgaggtg ggagaatcgc ttgagcctgg gaggtcaagg
115861  ctgccctgaa ctgtgattgt gccattgcat tccagcctgg gtgccagaga gagaccctat
115921  ctctaaataa ataaataagt aaataaataa acagcaacaa caaaaacact caaagcaaat
115981  ctgtactaaa ttttgaattc attcctgagag gtgacagcat gctggcagtc ctggcagccc
116041  tcgctcactc tcagggcctc cttgaccttg acgcccactc tggctgtgcg tgaggagccc
116101  ttcagccctc ccctgcactg tgggagcccc tttctgggct ggccaaggcc agagccggct
116161  ccctcagctt gcgggaggt gtggagggag aggcgctggg ggaactgggg ctgcgggtgc
116221  cttgtgggcc agcgcgagtt ctgggtgggt gtgggctggg cagcccgc actcggagca
116281  gccggccggc ccgcgagcc ccaggcagtg aggggcttag cacctgggcc agcagctgct
116341  gtactcgatt tctcactggg ccttagctgc ctccctgcgg ggcagggctc gggacctgca
116401  gcctgccatg cctgagcctc cccaacct gccgctgcag tgggctcctg cgtggcccaa
116461  gcctcctgac gagcaccgcc ccctgctcca cggcacccag tccatagac cgcccaaggg
116521  ctgaggagtg tgggtgcagg gcgcagggct ggcaggcagc tccacctgca gccccagtgc
116581  gggatccact gggtgaagcc agctgggctt ctgagtctgg tggggacttg gaggatcttt
```

FIG. 1 (cont.) (SEQ ID NO: 1)

```
116641 atgtctagct aagggattgt aaatacacca atcagcactc tgtatctagc tcaaggtttg
116701 taaacacacc aatcagcacc ctgtgtctag ctcagggttt gtgaatgcac caatcagcac
116761 tctgtatcta gttaatctgg tggagacttg gagaaccttt atgtctagct aagggattgt
116821 aaatatacca atgtgcactc tgtatctagc tcaaggtttg taaatacacc aatcagcact
116881 ctctgtctag ctcagggttt gtaaatacac caatggacac tttgtatcta gctaatctag
116941 tgaggaggtg gagaactttt gtgtctagct cagggattgt aaacgcacca atcagcaccc
117001 tgtcaaaacg gaccaatcag ctctctgtaa aaccaatctg ctgtctgtaa aatggaccaa
117061 tcagcaggat gtgggtgggg ccagataaga gaataaaagc aggctgcctg agccagaagt
117121 ggcaacctgc tggggtctgt agaagctttg ttcttttgtt ctttgcaata aattttgcta
117181 ctgctcactt tttgggtccg cattgcgttt atgagctgtg acactcactg ggaaggtctg
117241 cagcttcact cctgaagcca gcgagatcac gaacccacca gaagaaagaa actcctaaca
117301 catccgaaca tcagaaggaa caaactcagg acacgcggcc tttaagaact ataacactca
117361 ctgcaagggt ccttggcttc attctcgaag tcagtgagac caagaaccca ccaattccgg
117421 acacaatttg actgcagaaa atggatgtcc aaccctgtgg tttccctggg ccacattgga
117481 agaagaaagg agttgtcttg gccacacat aaaatacact tactatagca gatgagctaa
117541 agaaaagaaa aagtccatg cgtaatcttt gtgatatgtg ccaccaccaa taagcaaaat
117601 tgttctctta ttcaaaggt tggacacagc tgctctagat attttattat taaatatgca
117661 ggcaattact gtttaaatga agatttcctc acagaatgag attaaaagta tatattagtg
117721 gcttagcatt cattttagac aaccatttta gagattcaaa tcacacactt gcttacagaa
117781 attttgttgt cttcaatgtc ccattgtgg tttctttacc aagcctctac tgttcttcac
117841 atccaccaagt taaaaaaaaa aaggggcgg ggggcagaa tgaaaattgc atggtaggcc
117901 acaagttcag atcctcatcg acacaagagg tgcctgaagc agtggatgag gcttttctat
117961 ggatcatgag cagccacata aatgcttaaa agggcctggc agggagcatc agtgggtgat
118021 gtggctggga ggctgaatgg agagcatttg ttcttcagtt atctatagaa ggcagctgtc
118081 actcagcacc agctaagggc ttcccatgga ggaactgggg atcaggtttc ccagatcttt
118141 ttatgtaaca ggataagaca gagatccagc ttttttttggg taattatttc ctattttaaa
118201 atacgggtag ttgattaaat aaaaacaaac gaatgaacac catatgggca caacaaaaca
118261 catctgtggc ttggattcag cttgtgaatg attactgcag atatttattc tagaggacac
118321 ccctgggtat gtcctaatat aaaacctaaa tctaaactca agtcccatgc taccttcaga
118381 gaataaatga cccagaaaaa gaaccacctc tcctaaggaa gtataaattt gtaaataact
118441 gagacccaaa cttacaactg tacattttc ttattgttgg gctgttgcta acctcaatta
118501 agaaggcttg atgatatttg taaagtgtca tcactccacc atggtccagt aacatctgat
118561 cactccacca tggtccagta acatctgaat ggtcaagaaa tatctaaacg tatgtaccaa
118621 aaatttgtgt atactactgt accaataaac catttgtttc catttgatct ctgagtgtgg
118681 taatacatgt tatttgccct gctgttgtaa ataaacaaac caaatggagg cttgatgcaa
118741 gatgcagtgt agcatagtgc caactctgga ctccgactac tcagggtgta aattctaact
118801 ctgttctatt aacaccatga aactgagcaa gttagttaaa actcgctggg cccatttttct
118861 catttataca atggagattt taatagtaca gctacatagg ccattttgtg gtttaaaata
118921 catcatgatt atgaaacact taatgtaggg cttgctacat aatgagcaag gtttgttgct
118981 gttatcatta atatccttaa ttctcattat tataaaactt gagatagtat gaggtgaaca
119041 agttcataac agcaatataa tgaaaatttt aataattcct tttatacttt aacaaaaata
119101 cgagattggg taatttatta ttttttacatg agtaataaat attgcattaa aatatatttta
119161 aaatttacca cattaatgtc tgccagtcat gccaaatgac caacatgaat gtgaataaaa
119221 ctcagtctgt gccatttaa tcttaaccaa ccctttataa ttgttaatga tttgaacctc
119281 tgccttgaaa gatcacatta cttgattgtc ttcaacttat ctgaatgtgg tagtgatttc
119341 tgtaaattta taggaccttt gtctcatgca gctccatgga gttgaactta tgcacctta
119401 aaatggtata tacttaatta attaagtgtt gatctgcttc acatgtgtat aatattatta
119461 gctcactaaa ccaagaaaac agtggtcctt tagggaaaga aactaaatta aacagagaa
119521 tataaatacc atataaatat ctattattta ttgaactgtc acaattattg caaaaaatta
119581 cctttagtg gacaaaacaa ttgatattgc ccttttctgg aaagaaata atgtaatata
119641 tgatgaatag ttttggccag tatcctctag accttgccag ttaactggct ctcaaatttt
119701 tgaataataa aaacttggtg atagtagaaa aatagtaatt ttttaaaagt atgtgcacaa
119761 ttatacaact aaacaattca ttccagtg ttcacaattc tattgccttc tttgaatcaa
119821 aatttacata gttttctttt tagactaagc tcctttatga taccagtgtg cccatttctc
119881 attaccattg aaatgtctca tgagcatgtc acattctggt acaactgcta atccaggatg
119941 acagttagt tctttttaaat ccaattgaga gcctctact catgaccaga gaacctaaag
120001 aaaggttaag atacatttat tccttggtgt aagtgatttg tctatttta gttttcctaa
120061 gggtcatatt tcaatttaga tttttttttta taggttaggt aaaataggct tcccttttgc
120121 aatatgaaat atgtagtctt ttaaaaaatt tcttcaaagc tattaaactg aaaaaaaatt
```

FIG. 1 (cont.) (SEQ ID NO: 1)

```
120181 aatttggtct attcagtttg ttagcactta ccattttgga aagagagtga ctctactttt
120241 gtatttggta acattttccc tactacaggg cagtatcttt tgtaagttct tagatattag
120301 caccaaataa ataggcaaaa aaaatctatt atgttaattc ttagaacccc tgcttggcag
120361 tgcatcattg actagatgga gaagaaatga aaataataca ttaggaagca gtttcctggt
120421 tcttttgaaa caactagag agtcttgttg ttgactggaa tatctgaaga tcctgtttaa
120481 tgctttcatt ctatgattgt taagaatatg tcatagaact gctgtatcct gtttctttat
120541 gtcttcctt ctgtttgttg attagaaatc cctgagtggc tttacattat tagtacagta
120601 gatatgtagt atattcccat aataccactg ctgctattga ctaatagtaa taattttagg
120661 gcagctttat gacagttggt ttatgtttta gggtgtcatt tgacttgtga agcattgaaa
120721 tctgggtatt aagcacactg ttttctatgt ggtatggaat gattcttaaa gccctgagaa
120781 aatggaaaat aaaatatttt ttccttttta ccataatcac ctatgactgt cactctatca
120841 taaactgcat aaactttata acctcaaaac attttggaaa tgaaatgaca gaacttgctt
120901 actcaattgc ttctatatac accaaatatt tttttaaagt attatgttaa gtccttgaaa
120961 atatttgtt ctactcaata gaagcagttt aggttggtag ttctatgtgg aaaccgtgag
121021 gaaataattt tatattatga tgactagacc agtcttgaa catcactttg gttattgttc
121081 cattagtaaa tattataatt atttctgaga tttactcacc ttcaaagaat gttggcaatg
121141 ccagcattat taacactcct ctagttagaa caaagaggaa atgaataac aaaacataat
121201 aatagccaaa taaagagtga cttagaatgt cacccttat ctaggatcct gagtaattcg
121261 attattctta ggaaatacac ttttgtgcta gaacaaagac ttttgaaata gctaatttct
121321 gggtttcttt tcattttgaa ttaacttgaa tttcaaggaa acaagggtag ttttttacaga
121381 tacagtgcat agaagctctg tgtacaatga agaaagtag gaaagtgaga aaaatgccat
121441 tagattttc atcgttatac tatctgatat gtgaatttaa ctaaaactta tatacctcat
121501 tatagtactt cctaatgtaa tttcttaatt taagtgttcc ccataaggtt tttttttata
121561 taaacttaag tactgttaaa tatttaaggc aaattcaggt ataaaataag acttgttgat
121621 atcttattcc aagcatattt gtttctctcc tatttatttt tattctgtgt tcatttccaa
121681 aattgtttta ctcacaactg tttgttttt ctgtttcatt ctgtggtaaa ggtatcattt
121741 ggctaattgt ataatttcag tgtcatttct aatattccaa ttgtgatagt atcaacacaa
121801 gattaaattt ctctacatgg tttatgagaa tggaatgcca aattgaaata gaacagagca
121861 cagatgatct aaatataaaa agaactacaa aaatcacagt tgtttaaaaa ggttttttgt
121921 ttgtttatat atggtgcaga acatttgttc cttagccaaa tgtttccacc ttgagaaagc
121981 tatagagatt ctatgtagtc ctagtaccaa taatatgttt taacctgaat gtaccttatc
122041 tttattcata aactgtgact ttttacactg ctgaaacttt tttttttaag acaatctcac
122101 tctgtcgtcc agtctggagt gcagcagtgg tgtgatcttg gctcactgca acctctacct
122161 tctgtgttca agcaattctg gtgcctcggc cacctgagta gttgggatca caggtgtaca
122221 ccaccaggcc tggctaatag ttttgatat ttctagtaga gatgagtttt gccacattgg
122281 ccaggctggc ctgaaactcc tggcctcaag tgatctgcct gccttggcct cccaaagtgt
122341 tggtattcca agtgtgagcc actgtgcctg gctgaaact cataattcat ttccattaat
122401 attaatctca ccttttccaa taattaattg atttcacaag tattagtccc ctataatcat
122461 tgaatggcta ataaaattat ttatagacaa cagattaatt atctgccagc agtctgagat
122521 tagtttcttt aaaaaatgtt tattatttaa aacattcagc tgtgatcttg gctttcttgt
122581 gaggttcaat agtttctatt gagtaaagga gagaaatggc agagaattta cttcagtgaa
122641 atttgaattc cattaactta atgtggtctc atcacaaata atagtactta gaacacctag
122701 tacagctgct ggacccagga acacaaagca aaggaagatg aaattgtgtg taccttgata
122761 ttggtacaca catcaaatgg tgtgatgtga atttagatgt gggcatggga ggaataggtg
122821 aagatgttag aaaaaaaatc aactgtgtct tgttccattc caggtggctg cttctttggt
122881 tgtgctgtgg ctccttggaa agtgagtatt ccatgtccta ttgtgtagat tgtgttttat
122941 ttctgttgat taaatattgt aatccactat gtttgtatgt attgtaatcc acttttgtttc
123001 atttctccca agcattatgg tagtggaaag ataaggtttt ttgtttaaat gatgaccatt
123061 agttgggtga ggtgacacat tcctgtagtc ctagctcctc cacaggctga cgcaggagga
123121 tcacttgagc ccaggagttc agggctgtag tgttgtatca ttgtgagtag ccaccgcact
123181 ccagcctgga caatatagtg agatcctata tctaaaataa aataaaataa aatgaataaa
123241 ttgtgagcat gtgcagctcc tgcagtttct aaagaatata gttctgttca gtttctgtga
123301 aacacaataa aaatatttga aataacatta catatttagg gttttcttca aatttttaa
123361 tttaataaag aacaactcaa tctctatcaa tagtgagaaa acatatctat ttcttgcaa
123421 taatagtatg attttgaggt taagggtgca tgctcttcta atgcaaaata ttgtatttat
123481 ttagactcaa gtttagttcc atttacatgt attggaaatt cagtaagtaa ctttggctgc
123541 caaataacga tttcctattt gctttacagc actcctcttc aagacaaagg gaatagtact
123601 catagtagaa ataacagcta tgcagtgatt atcaccagca ccagttcgta ttatgtgttt
123661 tacatttacg tgggagtagc cgacactttg cttgctatgg gattcttcag aggtctacca
```

FIG. 1 (cont.) (SEQ ID NO: 1)

```
123721 ctggtgcata ctctaatcac agtgtcgaaa attttacacc acaaaatgtt acattctgtt
123781 cttcaagcac ctatgtcaac cctcaacacg ttgaaagcag gtactttact aggtctaaga
123841 aatgaaactg ctgatccacc atcaataggg cctgtggttt tgttggtttt ctaatggcag
123901 tgctggcttt tgcacagagg catgtgccct ttgttgaacc tccatttgac tggcatgcac
123961 atgtctcaga tattataggt tatcatatat tgttgctcct aatatttctg tgttagataa
124021 ttagagtagc ttggtttgta agaatgtgat gttggtggga ctgtagcaga acaagaaggc
124081 ccttatgggt cagtcatacc tctcttttca aatatttggt ctagctctct tctgggcatc
124141 ttgttgccaa tatatagtat tgctcaaaag ggcaggagat ttgaagtgat caaggaaaat
124201 atattttttc tattgattaa gtcttttgat ggggtagaat aatctaattt catgtaactg
124261 ctcaaagtta tatggtaggg ggatcccaaa tgtattttaa aactatttttt atatcatcat
124321 atttgaagta atagaaagtc agagtagcag aataaaggta ctaaaaattt taaaaactaa
124381 taaggtactt tgaaagaaat caattatgtt gattcctcat taaacaaatt tgcacttaaa
124441 gactgaggtt aataaggatt tccccaagtt ttttcatagc aacctgtgag cactttctct
124501 gttgaggcat ttatggtatg aaagatgag taaggcacag ttcttgccct ggagaaggtc
124561 acaggtgaga ggaggagttg acacagaaac atttgatata aagcaaggaa taaattccaa
124621 gactaaaatt ttcagaaatc taaaaaactc aagataagaa aaaccatta tattttctgg
124681 gtaacaaaat ttcagtgtta ttaacatgta ggaagatctt gatatttatt ctgaagccca
124741 tgtgtgttgc tgaaatattg ccgcatttgc atatactcat caccatcctc tgttttggag
124801 ctaagaattt tagactcaag atgtctaatt aagttgatcc attgatttta ttttttatgg
124861 aaatctgaga cccacagaag gcagggatt tgcccacatt tctagaagag tcagacatga
124921 gcgatgaggc acagtggaaa gaacatgagc attgcctgag ctctgagttg gcgctataag
124981 agcagtgatc atgggcaagt gactcttctg agccttggcc tcctcacctg ttaagtgaag
125041 aaaagaatat tcagaagat ctttgtgaga atgaaacaag gcaatttact tgcctgctac
125101 atagccaatg ggaaatcaat ataagttccc cgtggttccc ttctgtgggg ttttgttccc
125161 acagagggtg cactggccat tccacttctt cttttccaag ctcctcattc cctttaacgc
125221 tgttcatagt tggttccaaa ccatttgaaa tataataagc accaggatgg ttttttcttt
125281 ccaccaaagc aaatttcatt ttctaaacac tgtttataaa tatcaatggc tatttttca
125341 attttttgatt atcatgaaaa tatacaaata tgtttaatta aatatgctaa agaatgtatt
125401 aataaatatg tattaaataa ttcctacata taaggccttt ttgcttgggg tatgggtgat
125461 acaaaataaa tgtggcatga acccactgac ctctagcaat ttataaccta gaaaaagagt
125521 tatgatatgt ttataagttc ctgtgatata agacatgcat atagtcatta taacagaggt
125581 gcaaacaaga tgtatcaagt atgtccagag gaggaagaga ttaatcccag ctggaggaaa
125641 cactgatgct ttcttgcagc aggggcattt gagttgagaa agggaggaaa catagatttt
125701 gacaatgaga gctgagggga aaggggtttc aggtggaggg aaccgcatgt ggaaagcagg
125761 gaggtaggaa agtgtagagt gtgtttaaag aatagaccag tttggctgaa acaggatatt
125821 tgagcagagg aagcttgtac taggtaggtg ggttgaggcc aaattatgca aggcattaaa
125881 tattaaacta ggaattttgg actttatcct gcagtttatg gggggtaaat gataagattc
125941 aatatcactt tatttgtaca gtattatgtt acattttatc taattgtttg tttaattcct
126001 gtctagacaa tgaattcctc aagggcaagg agcatggctt attcacctca gtaatttcag
126061 tgcctagcat tgtgcctggt acaaagtgga cacttgtata taacctttt taattgaagc
126121 aacaagttgt caaccttaca aatgtgaatc cgtgattcag atgacaggtt gaaatgtaga
126181 ttgtctgcga agagggcaga aagagagtat gacaaaggag gacaagacag tggggcaggc
126241 agggagagag agcagccagg gtttcggtag aggtatgtca aaaaggtatg gaagtcagag
126301 gagaaggaga cccctatgtt atagaataca aatggaaggg aaatgatgac aacagtaagt
126361 tgtcattaaa tgcaaggttg caaagtaag attgtaaagc aggatgagta cccacctatt
126421 cctgacataa tttatagtaa aagctatttc agagaaattg gtcgttactt gaatcttaca
126481 agaatctgaa acttttaaaa aggtttaaaa gtaaaagaca ataacttgaa cacataatta
126541 tttagaatgt ttggaaagaa acaaaaattt ctaagtctat ctgattctat ttgctaattc
126601 ttatttgggt tctgaatgcg tctactgtga tccaaactta gtattgaata tattgatata
126661 tcttaaaaa attagtgttt tttgaggaat ttgtcatctt gtatattata ggtgggattc
126721 ttaatagatt ctccaaagat atagcaattt tggatgacct tctgcctctt accatatttg
126781 acttcatcca ggtatgtaaa aataagtacc gttaagtatg tctgtattat taaaaaaaca
126841 ataacaaaag caaatgtgat tttgttttca tttttatttt gattgagggt tgaagtcctg
126901 tctattgcat taattttgta attatccaaa gccttcaaaa tagacataag tttagtaaat
126961 tcaataataa gtcagaactg cttacctggc ccaaacctga ggcaatccca catttagatg
127021 taatagctgt ctacttggga gtgatttgag aggcacaaag gaccatcttt cccaaaatca
127081 ctggccacaa agtgtgacat tttggcattg gcatcactat tgatggaag ccaacctccc
127141 cccaaaaggc ctgtattaga atgaagatgg attccctggg tgggttacac ttgaaactag
127201 cctcacccat gaacactttg gcacagatta gctagcccat tcccccacag taaggaccat
```

```
127261 aaggaaggga cagaagcaaa gataagtttt agaacaaaag agagggaaa gaaaaatct
127321 agggttttat gagggctgtc cctgagtgat agatgtgaat aggcctccag ggcaggctgg
127381 ctcagaggct gactctttgg gttggggtga ctgattggtg gtgaggatgg agaagaaaag
127441 gggagtggag gaggtgaaag tgaccttggg acattaggtc tccataagtg acaggattta
127501 aggagtgttg taagctgtgg ttgttggacc aggtttaagc acagcttcct gagcttcctg
127561 actggtttag gtcaagctcc agagagcaaa tgccacagtc tcagtgatct ccttggagaa
127621 acagttggaa taggatgttg cccatgttgg gatgagtcat tgtccgctct tgctctttcc
127681 ctaccctgc aaaataataa tactgtattt gattgaacat ataaaacaaa agaaggatta
127741 tcacataagt atgtatatat aaccaacatt ggcaggtgca gaaaaccag actgtcagtt
127801 tgcctcatct gaaatgattg acacaaacaa atatatttac tgtcccaagt gaactttggc
127861 attttggata tccttcagtt gttctgttta aagatataac ttagaagcag ctgatggaat
127921 atttaaatcc atgcgttgaa ttcatgcatt caaagaaaca tgtcctgagt cactaaatgc
127981 tgacatttgt ttttcatgtt aagagtgtaa ataactggtc ccaaatataa tattattaca
128041 tcagataaaa actggaatgt gaacctctta acttgattgt gaaagtattt gccaatggtg
128101 cctcttgata attatttgag gctcacttca gaactcctct ggaagggtta attttaaat
128161 agtcatttta taaattaaca ttttgacat atgtgatggc tctcaaattt ttttcttttat
128221 gccagtttga atcatttctg ctcaattttt tttttaatt gggatggagt ctcactctgt
128281 tgcccaggct ggagtgcagt gatgcaatct tggctgactg caacctccac ctcctcggtt
128341 caagcgattc tctcgcatca gcctccagag tagctgggat tacaggcgcg caccaccatg
128401 cctggataat ttttgtatta ttactagaga tggggtttca ccacgttggc caggctggtc
128461 ttgaactcct gaactcctga cctcaagtga tccacctgcc tcagcctctt aaagagctgg
128521 aattataggt gtgagccact gcaccaggcc ctgttcaact tttaatgcta agattcattt
128581 gttgttgttt cacaagtgat taggcagagg tctttatat taatttaccc attttatttg
128641 taagagagtc tcatattaag gaagcataat atatgacaat ccaaatacag tacaaatttg
128701 gttaattttg attttgttaa ataattaatc acagggtcc ttcaaattgt gagctcctct
128761 ggttatactt atgttttacc tctggttata cttaatttca aacaaatgaa atttcattct
128821 attcatgata tttcagaagc agatctgttg cacaaaataa agcataccta taaatttct
128881 ttttttaaaa aaagtctct gttcactcta ttttctatta ttttctctt tttaaattt
128941 gaattttatt gtggcaagtc cacttaacat gagatttacc ctcttaacag attttatgt
129001 gtaaaataca atattgttca ccatgggtaa atgttgcaca gcagatctct ggaacttatt
129061 cattttgcac tactgaaatt ttatacctgt tgattagtat ctccccattt ccctctctcc
129121 cctgtcctgt tacccatggt tctgttcttt gcttctttga gtttgagtat tttgatacct
129181 catgtaatct tcattctatt ttctaacttt gacaatgttc tgacaaattt gctttccgga
129241 ttggagcact gtatagtgaa aattgaaaat cttggttatt ttctacagat tcccactatt
129301 ttaccttgag cagacactta tcttgaaggg tctcagattt gtcacttgta gaatggggaa
129361 tataaacctg ataatggtcc ctttcagttc taaagttata tcagttgaaa atacatgtgt
129421 cacttatggt aacgggtaga gaactggctc actgaacagc atatggatat tataaagtgg
129481 tttttttttaa tcctttctgc agacagttac tttatacttt attcaaatgg attattgtga
129541 agtacatgtt agcggacttt gtacctttta aaaatgtatg tatttggtgt aatgtagaaa
129601 tatagaaatt tattaagtat gatttatttc aatgttaagc atgagaaaat atgctccgaa
129661 aggttagata gcttgcctaa atgacaagct tgtatttcaa gcagaacttt ctgaatcaaa
129721 agactccaag acgaatgccc agctttcaaa aactgtctaa ccaaaataaa tcctaagatt
129781 caccttcata ctaaaattat ttaaaaatag tttattttaa attaatattc acttaaaatg
129841 tatttatcat gcaatacttt aaagtgtctg ggaaatgaaa atatccaaag atcaaagaac
129901 accatgtttt caaacttcaa aaatgttatc agtgacctaa acaattttta aaatttttcat
129961 agagcctatg aaaaatgtac ttgcaaatgg ctactttctg actaggaata gaatggggag
130021 agtatttagt ccaacaatga tagactggat taagaaaatg tggcacatat acaccatgga
130081 acactatgca gccataaaaa atgatgagtt catgtccttt gtagggacat ggatgaaatt
130141 ggaaaacatc attctcagta aactatcgca agaacaaaaa accaacacc gcatattctc
130201 actcataggt gggaattgaa caatgagatc acatggacac aggaaggga atatcacact
130261 ctggggactg ttgtggggtg gggggagggg ggagggatag cactgggaga tatacctaat
130321 gctagatgac gagttagtgg gtgcagtgca ccagcatggc acatgtatac atatgtaact
130381 aacctgcaca atgtgcacat gtaccctaaa acttaaagta taataaaaaa aataaaaaa
130441 agtttgaggt gtttaaagta tgcaaaaaaa aaaagaaa taaatcactg acacactttg
130501 tccactttgc aatgtgaaaa tgtttactca ccaacatgtt ttctttgatc ttacagttgt
130561 tattaattgt gattggagct atagcagttg tcgcagtttt acaaccctac atctttgttg
130621 caacagtgcc agtgatagtg gcttttatta tgttgagagc atatttcctc caaacctcac
130681 agcaactcaa acaactggaa tctgaaggta tgacagtgaa tgtgcgatac tcatcttgta
130741 aaaagctat aagagctatt tgagattctt tattgttaat ctacttaaaa aaaattctgc
```

FIG. 1 (cont.) (SEQ ID NO: 1)

```
130801 ttttaaactt tacatcata taacaataat ttttttctac atgcatgtgt atataaaagg
130861 aaactatatt acaaagtaca catggatttt ttttcttaat taatgaccat gtgacttcat
130921 tttggtttta aaataggtat atagaatctt accacagttg gtgtacagga cattcattta
130981 taataaactt atatcagtca aattaaacaa ggatagtgct gctattacta aaggtttctc
131041 tgggttccca aatgatactt gaccaaattt gtccctttgg cttgttgtct tcagacaccc
131101 tttcttcatg tgttggagct gccattcgt gtgccccaa actctacttg agctgttagg
131161 gaatcacatt ttgcagtgac agccttagtg tgggtgcatt ttcaggcaat acttttcag
131221 tatatttctg ctttgtagat tattagctaa atcaagtcac ataaacttcc ttaatttaga
131281 tacttgaaaa aattgtctta aaagaaaatt ttttagtaa gaattaattt agaattagcc
131341 agaaaactcc cagtggtagc caagaaagag gaataaatat tggtggtaat ttttaagtt
131401 cccatctctg gtagccaagt aaaaaaagag ggtaactcat taataaaata acaaatcata
131461 tctattcaaa gaatggcacc agtgtgaaaa aaagctttt aaccaatgac atttgtgata
131521 tgattattct aatttagtct ttttcaggta caagatatta tgaaattaca ttttgtgttt
131581 atgttatttg caatgttttc tatggaaata tttcacaggc aggagtccaa ttttcactca
131641 tcttgttaca agcttaaaag gactatggac acttcgtgcc ttcggacggc agccttactt
131701 tgaaactctg ttccacaaag ctctgaattt acatactgcc aactggttct tgtacctgtc
131761 aacactgcgc tggttccaaa tgagaataga aatgattttt gtcatcttct tcattgctgt
131821 taccttcatt tccattttaa caacaggtac tatgaactca ttaactttag ctaagcattt
131881 aagtaaaaaa ttttcaatga ataaaatgct gcattctata ggttatcaat ttttgatatc
131941 tttagagttt agtaattaac aaatttgttg gtttattatt gaacaagtga tttctttgaa
132001 tttccattgt tttattgtta aacaataat ttccttgaaa tcggatatat atatatatat
132061 gtatatatat atatatatat atatatatat acatatatat atatagtatt atccctgttt
132121 tcacagtttt aaaaaccgat gcacacagat tgtcagatag caattctgtg attgaagggg
132181 aaatatgtca cctcttcata ctcatattgg tgaagggtcc tagcttcaaa attaatagat
132241 tcctaaagag gggaaatgaa acatccgcat ttacacacac acacacac acacacacag
132301 agttcctctt gtcggtaagt tttgttttt ttaaatctct actagataaa atttgttatc
132361 taattgtgag ttttacacaa agaaaaactg tcacagaaaa gaaagacagt gtcacatttt
132421 tcaaagaaaa aagaagaaaa gaagtgcca tgttttcaa atacaaatgt tctggattga
132481 ttttaggatc tttagtgaaa aacaagtat ttcataataa gtaaaataaa aatctatgta
132541 ggtaaatttg tttctctaat ttaagaattt gaatttctga gtatttatga taagtgttga
132601 aataacttct tatatgtgac agtgaatact ggcagagcaa atgccaaatc aatgccaaat
132661 ctgtaggatc atttgattgt aggaacagaa ttctactcaa accgaaagca ggcatttgct
132721 ggagttacag aaaggcctca tggaacaccg agaaggtggt gccattcgac tcttaaagaa
132781 gctgcaacag gcacaagaga gtcagctgca gctcttcttc ttgagtctat atctgtcctg
132841 ggtccattcc ttttttgtggt tgcttcattc ctttctctct ctgaagactg gtttttctgg
132901 tctaccaggg ctatgccaca ttgactttat gtagtgtctc cattctggcc tcctgaattt
132961 acaggagagt tcctctgtac aaactcaaag tcctggagag aacagaaaac agcttccttt
133021 tggctcaggg gtccaactgc agtctactct gctgctatga ggatagtggg ttcaccacct
133081 ttgttgttct ctcagctagg gcagtgggaa atgactctat gaaaggaata tacatgggca
133141 ggcaaatgta ctaatcctca tcagtactgt aattttaagc aactttaaaa aattcttta
133201 agttatttga aaataagatc aaagaaggct gaattacata aatgaagatt tgttaacaat
133261 taattcaaac caatataaca catgctataa catggttgag tgtgattgag tcttgattta
133321 ttaggggcaa taatcaaaac atttaacaat cattatagta cagaacttac caatcaaatc
133381 agatgctcag ccggagtgga tgttggccac ccagctatta ttatccctgg ctcaattggt
133441 cttcagctgt gttaacttgc aaacattaat taactatcta agccctcat ttcctcaag
133501 tgtaaataga cacaataata ttacctattc cataggtgtg gggtgaatag taaatgtaat
133561 aatttgtcca aaacacttag tatagtgcct ggtccatggt aaatactaaa taaatgttat
133621 ctgacttatt attaaaattt tatcttctca gcttaaccctt cagaacagta atatattggg
133681 gtctagataa atcttgccta tatgaaaata atttaatact acatgcagat atatgctgtg
133741 tatattatgc cttctgttag aggaattgca gaaacaaaaa tttcaattaa taataagatg
133801 aattattct cccaattgta gaatctttg acaatttat catgcattac agatgtaaga
133861 actcttgatt gggacttgat agtctaactt tataataatt taagaacatt cctcttagag
133921 aatttctatg gccataatac tgaacacatg aatttaatt agctgtcctc tttagcccta
133981 aaaaaaaat tactgtaatt taacacttaa gtgttgttct cccaggtac agtaatcttt
134041 tttttttt ttttttttt ttgcatagag ggtaatcttt tctctttcca aatggcagaa
134101 ctgttagttt tctgactgtc cggtgaaatt ctaagtccac ttacttccca atagcatgca
134161 attagcaaag gtcctccttg caaaggcaca gaacacacct aaacatcttg cagatgctgt
134221 ttggacactc ttcccctgct tttggtctct ttgtaaagca gctcatctgg atacaggatc
134281 tcttttcccc attgcccatt ctaatatatg ttaccgttat tacttataga ataatagtag
```

FIG. 1 (cont.) (SEQ ID NO: 1)

```
134341 aagagacaaa tatggtacct acccattacc aacaacacct ccaataccag taacattttt
134401 taaaaagggc aacactttcc taatattcaa tcgctctttg atttaaaatc ctggttgaat
134461 acttactata tgcagagcat tattctatta gtagatgctg tgatgaactg agatttaaaa
134521 attgttaaaa ttagcataaa attgaaatgt aaatttaatg tgatatgtgc cctaggagaa
134581 gtgtgaataa agtcgttcac agaagagaga aataacatga ggttcattta cgtcttttgt
134641 gcatctatag gagaaggaga aggaagagtt ggtattatcc tgactttagc catgaatatc
134701 atgagtacat tgcagtgggc tgtaaactcc agcatagatg tggatagctt ggtaagtctt
134761 atcatctttt taacttttat gaaaaaaatt cagacaagta acaaagtatg agtaatagca
134821 tgaggaagaa ctatataccg tatattgagc ttaagaaata aacattaca gataaattga
134881 gggtcactgt gtatctgtca ttaaatcctt atctcttctt tccttctcat agatagccac
134941 tatgaagatc taatactgca gtgagcattc tttcacctgt ttccttattc aggattttct
135001 aggagaaata cctaggggtt gtattgctgg gtcataggat tcacccatgc ttaactgagt
135061 ggtgccaaat tgtcctcaag tctgttgtac tgatatatat ccccatcaag agagtacaag
135121 aattctcata gctatgtatc ttcaacaaca cttggtgtct ggtagatgtg aagtgattac
135181 taaaaatata gggaagctgc atacataatt attggctttt gctgttctct tacattaatt
135241 tcttattcat gttgattact catttgtcac ctagttttt cttccttaat taaattgtag
135301 gaatttatga attatggatt gatcatcagc tctatacatt tcaaacataa tccctcagtc
135361 agtggcttgg cttatagagt cttttgatga aaagaagctt taagtttaa taaagttcaa
135421 tttattgtct tttcctttat gttttgtgct tttggtatct tgattaagaa ctccttcctt
135481 atattgggtt ctcaaattta gcagcataac attttcatac tattatttaa atttttttca
135541 cattatttag tgatagcacc tttcttattc ctaaagtgtt tatcattgcc ttctgtcttt
135601 ctgcttgata aatattgcca cacatttgta tactttatta gtgtgtacaa agaccacatt
135661 ttagttgtgt tatttctctt gttttggttt tctagaatgc agagccatta atattatagt
135721 aatgcttatg tgctaatacc atatcagggg cacaaatccc attgcagcgg gactgagaaa
135781 ttaaaggaaa tgatgcacat ttactcattt ttgtttaaaa aatcaaatgc atattttca
135841 atcagactat atggttggtc tggatagctt catcattgaa tttttaaagt attttttgtac
135901 tactgtattt aaaattattc attcaccact gcttttgtag atggtttaga acccaagtt
135961 aggaatgact gtgcaacact attattatac tctttttaaa attatacttt ttgcttaagt
136021 ttctttcctt gttctctgag acagtgttca tgttcccaaa ccacacacat ttattcagct
136081 ataaaatttg tatgatcaac tcctgtcaga acaaacatca ttataaaaaa tatctccagg
136141 aaaaagaaaa ccctttaat gctctcttct ggttcatgtg tcttcttatt ttctttaagc
136201 attttcataa cccattgagc tgtaatttaa ttggaacatg atttatacta aagttggttt
136261 ctttacctt aactttttt tttagtttga tcagctctct ttagcttctg tagttcggtc
136321 tttaattcca ttccagtatg cttttggagt tgggtctcat aaatgtatag aaatgtttct
136381 gttgggaaac agcaggagaa tattaaataa atattgtgct tacatctatt taattctttg
136441 cccaactttc tacaactttg actttacatt taagctcctc atgcacttac atgtttcttt
136501 acctaaaaat atcttttcac catggtgtg tacaattcct ttgtccttgc tgtattaatt
136561 ttcttggttt acatagtagc ctctacacat tgatgtcaaa acctctgttt ggtgcatttc
136621 tactctgcgt gttcaatctc catgaaagtt tctgtaaggt attttcattc ctctagtttt
136681 tcacatgtgc atcctggctt tgtgacctgt gctttgatat cgtgcctttc atcttgtggc
136741 attgaaggat ctttgcaagg acctattgtg ttataataca gtctatgaaa aatatcaata
136801 tttgcatttg atcacatttta aaaaatcac attcttttgt ttgaatatca aagctaatat
136861 gtgagtgatt tccctgccaa atagcacaag tagcctttcc tgggtgttta tgggcattta
136921 tctggttaat gattcccatc atagtgctgt cacccatgcc attgctaaac ttatacagta
136981 acttttttgt tttcacctca gcatatgttg agagtaggaa atagatagga ctatgccctc
137041 aaatttttacg tttatatgat gttaatccta aaggtccttg tgacttctga agtaaaaact
137101 cagtgttgtc attttactta ctgaattgtt agctgagttt agagttgagt ttacaatgga
137161 gtaaacaagg tgtttagttt gatgtatgct tttagtcttt cagaaaaaaa tgtttatact
137221 tggaaagaat agtttattta cccatctggc ctagtttaga caaaacaca gagtcaaatg
137281 tcaacagaat tctgaagtta taaaaatgac agtgtggctt ttttttttt taaccttcca
137341 cctggtgctt atgcccaagt gcctagcttt ctttagctct caactaataa aggtaatgtt
137401 tagataacat ttaacgttaa gttgcattgt gtttatgatc acatatctca aatattggta
137461 cacgaaactg tacaacaacc ttttttatta gatttttccta cgaaattcct tattatattc
137521 cctaagatag cttttttccca ccttcttctt ccttctccct tctcaggtgc tccaataatt
137581 ccaacccctg cagccagtga cttattata tcttttttta aaatctaaa aaaaaaatt
137641 gatgcaacca ggaagaattt tctcatttct ctccaccagt tgtaccagcc tactgcacct
137701 ctcctcatgc accaccttct gcctgtgttc ttgctcctat attcaggagc aagtaatatg
137761 caataccttcc ctctttgtgg gatctttctc attagcataa aaatactttc ccttgatctc
137821 cagctactac cccatttctt tgacctacat atagcaaaat atttgagaaa ggaccacttt
```

FIG. 1 (cont.) (SEQ ID NO: 1)

```
137881 ccatcttttc ctcaatctac ttccattttt ttctcaatcc actttcattt cattgttctc
137941 ctcaacccat tctttccaca acctacttca ttttatttcc atcagcccca taactcagga
138001 tcaacatctt gccagagcca atttccttgt ctcccttaac agctccagca gtatttatgc
138061 catggacaaa ttattcttct tgtgatactt tctctcttgc ttccatgaca ctactcccac
138121 ttcattttct ttctacctct ctggctcttc cttggtccct tttcctggcc ccttctctct
138181 ttcagatctc taaacatcag ctatatctca gccctgttct actgacactc tctagctgtt
138241 attttctaaa cccatgtttc agaaaccata tcttgatgaa tcttggaagg ccgaggcagg
138301 cgaattactt gaggtcggga gtttgagacc agcctggcca acgtggtgaa accccatctc
138361 tcctaaaaat acaaaaatta cctggccgtg gtggcatgca cccagctact gagaggctg
138421 aggcacaaga atcgcttgaa cctgggaggt ggaggtttca gtgagccgag atcctgccac
138481 tgcactccag cctgagcaat agaggagact ccgtctcaca cacacacaca cacacacaca
138541 cacaaagaaa ataaaccatc tcttgatgaa tcataaattt gtgtctctag tttagacctc
138601 tatcctgctc tctaaatgat gtatccaact atcatcttga caccatcata tgttcataaa
138661 acataattat agaatatctt tcagtaggct tgacatttta aggcatgagt ttccgttcag
138721 tatctcctta aaatataccc agggtctcag gagactattc aaacaggaca aagcttctat
138781 tctacttact aatgtgtctg gccctatttg gcaggttgga taaaaagtca tctgaacatt
138841 gtcactttat gaataatata gtttaatagt ttgtgaatca ccctgcaat ttaaaaaata
138901 gtaaaattat cagaatctaa tttaataatt cctattggaa cacccatgt tagggatt
138961 ccagttattt caattgatat ctcaatgttt taaagattgt ttattctat tactaattca
139021 ctctttattt taacataaat tgtggctatc tatctctatt catttcaatt atatttctca
139081 taccattcta tagatggggt gaaagaaaaa gtgttaattt tttaaaactc catacctcaa
139141 atactatatg aatttatagt tgttattgct aaagcaatta tcttacatct tttcctccaa
139201 aacaaagtta tgtgctggtt tattttcttt gtactcataa gatgccttcc attttttagta
139261 acataagtct tgtctttctc ctattcttag ctacttaagc attatgtagc ttaaataagc
139321 actaaagatt cctatctgta tgaaaaaata aagattaaat aaataagatc tagaagggt
139381 gacaaggtga tgcttcaaaa tgaaccatac caagccatct agcgattgat aaattactca
139441 cactcataat cacattgttg gaagaagcc attgacaatt cagttgttt cacaactgtc
139501 tatcacatag tgagcacaac taaagacta cttttgtct tttactgctt gttttgttga
139561 tcaagtgact gattgtacaa tgaccaacaa gaagtctgat gtgtagagaa aaggggaacc
139621 tggcttttct gccttactcc tgatgcctaa ttctgagcat gtgaatatta ttctgtttct
139681 ttaattctcc aagtgaagca gcagataaac catccttgtt tccattagct gtctaccctg
139741 ttcaactgtg tgtttctaat aacataagaa taagaaagcc accagggtga gcagggaagg
139801 caatgagtct gcaaggcttg tggatagatt tctgttagtg aggctctaga aagttcttcc
139861 aagattgatg caatctgaga agagtttct gtcaatacaa actccctggg tttctccttt
139921 gtcctttac tgcctgtgtt tgttttgggt tccagtaaag atcaagtgac tgattgtacc
139981 atgaccaaca agaagcctga tgtgtggaga aaaggggaac ctggcttttc tgcattactc
140041 ctaatgccta attttcttgt actgaaagta gtttttgctg taagaatctg aggggaggag
140101 tcatttcttc aatttttttt tttggtctcc ttttaatggt ttcttgatca tgtctatcct
140161 tattttctg ttttcacaaa tttttgtggt atattttcct ctcatgacct ctgtctcaag
140221 acttctttcc atccatctct tctcatttca tcctgtagag tgtctgtggt aagagcctg
140281 cattctactc tggccttgcc atgtgtggcc ttgggcaagt cctagcctcc ttgagggtct
140341 tattttctc atttgtaaaa tgaaacagtt tgatgagaag ttttctaagg ttccttcaag
140401 ctttgacaat ctctctcttc tggatctttt tcccatgaaa aatttcaact cttgattagc
140461 atgtaggcag ggattattcc acatccttat aggaatcaca ttctgctac tgtccctgaa
140521 tgctagagtc cattgattaa gttattcact gctgcaattg tcagagctga tcaaagaact
140581 ctgaaccagt gtgttactag aactaacaaa gaaaatgcca ttatgatgtt ctagagtctt
140641 gaattagtag aagaggttta ataagaaccc taagggattg ctagaatgtt aaaaacaaac
140701 aaacaaaaaa aaaggttgaa aagtttagaa aattcactgg tctttgtgcc catcattta
140761 cttccagggt ttagataatc tcatttttgc aatgaaggaa tggattagat cacaagttct
140821 catcctagta gcacatgcag aatctttata aaaacacaga gtagccaggt gcggtggctc
140881 atgcctgtaa tccagcact ttgagagcct ggggcaggtg gatcacttga aataggagt
140941 tgaagaccaa gctggtcaac atggcaaaac cctgtatcta ctaaaaattc aaaaattagc
141001 caggcatgat ggcacatgcc tcccagctac tgggaggct gaggcaggag aatcgattga
141061 acccgggaga tggaggttgc agggagctga gatagctcca ctgcactcca gcctggtgac
141121 aggtgagac tccatcacaa acaaaacaaa acaaagaaa gcaaaaacac agattactca
141181 gggtccacta agaccagtga agtcagttct cttggtaggg ggcagggtga ctgagcatga
141241 tgtttgtaat tttaaaagtg ctccaggtga ttctagcgtg tatcaagcaa gacttgtgaa
141301 ccactgaact acatgctaag actcatttta gctctgattt tctgtgagtc atagcagagg
141361 gctcagcaaa cttttctat aaatgctaag atagtaaata ttttcagctt tgtgggctgt
```

FIG. 1 (cont.) (SEQ ID NO: 1)

```
141421 atcgtcttta tgacaactca actcagtctt tgtagagaaa agcagctgta cataatatgt
141481 aaactaatgg gagtagctag atgtgtcctg tgggccatag ttttgctgac tcctggtcta
141541 tgtcatagaa ttttccttttg aattgatgga ccaccagcaa atgatttttg tcctgtatca
141601 atcaatgata catacataaa tctctacaag acatgtaaag gatgaggctt aatgacagag
141661 tactttgggg aagacataat attgcaaaat taagatgctt agagaaaaat catattaaaa
141721 tagtgaaaac tgtgagaagg tattttgatt tgttgttttg gattcctctt tttgcaaatt
141781 cttttgaaat attttcagtg gaagctacat agatccaatt gtattcacca agctagattg
141841 taattaagct ccagagtaag taatagattt gatgagtgat gtccaacctt ttacatggaa
141901 gagtaagttt gagtcttcct ttgcccattg acacacttag taccatgttt accaaagttc
141961 ttagttattg aaatgggcac cagcatattt tgaaacgttg gtgttaactt gggatatgcc
142021 ttttgtcatg ttgcaaatag atttttgtttc tgttttgtga agatcaccat ctctgtcact
142081 tctgatagaa aaagtgacac tgacttctca agtgatttga cacaggttaa aatatgtaaa
142141 ccatttctgt agagagcaag ctgtaataat atactaaagg gctaggttta tagtataata
142201 taaataactc atttatgctg ttaataattt atagcaacat ggcatttgac tgacttttta
142261 tgtgctctag tcatgtaagt aatagatgtg gaaacataga ccagagtttc aagaacatgt
142321 tttgggcaga gtctgttttc ttgctattat ctcttaagtt tatgttcatg gcctaaagat
142381 tatgctaatg gatctgcctt ggtcttgggt gtcaggtctg tgttagcgag tattgaaaag
142441 catagttttt gcctactggg aaggatttat gatttaaaag ccctaaatct ccctttttat
142501 gtacttcata cttagaaaat ttttcctgta aactgtgtga cttttttaca ttgtgccagt
142561 tttctagatg actctcgtca tatttatttc ttgcaatcct tctataacta tcagttatga
142621 agtctcttta tagtgttgcc agccaggtct caggtgtgtg aaatgtattt tctattatgg
142681 attttggggt atgatggcac atagtttggg tgttaatgcc taatcttgat gtactggctt
142741 ctgaacaacc aaaaggatga aaggaaatag aacaaatatt tttgtgaggg agaggagtct
142801 ggcttcttga cttactctag aaaaagcctg taagcctcct cttccctcct tgtcacacaa
142861 agtgacaaag aaaatcaaga attgttttct tcttggctta aatgcatccc ttataaagta
142921 aggctgagat caggctgtga agctatcttt ttgtcaagac tgtcataatt ccaaaacact
142981 ttgttcttct aatgcttagg ttagtaactt taaacatttt tataaagata gtgaggtcca
143041 gttttaagga ttgacccctt ctcaaggggc tcagaagagg ttttggagaa taataaaatt
143101 aaataatgaa accaataatt taaaccagat catgatcctt aagaaaaaat cccatcaaat
143161 ttgggctaaa ctctaataca cagaggtctg cacaacttat gtcaagtatt cttccccaca
143221 aatgaagaat ggggttcatt gtgtcattgg ttgggtctca ttttggcttc atcttctatt
143281 tctcaaagtc taagaaaagt gctcctacgg aagtgggtgt tggctatcat gagactttgc
143341 tgctggcagg ccagcttgct gctctagaca gagatatccc tcgatcctcc ttggacaact
143401 gttttctgtg cacaggaagc agcaggctgg ggttaaggag tttgccaatc cagtcattct
143461 gataattgct gaatatgaat ttctatccag cacaatctag gtagctacaa tggcacagta
143521 gtttttatgt atcaggtgaa aatgtttaat aggcactcta aatgagagaa aaggttaagt
143581 gaggttaaaa gctcaatgaa aacaaataga tgagactaaa aatagttcaa taggttgtaa
143641 cttccatctc atccaaacag caatgaatat tttgaggctg aggcgctgag gggtaaaatt
143701 gcagcctgga ctacttgcta atgtagacct acagcactgt cattcttact gcacagacac
143761 tgctttctgc ataggaggta gaataatgaa ttcatttatt attaacaaag atttattaag
143821 tgactgcatg gtgctaacca ctagatgggg agggatgttt tgaactgtcc attgtttgac
143881 tataacaagg aacgctttga acgaggttac tatcataggc agaatttgtt taacatgaag
143941 cctatgagac ataagccaca ggtcctctca cgtgcaggaa ctcctttgaa ggccctatac
144001 ttaattttat atgcatagtt tggatttgga ttcttttttt tttaagagtt ccccaaatta
144061 cttaagcttc aggctccaca aaacctggat ctaccctgg tagcagctat gaatctttga
144121 ctatgaaatt aagtgtacaa gaaatatgac tttacttttt ctgtgattga gtttatttc
144181 tatttgagca cgcattccac tgagtgaaag aaataatatc attgaattca gagattttgc
144241 tgggttctaa gtggagttta cagaatgcca tgatattagg aattaaggag tgtgttgccc
144301 tacatcatct tttgtccgtg ctcactgtct ctgaggcact gatgttccta tgtgacctag
144361 agggcatgg tccaggtaga tggagtctgt ccttgttctc actgtgagct ctcgcttgct
144421 gacccttctt cagtttcttc catgccctg aggggtaaaa agattcaaat ctgaagctat
144481 atcaagccat ctgtgcatag acattccaag caaccatgtt cactctactg ctcccatgtc
144541 atgcaaggca caggaagctt cactatggca tgagtatttc ctgggctttg ccttggaatt
144601 gaggcacggg cctcctttgt tctaaaattc cccaaatcta cttgaggata gaaccaggat
144661 ttggttgcaa ggcagaactt ttcttagagg acctggtatc taaaccctct tgttacccc
144721 atttatggac cccatttatg gggtgaggag agtgactgct tctaatccat cataattttt
144781 gtctatggct actgttttg catagacact atgttttgag tccttaggct ttggcttttg
144841 gcgcttaatg gccaatattc acatggctca aaattttcaa atgatccata tctgacttga
144901 gtttcaaaag tcagttttg aaacttaaat gatcagaatt gatttgttct gctctggttc
```

FIG. 1 (cont.) (SEQ ID NO: 1)

```
144961 tgatgtggcc tctccttcca gaggtactgg aggtagaata tccaaggtgg aaagcccacg
145021 actacaagga attggttagt aattcataat gttagctgtc cacatctatt cagtaatggc
145081 atttcagtgg ctgcacaact gaccatggtg aaagtgtctg cacaagccac ttttcttcc
145141 tgtcagaaaa tgttctcacc cactgaattg aatgactgtc tgctcatatg ctgtgaatga
145201 gtgcccagtc ttaagattaa atcacacgtt cttggctatg catatttggg catgctgtgg
145261 ggagttataa taggctgtct tagagtcaca ttaagcagct agacagacaa tgagttggaa
145321 agttacattt tctaaatttg attggtacat tccatttgtc acatttgaca ttagaagttc
145381 tggattcacc ctctatggtg agcttcacta atggagaatg taatttgcaa tgctcaaaca
145441 caagtcctaa acagaaaaca ttgtatgtta cattccagtg ctaccaaaat agtggttttg
145501 aaagtcctta ttttctaata ctactatgtg taattttgag tcatttagat agcaacagtt
145561 aaatgtttta tagattgttt ggaagtatta aaatgtgaag gattttttgtt atatagtgtc
145621 tttcctatct tgcttaataa aatataagtt tagaattgtg tatagaatta acatgcaaaa
145681 atatcaagtc tcaactttat acagttaatc tacatttgtg tataccattc aattatttca
145741 agagagggat actattctta tgcaggataa atacaataag atattttaaa tgaatttaa
145801 ctacatctct ggcagtttca tctcaatagt agttgtaatt ttatctccca gaccttatta
145861 tagactagca gctctctatg aaaattagtg acagtgtgag tgtatttaa ttcaaagtta
145921 atcaagaatg actgagtcaa gagttagcta ccctgaaag taactcataa ttcagaattt
145981 aaaatattac atgtggaaca atcatgacta tatgcctttt actttctcta tcattattta
146041 ggttgtgggc tttgggtcct tttcacatcc gttaacagtg ggcttgactt caaaggatta
146101 ttttcttgaa tcttgaataa ttgctgaaga caatttgaag atattttcaa gatgaaggaa
146161 actgaagcac agaatcacta gagtgaaaaa agaacttcac aaacagtgca ggcttgatca
146221 atggcatggg aaaacaggca atacagttag aattgctaag atggaatttt aacgttcaat
146281 taaggatcta tctctaaact cctctgcttt atccaccaat cattccatat taaagatgaa
146341 gaattgttcc catttcacct tttgataagg aaaaatagaa ataacagaag caaatacact
146401 tttgcccaca ttttttttcca aaaagaataa ttttttgaagt ctaaacgttt ggtgtaaata
146461 agatgatgtg ttaatattgt aaaggaaagc tagttaagtt tttgactgaa taaagccagc
146521 atcaataatt actagtaaga ctaaaaataa gagcagtaaa attgtgtcta atcagctact
146581 aatatctggg aaggattgag ccacaggatc aaagatggta tcttttaaaa atagaagttg
146641 agtgaattcg gtcttcaaat tctttctttt tattcattta tatttattta ctcattagta
146701 tattcattcc tttattcatg tattgttcaa atatatattg ggtactatt atatgccaag
146761 ttgtttttaa aatcacattc caaattcccg taagtcataa ttattcagag atgtatgttt
146821 tttttaaaaa aaattgaaca cctttaaaaa ttatcaagtc cttttatttc tgtatgcatt
146881 aaagataaac tttactaaat gttacatgaa tagatttata aagcagataa atatttaatt
146941 tcaaatataa ccttatatg caattatatt ttccttagca ctaaaaatga atatttaagt
147001 aatttatatt aaaagtgtaa ttatttaact gcagatgtat gccaatgact taaattgttt
147061 aaagattata gcaaagttgt ttaaaattgt ctaatcatga agagttcact taaccacctg
147121 gttgacacat aaaattatag ttagttacta aggtagttcg agagaaagag aagaatcttc
147181 agtagtggtt ttgaggtgtg gtacatttta ttataatata ccggttatac agcattgtgc
147241 agtgctgctc atagtagaaa taaattttct ctttgatgtc atctattccc ttgtgtggct
147301 tacataactg agaattaggt gatcacaaaa ataaacaggc ctatacagag cccatttata
147361 taagtcctgg ttatttctct tcagttaaac ttttaattat atccaattat ttcctgttag
147421 ttcattgaaa agcccgacaa ataaccaagt gacaaatagc aagtgttgca ttttacaagt
147481 tatttttag gaagcatcaa actaattgtg aaattgtctg ccattcttaa aaacaaaaat
147541 gttgttattt ttatttcaga tgcgatctgt gagccgagtc tttaagttca ttgacatgcc
147601 aacagaaggt aaacctacca agtcaaccaa accatacaag aatggccaac tctcgaaagt
147661 tatgattatt gagaattcac acgtgaagaa agatgacatc tggccctcag ggggccaaat
147721 gactgtcaaa gatctcacag caaaatacac agaaggtgga aatgccatat tagagaacat
147781 ttccttctca ataagtcctg gccagaggt gagatttgaa cactgcttgc tttgttagac
147841 tgtgttcagt aagtgaatcc cagtagcctg aagcaatgtg ttagcagaat ctatttgtaa
147901 cattattatt gtacagtaga atcaatatta aacacacatg ttttattata tggagtcatt
147961 attttaata tgaaatttaa tttgcagagt cctgaaccta taatgggt tatttaaa
148021 tgtgattgta cttgcagaat atctaattaa ttgctaggtt aataactaaa gaagccatta
148081 aataaatcaa aattgtaaca tgttttagat ttcccatctt gaaaatgtct tccaaaaata
148141 tcttattgct gactccatct attgtcttaa attttatcta agtccattc tgccaaacaa
148201 gtgatacttt ttttctagct ttttcagtt tgttgtttt gttttctttt gaagttttaa
148261 tcagacata gattatttt tcccagttat ttactatatt tattaagcat gagtaattga
148321 cattatttg aaatccttct tatggatccc agcactgggc tgaacacata gaaggaactt
148381 aatatatact gatttctgga attgattctt ggagacaggg atggtcatta tccatatact
148441 tcaggctcca taaacatatt tcttaattgc cttcaaatcc ctattctgga ctgctctata
```

FIG. 1 (cont.) (SEQ ID NO: 1)

```
148501 aatctagaca agagtattat atattttgat tgatattttt tagataaaat aaaagggagc
148561 tgaaaactga attgcaaact gaattttaaa actttatctc tctgtggtta attgcaaaca
148621 cagatacaaa aatatagaga gagatacagt tagtaaagat gttaggtcac cgttactaac
148681 actgacatag aaacagtttt gctcatgagt ttcagaatat atgagtttga ttttgcccat
148741 ggattttaga atatttgata aacatttaat gcattgtaca aattctgtga aaacatatat
148801 ataggatgtg cgaaaagtcc ctgtgtatca tgtgaaatgg cttaaaacag aacaccatag
148861 gtattcatat cagtgaatac cataggtagc tgaaagtgtt ttttcctggg gtcgccaaga
148921 tgaatgccaa aagtgatatc attattataa acaatagcca gaataggttg gtataaacct
148981 ggtagaaagc cttgataaat tgactttctc tcctcctgac atcctgccac ccctttgctt
149041 tgctgatgct catttgtcca ctaaattaaa ctcaagcaag ccctagtaaa gtaatagaat
149101 ttgtggagtc ctcattagta taggaagttt ccctgatgtg agattagtaa ttagagatgt
149161 agcaaaatga gaaagaagta atatgcttag atatttcatt ttctctgaac ctgtatatac
149221 aaaataggcc atgcgtgttc agtaactatt cactgcaagg cactctctag gtactttggg
149281 ggaattggaa attactcaca taaggctatg gattgtgcca tttgtcaaaa gacaaaatga
149341 caacaaattt agtttaaaga cctcagtcag cttatttttc tattctagat ttggacagtc
149401 cttcatttca caaattggag taagtgttcc aataagttga gcaaaggagc ttggctttat
149461 agacccaaaa aaagggccaa aggaagcaga aacaaagaac aataagagaa ttggtcattt
149521 caaagttact tttcttgaaa ggtgggaca aggagacaga ataatagaaa agtcactgat
149581 tggttaacat tggattaaga attaaaacag aggaaacttt aagattgaag tttgaaactg
149641 acttgtttgg gaaatcaggc tgtcttcttt cttgatttct tagaaggccg gataacaact
149701 gagttttgct ttggtgaaca tgggtgactc cattttact tttagtctgg tctgttgagg
149761 cctcgtgaga gagcttaatc taaacaatg acttcctata atttttgttt gacacatcca
149821 aagagggact ctaatattta ttgagagctt atcatatctt aagtactgtt taaacacttt
149881 tatttgctat tacatttgat cttattataa ctctaaaggc agaaatgatt gcttttattt
149941 tccacaatgg aggaaactga ggttcaatta agtgagtaag gaagcaggga tcttaaaccc
150001 agataccatt gctcctcttt aaaggtggaa gaacagaaaa catggggcag gggaagagag
150061 aaagtttctg tccaggaca tgataatcta aaagggaaaa cgtaagatcc actgaaacct
150121 gaggcagatt tattgtggca ataacaaagc ttaagtttca cagaccttca tttgcctgag
150181 ccaactttga aggccatgta tctaatttgg tttttataat tctataatct ttattcttga
150241 aaagagccct ccctccaaat ttacaagctt gggcccca aaatccttga aatgcccttg
150301 aataagagat atccaggtaa atgctatggg aattcagagg aggaagcagt tagtatcagt
150361 tggcggagag ttaggctatt aagagaaggt tttatatagg aagtggcatt tagaatgaag
150421 ctttgagaac tgagctgtgt atttgaacaa gtaaggtgg tgttgcagaa ttttgctcct
150481 tagttctatt aaaaacccgg gttcttgtca catgatccgg aaaatttagg cacacagata
150541 cattgaagca tgagtagagc aggattttat tgggcaaaaa ggaaaaaaag aaaactcagc
150601 aaatcgagat ggagtcttgc tcacagattg aatcccaggc caccacaaag gaactgaaga
150661 gatcgggctt ctcccctgca taaggtgcaa attccccatg gctccaccca cttccccta
150721 gtgtgcatgt ggggctccag tccacggtgg gcatgcccag acaagccttg ggcaggttcc
150781 ctcatctgtg caaaagcatc tgatgtaaac acttgagggg tggttcggag attctctggg
150841 acccttttat tttcttatct gcctaggcat ttggctgtct cagtgggtgg gaaagggtgc
150901 tccaggcaaa gggcataaca tgaggcaaag ggcatgcaca gaaaacagtg actggttcag
150961 tcaggttggg ggatgccaaa ggaagtaatg ggagacaaga ttggagcaag atagataaga
151021 gattgtggat ttttttcctt tttttatctat ataaatacag agacagggtc tcactatgtt
151081 gcccaggctg gtctcaaact cctggcctca agtgatcctc ccacctcatc ctcccaaagt
151141 gctaggatta caggcatgag gcactgtgcc caacctccaa ttttggattt tgagagctaa
151201 agcaatatag tcgaaaactc agataatcca ggtagatttt gctattaggt gctatttggt
151261 tcctggtaca gagctaaaac ccttggaatt tcctaagtga taagagctac aggagcatct
151321 tttgttatat gtttcccccc ctagttcctg aaatagctct agagaaatac aggtgaataa
151381 catcctttgt tattcatatc aagcccctat caaccatacc ccagtttcta tttatgaagt
151441 ggcttttggg aagtccctaa agacaggagt ggggaaaggc tggttgtcag ggggatgggt
151501 tgaaactttc atcttccccc cttgacctcc agggagggat gagtggctga aaattgtgta
151561 aaatcaacaa tggccagtga tttaatcaac catgcctatg taatgaagcc acccgataag
151621 ccttaactgg aacttttgg agagcctcca ggctggtgaa gacattgagg tgctcagaag
151681 gtggtattcc agagagagca cagaatctct gttccccttc ccacattcat tttgctatgc
151741 atctctccca tctggctgtt cttgagaggt atccgtttat aataaactgg taacctagta
151801 agtaaactgt taccctgagt tctgtgagcc attctagcaa attatcaaac ctaaagagtt
151861 catggatacg tgcaatttac agatgcacag tcagaagcac agatgacaat ctgggcttgc
151921 cattggcatt tgaagtgtgt tgggaggcag tcttacagga atgagccctt atcctgtggg
151981 gtctatgcta ataacagaca gttgtcagca ttgcttggtg tcgaaaccc acattgttgg
```

FIG. 1 (cont.) (SEQ ID NO: 1)

```
152041 tgtcagaagt attgtcagta ggatagggaa aacagtttgt tttcttttt tagtggtctt
152101 tggtcatctt taagagcagg gcttctcaaa gtgtggtcct tgaaccagca tcacctgtac
152161 cacgtaagaa cttatgagaa atgttcattc ttgggcccca acaaagaatt aaaaattctg
152221 agggtgtgaa cggggtctga gtttcagcac aacttcccga ccatgctgat gcattcttgc
152281 ccaagcatga aagccctccc ttgtttaaga aggccattag ggccgggtgt ggtggctcat
152341 gcttgtaatc gagcactttg agaggacata gtgggaggat cacttgagcc ctggagttct
152401 agacaagcct gggcaacatg gcaaaatgct gtctccacaa aaatcacaaa aattaggtgg
152461 gcgtgtgttg tgtgcctata ggcccagcta cttaggagac tgaggcagga ggatcgcttg
152521 agcccaggag attaaggctg cagcgagctg tgatggcacc actacagcct ggatgacaga
152581 gtgagacact gtctcaaaaa aaaaaagaa aagaaaaag aaaaagaaa ggaaaatgaa
152641 aaagaacgcc attaggtata aaggagcaat ggtaaaagac cagttgcaaa aggttaggga
152701 atgggtggtt actgaaataa gaagctatgt agaacactag tgttggtggc aggaagtaga
152761 aagcaagagc actgctctgt gggggatggt catagcaaat gcaatatgga ggcatttgcc
152821 tctgcactga ggagaaaact atcttttcca agataggagg aaaggagata agtggaatta
152881 aagagaacct ttgagcacag agttgggaaa ctgaaggtat ttgtgttgtg ctccctcaat
152941 cttttaattc aactataagc taaacccatg aaacttgagt agtttcagtt atctgacttt
153001 tttcttctct tttgatacag tgttggctat tctgggtctt ttgcctctct ttatgtactt
153061 aagaatcagt ttgccaatgt atgcaaaata actggctggg attttgattg tgattggctt
153121 gaatctatag atggagttgg gaaggactga catcttgaca atgttgaagc ttcctattca
153181 tcattatgaa atatttctcc atttgtttga ttctttgatt tcttttatca gaatttagtt
153241 ttcctcatat agtcttttaa aatatttgt tatattttgt tcaagtattt tgttttttgag
153301 gaatgccaat gtaaatggta ttgtgatttt aatttcaaat tccatttttt cattgctgtt
153361 ataggaaaa atgatttttt ttgcatgtta gccttatatc tttcaacttt gctataatca
153421 attattgata gtttcaagga ttttttggtc aattattttg aatcttctac atagattatc
153481 atcatctgaa cttagtttta tttcttcctt cccaatctgt atacctttat ctccttttct
153541 tatttcatta gctaggactt ccagtatgat gttgaaagta gtggtgagag ggatatctt
153601 ggtcttgttc ttgatcttag tgggaaaact tcaagtttct tatcattaag tatgatttta
153661 gctggagggt ttttgtagaa gttttttttt tttaagttga agaagtctcc ttctattttt
153721 agtttgctga ttttttaaaaa gaatcaggaa tgggtgttaa attttgtgaa atgcttttct
153781 gcaactattg atttgagcac tttattttc ttctttggct tgttgatgtg aagtacatta
153841 attgattttt gaatgctgaa tcaacctttt gtacctgaga ttaatcccgt ttggttgtgg
153901 tatataatta tttgtataca tgttgagttc gatttgctaa tactttttga gaattttgc
153961 attggtgttc atgaaaaaat attggtgtgt agttttttgt gacatcttta tctgcttatg
154021 gttttaaggt aatgctggcc tcatagcatg agttagggag tatttcctct acttttacat
154081 ttgagaagag attgcagaga attagtaaaa ttcctacttt aaatatttg tggaattcac
154141 cagtgaaccc atctggacct ggtgctttct gttttggaag gtcattaatt attttaaaat
154201 agatataggc ctattcagat tacctatttt ttctcatgcg agttttagca gattgtcttt
154261 caaggaattg gtctatttca tttaggttat caaatatgtc aacgtagagt tattcatagt
154321 attctttat tatcctttta atgtgcaagg gatctgtagt gatgtcccct ttttgtttt
154381 attgatatta gcaatttgtg tcacatcttt tatttgctt tgttagccag gctagagata
154441 tctctatttt tgatgttttt gatgaaccaa cttttgttt tattgatttt ctctgttgat
154501 ttcgtgattt caatttcatg attttaaat tatgcttaca tttgatttaa tttgatcttc
154561 ttttgctagt tatccaaggt ggaagcttat attgttaaga tccttttgca ttcttatgca
154621 ttcaatgatg taaattccc ctaagcact gcttttctg catctcacaa atattcatga
154681 gttgtatttt catgttcatt tagtttgaaa tatttttaaa tttctcttga tatttctctt
154741 ttgacccatg tgttacttag aagtgtgttg tttaatcacc attttaaaa atttctagc
154801 tatctttctg ttattgattt ctagtttaat tccattgtgg tctgagagca tatattgtat
154861 aattttaatt tttataaaat ttgttaaggt gtgatttatg gccagaatg tggtctatct
154921 tggtgaatgt tccatgtaag ctttggaaga ctgtgtattc tgctatattt gaatgaggta
154981 gtctatagac atcaattatg tccagttgat tgatggtgct gttgaattca actatgtcct
155041 tactgatttt ccacctgcta gatctgtcca ttctttgcag agggacactg aagtctccaa
155101 ctctagtagt gaatattcta ttcttgtta cagttttatc aacttctgct tcatgtcttt
155161 tgatgctttg ttctagaaa catacacatg aagaattggt atgtcttttg gagcatgacc
155221 catttatcct catataatgc ccctcattat ttcctcgccc tgatgtctgt tctctctgaa
155281 agaaatatag cctctccagg tctcttttgg ttggtgttaa aatgacttaa ctttctttat
155341 cccccttact tttagtttat atgtggtttt aaatttaaag tgggtttctt gtagacagca
155401 aatagttcag agttgttttt cgatccactt tgacaatctt tgtctttaa ttggtatatt
155461 tggactattg atattttaag tgattattga tatagttaga taaacatcta ctatatttat
155521 tactgttttc tgtctgttac actacttgtt ctttgtttat atttttattg tctactcttt
```

FIG. 1 (cont.) (SEQ ID NO: 1)

```
155581 ttctttccat tgtggtttta atcgagcatt ttatatgttt ccatttcttt ttcttagcat
155641 agtaattctt ctttaaaaaa acattttta gtggttgccc ctagagtttg caatatacat
155701 ttacaactaa tctaagtcca ttttcaaata atactaaata atttcatgtg tagtgcaagt
155761 accttttaat aataaaacac tcccagttcc accttccagt ctcttgtatt atagctataa
155821 tttagttcac ttacatatat gggtatacct aagtatatac attatcatat ttatgattga
155881 atatattgat gaaattattt tgaaaaaact gttatcgtta aatcaattaa gagtaagaaa
155941 aatagttcta attttattat aaaatgaaat accttcattt attcattctc taatacactt
156001 tctttcttta tgtagatcca agtttctgac ctgtataatt ttccttttct ctcttcagct
156061 tctttgaaca tttcttacca gccagaccta ctgacaacaa ttttccccaa tttttgtttg
156121 tctgatagag actttatttc ttcttgactt ttgaagaata attccacagg gcacagaact
156181 ctagattggt gatttcttcc cctcaaaccc ttaaatattt cattccactg ccttcttgct
156241 tgcattgttt ctgagaagtt agatataatt cttatctttg cctttctata ggtaagatgt
156301 tttttcctct ggcttctatc aagattttt ctttatgaac atgatatgcc tttcttttg
156361 aacatgatat gcctttcttt ttgaacatga tatgcctttg tgtcggattt tttttggcat
156421 tattctgctt ggttttctct gagtttcttg gatatgtggt atggtatctg acactaattt
156481 ggaaaaattc tcagtcatta ttgcttcaaa tatttcttct gttctttttt ttcctttatt
156541 ctccttctgg tattcccatt acatgtatgt tacagttttt gtagtcatcc cgctgttttg
156601 gatattctgt ttttttcagt tttttttcc ttcgcatttc agtgttggaa gtttctattg
156661 acatattctc aacctcagag attctttctt cagctgtgtt cagtctacca atgagtccat
156721 caaaggcatt ttacattttt attacagaat ttttgaccta tagaatttct tttgattcca
156781 tctttgaatc tccatttctc ttctgctttt catctgttct tgcatgttgc ctactttttc
156841 catgaaaacc tttagctttt ttttttttc ttttgaggt ggagtctcac tgttgccag
156901 gctggagtgc agtggtgtga tcttggctca ctgcaacctc tgcctcctgg gttcaagtga
156961 ttctcctcct cagcctccca agtagctggg attacaggtg cctgccacca tgcctgagta
157021 attttttgtat ttttagtaga gatggggttt tatcatgttg gccaggcggg tcttgaactc
157081 ctaacctcaa gtgatctgcc cacctagcc tcccaaattg ctgggattat aggtgtgagc
157141 caccatgccc tgcctttagc atgttaatca tagttgtttt aaattcctga tctgttaatt
157201 ccaacatccc tgtcatatct gactgtggtt ctgatgcttg ctctgtgttt tcaaatggtg
157261 tttttttttt tttgcctttt agtaagcctt gtaatttttt attgaaaggt ggacatgatg
157321 tgctggtaa aaggaactgt agtaaatagg ccttagtaa tgtactggta ggtgtagcag
157381 agggtgaggg aagtattctg tagtcctatg attaggtttt agtcttttag tgagcctgtg
157441 cgcctgcagc ttggaagcac ttgtgaagtc tttttcacc ccttttggtg ggacatagtg
157501 actagtgtga gcgggagttg agtatttccc ttccctagg tcagttaggc tctgaaaaaa
157561 ccctgatagg ttaggcatgg taaaatagtc tcttttgagg gcaggcattg ttataagaat
157621 agaatgctct ggggccaggt gcggtggctc acgcctgtaa tcccgcact tgggaggct
157681 aaggcaggtg gatcacctga ggtcaggagt cgagaccag cctggccaac atggtgaaac
157741 cccgtctcta ctaaaaatac aaaaatcagc caggtgtggt ggcacacacc tataatccca
157801 gctactcagg aggctgaggc aggagaactg cttgaaccca gtaagtggag gttacagtga
157861 cccaagattg tgccactgca gtctagtctg ggtgacagag caagactccg tctcaaaaaa
157921 aaaagaatgc tctggcatat ttgaaaatgg ttacttttcc ctttttttct ctgatcttca
157981 ctgtgagaac ctggtaagca tcctataggc aaaattcata aaagtataga agtcggccag
158041 tgacttggac ccacttggaa ttttcttgct ctcacatcat gcacactgaa tctccagcaa
158101 tttttcactt acagtttagg ttttcctacc ctactactgg ttctctcaga ggtttctgct
158161 tattggtttc tgttttgtaa gttgtgattc tctgtaccta actgcctgtc tcccattttg
158221 ggggcagtg gtttgccctg tgacctcact tctctgacag atctaagaaa agttgtttat
158281 ttttcagtgt gctctgcttt ttacttgtta cgatgaagcc aaccactttc agaatttcta
158341 caaccagat cagaatctgg aagtcctgtt ttttatttt ttttatccct ttgtttagca
158401 tgttacctat cttaacacat tttaaataag tgaatgcata gcttatatct acttctaggt
158461 tatatgcttc cttagaatag gaattgattc ttaaaatgtc gttctgctca cgcctgtaat
158521 tccagcactt gggaggcca aggcaggcgg atcactggg gtcaggagtt caagaccagc
158581 ctggtcaaca tggtaaaacc ctgtgcctgc aaaaaataca aaaattagct gggcatggtg
158641 gtggccatct gtaatcccag ctactaggga agctaaggca tgaatcac ttgaacctgg
158701 gaggtggagg ttgcagtgag ctgagatcgc gccactgcac tccagcctgg gtgacaagag
158761 caaaactcca tctcataaat aaataaataa ataaataaat aataataaa aataaaaaaa
158821 taaaataaaa caaaaatttt attctgagca gtctctgaag aatataaatt ctactgcctt
158881 gcctttagaa cttataacag catctcgcaa actatcacaa gatgctccaa acatacttct
158941 tatgtgctga attaagaagt caactcaaat ttagtatact agtaatattt ttggatatcc
159001 caaacactg ccagctcagc ttaggctgc ccttcttggg ggggaaaaaa gcagttgaaa
159061 tttaggactt aagtgggcat ctcgtttaat ttttaatgga tttctatgtt gttggttatg
```

FIG. 1 (cont.) (SEQ ID NO: 1)

```
159121 gtgaagaggt gaaaagaata aatattctgt gcagaaaaat tattcagtct tcatgtgaaa
159181 acactttgtc catagcaatt acttatgaa aagatgtgg tattactttc tttgctctta
159241 actgagacct taatttaaa gaacctatac tttacaagtt tttattttca atgcatgaaa
159301 aatgtagcag ctatttcaca acctttactt ttaaaatcca ttttctttt taatctcaaa
159361 tagttttttc ttaaaacctt ttgacttttt atctaaattg taatagccag agcaccttcc
159421 cacaactaga atatctcatc ctttttgtct tttctttttc ctctcaaaat gcctactggg
159481 aacttaattt ggagtcagat tcttcatgat aaatctggac ttaatcaaaa ttcctcatat
159541 ggtatattgt atatatcaca gtactggata gtcctctgat taaatagata tttgatagta
159601 ctttaaggtc tatacttttg gatgaactta actgctttct ccatttgtag tctcttgaaa
159661 atacagaaat ttcagaaata atttataaga atatcaagga ttcaaatcat atcagcacaa
159721 acacctaaat acttgtttgc tttgttaaac acatatccca ttttctatct tgataaacat
159781 tggtgtaaag tagttgaatc attcagtggg tataagcagc atattctcaa tactatgttt
159841 cattaataat taatagagat atatgaacac ataaaagatt caattataat caccttgtgg
159901 atctaaattt cagttgactt gtcatcttga tttctggaga ccacaaggta atgaaaaata
159961 attacaagag tcttccatct gttgcagtat taaaatggcg agtaagacac cctgaaagga
160021 aatgttctat tcatggtaca atgcaattac agctagcacc aaattcaaca ctgtttaact
160081 ttcaacatat tattttgatt tatcttgatc caacattctc agggaggagg tgcattgaag
160141 ttattagaaa acactgactt agatttaggg tatgtcttaa aagcttattt gcgggaagta
160201 ctctagcctt attcaacaga tcactgagaa gcctggaaaa acaaatcccg gaaactaatt
160261 attatgtgcc agttatataa acaagaagac tttgttgggt acaaaccagt gattccttgc
160321 ctttgaaaaa tgtgtcagat atcatgcatt accagcagtt caatgatata aggaaaccag
160381 agtaatagct aaaaccttta aagctaaacc aaagatttac aaattgcctc ttcatccagt
160441 ctttcccaac ctaaaaactg agttctctaa aaatttagt atttttttct gaagaaaagg
160501 gaacatggac atttatctaa tcctcattag aaatctgact aatgataaca aggatttaga
160561 cctcaagcac ttcttaccaa aattcttgat atgaccttat agcaaattac tttcacctgt
160621 tgaactttcc tttctttat tccctgtac ctcacctgca ctgggcatat tcaagttgct
160681 tatacaacac tttactattg tgttagaaaa atcatgacac atgatgaatg tgtttgtgca
160741 acatgagctg attcataaat gaaaatgtgc attgaaattc cacaatattt taaaattagg
160801 agtttatcta gcaattgaac aaaattgatt aaatccatta tttgttagat cagctaaatt
160861 acataagttc attcatctgc tcataaatcc atccattctt ccatctggct atcccttagt
160921 caattcaaat aaatatttat ggggcacttt gggtaagcca ggtgctaaga attcaatgca
160981 aaacaagata gactcccctg tccttgttga acttatattt ttggtacaaa caaaagcaat
161041 aatcaagaaa aataaaaaa agtactgatt gtgattaata atatgaagaa attcaacaga
161101 gtattgtact taacatttga ttgatctgat tttctcagtt gtctgagaac aaacatttgt
161161 gaaaatctca ttgtagagtt cttacgatgg ataggggtc aactgtgtca ttattgctta
161221 tcagcttatc ccaagaccct agtttattac cagattgcaa atagtgttca ataaattatt
161281 cttattaagg gttgttatgt actctaaaac atttattgtg gtcccttcac tggttctggt
161341 ttacaaactt acttttctat gatgacatag tatagaaatt gagagtgaat atttagaagt
161401 tcatttttat tatatatttt tgaagtattg atatgtagtg aattagaaat ttaaaaagaa
161461 aacaaaactg tccttcacta cagattgaaa agcatatac taaaagacca tttgctcagt
161521 tatagtatat aaaggccaaa tgacttaaaa acaaattatg taaggagaag gaaacaacca
161581 tttattcagt gccactaact gtcagccagt tttttcagtg gtcagttaat gactgcagta
161641 gtgttctacc ttgctcaaag caccctcctc aagttctggc atctaagctg acatcagaac
161701 acagagttgg ggctctctgt gggtcacctc tagcacttga tctcctcatg cagtgcatgg
161761 tgctctcacg tctatgctat gttcttatgg tcttaggta acaagaataa ttttcttttct
161821 tttccttact atacattttg ctttctgaaa ttccttctc gccaatccag gtgaatgtca
161881 gaatgtgatt tgacaactgt ccaagtact cattcactga ggagtggtaa ggccttcgcc
161941 caacctgcct tctctgggaa tatactgctg cctgaacata tcattgttta ttgccaggct
162001 tgaacttcac caaattaatt tattagggtc aacatctaaa tattagaact atttcagatt
162061 aattttttaag tcgtatccac tttgggtact agatcaaatt gcaggtctct gcttctggct
162121 tgagcctatg tttagagatg atgtgcatga agacactctt tgcttttcct ttatgcaaaa
162181 tgggcatttt caatcttttt gtcattagta aaggtcagtg ataaggaag tctgcatcag
162241 gggtccaatt ccttatggcc agtttctcta ttctgttcca aggttgtttg tctccatata
162301 tcaacattgg tcaggattga aagtgtgcaa caaggtttga atgataagt gaaaatcttc
162361 cactggtgac aggataaaat attccaatgg ttttattga agtacaatac tgaattatgt
162421 ttatggcatg gtacctatat gtcacagaag tgatccatc acttttacct tataggtggg
162481 cctcttggga agaactggat cagggaagag tactttgtta tcagcttttt tgagactact
162541 gaacactgaa ggagaaatcc agatcgatgg tgtgtcttgg gattcaataa ctttgcaaca
162601 gtggaggaaa gcctttggag tgataccaca ggtgagcaaa aggacttagc cagaaaaaag
```

FIG. 1 (cont.) (SEQ ID NO: 1)

```
162661 gcaactaaat tatattlltt actgctattt gatacttgta ctcaagaaat tcatattact
162721 ctgcaaaata tatttgttat gcattgctgt ctttttttctc cagtgcagtt ttctcatagg
162781 cagaaaagat gtctctaaaa gtttggaatt ctcaaattct ggttattgaa atgttcatag
162841 ctttgatagt gttttcaga agaccaaatt tacagtggga gccttgggct tttgtttttt
162901 aacagctctt ttttgttcct gcttcagtgg cctgacctcc aagttagcaa tcgccaggtt
162961 gagaaatgct ttgcgagaca taacagatgc tcctgaaata acaaacactt ggaatcatga
163021 ggtagtggaa ttgaaaatag aaagtgtagt gattgttttt tgttatttgg atgggatgaa
163081 caatgtcaga ttagtctgta actattttt tttaatgtca ctctgatttg gtcacaaagg
163141 atctctagtc tcattgcctt agtatcattc tacgaattag aatgtgttac tgtgtaagag
163201 cacttcttgt atatgagaga aatagcaaca gttccagttt aaagtgatat aaatggaaac
163261 caagaaatgt ctttactggg accaaatctg acagcatttt actgtatttt gctggtatt
163321 ttctctagtc tttccgggta tattcacatt taatgatcac ttttctccct tgtgctaat
163381 ggacactgaa tccattccac taccatagtt cttgctaata ctactctact ttttacacaa
163441 aattaaaatg ccaggagcac ctccaggtag actgactata aatctagact gaaaaaaaag
163501 cttgtatttc ttaacagatt accttgtgga acatttgctc ctttcaacta atgaggcact
163561 aaatattgta actgctcaac tggtgctttt aatttatttg tctagacttt gtcatgttgc
163621 cagaagcttt atcctggttg gagttttgaa acagtattg tttcttcaga agaaaaaag
163681 ggattgtcag atgatctaaa aataaagaaa cactggaaat acaagtatcc caaggtgata
163741 gcattaggca agataaaaat gttgaaaagc gaaaagaac tggttgatag agaagtgttg
163801 ttattcagta gaacctaagt cttgtggtcc cattttaat gaaaaatggt gaattttttg
163861 gttttattg ttcttgttca cacaaatctg cccattagaa taagccaagc cctaaaaatt
163921 aatttcagtt tcactgggaa tcctttagtt tatctactat gtagtagaga ggttttgttt
163981 tattgcatgt ttgacgtagg aacgtatata tgcaagacat ggaggaaaac caagtgggcc
164041 agagttttga aaattcttta tcttttcttt ctgccaaagt gagtctccca agtttgtctt
164101 ttttttttca tttccactct tctatggttt ctagcattat ataaccaaa caaaaaaat
164161 acgttcagag attccttcag aaatgctgga tgatcttgat atcgatgctt ttcatatatg
164221 tgtttatgat gctggttct ggggctggct ctcagtatca caaagatgtc tgtaaacaga
164281 atatgctatt tcttctttgt gacaaatttt gaacattatg tgaatgtcca agaaagagca
164341 aaagagggca aacttctcat acatttttga tgtcgaaacc aagagacgct tttatttcc
164401 taactttcct ttgaaagttc aaattaagta attttatcct gtcctaaagt ttaaaagaa
164461 aaaaaaaagg aagaaggaat taaaaatcca agaaaatta tgtttgtttg cttttctgtt
164521 ttttttcttcc ttccaactcc gagactttgc aagggcatag ttctgaagat ctctgacact
164581 gagacattag agatctctgt atcaatggat catttgtttt cagacatatg aaacaggaac
164641 tttgaacaag aaatttcccc tcttttttctc atagtgatcc tgagacatca gctgtggaat
164701 cacaacacgt cattagtttt ggcaggtcct tgcaggtgtt ttgttttgtt ttattaatgt
164761 tcttccctcc tgtagctaga cagcaatctt ggagaatctg ccagcttgga agactattgt
164821 gtaaatttca aggtggagcc tccttaatt tgttctgtgt tacctgtgag ctgtgaggtc
164881 atgaagagga gacaatgagg ctaatcatga gagcccctt ggtttaggca attagaacaa
164941 caagatctaa aatggtttat tagccttgaa ttgtgttaag cacataattc ataaaaaaca
165001 gaaaaaatat ttttaaatgt atgtctaaat cttcagttac aagtttgaaa ggtgacaaac
165061 tattctgagg aaatgattag gcctattctt gcaacgagtc tttatgatct gaaaagaatc
165121 tatgtccaca cataactccc acctcaaaga tggggcatct tttgctctgg gagatatcaa
165181 atgcgaccaa aacaagtgtt tgtagatttg aatgatgatt cagcagtgta gcagttctca
165241 ctcatttat aataattaac aacttaataa ttaattatta aactcctaca tgcttaacat
165301 tataagtatg ataacttctg tggttacata aaagatatac atagcacttg tccttgatct
165361 gtcacagtga ggtcccaatc caacctatga gcttcaaatg aaagttcaa aattacactc
165421 attgtcataa gtcagagatc aaggaagaa aggatttaac caaaatgata aattaaatat
165481 aggtgattaa atatagtcat ggttcaaggc atgggccagt tagggagtgt gatgtgggta
165541 attatgaaag gccagctccc aagccctgtt gttgctactc ccccacatca gtcatccttc
165601 ctttttttct acttctactg cagtgccttc ctcatctttt ccttgcatc cctccattat
165661 atgagtcata caaattagac ttttcaaagc aacattaaca ttgtgtgaat ttggggtttt
165721 tgactaatcc caacattcca cccccacatt ccagtcccac atgggatttg gagccttgtt
165781 tataaacctg gcacttctaa tatatcttat cttagagtaa tccttgtatt tgtttaattt
165841 ccacttagca ttgtaaatac ttgcaggtat cctagttaag aaagcaaggt taaacacaa
165901 aatcatcacc aattaaagca ggctagataa agaatgtaat agaaatgcta gataaaacag
165961 attttttctt actaagtttt ctgtcccttat tagagtgcat aacacaataa cttgcttgat
166021 aagaattcaa tgtacattgt tttgtgctga atcactaaat gcttgatttc tgtaacaaga
166081 gattgtggtt ccatcagtat ctggatttta gtctgtgtaa tcttaggcaa gttatttgat
166141 ttctctgtgc ctctgttttc ttgtctgtaa aatgagtata atggtagtaa ctaattcatt
```

FIG. 1 (cont.) (SEQ ID NO: 1)

```
166201 gtgttttttgt gaggattaaa tgagttaata actagtactc ctccctggca catagtaagt
166261 acaatatgct gtgctgtggt ggttgttatt atttttata gttccttgag caaaagaaat
166321 aatgtcccca tcttagtata atattggagg tatataccat agaagtgaac aaaagaatat
166381 agtttcacaa agaaagtgat aattaaggcg gttcataaag ggtcataaag cttgtagatt
166441 ttagaaatgt ggggggcatga ggatgtggag agggtattcc aggatgccag acaggggagat
166501 tatggatgag tactaagatg agaactagaa aaagctgagg ggcaaaaggt cagagggggc
166561 cacaagttag ggagtattag gaaaagaag ttaatacttg acaagtgcca acatggcttc
166621 acgaggaatg ggttgggcct ttttgagtga ggaagaggct ggtgaaaggg tggtggagga
166681 cactgctgct gctgatggca tggggtgtag gtggcaggag aggcagggac atgagctagg
166741 aaactctcca gctatgaagt gatgagtctg gagtaatata aggacagtag gggtggagtg
166801 ctgaacttaa gggaggagag aaaaataatt ggtatggaag taggtacaat gcaattttat
166861 tatttctgag cctaaaaatg tgaaatttt gattatttgg tcagaccagg gaagtatttt
166921 cttttatgct atctctgaaa atgtatacac taaaaagttg tagtataaaa aggttgtaaa
166981 gcattaagta attttagagg aaacaataat ttggatattt tacatgcaat catttatatg
167041 caaatatatg taaatattac aaaattattc tctatttgtt acaaaccta aatattttg
167101 actgaggaat atttattca tctaattata gctactttgt tctaactaat agatattctt
167161 gaaaacaaag caacactttt ttggagacag agtcttgcac tgtcacctag acttgagtgt
167221 gttaccttga actccagggc tccagtgatc ctcccacctc agtctcttgg gtaggtggat
167281 tacaggccca cactaccatg cccagctgta ttagtccatc ctttcattgc tataaagaaa
167341 taccggaaac tgggtaattt ataaagaaaa taatgtaac tggctcacgg ttcttcaggc
167401 tgtacgggaa gcatagcagc atctgcttct gaggaggcct caggaagttt tcaatcatgg
167461 tggaaggcaa ataagaagca ggcatgttac acgacgaatc aggagcaaga caaagtgagg
167521 gaggaggtgc cacacacttt gaaatgagca gatctcatga aacagcgcc aagaggatgg
167581 tgctataccg ttcatgagaa atccaccccc atgatccagt tacctcccac caggccccgc
167641 ctccaacact gggaattaca attcaacatg agatttgggc agagacacag atccaaacca
167701 taccaccagc taataccaaa aaaaaaaaa aatttttttt ttaagacatg gtcttactat
167761 gttctacagg ctggtcttaa actcctggcc tcaagtgatc ctcccacctt ggcctcccaa
167821 agcactggga attcagacat gagtaacagt gcctggccaa tacttattt taaacattct
167881 ctaccataaa cttaggatct tgatttgttc acattgaaca gatttttatt atacagattg
167941 aatttataag aaaatgttgc agacattgtc aaaagggac gtccaaacca ctgtgatatt
168001 tataagcatt tgggccacat tttgatagaa ctatacacgg agtgtgtgtg tgtgtgtgtg
168061 tgtatatata tatacacaca cacattattt atatatatgt atatatgtat atatatatat
168121 gtatttatat atatatgtgt atatgtatgt acacattatt tacctaccta ctgtgtgagt
168181 gtgtgcatat atacacgcac acacacacac acaaatatat atatttccct tctgagacaa
168241 agccaaacag cactgtatgc ttaaagaaaa acagtcacac ttcccactta tgtaatttat
168301 attacatcca gtcaccacac cagccaaact gctttattgt tttttgtttg acatccaatg
168361 ctaaagcata atgcctgttg cagtgaaata tacatgagca accctgagaa tcaatatag
168421 cctcacgtgt tgccactgag ttgagttgag gagtcaagct gtagcaaaaa ggtttgtcac
168481 cgggtgagta atggtgctct tattttctc tgggtctcaa gaagtgctct ttatgacata
168541 tatggcatta aataaatatc agatatttgc acatcctaac tttcctattg gtgaagtttc
168601 ttaaagaga gataaagggc cattgtgtga ttgatagttt caggtatatt tttgctgcac
168661 agtcagtccg agtgtaccac gtagggcaaa ccacgtaact tctcagggcc ttgactgttt
168721 catttgtaaa ccagagaaaa ggacttgggt gacctccaaa gacctttcaa atttggagat
168781 gagtttgtgg aaagttcaaa cagtttagaa aacagaacta agacacccac tggcacccct
168841 ggaagcaaga gagtgccagg tactatttgt aatacaggaa tgaaatacct aattgtatga
168901 aattgaattc taactgaacc agtttgttca gttaaatttt ttttttcaat tagagtgctt
168961 acttcagtat ctaacactag acagtaaact gtagacaaaa gacctacaga atttctgaat
169021 ggtatcaaat tcaccacact taaaactttg ggatgtctaa tttcaaccaa cagctttctt
169081 tcttcataat gttgaatata tgtgtatcta ttttagctaa atttaatata tatcaatata
169141 ctttgataga tattttatat aaactattag actatagtat tatgagtaaa agacccacca
169201 tttcccaagc aattataaag aacgatcaaa attttaatgg gttgttagta ttatttcttt
169261 aaagattgtg atactgataa atatttggcc acatttttaat agaattatac atgggatgtg
169321 tgtgtgtgtg tgtgtgtgtg tatatgtgtg tgtgtatata tatatggcag tagagatata
169381 tatatctaca cacatctaga tatatatata catgtatatc tatatataca cacatatatc
169441 tgtgtgtata tatacatatg tatatatacc tacatacata tgtacatata catacatgca
169501 tatatctgta catatatata tagtgtgtgt gtgtgtatat atatatatat atatatattt
169561 ttttttttcct gagccaaaac aaaatactag gttgtaatag ctgttctttc agaaggaaga
169621 aaaacaacat gtgctgaact ctgagtttga tgttttttgta ttttacttcc tattttcata
169681 tcagtccatt tatttattca ggaagaattt attgagcata tattatgaac acagcttttg
```

FIG. 1 (cont.) (SEQ ID NO: 1)

```
169741 ctaaggacag ggtatgcagc agttatggcc tagtaggaga tatggatgtt aaaaacaaaa
169801 tgctcacaaa tgcacatata atcttaatac tcattgtaag ctatgaaagc agagtgtgag
169861 tattatgaga ccatatgttg ggagatttta tttggtattg aggatcagga aagatacccc
169921 tgaggaagtg atatttaatt tgaaacctaa agaaagcagt tggccatggg aagaaggtag
169981 ggaatgagat tcccaagcaa taggaatcca atgtgtgaag aagctgaggg agtgaaagaa
170041 agctagtgtg gtggcaggaa gaaagagaag agaatggaga agggcactaa atgagtcaga
170101 gaagtaggag gggctaaacc atgtagggtc gtgtaggcca tcttaaaggc ctgagtgtag
170161 tggaaaacct ttgaaggttt gttaaaaggt caatgaaatg ttctaatttc tgttgtagtg
170221 aattgctttg attgctgaat gcgaatggat gggtagagat gcaagagtga aagggaagaa
170281 atcaattagg aggctcttgc cctgctccag ataggactga taattaattt tatttgggaa
170341 gatcagggag aaagataagt catgaatgac tcccaagttt ctggattgaa gaaatgaagg
170401 taccatacac tgagatggga aagcctaggg gtagagtagc tttgagaaga aaggtagcat
170461 ttccccattt cataaaacat ggaagaacaa agaggctgga ttcctgtttg tagacatacc
170521 ttccaggcca gaactgcatt actacaacat ctttgcaagc cacattgcct ttcataactc
170581 tgtgtcagtg ttgatgccgt aacatctttg gccttccccc taccatcctc ccgcagtcct
170641 ccatgataat gccattattc cgtttcaaat tgtgtgcttc cattggatgt gtgagtctcc
170701 ttgaaagtta taatgaggct gtagcccata tgaaatgctt caactcaggt cctgcatagg
170761 aagaggaagc taatctctcc aggaactgag cctgtggcta gagggatgga taattgttta
170821 aataaagaat atgctgctga gtactgatgg gctctttatg tacccatttg gctgctgctg
170881 cccaaccttt aatctttcct gagctttaaa taggaaggaa aaaatggtcc acaaaggatt
170941 tgagccattt tgctgtggtg atgaggagca cgggtttaga gacaaacact cctgtgtttg
171001 aattccagct cctactatct cctagctaag tgaccttgga caagtcactt accttctcca
171061 acctgctgtt tcttcatgta cgtaatagga tttacctcat gaggttgaca tgaagattga
171121 aagaggtaac atatagaatg agcctgtccc aggacatggt tcatgataag tctgccataa
171181 atgggagcta tgtgtcccac cctttggag gagataactg ttctgtagca ggtaatatat
171241 tgtttgatac ttggttaacc cttacaatta tcatttcctg ttcttctcaa taatgctaga
171301 aaccttttat ttaaagaacc acaatataaa atgaaaaata tataaaaaaa gcaaatggaa
171361 aaattctatt ggcaaggctt tttaacttta tatactaaat aaatccaatt gcttaaataa
171421 tgaactgact caagttctca gcactgcttc ttgtttaatt ctctttagtt tttcagaatt
171481 ctccaataat gacctttgtc tactctcttc agtttattca gaattactt ttatttacat
171541 agaagtttgg aagtggatac acaaacatat ccctcacata tcttatgatc ctatgagtca
171601 tatactcatc tcttatattc cctctgtaaa gcaatgtagg tacctttcag gaaggtgatt
171661 tttatgtagg ttgagaaata tcagcatgga ggtcctagct gacctctcta gagagtttct
171721 gagacatttg acaacaactt tttctttaag tcatcagtta tgccccgggg tatgaaattt
171781 ctaacatgat cctcagtaaa cttggctgcc ttgctgagga tactctccat ctgcctgaga
171841 gacacagaca ccattaattg ggaattgact tgacttgtgt ggtccttgt ggaccagatg
171901 gccactaaat attctcattt caaggcaatt ggtaaaaact acacttcaag aaatttcatt
171961 cttaattccc cttagtggat gttattaacc aaaggcaaaa gaaaaaaagg gtaaaaaaaa
172021 tattctaaat gttaatatca aaaatattat tttcaattca ccccaggcac agagaactaa
172081 gtattattat tgctattgca ccggcattcc ccaatgagac agtgattttc ttttaagaca
172141 tttttaaata atataggcag aattaagtag acggtgatct ggtaagtaga tgtttcaggg
172201 taacagctgt gcaatgctcc atgcagggaa ttagattgtc attttattcc ttaccaggaa
172261 catacattca gttaaacaat tatttgactt ctgctcttcc actgatttct aagttgaggc
172321 tctctcttgt gcctgtctga tcagataagt agagttgtgc cttggtttat agatgagata
172381 aatgtgtatt tgaataagca taagttaaag aaatttaaa atcccttagg aagctaggct
172441 tatcagagaa atccaaggaa atacattaac aaactaggaa tttgttctaa caggttaatt
172501 ataactcata aacttattgg gtttttttac cttttaattt tatattacat ttgcttataa
172561 taaggaatat tgctaggaat aaaattttt aatattctac aattaacaat tatctcaatt
172621 tctttattct aaagacattg ggattagaaa aatgttcaca agggactcca atattgctg
172681 tagtatttgt ttcttaaaag aatgatacaa agcagacatg ataaaatatt aaaatttgag
172741 agaacttgat ggtaagtaca tgggtgtttc ttatttaaa ataattttc tacttgaaat
172801 attttacaat acaataaggg aaaaataaaa agttatttaa gttattcata ctttcttctt
172861 cttttctttt ttgctataga aagtatttat tttttctgga acatttagaa aaaacttgga
172921 tccctatgaa cagtggagtg atcaagaaat atggaaagtt gcagatgagg taaggctgct
172981 aactgaaatg attttgaaag gggtaactca taccaacaca aatggctgat atagctgaca
173041 tcattctaca cactttgtgt gcatgtatgt gtgtgcacaa ctttaaaatg gagtacccta
173101 acatacctgg agcaacaggt acttttgact ggacctaccc taactgaaa tgattttgaa
173161 agaggtaact cataccaaca caaatggttg atatggctaa gatcattcta cacactttgt
173221 gtgcatgtat ttctgtgcac aacttcaaaa tggagtaccc taaaatacct ggcgcgacaa
```

FIG. 1 (cont.) (SEQ ID NO: 1)

```
173281 gtacttttga ctgagcctac ttctctcctc actggtatgg ctccaaccat caggccctat
173341 cttggtccat ttaggctgct aaaataaaat accaaagact gagctgctta taagcaatct
173401 ttggaggctg agaagtcaaa gatcaaggtg ccagcaggtt tgctgtctcg tgagagcata
173461 cttcctggtt cattgatggt gctttcttgc tgtgtcctca cataatggaa agggcaagac
173521 ctctctggtg tctcttttac aatggcacta atcccatcat gagggctttg ttctcatgac
173581 ctaatcacct cccacatgtc ctacattcta atactatcac cttgggggtt aggattttaa
173641 catatgaatt tgaggaggtg gcgggggggga cacaaatatt tagaccatag catttcactc
173701 ctgacctcca aagttcatgt cttcttcaca tgcaaaatac attcattcca tcccaatagc
173761 ccccaaagtc ttaacttgtt ccagcatcaa cttacaaggc taaagtccaa ggtttcatct
173821 aaatatcagc taaatcagca caaacagcta aatcaggtag agtgggactt aaggtgtgat
173881 tcctctttag gcagattgct ctccaactat gaattgtga atcaaacct attatgtact
173941 ttcaaaataa aatggtgaaa caggcacagg ctagacagtc ccatttcaaa aagagaaat
174001 agaaaagaaa aaggagtga caggtctcta taagtctaaa actttaaggc ttgagaataa
174061 tttgctttgc tttgcctcca ggctcactgg ggtggtgtct tacctctgga cacactgggg
174121 tggaggctct atcctcatgg atttgagtgt ctcattcttt gtggcaggtc tgtgctccaa
174181 tcccacacct atggctccct gagtgtgcaa ttgcatgcct ggtggttcta ctggtctggg
174241 attgcatagg tggcccagcc ttcatagctc cactgggcat tgcctaatg tgggctctat
174301 gtggtgacct caccctggg cctctacctg ggccctgtga ctccctgggt tcttgaaatc
174361 taggtggagg cagccatccc cctacagttg tgctgagtgt agtgcatgag tgctggggtc
174421 tgctagagct atacctaggg tggtggagat gtatggcaat ggagtatggg gagctgatat
174481 ggtttgggtg tgtccccacc caaatcttgt cttgaattat aatttccata atctccatgt
174541 gttgagggag ggacctggtg agaggtgact ggatcatggg catggttttc ccatgctgtt
174601 catgtgatag tgagtgagtt ctcacgagat ccaatggttt cataaggcag ttttccctgc
174661 tcttgcaccc tctttcttgc ctgtcaccat gtaagacata actctttccc ttccgccatg
174721 attgtaagtt tcctgaggcc ttcccagcca tgtggaactg tgagtcaatt aaacctcttt
174781 tctttataaa ttacccagtc tctttacagc aatgtgaaaa tgtgctaata caggagcaaa
174841 gactgcagtg tgaggtggca atgtgaagtc tgcaatgtga ggtggcacgg ggcagttgta
174901 gccctcctt tgaaatcttt cttccctacc ccaggcctct gcactctgaa ctatgatggg
174961 aaaggcagct tggaagatct ccaaatggct ttggagtcat cttccattg tcttggacta
175021 taaattctgg cttctgttta ggtggctgac taatatcccc actgtctgaa tgcatagcac
175081 ctagtttctg ttgagatggc tagtccatag taatttactt atcaaatttg gccacaccct
175141 ttgtattctc tcctgagcag gctttctcat cttcacaat atggatagcc tgagaatttt
175201 ccaaattttg aagttctgct tcccttttga tcaataattc catttaaag tcatttctca
175261 tcttgaattt tactatgagc agtcaagagt aactaagctg ctccttcaac tttgcttgga
175321 tatttcctca gtcaaacatt caatttcatt gctttcaagt tctgccttcc acaaaacact
175381 aggacacaaa cagctcagcc aagttctttg acatttata agaaggatag cttttcctcc
175441 attgtccaat aacatgttcc tcatttccat ctgaaaaccc atcagattgg cctttaccgt
175501 ccatatttct gggaacattc tgctcatgac cacttaggta ttcggtaaga agatagtagc
175561 tttctctata gctctcctcc tctctggagc cctcaccaga atggccttta attgtccatt
175621 cacagcaatg taggcttttt ctagcatgta cctgaaaact cttccagcct ctactcatta
175681 ccttgttcca aagctgcttc cacattgagt atttgttaca gcagtaccca gatcccagta
175741 ccaatattct gtcttagtcc attggggcta ctacacgatg tcttataaac aacagtaaaa
175801 tttatttttc acagttgtgg aggctgggaa gttcaaaatc tggtgccagc agattttgtg
175861 tctggtgaag gccttcttcc tcacagatgg ctgtgttctc actgtgttgt tacatggcag
175921 aagagtgggc aggctagctc tctgggatgt cttttataag ggcagtaatc caaatcatgg
175981 gtttagggta gagccctcat gacctaaatc acctcccaaa ggcccacct cctaatacca
176041 gcatctttga agttaggatt tcaacatatg actttggcag gggacagaa gctttcagtt
176101 tatagcaaac cctataggta gcactacttt gtcctttcct aatcaatttg cgtcaatgaa
176161 acatgaatta aagagacct aggcgactcc actatactgg gattattccc agtataaatt
176221 atcatctctc cacaccttct catctactcc ctatctgagt tctgaagctc tccactacaa
176281 gaaggaggct ttggtttgac ttgatatact tctctgggaa acaggttag cataaaacag
176341 tgatgctcat tctagaacac ctgcaaatga caatagtttt cttcgaagt cgccaggaat
176401 cgtctgcctt tgggtatgtg gctgtgagca ctgccgggca aatgccata tgacctagat
176461 gaggcatatg ccatcctttg aagccattag gacattatat aggaaatata ttaactaaaa
176521 tggaataaaa ttttctaaat aacaccttat gtttatccaa caggtggttc attatacttg
176581 agagcattat acagaggaat ttgatgggga ggagagctgg agaaattctc gaaattctgg
176641 gtttctttaa cagaatactc tagctataaa cttataattt taaaaaataa gcattatatt
176701 aaagaaaagg gaacataaat tattttgttt tattaaactt aagtccaaag gtctggattg
176761 tggcagaata ggatcagggg acctaaaatg ttgagcctca aaggtcttct tagagaacaa
```

FIG. 1 (cont.) (SEQ ID NO: 1)

```
176821 ctgtattcca ctattagcgc ttttggtcct tttagcccaa tttctgttta tcccaaatgt
176881 tcttcccttt tctgccttcc ttcacagtgg accctgccag gagctttgaa atgcctgtga
176941 gtgttaaaca cttacccatt gagtgcccaa ccttaacatg cccctaataa aatgtactta
177001 gattaaccgt tttcattatc aaagtttcct tattacccaa caaacacagg cgctttaaag
177061 aaaacattaa ctaaattgca agtgacacat tttaagatct ttgatatgac ttcagagaat
177121 gcactatagg aacacaatgc aatgggaggg aaacttggga gggaagacat tagcctttat
177181 aaaatctgca agtattgcca aatcaaaata aaatttacag gaaagcagga tcataaatat
177241 aatctaaaat cttagaacct gtggttatga ttttaaatac taatacaatg caaatttttt
177301 acctgtttag gttttatttt catcagttca tatttaggta tatactttta ctgttctcct
177361 tttttataat ttaccattca caaagatgat gatgttagtc taactttaat gtcatgagtg
177421 ctttgagtag tagtgctaag ttttgttga gtagtagtgt gctttttga ttagtagtga
177481 taggtttttg atgagtaagc ctgctagcag catacaaaca aacaagcaag tatcagccta
177541 gagaagcaga aaaggcattt gggtttcaaa gtcacaaggc ctaggcttta gtctaataca
177601 gctgataata caatttgtcc aaacaggaca ttttgggtg tgtcaaacac taaactggac
177661 aggacattat gacaaaagtg caaagcagga ctttccgggg caaaccagga tgtatgtcat
177721 ctcactgagt cctctctttg tccttgccat gactagtatc tctagaggta aatgaacaga
177781 gtaatgacaa atagccagac acctgaatct tatcccaaca gcacctccta cataattccc
177841 cattatccca aatggaaatt aaaatatat acagtgataa ttccaggcca agaaatgctt
177901 tatttctagc ttggacttgg cttccatgtc cagtgtagaa tcttatcctt gctgatctgg
177961 actgtatctc atgaagccat gacttgtacc tagttactag ctggaaggct tagaacaaaa
178021 gctggtccag agagcctcct ttttccttat ttcctgggtc cacacccttta ccatggcagt
178081 ctgcctatca tttgatggag gaatttaaag caagtccaag ggaagggaag agagtttcta
178141 aaatctagaa cttggatagt ttaatttacc tatcccaaaa cagcttaggc ccagacagct
178201 tctctccaag attggtgcca aactgaaatt accagctgtg tagaccaaag agaatttcaa
178261 aagaaactga atcccaagag aaaaaaaaaa gacttctggc attgtggccc aataaattgg
178321 taggattgtt gtgacttttc aagtttacat gtaaatggg cccagcgcag tgcctggcaa
178381 atatgggtac taagtaaaag taactataat catgtttttt taatctggac ttcacttggt
178441 catcctttaa atggtgtctg acagaatcct agttcttgtc tcactttact tagtttccct
178501 gggaaatttc atgtgtcctt ttggctttaa ttaatatctc tattttgatg acctccatta
178561 tctgcctatt cccagagctt tccacctgat atctcagcac atgaaaagca ccttatgtca
178621 ataagtgagt tccttcctg ccccaccaca tacctgtcct gtgttcctaa ttccactgaa
178681 tggcatccca tcctccagtt tcccaaggcc aagacctggg actcatcttt cactctcaag
178741 ttcctccacg ggtacccaca tgtcacatcc tgtcaatgct gtccctgggg agtatctgaa
178801 atatattcac ttttcttcat ttccacctga caccactatt aacacttgca caaatttctg
178861 aggttcctgg ctcatttccc tcattgaccc ccaatagttc attctgctct ttgcagctct
178921 ggtgatcttt ccaaacccca catctgatca cttgtttctt cccttcatat ggctccttaa
178981 tgccttctgg actaagtcca cactgcttaa ggtggcttac caggtccttc atgattttgt
179041 ctttgtttgg cttttctacac tcactgccca acttcccctt acttcccatg attcagttat
179101 actgaatttc tttggttctc taaagcacat gtgctttctg ttctgcagag gcttttttgt
179161 tcacttgcta ttctctacct gggaaactcc cccagccctt cactgcctcc ttctaccatc
179221 tttcaggcct ctccttacac atcacttctt tccaaaaatc tgccttgaca ctccaggtct
179281 cggtttccta ggtgtaccct ataactccac ccctttcata gcatttctca ctctggctgg
179341 agatttacct tttaacttgt ccatgtcccc cactggagtg gaagttcctg gaggtcaggg
179401 attatatcct attaattgtt gtatttccag tgcctagagt agtcttgcat acatggatgg
179461 tattcaataa atattggttg aatgaataag gagttctttc atttcatatg taatagatca
179521 tggaaatagc cttgtgattg atacacagca ggtattacca tcctcacttt agaatgagga
179581 ctcagagcct tgagatgtct gagggccttg actgggacag ctggcagatg caggagcaga
179641 gctgcatcac ccctgtgggc tatctcaggg ttgtctgtaa tctaagtaca atgtctgttg
179701 attttggact gaaggctttt tgggtaattg tttgcttttt caatacttat aaaatagttt
179761 ccatccttac tcattgatag taaggttagt tattttagaa aacaagctaa atagcagaaa
179821 tagtggcctt ttaagtgaa aatttaccct gaaaaatcta cagagtagca aacagagtat
179881 caaaggagt tgactgtatc tatttttata actgccactt atggattatt cagtaaaacc
179941 acaattcact tttatgattt tttttcatgt ttctctgtca caagagcaaa ctcttgctcc
180001 ataataacat tccagaatac agcaatagca aaagtcaaca ttttgaatcc tttacaaact
180061 cttagacatt tttttttttt tagtttaaca tgttacaaaa caaaatttct tcttttttca
180121 cagcagtttg ggaagtacat actatttatt agctcatcag catgaagctg gaaaattctt
180181 tttcctaaag ttctttatat ctacaaactg ttgatgtttt catttattta tttttaatgc
180241 tacgttgtaa tgaaaatcat tggaaaactt tagattctag taattttgaa gtcttcttag
180301 tttggacagg actgagctaa agtttgtact ttttttaatt tattgaaaaa tggtttctaa
```

FIG. 1 (cont.) (SEQ ID NO: 1)

```
180361  tgatagtatt aacaagatta tattgggggc aggacgcagt ggctcacact tgtaatccta
180421  gcactttggg aggccgaggc ggttggatca cctgaggtca ggagttcaag accagcctgg
180481  ccaacatgta gaaatcccct ctccactaaa atacaaaaat tagctgggca tggtggcagg
180541  cactgtaatc ccagctactt gggaggctga ggcaggagaa ttgtttgaac ctgggagtcg
180601  gaggttgcag tgagcccaga tcgcaccact gcactccagc ctgggcaata gagcaagatt
180661  ctgtctcaaa aaggaagaaa gaaagattat attggggata tatatgtgtg tgtgtgtgtg
180721  tgtgtgtata tacacacaca tatatatata catatataca tatatataca tatttaaagg
180781  ataaaggatt ctgctgccac agatcactaa atcagatgat ctctagcaat ttcctgtttg
180841  tttgttttt  gcccatagtg cttatctctt tgaacagtaa ttttccactt actattttc
180901  tcccctttg  gaccataatt tcctttaagg cagagcctcc tgttactcat ctttgaatct
180961  ggggtctgtc agagtaccta gaatttaata aactctcatt aagagccagt tgaaagaata
181021  tatgactaag cagtcattta catccaaaag atccgtagga gaattcttat cagcacatgt
181081  gattggtaac aataactttg tacttttcaa aaacaattac taatctatct tgctttccat
181141  tatctcacca aaacctatta gcatgtctgg cagaaaatag atacttaata aatttcttaa
181201  atgtttactg acttcaattt taagttttat taactatgtt gacttttctc taatgaagat
181261  gattctaaaa agcttttac  tatacttcac agtgaataaa acagtgagat aggaatattg
181321  caaaatgtcc cctgtgttgg tcagtcttag tgtcattcat tttaaaaatt ctgttctcta
181381  aatattgaca gttatatata aatttatgta attgtttact tctaataaag aatttcatct
181441  ggggaaaaac atactttgct cagctctttg ccacaagtgc aaagtctaag acagtcaaat
181501  agctttccta gtacggcctt aggaacttag tatatgactg gtgtgaatct agagggagca
181561  tactgcattc tgaccaaaat ctccaccctg ttactatggc catcactaac ttcgcagtat
181621  tgcagtactt cctgctagct tagttcccaa ggcaacttgt gaaggaaaat ttttacaaag
181681  ctgttgtcac acaaaggtag tgtttcagtt cctgagccca tgtccttgga gttgcccagg
181741  ctccaataat actaataatt actgtacatt aggtacttac catgtgccat attctgcggg
181801  agccgctttc cacaaattat ctctggtaat ccttgtaaca ccctttgac  atcaatatta
181861  ttattttctc catttttta  catatgagat aaatgagact taaaataatg tgcctgatat
181921  catcagcaaa tgagctgagg agggcagatt caaagctgat tgtgtttgac tctagagctg
181981  cagtcttaag ccagaccttt tcttgctggt taattttact gaaaaaaaaa aaaaaaaaaa
182041  aaaaccctca aatactgctg attgatctaa agtactaaca tttctatcag tgttagggaa
182101  attttaattt tataatttga ttttgtgaga aatttatagc atcttgaata ctcacatgca
182161  aagtgatatg tcttagataa cattttacaa tggcagagct taagccagtg ctcagtcatt
182221  cattcatcct caagttttga ttcatttatc attcatcaaa actctgtttt gtttggccac
182281  ccacattcta ggagctcagt acatatttga taaatgaatg aattgttgag gttgacagtt
182341  acccaggact ggcattagga acacagagct gaagagcacg ttttacccct caagaagctt
182401  acagtctaac gagggaactt gcacaaatac tactatcact aggtgcctgg ttgaatggct
182461  taagagatga tcagggatat tcagaaggat atgtcaggct cagcaatggc atcacttgag
182521  agcatcaagg tgtttaggga actacaagat gtttggttct gctgggaata agagtgaagg
182581  gggctccatt tggatgcctc atacaccagg tgagagatct tagatttat  tccaccagga
182641  ggagaactac cataggattt aaaacagaaa tgatatggtc aaacctacat cttaggaaga
182701  tccctgggt  gtttgtatgg tggacttgca atttgactaa ttgagatttg taggatgatt
182761  cttaagagat gatgatgacc cagactggga tcactataat agagttggta aggaggagaa
182821  tgatttaaaa agtagttgga agaattctag ggatggagat aaacatttga aaattattaa
182881  cttataggtg gtcatcaata ccctgaaaat gactgggatc tcagaggaga gtctggagag
182941  ttggaaatga caaagactaa tattcaaggg ggcaggaaga gggagagttg ttcacacatg
183001  acaataggaa gaaatggcca tagagtgtgt ggttctctc  agccaagga  atagatgttt
183061  taagaaagga aaattcttgt ggtgggaagc agtagagatg acagatacac attaatttct
183121  tgagatttct agatgactaa atgggcagat gttgaatgat agctaaagga gaacccagaa
183181  acaagggagg gattttgttt ttgttttta  aaaaagatag accatagcag cttcatagac
183241  tgaaacaata aaaagttga  aggcacaaag aaagacacag gtcctctaac tccctgccca
183301  gtgcccttta ttcatattct cagcacttgt atttctaagt tttatgtttg agtcttcggg
183361  gatacatcag agtagtcccc cttgtctaat aaatgtgttt acatttcctg ccataccaga
183421  aaccccttctc aaactttaat gaatttctac aaggtgagat tactttaatg agaaaccaac
183481  caaggaaagg agtatcatct gcaatatact ttcaaatgtt ttttgcttgt tgtttcttg
183541  tccagctaaa aaaaaaaaaa aaaacaagc  cattggtcct aacacaactt tcatattcta
183601  ccccaatatc aaagaggctt aaaatctcct ggtcgtgtga tgggcacaca gttaattttt
183661  tgtgaacaaa cacagtgtta tgggccattt ctgaatttat ctctgaaatc ataagattct
183721  ttctgagcca ttatctcatt ctatattaca gtcaggtgga gccatctta  cctcctcata
183781  ctaaattcta gacttctcaa gggcaggaga caatcatctg tatatctctt tggccttcat
183841  acactcagga gtacttgcca aaaataaaca tttaatgcac atttatttga ataattgata
```

FIG. 1 (cont.) (SEQ ID NO: 1)

```
183901 agatccaata cttcaataac tttgtcatat ttttatagaa tgggtttcta tatctcattt
183961 gcattttcaa actttacttt tactgtctag cttaaaaaa aaagcctttg actctaatac
184021 agccctcata ttctacccca atatctaaga ggctttatat ctcctagtgt tgtaccacta
184081 ttttaactcc agtattttt acttcatagt tttacctatt tgttacagtt agttttatg
184141 aattcaagag atgaatagca attttccata tgtaatttaa aaaaccccac agttgactat
184201 tttatgctat cttttgtcct cagtcatgac agagtagaag atgggaggta gcaccaagga
184261 tgatgtcata cctccatcct ttatgctaca ttctatcttc tgtctacata agatgtcata
184321 ctagagggca tatctgcaat gtatacatat tatcttttcc agcatgcatt cagttgtgtt
184381 ggaataattt atgtacacct ttataaacgc tgagcctcac aagagccatg tgccacgtat
184441 tgttttctta ctactttttg ggatacctgg cacgtaatag acactcattg aaagtttcct
184501 aatgaatgaa gtacaaagat aaaacaagtt atagactgat tcttttgagc tgtcaaggtt
184561 gtaaatagac ttttgctcaa tcaattcaaa tggtggcagg tagtgggggt agagggattg
184621 gtatgaaaaa cataagcttt cagaactcct gtgtttattt ttagaatgtc aactgcttga
184681 gtgttttaa ctctgtggta tctgaactat cttctctaac tgcaggttgg gctcagatct
184741 gtgatagaac agtttcctgg gaagcttgac tttgtccttg tggatggggg ctgtgtccta
184801 agccatggcc acaagcagtt gatgtgcttg gctagatctg ttctcagtaa ggcgaagatc
184861 ttgctgcttg atgaacccag tgctcatttg gatccagtgt gagtttcaga tgttctgtta
184921 cttaatagca cagtgggaac agaatcatta tgcctgcttc atggtgacac atatttctat
184981 taggctgtca tgtctgcgtg tgggggtctc cccaagata tgaaataatt gcccagtgga
185041 aatgagcata aatgcatatt tccttgctaa gagtcttgtg ttttcttccg aagatagttt
185101 ttagtttcat acaaactctt cccccttgtc aacacatgat gaagctttta aatacatggg
185161 cctaatctga tccttatgat ttgcctttgt atcccattta taccataagc atgtttatag
185221 ccccaaataa agaagtactg gtgattctac ataatgaaaa atgtactcat ttattaaagt
185281 ttctttgaaa tatttgtcct gtttatttat ggatacttag agtctacccc atggttgaaa
185341 agctgattgt ggctaacgct atatcaacat tatgtgaaaa gaacttaaag aaataagtaa
185401 tttaaagaga taatagaaca atagacatat tatcaaggta aatacagatc attactgttc
185461 tgtgatatta tgtgtggtat ttttcttctt ttctagaaca taccaaataa ttagaagaac
185521 tctaaaacaa gcatttgctg attgcacagt aattctctgt gaacacagga tagaagcaat
185581 gctggaatgc caacaatttt tggtgagtct ttataacttt acttaagatc tcattgccct
185641 tgtaattctt gataacaatc tcacatgtga tagttcctgc aaattgcaac aatgtacaag
185701 ttcttttcaa aaatatgtat catacagcca tccagcttta ctcaaaatag ctgcacaagt
185761 ttttcacttt gatctgagcc atgtggtgag gttgaaatat agtaaatcta aaatggcagc
185821 atattactaa gttatgttta taaataggat atatatactt tttgagccct ttatttgggg
185881 accaagtcat acaaaatact ctactgttta agattttaaa aaaggtccct gtgattcttt
185941 caataactaa atgtcccatg gatgtggtct gggacaggcc tagttgtctt acagtctgat
186001 ttatggtatt aatgacaaag ttgagaggca catttcattt ttctagccat gatttgggtt
186061 caggtagtac ctttctcaac caccttctca ctgttcttaa aaaaactgtc acatggccag
186121 gcacagtggc ttacatctgt aatcccaata ctttgggagg ctgaggtggg gggattactt
186181 gaggccagga attcaagacc agccaggca acatagtgag gccccatctg tcttattaa
186241 aacaaaacaa aactgtcaca gcttctttca agtgatgttt acaaattccc tatggtttag
186301 tcacaaggaa gttctgagga tgatgtatca cgtcatttct gttcaggctt ttgagcctcc
186361 tggaggtaaa tggtttcctt actgaaggct tgttattacc atgattatca ctaagcttga
186421 agtaacaaat tagggggca gactcacaac ctcttgccct gccatggaca agttcaagaa
186481 tctaagtaaa gtcctctatt gtctgatctt ggatttgctc aacctgaaca agccaaggag
186541 gtgtattaaa ctcaggcaca tcctgaccaa tttggaattc ttaagcttca gatcactgtg
186601 gaagaggctc aactctttat ggtgctgtag acttacgctc attttctagg taatttataa
186661 gggacctaat attttgtttt caagcaact tcagttctac taaacctccc tgaagaatct
186721 tccagctgct gagtagaaaa tcacaactaa tttcacagat ggtagaacct ccttagagca
186781 aaaggacaca gcagttaaat gtgacatacc tgattgttca aaatgcaagg ctctggacat
186841 tgcattcttt gactttatt ttccttgag cctgtgccag tttctgtccc tgctctggtc
186901 tgacctgcct tctgtccag atctcactaa cagccatttc cctaggtcat agaagagaac
186961 aaagtgcggc agtacgattc catccagaaa ctgctgaacg agaggagcct cttccggcaa
187021 gccatcagcc cctccgacag ggtgaagctc tttcccacc ggaactcaag caagtgcaag
187081 tctaagcccc agattgctgc tctgaaagag gagacagaag aagaggtgca agatacaagg
187141 ctttagagag cagcataaat gttgacatgg acatttgct catggaattg gagctcgtgg
187201 gacagtcacc tcatggaatt ggagctcgtg gaacagttac ctctgcctca gaaaacaagg
187261 atgaattaag tttttttta aaaagaaac atttggtaag gggaattgag gacactgata
187321 tgggtcttga taaatggctt cctggcaata gtcaaattgt gtgaaggta cttcaaatcc
187381 ttgaagattt accacttgtg ttttgcaagc cagatttcc tgaaaaccct tgccatgtgc
```

FIG. 1 (cont.) (SEQ ID NO: 1)

```
187441 tagtaattgg aaaggcagct ctaaatgtca atcagcctag ttgatcagct tattgtctag
187501 tgaaactcgt taatttgtag tgttggagaa gaactgaaat catacttctt agggttatga
187561 ttaagtaatg ataactggaa acttcagcgg tttatataag cttgtattcc ttttctctc
187621 ctctccccat gatgtttaga aacacaacta tattgtttgc taagcattcc aactatctca
187681 tttccaagca agtattagaa taccacagga accacaagac tgcacatcaa aatatgcccc
187741 attcaacatc tagtgagcag tcaggaaaga gaacttccag atcctggaaa tcagggttag
187801 tattgtccag gtctaccaaa aatctcaata tttcagataa tcacaataca tcccttacct
187861 gggaaagggc tgttataatc tttcacaggg gacaggatgg ttcccttgat gaagaagttg
187921 atatgccttt tcccaactcc agaaagtgac aagctcacag acctttgaac tagagtttag
187981 ctggaaaagt atgttagtgc aaattgtcac aggacagccc ttctttccac agaagctcca
188041 ggtagagggt gtgtaagtag ataggccatg ggcactgtgg gtagacacac atgaagtcca
188101 agcatttaga tgtataggtt gatggtggta tgttttcagg ctagatgtat gtacttcatg
188161 ctgtctacac taagagagaa tgagagacac actgaagaag caccaatcat gaattagttt
188221 tatatgcttc tgttttataa ttttgtgaag caaaattttt tctctaggaa atatttattt
188281 taataatgtt tcaaacatat ataacaatgc tgtattttaa aagaatgatt atgaattaca
188341 tttgtataaa ataatttta tatttgaaat attgactttt tatggcacta gtatttctat
188401 gaaatattat gttaaaactg gacagggga gaacctaggg tgatattaac caggggccat
188461 gaatcacctt ttggtctgga gggaagcctt ggggctgatg cagttgttgc ccacagctgt
188521 atgattccca gccagcacag cctcttagat gcagttctga agaagatggt accaccagtc
188581 tgactgtttc catcaagggt acactgcctt ctcaactcca aactgactct taagaagact
188641 gcattatatt tattactgta agaaaatatc acttgtcaat aaaatccata catttgtgtg
188701 aaa
```

FIG. 1 (cont.) (SEQ ID NO: 1)

| | | | | | | |
|---|---|---|---|---|---|---|
| 1 | aattggaagc | aaatgacatc | acagcaggtc | agagaaaaag | ggttgagcgg | caggcaccca |
| 61 | gagtagtagg | tctttggcat | taggagcttg | agcccagacg | gccctagcag | ggaccccagc |
| 121 | gcccgagaga | ccatgcagag | gtcgcctctg | gaaaaggcca | gcgttgtctc | caaactttt |
| 181 | ttcagctgga | ccagaccaat | tttgaggaaa | ggatacagac | agcgcctgga | attgtcagac |
| 241 | atataccaaa | tcccttctgt | tgattctgct | gacaatctat | ctgaaaaatt | ggaaagagaa |
| 301 | tgggatagag | agctggcttc | aaagaaaaat | cctaaactca | ttaatgccct | tcggcgatgt |
| 361 | tttttctgga | gatttatgtt | ctatggaatc | tttttatatt | taggggaagt | caccaaagca |
| 421 | gtacagcctc | tcttactggg | aagaatcata | gcttcctatg | acccggataa | caaggaggaa |
| 481 | cgctctatcg | cgatttatct | aggcataggc | ttatgccttc | tctttattgt | gaggacactg |
| 541 | ctcctacacc | cagccatttt | tggccttcat | cacattggaa | tgcagatgag | aatagctatg |
| 601 | tttagtttga | tttataagaa | gactttaaag | ctgtcaagcc | gtgttctaga | taaaataagt |
| 661 | attggacaac | ttgttagtct | cctttccaac | aacctgaaca | aatttgatga | aggacttgca |
| 721 | ttggcacatt | tcgtgtggat | cgctcctttg | caagtggcac | tcctcatggg | gctaatctgg |
| 781 | gagttgttac | aggcgtctgc | cttctgtgga | cttggtttcc | tgatagtcct | tgcccttttt |
| 841 | caggctgggc | tagggagaat | gatgatgaag | tacagagatc | agagagctgg | gaagatcagt |
| 901 | gaaagacttg | tgattacctc | agaaatgatt | gaaaatatcc | aatctgttaa | ggcatactgc |
| 961 | tgggaagaag | caatggaaaa | aatgattgaa | aacttaagac | aaacagaact | gaaactgact |
| 1021 | cggaaggcag | cctatgtgag | atacttcaat | agctcagcct | tcttcttctc | agggttcttt |
| 1081 | gtggtgtttt | tatctgtgct | tccctatgca | ctaatcaaag | gaatcatcct | ccggaaaata |
| 1141 | ttcaccacca | tctcattctg | cattgttctg | cgcatggcgg | tcactcggca | atttccctgg |
| 1201 | gctgtacaaa | catggtatga | ctctcttgga | gcaataaaca | aaatacagga | tttcttacaa |
| 1261 | aagcaagaat | ataagacatt | ggaatataac | ttaacgacta | cagaagtagt | gatggagaat |
| 1321 | gtaacagcct | tctgggagga | gggatttggg | gaattatttg | agaaagcaaa | acaaaacaat |
| 1381 | aacaatagaa | aaacttctaa | tggtgatgac | agcctcttct | tcagtaattt | ctcacttctt |
| 1441 | ggtactcctg | tcctgaaaga | tattaatttc | aagatagaaa | gaggacagtt | gttggcggtt |
| 1501 | gctggatcca | ctggagcagg | caagacttca | cttctaatga | tgattatggg | agaactggag |
| 1561 | ccttcagagg | gtaaaattaa | gcacagtgga | agaatttcat | tctgttctca | gttttcctgg |
| 1621 | attatgcctg | gcaccattaa | agaaaatatc | atctttggtg | tttcctatga | tgaatataga |
| 1681 | tacagaagcg | tcatcaaagc | atgccaacta | gaagaggaca | tctccaagtt | tgcagagaaa |
| 1741 | gacaaatatag | ttcttggaga | aggtggaatc | acactgagtg | gaggtcaacg | agcaagaatt |
| 1801 | tctttagcaa | gagcagtata | caaagatgct | gatttgtatt | tattagactc | tccttttgga |
| 1861 | tacctagatg | ttttaacaga | aaaagaaata | tttgaaagct | gtgtctgtaa | actgatggct |
| 1921 | aacaaaacta | ggatttggt | cacttctaaa | atggaacatt | taaagaaagc | tgacaaaata |
| 1981 | ttaattttgc | atgaaggtag | cagctatttt | tatgggacat | tttcagaact | ccaaaatcta |
| 2041 | cagccagact | ttagctcaaa | actcatggga | tgtgattctt | tcgaccaatt | tagtgcagaa |
| 2101 | agaagaaatt | caatcctaac | tgagaccta | caccgtttct | cattagaagg | agatgctcct |
| 2161 | gtctcctgga | cagaaacaaa | aaaacaatct | tttaaacaga | ctggagagtt | tggggaaaaa |
| 2221 | aggaagaatt | ctattctcaa | tccaatcaac | tctatacgaa | aattttccat | tgtgcaaaag |
| 2281 | actcccttac | aaatgaatgg | catcgaagag | gattctgatg | agcctttaga | gagaaggctg |
| 2341 | tccttagtac | cagattctga | gcagggagag | gcgatactgc | ctcgcatcag | cgtgatcagc |
| 2401 | actggcccca | cgcttcaggc | acgaaggagg | cagtctgtcc | tgaacctgat | gacacactca |
| 2461 | gttaaccaag | gtcagaacat | tcaccgaaag | acaacagcat | ccacacgaaa | agtgtcactg |
| 2521 | gcccctcagg | caaacttgac | tgaactggat | atatattcaa | gaaggttatc | tcaagaaact |
| 2581 | ggcttggaaa | taagtgaaga | aattaacgaa | gaagacttaa | aggagtgctt | ttttgatgat |
| 2641 | atggagagca | taccagcagt | gactacatgg | aacacatacc | ttcgatatat | tactgtccac |

FIG. 2 (SEQ ID NO: 2)

| | | | | | | |
|---|---|---|---|---|---|---|
| 2701 | aagagcttaa | tttttgtgct | aatttggtgc | ttagtaattt | ttctggcaga | ggtggctgct |
| 2761 | tctttggttg | tgctgtggct | ccttggaaac | actcctcttc | aagacaaagg | gaatagtact |
| 2821 | catagtagaa | ataacagcta | tgcagtgatt | atcaccagca | ccagttcgta | ttatgtgttt |
| 2881 | tacatttacg | tgggagtagc | cgacactttg | cttgctatgg | gattcttcag | aggtctacca |
| 2941 | ctggtgcata | ctctaatcac | agtgtcgaaa | attttacacc | acaaaatgtt | acattctgtt |
| 3001 | cttcaagcac | ctatgtcaac | cctcaacacg | ttgaaagcag | gtgggattct | taatagattc |
| 3061 | tccaaagata | tagcaatttt | ggatgacctt | ctgcctctta | ccatatttga | cttcatccag |
| 3121 | ttgttattaa | ttgtgattgg | agctatagca | gttgtcgcag | ttttacaacc | ctacatcttt |
| 3181 | gttgcaacag | tgccagtgat | agtggctttt | attatgttga | gagcatattt | cctccaaacc |
| 3241 | tcacagcaac | tcaaacaact | ggaatctgaa | ggcaggagtc | caattttcac | tcatcttgtt |
| 3301 | acaagcttaa | aaggactatg | gacacttcgt | gccttcggac | ggcagcctta | ctttgaaact |
| 3361 | ctgttccaca | aagctctgaa | tttacatact | gccaactggt | tcttgtacct | gtcaacactg |
| 3421 | cgctggttcc | aaatgagaat | agaaatgatt | tttgtcatct | tcttcattgc | tgttaccttc |
| 3481 | atttccattt | taacaacagg | agaaggagaa | ggaagagttg | gtattatcct | gactttagcc |
| 3541 | atgaatatca | tgagtacatt | gcagtgggct | gtaaactcca | gcatagatgt | ggatagcttg |
| 3601 | atgcgatctg | tgagccgagt | ctttaagttc | attgacatgc | caacagaagg | taaacctacc |
| 3661 | aagtcaacca | aaccatacaa | gaatggccaa | ctctcgaaag | ttatgattat | tgagaattca |
| 3721 | cacgtgaaga | aagatgacat | ctggccctca | gggggcaaa | tgactgtcaa | agatctcaca |
| 3781 | gcaaaataca | cagaaggtgg | aaatgccata | ttagagaaca | tttccttctc | aataagtcct |
| 3841 | ggccagaggg | tgggcctctt | gggaagaact | ggatcaggga | agagtacttt | gttatcagct |
| 3901 | tttttgagac | tactgaacac | tgaaggagaa | atccagatcg | atggtgtgtc | ttgggattca |
| 3961 | ataactttgc | aacagtggag | gaaagccttt | ggagtgatac | cacagaaagt | atttatttt |
| 4021 | tctggaacat | ttagaaaaaa | cttggatccc | tatgaacagt | ggagtgatca | agaaatatgg |
| 4081 | aaagttgcag | atgaggttgg | gctcagatct | gtgatagaac | agtttcctgg | gaagcttgac |
| 4141 | tttgtccttg | tggatgggg | ctgtgtccta | agccatggcc | acaagcagtt | gatgtgcttg |
| 4201 | gctagatctg | ttctcagtaa | ggcgaagatc | ttgctgcttg | atgaacccag | tgctcatttg |
| 4261 | gatccagtaa | cataccaaat | aattagaaga | actctaaaac | aagcatttgc | tgattgcaca |
| 4321 | gtaattctct | gtgaacacag | gatagaagca | atgctggaat | gccaacaatt | tttggtcata |
| 4381 | gaagagaaca | aagtgcggca | gtacgattcc | atccagaaac | tgctgaacga | gaggagcctc |
| 4441 | ttccggcaag | ccatcagccc | ctccgacagg | gtgaagctct | ttccccaccg | gaactcaagc |
| 4501 | aagtgcaagt | ctaagcccca | gattgctgct | ctgaaagagg | agacagaaga | agaggtgcaa |
| 4561 | gatacaaggc | tttagagagc | agcataaatg | ttgacatggg | acatttgctc | atggaattgg |
| 4621 | agctcgtggg | acagtcacct | catggaattg | gagctcgtgg | aacagttacc | tctgcctcag |
| 4681 | aaaacaagga | tgaattaagt | ttttttttaa | aaaagaaaca | tttggtaagg | ggaattgagg |
| 4741 | acactgatat | gggtcttgat | aaatggcttc | ctggcaatag | tcaaattgtg | tgaaaggtac |
| 4801 | ttcaaatcct | tgaagattta | ccacttgtgt | tttgcaagcc | agattttcct | gaaacccctt |
| 4861 | gccatgtgct | agtaattgga | aaggcagctc | taaatgtcaa | tcagcctagt | tgatcagctt |
| 4921 | attgtctagt | gaaactcgtt | aatttgtagt | gttggagaag | aactgaaatc | atacttctta |
| 4981 | gggttatgat | taagtaatga | taactggaaa | cttcagcggt | ttatataagc | ttgtattcct |
| 5041 | ttttctctcc | tctcccatg | atgttagaa | acacaactat | attgtttgct | aagcattcca |
| 5101 | actatctcat | ttccaagcaa | gtattagaat | accacaggaa | ccacaagact | gcacatcaaa |
| 5161 | atatgcccca | ttcaacatct | agtgagcagt | caggaaagag | aacttccaga | tcctggaaat |
| 5221 | cagggttagt | attgtccagg | tctaccaaaa | atctcaatat | ttcagataat | cacaatacat |
| 5281 | cccttacctg | ggaaagggct | gttataatct | ttcacagggg | acaggatggt | tcccttgatg |
| 5341 | aagaagttga | tatgcctttt | cccaactcca | gaaagtgaca | agctcacaga | cctttgaact |
| 5401 | agagtttagc | tggaaaagta | tgttagtgca | aattgtcaca | ggacagccct | tctttccaca |

FIG. 2 (cont.) (SEQ ID NO: 2)

| | | | | | | |
|---|---|---|---|---|---|---|
| 5461 | gaagctccag | gtagagggtg | tgtaagtaga | taggccatgg | gcactgtggg | tagacacaca |
| 5521 | tgaagtccaa | gcatttagat | gtataggttg | atggtggtat | gttttcaggc | tagatgtatg |
| 5581 | tacttcatgc | tgtctacact | aagagagaat | gagagacaca | ctgaagaagc | accaatcatg |
| 5641 | aattagtttt | atatgcttct | gttttataat | tttgtgaagc | aaaattttt | ctctaggaaa |
| 5701 | tatttatttt | aataatgttt | caaacatata | ttacaatgct | gtattttaaa | agaatgatta |
| 5761 | tgaattacat | ttgtataaaa | taatttttat | atttgaaata | ttgacttttt | atggcactag |
| 5821 | tatttttatg | aaatattatg | ttaaaactgg | gacaggggag | aacctagggt | gatattaacc |
| 5881 | aggggccatg | aatcaccttt | tggtctggag | ggaagccttg | gggctgatcg | agttgttgcc |
| 5941 | cacagctgta | tgattcccag | ccagacacag | cctcttagat | gcagttctga | agaagatggt |
| 6001 | accaccagtc | tgactgtttc | catcaagggt | acactgcctt | ctcaactcca | aactgactct |
| 6061 | taagaagact | gcattatatt | tattactgta | agaaaatatc | acttgtcaat | aaaatccata |
| 6121 | catttgtgta | | | | | |

FIG. 2 (cont.) (SEQ ID NO: 2)

| | | | | | | |
|---|---|---|---|---|---|---|
| 1 | mqrsplekas | vvsklffswt | rpilrkgyrq | rlelsdiyqi | psvdsadnls | eklerewdre |
| 61 | laskknpkli | nalrrcffwr | fmfygiflyl | gcvtkavqpl | llgriiasyd | pdnkccrsia |
| 121 | iylgig1c11 | fivrtllllhp | aifglhhigm | qmriamfsli | ykktlklssr | vldkisigql |
| 181 | vsllsnnlnk | fdeglalahf | vwiaplqval | lmgliwellq | asafcglgfl | ivlalfgagl |
| 241 | grmmmkyrdq | ragkiserlv | itsemieniq | svkaycweea | mekmienlrq | telkltrkaa |
| 301 | yvryfnssaf | ffsgffvvfl | svlpyalikg | iilrkiftti | sfcivlrmav | trqfpwavqt |
| 361 | wydslgaink | iqdflqkqey | ktleynlttt | evvmenvtaf | weegfgelfe | kakqnnnnrk |
| 421 | tsngddslff | snfsllgtpv | lkdinfkier | gqllavagst | gagktsllmm | imgelepseg |
| 481 | kikhsgrisf | csqfswimpg | tikeniifgv | sydeyryrsv | ikacqleedi | skfaekdniv |
| 541 | lgeggitlsg | gqrarislar | avykdadlyl | ldspfgyldv | ltekeifesc | vcklmanktr |
| 601 | ilvtskmehl | kkadkililh | egssyfygtf | selqnlqpdf | ssklmgcdsf | dqfsaerrns |
| 661 | iltetlhrfs | legdapvswt | etkkqsfkqt | gefgekrkns | ilnpinsirk | fsivqktplq |
| 721 | mngieedsde | plerrlslvp | dseqgeailp | risvistgpt | lqarrrqsvl | nlmthsvnqg |
| 781 | qnihrkttas | trkvslapqa | nlteldiysr | rlsqetglei | seeineedlk | ecffddmesi |
| 841 | pavttwntyl | ryitvhksli | fvliwclvif | laevaaslvv | lwllgntplq | dkgnsthsrn |
| 901 | nsyaviitst | ssyyvfyiyv | gvadtllamg | ffrglplvht | litvskilhh | kmlhsvlqap |
| 961 | mstlntlkag | gilnrfskdi | ailddllplt | ifdfiqllli | vigaiavvav | lqpyifvatv |
| 1021 | pvivafimlr | ayflqtsqql | kqlesegrsp | ifthlvtslk | glwtlrafgr | qpyfetlfhk |
| 1081 | alnlhtanwf | lylstlrwfq | mricmifvif | fiavtfisil | ttgcgcgrvg | iiltlamnim |
| 1141 | stlqwavnss | idvdslmrsv | srvfkfidmp | tegkptkstk | pykngqlskv | miienshvkk |
| 1201 | ddiwpsggqm | tvkdltakyt | eggnaileni | sfsispgqrv | gllgrtgsgk | stllsaflrl |
| 1261 | lntegeigid | gvswdsitlq | qwrkafgvip | qkvfifsgtf | rknldpyeqw | sdqeiwkvad |
| 1321 | cvglrsvicq | fpgkldfvlv | dggcvlshgh | kqlmclarsv | lskakillld | cpsahldpvt |
| 1381 | yqiirrtlkq | afadctvilc | ehrieamlec | qqflvieenk | vrqydsiqkl | lnerslfrqa |
| 1441 | ispsdrvklf | phrnsskcks | kpqiaalkee | teeevqdtrl | | |

FIG. 3 (SEQ ID NO: 3)

```
   1 gaattcaaag gaaaacataa gatgcaattc gtgcctccaa ggaggttgta gggaagaggg
  61 gttatgaatg tatgtaaata gaagttggtg tgcgtgtgtg tttataaaca gaattgtcag
 121 accaaacatt attttggaag cagtaaaagt aaactagaat ctggcctagt catgtcccag
 181 gacacctctt tcaagtcctg aaacatcttt gtaagactgt aatgtgtgtt tacatcctag
 241 gtaatcactg tggcccactg ttgaagagct gtggctgttc ttacccttct agttagataa
 301 acttataagc acaaccagac tacatatatg aagctgaaga gaccttgtct ttttttaacg
 361 agcttttctt cccgatagga gtgactattt cttttcttct tccacatttt caggtttag
 421 tgtacttgtg attgctaccc acttatcact attaaagtct actcaggaga gaatctgaga
 481 aacactctca aattaagttg aacatgatgg ataagtaaag tattgtgaaa gttcactctc
 541 atgatttcta atggtgaaac ctggcagggt gactaatctt tgacgagaag gttatcactt
 601 ataatctttc atatattgag atcatttgta agaagcaccc agcacattgc tgaacacaaa
 661 gtaggtatta aataaatgtt ggcttccttt tctcctactc atcctcgctc ttcttttaa
 721 tataccttta aaatgatgcc acagaaatgg ccacccaatc ttctatattt aaggtcagtt
 781 cttgcattag gaaattctat aggggaagta tgtgaagtat gtgtagtcag tcattaaatg
 841 cttgggctct ggccacagat tgtttaggtt taaatcccag tttcctcttt tattattaat
 901 tgtgcaactt gcttgggaaa acatgaaact tgttttttcct caggttcatt atctgtaata
 961 tatagtgaat gaagaagttt cctgtcccat gaaggtgttg taaagattaa aaaaggcaaa
1021 ttaggctgtg tatttgtcat aataattggc atatatggta agtgaccaac aaccataagg
1081 tattataaaa ttgttataaa atgatatgag ctatcattga gcagcatgaa agaagagctt
1141 cactgtttca cctactatca ccctggccca ttaatctctt tcctgttcct gacatttcag
1201 agatacgttt aggatttcaa tcatgacctt aagccacatt tgaacaattt ctggtggat
1261 aagtcctcat tcccacatta tgtatgtacc tagatgcaaa tcctgaatat catgtcgcaa
1321 ttagtgcatc tggacatgct tgctaactgt gttaaagctc tgaataatgg taaagtttta
1381 tttctaccaa aacaaatttg ggctgtaatg ttttatgata aaaatctgtg gtcttcctat
1441 gtacatgtgt gtgtacatgc ttaaaatgca atgttatagt taaatgtaat tcattaaaag
1501 tatgtaactc cagtggctac ttagtttggc tacttggttt gtagatttct gctttcctgt
1561 ttcattgtta aacaggtcta gaagttatta tttcatgaaa ctaatgtgag gaaaaagact
1621 atgttgatat ataagtgaca ttatataaat acatgaggga tgatttgatt agaagcagta
1681 ttacacagtg ataggagtaa tggtttagaa ctagactcag gtttgaatct tagctctatc
1741 attataggca tttacttaac ttttcttgtt tgcttaactg aaaactgaag ataataacac
1801 ctatttacat ggttgttata agggttatat gaataatgtc tggcaaatag taagaactca
1861 agtaactgtt tcactctttc cagaaggaga ttggctgaaa aatatttgga gtctcctcca
1921 gccatattcc ttggtcagct tctatgatcc tctttggagc ttaattctta atccctttat
1981 tttcacttgc ttgttgataa caaagaagaa ctaattatta atttatttca aaatgcatgt
2041 attatatttg atgggccaca ctaacagtta taaaccaaac aacagattgg gaatgggggaa
2101 gtggatgtgg tgagttcaat cacatgtctg ggaaaagtca atagtgaaga cagagtctca
2161 caattttttg tcataatgga gagatgaaaa cacaggtaga ggatttcaaa caacagagtg
2221 gatggtgagt taaaaatgct gaaattcttt cctggtgtct aacttaatgc aatgtggttt
2281 atctctttgc tcttttctct actattcaaa tttaggataa taaagattaa atgtttctaa
2341 atcttacttt acaatatcaa gaaaaaaagg tatgcttttg cccacggaag ggcaaagcag
2401 agctatgaaa acctgctgaa cacattcttt attttcaaca caggttcttg tctttccatc
2461 atgaaatgca cattttattt gtactgtatt tgggtgacca caagtcaaca acaagataat
2521 tcacaagacc cttgccttag atgtgtcggc aataaagtaa tcaggccaaa attttactt
2581 tcctttgaat ttttcaattc aaacacaatg tatgcttgct tttacacagt aggggtcagg
2641 gattagaggg ttggctcctt taaaaccgtc agagacacag gcaatcctac acaaaattct
2701 cagaaggaag gcgcctacgc ctgggaatgc ccagatgccc ctcagagagt tgaagatggc
```

FIG. 4 (SEQ ID NO: 4)

```
2761 gtttctctga gtcaggtcaa agttaacaca ttaccttcgc ttcaaagact gcttggcttc
2821 ctttcggtgg attagtcaag atgttttgct gactgagact aggaaatcta taggagggcg
2881 ggttagttta cattgttcct tgtcattatc gctaaaacac tccaaagcct tccttaaaaa
2941 tgcgcactgg gctaaaaagg atagacaagg aacacatcct gggccggtaa ttacgcaaag
3001 cattatctcc tcttacctcc ttgcagattt tttttctct ttcagtacgt gtcctaagat
3061 ttctgtgcca cccttggagt tcactcacct aaacctgaaa ctaataaagc ttggttcttt
3121 tctccgacac gcaaaggaag cgctaaggta aatgcatcag acccacactg ccgcggaact
3181 tttcggctct ctaaggctgt attttgatat acgaaaggca cattttcctt cccttttcaa
3241 aatgcacctt gcaaacgtaa caggaacccg actaggatca tcgggaaaag gaggaggagg
3301 aggaaggcag gctccgggga agctggtggc agcgggtcct gggtctggcg gaccctgacg
3361 cgaaggaggg tctaggaagc tctccgggga gccggttctc ccgccggtgg cttcttctgt
3421 cctccagcgt tgccaactgg acctaaagag aggccgcgac tgtcgcccac ctgcgggatg
3481 ggcctggtgc tgggcggtca ggacactgac ctggaaggag cgcgcgcgag ggagggaggc
3541 tgggagtcag aatcgggaaa gggaggtgcg gggcggcgag ggagcgaagg aggagaggag
3601 gaaggagcgg gaggggtgct ggcggggtg cgtagtgggt ggagaaagcc gctagagcaa
3661 atttggggcc ggaccaggca gcactcggct tttaacctgg gcagtgaagg cgggggaaag
3721 agcaaaagga aggggtggtg tgcggagtag gggtgggtgg ggggaattgg aagcaaatga
3781 catcacagca ggtcagagaa aaagggttga gcggcaggca cccagagtag taggtctttg
3841 gcattaggag cttgagccca gacggcccta gcagggaccc cagcgcccga gagaccatgc
3901 agaggtcgcc tctggaaaag gccagcgttg tctccaaact ttttttcagg tgagaaggtg
3961 gccaaccgag cttcggaaag acacgtgccc acgaaagagg agggcgtgtg tatgggttgg
4021 gtttggggta aaggaataag cagtttttaa aaagatgcgc tatcattcat tgtttttgaaa
4081 gaaaatgtgg gtattgtaga ataaaacaga aagcattaag aagagatgga agaatgaact
4141 gaagctgatt gaatagagag ccacatctac ttgcaactga aaagttagaa tctcaagact
4201 caagtacgct actatgcact tgtttattt cattttcta agaaactaaa aatacttgtt
4261 aataagtacc taagtatggt ttattggttt tcccccttca tgccttggac acttgattgt
4321 cttcttggca catacaggtg ccatgcctgc atatagtaag tgctcagaaa acatttcttg
4381 actgaattc
```

FIG. 4 (cont.) (SEQ ID NO: 4)

SEQUENCE LISTING

```
<160> NUMBER OF SEQ ID NOS: 72

<210> SEQ ID NO 1
<211> LENGTH: 188703
<212> TYPE: DNA
<213> ORGANISM: Homo sapiens

<400> SEQUENCE: 1
aattggaagc aaatgacatc acagcaggtc agagaaaaag ggttgagcgg caggcaccca      60
gagtagtagg tctttggcat taggagcttg agcccagacg gccctagcag ggaccccagc     120
gcccgagaga ccatgcagag gtcgcctctg gaaaaggcca gcgttgtctc caaacttttt     180
ttcaggtgag aaggtggcca accgagcttc ggaaagacac gtgcccacga aagaggaggg     240
cgtgtgtatg ggttgggttt ggggtaaagg aataagcagt ttttaaaaag atgcgctatc     300
attcattgtt ttgaaagaaa atgtgggtat tgtagaataa aacagaaagc attaagaaga     360
gatggaagaa tgaactgaag ctgattgaat agagagccac atctacttgc aactgaaaag     420
ttagaatctc aagactcaag tacgctacta tgcacttgtt ttatttcatt tttctaagaa     480
actaaaaata cttgttaata agtacctaag tatggtttat tggttttccc ccttcatgcc     540
ttggacactt gattgtcttc ttggcacata caggtgccat gcctgcatat agtaagtgct     600
cagaaaacat ttcttgactg aattcagcca acaaaaattt tggggtaggt agaaaatata     660
```

```
tgcttaaagt atttattgtt atgagactgg atatatctag tatttgtcac aggtaaatga    720
ttcttcaaaa attgaaagca aatttgttga aatatttatt ttgaaaaaag ttacttcaca    780
agctataaat tttaaaagcc ataggaatag ataccgaagt tatatccaac tgacatttaa    840
taaattgtat tcatagccta atgtgatgag ccacagaagc ttgcaaactt taatgagatt    900
ttttaaaata gcatctaagt tcggaatctt aggcaaagtg ttgttagatg tagcacttca    960
tatttgaagt gttctttgga tattgcatct actttgttcc tgttattata ctggtgtgaa   1020
tgaatgaata ggtactgctc tctcttggga cattacttga cacataatta cccaatgaat   1080
aagcatactg aggtatcaaa aaagtcaaat atgttataaa tagctcatat atgtgtgtag   1140
gggggaagga atttagcttt cacatctctc ttatgtttag ttctctgcat gtgcagttaa   1200
tcctggaact ccggtgctaa ggagagactg ttggcccttg aaggagagct cctccctgtg   1260
gatgagagag aaggacttta ctctttggaa ttatcttttt gtgttgatgt tatccacctt   1320
ttgttactcc acctataaaa tcggcttatc tattgatctg ttttcctagt ccttataaag   1380
tcaaaatgtt aattggcata aattatagac ttttttttagc agagaacttt gaggaaccta   1440
aatgccaacc agtctaaaaa tgcagttttc agaagaatga atatttcatg atagttcta   1500 aatactaatg aactttaaaa tagcttacta ttgatctgtc aaagtgggtt tttatataat   1560
tttcttttta caaatcacct gacacattta atataggtta aaaaatgcta tcaggctggt   1620
ttgcaaagaa aatgtattac aaaggctgct aagtgtgtta agagcatact catttctgtt   1680
ctccaaaata tttcataagg tgctttaaga ataggtatgt ttttaaaagt taagttccta   1740
ctatttatag gaactgacaa tcacctaaaa taccaatgat tacaaacttc cttctggcct   1800
tctggactgc aattctaaaa gtgtaaaaaa catattttct gcattaagtt aggcagtatt   1860
gcttagtttt caaagtggta ggctttggag tcagattatt ttgattcaga tcctacatct   1920
actgtttagt agctctgttg cctgaggcag gtcccttaac atctctgtgt gtgacttgac   1980
ctttaaaatt tggagactgt catagggggtt aatcccttga gaaaatgaat gtgaaaagtt   2040
agcctaatgt taactgctat tattatggat taccatattt tcacattcat cacagtacat   2100
gcaccttgtt aatataagat gctcaattca tctttgagta taattttgtg actctcaatc   2160
tggatatgca atgagtgggc ctgtatgaga atttaattta tgaaaaattg tgtttcacat   2220
ggccttacca gatatacagg aaacacgtca catgttctca ttgtatgttg ttaaatgcct   2280
tagaatttaa ctttctgaat aggatccctt cagtttgaga gtcataaaag agtaaaatta   2340
ttatggtatg agttatagat tgtattgaat atctctttat atgtctaggt tttgtcattg   2400
gaaaaccaaa aagtttggaa aaaaaatcta agttatttct tactttctta attttgtgtg   2460
gatttcacat caagtataaa atttgaagaa catctgaact atcataatcc atatatatat   2520
ataaaataaa cataatctaa gagagaattt caccatgaaa aattcaggta gttcatgact   2580
atcagagcaa acaagtacat taaattgaaa cttttatgaa aataacattt atgaaatagg   2640
aagctatttt taaactagaa gtgatatatt agcatataat ttataattca tatacaagtg   2700
ggattgattt ataaatggtc accaacagag attgtgctat ttaatttggg aaaattttt   2760 aaatttacat tttctcacaa cttttaaggt agttattcag tttgttcctc tctgtctctt   2820
ctctcatgcc ctgaatttt catatttcgt ttagttgtaa gagtgtatat caaaccgtgt   2880
gtcacatgac ataacttgaa ttttcgtcgt gatatctgtg ctatgtctag gtctatactg   2940
aggaactgtg ggaaccccac agaatccaag tatacagtgc cactgatttc ttacaaggga   3000
```

```
tgtggggtct cctgtaaact ctgcagttag tctcaagtaa gaccaaagag taaaatattg    3060
ttaggatcta aggtggaaat tcagcaaaga atcacatagt ctaagtctcg agtttaacag    3120
taagataatt tgagatactt tgtaattat taaacacaaa gtaatgagag atttttaaaac    3180 aaacaaatac acctgaattt atatatcaga ataggtatgg tggttcaaaa tagctatcta    3240
ataaaaacca cactcctatt ctaaacattt gcctttgatc aaaataattt tgggtctctt    3300
attatgaaat tgcctttcta aataatacat aaatttcttc tcataagtat atattagcca    3360
cattatttta ttgttattgt tttatattca tagcttgctt tagattaaaa attatattac    3420
ccagactggt ctcttggact tgcttccaag tgactttga ctgtatcaca aaatcaaatt    3480
cactctgaaa atataaagat ttttcatcat aatttccttt gttaacagcc aagtgctacc    3540
taattttagg tgttttcatt aaaaaaaaat gcattgcaaa cttttaaagac aattcttttg    3600 tttgtttgtt tttaaaagac agagtctcac tctgttgccc aggctagagt gcagtgacac    3660
aatcataact cactgcaacc tccacctcct gggctcaagt gagccttcca tcttgcctca    3720
cgagtagctg ggtcttcagg tgtacaggtg tgtaccacca tgcctggcta actttttttt    3780
tttttaagtt atatagagac agtatctcac tatgttgccc aggctgctct tggagctcct    3840
ggcctcaagt tatcctccca ctcagtctcc caaagtgctg ggattacagg cgtaagccac    3900
ctcaccctgt cagcctaaag acagtgctta atgaagagaa atataagtgc tttgagcaat    3960
ggaagtataa ttaaaattat actatgaaag attttataaag atgaccattt tgaatgggac    4020
cacacttatt tggttatata aattatgata cactattaaa aattcatcat gatgattttg    4080
tatttacatt ttatttacat gtttgcaatt tgtgaggaaa gctaaaatta tggctaagcc    4140
ataaatattt ttgcagtttg ttgagggtgt ttgtaaaagt gttgccaagg aagaccagtt    4200
ggctacccaa acaagggttt agtctaggtc tgatcaatac atacacatta tctcaggttt    4260
gtctatcaga aaaaccttag gttatccaaa tcaaaataaa atagatgcat aaaacaaagg    4320
ccaatatgtg ttgaacaatt atattgtgat atacaactgc caagcattcc cgattaccat    4380
gactccattt agtcagtcca tgggcaaatg ccatcaatga ggacagccca gggtttccat    4440
attctctctt ggctttacat cctataggaa ttggaggggc ccacctctgg gataggagcc    4500
cttctgtctt gaacaatgtt gtctgaacac taacaaatgt tgactttcta caccagtccc    4560
tcaatagtct tttctatttta tccttttgct gaccatgttt tgttattaca cagttgagat    4620
ttttcagctg ggaatctgtg ttaattttgt attaattttg attagcttaa ctctcagagt    4680
tctaaaagta cctcctgtac ctgatatatg acaaaaatta taattacatt tatttatata    4740
taaaatatct ttgtatatgt aaaatatctt tgtatatata attatataat tgtttctttt    4800
aattttgcaa attttaaaaa gttctccttt gttttgaagt ttattcctat agtttttat    4860 atgctagtta aattattaat cacttgattc aagtaatatt cttatatact tataaggaat    4920
agtgtagttt taatatttaa ttccttgcta aagagagaag tggaatctat ttttcttagc    4980
tacttcatca atattttatg tttgatgtga cagtcaaaat atccctcaga gctaactgtt    5040
acactaggga aatcacggtt ttccagtttt ccatttatgt gttatgggag ggagtggaac    5100
ttagtgtaat aatattcaat acataaatgt taacacttgt ttaaaggtcc ttgagtgagt    5160
actgctataa aatgcattat tattgctagt gtcatttcac aagagcctat aatttcagtg    5220
tgatagagct acaatataag tatagtattg caaaaccatc aggaagggtg ttaactattt    5280
agcatgcagt tatgtgttgg ttgtcaaaac gttaaaaaca tctctgactc agcagcaatt    5340
ttggcaattt tgatcctgag gcatctgtgt agggcatctt cctggagaaa aacctctgag    5400
```

```
atgcaatgag gtcaaaaggg gaaaacagac tatgataaag atcaagttgt ttggagatct    5460
tgtagaaaga ttaatttaca aatatgtcaa gtgcattatc atggaggaaa acattgctat    5520
ttctgttggt tctcttcaga gctctagaat caatttacca catagttgtt tcagtgtgaa    5580
attagcatta cagagtggct ttacggcttt actgtagggc attgtgtcag caaagagctt    5640
aggcttcttt tagcaagaag cttgtaaaaa tttaatttac tcttagattg cttgatgtag    5700
agaattacat tcctacagag ctctgaaaaa tcttttttca gagttttttca cagctgtatt    5760 caagttgcaa ggcttgtcaa ctttgctatt tttctgtgca gctctgttaa cttattatta    5820
tcttttgaca taaattatga ttccaaattg taaagctctg gatgtcaggg ccttttctaa    5880
tttgtttagt atgatattca gaccatttca agactcttcc gtggaacaat ttaataaaga    5940 ttttttttgtg atgttaatga gttcatggtg atcaaccccta gagacctgtg tctattgtag    6000
atcgatgaca ttcaacagtc ctgcagtgct ggcatcattt tgataaaaag gggtcaaagc    6060
aagtgggact gtgggcagat ttttaatgct tagaacaatt attccatcga agttttcttg    6120
tgtcccttct gccttagcct tgtaggata gcatgcttgc taatttcttg ctcatggggt    6180
aaggaaatga agattttttgc taggtccgta ggattattag gactactcag gcctgaagct    6240
atgcctggat atagccagaa aactctccca tagcttgctc caaggagctg agatacagca    6300
gtacttcctt tgtaggtcat gattctgggt aacctggaag atgacctcat tcatattctg    6360
tattctatgt gagacgttaa aaggtagag gtggccaaga aggaaattgt tgctgccttt    6420
atggaacaaa ttatctgaaa cccagctttc tcgaggcctt cattgaagta ctcaactggg    6480
gcacttaacc cagtctaagg ctggtcaagg aaggcttgct gggggaagtg tcttttgtat    6540
tcacacctaa aggaggttat tcaattagaa ttatccaaag agggtaggga tgggctagga    6600
aaaatttaaa caggtagtgt ggaggactga caggataagt aagcatggca ccttcaaaat    6660
atcctgagaa gttccctatg acgggaacat aaaatatgtg acagagattt gtgggagatg    6720
ggtctggaaa ctctagcagg ggccagatcg taaggggggct ttgtaggctt tgtaggcttt    6780
gtttgggctt tatcatactg gaagtgaaaa gccatggctt ttaaacagga gagggacata    6840
atcagttcat atactgttgc agttttgtaa aagaaaagat gagctgaaag agtggccatg    6900
gtggaggtgg gtgggttggg ggggagggggg cggggagaga gagagagaga gagagatttg    6960
aaagacattt aggaggtaaa atcaactggt ttggtaatca attagtagtt gaaggtgaag    7020
gaaagagaag agttaaggat aacatctata tttgttgatt tggataatag aggggacagt    7080
ggtgctgctt attgaatgag aaaatttaat cggagaagaa ggcatggagc aggagtgcag    7140
acctatgtga ctctacttct ctcaaaacca gaaacggaaa tgatgtatat ggctcagggt    7200
taggtaatat ggttatttga aaatgtatta aagtgattta gagcttagtc ttaggtaaga    7260
gatataagat gtctgaggtg acagttttat aaatatgtag agtgcccact tgtttggcct    7320
tattgtggca tagtgtgacc tgagagtgtt aggaagaagc agctgagttc tagggacagt    7380
actggttaaa ttctacttag aaattatact tagaactctc ctatataacc tgctaactga    7440
tgtctgaacc tcctgataac ttcactcctt taggcagtgc ttttcacatc acggacaca    7500 acatatgaga gatcatagaa attcaatgtg gtatgaaaat ctgcttggga cttcagatat    7560
tgtctccagt gattgaataa aaataggagc tcacctacta tgatgaggtt tctgtgtgtg    7620
ttaaaagaag gttttcatta cttttgaaaa ggttatgtat ccttgtttta tgttaaaact    7680
ttgagctttg ttaaatatgc agagttctct ttcttagcat ggactacaga ggtgcaacta    7740
```

-continued

```
cctcctacct gacttcacat ctactcccaa atgcctagtg aaggcttaat aatttcaaaa    7800
agggactcta gaatttcatt tgataccagt cagacaaatg tgtgaaaatt aagcataata    7860
ggcagaatcc cagggtact gacagctgta ttaagaggtg attcaagggc taaaccttag     7920
agtccagcat tggttatggg tgtgacaaga aaatgaagcc tatgttggct gggattagca    7980
accacagttc tagaggaagc aaggtggaga aactatatag ggggctccct ttgtacgttt    8040
tatttatttt aaacatctct ataaactcta gaaattaaaa caacaatacc aacacaaaag    8100
catcactttt tcgaccaaag accattgcta tactttttg tgtaaagggc tagatagtaa    8160
atattttcag ctttgtgggc cacataagtc tctgcaatag acaatatgca aacaaataag    8220
catggctgtg tttcaattaa actttattat gaacattaaa atttgaattt catataactt    8280
ttacatgttg caaatattc tttatttaaa ttctattgca atatgcttta aaagatacag     8340
tttttagtct ttcttagttt aaaataaaat ctagaaaaaa ttttaagtct tctataactt    8400
tttttcggta actgaataat tttaaaagta agtgaaacat ttagacatgc aaaatggact    8460
tttcagaaga agaaaatggt agcttaacag ttattagatt attgtccaga ataatttttg    8520
acttataagt ctctgttgac catttcattg cctctttttt tggaatatgc atctttaat    8580 gtgtccttca aggcaaggc tctatcttat ctatcttgtg tcttgcattt tcccagggca     8640 atgttttca caattttttt aaaaacaat actgtaatca attttcaaat aaaatttcc      8700 atgggaccgc agtgtataca aatagcagtg acaataaaag ataataactc tcccataaat    8760
acaaagaaac agttaaccta gtgctctaaa gtaaaggcta cagtgattt gtataacatt    8820 tatatgtaat tttcttgatc ctacatggtt gtgtttttca cagtgttatg tttctgaaat    8880
cgagatgcct tttataattg atgtcaaaag aaacttgtca gccacaaggc ccaggaataa    8940
gttgtaatat gggaacttag caatacataa aggtatatat actcctgtga cctcagctga    9000
attatttgca ttggttgcat cccacaaggt tgactcttaa ataaatttag tttgttgctt    9060
gaaatttctt gggataaatt actttgtgat gtagttttga aaaaaaaaca ggtaatattt    9120
agtctgaagt ttgtctgaca tactaagcaa tgtaattaaa gtagaagtcg cctaagctca    9180
gcactttatt atgccttgaa attatactgc ctgtcctaca ggtgaaggtg ttatgaatgc    9240
agtttgtcac tgtaactcta ttcatagctc tgaaaggctg agagtgactc agaagaatat    9300
ttttgctctg aatatgaaga acgcttagac taaaacttta attacgatgc tgaagaagaa    9360
agtggtaggt gattgcatga ataagtatgt aatattgtta atttctaaaa actgtgtata    9420
gttaatgtag tgcttctttt tggaaaggct attgttaaat tgatggtaaa ttctataacc    9480
aatatcacct taaagcaagt acgcatgata aagtattata aaaccatgat aatatcatat    9540
gtggcttatt attgttccct gagtgttgta caactctgtt atgctgtgat gaaacctcat    9600
gcaaacaggt atgtcaaaga tatgatgggc tgttaactga gcttggccca catatggtgt    9660
agtgacatgc tcactaatgc agtgcagaga taaccaataa cagatcataa caggtttaaa    9720
tatgtgcaag gagatgtcag cagaagcttt cctacatagt gaatactaaa caagcctgac    9780
agcccaggat catgttcgga tcaatctagt gtgctaaaat taacatatag tcctacattt    9840
gagaatgtgt gattttcttg gttcctgtct ataaataat attttaaaat acatacattt     9900
caaatcagaa gttggtgaat tcactgaaat atttctagag aacactaggt attggggctc    9960
atagtgtgaa aaccactgac ttaattcttc ccccatcttg gttgttcctg atcttccctt    10020
gtgtccccat tccagccatt tgtatcctta gaaaatgatc tcatattcta cttcatcttt    10080
atcttcattg tcaactgtca ggtagcaata tatgatggaa gaagcatgta ctttggaatc    10140
```

```
agacagacct ggctggaatc ctaactctgt cacttattaa caatgtgatc ttaggcaatt    10200
tacttaatct ctctgaacct cagctactct cgtcagtaca atgagttatc cttatcttta    10260
catggcacag tattattatg atatcaaaaa ttcattgagt atttactctg catattagtc    10320
aaggttctcc agagaagtag aaccaatgat acacacacac acacacacac acacacacac    10380
acacacacac acaatttatt ataaggaatt gacttacatg attatgatgg ctaacaagtc    10440
caaaatctgc agtatgggtc agctggcagg aaacccagga gagtcaatgt tccagtttga    10500
gtctgaaggc agtctgttgg ggaatttcgt ccttctctgg gaggccagcc ttttgttct     10560 atacaggcct tcaaccgatt ggatgaagtt cacctttatt agtgagggca atctgcttta    10620
accaaagttt actgatttaa atgttaatct catccaaaaa cacccaccca gttgacacat    10680
aaaattaacc atcactctct gtaagcactt tctatgcatt aagtgatagc aaataatgcc    10740
agacataggg cgtctttaat aaatggtaag cactgttatc agcaacaaca ggattattat    10800
aattagcacc ttttcatctt tctgtctggg ctctgagaaa gtacctctct tctctaaatt    10860
tatccctcct ttcctatgaa ttagacccag tgctttctct gaattatgaa ggtcacactc    10920
ctacaaatgc cccttcccaa ttgcacatct gtcggctttc tttgccattg acttttatct    10980
ctagctttta aatttacagg catatgtcag ttaacaatgg aatgcgttc  tgggtaatat    11040 gtccttaggc aattttatcg ttgtgagaat actatagagt atacctacac aagcctagat    11100
gtcgtatagc ctactacaca cctaggcaat atgacatagt cttttgcttc taggctacaa    11160
acctgtacgg cttgttacta tactgaatac tgcaggcagt tgtgacacag tggtatttgc    11220
atatcggaac atgtctaaac acagaaaagg tgcactaaaa atactatgta gtgatctcat    11280
gggaccacca ttgtatatgc agtctgctgt agactgaaat gtcatgcagt gcataactgt    11340
atcttaaata ctcaaagtat cacctttgtt tgtttgtccc cttgtgtgca tcatcctaac    11400
gtggaatttc tctgttgatt agggccagcg tattagtttg ctagggctac cataacaaaa    11460
taccacaaat ttggtggctt aaataacagg aatttattat cttatggttt tgaagactag    11520
aagtacaaga tcaaggtgtt ggcaggtttt tcttctaagg gccatgagga agagtctatt    11580
ccatgccttt cccctacctt ctggtggttt gctagaaatc cttggcattc cttgacttac    11640
agaggcatca ccctgatctc tgttttcatc ttcacatggc attctccctg tgagcctgtc    11700
tctgtgtcca aacttcttta ctattaatat aaggacacca gtcatattgg attagggtct    11760
actttagtga cctcattgga atgttattac ctctgtaaag atcctatctc taaataaggt    11820
cacatcctta ggtaccgggg gttaggactc aaacatacct ttttttgggg aaacacaatt    11880
caacctataa caattgataa cactctttag gagcagaatg cgatatggaa gtaatttgag    11940
accataaagt atatacatgt agggagttaa tctatgaaac ctattgaaag ccatatatac    12000
ctcatgtata gtggtccata aatagcatgg agacattgca gaggatgtta agtgatatga    12060
tacaggaaca atccaagaag gtcataagaa aaaggacctt ttgctcttga gaggactgaa    12120
gaatgacttt ccatttatga aattttggta catgtccact aaaaatagga tgaaggccaa    12180
acttaggaag aatattttga taatggagaa ggttgcatat aaaaacattt tattgaggac    12240
aattaaataa tgttggctgg aagttttagg atgatcatct ttaggactca gaaaagaga    12300 agaaacatta ttaaagaatt gtccctgaac aagtataggc accctcacat ttgcattgca    12360
tttactatag aattgaaaaa tgttttgacc ttttttttt  ggcttttaat atatttgacc    12420
aagagtaaca gctaagcaat acctatttgc aatcagtgtc atcatgtggg ctccaaacat    12480
```

```
atcatgtttg tgtaattaat tgattgaccc attaatttgt tcaatttctg ctctgttcca    12540
ggcactgaac aacatgatgg agataaaaga taaatattac acctgccttg tcctcaagaa    12600
gttagtcttc tgagggaaag aaattagcaa acaaattgta atctcagtta tgtgccatgt    12660
tccatgctgg gcacagggga tacagtagtt taaaaaaaac acaagatcta taaggtgttt    12720
cttcttgtgg accttacagt ctagggtgct tggaaacatg gggcgttggc agacaagtaa    12780
atacacattt tgtggtaaag gctcaggtag aagaagtaca ggatagaata gagcacacca    12840
tggggaatta atctagactt cagagaggct cacacataca taatttatgt gtgactatttt   12900 caatgcatt gaggtttctt ggaaatagag gttaggtttt attttaagga agttaccatt     12960 tttttttca gtgtgatgtg gttgaaccaa agaatgccat gcccagtgat ggtaatagga    13020 taatctttt aaaaattaag agccacctaa taaatcaata gtttcattca gcgggagctc     13080
ctgcagagtt caaaagaag agaatctggc acagcgtttc ctttaaagtt cattttccta    13140
gagtgtgaat ggaagcaaga gattataaca ttttgaggtc aaaaaaattc tgaaatgcct    13200
ataaaaatta ttttctccaa attatcatca tttgtgcttt taatgacctg attgcaaaga    13260
tgaacatttt gaattcttaa attgctatt aggattggtt aatgaatcaa ttatctatta    13320
ctgtatgttt tgctattgga aaaaatagca acttaagtgt tttgcagacc tttacttagg    13380
tatatgttgc ttttatgaaa aaaaagatgt aaatattaag taaaagggat ttaaagcaag    13440
gcttttgagg tagagtctta ttaattcctt ggtaaaccttt gagccaattg ttgtctatgt    13500
tctctgcctc tgtcttgctc cttccttctg ggattcactg tgggaatgcg ggattgttaa    13560
tctggggatg ctgtccaatc ctgcctctct caagctttgc tattgatctc cctcccagtg    13620
ataataaagc ttgaagaaaa tgaaagtagc gttagtattg gtcctcaaac tcaagaacag    13680
gatgaaactt aaatcttgag tcatacaatt gtgtctacat actgctcccc aaaaagagaa    13740
gtaaagaaga tgctaacttt ccctttaat ttgcagtact tagcaatttg ttttcttgag     13800
ggttaagtaa taacagtgga agaaaaaagg gttaaaatgc caccaagaac ccaattccat    13860
gtttagtttg aaagtgggaa atcagctgcc actgggaagt ctgaatccaa tgccatgatg    13920
ttctttgaat ccttctgaga aataatcatg tgtagccata acatacctgt ataacagagc    13980
agagaacata aacaaatgaa ggtgaaggga agattaagac agaagagaaa aattccagaa    14040
tcgactgatc attttttatct gtttagatga tttcaggcag aatcctagag accaacttta    14100
tcacaactga attttaaaaa tcaccagctt tgtcattgtg atgcagcatc agtttcagta    14160
ttatccttgg agtattaatt cttaatcatc ttcatcttag aacattttg aggtcacttc     14220 tagtctctat ttcaccagtg aagaaacaaa atccccaaa ctatatcagg tggaattaca    14280
cagtattttt tttttaattt tggggaaagt cgattcaagg cagtaacttg caagctagtg    14340
ttagaaagga tttaataaat agtggttttt ctgtacacat agtgagaggt cattacatca    14400
tttggttgtt gaaagtcata aggatgtcta gcatgcgctt tgcctgtagt ggttcatgcc    14460
aggcagattc ctgactccta tacccagag cttatcagag catttatgtc cccaaagaga    14520
aatgtcacct ccatctttca ataaacactt tagcaaagaa aaatcaagta ctttaattcc    14580
aaatcttgag ttaattccag aataacaatg atggctcgga aaaatatggg tatttctgtc    14640
aaaggacaga gaaacctagt agagagtatt tactttgggt cctagtgatg gtatctgaac    14700
aagctaggtg aacaaagagc ctcaataagg gattttgagg tctagaaaaa gagaggaaat    14760
accaaataaa tggaataatt ataaaataaa taccagcaaa gttaaatcaa tatatcatgt    14820
gggagatatc cttatatcac tcatgtgatt tctattttgt tcctatatta ggccaaggag    14880
```

```
aggtggaact tgttttcctt tttccctctc agctacgaat ggacatactt aaaactgttt    14940
ctctgcttct gttctctaaa atgtgattgt ctaacagtaa ccgtgatgac gttttgacag    15000
ttgcacaagt ttcttctttt aagctttaaa aatgccagcc agtaacccag tggcatttct    15060
actataaaat cttaaggcca atccattcc ccttttcctt attttcttgg tttcaaatat     15120 attttattg ccaatggaaa taaaaatcct aaattagaga gcaatggcat cccttgtctt     15180
gtgaataaag agctcctaaa tgtgaactta tacaggatgc agcaatttat agggtagtta    15240
atcattcttc tttctagcca gttgttccag ctacagtttt gtggctcttg ttagtggctt    15300
cattcccaga tagaataaaa atcaaaccaa atcctggaa aggcactctg aggatgcttc     15360
tctaaagtag atgggcatca actataaatc acaatgcttt gtttcctctg ttatgtttca    15420
agatgggtgg gatttttttt gtagcattac ttattattgc ctctcaagtg cttgagtctt    15480
tgaaatccaa gtcatgtgag tgaattagat acagctgtta gaagtggcct ttcaatgcca    15540
atggtacaca ttccttggtt tctttacgat actattgctc ttacaacttt tatctgaagt    15600
cataaattca tagttgtccc agaagttaag ttccttgctt ctagaggaca gaaaacaaac    15660
aatttacaca actcatggtg catgtcacca gtccttagat ctcatgaaat atgcatgaaa    15720
tcttaaatca cttgctgtag ccacccagcc attgacatat ttgaaagact ttagtgtatc    15780
aaagtcacta taatgaaaat tttgatttca ccagttctag gagtgaaaaa tcaaatgttt    15840
agtaaaactt tctaaaatta acactgacag ttgatttctg tatactgttg ttcttaataa    15900
tagctttatt gagatataat tcatattcaa acaacttac ccatttaaag catacaatcc     15960
aatgattttt tagtatcttc aaagagttgc ctatcaccat aaccaatttt agaacacttt    16020
catcactgta aaaagaaact ccattcctat tagcagtcat tccttattcc aaatcccct     16080 gctcgcccta gacaactaca aatgtacttt ccatctctat agatttgcct gttctggaaa    16140
ttttatgtaa atagaacaaa gtgttctttt gtgactggct tatttcactt agcattttt    16200 ttcaaagatt catccctgtt gtagcgtgta tcagtgcatc attcttttt attttttag     16260 agacagggcc ttgctctgtt gcccaggttg gaatgtgcag tggcatgatc atgggtcact    16320
atagctttga agtcataggc gaaagcggtc ctcccacctc agtctcccga gtagctgaga    16380
ctacaggctt gcaccacatg actgtctaat ttataatttt ctttagagac agggtcttgt    16440
tatgttgtct aggctgctct caaactccag ggctcaagtg gtcctcctcc cacagcatcc    16500
taaagtgctg ggattatagg tgtgagccac agcacctggc ttgcatcatt ctttttattg    16560
ttgaataata tcccacttgt aagaatatgt attttattta tcctttcccc agttaataga    16620
tatttcgatt gttcctaatt cttgtctatt ataaataatg gtgctatgaa catttgtgta    16680 caagttttg tgcagacatc catttccctt tcttttgggc atatacctac gagtgtaatg      16740
gatgggccat atagtaactt tatgtttaat attttgagga tttttcaaac tgttttccaa    16800
agtggctgca tcatttttaaa ttccttccac cattgtgtga gtgtttcaat ttctccacat   16860
atttgcaaca cttactatta tctactctta aaaattacag ccatcctact gggcatgaag    16920
tggtatttca ttgtgagttt ttttttttctt tttctttttt tctttttttg ctaatgtttg   16980
tggattttct tttcattttc ttgatggtgt cctttgaagc acaaaagtat ttaatttga    17040 taatttccaa tttatttttt gttattgctg tttgtgcttc tggtgttgta tctaagtgta    17100
tgctacttta aaaaattagt tgtaaatatgg caaattggat acatgtgtag gctttggtgt   17160
cacaatccta attttaaaat tctgactctg cccttgacaa attaactaat taagcttcct    17220
```

```
tagcctcagt ttctcaactg taagttggag atattaccaa gacctacctc ttgaattgtt    17280
gtggggatca gatgaaataa tgtatgtgaa atatttagaa ttatgcaagt ctgtggtaat    17340
gaatactaat gttagctatc attattgtta aatcccaat aataaattct ggtgctttga     17400
aaattaaacc aaagccaagc agttgatatg aagaagcatg taataatgta cagacataat    17460
gctttataga caacattgaa tttggctctc atgaacatca ggaatagtgg tcatggtagt    17520
tattatctcc agcaggaact gtagctgaga gatcttcaga gctttttcca aggcgatatc    17580
actgggaaat aatagagaca aggttacaag ctagggctgt gttttcttct taaaatcttt    17640
agttcagttt ttttcaataa cagatttgta gtaggcatca ggtgactggg gattcgtatt    17700
cttcaagttg aaatattacc ttgttgagaa agaaaccatg tgtgagacaa ccatgttgag    17760
aaagaaaaag tgattttata gaaaattaat attgatagtg agcattatat gaaaatcatg    17820
aagttagaac atatttggcc agaaaattta cattaatagt tacccatagc aattaatgca    17880
ttataattac acatcctttt ctttaatga aaagaattc tttccttcca aagttatgca      17940
tgctattgtt aaacattaga gaatatagag aagcaaaaaa gaaaatatct ttttgatat     18000 tttcttaaca tacgtctgtt cctaataatg tttatagttt agaagcattg catgaaatgg    18060
gtagatcaat tttctatta atgtttggat tcattaggta cgaagttagc aaattaattt     18120
ccattagggt gcctgtatgg ttgtaaatcc tggacctgca gaagattttt cagtattggt    18180
ttgtagtctt ttgtttagca gcaaataatt agttctccag agcttctgaa attaattgac    18240
cactttaatg gtgtttacct acctagagaa agaaaaagaa cttctccaag tcccttggta    18300
aaattaagcc tcatgaacaa ttaactcaaa tatacacaag gcttgtcttt agcgagcata    18360
tactccctaa agttgattaa gctgaccaag tgattactgc ttataaattc accattttat    18420
ggagaagaag caaacactgc taaataccctt gtggaatcag aggaggggaa attagtaact   18480
tgaccccaat actgcgattt taaattgaat tcttgaagcc tacaagttt acacaggact     18540 ttagagagct ggatagtatc actttgtcaa gtcctacttt tactatgatt ctttgagaaa    18600
aatacatctg actaaataac tctgaatcta aattggataa aataaatgtg acattcaaaa    18660 tgttattat gattttagaa aaatatcctt atagacacta gatgagtttt agtctcaaat     18720
caatcctccc tatcatagtc acttatcaaa ataactaaag caaagtggta gagctgtgct    18780
ctagaagttt gggatttatg atcacaatct tttccaatga gtcccctctt tcctctgcct    18840
gtcttcaaca tttgtttttt ttttttttg gttaggacta tccagattgt gtggcctatt     18900
tcaaactcat ggcaaataca ttggatgatc agaaattttc taatgtattt gaatttgtct    18960
acacaaacta gagtaattgc tattaattcc tcaagtgtta attatttcat gcaaaaagga    19020
aaaaggctat tagtctttaa gtgtattagt atgtcaatat ttgggagaag tgtcatgcaa    19080
ttagtggttt gaatttccta ttttatttta ttgcatttta ttttatttgc ctagtcaaat    19140
aaaaagtaat gttaaataca tggaagcatg attgttttct acactaaaaa tcattttgac    19200
ttgaaaagat ctgatatcca tgaccttcat ctgaagtttt ggcagatgaa aatgtcagat    19260
gcgtcttttg gattaataaa aggcaaaagt cagatcgaaa aatgagtata agctttaatt    19320
atatgacttt aggaggatat gttatgaaaa tcaaagcttt aatagtgatt ataattggca    19380
agttcttttt ttataaggaa ttacaagtca ctctatacaa aaattggaat ttttgtccta    19440
agaaatgaaa tttactatag tttcatctgt gtgtgtgtgt gtgtgtgtgt gtgtgtgtgt    19500
ttaaaaaatc aagtgatagg gcttttcctc aataaaatct gaaatctctt atagttaagt    19560
gaacagaaca gtgtatctag gatgctagac ttttttttca aagttagttt aaaacttata    19620
```

```
catagtaaaa tctgtatgcc ttagggatct ctgtttgcta tcccatagtg aatgattaat   19680
tagtttctgt tagaaatagt cagaactagg ctgggtgtgg tggtggctca tgcctgtaat   19740
tccaggactt tgggaggcca aggcaggagg atctcttaag cccaggaatt tgcaaccagc   19800
ttgggcaggc tggtgagatc ctatctctac aaaaacaaac aaacaaacaa aggacaataa   19860
gaaagaaaga aatagccaga gctttgaaca aaatttctaa gtagaccaat gtaaaagtct   19920
gtcgtcaata tgtagtggct atgaatggag gttatgaatg aaagagaagg ataagatgaa   19980
ctagaggtga gaggggaaga cagcaggccc aagtgaaagg cagagccgag tttattgctt   20040
tttggttatt ccaggtgtgt ctgctttgtc tcatgaaaca cctggatgat cactgatttc   20100
tagtggaaga aatgctgaaa agtccttact gtgcatttaa acattctagg tttaatatac   20160
tcagggtttt tcaaaagaaa gggtggctgg agttttgcac taactaatat ttcataaagt   20220
gtctaagtat agatgtctgg tttttttttg tatttctaag actggcttga ggtaggcatg   20280
gagaattctt tgatgggaca taattttctt cctttctttt tttttttttt tttttttttt   20340
tgagacggag ttttgctctt gttgcccagg ctggagtgca atggcacaat ctcggctcac   20400
tgcaacctcc gcctcccagg ttcaagcaat tctcccacct cagcctcccg cgtagctggg   20460
attacaggca tgtgccccca tgcctggcta atttttttg tattttagt agagatgggg   20520 tttctccatg ttggtcaggc tggtctcgaa ctccttacct caggtgatcc acccacctcg   20580
gcctcccaaa gtgctgggat tacaggcgtg agccaccgcg cctggcctga tgggacatat   20640
ttttcattca attttattga tttaacctca caaataaaa tatttcctta agatgactct   20700
gtggtcattg ttgggcagca taagcttaat ggattttagt tatcataatt taccttaaac   20760
ccaatttgta tttcaggata taaatagagg tttattgtag tgaatcttcc aggaaatact   20820
aagtgatact aataattata gatggtgaac ttaagtcttt atattactga atttgtttgg   20880
tttgatgatg ctaggctatg gcattcttgc taatcaaaac gatgtgtcat ggtgtaacat   20940
aacttattaa aatgggcaca gataacacag gaagcttttt ataaaagcag ctcacaaatt   21000
gtgttacttt gaactgaact ggccatttat gggaaaggtc actgggttgt aaataaggac   21060
caaaagagtt acgtttatat ttttaaaag agattgagga gatttatttt tacatttctt   21120
gaaaatgcct tattttggta tggtattgac agatagtgaa attctgctca tttgtaaata   21180
tagtgtcata ttttaataat ttcaaacata ttgaaaatgc agaatttatt aatagtggga   21240
gcacattttc cttttactaa atgttctac aggttctttt ctttccatcc acacacagtg   21300
ccattaccct cattctaagc ctttcaaaca tctggcagta agtgatctgc tgcacttagc   21360
tctttccagc tgagctgatt tttaaatttt cagaaaattt gtgagctaat tgttaaacat   21420
ggccattatt aaaattaaa ttatttcaac ttataattaa ataaattata ttaaaacaaa   21480
agtattaaaa actcaaaagt tggctgggcg cactggctca cgtctgtaat cccagcactt   21540
tgggagaccg aggcaggtgg attgcctgaa gtcaggggtt cgagaccaac ctgaccaaca   21600
tggagaaacc ctgtctctac taaaaatata aaaaatagc cgggcatggt ggtgcatgcc   21660
tgtaatccca gctactcagg aggctgaggc aggagaattg cttgaaccca ggaggtggag   21720
gttgtggtga gctgagattg cgccattgcg ctccagcctg gcaacaaga gtgaaactct   21780 gtctcaaaaa aaaaaaaaa aaaaaaaag aaacaaaaaa aaaaaaaaaa caaaagcaa   21840 acaaacaaaa aaacaaaaat tatcacttcc taattatttt gcatttact attatctatg   21900 ctattaacgt tatttgcctt cattgtattt gaaaggtgga ctatattcta ttgcactttc   21960
```

```
attgtactat attctaatat gcaactgtgt atcccttccc aactctgtgt tcaatgactt   22020
tatatttggt tgctttaaaa tgatgacgat gagagtattt atatcataga aattggcaaa   22080
tgccgtaagt cagttttttgt ttttgttttt gttttccgga gaggggattg ttaaatattt   22140
gcctgcatgc aacaccacta catgcagtct gctatctttt gttcttcctg ctttcaggct   22200
cctctcccag ctgtctgtct agcacaaccc agcataccaa attttcttaa atagggaaag   22260
ttgaacatgg taaaagaatg aatgaagtca aaagaatgtg gaaagaccta ggctttgcca   22320
tttagtaaag tttagcatct ctaagcctcc atctctttat caataaaatt gagcaatgat   22380 ccctttagt tctacccatt taagaagatt ttcaaatgaa aaccacaacc tgctcatgtt   22440
tatgaaggca ctttggaaag cgctaaatac acgggttttt attagtagta aacacttact   22500 tcacctttt cacttcttga ctttagttta caagggctca taatctaaat tatatcataa   22560
attgctgtcc cagattttttt tacagcctaa ttgccacctg tatgttcgac tttccttctg   22620
ttctttatgt tagatactgg gatagtatgc accaggtggg tgtgccatca ctttctcaga   22680
tgatgtccac tgaagacctt gcatgatcat ggcattcatt ttcctgctgt attcagactg   22740
gcctcaacta ttttctttat tgctctccag gaaaaattac aaatgaatca gactgggcaa   22800
tgaagggtaa acctaattat cgctctttgt taaagacagc tcttgttaaa atgcggatat   22860
tgcaaattaa tggaaaaaat atgacatagt aaaccatact cacttattaa tatcttagta   22920
aggaataatt gatgaagtta cttaaccttta gagccctaat tcagttaagt tttaatgaag   22980
gacaagttgt agagatatcg agaacccagg gcaggtgcct actgaagaag ttccagacca   23040
aggaagtata aagaaggacc tgggtgggag cagtgagatt ggatatgagg gccactggca   23100
aagttttgcc ccagaacagt gtcaaaatgt ttgcatttgg catagcccttt tctctttttg   23160 ttctgaatgg ctttgctaga atatcttttc tataatgaat ttatcctgct tctcagatat   23220
tgctaaagca ctccctttg aattttggtg cttaacatg cattttgata cattaccaaa   23280
taaggtctga atgacacaaa ttttagaact ctccagagaa aagaaagatg ctgagggaaa   23340
aagcataggt ttgggactca ctaaatccca gttcaattcc tttctttaat aaatatattc   23400
aattttacct gagaaagctc tcgtgctctc gaattttatt tagaaatttc tctttgtaca   23460
tgattgattt cacaatcctt cttctgcctc ctcttctact ttcttctttc tagattttcc   23520
tatctttatg aagattattc tgccttatcc tcaacagtta gaaacaatat ttttgaaaat   23580
cactacggta tcctgcatag tgatttccca tgccaacttt actaatttcc attataaatt   23640
attatttatt gatgcctaga gggcagatga gtgtagctgc tatggagtga ggagacaaaa   23700
cataagaaag ttatgatcct accctcaggt aatgattcag acatgataat taagtcaaca   23760
aattgataga aactaatcac taactctctg gctatagtca ttctttcaat gaatagctca   23820
ttactgagta tgcatgctac agtaacaaaa ttatataagg ctgttgatta aatgttgatt   23880
aagtgcatgt cttattcaga gtttttttat atttgaaatg gaagaggctg gacttcagta   23940
atttgctata aactgctagt atatgattat ttggggcag ttattttta aagaataatt   24000 taaatatgga atgtttagca gtttgttttt tccctgggaa aaaccatact attattccct   24060
cccaatccct ttgacaaagt gacagtcaca ttagttcaga gatattgatg ttttatacag   24120
gtgtagcctg taagagatga agcctggtat ttatagaaat tgacttattt tattctcata   24180
tttacatgtg cataattttc catatgccag aaaagttgaa tagtatcaga ttccaaatct   24240
gtatggagac caaatcaagt gaatatctgt tcctcctctc tttatttag ctggaccaga   24300 ccaattttga ggaaaggata cagacagcgc ctggaattgt cagacatata ccaaatccct   24360
```

```
tctgttgatt ctgctgacaa tctatctgaa aaattggaaa ggtatgttca tgtacattgt    24420
ttagttgaag agagaaattc atattattaa ttatttagag aagagaaagc aaacatatta    24480
taagtttaat tcttatattt aaaaatagga gccaagtatg gtggctaatg cctgtaatcc    24540
caactatttg ggaggccaag atgagaggat tgcttgagac caggagtttg ataccagcct    24600
gggcaacata gcaagatgtt atctctacac aaaataaaaa agttagctgg gaatggtagt    24660
gcatgcttgt attcccagct actcaggagg ctgaagcagg agggttactt gagcccagga    24720
gtttgaggtt gcagtgagct atgattgtgc cactgcactc cagcttgggt gacacagcaa    24780
aaccctctct ctctaaaaaa aaaaaaaaaa aggaacatct catttcaca ctgaaatgtt      24840 gactgaaatc attaaacaat aaaatcataa aagaaaaata atcagtttcc taagaaatga    24900
ttttttttcc tgaaaaatac acatttggtt tcagagaatt tgtcttatta gagaccatga    24960
gatggatttt gtgaaaacta aagtaacacc attatgaagt aaatcgtgta tatttgcttt    25020 caaaacctt atatttgaat acaaatgtac tccctgggaa gtcttaaggt aatggctact      25080
ggttatcaaa caaatgtaaa aattgtatat ttttgagtac ctgttacatg ccaggtagaa    25140
tatctcctct cagccactct gagtggaaag catcattatc tctattttac agaaaagcaa    25200
actgaggctc agagagataa tatactttgc cagttaatga atgatggagc catgattcca    25260
gctgaggtct gtattgcctt gctctctagg aatggtagtc ccccccataa agaatctctc    25320
agtttccttt ccaatcaaaa ggttaggatc cttttgattg ccagtgacag aaacccaatt    25380
tactagctta agtaaataaa aggaacgaat ttattggctc atgaagcctg aactatgtga    25440
agacctaggt ggagaactgg ccttaggaac tcaatgggac caaggactca aatgccacct    25500
ggtggcattt gccttatgct ggttttattt tctcagaccg gaccagcttt ctacataaag    25560
tgggtccctg gttagaactc tttgctccta tctttaagga ccacgaaaga aggagcccctt   25620 tgtccttggc taaatgtgaa aaatcccaga gactcttgag tcatagtgct taccccttgg    25680
gccactcata gtctagaatg aactaggctg agtctcgtgc caacagcaca ggcctgatgc    25740
cagataaaag ggtgagtgaa gggggataaa aaataagaca tagctactaa attattgcac    25800
caaagtaaaa acattgagtt gacttgcaat ttgtttcttt taattaaatt catttccttt    25860
ttttggcatt tgaaggcaa agtaagatat taaactttat ttttattgat tttattcaaa    25920
gaattaagct agtgggagta gcagattcac acttctaaga tcaagggcca gcttctatta    25980
ttgaacactt ggtgtgtgca aatgccatga ggtagggata ctttgttttg ttttttattt    26040
tttattgggt tcgatctctt ttgtttatga tgtatcccca agtgcctaga ataggggcctg   26100 gcatatggta tatactcaat aaatatttgt tgaatgaatc catgatggaa tgtgaaatgg    26160
ctagcattac atagaaacct gtagcattgc tggagagata aaatatataa acataatcca    26220
ttgcaggtat attgacaagt tcaaaataat ataatgggta ttgaatatct aaatgtttgt    26280
tgttgttgtt gctgttgttt ttgagacaga gtcttgctct gttgcccagg ctggagtgta    26340
atggtgcaat tttggctcac tgcaaacttc gtctcctggg ttcaagtgat tctcctgcct    26400
cagcctctcg agtagctggg tttacaggca ctcgccacaa tgcctggcta atttttgtat    26460
tttagtagat gtggagtttc gccatgttgg ccaggctggt cttgaactcc tgacctcaag    26520
tgatctgccc accttggcct cccaaaatgc tgggattata ggtgtgagcc actatgccca    26580
gctttgaata tctaagtttt aattggatgc tgagggaatg attaatcaga gtagggctgg    26640
gttaattgaa aaatgtgata catttgtatt tatggccaga tagagaacat gaatctgaat    26700
```

```
ttgcagaatt atctggctta acattttttt ctttccagtt ttcactgtat cccccatgtt   26760
gattcaattt aaaaaatata cctattttac ttcaattcaa caatgctatg ccagtacaaa   26820
cccatacgtt ctattatttt tgttttgttt tgttttttgta tctccaccct gttacttctt  26880
ttcttataaa attggtattt gaaatttatt gaaatatttt ggaagagtga cataccattt   26940
ttggtacttt gtacctctgc acccttggga agtgaccctg gcttacatt tcataactgc    27000 cttgtgacca tggccctcaa gtggttgcca gatggttgaa gaacattaac ctatctggct   27060
caattttgtg accatggatt gaatcctcta cataactgca gtgtgcaaac cacacatccg   27120
ttccaagatt gtagtcagga tatgaacttt ttaagaataa aacttcttcc cttctgatct   27180
gggcctggta tgtggtccta ctagaaccac atcacctact cttggtgcta acaatttgtg   27240
gcaccaagtt gttcaagttt cacccattaa agaaattccc cgaccttgcc ttctcctcag   27300
gtaactaccc cattctattt tttctttcat agctaacatt ctctgctctc ctggtctctc   27360
tacttcactt tcatttacat ctcagctcct gaagtatggt ttccaccatg ttcctaaaac   27420
tacattgccc agggtcacta gagacctctt atgaaatata caacacctt tctacattac    27480 ttccgtgtgg accactttttt cacattgaac ccattttgtt ggtttatgta cacacccctt  27540
ccttggcttt cccatctgat ccattctcc tttgatggag aaggtgagtc tgctccatat    27600
ttagcttctt actctgagta accaaatgtt atggatggga ggttagctct gtgtgtgaga   27660
gaaaggtgga gaagcatgtg gggagggaaa tagatgggaa aaggtaatta ggctttatag   27720
aagggctctc attagcaagc ttctagggga tgccaagatc catgcttaga gattgccagg   27780
cttgtcttca aatctcagct gtgtattact cctttatgtt ttttgtttgt ttgtgttgtt   27840 tgttttttgag acagagtctc gctgtgtcac ccaggctgga gtgtagtggt gtgatctcag   27900
ctcactgcaa actctgcctc ctgggttcaa gcgaatctca gtctcctgag tagctgggac   27960
tacaggcatg caccaccagg cctggctaat ttttgtagag acggggtttt gctatgctgg   28020
ccaggctggt cttgaactcc tgacctcaag tgatctgccc gccttggcct cccaaagtgt   28080
tgggattagt ggcgtgagcc actgccccgg cctattactc ctttagagtg atttagagcc   28140
atgtttactt atggtaactt gacagtaatg ggaataacca ctgatgaaac gtaaagcctt   28200
tgtctaattg tttacctagt tcttccttgt ggttcatgaa attttttcatc tctgtacagt   28260 ttgaaaatta agatgataat atttagagat attttattcc tttgtgaaga gaaaaaaggc   28320
tttcattaac agaaatcagt ggcaataact taataaatac aatcagctgg tgttcctata   28380
gtatttaaaa gaaaacagaa agtttactag atttcagcca gttttcagac tatttaatgt   28440
ctattcttac tataatagaa aatatataat ttgatcttgt tctcattttt caaagacctt   28500
taatacatga ttttagtagt tgaaaatgaa gtttaatgat agtttatgcc tctacttttta  28560 aaaacaaagt ctaacagatt tttctcatgt taaatcacag aaaaagccac ctgacatttt   28620
aacttgtttt tgatttgaca gtgaaatctt ataaatctgc cacagttcta aaccaataaa   28680
gatcaaggta taagggaaaa atgtagaatg tttgtgtgtt tattttttcc accttgttct   28740
aagcacagca atgagcattc gtaaaagcct tactttattt gtccacccctt tcattgtttt   28800 tttagaagcc caacactttt ctttaacaca tacaatgtgg ccttttcatg aaatcaattc   28860
cctgcacagt gatatatggc agagcattga attctgccaa atatctggct gagtgtttgg   28920
tgttgtatgg tctccatgag attttgtctc tataatactt gggttaatct ccttggatat   28980
acttgtgtga atcaaactat gttaagggaa ataggacaac taaatatttt gcacatgcaa   29040
cttattggtc ccactttttta ttcttttgca gagaatggga tagagagctg gcttcaaaga   29100
```

| | | | | | |
|---|---|---|---|---|---|
| aaaatcctaa | actcattaat | gcccttcggc | gatgttttt | ctggagattt | atgttctatg 29160 |
| gaatcttttt | atatttaggg | gtaaggatct | catttgtaca | ttcattatgt | atcacataac 29220 |
| tatattcatt | tttgtgatta | tgaaaagact | acgaaatctg | gtgaataggt | gtaaaaatat 29280 |
| aaaggatgaa | tccaactcca | aacactaaga | aaccacctaa | aactctagta | aggataagta 29340 |
| aaaatccttt | ggaactaaaa | tgtcctggaa | cacgggtggc | aatttacaat | ctcaatgggc 29400 |
| tcagcaaaat | aaattgcttg | cttaaaaaat | tattttctgt | tatgattcca | aatcacatta 29460 |
| tcttactagt | acatgagatt | actggtgcct | ttattttgct | gtattcaaca | ggagagtgtc 29520 |
| aggagacaat | gtcagcagaa | ttaggtcaaa | tgcagctaat | tacatatatg | aatgtttgta 29580 |
| atattttgaa | atcatatctg | catggtgaat | tgtttcaaag | aaaaacacta | aaaatttaaa 29640 |
| gtatagcagc | tttaaatact | aaataaataa | tactaaaaat | ttaaagttct | cttgcaatat 29700 |
| attttcttaa | tatcttacat | ctcatcagtg | tgaaaagttg | cacatctgaa | aatccaggct 29760 |
| ttgtggtgtt | taagtgcctt | gtatgttccc | cagttgctgt | ccaatgtgac | tctgatttat 29820 |
| tattttctac | atcatgaaag | cattatttga | atccttggtt | gtaacctata | aaaggagaca 29880 |
| gattcaagac | ttgtttaatc | ttcttgttaa | agctgtgcac | aatatttgct | ttggggcgtt 29940 |
| tacttatcat | atggattgac | ttgtgtttat | attggtcttt | atgcctcagg | gagttaaaca 30000 |
| gtgtctccca | gagaaatgcc | atttgtgtta | cattgcttga | aaaatttcag | ttcatacacc 30060 |
| cccatgaaaa | atacatttaa | aacttatctt | aacaaagatg | agtacactta | ggcccagaat 30120 |
| gttctctaat | gctcttgata | atttcctaga | agaaattttt | ctgacttttg | aaataataga 30180 |
| tccataatat | atattcttat | ggaaatctga | aaccatttgg | gcatttgggg | gtaaaaagta 30240 |
| ttttattagt | aaatttaaat | gaggtagctg | gataattaaa | ttacttttaa | gttacctttg 30300 |
| agatgatttt | tctcaatcag | agcaccaccc | agagctttga | gaaacaattt | tattcacagc 30360 |
| ttctgattct | atttgatgta | attttttagaa | aataagtttt | gctggttgct | ttgaatcagg 30420 |
| gtatggagta | cagttcactc | tgatcctatc | atataaatca | tgtaagtata | taacatttc 30480 |
| aataagtgat | tgttggattg | aagtgaatga | tatttcaagt | aattgttatg | tcatggccaa 30540 |
| gatttcagtg | aaactcaaaa | tttctcctgg | ttgtgttctc | cattgcatgc | tgcttctatt 30600 |
| gattaaccta | agcactactg | agtagaagct | ggaagagggg | tctaattaga | aggccccttt 30660 |
| ctatgctctg | cttggcttgt | aaaataattt | atttctctag | atcccaccaa | catagtagtt 30720 |
| tcatgtatgc | aaaaacaccc | acctaaatgt | caaagtttgt | atgatacatg | gacatatcta 30780 |
| tagaatttt | tttggtctgg | tgcatgccaa | aaaataaaca | tgatatagaa | gaatttaata 30840 |
| tttattgagt | acctaatctg | ttccagttca | atatgaaggt | ctttatgcag | attattttac 30900 |
| ttaattttcc | tagtaactcc | atggagcaaa | aattatctct | aatttatata | acaggaagtt 30960 |
| gagcgtgagg | caaattaagt | aactttccca | aagttacaca | tatggtaagt | ttgagagata 31020 |
| tcccagtctc | tttagctcca | aagcctttga | ccctttcacc | ataccagatt | atgattgcta 31080 |
| ttaatatata | attataatta | taatgattgt | atttaggtac | tcaacagaat | ggtgactcta 31140 |
| gtaaccagcc | ttggttctgc | tgagcttctc | tgcgtcttct | caggagacac | aggctacaga 31200 |
| gcttgaaggc | tgaggattct | tccagggtca | cttcaggggc | aaatctgaaa | ctttcttcag 31260 |
| gacaggaatc | aacgagatct | tctcacttac | ttatacctgg | gggaggaact | gtatgaaatc 31320 |
| cacccaagaa | ccagtcatgc | taagggccaa | acctatagac | aaaaaaaggg | ataggagaat 31380 |
| ggagtatgta | tggagaaaga | ctaaattgtt | cttaaacttc | tcaagcttaa | aaatatccca 31440 |

```
gcaaaagaga tcgtaaaagc ccttcatggc gtattaatta tccatgcatg ggggtgagtg   31500
gaaaggtact cctgagcccg aggctacagc tttggaacta gcagcacctt tgaaggggaa   31560
agcgtgtttc catcatctca actcctactg ataaccaatg aatattggt gagtaaagga    31620 tcctggggga agaagcagct gaaatgtgta ggtgagaagg cagagagaag aatatttata   31680
ttgggaatgg cacaagtgtg atgaggctgc aggttttca cccttgtcat agagaaaaaa    31740
ccacgctgac accatgcagt tttaaatagt gagaaatttg caaattgtta gatcttaaat   31800
aatttagata aacatagtgg ccatttagat tattgcagtt ttttcaggat atctgatctc   31860
ttgatttcat tcttttttgtc tcttataaga ataaaagggg gggagaaaat ttagccatta  31920
tagtatttct ctacattttc tctgtccttt tacataactt acaccagtgc cttcctattt   31980
atggtattat ttatgggtat ttcttctttt ctttcactga gcaaggataa atgagccagg   32040
gattcttgaa actactgtaa cacttctctt agaaatagat ggtcatactt tcagaatctc   32100
tacacattct tagtccctct aaacaatgat agttgtggca taaaaatatt tgcttggttt   32160
caggactgat agagaaaagt actataaaat ttgctgttaa ctgtgaaagg ttaaaaaaaa   32220
ggaggtgcca tcatgaagga gctaatcttt ctgaagtact gctgtagttt taaatattat   32280
tagctatgac ttctcaccat taactatgca cttgcttttt cttcatctga ctcagcagcc   32340
agatagatgc aacattgtct ttaacattta agactcctag caagtccggg cacggggct    32400 cacacctgta atcccagcac tttgggaggc cgaggtgggc aaatcacaag gtcaggagtt   32460
tgagaccagc ctggccaata tggtgaaacc ctgtctctac taaaagtaca aaaatcagcc   32520
aggtgtggtg gcgtggtggc gggcacctgt ggtcccagct acttgggagg ctgaggcagg   32580
agaatagctt gaacctggga ggcagaggtt gcagtgagct gagatcgcac cactgcactc   32640
cagcctgggt gacagagcga gactccatct caaaaaaaaa aaaaaaaaaa aagactccta   32700
gcatggaaga gaaactggct gttgaaaacc tgaatgtgag agtcagtcaa ggatagtttg   32760
agggaagcca agtagaggaa gctctcacaa gcagattggt gagagaatat gattatacaa   32820
tgcatttatt atgataagaa attcacaagc attcattcaa aatactcttg attcctaggc   32880
agctctgggc atatttccac caacaaattg aggcatatgt cagtgcagcc taggtcagac   32940
tacctttttt cattaaacct cacaaaatta aggacatac aggagaagtc ctggtactca    33000
tgttgcagac tacagtctat atggcaaagg aggatctctg tcccttatgt ttggatgaaa   33060
acattgggta ggcatttgaa tacaagccta ctgctaatat ggggctaagg tcttggccc    33120 cctaaaggtt tgctgaaata ttactgacag gaggcagatt gataagagga aaagcacata   33180
aatgtatttg acatgtatac atgggagcct tcaggatgaa gacctaccct ctcagtgcag   33240 tatgaagct tgtataccat cttgaggtta cagaaagaat gggggtttgg atctttgtaa    33300
aacaggtttc agtggcaaga caggttatga gaaggagaaa ggaagagact tgggtagcaa   33360 aggggggtctt gttttgtagg taaatcgttg gcagcccaca gagaaaatag atggagaatg   33420
tttcttttca gaccttggca ggtgtcagat tctcagttaa tctctcctag atttgaaaaa   33480
aaaaaaaaag gtctagaaag ggagagcctg gctgcactaa cacatttttct acagatgcaa  33540 atttctccca caaatacag ctttgcaggt ccacttctat ctgctgggcc tgtggcaacc    33600
atttcaaaat atgtgaatga aatatatgtg ggggtaaact ttttttattt acttccctaa   33660
agaagggatg gtgttctctc gggaattctg tgcatagaga gcctgtggct taggcacttt   33720
gatttatgta tatctcttcc tgtgattggc tatctaggga ctgctatctc cagcaaatct   33780
tctaaatgtc tgccatgtag aattcctttc tcatctttct gtctcacccc cttatctagc   33840
```

```
tgcttctcta accctagagt gacactgcac tccccacaat ctcctatgtc ctgaatatttt    33900 taccccatcc taaactccat ctctaacaca gatgcacttt cttgtgctgc ctactgcatt    33960
gtacatcttc cccttagttc ccatgatgca actctgccct accccagaaa atgtaattta    34020
attggtctgg gataaaacct gggacactat cattcttgaa atattcccca agcgattcta    34080
attatatagc caaagttgag aactatttgt agacaggcat cagcatgatc acttaatgat    34140
ttgacttttg ctagatctaa ggtgaggaaa ttggagagtg gtatccatag gaagaactgt    34200
ttagtttaat ttttttttta ttttttcttc taaaaaaaaa tccaacaacg agatacatgt    34260
gcggaacatg caggtttgtt acataggtat aatgtgccat ggtagtttgt tgcacctatt    34320
gacccatcct ctaagttccc tccctactc cttacttccc aacaggccct ggtgtatgtt    34380
gttcccctct ctgggtccac ctgttctcaa tgttcaactc cctttacga gtgagaacac    34440 atggtgtttg attttctgtt cctgtgttaa tttgctgagg atgatagttt ccagcttcat    34500
ccacgtccct gcaaaggaca tgatctcatt ccttttatg gctgcatagt attccatgat    34560
gtatatgtac cacattttct ttatccagtc tgtcattgat gggcatttgg gttggttcca    34620
tgtctttgct attgtaaata gttctgcagt aaacatatat gtccatgtgt ctttatagta    34680
gaatgattta tattactttg ggtatatacc cagtaatgag attgctgggt caaatggcat    34740
ttctggttct agatacttga ggaatcgcca cactgtcttc cacaatggtt gaactaattt    34800
acactcccac taacagtgta aaagcgttcc tatttctcca cagcctcacc agcatctatt    34860
gtttcctaac attttaataa ctgctattct gactggcatg agatggtatc tcattgtggt    34920
tttgatttgc atttatctga tgatcagtga tgctgagatt tttaaaatat gtttgttggc    34980
catgtaaatg tcttttgtga agtgtctgtt catatccttt gcccacctta atagggtttt    35040 tttttcttg tgaatttgtt taagtgcctt gtaaattctg gaaattagat ctttgtcaga    35100
tggatagatt gcaaaaattt tctcccattt gtaggttgc ctgttcactc tgatgatagg    35160
ttcttttgct gtgcagaagc tctttagttt aattagatcc aatttgtcaa ttttggcttt    35220
ttttgcaatt gcttttggca ttttcctcgt gaagtctttg cccgtgccta tgtcctgaat    35280
ggtattgcgt aggttttctt ctagggtttt tatagttttg ggttttacat ttaagtcttt    35340
aatacatctt gagttaattt ttgtataagg tataaggaag gggtccagtt tcagttttat    35400
gcataatggc taggcagttt tcccaccacc atttactgaa taggagatct tttcctcatt    35460
gcttgttttt gtcagatttg tcgaagatca gatggttgta gatgtgtggt gttatttctg    35520
aggtctctgt tctgcaccat tggtctatat gtctgttatc gtaccagtcc catgctgttt    35580
tggttaccgt agccttgtag tatattttga agtctggtag cgtgatgcct ccagctttgt    35640 tcttttttgct taggattgtc ttggctatat ggagtcttct tgattccat atgaaattta    35700 aaataatttt tttttattct gtgaagaatg tcaatggtag tttgatggga atagcattga    35760
aattataaat tactttgggc agtatagcca tgttcacaat attgattctt tctatccgta    35820
aggacgacac ttttttccatt tgtttgtgtt ctctcttatt tccttgagca gtggtttgta    35880
gttctcctta aagaggtctt tcacatcctt tgttagctgt gttcctaggt attttgttct    35940
ctttgtagtg attgtgaatg ggaattcatt cttgatttgc ctctctgctg cctgttgttg    36000
gtgtaaacaa aattcatttc ttgttcttat ttgtgaaatt ttggaaccaa atctattttc    36060
aaattagaaa ttgcttgtga taatggtttt gcaacttaga ctggatatga gacgatgaga    36120
tattagttct ttcattcctt tgtaggaata tggtgcatct tgcattattt tagctaacta    36180
```

```
gtgtccttta atgactaatg aatatgacat ggtgaaacaa agtaaaatat atatgatgca    36240
ctaagtatgc attgtttcca aaggttcagc atttttttt tgttaactct gctgggatct     36300
gctttatgca ctgataacat aacttatttt atgatcttaa gcaaataaaa acacttatct    36360
ggacctcagt ttccttaact gtacaactga gggaaactgt atagtatagc tatagtacag    36420
tataccatct ttaccgtcac ttccatcttt taaattatgt gtatataaga tagggcctag    36480
ataaatggta tttatcttaa attacagtga tactagctta taacttaatt tgctaggtca    36540
tgttgaactg ataacaatgt gtgaactgat gagcaactga gaagtaacca ggttgtgtta    36600
taacagtttg ttttttgattt agggttatca gtgagggtgg cggtggggag gggactttgg    36660
agtctaactg tctagttcaa atattagttt ttgtttatttt ttatttttaa ttttttgtggg  36720 tacatagtag atgtatatat ttatgggta catgtgatgt tttcatatag gcatgcaatg     36780
tgaaataagc acatcataga gaatggggta tccatcccct caaacactta tcttttgagt   36840
taccaacaat ccaatgacac tctttaagtt atcaaatcac agttttgcca gctactagcc   36900
atgtgatttt gggtaggtta cttaaattct cttcatctca atttcattat tgtaaagtgg   36960
agataatgat agcacatttt ttcttttttct ttttttctttt atttttttatt attatacttt  37020 aagttgtgtg atacatgtgc agaatgtgca ggtttgttac ataggtatca acaactctat   37080
aaaacatgtt ctatccagga aaagaaacta tcatcagagt gaacaggcaa cttacggaat   37140
gggagaaaat gtttgcaatc tagatggcga ttgcaatggc ggttcgctgc atccatcagc   37200
ccatcatcta cattaggtat ttctcctaat gctatccctc cccttgctcc ccacccctc    37260 acaggccct gtgtgtgatg ttcccctccc tgtgtccatg tgttctcatt gttcaactcc    37320
cacttatgag tgagaacatg tggtgtttgg ttttctgttc ttgtgttagt ttgctgagaa    37380
tgatggtttc cagcttcatc catgttcctg caaggacatg aactcatcct ttttatgg    37440 tgtatagtat tccatggtat atatgtgcca cattttcttt atccagtcta tcattggtgg    37500
acatttgggt tggttccaag tctttgctat tgtgaacgct gcagcaatga acatacataa    37560
gcatatgtct ttctagtcaa ataagttata atcctttggg tatgtaccca gtaatgggat   37620
tgctgggtca aatggtattt ctggttctag attcttgagg aatcgccaca ctgtcttcca    37680
caatggttga attaatttac actcccacca acagtgtaga agcattccta tttctccaca   37740
tccgctccag catctgttgt ttcctgactt tttaatgatc accattctaa ctggtgtgag   37800
atggtatctc attgtggttt tgatttgcat ttctctaatg actagtgatg atgagcttct   37860
tttcatgttt gttggctgca taaatgtctt cttttgagaa gtgtctgttc atatcctttc   37920
cccacttttt gatggggttg ttttttttcct gtaaatttgt ttaagttcct tgtagatttt   37980
ggatattagc cctttgtcag gtggatagat tgcaaacatt ttctcccatt ctgtaagttg   38040
cctgttcact ctgatgatag tttcttttgc tggatagaac atgttttata gagttgttgt   38100
gagaattaaa tgcattaagc acatagaata gattctggta catagcaagt gctctctcta   38160
tatatggaac tctatatgta gttggtgcaa aagtaattgt ggttttcacc attgaaagta    38220
atggcaaaga ccatcattac cttttcacca atttaaatat atggaaggaa tatatatata   38280
aaacctatat atatatgtca catatatgtc tctaacccat tattaataa tataatacaa    38340 tatatattat aattataatt gtatataaca tatgttatat aataatatag taatatttat   38400
tctaaataaa tatataatac tataaataat ataataattt atatatatga ttataatata   38460
taataggcta tattatatat tattaacata tacatatgtg tatatatatg tctttcatag   38520
acttaaatat atagagcaat aataggttag aaaatagcaa acatgtatat ataaacatat   38580
```

| | | | | | |
|---|---|---|---|---|---|
| atacatatag | aaaacatata | taaaaacata | tatatatata | tatatatgtg | tgttttctgc 38640 |
| ctttcatttt | tagagacagg | gtctcatcat | gttgcccagg | ctggtctcaa | actcctgggc 38700 |
| tcaagtgatc | ctactgcttt | ggactcccga | agtgctggga | tttcagacat | gagacactgc 38760 |
| acccagtcca | gtccctgtct | ttttaaatag | actctctacc | taagtgcaca | aatactcatt 38820 |
| atttacattt | agttatttct | gtatatatgc | tataagcaaa | tcttgtagca | ccagtttgat 38880 |
| ttttataagg | cacaagaata | tattttacta | atgctttaaa | atggcagcta | gattctagta 38940 |
| ttactttaga | aattaaaatt | aatattttaa | cacatctttc | attattgtgt | tatctgaacc 39000 |
| aaacctatta | ttgctgctat | ttcagcaaat | ccaggggctt | tttcttataa | aatatgaaga 39060 |
| atatagctta | gatttctagt | gaagatgtta | ccagtaataa | ttaataaaat | cagtaagcac 39120 |
| taaaaggaaa | ataccaaaac | taaagcattt | tgaattagtc | attgaatcta | aaagaaaggt 39180 |
| agatttttt | ctgagattct | gttctaggtg | tggtatatgt | gtattttgc | aaaaactata 39240 |
| aacaattgtg | gcaaaatgaa | ggaaatattt | aaaaacaaac | ctcttaattc | ttcagtggat 39300 |
| taagcgtgaa | tatgttttta | ttttctatga | tgaatatgga | aaaattcatt | tccttagcaa 39360 |
| tttgtatgag | cccaaaaact | attgtcagac | tctgctgtat | caaatagac | aaaaaattga 39420 |
| cactcacttt | taccctgcca | aaagcaaaat | cttaaacttt | tgctttagta | tataagccag 39480 |
| cattcattgt | atcctatgat | gggttctgag | tgtaggtgta | tttgctttct | tccattttt 39540 |
| gtatgcatgt | tttctttta | tttattattg | taagttgtat | gaaatttta | tccaatttt 39600 |
| tattttcttc | tgattaataa | tcagaataat | cagataatta | ctggtaaatt | tgatgttaat 39660 |
| ccttccagct | ttttcccatg | ggaatttata | cttaataaag | gggagaagtc | atcattacat 39720 |
| aatgtgcata | ttaatctgct | tctcccttta | atgtgttgtg | aatgcctttc | catgtcatta 39780 |
| gatgttttc | tacctagtta | ctttcatgaa | tcatatggct | gtaccatgat | ttatttaatc 39840 |
| agttcctcat | cattgagtat | gtaaattgcc | tccattttt | tattactata | aaaggtcctt 39900 |
| cagtacacac | ccctttaaaa | gctgactctt | agaaggtgtt | cttgactctc | tacctaagtg 39960 |
| taaaaataca | aataaattgc | tttccagaaa | aggtgcacta | ctatttact | ttcctgatac 40020 |
| taaactatga | aaattcagtc | ctaacaatag | atatttaaat | aaagttttaa | aaatgccaag 40080 |
| tgaaaaagag | catattatta | ttttcatttg | cattacttt | ggttcctggt | gagtttaatc 40140 |
| tgttttgta | tattaattat | gcattatat | ttcttttgt | gtgtgtgaat | tgcctttcat 40200 |
| gttcttgtg | tgttttatt | tgttgtatt | tgtctctttc | ttgatatatg | agagaatatt 40260 |
| ttccctagcc | tgtcaattgc | cttgtaattt | tgttctagt | gagttttt | ttttttttt 40320 |
| acaattaaaa | gctttaattt | ttgaaaattt | tgctggcaaa | tctatatatc | tttttctttg 40380 |
| ttttctgctt | tgacattatt | cttttataaa | ggcccatgcc | acccaaatat | tatgtaagca 40440 |
| tgcatctatg | tttttattac | ttcatctttt | acatttaaat | atctactcta | tttagaattc 40500 |
| attgtgatgc | atgtatgagg | tagaaatcta | atttcaaaaa | gatgagtatc | cagtttgtcc 40560 |
| atcatttatt | gcatgatctc | tttctccact | gaattaaaat | gccgtatttt | ataatatatt 40620 |
| aaagtattac | atgtgcttgg | acatgttcct | ggacttttga | gataaatcag | tctatttctt 40680 |
| tgtcatgtca | catattatta | tggctttatg | atttaatatc | cagtaatgta | aaccctctga 40740 |
| cacattattc | ttattcctca | aatgttttg | atgagttttc | ttccaaatga | aatttataat 40800 |
| cattttattc | attgattcaa | caaatatttg | ttgaatggat | attctgtgct | tggtattgtg 40860 |
| catggtatta | ggattgttgc | aaaaattgag | actgacagtc | cctactctta | cggtgctaaa 40920 |

```
aattcacttc caaaaaaatc tttaaatgtt gatgaagatt gcactaatct tataaaataa   40980
cttggagggg aatgtaatct ttgcaacatt aagttcttca ttttagaaag ttttaagact   41040
ctccatttat ttgagacttt taaaatatgt cccaataatg ttttgtgaga tgtatatttt   41100
aagatatata tcttattgct attacattgt atcttttgtt atattgttac tatgaatggg   41160
atactcattt aattagatgt cattttggt atatagaaat ctattttctt agcatagtca   41220
ttttttaaac ctcgatctat taaattcttg attcatttac atttgttaca caatcatatt   41280
ctatgctgat aatacttctt gcttctttcc aatatttgta cctcgatcat ttttcttgtt   41340
gagttgtatt agctagaagt tctagaaaaa tgttaaatgg tagtaatagc tagtattctg   41400
ttttttcctg actctaaatg taatgcatct agactttat aattatggca ttgattgtaa   41460
cattttgagg aagaaatcct ttttcaggtt aataatgtat ctttatattc aagtttatta   41520
agaacattta ttggaaacat attgaaattt tatcagattc cttttcagtt gttactgaga   41580
taatcatagg ttcttctgta ttcttttaat taatttctca aaattaaact gtcctattat   41640
tcttggaata acgacatata aagtactgta tatttaaaag aagttaaaat gataatggtg   41700
attttattaa gtgacctcac acaatagaaa acagtgtagc cttagaagtt ttccaagtga   41760
ccattctact tagaaacaac cctgctttgg gatcagaact gtaattttta aagtaaagtt   41820
ttctgggttt aattcattta gtgtaattac aagcatgagt tcaggtttct attttttttca   41880 cctgaacttt ccttcatggt ttgaatatct agaaaaagca gacttcccta tctctagact   41940
aaacatttga tcctatctta ggtatgcatt acaattttt aaccataaat ggttaaagaa   42000
tttagactca tctacaataa ctttgaagct ctggtcttga agaacatgtg agaaatgaga   42060
tataactcct agaagatata ggagacattt ttagtcttcc aaattttccc tgggaggctg   42120
atctaaattg agtcacaaaa ttgttcccac caggaatgca atcacttgag ctgttttcta   42180
atctgagccc ctctacccag atgatcttct gaactcatac tgttcagact ttcatccttc   42240
tgagtagaaa acagccatag tcatggcagg atgagggcta ggacaattac ccaaggaatt   42300
cttggcctct gccatgggac tctgcagact cagatcatat aatcagagat gttagcactg   42360
gaggggacat cacaattagc tttctccacc tcttagtttta tcagtgagga aaactgtcca   42420
gagcgcggaa gagactaaaa taacacagcc aatgtaggta atgtgctgga taagaatttg   42480
gaattcacga ttttgaattc agtgtttatt tcaccatcac gctggcttac acgttggtat   42540
caggcttctt ctattattga agtgagccat taagtgaatt ccatcttgat ttgtgtctga   42600
tacagagtaa taaactattt tattaaatat ccaaataatt atacattcct ccttcttaca   42660
tgcaagccta agtttgcttg tactatttca tgtggtagca aatcaggacg cttcttgtgt   42720
ctctgaaaat actctgagta atggagtaca gtcagctttc ttgtaccaag aatataggga   42780
ctatgtttct cccagtcatt ctggggataa ttttgtgaa ggattgcact tcataggtta   42840
agctaggtat cagttaccag tgttttttcc aaataaaaaa aaaatcaggt gatatctgta   42900
aatggttcca ttgtaaatat taagaacat gatgcttaaa acagattagg gaaaactata   42960
gaaggggtgg ggtttcggag tgctaatttt gtccttgaat ggtaacagct ccatgtggtg   43020
gtgaggttta tgttggtttg ctgtttgcag atgatcttat tattagaatt tttcataccg   43080
aaaataaact gcattttagt ttgtaaacat gcccttccag agtaatgcta ccagttcttt   43140
gtgaaatagc tactgttgtt caaggatga ctatgtcctc ttcggttgag gaaagatgac   43200
aacaaactca gtaatgacat gtaaaatagg tattacaaac caggtatggt ggcatagcc   43260 tgtaatccca gctacttgag aggctaaagc aggaggatct gttgatctat ggatttgagg   43320
```

```
ctgtagtgtg ttgtgatggc acctatgaat agcccttgca ctccagccca agcaacaaag   43380
caagactgtc tctgaatttt tgttttgttt tgttttttgt tttttttttt ttgagacaga   43440
gtcttgctct gtcacccagg ctgaagtgca gtggcgcgat ctccactcac tgcaagctcc   43500
gcctcctggg ttcacgccat tctcctgcct cagcctcccg agtagctagg actacaggcg   43560
cccgcctcca cgcccagcta aattttttgt attttagta gagacgaggt ttcactgtgt   43620
tagccaggac ggtcttgatc tcctgacctt gtgatcctcc tgcctcggcc tcccaaagtg   43680
ctgggattac aggcgtgagc caccgcgccc ggcccctgtc tctgaatttt ttaaaaaggc   43740
attccactca aattaataca catttttaatt gtgttttgtt gtaaattaca actgaataaa   43800
aattcagcaa ataagtctgt tgtggtaggg aaaagtctat tgtgatctgg aaaatataat   43860
ggagaaatcc agtggaagag atttttatttc acattactca aaataaaaaa atcttataca   43920
agtctttaca cttgtaactt gaaaaattct gtgctaaaat ttagcttggt tgctaaaata   43980
tttctctttt tttctcagaa gcttcttttt agcatcctat agacacaagt tacttttaa   44040 aatatttgca tacttgcttt gcaatgtatt gtttatcagt agttctatat tctttgagat   44100
agtctatcca gtcttctgt atttatcgta tgtctgtata gatatatatt agcagataaa   44160
tgagttctga aaggggagaa atgtgattat gctaatcatg atataaagaa ttgactttat   44220
aagcagtgtt cacaggtcat acctttcccg ttactgtctt acagtgaaca agaaatgatg   44280
ctttgtctgg tatgcatggt aaataatgcc ccttgctctc tgcttcatga tcacatgtga   44340
tacttctaac atagatagca catgtaaatc cagtggcctt gactgcaact caagagagca   44400
ttttggccaa gtacaaaccc actagtcatg aaaaaaaaaa aaaaaccaaa tcaaagtaaa   44460
ttgatggtat tgacatttgt ctatgaaaaa caacataata tagaacaatt ctggggtaaa   44520
atattgatct aaaataattt taaggattaa atattgccat tgtaagcata ctatgagcaa   44580 ttatgttttgt aatgcagata tatttataat ttttaaatcca agatttaccct taattgtaca   44640 ttttcctaat ttaaaaaagt tatttttgaaa aaaaaatcct cgaatctaga gaaaggttgg   44700
caaatacata tggaactttg taaaaaaacat ccagggcagc actttcactg attgcagtag   44760
cttaggagtg aaaaacaaca caactgctcc aatgtatggc aatgggcaaa tatcccgatt   44820
tattcacagg gtggcatgtt aggcagtgct tagaataaat gagttggtta tacaagtatc   44880
aatagggata aatgtgaaaa acacagtgtt aagttttttaa aaagttgtaa aaagcacagt   44940
aggatgttat ttatataaaa tttaaaaacc tcaaaaacca ttcttctttg atatatattc   45000
taaagatgaa catatatgta atagaagtac aaaacataca taaaataata tacactatgc   45060
agtcatttgt gtacttactt ttcaaaaata tttcagtaga tatagcaaac agttaacatg   45120
taatatttgg ataggaggtt ggcaattttc ttttttagcac ctgcctgtct gctatcattc   45180
aaactcacat ttaaaatgtg gctatgtgag atgagagaac tataatattc caggtttgtg   45240
attagtttgg aaactttta aaagtttgaa tgtggtctga gagatagttt gttataattt   45300
ctgttctttt acatttgctg aggagagctt tacttccaac tatgtggtca attttggaat   45360
aggtgtggtg tggtgctgaa aaaaatgtat attctgttga tttggggtgg agagttctgt   45420
agatgtctat taggtctgct tggtgcagag ctgagttcaa ttcctgggta tccttgttga   45480
ctttctgtct cgttgatctg tctaatgttg acagtggggt gttaaagtct cccattatta   45540
atgtgtggga gtctaagtct cttttgtaggt cactcaggac ttgctttatg aatctgggtg   45600
ctcctgtatt gggtgcataa atatttagga tagttagctc ctcttgttga attgatccct   45660
```

```
ttaccattat gtaatggcct tctttgtctc ttttgatctt tgttggttta aagtctgttt   45720
tatcagagac taggattgca acccctgcct ttttttgttt tccattggct tggtagatct   45780
tcctccatcc ttttatttg agcctatgtg tgtctctgca cgtgagatgg gtttcctgaa    45840
tacagcacac tgatgggtct tgactcttta tccaatttgc cagtctgtgt cttttaattg   45900
gagcatttag tccatttata tttaaagtta atattgttat gtgtgaattt gatcctgtca   45960
ttatgatgtt agctggtgat tttgctcatt agttgatgca gtttcttcct agtctcgatg   46020
gtctttacat tttggcatga ttttgcagtg gctggtactg gttgttcctt tccaggttta   46080
gcgcttcctt caggagctct tttagggcag gcctggtggt gacaaaatct ctcagcattt   46140
gcttgtctat aaagtatttt atttctcctt cacttatgaa gcttagtttg ctggatatc    46200 tctcagacca cagtgcaatc aaactagaac tcaggattaa gaatctcact caaagccgct   46260
caactacatg gaaactgaac aacctgctcc tgaatgacta ctgggtacat aacgaaatga   46320
agacagaaat aaagatgttc tttgaaacca cgagaacaa agacaccaca taccagaatc    46380
tctgggatgc attcaaagca gtgtgtagag ggaaatttat agcactaaat gcctacaaga   46440
gaaagcagga aagatccaaa attgacaccc taacatcaca attaaaagaa ctagaaaagc   46500
aagagcaaac acattcaaaa gctagcagaa ggcaagaaat aactaaaatc agagcagaac   46560
tgaaggaaat agagacacaa aaaccccttc aaaaaatcaa tgaatccagg agctggtttt   46620
ttgaaaggat caacaaaatt gatagaccgc tagcaagact aataaagaaa aaagagaga    46680 agaatcaaat agacacaata aaaaatgata aggggatat caccaccaat cccacagaaa    46740
tacaaactac catcagagaa tactacaaac acctctacgc aaataaacta gaaaatctag   46800
aagaaatgga tacattcctc gacacataca ctctcccaag actaaaccag gaagaagttg   46860
aatctctgaa tagaccaata acaggctctg aaattgtggc aataatcaat agtttaccaa   46920
ccaaaaagag tccaggacca gatggattca gccgaatt ctaccagagg tacaaggagg     46980
aactggtacc attccttctg aaactattcc aatcaataga aaagagggga atcctcccta   47040
actcatttta tgaggccagc atcattctga taccaaagcc gggcagagac acaaccaaaa   47100
aagagaattt tagaccaata tccttgatga acattgatgc aaaaatcctc aataaaatac   47160
tggcaaaccg aatccagcag cacatcaaaa agcttatcca ccatgatcaa gtgggcttca   47220
tccctgggat gcaaggctgg ttcaatatac gcaaatcaat aaatgtaatc cagcatataa   47280
acagagccaa agacaaaac cacatgatta tctcaataga tgcagaaaaa gccttttgaca   47340 aaattcaaca accccttcatg ctaaaaactc tcaataaatt aggtattgat gggacgtatt   47400
tcaaaataat aagagctatc tatgacaaac ccacagccaa tatcatactg aatgggcaaa   47460
aactggaagc attccctttg aaaactggca caagacaggg atgccctctc tcaccgctcc   47520
tattcaacat agtgttggaa gttctggcca gggcaatcag gcaggagaag gaaataaagg   47580
gtattcaatt aggaaaagag gaagtcaaat tgtccctgtt tgcagacgac atgattgttt   47640
atctagaaaa ccccatcgtc tcagcccaaa atctccttaa gctgataagc aacttcagca   47700
aagtctcagg atacaaaatc aatgtacaaa aatcacaagc attcttatac accaacaaca   47760
gacaaacaga gagccaaatc atgagtgaac tcccattcac aattgcttca agagaataa    47820 aataccctagg aatccaactt acaagggatg tgaaggacct cttcaaggag aactacaaac   47880
cactgctcaa ggaaataaaa gaggacacaa acaaatggaa gaacattcca tgctcatggg   47940
taggaagaat caatatcgtg aaaatggcca tactgcccaa ggtaatttac agattcaatg   48000
ccatccccat caagctacca atgactttct tcatagaatt ggaaaaaact actttaaagt   48060
```

```
tcatatggaa ccaaaaaaga gcccgcatcg ccaagtcaat cgtaagccaa aagaacaaag    48120
ctggaggcat cacgctacct gacttcaaac tatactacaa ggctacagta accaaaacag    48180
catggtactg gtaccaaaac agagatatag atcaatggaa cagaacagag ccctcagaaa    48240
taacgccgca tatctacaac tatctgatct ttgacaaacc tgagaaaaac aagcaatggg    48300
gaaaggattc cctatttaat aaatggtgct gggaaaactg gctagccata tgtagaaagc    48360
tgaaactgga tcccttcctt acacctata caaaaatcaa ttcaagatgg attaaagatt    48420
taaacgttag acctaaaacc ataaaaaccc tagaagaaaa cctaggtatt accattcagg    48480
acataggcgt gggcaaggac ttcatgtcca aacaccaaa agcaatggca acaaaagcca    48540
aaattgacaa atgggatcta attaaactaa agagcttctg caaagcaaaa gaaactacca    48600
tcagagtgaa caggcaacct acaacatggg agaaaatttt cgcaacctac tcatctgaca    48660
aagggctaat atccagaatc tacaatgaac tcaaacaaat ttacaagaaa aaacaaaca    48720 accccatcaa aaagtgggcg aaggacatga acagacacta ctcaaaagaa gacatttatg    48780
cagccaaaaa acacatgaag aaatgctcat catcactggc catcagagaa atgcaaatca    48840
aaaccactat gagatatcat ctcacaccag ttagaatggc aatcattaaa aagtcaggaa    48900
acaacaggtg ctggagagga tgtggagaaa taggaacact tttacactgt tggtgggact    48960
gtaaactagt tcaaccattg tggaagtcag tgtggcgatt cctcagggat ctagaactag    49020
aaataccatt tgacccagcc atcccattac tgggtatata cccaaaggac tataaatcat    49080
gctgctataa agacacatgc acgtatgt ttattgcggc actattcaca ataggaagaa    49140
cttggaacca acccaaatgt ccaacaatga tagactggat taagaaaatg tggcacatat    49200
acaccatgga atactataca gccataaaaa atgatgagtt catgtccttt gtagagacat    49260
ggatgaaatt ggaaaccatc attctcagta aactatcgca agaacaaaaa accaaacacc    49320
gcatattctc actcataggt gggaattgaa caatgagatc acatggacac aggaagggga    49380
atatcacact ctggggactg tggtgggtc gggggagggg ggagggatag cattgggaga    49440
tatacctaat gctagatgac acgttagtgg gtgcagcgca ccagcatggc acatgtatac    49500
atatgtaact aacctgcaca atgtgcacat gtacctaaa acttagagta taaaaaaaa    49560 aaaaaaaaaa gtttgaatgt tttcttgcat tcagagcctt ggttgacata gttaattaaa    49620
aataaaacat tgtatataaa gcacagaatg agcagctaca caaagctgct caatcaatga    49680
cagctctata tgggttaggg tttcttgtgg ggatgacatt gatgtagaaa gcatggtcat    49740
ctattgagaa tgatggggct ggaggtattg gatacttgag gtttagaaaa tacattgtag    49800
aaaatggaca aaaaccctc aaattaaggg atgaggcaga ataatgcttg gcaataccag    49860
gggtaggctg cagtctttct tggaaatata tattttaaat ggaaccaatt atcatagcat    49920
catttcctct cagggttacc ctctgatccc tattttacta aatcgttata aaacaaaatg    49980
aggaattatg tgtccttccc ttttgaagcc aatgtaacaa gatgggtaag aattagacct    50040
cctgagttca aaatccctgg attcagatct attcctgtat attcaggaga agtggtaata    50100
aattcgatgg acaatttggt ttagtagtcg attgaggacc ctgatgaggt atatttggga    50160
aaacataact tccgctctct ctcattgact cacgggcctt tgaggagtcc aggagtcatt    50220
ggaatctggc ctgaggttga ggctgctggc aaaactcctt ccccaaagtc cattcctatt    50280
gctgactgag aagggactag cattggaagt ggctgatttt aaataccgct agtgctggtg    50340
tgctcctccc tcccattccc agctctgctt tgtgtagttg ccttgagaag ctaagttcat    50400
```

| | |
|---|---|
| tctgaaaata atgccattgc acaaaacact tttgaaagtt ctagtttgaa attacatcag | 50460 |
| gtcacttggt ctgtgtggcc tcagtttctt catctgccat gtgaaaataa taatgcctac | 50520 |
| tctgtagcaa agaaagtctc tatagtaaac aaaaaaaaag cctactctga tactgaaagt | 50580 |
| tgttatgaaa aataaaaaag ggaaatgctt tagaaactgt taagtgctat gtagatgtta | 50640 |
| ctaattaaca aaccatttca gaaactatac tttttatttt atggccacta ttcactgttt | 50700 |
| aacttaaaat acctcatatg taaacttgtc tcccactgtt gctataacaa atcccaagtc | 50760 |
| ttatttcaaa gtaccaagat attgaaaata gtgctaagag tttcacatat ggtatgaccc | 50820 |
| tctatataaa ctcattttaa gtctcctcta aagatgaaaa gtcttgtgtt gaaattctca | 50880 |
| gggtattta tgagaaataa atgaaattta atttctctgt ttttcccctt ttgtaggaag | 50940 |
| tcaccaaagc agtacagcct ctcttactgg gaagaatcat agcttcctat gacccggata | 51000 |
| acaaggagga acgctctatc gcgatttatc taggcatagg cttatgcctt ctctttattg | 51060 |
| tgaggacact gctcctacac ccagccattt ttggccttca tcacattgga atgcagatga | 51120 |
| gaatagctat gtttagtttg atttataaga aggtaatact tccttgcaca ggccccatgg | 51180 |
| cacatatatt ctgtatcgta catgttttaa tgtcataaat taggtagtga gctggtacaa | 51240 |
| gtaagggata aatgctgaaa ttaatttaat atgcctatta aataaatggc aggaataatt | 51300 |
| aatgctctta attatccttg ataatttaat tgacttaaac tgataattat tgagtatctt | 51360 |
| ctgtaaactg cctctgttgt agtttttttt ttctcctaat catgttatca ttttttttgga | 51420 |
| atccatggtt tcctgttaag atgactcaca cagcctacat aaaagtaatt gacaaaatat | 51480 |
| catcttatag taaaatgcca catatcttta tgttcagcaa gaagagtata atatatgatt | 51540 |
| gttaatgata acccaaacaa caaaagattt caccttaact ggttgtcata agtagtagta | 51600 |
| tccaccgcct tattttgagt tggatttta tcatcctatg agcccctacaa atttaaagtt | 51660 |
| tttggaacag cacgtgcatt gaacccataa gaacctactc tgcttttctg catgtattgt | 51720 |
| ccagacaaga gaccaaattg ccgaggcatc atttaggtga attctaatta acatttagct | 51780 |
| accttacaac cacaattcaa ggttgtttca aaggcatgtg cttgcatcat cctgattcac | 51840 |
| taccatgtgt tactaacttg gatctgcaaa gtcattataa aaagctgttt tgatggactt | 51900 |
| atttggatat tgctttaccc ttcttctctc tttttctttta tcaatgtaaa aacattatat | 51960 |
| gttaaatact tggcttttaa gagcatagat ctgaaatctg cctctagcaa ataacccata | 52020 |
| acacttctaa gatatacctg caaggtcaat tgtgttgtaa aaccttgata accatacttt | 52080 |
| attgttcaaa aaagcctttt atgaaggcag aagttaaaaa aaaaaaacaa aaaaaacaga | 52140 |
| gtccacagtt atcacctcag ctacaatctc atcagttcac aagtaccagc aaaacatgtg | 52200 |
| ataagtcaac aaatgtttta tttcaatctg aacattttac gtaagtgaag actttgttag | 52260 |
| atatcatttg gaatgtggaa tctacacagt tggcatatca gagaaggttg aattcagttt | 52320 |
| aataaatgtt tatagaaagt gcttgttatc ataatgataa tagctcagga tgtgcatgac | 52380 |
| aagcttttaa gcgattgggt acactatctc atttgatctt ctgcacaact attaatggta | 52440 |
| ggtactatta tccctatctt atggataagt aaactaagat ttaaaaagta cagaacatgg | 52500 |
| tgtgaacact gcttcaaaat ttctaaaata ggtaaatcac gatctctaaa ctggagggtt | 52560 |
| gtccaaccac tagggacaat agagtactga tatttagtgg tcagactgta atgcgggaag | 52620 |
| agacaggcat gggctaaacg ggtgtagaga tcaaataagg ggcaggttag tttgtaaaca | 52680 |
| tgtccatatg taacatttag cacaaataca ggatataggt gctttcagac ccagctgcat | 52740 |
| tgataaaaag ttaggtggta ttgtatctgt cttcctttct caatgttgca tatctgtgtt | 52800 |

```
cttgcccagt tgcttcatc tctctagcca cacttattgg cctacaatgg catcatcacc    52860
aaagaaggca atcccatctc cgtgtggctt tggtttgctc cctaaagtaa accttgtgtt    52920
tacttttccc aggtctcatg ctttcccata tctgacctgt tttgtcctca tggccaggat    52980
atgtgggacc tttcctacaa tgttccaaag tttgtaatag agctcttctc tgctttgttc    53040
caaattctgc aacattttac tttaaataat gaatttaaat acaacaaac ttgagctttg     53100 cctatacttt tcaagaatgc agagataact aaattaataa aaatattcat tgagtcctta    53160
ctgtgcacac agctctatgt taagccttgt gcagaactca aagtcactcg agattaagcc    53220
tgttactaag ttatgtgcaa tttagctcag tggatttccc ccacttcata ttgctctgat    53280
aatgttttgg aattaactgc cttgattcct tcttttctct gcttgtctat acactattta    53340
ttattctaca ccatctcaaa ttctaactcc tcaagaaaat ccttccagat gatttttcta    53400
accaggagtt ttaacttcct tttaactacc ctattacttt ctacttcctt aactcatcta    53460
tcatattata tttagttatt tatatactag gtcgccttga agaagggatt gtgttttcat    53520
aaatcttaat aatccctgag gcatcaagta cagtgatttg catttactaa atgctcaaca    53580
aatatgtgag ggattcactt gaaactaata ttagataatt cccagtcaaa gtgatctaat    53640
agcaaatcaa ttcttcagtt ttataggcaa agtatgactc tggttttcca taatcataat    53700
taatttgtca actttataat tttaattaag taaatttaat tggtagataa ataagtagat    53760
aaaaaataat ttacctgctt aactacgttt catatagcat tgcattttc tttgtaaaat     53820 ttaagaattt tgtattaata aacttttta caaaagtatt aattattcag ttattcatca     53880 tatacttta ttgacttaaa agtaatttta ttcaaaagag ttagtatagg actacatgaa     53940
aaattcaagg ccaaggctta atttcaaatt tcactgcctt tggctctatc ttttaaaaca    54000
aaacaaaaaa ctcccgcaca atatcaatgg gtatttaagt ataatatcat tctcattgtg    54060
aggagaaaaa ataattattt ctgcctagat gctgggaaat aaaacaacta gaagcatgcc    54120
agtataatat tgactgttga aagaaacatt tatgaacctg agaagatagt aagctagatg    54180
aatagaatat aattttcatt acctttactt aataatgaat gcataataac tgaattagtc    54240
atattataat tttacttata atatatttgt attttgtttg ttgaaattat ctaactttcc    54300
attttctttt tagactttaa agctgtcaag ccgtgttcta gataaaataa gtattggaca    54360
acttgttagt ctcctttcca acaacctgaa caaatttgat gaagtatgta cctattgatt    54420
taatctttta ggcactattg ttataaatta tacaactgga aaggcggagt tttcctgggt    54480
cagataatag taattagtgg ttaagtcttg ctcagctcta gcttccctat tctgaaaact    54540
aagaaaggtc aattgtatag cagagcacca ttctggggtc tggtagaacc acccaactca    54600
aaggcacctt agcctgttgt taataagatt tttcaaaact taattcttat cagaccttgc    54660 ttcttttaa aactttaaat ctgttatgta ctttggccag atatgatacc tgagcaattc     54720
ttgttctggg ttgtcttatg tgaaaaataa attcaaggtc cttggacag ataatgtgtt     54780 ttatttatct ttgcatatcc attacttaaa acagcattgg acccacagct ggtacaaaat    54840
taattactgt tgaattgagc aaatatttat tctaaatgtc tctgtcaaat gacagagtgt    54900
ggttgtgtgg attaagtccc tggagagagt tctttgttct ctcatgttct atgctgtggt    54960
tcttgcttta tgcaaaaaga agtaagttac ttaaaacctg gacatgatac ttaagatgtc    55020
caatcttgat tccactgaat aaaaatatgc ttaaaaatgc actgacttga aatttgtttt    55080
ttgggaaaac cgattctatg tgtagaatgt ttaagcacat tgctatgtgc tccatgtaat    55140
```

```
gattacctag attttagtgt gctcagaacc acgaagtgtt tgatcatata agctccttt   55200 acttgctttc tttcatatat gattgttagt ttctagggt ggaagataca atgacacctg   55260
tttttgctgt gcttttattt tccagggact tgcattggca catttcgtgt ggatcgctcc   55320
tttgcaagtg gcactcctca tggggctaat ctgggagttg ttacaggcgt ctgccttctg   55380
tggacttggt ttcctgatag tccttgccct ttttcaggct gggctaggga gaatgatgat   55440
gaagtacagg tagcaaccta ttttcataac ttgaaagttt taaaaattat gttttcaaaa   55500
agcccacttt agtaaaacca ggactgctct atgcatagaa cagtgatctt cagtgtcatt   55560 aaatttttt tttttttttt ttttgagac agagtctaga tctgtcaccc aggctggagt   55620
gcagtggcac gatcttggct cactgcactg caacttctgc ctcccaggct caagcaattc   55680
tcctgcctca gcctccggag tagctgggat tagaggcgca tgccaccaca cccagctaat   55740
ttttgtattt tagtagagac agggtttcac caggttgccc aggctggtct cgaatgcctg   55800
acctcaggtg atccgcccac ctcggcctcc caaagtactg atattacagg catgagctac   55860
cgcgcccggc ctaaaaaata cttttttaaga tggtgtaaat attactttct gtatcaatgg   55920
tacatttttt acttgtcagt ctctagaatt tctttataaa tatgttgatt cagttcattt   55980
ttgtagatta taaaacaggt aaaaaaggat aaaacattta tgtgaattaa agggaatacc   56040 taattttgt gtagagttta ttagcttta ctactctggt ttatggatca tcacaccaga   56100
gccttagtta ctttgtgtta cagaataact aatatgagtg aatgaatgac ttacacaagt   56160
cactgcttag gataaagggc ttgagtttgt cagctagagt atgacagaaa gtatctaagt   56220
tttggagtca aatagcactt tgtttgaatc ccagattgca tgcttactag ttatgtgacc   56280
ttagtcaagc cacttcacct cactgagtct ttgctttttt catctctaaa atagagatac   56340
ccaccgctca taggctgtca taagggatag agatagcata tggaatgagt ctgtacagcg   56400
tctggcacat aggaggcatt taccaaacag tagttattat ttttgttacc atctatttga   56460
taataaaata atgcccatct gttgaataaa agaaatatga cttaaaacct tgagcagttc   56520
ttaatagata atttgacttg tttttactat tagattgatt gattgattga ttgattgatt   56580
tacagagatc agagagctgg gaagatcagt gaaagacttg tgattacctc agaaatgatt   56640
gaaaatatcc aatctgttaa ggcatactgc tgggaagaag caatggaaaa aatgattgaa   56700
aacttaagac agtaagttgt tccaataatt tcaatattgt tagtaattct gtccttaatt   56760
ttttaaaaat atgttatca tggtagactt ccacctcata tttgatgttt gtgacaatca   56820
aatgattgca tttaagttct gtcaatattc atgcattagt tgcacaaatt cactttcatg   56880
ggctgtagtt ttatgtagtt ggtccagggt gttattttat gctgcaagta tattatactg   56940
atacgttatt aaagaatttc ctacatatgt tcactgctgc tcaatacatt tatttcgtta   57000
aaacaattat caagatactg aaggctgatt ggtaactcac atggaactgg gagagtatac   57060
aattctgaac caaatagatg attctctatt attatatctt aatttatgtg ttatggtata   57120
ttaaacatga aaaaattgt atttggttag aatatgtttg ctcttcctta actcgggaat   57180
gacatagggt aatattcaca gattgggttc ctataaatcc tccacttgaa gtgaagtcag   57240
ttcaagtaat gaaagctacc tcctgagata gaatcagtac ttggcaccta tctctagtgt   57300
tctttcacct catataacct ttcactgatt agtaaagatt atatccaaca aagaaagtac   57360
agcacagact gagatatgat tactgagata aatttgggca aaatataaac tacagcattt   57420
ctgtagcaat gagaccattt ttcttcagtt gagctccatg ttctacaaac ttcaatcaaa   57480
aaaggttcta ggagactcag tgaaagttga tacactgttc aaggaacaaa taatttcagc   57540
```

```
acatgggaat tcacaggga aaaatatact aaaaagagag gtaccatttt ggatggtgtc   57600
aatatgggtt atgaggaatt caggctgctg agtccagtgt acaatggaaa ctgagctgca   57660
ggtgtgtgat tgtaacaaca aaagaaatgc tgaaatatta agtcctttgc catgtaaata   57720
gaaaaagagt atttatttcc caaacattat tgctcacctg tttttgttat gcctttcaag   57780
ataaatccag gaaaggaatt gcattttctt tccagaaaac aagttcttgg gggaattgtt   57840
caattggtag atgttgtttt tctcattaac aagtgagtgc tccatcacac ttgctgagtg   57900
ctccatcaca cttgctctct gcattactcc tctgcctgca aacacatata tagcaagggt   57960
gatgacaagg atatcagagg gtctggtttt ctcaaactca tgataaactc atggctgggt   58020
cattcttggt gctgatttta ctttgttttt tgttgttatt gttccctctt cctcaaaaga   58080
tgaaatctat ccctcttact tggaatttct ctttgatata tagcgaatgt ttggttgtaa   58140
cctgtataat ctggcatgaa attgtcactc gaaaaggcta gaagtgttga cataaatatg   58200
ggacagcaag agttgctcct actcaagaga gcaaatataa tgttctggaa gagattggca   58260
gaattcacat caaaggagtg attacttcag cctgggccac tgttgtactg gtcaaaaggc   58320
tgtgcaaagc tctctgaaaa tccactcttt tattgctctt tagtaataaa gtcactttca   58380
attttaaaaa taacaaactg atatatttt atgactcata aaatgttagc aattatatta   58440
tggagaatct actttctggg tgattcttac aaatgttctt ggatctattt ttttttctta   58500
tagtacctat tcttcccatt tttctcagct ctagttaata tatttcaaca acagttcaac   58560
aaatttaaca ttttataaa aagtgtttcc tatcatttta taaataccag cctagtccat   58620
gttattcctt ttcttgttga ggagaaagga cacacattgt aaattcaaat atagacctct   58680
actgtgctat ttaatcttgg taacaactcc acaaaggaga tgcatgtttt tccttctata   58740
gaggtagatt ctgtaaagtt agagggaaga gtgacttgct taagatggca taagctgtaa   58800
ctggcagaac caggattcaa agccaggtgg gatgccaaaa tcataatctg tcttcagtgt   58860
caagttactg aaattggtaa acattagacc taaatagacg gaattgcaat ccgggttggg   58920
cacattaaac tccattttct tcatcaatgt gctcagatta catttactt ttcaggctaa   58980 aaatggaaaa aaagagtccc tcttagttct gcacttgaga atgagaatag cttttctgaa   59040
ttatacaagg aagaagaact aatgcccaaa tgccaggtac ccacatgcac tatgccatgg   59100
cacagctgtt gccccttc accagagccc tctctctgta tcctggttga cctttccttg   59160
ggcaagagct gggtggggag gatcacaagt gactccaatt tggatggctt cgggaagact   59220
gggaccgagc tgaaggcagt gttgtcctct gcactccctg ttttctgtct gctggagcac   59280
tgaagcctca catatgtatt aaaaaaataa tttccatttg catttcagac tagaagattg   59340
aacgtatagt gtaatgtgat tgcaaataat tatattgaaa tgagacagag aggatgtagt   59400
atctactgtc ataattttc aaacccacc tgcaacttga attaaaagaa ccacttgggt   59460
tttttttttt gttcaaacg caaatcctgg aaacctactg agactcattc agtcagtatc   59520
tctaagaggc aagcttgaga ctgtatattt aaaaagcatc tcaggtgatt tttacacatg   59580
ctaaggctta agaaccactt ctctgtagct tatatgttat tttcaatgtt cctcaaagcc   59640
aagttagaat ttccaaagtg ttaagaatcc attagacaat cacagaattg tctttttcct   59700
ttataaatct tgcaatgttg ttctcatttc catacttaat tacttaaaac accaaccaac   59760
caacaagcaa aaaatgatta gtctaactaa tattacaagt taataatgaa gtaaaggttt   59820
aaaaataatg tcataataat gttaataaca aattattaat tataatttaa aaataatatt   59880
```

```
tataatttaa aaataatatt tacaagtact acaagcaaaa cactggtact ttcattgtta    59940
tcttttcata taaggtaact gaggcccaga gagattaaat aacatgccca aggtcacaca    60000
ggtcatatga tgtggagcca ggttaaaaat ataggcagaa agactctaga gaccatgctc    60060
agatcttcca ttccaagatc cctgatattt gaaaaataaa ataacatcct gaattttatt    60120
gttattgttt tttatagaac agaactgaaa ctgactcgga aggcagccta tgtgagatac    60180
ttcaatagct cagccttctt cttctcaggg ttctttgtgg tgtttttatc tgtgcttccc    60240
tatgcactaa tcaaaggaat catcctccgg aaaatattca ccaccatctc attctgcatt    60300
gttctgcgca tggcggtcac tcggcaattt ccctgggctg tacaaacatg gtatgactct    60360
cttggagcaa taaacaaaat acaggtaatg taccataatg ctgcattata tactatgatt    60420
taaataatca gtcaatagat cagttctaat gaactttgca aaaatgtgcg aaaagataga    60480 aaagaaatt tccttcacta ggaagttata aaagttgcca gctaatacta ggaatgttca    60540
ccttaaactt ttcctagcat ttctctggac agtatgatgg atgagagtgg cattttatgc    60600
caaattacct taaaatccca ataatactga tgtagctagc agcttgaga aattctaaag    60660 ttttcaagtg ataagactca atttatacaa agctaattgg ataaacttgt atatgattaa    60720
gaagcaaata aatacttatt atgcttttt gctgtttatt taaatattta acccagaaaa    60780
taagtcactg tgacagaaat aaaaatgaga gagaagggtg agccactctt aggtagttct    60840
ggcattattt aatctaggcc agaggttgca aatggtgtcc catagaacta attttggctc    60900
ctagacctgt cttatttaac ctttcattta aaaatttgt attggttgcc agcaattaaa    60960
aattgggaga tgtctcacac acacacacac ataaacacac acactcatgt gtgcagcctc    61020
ttttgaagaa ttggaataac tagtcaactg cgtcctcctt ttccacaagc tgtgacagct    61080
ccctgctcac agagcacctg ccctctcctg ttcatcatgc tctcttctca gtcccattcc    61140
ttcattatat cacctatttg gtcctgagac taagtgagtt tgagatctgt gatttagaca    61200
aagtggtgaa tctagctctg aatcatagta agtagctctg ggaatcatct tgtcttctgt    61260
tagcccattg agagagaaat agagagagag agagagagaa agaaagaaga agaaacagat    61320
ctggggagag tcactgaatg ggagcataga gacagagaaa cagatctaga aaaccaaact    61380
gggagaaaat gagagaaacc aaaagagagg tagagaggag cagagaagaa aatgaagaag    61440
caaggcaagg accaggcttt ttcattattt cttatggcca agacttcagt atgcgtggac    61500
ttaattcttc cttatgctcc taccttccct agggaaactg atttggagtc tctaatagag    61560
cccttctttt agaatcacag tttgatgcct taaaactagt tatataccct cacatgcttc    61620
cttaacccac agaagtgatg ctaatgaggc ccttaataag gagcgtgcta ttaagatgaa    61680
gacattcatt ttttttctcc gtccaatgtt ggattaaggc acattagtgg gtaattcagg    61740
gttgctttgt aaattcatca ctaaggttag catgtaatag tacaaggaag aatcagttgt    61800
atgttaaatc taatgtataa aaagttttat aaaatatcat atgttagag agtatatttc    61860 aaatatgatg aatcctagtg cttggcaaat taactttaga acactaataa aattattta    61920 ttaagaaata attactattt cattattaaa attcatatat aagtgtagc acaatgagag    61980 tataaagtag atgtaataat gcattaatgc tattctgatt ctataatatg ttttgctct    62040 cttttataaa taggatttct tacaaaagca agaatataag acattggaat ataacttaac    62100
gactacagaa gtagtgatgg agaatgtaac agccttctgg gaggaggtca gaatttttaa    62160
aaaattgttt gctctaaaca cctaactgtt ttcttctttg tgaatatgga tttcatccta    62220
atggcgaata aaattagaat gatgatataa ctggtagaac tggaaggagg atcactcact    62280
```

```
tattttctag attaagaagt agaggaatgg ccaggtgctc atggttgtaa tcccagcact   62340
ttgggagacc aaggcgggtg gatcacctga ggtcaggagt tcaagaccag cctggccaac   62400
atggtaaaac ccggtctcta ctaaaaatac aaaaaattaa ctgggcatgg tggcagatgc   62460
tgtagtccca gctgctcggg aggctgaggc aggagaatca cttgaacctg ggaggcgag    62520
gttgcagtga gctaagatca cgccactgca ctccagcctg gcaacaagg cgagactctg    62580
tctgaaaaag aaaaaaaat aaaaataaaa ataaaaagaa gtggaggaat attaaatgca    62640
atataaaagc ttttttatt tttaagtcat acaatttgtt tcacataaca gatcaggaaa    62700
taatacagag atcataagtt ttggagctgg gtttgaatcc tggctctgcc atttactttc   62760
tgtgtaatct aagtcaagtt actgaacttt gtgggccctc tggctctcca tgtgtaaaat   62820
ggagaatatt aatatttacc ttgcaagttt gttgtgaaga ctgaaggaga gaatttaggt   62880
aaaacattca tcagagtacc atgcacacag ttgttcctca ataaacatta gcttctctga   62940
ttgcaagttc cagtctaaag tgctttatat ataccagcca ataaaggat gcgagagaga    63000
tataccagtg tattgttttc taccatttta aacctatttt catccactgt tacaaattct   63060
atcatactgc tccacataaa aaatattatc aatgattttt agtctctgaa gtgcaatatt   63120
tgattattga gcacacctgt tgaagtttta gtttcttctc acttacatgg ttgtgtaaa    63180
ggtaggaggt ataaaaccag tgtcctaggt ctaaatcttt cttaatgtca tactttggat   63240
tcattgatat aagtaacttg agcaccagcg cttcatttta cttcattttt taaagatata   63300
gtaagagtaa ttcccatctg cctagcaaaa ttgttttgta gaaaagtttg tggatcagat   63360
ttattttact ttgattttag gaatttcaag tgtcttcgtc ggcatgaagg aaaaatatgc   63420
agtttgacat tttctactac tttcaggtca ttattttcct actctggtgc aaaaaccctc   63480
aattcctgtc tcactccatc taatcaaata ggtagcatgc ttgagccctt actatgtgcc   63540
aggcactagg ataagcactt tatatgtttt gtcccaatta attctcacag catttctatg   63600
acctaaataa aattaatatt ttcatttcac caataataaa atggaggctt caaaaagttt   63660
agggacttgg ctcagctcac acaactggca aggactgaaa atggatttta gtcccaaatg   63720
tcataggcta gagccctttc actaaactgt tgtcttccat ctggtggcat cctcttcctc   63780
cagtctttgt cacctaaact ctgggcaccc cttgatggca tttacttatg atggtgatgc   63840
ttgttaaact tcctgtttgc gacttcaacg tccatataaa tgagtcttcc aatactgtac   63900
ttagaactta tattttgtag tgacttcttt aaaagctttc tctcttagtc atatcctgag   63960
ttttgttagc acctggactt accttacttt ggaaatgttg cactctgaaa tctctttctc   64020
agcttggaat ttcctaatct tccaactgtt tgagtctttt aattctacat ttactgcctt   64080
tccatttcat caggatttct agtctcttta attcttcctt ttgaactcct cctgatttaa   64140
cctctgctta ttcgaagaac aataatttta ttctctcagc tgcactctca attccctttt   64200
ccttttggtg atttttcttt ttcctacaga acacttactt tatcagtttt ggagaaggaa   64260
gtgctatctg ggtaacagta gtgctatctg ttgactctag tcaactgtaa gttttataca   64320
tttattgttt aaaccttata tgggtctata atccttcttg ggaaatcctt tcatttgtct   64380
ttaatttcct ttaccatttc cctaaaggct attccagatt tttatcacat tcacaaaatt   64440
cccgtctttt ctcaggatct gttcaccccc agtagatagc cttgtctccc acaatacatg   64500
gagaaaatag aggccaccgt catatttgaa tgtttccaac ttctctcttc accttttgaa   64560
ttatcttttt cttcttttgt gtctaagaga aagatgtata cttcttctta cccttgtctg   64620
```

```
aactactcta ttttgcttca tcttctcaga acaggggacc agcaattatt cttcctccag    64680
aagcttcaac atcttttgtc aactgactcc ttctcatgtt taaatatttt caagttaaac    64740
aatttctttc ctgactttcg ctcacgcaac ctcatgccca aaaccttatc actcttcttc    64800
cctttgctgt caaggctgtt ctcacttctt cactttttgt ggacttctcc ccactacaac    64860
atagattctg ctatcaccaa tctattaaaa ctgttatact cttgtggaat ttatcattta    64920
atttagcttc agtgaaccgt tctttccaga ttattttggc ctcagaccat gacttctaag    64980
tctgccgtgc ttgccactta agtgatgatg ggccagtggg tccccaccta ggcctctgtg    65040
ttagtctgtt ttcatgttgc tgataaagac atacccaaga atgggcaatt tacagaagaa    65100
aggggtttga gggactcaca gttccatgtg actggggagg cctcacaatc atggtggatg    65160
atgaaaggca tgtctcacat ggaggcagat aagagcatag aacttgtgca gggaaacttc    65220
cctttattaa accaccaggt cttgtgagac ttcttcacta tcacgagaat aggatgggca    65280
agaccctccc ccatgattca attatctccc actgggtccc tcccacaaca catgggaatt    65340
atgggagcta taattcaaga tgagatttgg gtgaggacta agccaaacca tatcagcctc    65400
cttctggctt tttatgttct ccgtgggtga cctctctcag gctcaagtga taaccaatgt    65460
gctgatgact ctcaaatgcg catctctggc ttcagtttct tccttgaact tcatacatat    65520
gtttccaaat ttcctgcgtg tacctcaagg ttcttgttca tcacttccca agcttcataa    65580
acgcactcat tttagtgtat tctctgtctc ctttgatagc atccctgaga ggcaagtccc    65640
tggtgagtta tatacaactc ctcccttgct ccaaacctga gagtaagtaa cattcctatt    65700
aacatattag gaagctgagg cttagacagt ttaagtaact caagcatggt tacacaacta    65760
gctagggcag agctaaaatg tcaggctagg cttctgtgac tccaaagccc tttctcactt    65820
agcatatcat cacttatttt ttttttttaat cacatatatg attttttttt ctttaagaga    65880
tagaatcttg ctctatcacg tgggctggag tgcagtggca caatcatagc tcactgtaac    65940
cttgaacttg ggctcaagtg atcctcctgc cttagcctac tgagtagcta gggctacaga    66000
cacacaccac catgcctagc taatttttatt ttattttatt ttattttttg agacagagtc    66060
tcactctgtc acccaggctg gagtgcagtg gtgcgatctt ggctcactgg aacctctgct    66120
gcccgggttc aagcgattct cctgcctcag cctcctgagt agctgggatt acaggtgcct    66180
gccactgtgc ccagctaatt tttgtatttt tagtagagac ggggtttcac catcttggcc    66240
aggcttgtct tgaactcctg acctcgtgat ccactcgcct cggcctccca agtgctggg     66300 attacaggtg tgagccacca cgcctggcca cctacctaat ttttaatttt tttgtagaga    66360
cagggtctca ctacgttgcc caggctggtc ttgaactcct gttctcaaac aatcctcctg    66420
cctcggacac cccaagtgca gggattacag gcatgagtca ttgcagctga cctgtatata    66480
tgatttttag tatatgtaaa tatacatatt tattaaatgt aaatataaat ataaatgtgt    66540
ggagtgatat ccattgaaat gttaaacata gttctcagtg gtacaactac aggtgatttc    66600
tcttttctta tttctggttt tctgtgtttt ccaaatttct tgaaatgtgt cttctgtaat    66660
cagaaataaa agttattagt aacaacagtc ttccactggt acaagtgctt attggataaa    66720
agtcccactt ctaagcatga tactcacaac ttttaggtta atagcctttg tcaccttgcc    66780
atatacatct gatccagcca ctcacaccat tcctgagata tattttgttc ctttgtgcct    66840
aaatcattgt gcatgcagat ccatcttcct ggaacaccta taaccatttc ttagtcctgt    66900
gaaatcctac ttcatccctt catagcctag catgtatgtc atttatttgg tcaagggtga    66960
gttggttgtt ctcttgaatg tactgccata tgacgtggtg tgatttcaat tgtagcacca    67020
```

```
agctcattgc aatattaatt cgtttgtcat tctcccatgt aggatgtttg aagtagtttc   67080
taacacagag attatactca ataaatattt attagataaa taaatgaata agggaataac   67140
aaatgccttt gtctcatttt aaaatacttt cattgttagc tacccatata ataaaaaact   67200
aaaagcagta gttttcaagc atgattgttt atgtatgcct taaaagaatt ttgaaaacct   67260
atgtacccct gacacacttt taagttaact tataaatttt tcaacatagt tttaagtggt   67320
ggcaaatgat gtagtttctt gtgtatttta aactgcttaa gtatgctata catggatttc   67380
ttcaaaaccc tgaagctgca gtttcagtgc attcaattta tggaaaagaa attaatttat   67440
aaaattggtt cttattgtca agtcaatcag ctaaatataa cttgctttct gtcaggaaaa   67500
gtctgacttt aaaatacaga taagtaataa ctattattaa ttaattaaat tattaaaatt   67560
aaaataatta aataatttgt taattaaaat gccttattcc cctacttatt tctgcaattt   67620
gactctaaga atagatagga catgtagatt gccttaggtt tgaaatctgg gtgaaataag   67680
atactgcctc cttcagtatt tctgcctttg cttttatggg agcctctttc aagaaaaagt   67740
cattctctca tggtcccttt gtttgagtcc cagaggtttt cctactccag aaagtgcaac   67800
gtagtgagac tagtactata ctcccttgca tggtaagtga aaggctgtc tgtataaaat   67860 gagggaagga ctcatgagag ggaagtaggt caggagaaat gataggttct caggcaggtt   67920 aatttagga aagagtgaat agagtcccct aaaacaaggt gcatctgctt cctcctgatc   67980
aatctttagg actgtttact ttgatttgaa gaccactatg ctaaagcttc ccacgggggc   68040
aatagtgagg caaggaattt ttaaaaggga attacttctt cgtagctact tttgtgaaat   68100
gaattcattt gaattatctg gcaatctctt catatttata ttcaacaata attacttaaa   68160
gaaatgcttt gagcttctca gaggagggtg ctaccagtgt gatggagtag aattcagatt   68220
tgggtagtga ctttaaagct gtgtgacttt agtcatttaa ctgctgagtc acagtctaca   68280
gctttgaaag aggaggatta taaaatctat ctcatgttaa tgctgaagat taaataatag   68340
tgtttatgta ccccgcttat aggagaagag ggtgtgtgtg tgtgtgtgtg tgtgtgtgtg   68400
tgtatgtgta tgtatacatg tatgtattca gtctttactg aaattaaaaa atctttaact   68460
tgataatggg caaatatctt agttttagat catgtcctct agaaaccgta tgctatataa   68520
ttatgtacta taaagtaata atgtatacag tgtaatggat catgggccat gtgcttttca   68580
aactaattgt acataaaaca agcatctatt gaaaatatct gacaaactca tcttttattt   68640
ttgatgtgtg tgtgtgtgtg tgtgtgtttt tttaacaggg atttggggaa ttatttgaga   68700
aagcaaaaca aaacaataac aatagaaaaa cttctaatgg tgatgacagc ctcttcttca   68760
gtaatttctc acttcttggt actcctgtcc tgaaagatat taatttcaag atagaaagag   68820
gacagttgtt ggcggttgct ggatccactg gagcaggcaa ggtagttctt ttgttcttca   68880
ctattaagaa cttaatttgg tgtccatgtc tctttttttt tctagtttgt agtgctggaa   68940
ggtatttttg gagaaattct tacatgagca ttaggagaat gtatgggtgt agtgtcttgt   69000
ataatagaaa ttgttccact gataaattac tctagttttt tatttcctca tattattttc   69060
agtggctttt tcttccacat ctttatattt tgcaccacat tcaacactgt atcttgcaca   69120
tggcgagcat tcaataactt tattgaataa acaaatcatc catttatcc attcttaacc   69180 agaacagaca tttttcaga gctggtccag gaaaatcatg acttacattt tgccttagta   69240
accacataaa caaaggtct ccattttgt taacattaca attttcagaa tagatttaga   69300
tttgcttatg atatattata aggaaaaatt atttagtggg atagttttt gaggaaatac   69360
```

| | |
|---|---|
| ataggaatgt taatttattc agtggtcatc ctcttctcca tatcccaccc taagaacaac | 69420 |
| ttaacctggc atatttggag atacatctga aaaaatagta gattagaaag aaaaaacagc | 69480 |
| aaaaggacca aaactttatt gtcaggagaa gactttgtag tgatcttcaa gaatataacc | 69540 |
| cattgtgtag ataatggtaa aaacttgctc tcttttaact attgaggaaa taaatttaaa | 69600 |
| gacatgaaag aatcaaatta gagatgagaa agagctttct agtattagaa tgggctaaag | 69660 |
| ggcaataggt atttgcttca gaagtctata aaatggttcc ttgttcccat ttgattgtca | 69720 |
| ttttagctgt ggtactttgt agaaatgtga gaaaaagttt agtggtctct tgaagctttt | 69780 |
| caaaatactt tctagaatta taccgaataa tctaagacaa acagaaaaag aaagagagga | 69840 |
| aggaagaaag aaggaaatga ggaagaaagg aagtaggagg aaggaaggaa ggaaagaagg | 69900 |
| aaggaagtaa gagggaagca gtgctgctgc tgtaggtaaa aatgttaatg aaaatagaaa | 69960 |
| ttaagaaaga ctcctgaaag gcaattattt atcaatatct aagatgagga gaaccatatt | 70020 |
| ttgaagaatt gaatatgaga cttgggaaac aaaatgccac aaaaaatttc cactcaataa | 70080 |
| atttggtgtc aggctgggtg cagtggctca cacttgtaat cctagcactt ttggaggcag | 70140 |
| aggcaggtga attgcttgag tccaggagtt tgagaccagc gtgggcaaca tggcaaaccc | 70200 |
| cacctctaca aaaacacaa acaaaagaaa atagctgggt gtggtggtgt gtgcctgtag | 70260 |
| tcccagctac ttgggaggct gaggtgggag gatcacctga gcctgagaag tggaggctgc | 70320 |
| agtgagccat gattgcacca ctgtacccta gcctaggtga taggctcaaa aaaaaaaaaa | 70380 |
| attggtgttt gcaatgctaa taatacaatt tggttgtttc tctctccagt tgttttccta | 70440 |
| catacgaaac agcttttaaa acaaaatagc tggaattgtg cattttttct tacaaaaaca | 70500 |
| ttttctttct taaaatgtta ttattttttct tttatatctt gtatattatt actagcagtg | 70560 |
| ttcactatta aaaaattata ctataggagg ggctgatact aaataagtta gcaatggtct | 70620 |
| aaacaaggat gtttatttat gaaaaggtag taattgtgtt tcatagaatt tttaaaatta | 70680 |
| attctgcgta tgtcttcaag atcaattcta tgatagatgt gcaaaaatag ctttggaatt | 70740 |
| acaaattcca agacttactg gcaattaaat ttcaggcagt tttattaaaa ttgatgagca | 70800 |
| gataattact ggctgacagt gcagttatag cttatgaaaa gcagctatga aggcagagtt | 70860 |
| agaggaaggc agtggtccct tgggaatatt taaacacttc tgagaaacgg agtttactaa | 70920 |
| ctcaatctag gaggctgcct tttagtagta ttaggaatgg aacactttat agttttttt | 70980 |
| ggacaaaaga tctagctaaa atataagatt gaataattga aaatattaac attttaagtt | 71040 |
| aaatcttacc cactcaatac aatttggtaa tttgtatcag aagcttaaaa gataacctaa | 71100 |
| tagttcttct acttctataa cttacccaaa tatgtttgca gagatcttat gtaaagctct | 71160 |
| tcattataac actgctttca ggagccaaaa attgggtggg ggagccccat aaatgttgaa | 71220 |
| taatagggt ttgattagat aaattttggt gtagttctat aatggcgtgt tattcagcca | 71280 |
| ataaaaggtt tgttaaagaa tgactgtgac ggatgtatat gatatactct taagtgaata | 71340 |
| aagagttaca aaatgttatg tacaagttac aaaatgtatg tacattatga tccattttc | 71400 |
| ataaaatcat atgtatgtat atatgtgtgt ctggaaggat aaatttatca agttgttatc | 71460 |
| tctgaaattt tgggtatatt ttatatttct agattttctg ttactttgtt actttactga | 71520 |
| taaagtaata acgttgttga cttttgtcac tctcccctat taataatcat ctaggctgca | 71580 |
| aaaggatcat gtcttcttta ttttatatt ccaaggactg tcaacaagtg cctagcactt | 71640 |
| gacaggtata ttatagaaat ttaactgaat atctttagga aatagatttt tgtttgtagt | 71700 |
| tgttctagtc tacattaaat gtcttgcgct tatgaaactt ccttgaatta ttttagtgaa | 71760 |

```
gcaatattag tatagaattt tgcatcactg gatgcccttg actgaaagct ggcttatggc   71820
atctcaccag tgtgtgggga gtttcagtcc ttctgttgtc tgcatcacag ctgaagcagt   71880
gctgttgctg acaattcctg acaccacctt gtctctatta ttgatcattg cctcactatg   71940
gtactgagtt ttagcttatt cttgtaataa ctgggactca tatgtataga ataagctatt   72000
agctcacgtt tttgcttgct ttttatacag aatacatgtc tgcaaatagt tttatcaata   72060
ttttggaatt ttgggagata tgaagttaaa aacatcattg aatatatata tatacacaca   72120
cacatatata tatgacacta tacatgattt attttattta atttttaaaa ttttattctt   72180
tttagagatt aggtcttact ctgtcaccca ggctgaactt cagtggtgtg atcatagctc   72240
actgtaacct tgaactcctg ggctcaattg acctttccgc ttcagcctcc caaagtgctg   72300
ggtttatagg catgagccac tgtgtctggt ccaatatgca tatatatatt tttaacctgg   72360
attatcagag ctatattgtg tttaggttta taaagctgta ctatgtgaaa atatcacttc   72420
taggtttaat tttgtacaaa ggaatttttat atagaaatga ggtaattcag atttttttccc   72480 atgtaataag aattgtaaaa tttactgaaa caaacatcaa aaagatatct gttacatgac   72540
cttcctttct tttgaatata tttcaggtga tattatttat taaaatttaa aaatgaaaat   72600
taaaatatat aaaaagttga aaattattcc tttctttact gtctctcatc tgtccatttt   72660
ccattctcct gcattccctc atccaaccaa ggtagccaat ccaggtaact ttttttagta   72720
tcttcccaga gatgtttctc tctatatata taatcaatat acatttttta ttattcccca   72780
cctctctttt tatgtaacaa tatgcagagt tttgcttctt gcttttccca ctatcttgga   72840
caactttcca tattcaaagc acagaggact tgcacatatg ttcagactgc tgaatatttc   72900
tgtctctccc ctgccattca tatgttgaaa tcctaattcc caaggtgatg gtattgcagg   72960
gtggggcctt tgggaggtga ttagtccatg agggtgaagt ctttagtaaa tgagattagt   73020
gtctttataa aagaaacctt agagagaccc tcacaccttta gagagaccct cacccctttc   73080
tgccatgtga gaacacagca ggaagacagc tggctatcca ggattcagga gtctcttagc   73140
agacccaaat ctgctggcac cttgatcttg gacttcccag cctccagaac tgtgagaaat   73200
aaattcctgt tgtttataag ccacacagtt catggtattt tgttatagca gcctgaacaa   73260
ggacacacac acacacacac acacatgcac acacatttaa atagatgcat agtattctat   73320
catatggatg gatattctat gatataatga atcactattg attgacattt gggttgtttc   73380
caatattttg ttaacacaaa gaacaacact acaaataact ttatatacat atcatttagc   73440
acatctgcaa ttgtatcagt aggcttccta taagtggtca agcatttgtg tacttgtgat   73500
tttggtagat gttgtcaaat gtccttccct gaaatttgta ccaattcgta ctcatgccat   73560
acactctaaa tagagtgctg atttccccac agcattacta acagatgata ttatctaatt   73620
taaaagtttt ctcatcttat agggaaaata gtatgtcaat gtattcttaa cttgcatttc   73680
ttttattata agtagtgtaa aatatcattt caacttatac acaggaggaa tttctctcta   73740
tataaagtga tcctagaatc ataatgaaaa atatcaccaa ctcattagga aaatgtacaa   73800
aggattgaat agatatctca tcaaaaataa aaatataagt ggcctttaaa cattgaaagg   73860
taacatttga acaaagactt gcaggaggtg agggattagg gaatgcagac tctgggaaga   73920
gtcttccaag tagcaggtga agcaagtgca aagctttcag atgggactga ctatacctgt   73980
ctggtttgaa gaacagtaag gaggtcactg aggctggcat agagtaagac agggagggta   74040
gaatactgtc agagaagtaa tcggcggtgg aggtaggggg taaaccataa agtgctcgta   74100
```

```
aagactaagg cttatttctc tgggtgagat tagaggccac tggagagttt taaacagaag    74160
taacagggcc actttggcta atgtttttag gctattctgt agggagacaa gggaggaagc    74220
aaggagatga gttaggagtc tattgtgcca gttcaggcaa gtgatgatgg tggcttgatc    74280
caggtagtag tggaagtagt atagtaggaa gtgatcagat tcaggacatg ctttgaagga    74340
agatccaata ggattaatgg ataagttgaa caatggcata tgagaaaagt cacagaggag    74400
tcaaagatga ttccaagctt tctggactga gtaactggaa ggataaatgt gccgtttact    74460
agaaagataa tgggagaaac aggttttgga tggagcttgg tttgggaata ttaagtttga    74520
aatgcctatt tgacatccaa atagagatgt tagttggatg tacaagtcta gtttcaagga    74580 agaggggct ggtagtgtga agatgggct ggataagatt ctaaaggaaa gagggttgat    74640
aagaagagaa aggggtgtag gggttagcct aagggcattc taagtattag aggttaagga    74700
ggtgggtgaa gaaaacccaa taaaataaaa gtctgagaag acaaagctag tgaatgaatg    74760
tggtatcccg gaacccaact gatgtcaagc agaagggtgt tatcaactag gtcaaatgct    74820
cattcatcaa gtaagatgaa actgttataa ttaaccggtg tcttctgaaa tacgagata    74880 actcgtgact taatgaaagc aatagtagag aaggtcaaac ttgaccagaa tgaaattaga    74940
aagaataaga ggaaagaaaa gaccaaatac agacaaccat tgatgcctta ttcttttgat    75000
atactcctgg agtccacttg ctaatacaat tgacccttaa acaatacagg cttgaactgc    75060
atgggtccac ttatttgtga atttttttc agttaataca ttggaaaatt tttgggtt    75120 tttgacaatt tgaaaaaact cacaaactgt ctagcctaga ataccgaga aaattaagaa    75180 aaagtaagat atgccatgaa tgcataaaat atatgtagac actagcctat tttatcattt    75240
gctactataa aatatacaca atctattata aaaagttaaa atttatcaaa acttaacaca    75300
cactaacacc taccctacct ggcaccattc acagtaaaga gaaatgtaaa taaacataaa    75360
aatgtagtat taaaccataa tggcataaaa ctaattgtag tacatatggt actactgtaa    75420
taatttggaa gccacttcct gttgctatta cggtaagctc aagcattgtg gatagccatt    75480
taaaacacca cgtgatgcta atcatctccg tgtgagcagt tctctctcca gtaaattgca    75540
tattgcagta aaaagtgatc tctagtggtt ctcgcatatt tttcatcatg tttagtgcaa    75600
tgccataaac cttgaataac atcaagcaat ccatacaaag tgccactagt gatgcacgga    75660
aaagttgtaa cagtacaaga aaaaagttga gttgcttggt atttaccata tattgaggtc    75720
tgcagctaca gttgcctgca atttcgagat aaatgaaccc agtataaaga ctgttgtaac    75780
aaaagaaaag aaaatgtgaa accatcagtg cagctatgcc agcaggtgtg aagtcttgca    75840 cttttttgcaa aatacaaaat atgaaatatg tgttaattga ctgtttatgt tatctgtaag    75900
gtttccactc aacaataggc tattagtagt taagttttg tggagtcaaa aattatacgt    75960
ggatttttga ctatacagtg ggttggcacc cctaaccttc atgttgataa agggtcaatg    76020
gtatattatt taatttttt gtatttatat tcataaataa gattaaatct atatttccaa    76080
gtaatctcta taagattttg ttattaatat tactattatt tttgagacag agtcttactg    76140
tcaccaggct ggagcacagt ggtgcgatct cggctcactg caacctctgc ctcccgggct    76200
caagcaattc tcctgcctca ccctcccaag tagctgggac tacaggcacg cacaaccaca    76260
ctcagctaat ttttgtattt ttagtagaga cggggtttca ccatgttggc caggatggta    76320
ttgatctctt gacctcatga tctgcctgcc tcggcctccc aaagtgttgg gattacaggc    76380
atgagccact gtgcacagcc attaatatta ttgttaccca ataaaaaaaa tttgaaaact    76440
tgtcttcttt tcccctgatt ctgtttaaat agcactggag ttacctgttt tgaattttt    76500
```

```
ttccaagcgg tcccttatga gtttctctca tgttttattt gtttcatttc tttttttttt   76560
tttttttttt ttttgagac ggagtctcgc tctgtcgccc aggctggagt gcagtggcgg    76620
gatctcggct cactgcaagc tccgcctccc gggttcacgc cattctcctg cctcagcctc   76680
ccaagtagct gggactacag gcgcccgcca ctacgcccgg ctaattttt gtattttag     76740
tagagacggg gtttcaccgt tttagccggg atggtctcga tctcctgacc tcgtgatccg   76800
cccgcctcgg cctcccaaag tgctgggatt acaggcgtga gccaccgcgc ccggcctgtt   76860
tcatttctta tatcgtattt ttgcaactcc tttattgata cttttcttcc tgattaggtt   76920
tctactaaaa ccaaacaagc tttccatgaa ttagctttta gatttactta ttagtttaac   76980
tgttctgttg tattgtaact cattaattta taatttatc tttattaatt attctatttt    77040
tcttcgcttt tttgttgttt ttctagtttt tgagttagat gtttgacgct tttttaaaaa   77100
gctgtgcatt ttcctctggg taatacttta gctgtatatt atgtattctg atatatagtg   77160
tttccattac attgttttct agaaaatctg tagctttgat ttatatttgt ttcctctttg   77220
acctaagata tcctaaggga aaatttaaca ttttccagaa agaaaacaaa ttttctttgt   77280
tttccaagaa tgttgttcaa attatttcta ctgcttggaa tttttatcat ttttgtgtat   77340
ccagtaaata gtcaatattt gtacttgctc tctgaccaca taaaagaata tattcgtgta   77400
gtttctatta atagattaga gttcaattca gatattaaat gtacatcatt attcatgata   77460
tttaggtctt ctacatcttc acttatcttt tttctacttg ctttgccatt aacagataaa   77520
gttgaattaa aggcttctac tacatacatt tctccctgtt attccttata ggttctgtaa   77580
tttttgcttc aagaatattg ctttttaaat ttaatatata gatacttata attacactct   77640
agcattataa agagccttt cttttcatt gaatgtattt gggcctgcat atgtctaaca     77700
tgaaaattat agtccttttt ttgtttctt gtttgtattt acagttttaa gttccatttt    77760
caacctttat gcactctttg ctttaggtgt gtctctttta gttagcataa agttaggttt   77820
gtctttaatt tcacctgaag tcttttcctc ttaatagatg ggttaagcca actgaaaaat   77880
aaaactgact tatatacttt tatttcaagt atgtcctcca caaatatttt ttgaatagat   77940
tagcttatat actttggaat ttgttaaaaa aagattttta taaaaaataa ttgtggtgaa   78000
atgtacataa cataaaattt atcatttga ccattttaa gggcatagct ctgtggcata     78060
aagtatactc acatagttgt gcaactatca cctccttttg attttttttt actaattttg   78120
taaatttgtt tcatctgagc tgtcttatta tgttttgttt tatgttttc tttcctttat    78180
tatgaagtca ctgtattgtc tgtaggctat atgtatctgt gagtgtgtgt gtatatgtgt   78240
gtattatggt ttttaaaaaa gtctatattt gttttccagt ggctatactt aatactaata   78300
actttatgtt aaattttca ttctatgtga ctctagttca ctaatatgag ctctgataaa    78360
atcagtgctt tttcgaggtt aggagatcaa gaccatcctg gctaacacag tgaaactccg   78420
tctctactaa aaatacaaaa aattagccag acgtgatggc gggtgcccgt agtcccagct   78480
actcgggagg ctgaggcagg agaatggcgt gaacccagga ggcagaactt gcagtgagcc   78540
gagatcgcgc cactgcactc tagcctgggt gacagagtga gactctgtct ctaaataaat   78600
aaataaataa ataaataaat aaataaaatc agtgcttttt cttcctctgc tacctccttt   78660
ccttctactc agttttagtc agtagtatta tcttttttca gatttatctt tgtattgtta   78720
aatctgctta tgcttctatt actttatta ttagctttaa atgatacctt ttgactttca    78780
gcttttctta ataaagcaat cagcaaattt cctttacact ccacacttat accccatttc   78840
```

```
ctttgtttgt ttatttggtt tttacttcta acttttctta ttgtcaggac atataacata    78900
tttaaacttt gtttttcaac tcgaattctg ccattagttt taattttgt tcacagttat     78960 ataaatcttt gttcactgat agtccttttg tactatcatc tcttaaatga ctttatactc    79020
caagaaaggc tcatgggaac aatattacct gaatatgtct ctattactta atctgtacct    79080
aataatatga aggtaatcta ctttgtagga tttctgtgaa gattaaataa attaatatag    79140
ttaaagcaca tagaacagca ctcgacacag agtgagcact tggcaactgt tagctgttac    79200
taacctttcc cattcttcct ccaaacctat tccaactatc tgaatcatgt gccccttctc    79260
tgtgaacctc tatcataata cttgtcacac tgtattgtaa ttgtctcttt tactttccct    79320
tgtatctttt gtgcatagca gagtacctga aacaggaagt attttaaata ttttgaatca    79380
aatgagttaa tagaatcttt acaaataaga atatacactt ctgcttagga tgataattgg    79440
aggcaagtga atcctgagcg tgatttgata atgacctaat aatgatgggt tttatttcca    79500
gacttcactt ctaatggtga ttatgggaga actggagcct tcagagggta aaattaagca    79560
cagtggaaga atttcattct gttctcagtt ttcctggatt atgcctggca ccattaaaga    79620
aaatatcatc tttggtgttt cctatgatga atatagatac agaagcgtca tcaaagcatg    79680
ccaactagaa gaggtaagaa actatgtgaa aacttttga ttatgcatat gaacccttca     79740
cactacccaa attatatatt tggctccata ttcaatcggt tagtctacat atatttatgt    79800
ttcctctatg ggtaagctac tgtgaatgga tcaattaata aaacacatga cctatgcttt    79860
aagaagcttg caaacacatg aaataaatgc aatttatttt ttaaataatg ggttcatttg    79920
atcacaataa atgcattta tgaaatggtg agaattttgt tcactcatta gtgagacaaa     79980
cgtcctcaat ggttatttat atggcatgca tataagtgat atgtggtatc ttttaaaag    80040 ataccacaaa atatgcatct ttaaaaatat actccaaaaa ttattaagat tattttaata   80100 atttaataa tactatagcc taatggaatg agcattgatc tgccagcaga gaattagagg     80160
ggtaaaattg tgaagatatt gtatccctgg ctttgaacaa ataccatata acttctagtg    80220
actgcaattc tttgatgcag aggcaaaatg aagatgatgt cattactcat ttcacaacaa    80280
tattggagaa tgagctaatt atctgaaaat tacatgaagt attccaagag aaaccagtat    80340
atggatcttg tgctgttcac tatgtaaatt gtgtgatggt gggttcagta gttattgctg    80400
taaatgttag ggcagggaat atgttactat gaagtttatt gacagtatac tccaaatagt    80460
gtttgtgatt caaaagcaat atctttgata gttggcattt gcaattcctt tatataatct    80520
tttatgaaaa aaattgcaga gaaagtaaaa tgtagcttaa aatacagtat ccaaaaaaat    80580 ggaaagggc aaaccgtgga ttagatagaa atggcaattc ttataaaaag ggttgcatgc     80640
ttacatgaat ggctttccat gtatatactc agtcattcaa cagttttttt tttagagccc    80700
cattcttatt ttttatacac tttgagagca taatgaaaag aaaagctacc tgcaaaagtt    80760
ttggacttac ctcaaagagg atatacttca ttccctcaaaa ggccttcttc caggaatagt   80820
atttcataac ctggaggttg gaaaaatctg gatttgttac aaaaaaatct gagtgtttct    80880
agcggacaca gatatttgtc taggagggga ctaggttgta gcagtggtag tgccttacaa    80940
gataaatcat gggctttatt tacttacgag tggaaaagtt gcggaaggtg ccttacagac    81000 ttttttttg cgttaagtat gtgttttccc ataggaatta atttataaat ggtggtttga    81060
tttcctcaag tcaaccttta aaagtatatt tagccaaaat atagcttaaa tatattacta    81120
gtaataaatt tagtactgtg ggtctctcat tctcaaaatg agcatttact aatttctgaa    81180
cactgtgcta ggtcctggga ataccaaatt gaataagaca tagtctattt ttctgaaggg    81240
```

```
tttatagcag agtcccctgt gttaataatg aaggagtgtg tggtatgtga atcatatatc    81300
aatagggttg ttaaaaataa tgaaaaaagg agaagaggaa gaacatcttt ttttttttctg   81360 attgcacggg cagccttaaa attattttg aagtgtacaa ttcagtgttt ttttagcata    81420
ttcacagggt tgtattatca tcaccatatt tttggcctct tgaaaagaaa tcctgtgcct   81480
attagcatcc aattaccgtt cctttgtagc taagtctccc ccattccagc tttaaacaat   81540
cacccatcta ctttctgtct ctataaattt gtctctttg  gacatttcac ataaatgaaa   81600
taatataata gggttttttg tgcctaaata agcttctaaa gaagaataag gtaaggaatc   81660
atcattcagc aaatatttat taagacttgc tttattttat acagtgtact aggagctgga   81720
gatgaaaata tgtgtagaac atgaatcata tacttcggga atttgtggac tagtgggaaa   81780
gattgacata tcaataacaa atcgaattag tgatgtaata gaggcatttt tacaggagta   81840
aaatgaggta gcatggactc tatctgggtc tgaataatgt gaggagtaac ctccttacac   81900
aaagaggcac aaggctaatg tcctctgatg gaatgattca ccatgcaatt ctaagggtga   81960
caagaatgaa agttagggcc ttgaagaaat attttgatta agagctgcca ataaagtaga   82020
gtaaagatta gattgatgtg aagaagtggg agattaatga gtaaatggtc actggcttgt   82080
tgagaagatt aaatgagatg tacatgtaat gtacctaaca caacgtcttg tacaaagtag   82140
ccattcagta gagactagct tgtattatct cccttttgagg taaagaaaac tgttagaaat   82200
agtatttcta ctactgatag tatttcttct acttatgcct ccctttgagg tgaagaatac   82260
tgttagaaaa catgacatag gagaaatacc cctgagagac agttcttatt agtgactact   82320
gtgcagaaaa gatggaggtt ggtgtaatta aggagaagga aagccatgaa gccaaagtat   82380
tatgaaaaag catcaatatg aatttttcatg ttgacaaagt ggtataaaag ataattataa   82440
agatggtcac ttataaatac ggtagttctg tgtgacacaa tttacagaag ttggtatatc   82500
gtgtggaaga aaacagcata agatcctgaa ggtttgaact gtgggcacat tggctccatg   82560
ctcaggaaat ggcaatgggg ttgggaagtg attccacttt atgtcccttt cagacacata   82620
aaaattactt gtgtgagtat cttatgccag acactattca ctgtgtagtg agcatggtgg   82680
gtatgaaatg acaactttat tgtctttcct gtcaaagaac ttgtaggctg gttggggaa    82740 agagaccatt tcaatatgaa gtgctgagct agaggtaccc ttagggcact acagaagcct   82800
agctgatggc ttttagcctg gctagacagt tcaggatctc taaaagcagg tgccttgaag   82860
gctgagtcaa atacaaaaat gtattttgga cagaggaaat tgtatgaaca gaaacacaga   82920
acatgaaact acttggttgg tgcagggtat catcagcata gaaccagaca gaaccagagt   82980
gtaaataagc cagaaggcca tgtcatggag gccttgtata ccagtctcag gaatttggtt   83040
gtggagagct ttcatcaggg gaatgatgta atcagcttgg aaatgtagat atatcactga   83100
ctgtgatagt gaggagcaga attaaggtgg acgtgattag aagctttgtg aatagcagaa   83160
agaacataga ttttgaaagc tggcagacgt aggttactga agaaagttac ttaaccttgc   83220 tatgtctttta gttttatcct ctgcaatatg gggataatac tgcctatttt gtagagtctt   83280
gtggattctt ctggcatata taatagaaaa taaaacagct attattatta ttgttgatgg   83340
tactatttgc tatatctgac tacaaggaga aagactaata ggaaaccatt tcaggaatcc   83400
agatatggtc atgatggaca ggaagagaca agagttacat agaggaattc tgggaagata   83460
agaaatgtca ttttttatgta ctgtttgcat ccatcagaca aggcatcagg aaaaatgatc   83520
cttcaggaaa gagtgatttt ttttcttcaa gaaattagaa gaggggagaa attggtttaa   83580
```

```
gattaaggac tccatgcata agagaaactg ggagggaaga caggtagaaa tgctatgggg   83640
ttaggaagga agaatgcaga ggtggattac ttagaattga dacatctgat caagacagag   83700
ggatcacagc ttttgctaac aaagtactag tggaggatgc cactaggtga ggtttaataa   83760
ataattgttg acaataagtt ccatttaaaa aataaacaat ttatgcttct tctttgccta   83820
agtgtcaaat aaaacattca gatttttatt tcaaagtatc cctgagtccc tgttcccttt   83880
tttgtcctgc tgactttttgg aactgattta ggcttcctta gtcatctcat aatagaaaaa   83940
atcagccagg tatttcctac atttcttgta ttttaaaaaa atgtaatgga tgtaatgaat   84000
tttaagcaaa tgtaatgaat acaataagta acttagtata tgctgttttc ttctctatgc   84060
tgaatgtttc atacatgtta ttttctatac aactacatgg tcaattcctt gaaaatatca   84120
actccaaaat ctttattttg gtatactcca cgtagcacat tgagagagtt ttaaactctt   84180
gttggatgac tgtttcaaaa gtgttttgaa gtaggcatgt cagttgcaaa aagtttgctc   84240
agcaaatgtt gttctgtctc acagtctcag acattgagca gatgattaca tgacagcacg   84300
tgattgctgg gagtaacaga caaaagtaac tgaaagtgct cggttatctt gacagtcaaa   84360
atcaaaagtg tccccctattt tcagtgacct aagagtttct ttttgtgttt ttggtattgt   84420
tgttaaataa gtgttctcac ctttgaaaag gtcaataaga attcaataca gtataatgtc   84480
tgtgtgccaa atgaaggtgc cccttatttt taagtgtgga ggagttttga tcataagaac   84540
ttgaaatacc tacagaatcc ttgatggtta agcagctggt gccagcacaa gaatccctca   84600
atatgttctc tatgaagccc cgatcaccaa atgcaaacat tcatgattca gtatattttc   84660
atcttgactg ccaaagttga tctgtttctt aatatattac atctagactt ggaactggag   84720
atgagaacag aatattatct tcctcatttt tgtgttttttg ttcaactcta atgtctgcaa   84780
agcacttgcg tatgtaatga tgctcagtgt cataggagca ggcaggtaag tgtaaatttg   84840
tctggatagg agaaagcatg cacaacatat ttcacatagt tttctgattt cagtttgttt   84900
ttgcaaatta ttcactcagt gagatagctt aaagacgtta tcacagggaa aggcatggag   84960
atagttctgt gttgatagaa aacttgtaat gtacagccat gagtgagaag tcaggttcag   85020
attcttcacc ttcagtcctc ctctttcata aacagctcca tgtcctattt tacatatcct   85080
actttaaaac gagattatag aagaatgaat ttctaggcaa agtgacactt atttttaaaat   85140 actattacgt atccctgtgc ccattaactt atcctaccat ttttcttccc ctgtgtccaa   85200 accacctttta gaatctccta aatatttgta gctattgtaa acagcactgg agactttgct   85260
agtttaaaag gagaaatcaa cgcaattaag ccctagttaa tttacttatc ccttatgaga   85320
ttataattgt attttgttat taaaaggggg acagagtaca ctgttctctt gcctttttaa   85380
tttccagact accacttctc ctgcacttga caataccgca gtctaccacg tagtcccatg   85440
gctgacagga ggagaattct aggcaggcca gtgtttgagt agtgagtaat tggactgtct   85500
ttacccagca actcactgtt ttgtaaatgt acctgagttt ggagaagtaa ttggcttttta   85560 taagggtgc ggggtggagg gttggggtgg ggagagtgag aaggaggtca gagctttagg   85620
atatataatt ggtctcccaca aagttgttgt gatacttttg gaaccacgta atggtcttca   85680
ttaactaagt gtctgtcatg acagccatta catatgcatt ataataaaaa tttatttaca   85740
gtgtaagttg aagaaggtaa aatctggatg tagtttctaa actctgcttg gcagttttca   85800
tatttaagcc actagaagaa aaaaattggg agggaagctg agaagaattt actgaaagaa   85860
aaaaatactt ggggagggaaa ttggcaagaa gtatgaaaaa gcttgggagg gaagtaagca   85920
aataaatgag ttaatgactg ttctggaaaa taaactctat catgcagata tcacatgact   85980
```

```
gattaaattt gaatttgacc tcctgctttc caggtctggt aaaaactaac ctgtaagaac   86040
ttgaaactta gcctttgaat ggtcaatcca ccactgtagg agaatttatg aatgttcagt   86100
tgagagaact gaaaataaag aagtaccata ggaattaaca tttgcattca gtagccaaga   86160
tataatggac atctgaaaca ggtatttgag gccaggcgtg gtgtctcatg cctgtaataa   86220
tagcactttg ggaggccgag gtgggtggat cacaggaggc caggagttca agaccagcct   86280
actaaaacac acacacacac acacacacac acacacacac acactagcca ggcgtggtgg   86340
tgcacgtttg tagtccaagc tacttgggag gctgaggcat gagaatagct gaacccaga    86400 aggcggaggt tgctgtgagc tgagattgcg ccactgcact ctagcctggg tgacagagtg   86460
agactctgtc tcaaaaataa aataaaacat atatttgaaa cacattgaat tatgtccctt   86520
aaacaagaat aaacatcact aaatgactgt accttgaact acctgtaatt ttctcctgat   86580
aggtaattaa gcttcaaagt actgacactt atttactgta atatgaagca ataacttaaa   86640
aaaaaaaaaa aactattgaa ccagaaccaa acaggaatgc catagcattt tgtaaactaa   86700
actgctattt catttcattt gagccctgga acttgaaaat aaatgctagc taacatctgt   86760
gaacagaaca tacccatcag tactgtgcta agcacctttc atgaactggt cattaaatcc   86820
tcactttcca tttatttagt gacaacttca cccagagttt gcagtcaaag tgaaaatgtg   86880
ctgaattcca aaagtgtgag ctaggtttta gaagttaatc acaattctgg aacaaattac   86940
tagcttaaca aatgagagtt cttatgtctc taaaaccaaa atagccctaa gtctgtccct   87000
cccagtaaga tttgggccag tcaatggaac agtaatatac aaatataatt acagctgtct   87060
aggagcaaac tatcctatga atagataata aaattaagac acttaagcca tgttttcata   87120
ttaaaacaca aagtaaaaaa tcattgtttt ccaaagataa aagccatact gtatcatgac   87180
atatatatgc ccgatgtttc gaccctcttg aagaattgag attctcgact ctacactctt   87240
agcgttttct atattgaaca gatgtttaat ttaaggaggt caagagaaat cttacactta   87300 tttttttaatg gtaccttaga catagaagga acctcagaaa tctctggctg aatatttcca   87360
tctgcagatg atcatgtcat taggcttctg actctatagc catagaaaaa tattcatgaa   87420
gacctttcag gaagggaatg ttggtatttc taaaaattga gtacaagtat tctctagaca   87480
aaacagctct tgaaatggca gattgtattc ccattattat atttcagaat caagacatta   87540
atacctactt tttatttacc aggtttagtt atccttgaat tagatttat aaattaaaga    87600 aatagatttc aataaatatt tgttgagttc ctagtatgga aacatcgtgt ttggcaccag   87660
ggatgttgcc tgcaagtata acaggagttc gtatttgtaa tgagtttatg atttacagat   87720
atttgggggg caaagatatc attcggtaaa tacttatgag tgcaaacttt gaactaggga   87780
ctgggccaaa ctctaggaac atatttgatg acagagacac aatccctgtc tcaaggagc    87840 tttcattcta gtagagaaga tgaaaaccag tacagtttgg taagttagat gatattggtt   87900
aatgtagggt tcttatgtaa gtctagagaa gtagcattta atctgttctt agaaggtcag   87960
gaaagatttc cctggaggaa gtgacattta agctgagaga ggatggataa acaggagtca   88020
tctgagtgaa caacagggag aacattccag aaagagaaca aaatgtacga ggcctgatgc   88080
caagagagaa cattcattgc attggggaac tatagtcact tctgtgtggc tgggatgtag   88140
aatgaaatga gcctggaccc aagagagcac tttgcccttt ggggaagctg taggtattac   88200
agtaaggttg gagtctggaa agaaaggggt atattgtgag atctgaattg ggagaggaca   88260
gttatatcca gacctttata tgctccagta agaagactga actttacact gggggccatg   88320
```

```
ggactcactg aatggcatta aatttgagag tggtcatatg accagatttg cattttacaa    88380
agattgtcat tgactgcaac atgaagtatg gagtattgga ggagcggtaa ggctggtggc    88440
agggagataa tttaggaggc tttaggtgag ggatgataat gacttgccag gtaggaagga    88500
gtaaatttct tctcagtgga taattagaag attgaatgga tggacttggt cactatttgg    88560
tatagaaggg gaaaaaagat gtcaaagatg atgccaattt ttaaaaataa tttaacattt    88620
atttttaaat attttttcag ccttattaag gtataatgga caacaattgt aggtatatgt    88680
catttacaac atgatgtttt gatttatgta tacattgtga aatgactgcc atagtcaagc    88740
tcattaacat atccatcact cacataatta acattttgtg tgtatgcagt gagaacatca    88800
ggctctactc tcttagcaat tttcaagtat agattacatt tgttaccaac tatagtggcc    88860
acactataca atagagctcc aggacttatt catcctgcct aactaaaact ttgtactctt    88920
tgaccaacat cttcccattc gtctctcctc cccatgccaa gtttccatct tggtcagttg    88980
ggtggatagt agtactatct gccgaggcag gttggtaggg tgaaaacaat gtgttccctt    89040
ttggaaatgc tgaggtgacc agggaacttc caagggaatc tgtctggatc tagagcttag    89100
aagagatgtt tgggctggaa acagacatca ggtattcttc agtatatggg ttgtaaatga    89160
agtcacagga gtgggtgata tcaccaatgg tgagtgtagt ataagaagac tggactgagg    89220
acagatttcc aaggaatttc aatacttaag aggtacgcag agaaaagagg ggctgtgaag    89280
gacaccaagg aggagactaa gagccaggag ggaaaacttt caagagagta ttgcattatg    89340
gaagggaaga agagagaaca ttttaaatga tacgcaatgc tcaataatgg tatccgcttt    89400
ggagaggcca agtaagattc ctaagtaccc attggatcaa ggtccttaat cttacaaaaa    89460
cttatgcaaa tcaataataa agagatgata acccgataat caaaaataga caaggcatat    89520
aagaagaaaa tgaattaaaa atattcaaag cattcaacat atacaaatgc gctcaatctg    89580
atatataatg aaagaaaagt aaattaaaac aacaatgggc atgactaaat aacagtatga    89640
gggagcctga ggagaaggag catttgaaat ttcagtacag aagagaaaag gggtgactta    89700
tagaaaaagg agacagaaac catagaacat gtttggagga taagactcaa acaggtagtg    89760
gggaccettt tctagagtag gatgaaaaca ggtaatgtgt gtggatgcaa atatgaggta    89820
ggatgtaatg ggaagttgag cgaattcata tttagtcatt cattcaaaaa tacttaattg    89880
agttactgct gtgtggcaag catcattcta caaacagagg gcacagtgat aagcaagcca    89940
gtttgtactc tcgtgtaact tacattctac tttgagaaga cagattataa ataggttaaa    90000
aagtcaataa tatgatgttt cagcatcaac aataaaaaat tagggtgata tatagagtgc    90060
cagggaaagt gctttcatgg acctcttcat tctctcctct cctggtgtca taagctactc    90120
cttcatccat gctgccattt tcttggtttt acggttccag tatagtactc atcacattat    90180
tactatagag ccatccacct tatgaaggtg aaggtgtcca tctccttact taaaaaaaaa    90240
aaaacaaac aaaaaacaa aaacccgaa aacaaaaaa agaggcagaa agacagaagg    90300
tcctccacta actttcacgt gccatgtaac cagcgaaatc caattatttt acagcattct    90360
agctatagaa gagtttggga agcgtagtgc ttagtgttct agcctttgta gcacaggaaa    90420
gggcctggaa ggaaaggaat tgtgtcttcc gcagttgctt ttctttatgg ggaagtgcta    90480
tagcccaaac aatattttag gaattttcat ctattgtcaa tatgcaaact ggaaggggat    90540
aatgaaaatg ttgtggttag aagtttatga aatattgtta ttcacatttt aaagtaaaaa    90600
gagggaatgt ttaagagact tgtttaagat cacatgtctc ataattggtg ggaccagcaa    90660
tacaatccaa atctaactac ttatcttttt gctatgccct attagtgttc atattagaaa    90720
```

```
agaaattcta tctcagacac taatgatttg ttctttggac accaatgact ttaagttaaa   90780
acttcatact agttaattta attatggtgt agcagtatta ttaaactatc aagactataa   90840
attttctatt tgtaaaggag attatgatac caaagattag tgaactaatg atattgagaa   90900
ttctatgaca taattttgaa aaatatttgc aggatattta ttttttgtgta aatgatgctt   90960 tcaagctacc ataatcctaa gtaagtgtat atttgggaaa accacctatt ctaacacact   91020
tgaaatttaa ataagtcagg aaattttttt ccagatcttc tcccaaatta tcttcatctt   91080
tttcctctcc ccttgggaaa gaatctcttc atgcctcata atatcaaatt taaactatgg   91140
aagtccaggt ggtggacagt cagcaaaggg gaagatgaga agcttgtgtt ataaagccag   91200
ctcttgtcag aataaggatc tggtaggaac ttcagaagtg atgggtaggt aagtatgaag   91260
gccaggtcct aagatctaaa ttacaaagca gaagacttac ttaccaggga gctgaaaaac   91320
atgttaggaa atccagagca ggaacagatt tcaagatagc acaataatat agcagtgaag   91380
tactgagaaa agagtttttt tcacgggttg gatttattct agcattttag gcagcatttg   91440
ggcatttcta agtggtcaga cttagaggag atagttaagg aattagcagc tgctaaatgc   91500
caattcttag accagttgaa tcaaaatcat ctaaaaagct ttcagaaacc agactttta   91560 agggccattt gagagactct caaatctgga atccagaaat ctatagctag atgagtttaa   91620
ggtagagcca gaataagaaa aataaaatag tttgtttgtt tcaggtatct tttccaatat   91680
tatttccgaa cctaccccaa acaccttaaa tcactgcatt ctatagccat tcttttaaaa   91740
atgcttgagt tattagtttt caaaaacaaa tacaaatctg cacacataca gaaataaaca   91800
ttaaagagac ataaagatat taaacagagt tacatatact tacaacttca tacatatata   91860
ttatatataa aactgaatat taagtgtttg atattagtga caaaatctgt aacatccatt   91920
atattagtgc ttttttgtact ttttgttggg tgtagtaaaa attgcattcg aatttgagtt   91980
ttctgctata tatttggtca gttcctatca gtgaaggaaa aacctttttt tattatttta   92040 ttgtttttt attttttgag acggagtcct gctctgttgt ccaggctgga gtgcagtggc   92100
atgatcttgg ctcactccaa cctctgcctc ccgggttcaa gcgattctcc tgcctcagcc   92160
tcctgagtag ctgggactac aggcacctgc caccaggtcc agctaatttt tgtatttta   92220 gtagaaatgg ggtttgcca tgttggccaa gttggtctgg aactcctgac ctcaggtgat   92280
ctgcctggct tggcctccca aagtgctgga attacaggtg taagtcacca cgcctggccc   92340 cttttatt tttaagctga ttgaagattc ttagttctca tgctttctag tggtgattaa   92400
tctttagcca atatttctat atacagttat tagtaatcat gtttgactta ggtcaacaaa   92460
caatctttcc taaaaaaaca gaaccccaat tttaatttct gaattattta gtatctattt   92520
tctgctgtgg aagttgaatt atgttgatag atatcataca gggccatgta acactctcag   92580
atacacgttc acatgtatag tagctgtata caaaaatgtt acttcattct ctctctcttt   92640
ataatactct tggctctctt acgttctctc acacactcta ctcttccctt cctctgttct   92700
ttctacttgt tccctctgct cctaccacac ttattcccc cttgtccatt ttccttgtgc   92760
ataaagcaca agtgcttagt aattatcaaa tattaataac aatgacacta accacccaat   92820
gatttagtgt taatgacatg ctttattgaa tggcattacc tctaaagttc atgtttcctt   92880
tacccaacca agcttcttac cctcctccct taccacaagc atctatattg tcaaggttgt   92940
tataaagagt aataagccag ccattaaaaa agggtttatg gtattttcct atctacaaag   93000
tcacaggaag ctcaaatgta ctcagtaaat attgcaaaat tacacaggac cattaaatgt   93060
```

```
aacactccac cctttctctc tctctctctc tctcttgctc tctctctctc tttctgtcaa   93120
tatagcaaca ccctatatca ttgcccttg tatgtgcaaa tcagagttaa taagctttat   93180
attagcaatt actccttaac aacttctggt ttgtttggtc cagttgaata atgtaagcac   93240
ttaaaaaaat gaaattataa acatttatgt gaaaagtgca tatatcacat tggatatgtt   93300
gttatgcact ccttaataat aaagtaagtt aatctttatt gcacacttat tataatatta   93360
ctttgaccct ctctagtact ctttatctaa gtattctcaa gtgctttaca atctcaaaca   93420
gacccaatgt gttgtataca cagaatcctt tgaagctgac atttgccttt ctgaccagct   93480
tgttgtaaag gaaatcagcc aaaaaacaag tatctagatg agtagctcaa acattagtac   93540
acatagtaat cacaggtcaa aatgcagata gattaccctg tccaaattct cctgagtaag   93600
agtaggtgaa acatttttaa ataagctccc caggtgattc tgaaattggt ccaaggacca   93660
catattaaga actaatgatc caaacaattt gacttttat tgtagattaa accatgctga   93720
gaaaattatt aaaaattgaa atggcagtgg aggatggttt gaaagaaagg ttttcaggg   93780
cccttcaac aataaaatta attgaacaca atattaaaac tctatatttg atttaagact   93840
aaggttttca ttgttttaa atctcagtaa ttttatgta acaggtcaat tcatacccag   93900
catcttaatt ccaatgaatg atttcccaca acaattttg tggataactc caagggaact   93960
cgaaggaagt tgtagtatga acaaagagaa gtagaatttg tccctgtgtg taaggcttct   94020
ctgataagca gcacaggctc tcatactgct ttttaaaaaa attatgatag catcaagtgg   94080
aattaatttt ttttagatta tactttcatg gaagggaaga tctactgtga aggctggaaa   94140
accaacaccc ttaagataaa tatattacca gatttgagcg ctcttagtaa tcagcaaaga   94200
taaatgttta acagtgcata caaaatgaag tgttttatgt taaatcaaat agagaaagcc   94260
aaacactaat aatgtggtta caaatgaaca ataaattagg taatcagaac aggtacagac   94320
attaatagca ggatattggt attattaatg tattttgttt taaaataatg aacttaatta   94380
caattctcct catcctaccc cactattta ttttattcca gattcagcag cttcatatta   94440
tgtctctgaa acacttatta ttaaagttat ccaaatgtac acatttctct ttatataaat   94500
gtttcagtcc agaaaaggag gccaaataca ttagctcaga acatcaaatc ttctcagatg   94560
tgggaatctt ttattttcac acttttaaag gtaatctgta tttctagcgt ctattataga   94620
cagaaaactt tcatatgaca acattcctat tttcttaact gccttgatag gggcgaagac   94680
aaattctaag taggactttt taccccattc ttcttaccat cattctttca caaacccccc   94740
agctttagac aatcgctatt atgaatttga catgtactat tccaatccat tcccataaat   94800
ttacacccat atatacatat agttatctat gaacaatatt tagtagcttt tttgtgtgtg   94860
gctttaaaat ttacataaat tgtataattt gtgcacattc ttctttaatt tgccttcttg   94920
gctacggtta tctttttgag atctagctat gctgctggta tgtagaattc tatttcattc   94980
tttttcatt gttgtttgt acccataacg tgtcacattt tatttatacc ttctgttcct   95040
gatggacatt tagattcttc caggatttta ctcaatactg caatgaaaat ctttgaattt   95100
ttctcttttg cacatattca agagactttt ctgacatata tatctatagg tgaattgtgt   95160
agtcatatga tacatacaca catttaaat ttcactagat actgccaatt tgcccttga   95220
aatagccata caatttatag taccaccagc cacttatgaa agttcccatt tcctcaaatc   95280
tttgaaagtt cttattataa acagacatat taattcttgc cattctgatt tgtaaatcag   95340
aatctctatt gttctacctc tagttctaat ttggaattcc ccaattactt gtaagatgct   95400
atatattttc atgtttgtta gtcattctga tttcatatcc tttaccaatt atcttttgg   95460
```

```
taagttattg tggtggccat gagatgtgcc ttacagaggc cttgctagag ggaatgtgat    95520
tgaatgagag ccccagatgc tgtgtattaa aatcctgcac tgagtttgtc tcaagatttc    95580
ttgcacgtga atgaatgagt acagctggga tactaaagca gatgtgtatt tgggagatat    95640
gagacttctt tagtggctga tttttggctc ataaatgact ttgccaaacc ttccttagac    95700
tgctcagtgt tctaacatct tccatccagc cttctaccct tctttccttt actagggat    95760 tgaatttaca ttgaggtctc atagccttct ctgcctctct ccttatttcc ttttatacaa    95820
atatttcccc taataaatcc atgcacattt aataccattt tgctatttgc aacctgcagg    95880
tcctggacta acacagttct atacattgca ttaccattct ctagagtggg atcttttgtt    95940
gtagagagtt ttaaaatttt tatgtagtca cttttatcca tattttttctt tatggtttat    96000 attttttgtgt cttctcttta acacatcttt tctagcagaa ttcataaata tattattcta    96060
tattgccaaa agtttgaaag ttgcaatcat tagaattaat ttttgtatat tgtgtaagtt    96120
aagaatctaa ttttattgtt tttcattgga aagccatttg tcccaagata atttttttagt   96180 agtccctcct tcccctattg tcattctgac atattttttc taggttccga tctatgcatg    96240
tgtttcttta tggaagagtt ggccctttgt atctttgagt ttcaaatcca tggattcaat    96300
caaccacaga tagaaaatat ttagaaaagc gtcagaattg aacatgtaca tacattttgc    96360
ttgtcattat tccctaaaca atatagtata acaactattt atgtaggatt tacattgtat    96420
taggtattgt aagtaatcta gagatgattt aaagtataca ggaagatgtg catatgttac    96480
atgcaaatac taccccattt atataagggt cttgagcatt catggatttt ggtatccaca    96540
gagagtcctg gaaccaattc cccacagatg ccaaggcaca actgtattta ttctatcatc    96600 tacttgtttta atctcacatc agtatctact tttgaaataa caataacttt attatttaac    96660
tttttttatt acttaggatt agagaatttc ctctggtgag gcatcatagt gtctcaagct    96720
ggccataaag acaagtgagg gctaggatcg gtaagactgg gcagaggaag atacaacaga    96780
tctcctatgc atgaagcaaa agtgcagctc agaagccagc tctttcatta agttgtcctc    96840
tataccctca ctagattgta agctcttgaa atgagaggct ataccttaat tgtctctgtt    96900
atctaaaata cttccactca ctgcttggaa catattgcct gcaataatta agcttgccct    96960
ggctcccaaa gcatagagca aatcacactc ctcccccttgc cttttgagaag ctcacagtct    97020 tcgaaggtag agatatgtga acagataaga aaatggatga caggagaaca gaaacgcatg    97080
actgtcagag aagtcattgg agactttaca gaggaaatta aattttttatt gatcttgaaa    97140 gagtttgcca gatgaagtag aggacaggca ttttagacaa agggaacagg aaatgtgaaa    97200
acacaaagtg atggaagtca tggtgagttt ggagaactat aaaacttcaa tgtggctgaa    97260
gggtaaggtg gatatagagg agtgctggga ggtgaggctg aagaaataag ctaggaaatg    97320 tcttttttatg ccattttttta aagtttggac tttattctga agttcacatg gatccaatat    97380
tttttgtttt gtgttgtttt aagcagaagc gtgacatgat cagcttgaat gatgaacaac    97440
ttgaattgtt taaagtggat cacacagtct actgttttac agttattctt tgaccaagat    97500
attctttatt aactgaggaa aaaaagggct ttcctgaatt ttgcagtcat gggatatatg    97560
ataagcattc ttgatttatc atcttcaatc ctgttacata acataataac cattgttatt    97620
acctttagca atgctttcct cagtattatc taatggccta taaaatgtga cttttcatttg    97680 caaatacagt acatctaaca agaacttacc acagctgcta tgcaaaatac caatacaatt    97740
gacccttgga caatgtgggg gttagggggtg ctgattcccc atgcagttga acatgttaca    97800
```

```
taacataata cataaccatt gttattatgt aacaggattg aaaatgataa atctttggaa    97860
agtggggcaa atgaattctt atgaattcca tatcttccac atgtgtttta ctttttttgat  97920
aagaagtagt aacctagttc agaaagaaaa taatcatccc cttttactta tgcaggatac   97980
caagtctatc ttagcaccat aatagtgaat gataggaatc aagctctatg aatacattca   98040
catgtacata tatatggcta tataggacac atgcatgcac atatacatat atacacttgc   98100
atatatgtgt atatacatgt acatatatgc atgtatattc aattgtatat gtgtatatag   98160
ccaagttatt gtacagttga cctttgaaca acacgggttt gaactatgca ggtccactta   98220
cacgtatttt ttttttccgt ttctgacacc cctaaggcaa caaggccaac tcctcccctt   98280
gctcttcctc ctcagctgac tcaacatgaa aactatgagg acgaagacct ttatgaagat   98340
tcacctccac ttaatgaata gtacatacat ttcttttttcc ccatggtttt cttaataaca   98400
ttttctttttc tctagcttgc tttattgtaa taatatagta tataatacat ataacatacc   98460
aagtatgtgt taattgactg cttatgttat cagtaaggct tctggtcaac agtagactat   98520
tgctagttaa gtttctggta gttacaagtt atatgtgggt gttcgactgc atggggagtc   98580
agcaccccaa ccctcatgtt gtccaagggc gttgtccaag ggtcagttgt aattggtatt   98640
ttggatagca gctgtggtaa attctggtta gatgtactat atttataaat gaaactcaca   98700
ttttataggc cattaaatat tattgaggag agcatttcta agggtaaaat cttgtctaat   98760
gcttgaaaca tcttcatttt cctgtcagtt tagatctttt tgaagtaatt ctgaaaatct   98820
ctcttttaag ctaaatttaa cacaaccaaa tagccaaata tttaagttcc actaatgaag   98880
atatctaaat ttctgttaaa aatttaagat atatgttaaa cccttctaat ataactcttc   98940
tctcagtcaa actttttttt ttaacagttg ctttgcttct tctttcaaag tcatacttca   99000
acaaagttgc tattgaatat gtctgactaa acatgttagc tatatgataa gatggctgga   99060
taagagataa atatagaaaa tgtagctttt tttctacttg caataaccct ttaggaatta   99120
aaatggaaaa ctaataacta tttgattcat aatagtagca aaccgtaaaa tatttagaca   99180
taaatctact aagaaattta taagacatat atggagaaaa ttcaattgaa taaaccgtta   99240
ttgaagtata taaaataaga tctggatgaa tagaaagatc ataattttta ataaaatttt   99300
gcatcttaaa aagtgaaccc tctccaaata tatgcacatt taataaaatt ataaatacat   99360
cccaatgagg ttggttttga aatttttgtta attggaactt aaatttcacc taagaagaaa   99420
aaataaagaa tagttaagag tgcatgcttt gtagacaaat tgccttagtt agaatcctgg   99480
ctctatcatc tattagctat gttatctttg ggataacatt catcttttct tatagatatg   99540
cttaaaacag tgcctgacat atagtaagca caaatatcca ttagctattc ttcttattat   99600
ttatgttatt agtattgtta atatttgtta ttatatggaa gactaaatga ccaaagagag   99660
tcaagaaatt tatgaataag atttatgcgt tgttagatat tagagccatt aaaaaaaaaa   99720
aaaccaaagt gccaaaaaac ctagcacagt gttaatacag gaataaaaaa atggatcaga   99780
ggaaccaaac agaaaagcca gaaatggatc ttaggaaaca tgagaatatg atatatgata   99840
gatgctaaat gaattcagta taaaaatatt aatgtaataa atcatgcttg ctattcaagt   99900
aaaagaaaat gaggttagat tcatgtctca taccaaatat aaccataaat tataccttga   99960
ttaaatttt taattaaaaa gcaataatat ttgaaaagaa atataggata ctcaatgtat   100020
aacctgaagg ttgggtagta cttttcaaca aatataggaa ttttttcactt gaaatactag  100080
aagaaaaaaa gatagcaaac aaatacagga attccaattt caagcagata taatgatttc   100140
atgaaatgtt aactgtgcac atgatagatg gtctatggat agtgcaaaag aaaaagagaa   100200
```

```
aagaaaaaat gtttttaac atatgcagca aaaaggttt ttaacatcta ttacatacaa    100260
ataaaaatga atgtataaca cagacttcaa taaaaatagg catttcacag gagaacaatt    100320
cagatggcca gtatttacaa tttcataggt attaaggaaa atacaaatta aaatggcaaa    100380
ttagcaaaaa ttgaggtgtg attatattaa tatctgttgg tggtggtgat tatggggaaa    100440
agggtacttt caaaacttgc taatataaat ataattcttt tggttgtttt gtaaaggaac    100500
ctgacaatat cttttaaaaa taagaaaac gcatactttt gacctagcca tcccattcat    100560
gagggtatgt cttagaaaaa taagatcaca aaatcataga gatttatgtg caatgatatt    100620
attggtaggt cattttatg aggaggggtg tggatagtaa atgccagggt aaatcacata    100680
gcatctaata aacgtattta tgaactacaa aagcttacac tttcagtcta gtctagtcca    100740
gactgcaaat aaatgtgagc aagtgaattc aagcacagaa gtgcttgaag gcaggtttca    100800
taaatctact ttcttacagt atcctgatat tgacttatcg agacagttac tgtggggttg    100860
attattaaaa tatttatgta tctaggtatt tttcattcag tagtatgtta ttcaattagc    100920
aacaagtgtg gggatttaaa gatattcttg tttgttttta ctgctgaaac atattctagt    100980
ggaaatttcg aataaacgat tagtcatcct aaaagcaaga tacatttct cagaaaagac    101040 aaggtaaaga acttgtatat cctccctcaa ttcgtttata aggtaataag atgaataaaa    101100
atatcatagt acaatttagc attgtaaaat aaaattaatt ggtcatctct agtgtggtcg    101160
tgcttggaag gtgaaagaag ccaagatctt gtctgggaat atcatgtcta ccttgacctc    101220
acccttaaga atcctagcct ttagtttaaa atcacatggc tacatacata ccaacttcaa    101280
caatagtaca tctggcaagg tcatgcaaac ctgggacttg agcttctgat tctaagtcca    101340 gtgcttttg tgtacatcat ctcttgtaca taccttatga tgatatgcta ataaaagcta    101400
cgtgatcagg ccttaaaaat ctgcttttt tttgtaatgg tagaatgggg catattatca    101460
catcaggtaa acactctatt caaggataaa tggaaatgaa tgtcatatat agatcattga    101520
taaatatctc attacaaaat tatgagagtt accaatgttt gagtgtatat tatgggccag    101580 cccttatat taaattactt caaattttta caactgttaa aggaagatat tattataccc    101640
attttataga tggacaagtt agggccagaa aagacttcct caaagctgtt agtccagtaa    101700
tggagacagg gctagaaaac aggtcatttt gctctttgac taatgttact actcatgttt    101760 tgtatttgt ttaaagtttt atttttatttt gctttattta ttttttgaga caagatctta    101820
ctctgtcacc caggctggag tgcaatggag tgatcacggt tcattgcagc cttgacctcc    101880
tgggctcaag cgatcctccc acctctcaat ctccagagta gctaggacta ctacaggtgt    101940
gtgccaccat acctggctaa attttgcatt ttttgtgggg acagggtttc actatgttgc    102000
ccaggctggt cttgaactcc tgggctccag cgattcacct gccttgacct cccaaagtgc    102060
cagtatcaca ggcttgagcc accatgtcca gccaagtttt attttagaat taaaaaaat    102120 tccacttgga ttgttacatt ttatctcatt gctttatatt tatagaatta ctttataaat    102180
gccactttct taattttcat agttagcact ctttatgaaa cataaactat tatttgaccc    102240 aggttttgt tagaggaatt gagtcagaga gctgttaagt aactgagatt tcacaataag    102300
ccagacagac cagggttcaa attctgggtc tcacattatc caattcaata ttccagcttt    102360
gttacttatt gagcaaccac tacaagcaca gtttacatga catctgatag ctctcaaaat    102420
gaattttaca aacataattc agatttcaac tcagcagtga ctcaggagaa aggcacttg    102480 gatgcatttc tttatggcat ttttcccagg gtacacgcaa cctggaagat ctcccaagta    102540
```

```
tgggggaagg tttcaccctg aggaatccca ttccctctaa tctgggacaa gggggaggag 102600
agtactgtct cttatcagcc atctccccag ggaggcctgg gccctcctgg aatgcatacc 102660
atggcttact gactcaaagt gttgaaaaga ccaggcattg ggacacacaa cactactctt 102720
aaaataaaaa aagaatcaga gtagcttgtg gttataattg aaatggacag agtaacatgg 102780
taccaagaaa ctattagcaa ttccttccct aaatccctca ttttcttaaa gcattttctc 102840
cttttcctca acaagcttta agttggattt gaagaatgat aagactaaaa ggagggctgt 102900
ttctggtctt tggaggaatt tgatattcca ttcgatctga gtgtgcaaag cctgagttca 102960
catgaactct tctgatctct ttctctaata tttttttcacc ttattcatat gggaaagaag 103020 gagggaata ctttagttcc attctccctc ctcctatttc cttgacttgt ttaaaatata 103080
aatgttatag acacctaaga tagaaatttg actgaaacag cctcttaatt attgtcttaa 103140
aaaattggta taatgaaatt gcatttgtag tctttggaca tttaaatcca gaagggatat 103200 tttcttttc tttttaaaa atttaattca atagttttg ggctacaggt ggttttggt 103260 tacatggata agtgctttag tggtgatttc tgagattttg atatacccat cacctgagca 103320
gtgtgcactg tacccaatat gtagtctttt atcccccccc cgctccaccc ttcctttatc 103380
gtccccaaag cacattatat aattattatg cctttgcagc ctcattggtt agctcccact 103440
tgtaagtgag aacatgcgat atttggtttt ccattcctga gttacttcat ttagaataaa 103500
ttgtctctag ctccattcaa gttgctgcaa aggccattat ttcattccgt tttttggctg 103560
aatagtattc catagtgtat atatgccaca ttttctttat ccacttgttg attgataggc 103620
atttaggttg gacccatatt ttcgcaatta tgaattgtac tgctgtaaac atgagtgtgc 103680
tttttttttt tccatataat gacttctttt cctttgggta gatacccagc agtgggactg 103740
ctggatcgaa tggtagttct ccttttagtt ctttaaggaa tctccatact gttttccaca 103800
gtggttgtac tagtttacaa ccccaccagc agtgtaaaac tgttccattt tcagcacatc 103860
catgccaaca tctattattt tttgactttt taattgtggc tattcttgca ggagtaagat 103920
ggtatctcat tgtggtttta atttgcattt ccctgataat cagtgatgtt gagcattttt 103980
tcctgtgttt gttattgtt tgtatatctt gagaattatc tattctgtcc tttgcccact 104040
ttttgatgga attatttgtt tttttttctt gctgatttgt ttgagttcct tgtagatcct 104100
ggatactagt cctttatcgg atgcatagtt tatgaatatt cttcccact ctgtaggtta 104160 tctgtttacc atgctaatta tttattttgc tgtgcaaaag cttttcagtt taattatttc 104220
ccatctattt attttgttt ctgttttatt tgcttttggg atcttagtca tgaacttttt 104280
acctaaacca atgactataa gagtttttcc aatgttatct tctagaatgc ttatgttttc 104340
tggtcttaga tttaagtctt tgattcatct tgagttaatt tttgtataag gtgagcattg 104400
aggatccagt ttcattcttc tacgtgtggc ttgccagttt tcccagcacc atttattaga 104460
tagggtatcc tgtccccact ttatgttttt gtatgctttg tcaaagatca gttgacttta 104520
agtatttggc tttatttctg ggttctctat tctgttccat tgtctacttg cctatttgtg 104580
taccagtacc aggctgtttt agtaactata gccttgtagt ataatttgaa gtcgggtaat 104640
atgatgcctc cagatttgtt cttttgtgctt agtattcctt tagctatgtg ggctctttt 104700 tagttcccta tgaattttag gattttttc tagttctgtg aagaattatg atgatatttt 104760
gatgggaatt gtattgaatt tgtagattgc ttttggcagt atggtcattt tcatagtatt 104820
gattctaccc atccatgagc atgggatgtg tttccatttg tttgtgtcac ctgtgattc 104880 tttgagcagc attttgtagt tttccttgta gagatcttta acctccttgg ttaagtatat 104940
```

```
tttcatgtat tttagttttt tttttttgtt tgttttgttt tgtttttgtt tgttttttgca 105000
gctgttgtaa aagggattga gttccttgatt tgattctcag cttggttgtt gtcagcaggg 105060
acatttctca aagtatagac tgtagttcct tatcttctat ctgtttctta ctgtcccctt 105120
cagtattctt gtccttttt ccgctatta tcttttgac cttttaatat atagatatct 105180
acttctactt ctgacaattt ttgcttctcc aattttcttt cttttctcc tctgcacaca 105240
tttatttatt tccttctatg tacttcttta tttttaactt aatattgat taacttccct 105300
tccctgtctc ttttccttct ttccataaat cttcattaat tgcctgcact gagctaggat 105360
tctatactct ctaaatcaat aatctatttt ctatagtcaa ctgtgttata atcgtactgt 105420
caagataact acttattttt aatacttaaa aatattttga aattttaacc aatttaatta 105480
atacaatgtt gagttcaaat ttgaaaaaaa caatggaaaa ctgtaataat tctagcaacc 105540
tcctgcttt taataatgta ttagaaaatt tgcctcttt tcaaaagcct acagtgaatc 105600
tattcataca aggcaaaagc aaaccattct cttcattctc tttttttctc caaaagattt 105660
aagtgttttt tgtttgtttg ttttgttttg tttttagat attgagtctt gctctgtcat 105720
ccaggctgca gtgcagtggt gtgatcatag ctcgctatag cctcgaattc ctgggttcaa 105780
gcaatcctcc tccctcaccc tcctgagtag ctggggctac aggtgcatgc taccatgccc 105840
agctaattta aaaggaaaaa aattgtgtag agatgggtct tgctatgttg cccaggctgg 105900
tctcaaactt ccaatctcaa gcatttctcc cacccagcat cctgaagtgc tgagattata 105960
agtgagccac tatgcccaac cagatttagt ttttaaaaag agaatacgat ttgaaaaagg 106020
aaaaatgtga ggcaggagag aagaaataca cacgagct gttttgtaat tgctgtaaaa 106080
ctgaaatctt cagcctcact aaaggagcac ttgcatgaac acctctaaat taccttatta 106140
ccttctaaat taggtgtgaa gtctaacttc taaattatga gtgaaatcca ctgcaattct 106200
tgttatttgg atggaatcct aggtatgtgg tccagttcat gagttgaaca aaagcatgct 106260
catttaggcc aggtagaaag aaataaagac ctatgtttta catgtctcat aaccactgaa 106320
ggtccttctc ataagcagtg cttatgggta ttaacgacct ctctatattt tacttctcca 106380
gtgcctaagt agccgagtcc actgagtcct gctacatctc ctccaacatg tcagcatttt 106440
tttcacaggc cttttgttac tctagatcag aaatgttgat agcaacagtt ccttgagggc 106500
agcagctagc atgatgccag ccaacaggaa ccaccaaatg gttcttaata taaattacta 106560
cttattaatc tatttacttt gtgcatttgg agttttgcat gtaaagtcct atttatgtcc 106620
atatggtaga taaatggaac aaatgaataa cagaagtaac cattttgata ctttagatat 106680
agataatatt ggattatttc tggattgtga agaagaagg aagaagcata tggaagagaa 106740
gttttagtag aggggaggaa ggaggaggtg gaaacgaatg tacaaggatg ggaggagaaa 106800
agggagagag acttttttt ttttaaggcg agagtttact acctatctaa ctcttcgcat 106860
tcttgaagtc tcagaccaaa tcccatcggt ttgaaagcct ctagggtatt ctatctattg 106920
tatacttctg ttatgtacaa aattaatttg ccaattaatt gtgaactgtt ttataaacta 106980
tcttaaaatg gttagtttaaa tctttgggat agtatttagc tttctccagg attatgactt 107040
accttctaaa ttagacatac aatgcctagg agtcaaggac tattttgcat aaattccagt 107100
cttcttttac aatgcctaga atgattgtta ccacagaaat attcattacc tgggagaaag 107160
gatgacagga ggggcagaat gaatggggag aggtcgtgag aatgaggtgc tgaggatgga 107220
cgaggaagaa agctgtttta gttgggagga taggtgacag aagcatggaa aggaattgcc 107280
```

```
ttggacccat ggaagcccag tgaagatact tagatcctgc aggggtgtga ataatgttct 107340
tttagtttct cttcttagga ggtttgttca ttttgggaga tttcttttga aaagagtgaa 107400
cttaaattgg agaaaagtac attttagtat gttgataaca tttgaatttg taaaatggac 107460
ctatggatga tctacacata tttatatacc cataaatata cacatatttt aattttggt 107520 attttataat tattatttaa tgatcattca tgacatttta aaaattacag aaaaatttac 107580
atctaaaatt tcagcaatgt tgttttgac caactaaata aattgcattt gaaataatgg 107640
agatgcaatg ttcaaaattt caactgtggt taaagcaata gtgtgatata tgattacatt 107700
agaaggaaga tgtgcctttc aaattcagat tgagcatact aaaagtgact ctctaatttt 107760
ctatttttgg taataggaca tctccaagtt tgcagagaaa gacaatatag ttcttggaga 107820
aggtggaatc acactgagtg gaggtcaacg agcaagaatt tctttagcaa ggtgaataac 107880
taattattgg tctagcaagc atttgctgta aatgtcattc atgtaaaaaa attacagaca 107940
tttctctatt gctttatatt ctgtttctgg aattgaaaaa atcctggggt tttatggcta 108000
gtgggttaag aatcacattt aagaactata aataatggta tagtatccag atttggtaga 108060
gattatggtt actcagaatc tgtgcccgta tcttggtgtc agtgtatttg tttgcctcat 108120
agtatagttt actacaaatg gaaaactcta ggattctgca taatactgga cagagaagat 108180
gtaaatatct gttagttcca tcatagaccc tgccactcca atgtacacac cagctttagg 108240
cttcttggta tagataaaca tacattttca aaattttca tcataatttt cataacaaaa 108300
taggaaggca aatgatgtca cttggcttaa aatctataat attaaaata aacaggacaa 108360 atgcattaac attgttgggg gaggaggtcc cttagtagaa acactcttgg tccaagcatt 108420
ttaaagctgt caaagagatg taaatataga taatgtatgt caaggagaga gctttgtggt 108480
taaactgtaa ctttcagttt aaacaattat tggtgactct gatgtcaaat gtttctcaag 108540
ctttatctga acaaaattct tctcactttg ttgccaaagt cgttaacaag aaatcacatt 108600
gactcattga tgttttggct cctttcccctt actttctgtt gctttccaaa agctgagaca 108660
ggaaactaac cctaactgag cacctgcaat tgcctggtag tattctagtc atgtgtgtac 108720
ttttgtgtgt atgtaatccc cttacagctc tgcaaagtaa gaattgttct ccctgcttta 108780
cagaagagat cataagataa ttgaggctgt tagatgttaa cttgccaaaa gccatacagg 108840
aaaatggtag agtcacagtt tgaaccaggt cctttttgatt cttttacatta aaccatgctt 108900 tgatcttgga aatacactgt aaggcaataa atcaatagat acggataatt cacaggcttc 108960
taaataaatg gaagttgatt gttttttatct gtgagccaaa gtaagactta ttctaagaat 109020
tccacaaatt tagataagat agagtatatg gcttctagac atccaacata gaactgagtt 109080
tgtgttatca gtttaagatt tggttttgct gtaaggtgca cacactttga ggaactaaaa 109140
ataattgtct gttcttattc tgatcagaat gtgtaatgtg ttgtccagtt ttggatgatg 109200
aatttcttat ttctaatctc ataagaaact tgtcatagat gtgagggaga gaattaagaa 109260
cagagtgtgg ggaagaaact gtgtacattt tgatgggatc cattatgtag ctcttgcata 109320
ctgtcttcaa aaataagtta cactataaag gttgttttag acttttaaag ttttgccatt 109380 ggttttaaa aaaattttta aattggcttt aaaaatttct taattgtgtg ctgaatacaa 109440
ttttctttat tacagaagta ccaacaatta catgtataaa cagagaatcc tatgtacttg 109500
agatataagt aaggttacta tcaatcacac ctgaaaaatt taaatgttat gaagaaatta 109560
tctcatttct attaatatgg gaactgtgtc ttcatcttta ttactgttct aaggtcaact 109620
caatgtagat tttacttgct tatggtttca tattttagct aaatagtaaa ataatatgga 109680
```

```
tatacatttt gttgtgactt actcatactt tccttatttg aactttttat gaatatgata 109740
tagagactga aactacaagg aacaaaatgc aatatcaatt atacagttgt ggcagcactg 109800
ctatcaattt gttgatagtg gttaacactt agaaaaacat tttaaaaata atttcacata 109860
agtaatgtaa tttattagct gtctctgaca ttttacagtt tggaatagtt tattttcttt 109920
ttggtgtcct caccaaaacc caacatcttc aagggcagga actgtataat ttttgccatt 109980
gtattttgag cacatagcat ggtacttgcc tctaaataga tactattgtt aaaatatttt 110040
ttaaggtaat attttaaagt gtatgctatg gtacagttca gtttgtgact tttgctagtt 110100
tatgccactt acagttagca aaatcacttc agcagttctt ggaatgttgt gaaaagtgat 110160
aaaaatcttc tgcaacttat tcctttattc ctcatttaaa ataatctacc atagtaaaaa 110220
catgtataaa agtgctactt ctgcaccact tttgagaata gtgttatttc agtgaatcga 110280
tgtggtgacc atattgtaat gcatgtagtg aactgtttaa ggcaaatcat ctacactaga 110340
tgaccaggaa atagagagga aatgtaattt aatttccatt ttcttttttag agcagtatac 110400 aaagatgctg atttgtattt attagactct ccttttggat acctagatgt tttaacagaa 110460
aaagaaatat ttgaaaggta tgttctttga ataccttact tataatgctc atgctaaaat 110520
aaaagaaaga cagactgtcc catcatagat tgcatttttac ctcttgagaa atatgttcac 110580
cattgttggt atggcagaat gtagcatggt attaactcaa atctgatctg ccctactggg 110640
ccaggattca agattacttc cattaaaacc tttttctcacc gcctcatgct aaaccagttt 110700
ctctcattgc tatactgtta tagcaattgc tatctatgta gtttttgcag tatcattgcc 110760
ttgtgatata tattacttta attattatta tacttaacat ttttatttac ttttttgtgtt 110820 agtattttat tctgtcttct ccttagatag taaccttctt aagaaaatat atatgctaag 110880
tgttttactg gtttaatatg cttagactac tcatctacct caatacttcc ttggagatct 110940
cctcctcagt cacacagagc tcaggactta tatttccttg gaactcctgt tagggtccaa 111000
tgtacatgaa attccctaga cagacagaca gtcagttata tggcttgatt tcaaagtttc 111060
aaaatgattt aatggactat caagtagttt attaggagaa cagttattat actcttctaa 111120
aaataaagac tttaagcaat aaagatgtat atgtatataa aatggctggg ttattcctag 111180 aagtacettt cttagaattt agttaaattt aatatccaag atactatctt ttcaaccctg 111240
agattgtgaa aagtaacttc tatcaatata aactttacta catttgtatt gtgttagtgt 111300
gttacagtat aatctagaac aatgtgtctt tctatatgat atatgacatt ttaatgccta 111360
aaaaaactga tatgtcttag atgattctag tcaggattta cttctagaat agattaaaat 111420
tctatttgag gagagtcaaa ttaattatcg aattctcagt tgttattatt gctgttttat 111480
ttttagtgaa acagattagt cttaatgtaa acacttgaga aataaattga tggtcaacct 111540
aaaatgtaaa aagaaatta atagaaaatt taaagagcaa caaagctctg acatttaaaa 111600
gaaatgaagt acaaatctct agggacctta aagatcatct aataatttcc tcattttcta 111660
gataaataaa ctgagagacc ccgaggataa atgatttgct caaagtcaaa tatctactta 111720
atataggaaa tttaatttca ttctcagtct gttaacatgc aacttttcaa tatagcatgt 111780
tatttcatgc tatcagaatt cacaaggtac caatttaatt actacagagt acttatgaaa 111840
tcatttaaaa tataataaaa ttgtatgata gagattatat gcaataaaac attaacaaaa 111900
tgctaaaata cgagacatat tgcaataaag tatttataaa attgatattt atatgttttt 111960
atatcttaaa gctgtgtctg taaactgatg gctaacaaaa ctaggatttt ggtcacttct 112020
```

```
aaaatggaac atttaaagaa agctgacaaa atattaattt tgcatgaagg tagcagctat  112080
ttttatggga cattttcaga actccaaaat ctacagccag actttagctc aaaactcatg  112140
ggatgtgatt ctttcgacca atttagtgca gaaagaagaa attcaatcct aactgagacc  112200
ttacaccgtt tctcattaga aggagatgct cctgtctcct ggacagaaac aaaaaaacaa  112260
tcttttaaac agactggaga gtttggggaa aaaggaaga attctattct caatccaatc  112320
aactctatac gaaaattttc cattgtgcaa aagactccct tacaaatgaa tggcatcgaa  112380
gaggattctg atgagccttt agagagaagg ctgtccttag taccagattc tgagcaggga  112440
gaggcgatac tgcctcgcat cagcgtgatc agcactggcc ccacgcttca ggcacgaagg  112500
aggcagtctg tcctgaacct gatgacacac tcagttaacc aaggtcagaa cattcaccga  112560
aagacaacag catccacacg aaaagtgtca ctggcccctc aggcaaactt gactgaactg  112620
gatatatatt caagaaggtt atctcaagaa actggcttgg aaataagtga agaaattaac  112680
gaagaagact taaggtagg tatacatcgc ttgggggtat ttcacccac agaatgcaat  112740 tgagtagaat gcaatatgta gcatgtaaca aaatttacta aaatcatagg attaggataa  112800
ggtgtatctt aaaactcaga aagtatgaag ttcattaatt atacaagcaa cgttaaaatg  112860
taaaataaca aatgatttct ttttgcaatg gacatatctc ttcccataaa atgggaaagg  112920
atttagtttt tggtcctcta ctaagccagt gataactgtg actataagtt agaaagcatt  112980
tgctttatta ccatcttgaa ccctctgtgg gaagaggtgc agtataaata actgtataaa  113040
taaatagtag cttcattat ttatagctcg caaataatc tgtatggaag tagcatatat  113100
aaggtatata aacatttagc ctcttgatag gactaactca cattctggtt tgtatatcag  113160
tcttgcctga atttagctag tgtgggcttt ttttatctt gtgagtttgc tttatacatt  113220
gggtttctga aaagatttct tttagagaat gtatataagc ttaacatgta ctagtgccaa  113280
tcttcagaca gaaattttgt tctattaggt tttaagaata aaagcatttt attttaaaa  113340 caggaaataa tataaaaagg agagtttttg ttgttttagt agaaaactta atgccttgga  113400
tgaaatgagc catgggcagg gttgtaatga attgatatgt ttaatagtat agatcatttg  113460 tgaataaatat gacctttgac aagacacaag ccattaacat ctgtaggcag aagtttcctt  113520
ctttgtaaaa tgagggaata aaatagatcc ctaaagtgtg taattttagt atttctaaac  113580
tttatgaagg tttcctaaat gataattcat ctatatagtg ttttttttgtg tgtttgtttg  113640 tttgtttgtt tgagatggag tctcgctctg tcacctaggc tggagtgcaa tggtgcaacc  113700
tcggctcact gcaacctctg cctcctgggt tcaagctaat ctcctgcctc agcctcctga  113760
gtagctgaga ttacaggcat gcaccaccat gccgagctaa ttttttgtatt tttagtagag  113820 aagggggtttc atcatgttga ccaggctggt cttgaactcc tgaccttgtg atccacccac  113880
ctcagcctcc caaagtgctg gtattacagg cgtgtgccac cacgtccagc ctgagccact  113940
gcgcccagcc catctatata gtttaatatc aatctaaatg aatttctcag tcctgagcct  114000
aaaaatttag ttgtaaagaa tgatatcctt gactaataat agtttctatt aatggattgc  114060
atctagtgct aggtggcata tatttagtcc ccacaactac cctggaaggt atttaaaatt  114120
ttcacatttt gcagataagg aaactaaagt tcagagttcg gcaacatgct tgaattcaag  114180
cagctcctag gatgttaatg gtggaggttg ggttcaaatc cagatctgtc tgactcaaaa  114240
aatgcatact cctaaccagt gcactatatc ccaattccat aggagcccctt ctttgtgatt  114300 catagccactt tcccatgagt tttgttgatt ttgtgagaaa caaactctt ttcctttgga  114360 actgtctgga atctctcttt ttcaaatttt tgaaatgtat ttctatgcca aaagacaaag  114420
```

```
atttctagag gaatatgcct aggatgagaa ttatgtaatt taaatcacag ctggaaagag  114480
agaaagtcct aagttactaa gaaatgttca aacacaaatg agctttcagt ctattggaag  114540
acctttatag ctagaagtat actgaactgt acttgtccat ggaccoctga agaaacaggt  114600 taaatcaaag agagttctgg gaaacttcat ttagatggta tcattcattt gataaaaggt  114660
atgccactgt taagcctttta atggtaaaat tgtccaataa taatacagtt atataatcag  114720
tgatacattt ttagaatttt gaaaaattac gatgtttctc attttaata aagctgtgtt  114780 gctccagtag acattattct ggctatagaa tgacatcata catggcattt ataatgattt  114840
atatttgtta aaatacactt agattcaagt aatactattc ttttatttttc atatattaaa  114900 aataaaacca caatggtggc atgaaactgt actgtcttat tgtaatagcc ataattcttt  114960
tattcaggag tgcttttttg atgatatgga gagcatacca gcagtgacta catgaacac  115020 ataccttcga tatattactg tccacaagag cttaattttt gtgctaattt ggtgcttagt  115080 aattttctg gcagaggtaa gaatgttcta ttgtaaagta ttactggatt taaagttaaa  115140
ttaagatagt ttgggatgt atacatatat atgcacacac ataaatatgt atatatacac  115200
atgtatacat gtataagtat gcatatatac acacatatat cactatatgt atatatgtat  115260
atattacata tatttgtgat tttacagtat ataatggtat agattcatat agttcttagc  115320
ttctgaaaaa tcaacaagta gaaccactac tgatattttta ttatttcata ttacatataa  115380
aatatattta aatacaaata taagaagagt ttttaataga ttttttaataa taaaggttaa  115440 gagattcgaa agctcaaagt agaaggcttt tatttggatt gaaattaaac aattagaatc  115500
actgttgata ttttattatt tcatattaca tataaaatat atttaaatat aaagataaga  115560 gttttttaata gattttataa taaatgttaa gagattaaaa aactgaaaat agaaggcttt  115620
tatttggatt gaaattaaag gccaggcatg gtggttcatg cctgtaatcc cagaatttta  115680
ggagactgag tggggaggat tgcttgagcc caggggtcaa gaccagcctg ggcaacacag  115740
tgagacaccg tatctacaaa ataattaaaa aattagctgg gcatggtggt gtgtgcctgt  115800
atgctaccat taactaagga ggctgaggtg ggagaatcgc ttgagcctgg gaggtcaagg  115860 ctgcctgaa ctgtgattgt gccattgcat tccagcctgg gtgccagaga gagacctat  115920 ctctaaataa ataataagt aaataaataa acagcaacaa caaaaacact caaagcaaat  115980
ctgtactaaa tttgaattc attctgagag gtgacagcat gctggcagtc ctggcagccc  116040
tcgctcactc tcagggcctc cttgaccttg acgcccactc tggctgtgcg tgaggagccc  116100
ttcagccctc ccctgcactg tgggagcccc tttctgggct ggccaaggcc agagccggct  116160
ccctcagctt gcggggaggt gtggagggag aggcgctggg ggaactgggg ctgcgggtgc  116220
cttgtgggcc agcgcgagtt ctgggtgggt gtgggctggg caggcccgc actcggagca  116280 gccggccggc cccgcgagcc ccaggcagtg agggcttag cacctgggcc agcagctgct  116340
gtactcgatt tctcactggg ccttagctgc ctccctgcgg ggcagggctc gggacctgca  116400
gcctgccatg cctgagcctc ccccaacct gccgctgcag tgggctcctg cgtggcccaa  116460
gcctcctgac gagcaccgcc ccctgctcca cggcacccag tcccatagac cgcccaaggg  116520
ctgaggagtg tgggtgcagg gcgcagggct ggcaggcagc tccacctgca gcccagtgc  116580 gggatccact gggtgaagcc agctgggctt ctgagtctgg tggggacttg gaggatcttt  116640
atgtctagct aagggattgt aaatacacca atcagcactc tgtatctagc tcaaggtttg  116700
taaacacacc aatcagcacc ctgtgtctag ctcagggttt gtgaatgcac caatcagcac  116760
```

```
tctgtatcta gttaatctgg tggagacttg gagaaccttt atgtctagct aagggattgt    116820
aaatatacca atgtgcactc tgtatctagc tcaaggtttg taaatacacc aatcagcact    116880
ctctgtctag ctcagggttt gtaaatacac caatggacac tttgtatcta gctaatctag    116940
tgaggaggtg gagaactttt gtgtctagct cagggattgt aaacgcacca atcagcaccc    117000
tgtcaaaacg gaccaatcag ctctctgtaa aaccaatctg ctgtctgtaa aatggaccaa    117060
tcagcaggat gtgggtgggg ccagataaga gaataaaagc aggctgcctg agccagaagt    117120
ggcaacctgc tggggtctgt agaagctttg ttcttttgtt ctttgcaata aattttgcta    117180
ctgctcactt tttgggtccg cattgcgttt atgagctgtg acactcactg ggaaggtctg    117240
cagcttcact cctgaagcca gcgagatcac gaacccacca gaagaaagaa actcctaaca    117300
catccgaaca tcagaaggaa caaactcagg acacgcggcc tttaagaact ataacactca    117360
ctgcaagggt ccttggcttc attctcgaag tcagtgagac caagaaccca ccaattccgg    117420
acacaatttg actgcagaaa atggatgtcc aaccctgtgg tttccctggg ccacattgga    117480
agaagaaagg agttgtcttg ggccacacat aaaatacact tactatagca gatgagctaa    117540
agaaaagaaa aaagtccatg cgtaatcttt gtgatatgtg ccaccaccaa taagcaaaat    117600
tgttctctta ttcaaaaggt tggacacagc tgctctagat atttttattat taaatatgca    117660
ggcaattact gtttaaatga agatttcctc acagaatgag attaaaagta tatattagtg    117720
gcttagcatt cattttagac aaccatttta gagattcaaa tcacacactt gcttacagaa    117780
attttgttgt cttcaatgtc cccattgtgg tttctttacc aagcctctac tgttcttcac    117840
atcaccaagt taaaaaaaaa aaaggggcgg ggggcagaa tgaaaattgc atggtaggcc    117900
acaagttcag atcctcatcg acacaagagg tgcctgaagc agtggatgag gcttttctat    117960
ggatcatgag cagccacata aatgcttaaa agggcctggc agggagcatc agtgggtgat    118020
gtggctggga ggctgaatgg agagcatttg ttcttcagtt atctatagaa ggcagctgtc    118080
actcagcacc agctaagggc ttcccatgag ggaactgggg atcaggtttc ccagatcttt    118140
ttatgtaaca ggataagaca gagatccagc ttttttttggg taattatttc ctattttaaa    118200
atacgggtag ttgattaaat aaaaacaaac gaatgaacac catatgggca caacaaaaca    118260
catctgtggc ttggattcag cttgtgaatg attactgcag atatttattc tagaggacac    118320
ccctgggtat gtcctaatat aaaacctaaa tctaaactca gtcccatgc taccttcaga    118380
gaataaatga cccagaaaaa gaaccacctc tcctaaggaa gtataaattt gtaaataact    118440
gagacccaaa cttacaactg tacattttc ttattgttgg gctgttgcta acctcaatta    118500
agaaggcttg atgatatttg taaagtgtca tcactccacc atggtccagt aacatctgat    118560
cactccacca tggtccagta acatctgaat ggtcaagaaa tatctaaacg tatgtaccaa    118620
aaatttgtgt atactactgt accaataaac catttgtttc catttgatct ctgagtgtgg    118680
taatacatgt tatttgccct gctgttgtaa ataaacaaac caaatggagg cttgatgcaa    118740
gatgcagtgt agcatagtgc caactctgga ctccgactac tcagggtgta aattctaact    118800
ctgttctatt aacaccatga aactgagcaa gttagttaaa actcgctggg cccattttct    118860
catttataca atggagattt taatagtaca gctacatagg ccattttgtg gtttaaaata    118920
catcatgatt atgaaacact taatgtaggg cttgctacat aatgagcaag gtttgttgct    118980
gttatcatta atatccttaa ttctcattat tataaaactt gagatagtat gaggtgaaca    119040
agttcataac agcaatataa tgaaaatttt aataattcct tttatacttt aacaaaaata    119100
cgagattggg taatttatta ttttttacatg agtaataaat attgcattaa aatatatttta    119160
```

```
aaatttacca cattaatgtc tgccagtcat gccaaatgac caacatgaat gtgaataaaa   119220
ctcagtctgt gcccatttaa tcttaaccaa ccctttataa ttgttaatga tttgaacctc   119280
tgccttgaaa gatcacatta cttgattgtc ttcaacttat ctgaatgtgg tagtgatttc   119340
tgtaaattta taggaccttt gtctcatgca gctccatgga gttgaactta tgcaccttta   119400
aaatggtata tacttaatta attaagtgtt gatctgcttc acatgtgtat aatattatta   119460
gctcactaaa ccaagaaaac agtggtcctt tagggaaaga aactaaatta caacagagaa   119520
tataaatacc atataaatat ctattattta ttgaactgtc acaattattg caaaaaatta   119580
ccttttagtg gacaaaacaa ttgatattgc cctttctgg aaaagaaata atgtaatata    119640
tgatgaatag ttttggccag tatcctctag accttgccag ttaactggct ctcaaaattt   119700
tgaataataa aaacttggtg atagtagaaa aatagtaatt ttttaaaagt atgtgcacaa   119760
ttatacaact aaacaattca ttcaccagtg ttcacaattc tattgccttc tttgaatcaa   119820
aatttacata gttttttcttt tagactaagc tcctttatga taccagtgtg cccatttctc   119880
attaccattg aaatgtctca tgagcatgtc acattctggt acaactgcta atccaggatg   119940
acagtttagt tcttttaaat ccaattgaga gccttctact catgaccaga gaacctaaag   120000
aaaggttaag atacatttat tccttggtgt aagtgatttg tctattttta gttttcctaa    120060
gggtcatatt tcaatttaga ttttttttta taggttaggt aaaataggct tccctttgc     120120 aatatgaaat atgtagtctt ttaaaaaatt tcttcaaagc tattaaactg aaaaaaaatt   120180
aatttggtct attcagtttg ttagcactta ccatttggaa aagagagtga ctctactttt    120240
gtatttggta acattttccc tactacaggg cagtatcttt tgtaagttct tagatattag    120300
caccaaataa ataggcaaaa aaaatctatt atgttaattc ttagaacccc tgcttggcag   120360
tgcatcattg actagatgga gaagaaatga aaataataca ttaggaagca gtttcctggt    120420
tcttttgaaa acaactagag agtcttgttg ttgactggaa tatctgaaga tcctgtttaa   120480
tgctttcatt ctatgattgt taagaatatg tcatagaact gctgtatcct gtttctttat    120540
gtcttccctt ctgtttgttg attagaaatc cctgagtggc tttacattat tagtacagta    120600
gatatgtagt atattcccat aataccactg ctgctattga ctaatagtaa taattttagg   120660
gcagctttat gacagttggt ttatgttta gggtgtcatt tgacttgtga agcattgaaa     120720
tctgggtatt aagcacactg ttttctatgt ggtatggaat gattcttaaa gccctgagaa   120780
aatggaaaat aaaaatattt ttcctttta ccataatcac ctatgactgt cactctatca    120840
taaactgcat aaactttata acctcaaaac attttggaaa tgaaatgaca gaacttgctt   120900
actcaattgc ttctatatac accaaatatt tttttaaagt attatgttaa gtccttgaaa   120960
atattttgtt ctactcaata gaagcagttt aggttggtag ttctatgtgg aaaccgtgag   121020
gaaataattt tatattatga tgactagacc agtctttgaa catcactttg gttattgttc    121080
cattagtaaa tattataatt atttctgaga tttactcacc ttcaaagaat gttggcaatg   121140
ccagcattat taacactcct ctagttagaa caaagaggaa atgtaataac aaaacataat   121200
aatagccaaa taaagagtga cttagaatgt acacccttat ctaggatcct gagtaattcg   121260
attattctta ggaaatacac ttttgtgcta gaacaaagac ttttgaaata gctaatttct    121320
gggtttcttt tcattttgaa ttaacttgaa tttcaaggaa acaagggtag tttttacaga   121380
tacagtgcat agaagctctg tgtacaatga agaaaagtag gaaagtgaga aaaatgccat   121440
tagatttttc atcgttatac tatctgatat gtgaatttaa ctaaaactta tatacctcat    121500
```

```
tatagtactt cctaatgtaa tttcttaatt taagtgttcc ccataaggtt ttttttttata  121560
taaacttaag tactgttaaa tatttaaggc aaattcaggt ataaaataag acttgttgat  121620
atcttattcc aagcatattt gtttctctcc tatttatttt tattctgtgt tcatttccaa  121680
aattgtttta ctcacaactg tttgttttt ctgtttcatt ctgtggtaaa ggtatcattt  121740
ggctaattgt ataatttcag tgtcatttct aatattccaa ttgtgatagt atcaacacaa  121800
gattaaattt ctctacatgg tttatgagaa tggaatgcca aattgaaata gaacagagca  121860
cagatgatct aaatataaaa agaactacaa aaatcacagt tgtttaaaaa ggttttttgt  121920
ttgtttatat atggtgcaga acatttgttc cttagccaaa tgtttccacc ttgagaaagc  121980
tatagagatt ctatgtagtc ctagtaccaa taatatgttt taacctgaat gtaccttatc  122040
tttattcata aactgtgact ttttacactg ctgaaacttt ttttttttaag acaatctcac  122100
tctgtcgtcc agtctggagt gcagcagtgg tgtgatcttg gctcactgca acctctacct  122160
tctgtgttca agcaattctg gtgcctcggc cacctgagta gttgggatca caggtgtaca  122220
ccaccaggcc tggctaatag ttttttgatat ttctagtaga gatgagtttt gccacattgg  122280
ccaggctggc ctgaaactcc tggcctcaag tgatctgcct gccttggcct cccaaagtgt  122340
tggtattaca agtgtgagcc actgtgcctg gcctgaaact cataattcat ttccattaat  122400
attaatctca ccttttccaa taattaattg atttcacaag tattagtccc ctataatcat  122460
tgaatggcta ataaaattat ttatagcaaa cagattaatt atctgccagc agtctgagat  122520
tagtttcttt aaaaaatgtt tattatttaa acattcagc tgtgatcttg ctttcttgt  122580
gaggttcaat agtttctatt gagtaaagga gagaaatggc agagaattta cttcagtgaa  122640
atttgaattc cattaactta atgtggtctc atcacaaata atagtactta gaacacctag  122700
tacagctgct ggacccagga acacaaagca aaggaagatg aaattgtgtg taccttgata  122760
ttggtacaca catcaaatgg tgtgatgtga atttagatgt gggcatggga ggaataggtg  122820
aagatgttag aaaaaaaatc aactgtgtct tgttccattc caggtggctg cttctttggt  122880
tgtgctgtgg ctccttggaa agtgagtatt ccatgtccta ttgtgtagat tgtgtttat  122940
ttctgttgat taaatattgt aatccactat gtttgtatgt attgtaatcc actttgtttc  123000
atttctccca agcattatgg tagtggaaag ataaggtttt ttgtttaaat gatgaccatt  123060
agttgggtga ggtgacacat tcctgtagtc ctagctcctc acaggctga cgcaggagga  123120
tcacttgagc ccaggagttc agggctgtag tgttgtatca ttgtgagtag ccaccgcact  123180
ccagcctgga caatatagtg agatcctata tctaaaataa aataaaataa aatgaataaa  123240
ttgtgagcat gtgcagctcc tgcagtttct aaagaatata gttctgttca gtttctgtga  123300
aacacaataa aaatatttga aataacatta catatttagg gttttcttca aatttttaa  123360
tttaataaag aacaactcaa tctctatcaa tagtgagaaa acatatctat tttcttgcaa  123420
taatagtatg attttgaggt taagggtgca tgctcttcta atgcaaaata ttgtatttat  123480
ttagactcaa gtttagttcc atttacatgt attggaaatt cagtaagtaa ctttggctgc  123540
caaataacga tttcctattt gctttacagc actcctcttc aagacaaagg gaatagtact  123600
catagtagaa ataacagcta tgcagtgatt atcaccagca ccagttcgta ttatgtgttt  123660
tacatttacg tgggagtagc cgacactttg cttgctatgg gattcttcag aggtctacca  123720
ctggtgcata ctctaatcac agtgtcgaaa attttacacc acaaaatgtt acattctgtt  123780
cttcaagcac ctatgtcaac cctcaacacg ttgaaagcag gtactttact aggtctaaga  123840
aatgaaactg ctgatccacc atcaataggg cctgtggttt tgttggtttt ctaatggcag  123900
```

```
tgctggcttt tgcacagagg catgtgccct ttgttgaacc tccatttgac tggcatgcac 123960
atgtctcaga tattataggt tatcatatat tgttgctcct aatatttctg tgttagataa 124020
ttagagtagc ttggtttgta agaatgtgat gttggtggga ctgtagcaga acaagaaggc 124080
ccttatgggt cagtcatacc tctcttttca aatatttggt ctagctctct tctgggcatc 124140
ttgttgccaa tatatagtat tgctcaaaag ggcaggagat ttgaagtgat caaggaaaat 124200
atattttttc tattgattaa gtcttttgat ggggtagaat aatctaattt catgtaactg 124260
ctcaaagtta tatggtaggg ggatcccaaa tgtatttttaa aactattttt atatcatcat 124320
atttgaagta atagaaagtc agagtagcag aataaaggta ctaaaaattt taaaaactaa 124380
taaggtactt tgaaagaaat caattatgtt gattcctcat taaacaaatt tgcacttaaa 124440
gactgaggtt aataaggatt tccccaagtt ttttcatagc aacctgtgag cactttctct 124500
gttgaggcat ttatggtatg aaaagatgag taaggcacag ttcttgccct ggagaaggtc 124560
acaggtgaga ggaggagttg acacagaaac atttgatata aagcaaggaa taaattccaa 124620
gactaaaatt ttcagaaatc taaaaaactc aagataagaa aaacccatta tattttctgg 124680
gtaacaaaat ttcagtgtta ttaacatgta ggaagatctt gatatttatt ctgaagccca 124740
tgtgtgttgc tgaaatattg ccgcatttgc atatactcat caccatcctc tgttttggag 124800
ctaagaattt tagactcaag atgtctaatt aagttgatcc attgatttta tttttttatgg 124860 aaatctgaga cccacagaag gcaggggatt tgcccacatt tctagaagag tcagacatga 124920
gcgatgaggc acagtggaaa gaacatgagc attgcctgag ctctgagttg gcgctataag 124980
agcagtgatc atgggcaagt gactcttctg agccttggcc tcctcacctg ttaagtgaag 125040
aaaagaatat ttcagaagat ctttgtgaga atgaaacaag gcaatttact tgcctgctac 125100
atagccaatg ggaaatcaat ataagttccc cgtggttccc ttctgtgggg ttttgttccc 125160
acagagggtg cactggccat tccacttctt ctttttccaag ctcctcattc cctttaacgc 125220
tgttcatagt tggttccaaa ccatttgaaa tataataagc accaggatgg ttttttcttt 125280
ccaccaaagc aaatttcatt ttctaaacac tgttttataaa tatcaatggc tatttttttca 125340 atttttgatt atcatgaaaa tatacaaata tgtttaatta aatatgctaa agaatgtatt 125400
aataaatatg tattaaataa ttcctacata taaggccttt ttgcttgggg tatgggtgat 125460
acaaaataaa tgtggcatga acccactgac ctctagcaat ttataaccta gaaaagagt 125520 tatgatatgt ttataagttc ctgtgatata agacatgcat atagtcatta aacagaggt 125580 gcaaacaaga tgtatcaagt atgtccagag gaggaagaga ttaatcccag ctggaggaaa 125640
cactgatgct ttcttgcagc agggggcattt gagttgagaa agggaggaaa catagatttt 125700
gacaatgaga gctgagggga aaggggtttc aggtggaggg aaccgcatgt ggaaagcagg 125760
gaggtaggaa agtgtagagt gtgtttaaag aatagaccag tttggctgaa acaggatatt 125820
tgagcagagg aagcttgtac taggtaggtg ggttgaggcc aaattatgca aggcattaaa 125880
tattaaacta ggaattttgg actttatcct gcagtttatg ggggtaaat gataagattc 125940 aatatcactt tatttgtaca gtattatgtt acattttatc taattgtttg tttaattcct 126000
gtctagacaa tgaattcctc aagggcaagg agcatggctt attcacctca gtaatttcag 126060
tgcctagcat tgtgcctggt acaaagtgga cacttgtata taaccttttt taattgaagc 126120
aacaagttgt caaccttaca aatgtgaatc cgtgattcag atgacaggtt gaaatgtaga 126180
ttgtctgcga agagggcaga aagagagtat gacaaaggag gacaagacag tggggcaggc 126240
```

```
agggagagag agcagccagg gtttcggtag aggtatgtca aaaaggtatg gaagtcagag   126300
gagaaggaga cccctatgtt atagaataca aatggaaggg aaatgatgac aacagtaagt   126360
tgtcattaaa tgcaaggttg caaaagtaag attgtaaagc aggatgagta cccacctatt   126420
cctgacataa tttatagtaa aagctatttc agagaaattg gtcgttactt gaatcttaca   126480
agaatctgaa acttttaaaa aggtttaaaa gtaaaagaca ataacttgaa cacataatta   126540
tttagaatgt ttggaaagaa acaaaaattt ctaagtctat ctgattctat ttgctaattc   126600
ttatttgggt tctgaatgcg tctactgtga tccaaactta gtattgaata tattgatata   126660
tctttaaaaa attagtgttt tttgaggaat ttgtcatctt gtatattata ggtgggattc   126720
ttaatagatt ctccaaagat atagcaattt tggatgacct tctgcctctt accatatttg   126780
acttcatcca ggtatgtaaa aataagtacc gttaagtatg tctgtattat taaaaaaaca   126840
ataacaaaag caaatgtgat tttgttttca ttttttattt gattgagggt tgaagtcctg   126900
tctattgcat taattttgta attatccaaa gccttcaaaa tagacataag tttagtaaat   126960
tcaataataa gtcagaactg cttacctggc ccaaacctga ggcaatccca catttagatg   127020
taatagctgt ctacttggga gtgatttgag aggcacaaag gaccatcttt cccaaaatca   127080
ctggccacaa agtgtgacat tttggcattg gcatcactat ttgatggaag ccaacctccc   127140
cccaaaaggc ctgtattaga atgaagatgg attccctggg tgggttacac ttgaaactag   127200
cctcacccat gaacactttg gcacagatta gctagcccat tcccccacag taaggaccat   127260
aaggaaggga cagaagcaaa gataagtttt agaacaaaag agaggggaaa gaaaaaatct   127320
agggttttat gagggctgtc cctgagtgat agatgtgaat aggcctccag ggcaggctgg   127380
ctcagaggct gactctttgg gttggggtga ctgattggtg gtgaggatgg agaagaaaag   127440
gggagtggag gaggtgaaag tgaccttggg acattaggtc tccataagtg acaggattta   127500
aggagtgttg taagctgtgg ttgttggacc aggtttaagc acagcttcct gagcttcctg   127560
actggtttag gtcaagctcc agagagcaaa tgccacagtc tcagtgatct ccttggagaa   127620
acagttggaa taggatgttg cccatgttgg gatgagtcat tgtccgctct tgctctttcc   127680 ctaccctgc aaaataataa tactgtattt gattgaacat ataaaacaaa agaaggatta   127740
tcacataagt atgtatatat aaccaacatt ggcaggtgca gaaaaaccag actgtcagtt   127800
tgcctcatct gaaatgattg acacaaacaa atatatttac tgtcccaagt gaactttggc   127860
attttggata tccttcagtt gttctgttta aagatataac ttagaagcag ctgatggaat   127920
atttaaatcc atgcgttgaa ttcatgcatt caaagaaaca tgtcctgagt cactaaatgc   127980
tgacatttgt ttttcatgtt aagagtgtaa ataactggtc ccaaatataa tattattaca   128040
tcagataaaa actggaatgt gaacctctta acttgattgt gaaagtattt gccaatggtg   128100
cctcttgata attatttgag gctcacttca gaactcctct ggaagggtta attttttaaat  128160 agtcatttta taaattaaca ttttttgacat atgtgatggc tctcaaattt tttctttat   128220 gccagtttga atcatttctg ctcaattttt ttttttaatt gggatggagt ctcactctgt   128280
tgcccaggct ggagtgcagt gatgcaatct tggctgactg caacctccac ctcctcggtt   128340
caagcgattc tctcgcatca gcctccagag tagctgggat tacaggcgcg caccaccatg   128400
cctggataat ttttgtatta ttactagaga tggggtttca ccacgttggc caggctggtc   128460
ttgaactcct gaactcctga cctcaagtga tccacctgcc tcagcctctt aaagagctgg   128520
aattataggt gtgagccact gcaccaggcc ctgttcaact tttaatgcta agattcattt   128580
gttgttgttt cacaagtgat taggcagagg tcttttatat taatttaccc attttatttg   128640
```

```
taagagagtc tcatattaag gaagcataat atatgacaat ccaaatacag tacaaatttg   128700
gttaattttg attttgttaa ataattaatc acaggggtcc ttcaaattgt gagctcctct   128760
ggttatactt atgttttacc tctggttata cttaatttca aacaaatgaa atttcattct   128820
attcatgata tttcagaagc agatctgttg cacaaaataa agcataccta taaattttct   128880 tttttttaaaa aaaagtctct gttcactcta ttttctatta tttttctctt tttaaatttt  128940
gaattttatt gtggcaagtc cacttaacat gagatttacc ctcttaacag atttttatgt   129000
gtaaaataca atattgttca ccatgggtaa atgttgcaca gcagatctct ggaacttatt   129060
cattttgcac tactgaaatt ttatacctgt tgattagtat ctccccattt ccctctctcc   129120
cctgtcctgt tacccatggt tctgttcttt gcttctttga gtttgagtat tttgatacct   129180
catgtaatct tcattctatt ttctaacttt gacaatgttc tgacaaattt gctttccgga   129240
ttggagcact gtatagtgaa aattgaaaat cttggttatt ttctacagat tcccactatt   129300
ttaccttgag cagacactta tcttgaaggg tctcagattt gtcacttgta gaatgggaa    129360 tataaacctg ataatggtcc ctttcagttc taaagttata tcagttgaaa atacatgtgt   129420
cacttatggt aacgggtaga gaactggctc actgaacagc atatggatat tataaagtgg   129480
ttttttttaa tcctttctgc agacagttac tttatacttt attcaaatgg attattgtga   129540
agtacatgtt agcggacttt gtaccttta aaaatgtatg tatttggtgt aatgtagaaa     129600
tatagaaatt tattaagtat gatttatttc aatgttaagc atgagaaaat atgctccgaa   129660
aggttagata gcttgcctaa atgacaagct tgtatttcaa gcagaacttt ctgaatcaaa   129720
agactccaag acgaatgccc agctttcaaa aactgtctaa ccaaaataaa tcctaagatt   129780
caccttcata ctaaaattat ttaaaaatag tttatttaa attaatattc acttaaaatg    129840
tatttatcat gcaatacttt aaagtgtctg ggaaatgaaa atatccaaag atcaaagaac   129900
accatgtttt caaacttcaa aaatgttatc agtgacctaa acaatttta aaattttcat    129960 agagcctatg aaaaatgtac ttgcaaatgg ctactttctg actaggaata gaatgggag    130020 agtatttagt ccaacaatga tagactggat taagaaaatg tggcacatat acaccatgga   130080
acactatgca gccataaaaa atgatgagtt catgtccttt gtagggacat ggatgaaatt   130140
ggaaaacatc attctcagta aactatcgca agaacaaaaa accaaacacc gcatattctc   130200
actcataggt gggaattgaa caatgagatc acatggacac aggaagggga atatcacact   130260
ctggggactg ttgtggggtg gggggagggg ggagggatag cactgggaga tatacctaat   130320
gctagatgac gagttagtgg gtgcagtgca ccagcatggc acatgtatac atatgtaact   130380
aacctgcaca atgtgcacat gtaccctaaa acttaaagta taataaaaaa aataaaaaaa   130440
agtttgaggt gtttaaagta tgcaaaaaaa aaaaagaaa taaatcactg acacactttg    130500
tccactttgc aatgtgaaaa tgtttactca ccaacatgtt ttctttgatc ttacagttgt   130560
tattaattgt gattggagct atagcagttg tcgcagtttt acaaccctac atctttgttg   130620
caacagtgcc agtgatagtg gcttttatta tgttgagagc atatttcctc caaacctcac   130680
agcaactcaa acaactggaa tctgaaggta tgacagtgaa tgtgcgatac tcatcttgta   130740
aaaaagctat aagagctatt tgagattctt tattgttaat ctacttaaaa aaaattctgc   130800
ttttaaactt ttacatcata taacaataat ttttttctac atgcatgtgt atataaagg    130860 aaactatatt acaagtaca catggatttt ttttcttaat taatgaccat gtgacttcat    130920
tttggtttta aaataggtat atagaatctt accacagttg gtgtacagga cattcattta   130980
```

```
taataaactt atatcagtca aattaaacaa ggatagtgct gctattacta aaggtttctc    131040
tgggttccca aatgatactt gaccaaattt gtcccttggg cttgttgtct tcagacaccc    131100
tttcttcatg tgttggagct gccatttcgt gtgcccccaa actctacttg agctgttagg    131160
gaatcacatt ttgcagtgac agccttagtg tgggtgcatt ttcaggcaat acttttttcag   131220
tatatttctg ctttgtagat tattagctaa atcaagtcac ataaacttcc ttaatttaga    131280
tacttgaaaa aattgtctta aaagaaaatt ttttttagtaa gaattaattt agaattagcc   131340
agaaaactcc cagtggtagc caagaaagag gaataaatat tggtggtaat tttttaagtt    131400
cccatctctg gtagccaagt aaaaaagag ggtaactcat taataaaata acaaatcata    131460
tctattcaaa gaatggcacc agtgtgaaaa aaagctttt aaccaatgac atttgtgata    131520
tgattattct aatttagtct ttttcaggta caagatatta tgaaattaca ttttgtgttt    131580
atgttatttg caatgttttc tatggaaata tttcacaggc aggagtccaa ttttcactca    131640
tcttgttaca agcttaaaag gactatggac acttcgtgcc ttcggacggc agccttactt    131700
tgaaactctg ttccacaaag ctctgaattt acatactgcc aactggttct tgtacctgtc    131760
aacactgcgc tggttccaaa tgagaataga aatgattttt gtcatcttct tcattgctgt    131820
taccttcatt tccatttaa caacaggtac tatgaactca ttaactttag ctaagcattt    131880
aagtaaaaaa ttttcaatga ataaaatgct gcattctata ggttatcaat ttttgatatc    131940
tttagagttt agtaattaac aaatttgttg gtttattatt gaacaagtga tttctttgaa    132000
tttccattgt tttattgtta aacaaataat ttccttgaaa tcggatatat atatatatat    132060
gtatatatat atatatatat atatatatat acatatatat atatagtatt atccctgttt    132120
tcacagtttt aaaaaccgat gcacacagat tgtcagatag caattctgtg attgaagggg    132180
aaatatgtca cctcttcata ctcatattgg tgaagggtcc tagcttcaaa attaatagat    132240
tcctaaagag gggaaatgaa acatccgcat ttacacacac acacacacac acacacacag    132300
agttcctctt gtcggtaagt tttgttttt ttaaatctct actagataaa atttgttatc    132360
taattgtgag ttttacacaa agaaaaactg tcacagaaaa gaaagacagt gtcacatttt    132420
tcaaaagaaa aagaagaaaa gaaagtgcca tgttttcaa atacaaatgt tctggattga    132480
ttttaggatc tttagtgaaa aacaaagtat ttcataataa gtaaaataaa aatctatgta    132540
ggtaaatttg tttctctaat ttaagaattt gaatttctga gtatttatga taagtgttga    132600
aataacttct tatatgtgac agtgaatact ggcagagcaa atgccaaatc aatgccaaat    132660
ctgtaggatc atttgattgt aggaacagaa ttctactcaa accgaaagca ggcatttgct    132720
ggagttacag aaaggcctca tggaacaccg agaaggtggt gccattcgac tcttaaagaa    132780
gctgcaacag gcacaagaga gtcagctgca gctcttcttc ttgagtctat atctgtcctg    132840
ggtccattcc ttttttgtggt tgcttcattc ctttctctct ctgaagactg gttttttctgg   132900
tctaccaggg ctatgccaca ttgactttat gtagtgtctc cattctgcc tcctgaattt     132960
acaggagagt tcctctgtac aaactcaaag tcctggagag aacagaaaac agcttccttt    133020
tggctcaggg gtccaactgc agtctactct gctgctatga ggatagtggg ttcaccacct    133080
ttgttgttct ctcagctagg gcagtgggaa atgactctat gaaaggaata tacatgggca    133140
ggcaaatgta ctaatcctca tcagtactgt aattttaagc aactttaaaa aattctttta    133200
agttatttga aaataagatc aaagaaggct gaattacata aatgaagatt tgttaacaat    133260
taattcaaac caatataaca catgctataa catggttgag tgtgattgag tcttgattta    133320
ttaggggcaa taatcaaaac atttaacaat cattatagta cagaacttac caatcaaatc    133380
```

```
agatgctcag ccggagtgga tgttggccac ccagctatta ttatccctgg ctcaattggt  133440
cttcagctgt gttaacttgc aaacattaat taactatcta agcccctcat tttcctcaag  133500
tgtaaataga cacaataata ttacctattc cataggtgtg gggtgaatag taaatgtaat  133560
aatttgtcca aaacacttag tatagtgcct ggtccatggt aaatactaaa taatgttat   133620 ctgacttatt attaaaattt tatcttctca gcttaacctt cagaacagta atatattggg  133680
gtctagataa atcttgccta tatgaaaata atttaatact acatgcagat atatgctgtg  133740
tatattatgc cttctgttag aggaattgca gaaacaaaaa tttcaattaa taataagatg  133800
aattatttct cccaattgta gaatcttttg acaattttat catgcattac agatgtaaga  133860
actcttgatt gggacttgat agtctaactt tataataatt taagaacatt cctcttagag  133920
aatttctatg gccataatac tgaacacatg aatttttaatt agctgtcctc tttagcccta  133980
aaaaaaaaat tactgtaatt taacacttaa gtgttgttct tcccaggtac agtaatcttt  134040
tttttttttt ttttttttttt ttgcatagag ggtaatcttt tctctttcca aatggcagaa  134100
ctgttagttt tctgactgtc cggtgaaatt ctaagtccac ttacttccca atagcatgca  134160
attagcaaag gtcctccttg caaaggcaca gaacacacct aaacatcttg cagatgctgt  134220
ttggacactc ttcccctgct tttggtctct ttgtaaagca gctcatctgg atacaggatc  134280
tcttttcccc attgcccatt ctaatatatg ttaccgttat tacttataga ataatagtag  134340
aagagacaaa tatggtacct acccattacc aacaacacct ccaataccag taacattttt  134400 taaaagggc aacactttcc taatattcaa tcgctctttg atttaaaatc ctggttgaat  134460
acttactata tgcagagcat tattctatta gtagatgctg tgatgaactg agatttaaaa  134520
attgttaaaa ttagcataaa attgaaatgt aaatttaatg tgatatgtgc cctaggagaa  134580
gtgtgaataa agtcgttcac agaagagaga ataacatga ggttcattta cgtcttttgt   134640
gcatctatag gagaaggaga aggaagagtt ggtattatcc tgactttagc catgaatatc  134700
atgagtacat tgcagtgggc tgtaaactcc agcatagatg tggatagctt ggtaagtctt  134760
atcatctttt taacttttat gaaaaaaatt cagacaagta acaaagtatg agtaatagca  134820
tgaggaagaa ctatataccg tatattgagc ttaagaaata aaacattaca gataaattga  134880
gggtcactgt gtatctgtca ttaaatcctt atctcttctt tccttctcat agatagccac  134940
tatgaagatc taatactgca gtgagcattc tttcacctgt ttccttattc aggattttct  135000
aggagaaata cctaggggtt gtattgctgg gtcataggat tcacccatgc ttaactgagt  135060
ggtgccaaat tgtcctcaag tctgttgtac tgatatatat ccccatcaag agagtacaag  135120
aattctcata gctatgtatc ttcaacaaca cttggtgtct ggtagatgtg aagtgattac  135180
taaaaatata gggaagctgc atacataatt attggctttt gctgttctct tacattaatt  135240
tcttattcat gttgattact catttgtcac ctagtttttt cttccttaat taaattgtag  135300
gaatttatga attatggatt gatcatcagc tctatacatt tcaaacataa tccctcagtc  135360
agtggcttgg cttatagagt cttttgatga aaagaagctt ttaagtttaa taaagttcaa  135420
tttattgtct tttcctttat gttttgtgct tttggtatct tgattaagaa ctccttcctt  135480
atattgggtt ctcaaattta gcagcataac attttcatac tattatttaa attttttca   135540 cattatttag tgatagcacc tttcttattc ctaaagtgtt tatcattgcc ttctgtcttt  135600
ctgcttgata aatattgcca cacatttgta tactttatta gtgtgtacaa agaccacatt  135660
ttagttgtgt tatttctctt gttttggttt tctagaatgc agagccatta atattatagt  135720
```

```
aatgcttatg tgctaatacc atatcagggg cacaaatccc attgcagcgg gactgagaaa    135780
ttaaaggaaa tgatgcacat ttactcattt ttgtttaaaa aatcaaatgc atatttttca    135840
atcagactat atggttggtc tggatagctt catcattgaa ttttttaaagt attttttgtac   135900 tactgtattt aaaattattc attcaccact gcttttgtag atggtttaga aacccaagtt    135960
aggaatgact gtgcaacact attattatac tcttttttaaa attatacttt ttgcttaagt   136020
ttctttcctt gttctctgag acagtgttca tgttcccaaa ccacacacat ttattcagct    136080
ataaaatttg tatgatcaac tcctgtcaga acaaacatca ttataaaaaa tatctccagg    136140
aaaaagaaaa ccctttttaat gctctcttct ggttcatgtg tcttcttatt ttctttaagc   136200 atttttcataa cccattgagc tgtaatttaa ttggaacatg atttatacta aagttggttt   136260
ctttaccttt aactttttttt tttagtttga tcagctctct ttagcttctg tagttcggtc   136320
tttaattcca ttccagtatg ctttttggagt tgggtctcat aaatgtatag aaatgtttct   136380
gttgggaaac agcaggagaa tattaaataa atattgtgct tacatctatt taattctttg    136440
cccaactttc tacaactttg actttacatt taagctcctc atgcacttac atgtttcttt    136500
acctaaaaat atcttttcac catgggtgtg tacaattcct ttgtccttgc tgtattaatt    136560
ttcttggttt acatagtagc ctctacacat tgatgtcaaa acctctgttt ggtgcatttc    136620
tactctgcgt gttcaatctc catgaaagtt tctgtaaggt attttcattc ctctagtttt    136680
tcacatgtgc atcctggctt tgtgacctgt gctttgatat cgtgcctttc atcttgtggc    136740
attgaaggat ctttgcaagg acctattgtg ttataataca gtctatgaaa aatatcaata    136800
tttgcatttg atcacattta aaaaaatcac attcttttgt ttgaatatca aagctaatat    136860
gtgagtgatt tccctgccaa atagcacaag tagcctttcc tgggtgttta tgggcattta    136920
tctggttaat gattcccatc atagtgctgt cacccatgcc attgctaaac ttatacagta    136980
acttttttgt tttcacctca gcatatgttg agagtaggaa atagatagga ctatgccctc    137040
aaattttacg tttatatgat gttaatccta aaggtccttg tgacttctga agtaaaaact    137100
cagtgttgtc attttactta ctgaattgtt agctgagttt agagttgagt ttacaatgga    137160
gtaaacaagg tgtttagttt gatgtatgct tttagtcttt cagaaaaaaa tgtttatact    137220
tggaaagaat agtttatttta cccatctggc ctagtttaga caaaaacaca gagtcaaatg    137280
tcaacagaat tctgaagtta taaaaatgac agtgtggctt ttttttttttt taaccttcca    137340 cctggtgctt atgcccaagt gcctagcttt ctttagctct caactaataa aggtaatgtt    137400
tagataacat ttaacgttaa gttgcattgt gtttatgatc acatatctca aatattggta    137460
cacgaaactg tacaacaacc ttttttatta gattttccta cgaaattcct tattatattc    137520
cctaagatag cttttttccca ccttcttctt ccttctccct tctcaggtgc tccaataatt    137580
ccaacccctg cagccagtga ctttattata tcttttttta aaaatctaaa aaaaaaaatt    137640
gatgcaacca ggaagaattt tctcatttct ctccaccagt tgtaccagcc tactgcacct    137700
ctcctcatgc accaccttct gcctgtgttc ttgctcctat attcaggagc aagtaatatg    137760
caatacctcc ctctttgtgg gatctttctc attagcataa aaatactttc ccttgatctc    137820
cagctactac cccatttctt tgacctacat atagcaaaat atttgagaaa ggaccacttt    137880 ccatctttttc ctcaatctac ttccatttttt ttctcaatcc actttcattt cattgttctc    137940
ctcaacccat tctttccaca acctacttca ttttatttcc atcagcccca taactcagga    138000
tcaacatctt gccagagcca atttccttgt ctcccttaac agctccagca gtatttatgc    138060
catggacaaa ttattcttct tgtgatactt tctctcttgc ttccatgaca ctactcccac    138120
```

```
ttcattttct ttctacctct ctggctcttc cttggtccct tttcctggcc ccttctctct 138180
ttcagatctc taaacatcag ctatatctca gccctgttct actgacactc tctagctgtt 138240
attttctaaa cccatgtttc agaaaccata tcttgatgaa tcttggaagg ccgaggcagg 138300
cgaattactt gaggtcggga gtttgagacc agcctggcca acgtggtgaa acccatctc 138360
tcctaaaaat acaaaaatta cctggccgtg gtggcatgca cccagctact gagaggctg 138420
aggcacaaga atcgcttgaa cctgggaggt ggaggtttca gtgagccgag atcctgccac 138480
tgcactccag cctgagcaat agaggagact ccgtctcaca cacacacaca cacacacaca 138540
cacaaagaaa ataaaccatc tcttgatgaa tcataaattt gtgtctctag tttagacctc 138600
tatcctgctc tctaaatgat gtatccaact atcatcttga caccatcata tgttcataaa 138660
acataattat agaatatctt tcagtaggct tgacatttta aggcatgagt ttccgttcag 138720
tatctcctta aaatataccc agggtctcag gagactattc aaacaggaca aagcttctat 138780
tctacttact aatgtgtctg gccctatttg gcaggttgga taaaaagtca tctgaacatt 138840
gtcactttat gaataatata gtttaatagt ttgtgaatca cccctgcaat ttaaaaaata 138900
gtaaaattat cagaatctaa tttaataatt cctattggaa caccccatgt taggggattt 138960
ccagttattt caattgatat ctcaatgttt taaagattgt ttatttctat tactaattca 139020
ctctttattt taacataaat tgtggctatc tatctctatt catttcaatt atatttctca 139080
taccattcta tagatggggt gaaaagaaaa gtgttaattt tttaaaactc catacctcaa 139140
atactatatg aatttatagt tgttattgct aaagcaatta tcttacatct tttcctccaa 139200
aacaaagtta tgtgctggtt tatttttctt gtactcataa gatgccttcc attttttagta 139260
acataagtct tgtctttctc ctattcttag ctacttaagc attatgtagc ttaaataagc 139320
actaaagatt cctatctgta tgaaaaaata aagattaaat aaataagatc tagaaagggt 139380
gacaaggtga tgcttcaaaa tgaaccatac caagccatct agcgattgat aaattactca 139440
cactcataat cacattgttg gaaagaagcc attgacaatt cagtttgttt cacaactgtc 139500
tatcacatag tgagcacaac taaaagacta cttttttgtct tttactgctt gttttgttga 139560
tcaagtgact gattgtacaa tgaccaacaa gaagtctgat gtgtagagaa aaggggaacc 139620
tggcttttct gccttactcc tgatgcctaa ttctgagcat gtgaatatta ttctgtttct 139680
ttaattctcc aagtgaagca gcagataaac catccttgtt tccattagct gtctaccctg 139740
ttcaactgtg tgtttctaat aacataagaa taagaaagcc accagggtga gcagggaagg 139800
caatgagtct gcaaggcttg tggatagatt tctgttagtg aggctctaga aagttcttcc 139860
aagattgatg caatctgaga agagttttct gtcaatacaa actccctggg tttctccttt 139920
gtcctttttac tgcctgtgtt tgttttgggt tccagtaaag atcaagtgac tgattgtacc 139980
atgaccaaca agaagcctga tgtgtggaga aaaggggaac ctggcttttc tgcattactc 140040
ctaatgccta attttcttgt actgaaagta gttttttgctg taagaatctg aggggaggag 140100
tcatttcttc aattttttt tttggtctcc ttttaatggt ttcttgatca tgtctatcct 140160
tattttctg ttttcacaaa ttttttgtggt atattttcct ctcatgacct ctgtctcaag 140220
acttcttttcc atccatctct tctcatttca tcctgtagag tgtctgtggt aagagccctg 140280
cattctactc tggccttgcc atgtgtggcc ttgggcaagt cctagcctcc ttgagggtct 140340
tatttttctc atttgtaaaa tgaaacagtt tgatgagaag ttttctaagg ttccttcaag 140400
ctttgacaat ctctctcttc tggatctttt tcccatgaaa aatttcaact cttgattagc 140460
```

```
atgtaggcag ggattattcc acatccttat aggaatcaca tttctgctac tgtccctgaa    140520
tgctagagtc cattgattaa gttattcact gctgcaattg tcagagctga tcaaagaact    140580
ctgaaccagt gtgttactag aactaacaaa gaaaatgcca ttatgatgtt ctagagtctt    140640
gaattagtag aagaggttta ataagaaccc taagggattg ctagaatgtt aaaaacaaac    140700
aaacaaaaaa aaaggttgaa aagtttagaa aattcactgg tctttgtgcc catcatttta    140760
cttccagggt ttagataatc tcattttttgc aatgaaggaa tggattagat cacaagttct    140820
catcctagta gcacatgcag aatctttata aaaacacaga gtagccaggt gcggtggctc    140880
atgcctgtaa tcccagcact ttgagagcct ggggcaggtg gatcacttga aataggagt     140940 tgaagaccaa gctggtcaac atggcaaaac cctgtatcta ctaaaaattc aaaaattagc    141000
caggcatgat ggcacatgcc tcccagctac tggggaggct gaggcaggag aatcgattga    141060
acccgggaga tggaggttgc agggagctga gatagctcca ctgcactcca gcctggtgac    141120
agggtgagac tccatcacaa acaaaacaaa acaaaagaaa gcaaaacac agattactca     141180 gggtccacta agaccagtga agtcagttct cttggtaggg ggcagggtga ctgagcatga    141240
tgtttgtaat tttaaaagtg ctccaggtga ttctagcgtg tatcaagcaa gacttgtgaa    141300
ccactgaact acatgctaag actcatttta gctctgattt tctgtgagtc atagcagagg    141360
gctcagcaaa cttttttctat aaatgctaag atagtaaata ttttcagctt tgtgggctgt   141420
atcgtcttta tgacaactca actcagtctt tgtagagaaa agcagctgta cataatatgt    141480
aaactaatgg gagtagctag atgtgtcctg tgggccatag ttttgctgac tcctggtcta    141540
tgtcatagaa tttcctttg aattgatgga ccaccagcaa atgattttg tcctgtatca     141600 atcaatgata catacataaa tctctacaag acatgtaaag gatgaggctt aatgacagag    141660
tactttgggg aagacataat attgcaaaat taagatgctt agagaaaaat catattaaaa    141720
tagtgaaaac tgtgagaagg tattttgatt tgttgttttg gattcctctt tttgcaaatt    141780
cttttgaaat attttcagtg gaagctacat agatccaatt gtattcacca agctagattg    141840
taattaagct ccagagtaag taatagattt gatgagtgat gtccaacctt ttacatggaa    141900
gagtaagttt gagtcttcct ttgcccattg acacacttag taccatgttt accaaagttc    141960
ttagttattg aaatgggcac cagcatattt tgaaacgttg gtgttaactt gggatatgcc    142020
ttttgtcatg ttgcaaatag attttgtttc tgttttgtga agatcaccat ctctgtcact    142080
tctgatagaa aaagtgacac tgacttctca agtgatttga cacaggttaa aatatgtaaa    142140
ccatttctgt agagagcaag ctgtaataat atactaaagg gctaggttta tagtataata    142200
taaataactc atttatgctg ttaataattt atagcaacat ggcatttgac tgacttttta    142260
tgtgctctag tcatgtaagt aatagatgtg gaaacataga ccagagtttc aagaacatgt    142320
tttgggcaga gtctgttttc ttgctattat ctcttaagtt tatgttcatg gcctaaagat    142380
tatgctaatg gatctgcctt ggtcttgggt gtcaggtctg tgttagcgag tattgaaaag    142440
catagttttt gcctactggg aaggatttat gatttaaaag ccctaaatct cccctttat    142500 gtacttcata cttagaaaat ttttcctgta aactgtgtga ctttttttaca ttgtgccagt    142560 tttctagatg actctcgtca tatttatttc ttgcaatcct tctataacta tcagttatga    142620
agtctcttta tagtgttgcc agccaggtct caggtgtgtg aaatgtattt tctattatgg    142680
attttggggt atgatggcac atagtttggg tgttaatgcc taatcttgat gtactggctt    142740
ctgaacaacc aaaaggatga aaggaaatag aacaaatatt tttgtgaggg agaggagtct    142800
ggcttcttga cttactctag aaaaagcctg taagcctcct cttccctcct tgtcacacaa    142860
```

```
agtgacaaag aaaatcaaga attgttttct tcttggctta aatgcatccc ttataaagta 142920
aggctgagat caggctgtga agctatcttt ttgtcaagac tgtcataatt ccaaaacact 142980
ttgttcttct aatgcttagg ttagtaactt taaacatttt tataaagata gtgaggtcca 143040
gttttaagga ttgacccctt ctcaaggggc tcagaagagg ttttggagaa taataaaatt 143100
aaataatgaa accaataatt taaaccagat catgatcctt aagaaaaaat cccatcaaat 143160
ttgggctaaa ctctaatata cagaggtctg cacaacttat gtcaagtatt cttccccaca 143220
aatgaagaat ggggttcatt gtgtcattgg ttgggtctca ttttggcttc atcttctatt 143280
tctcaaagtc taagaaaagt gctcctacgg aagtgggtgt tggctatcat gagactttgc 143340
tgctggcagg ccagcttgct gctctagaca gagatatccc tcgatcctcc ttggacaact 143400
gttttctgtg cacaggaagc agcaggctgg ggttaaggag tttgccaatc cagtcattct 143460
gataattgct gaatatgaat ttctatccag cacaatctag gtagctacaa tggcacagta 143520
gtttttatgt atcaggtgaa aatgtttaat aggcactcta aatgagagaa aaggttaagt 143580
gaggttaaaa gctcaatgaa aacaaataga tgagactaaa aatagttcaa taggttgtaa 143640
cttccatctc atccaaacag caatgaatat tttgaggctg aggcgctgag gggtaaaatt 143700
gcagcctgga ctacttgcta atgtagacct acagcactgt cattcttact gcacagacac 143760
tgctttctgc ataggaggta gaataatgaa ttcatttatt attaacaaag atttattaag 143820
tgactgcatg gtgctaacca ctagatgggg agggatgttt tgaactgtcc attgtttgac 143880
tataacaagg aacgctttga acgaggttac tatcataggc agaatttgtt taacatgaag 143940
cctatgagac ataagccaca ggtcctctca cgtgcaggaa ctccttgaa ggccctatac 144000 ttaattttat atgcatagtt tggatttgga ttctttttt tttaagagtt ccccaaatta 144060
cttaagcttc aggctccaca aaacctggat ctacccctgg tagcagctat gaatctttga 144120
ctatgaaatt aagtgtacaa gaaatatgac tttactttt ctgtgattga gtttattttc 144180
tatttgagca cgcattccac tgagtgaaag aaataatatc attgaattca gagattttgc 144240
tgggttctaa gtggagttta cagaatgcca tgatattagg aattaaggag tgtgttgccc 144300
tacatcatct tttgtccgtg ctcactgtct ctgaggcact gatgttccta tgtgacctag 144360
aggggcatgg tccaggtaga tggagtctgt ccttgttctc actgtgagct ctcgcttgct 144420 gaccttctt cagtttcttc catgcccctg aggggtaaaa agattcaaat ctgaagctat 144480
atcaagccat ctgtgcatag acattccaag caaccatgtt cactctactg ctcccatgtc 144540
atgcaaggca caggaagctt cactatggca tgagtatttc ctgggctttg ccttggaatt 144600
gaggcacggg cctcctttgt tctaaaattc cccaaatcta cttgaggata gaaccaggat 144660
ttggttgcaa ggcagaactt ttcttagagg acctggtatc taaaccctct tgttaccccc 144720
atttatggac cccatttatg gggtgaggag agtgactgct tctaatccat cataattttt 144780
gtctatggct actgttttg catagacact atgttttgag tccttaggct ttggcttttg 144840
gcgcttaatg gccaatattc acatggctca aaattttcaa atgatccata tctgacttga 144900
gtttcaaaag tcagttttg aaacttaaat gatcagaatt gatttgttct gctctggttc 144960
tgatgtggcc tctccttcca gaggtactgg aggtagaata tccaaggtgg aaagcccacg 145020
actacaagga attggttagt aattcataat gttagctgtc cacatctatt cagtaatggc 145080
atttcagtgg ctgcacaact gaccatggtg aaagtgtctg cacaagccac ttttcttcc 145140 tgtcagaaaa tgttctcacc cactgaattg aatgactgtc tgctcatatg ctgtgaatga 145200
```

```
gtgcccagtc ttaagattaa atcacacgtt cttggctatg catatttggg catgctgtgg   145260
ggagttataa taggctgtct tagagtcaca ttaagcagct agacagacaa tgagttggaa   145320
agttacattt tctaaatttg attggtacat tccatttgtc acatttgaca ttagaagttc   145380
tggattcacc ctctatggtg agcttcacta atggagaatg taatttgcaa tgctcaaaca   145440
caagtcctaa acagaaaaca ttgtatgtta cattccagtg ctaccaaaat agtggttttg   145500
aaagtcctta ttttctaata ctactatgtg taattttgag tcatttagat agcaacagtt   145560
aaatgtttta tagattgttt ggaagtatta aaatgtgaag gattttgtt atatagtgtc     145620
tttcctatct tgcttaataa aatataagtt tagaattgtg tatagaatta acatgcaaaa   145680
atatcaagtc tcaactttat acagttaatc tacatttgtg tataccttc aattatttca     145740
agagagggat actattctta tgcaggataa atacaataag atattttaaa tgaattttaa   145800
ctacatctct ggcagtttca tctcaatagt agttgtaatt ttatctccca gaccttatta   145860
tagactagca gctctctatg aaaattagtg acagtgtgag tgtattttaa ttcaaagtta   145920
atcaagaatg actgagtcaa gagttagcta cccctgaaag taactcataa ttcagaattt   145980
aaaatattac atgtggaaca atcatgacta tatgcctttt actttctcta tcattattta   146040
ggttgtgggc tttgggtcct tttcacatcc gttaacagtg ggcttgactt caaggattaa  146100
ttttcttgaa tcttgaataa ttgctgaaga caatttgaag atattttcaa gatgaaggaa  146160
actgaagcac agaatcacta gagtgaaaaa agaacttcac aaacagtgca ggcttgatca   146220
atggcatggg aaaacaggca atacagttag aattgctaag atggaatttt aacgttcaat   146280
taaggatcta tctctaaact cctctgcttt atccaccaat cattccatat taagatgaa   146340
gaattgttcc catttcacct tttgataagg aaaaatagaa ataacagaag caaatacact  146400
tttgcccaca ttttttttcca aaagaataa ttttttgaagt ctaaacgttt ggtgtaaata  146460
agatgatgtg ttaatattgt aaaggaaagc tagttaagtt tttgactgaa taaagccagc   146520
atcaataatt actagtaaga ctaaaaataa gagcagtaaa attgtgtcta atcagctact   146580
aatatctggg aaggattgag ccacaggatc aaagatggta tcttttaaaa atagaagttg   146640
agtgaattcg gtcttcaaat tctttctttt tattcattta tatttattta ctcattagta   146700
tattcattcc tttattcatg tattgttcaa atatatattg ggtacttatt atatgccaag    146760
ttgttttttaa aatcacattc caaattcccg taagtcataa ttattcagag atgtatgttt   146820
ttttttaaaaa aaattgaaca cctttaaaaa ttatcaagtc cttttatttc tgtatgcatt  146880
aaagataaac tttactaaat gttacatgaa tagatttata aagcagataa atatttaatt   146940
tcaaatataa cccttatatg caattatatt ttccttagca ctaaaaatga atatttaagt  147000
aatttatatt aaaagtgtaa ttatttaact gcagatgtat gccaatgact taaattgttt  147060
aaagattata gcaaagttgt ttaaaattgt ctaatcatga agagttcact taaccacctg   147120
gttgacacat aaaattatag ttagttacta aggtagttcg agagaaagag aagaatcttc   147180
agtagtggtt ttgaggtgtg gtacatttta ttataatata ccggttatac agcattgtgc  147240
agtgctgctc atagtagaaa taaattttct ctttgatgtc atctattccc ttgtgtggct   147300
tacataactg agaattaggt gatcacaaaa ataaacaggc ctatacagag cccatttata   147360
taagtcctgg ttatttctct tcagttaaac ttttaattat atccaattat ttcctgttag   147420
ttcattgaaa agcccgacaa ataaccaagt gacaaatagc aagtgttgca ttttacaagt   147480
tatttttag gaagcatcaa actaattgtg aaattgtctg ccattcttaa aaacaaaaat    147540
gttgttattt ttatttcaga tgcgatctgt gagccgagtc tttaagttca ttgacatgcc   147600
```

```
aacagaaggt aaacctacca agtcaaccaa accatacaag aatggccaac tctcgaaagt 147660
tatgattatt gagaattcac acgtgaagaa agatgacatc tggccctcag ggggccaaat 147720
gactgtcaaa gatctcacag caaaatacac agaaggtgga aatgccatat tagagaacat 147780
ttccttctca ataagtcctg gccagagggt gagatttgaa cactgcttgc tttgttagac 147840
tgtgttcagt aagtgaatcc cagtagcctg aagcaatgtg ttagcagaat ctatttgtaa 147900
cattattatt gtacagtaga atcaatatta aacacacatg ttttattata tggagtcatt 147960
atttttaata tgaaatttaa tttgcagagt cctgaaccta tataatgggt ttattttaaa 148020
tgtgattgta cttgcagaat atctaattaa ttgctaggtt aataactaaa gaagccatta 148080
aataaatcaa aattgtaaca tgttttagat ttcccatctt gaaaatgtct tccaaaaata 148140
tcttattgct gactccatct attgtcttaa attttatcta agttccattc tgccaaacaa 148200
gtgatacttt ttttctagct ttttcagtt tgtttgtttt gttttctttt gaagttttaa 148260
ttcagacata gattatttttt tcccagttat ttactatatt tattaagcat gagtaattga 148320
cattattttg aaatccttct tatggatccc agcactgggc tgaacacata gaaggaactt 148380
aatatatact gatttctgga attgattctt ggagacaggg atggtcatta tccatatact 148440
tcaggctcca taaacatatt tcttaattgc cttcaaatcc ctattctgga ctgctctata 148500
aatctagaca gagtattat atattttgat tgatattttt tagataaaat aaaagggagc 148560
tgaaaactga attgcaaact gaattttaaa actttatctc tctgtggtta attgcaaaca 148620
cagatacaaa aatatagaga gagatacagt tagtaaagat gttaggtcac cgttactaac 148680
actgacatag aaacagtttt gctcatgagt ttcagaatat atgagtttga ttttgcccat 148740 ggatttaga atatttgata aacatttaat gcattgtaca aattctgtga aaacatatat 148800
ataggatgtg cgaaaagtcc ctgtgtatca tgtgaaatgg cttaaaacag aacaccatag 148860
gtattcatat cagtgaatac cataggtagc tgaaagtgtt ttttcctggg gtcgccaaga 148920
tgaatgccaa aagtgatatc attattataa acaatagcca gaataggttg gtataaacct 148980
ggtagaaagc cttgataaat tgactttctc tcctcctgac atcctgccac cccttttgctt 149040 tgctgatgct catttgtcca ctaaattaaa ctcaagcaag ccctagtaaa gtaatagaat 149100
ttgtggagtc ctcattagta taggaagttt ccctgatgtg agattagtaa ttagagatgt 149160
agcaaaatga gaaagaagta atatgcttag atatttcatt ttctctgaac ctgtatatac 149220
aaaataggcc atgcgtgttc agtaactatt cactgcaagg cactctctag gtactttggg 149280
ggaattggaa attactcaca taaggctatg gattgtgcca tttgtcaaaa gacaaaatga 149340
caacaaattt agtttaaaga cctcagtcag ctttattttc tattctagat ttggacagtc 149400
cttcatttca caaattggag taagtgttcc aataagttga gcaaaggagc ttggctttat 149460
agacccaaaa aaagggccaa aggaagcaga aacaaagaac aataagagaa ttggtcattt 149520
caaagttact tttcttgaaa ggtggggaca aggagacaga ataatagaaa agtcactgat 149580
tggttaacat tggattaaga attaaaacag aggaaacttt aagattgaag tttgaaactg 149640
acttgtttgg gaaatcaggc tgtcttcttt cttgatttct tagaaggccg gataacaact 149700
gagttttgct ttggtgaaca tgggtgactc cattttttact tttagtctgg tctgttgagg 149760
cctcgtgaga gagcttaatc taaaacaatg acttcctata attttttgttt gacacatcca 149820 aagagggact ctaatatttta ttgagagctt atcatatctt aagtactgtt taaacacttt 149880
tatttgctat tacatttgat cttattataa ctctaaaggc agaaatgatt gcttttattt 149940
```

```
tccacaatgg aggaaactga ggttcaatta agtgagtaag gaagcaggga tcttaaaccc    150000
agataccatt gctcctcttt aaaggtggaa gaacagaaaa catggggcag gggaagagag    150060
aaagtttctg tcccaggaca tgataatcta aaagggaaaa cgtaagatcc actgaaacct    150120
gaggcagatt tattgtggca ataacaaagc ttaagtttca cagaccttca tttgcctgag    150180
ccaactttga aggccatgta tctaattttg tttttataat tctataatct ttattcttga    150240
aaagagccct ccctccaaat ttacaagctt tgggccccca aaatccttga aatgcccttg    150300
aataagagat atccaggtaa atgctatggg aattcagagg aggaagcagt tagtatcagt    150360
tggcggagag ttaggctatt aagagaaggt tttatatagg aagtggcatt tagaatgaag    150420
ctttgagaac tgagctgtgt atttgaacaa gtaaggtgg tgttgcagaa ttttgctcct    150480
tagttctatt aaaaacccgg gttcttgtca catgatccgg aaaatttagg cacacagata    150540
cattgaagca tgagtagagc aggattttat tgggcaaaaa ggaaaaaaag aaaactcagc    150600
aaatcgagat ggagtcttgc tcacagattg aatcccaggc caccacaaag gaactgaaga    150660
gatcgggctt ctcccctgca taaggtgcaa attccccatg gctccaccca cttcccctta    150720
gtgtgcatgt ggggctccag tccacggtgg gcatgcccag acaagccttg ggcaggttcc    150780
ctcatctgtg caaaagcatc tgatgtaaac acttgagggg tggttcggag attctctggg    150840
acccttttat tttcttatct gcctaggcat ttggctgtct cagtgggtgg gaaagggtgc    150900
tccaggcaaa gggcataaca tgaggcaaag ggcatgcaca gaaaacagtg actggttcag    150960
tcaggttggg ggatgccaaa ggaagtaatg ggagacaaga ttggagcaag atagataaga    151020
gattgtggat ttttttcttt ttttatctat ataaatacag agacagggtc tcactatgtt    151080
gcccaggctg gtctcaaact cctggcctca agtgatcctc ccacctcatc ctcccaaagt    151140
gctaggatta caggcatgag gcactgtgcc caacctccaa ttttggattt tgagagctaa    151200
agcaatatag tcgaaaactc agataatcca ggtagatttt gctattaggt gctatttggt    151260
tcctggtaca gagctaaaac ccttggaatt tcctaagtga taagagctac aggagcatct    151320
tttgttatat gtttcccccc ctagttcctg aaatagctct agagaaatac aggtgaataa    151380
catcctttgt tattcatatc aagccccctat caaccatacc ccagtttcta tttatgaagt    151440
ggcttttggg aagtccctaa agacaggagt ggggaaaggc tggttgtcag ggggatgggt    151500
tgaaactttc atcttccccc cttgacctcc agggagggat gagtggctga aaattgtgta    151560
aaatcaacaa tggccagtga tttaatcaac catgcctatg taatgaagcc acccgataag    151620
ccttaactgg aactttttgg agagcctcca ggctggtgaa gacattgagg tgctcagaag    151680
gtggtattcc agagagagca cagaatctct gttccccttc ccacattcat tttgctatgc    151740
atctctccca tctggctgtt cttgagaggt atccgtttat aataaactgg taacctagta    151800
agtaaactgt taccctgagt tctgtgagcc attctagcaa attatcaaac ctaaagagtt    151860
catggatacg tgcaatttac agatgcacag tcagaagcac agatgacaat ctgggcttgc    151920
cattggcatt tgaagtgtgt tgggaggcag tcttacagga atgagcccctt atcctgtggg    151980 gtctatgcta ataacagaca gttgtcagca ttgcttggtg tcgaaaaccc acattgttgg    152040
tgtcagaagt attgtcagta ggatagggaa aacagtttgt tttctttttt tagtggtctt    152100
tggtcatctt taagagcagg gcttctcaaa gtgtggtcct tgaaccagca tcacctgtac    152160
cacgtaagaa cttatgagaa atgttcattc ttgggcccca acaaagaatt aaaaattctg    152220
agggtgtgaa cggggtctga gtttcagcac aacttcccga ccatgctgat gcattcttgc    152280
ccaagcatga aagccctccc ttgtttaaga aggccattag ggccgggtgt ggtggctcat    152340
```

```
gcttgtaatc gagcactttg agaggacata gtgggaggat cacttgagcc ctggagttct 152400
agacaagcct gggcaacatg gcaaaatgct gtctccacaa aaatcacaaa aattaggtgg 152460
gcgtgtgttg tgtgcctata ggcccagcta cttaggagac tgaggcagga ggatcgcttg 152520
agcccaggag attaaggctg cagcgagctg tgatggcacc actacagcct ggatgacaga 152580
gtgagacact gtctcaaaaa aaaaaagaa aagaaaaag aaaaagaaa ggaaatgaa 152640 aaagaacgcc attaggtata aaggagcaat ggtaaagac cagttgcaaa aggttaggga 152700
atgggtggtt actgaaataa gaagctatgt agaacactag tgttggtggc aggaagtaga 152760
aagcaagagc actgctctgt gggggatggt catagcaaat gcaatatgga ggcatttgcc 152820
tctgcactga ggagaaaact atcttttcca agataggagg aaaggagata agtggaatta 152880
aagagaacct ttgagcacag agttgggaaa ctgaaggtat ttgtgttgtg ctccctcaat 152940
cttttaattc aactataagc taaacccatg aaacttgagt agtttcagtt atctgacttt 153000
tttcttctct tttgatacag tgttggctat tctgggtctt ttgcctctct ttatgtactt 153060
aagaatcagt ttgccaatgt atgcaaaata actggctggg attttgattg tgattggctt 153120
gaatctatag atggagttgg gaaggactga catcttgaca atgttgaagc ttcctattca 153180
tcattatgaa atatttctcc atttgtttga ttctttgatt tcttttatca gaatttagtt 153240
ttcctcatat agtcttttaa aatattttgt tatattttgt tcaagtattt tgttttgag 153300 gaatgccaat gtaaatggta ttgtgatttt aatttcaaat tccaattttt cattgctgtt 153360 ataaggaaa atgattttttt ttgcatgtta gccttatatc tttcaacttt gctataatca 153420
attattgata gtttcaagga ttttttggtc aattattttg aatcttctac atagattatc 153480
atcatctgaa cttagtttta tttcttcctt cccaatctgt ataccttttat ctcctttct 153540 tatttcatta gctaggactt ccagtatgat gttgaaagta gtggtgagag gggatatctt 153600
ggtcttgttc ttgatcttag tgggaaaaact tcaagtttct tatcattaag tatgatttta 153660
gctggagggt ttttgtagaa gtttttttt tttaagttga agaagtctcc ttctatttt 153720 agtttgctga tttttaaaaa gaatcaggaa tgggtgttaa attttgtgaa atgcttttct 153780
gcaactattg atttgagcac tttatttttc tctttggct tgttgatgtg aagtacatta 153840
attgattttt gaatgctgaa tcaacctttt gtacctgaga ttaatcccgt ttggttgtgg 153900
tatataatta tttgtataca tgttgagttc gatttgctaa tacttttga gaattttgc 153960 attggtgttc atgaaaaaat attggtgtgt agtttttgt gacatcttta tctgcttatg 154020
gttttaaggt aatgctggcc tcatagcatg agttagggag tatttcctct acttttacat 154080
ttgagaagag attgcagaga attagtaaaa ttcctacttt aaatattttg tggaattcac 154140
cagtgaaccc atctggacct ggtgcttcct gttttggaag gtcattaatt attttaaaat 154200
agatataggc ctattcagat tacctattt ttctcatgcg agtttagca gattgtcttt 154260 caaggaattg gtctatttca tttaggttat caaatatgtc aacgtagagt tattcatagt 154320
attcttttat tatccttta atgtgcaagg gatctgtagt gatgtccct ttttgtttt 154380 attgatatta gcaatttgtg tcacatcttt tattttgctt tgttagccag gctagagata 154440
tctctatttt tgatgttttt gatgaaccaa ctttttgttt tattgatttt ctctgttgat 154500
ttcgtgattt caatttcatg attttttaaat tatgcttaca tttgatttaa tttgatcttc 154560
ttttgctagt tatccaaggt ggaagcttat attgttaaga tccttttgca ttcttatgca 154620
ttcaatgatg taaatttccc tctaagcact gcttttctg catctcacaa atattcatga 154680
```

```
gttgtatttt catgttcatt tagtttgaaa tattttttaaa tttctcttga tatttctctt   154740
ttgacccatg tgttacttag aagtgtgttg tttaatcacc attttttaaaa attttctagc   154800
tatctttctg ttattgattt ctagtttaat tccattgtgg tctgagagca tatattgtat   154860
aattttaatt tttataaaat ttgttaaggt gtgattatg gcccagaatg tggtctatct    154920
tggtgaatgt tccatgtaag ctttggaaga ctgtgtattc tgctatattt gaatgaggta   154980
gtctatagac atcaattatg tccagttgat tgatggtgct gttgaattca actatgtcct   155040
tactgatttt ccacctgcta gatctgtcca ttctttgcag agggacactg aagtctccaa   155100
ctctagtagt gaatattcta tttcttgtta cagtttatc aacttctgct tcatgtcttt    155160
tgatgctttg ttgctagaaa catacacatg aagaattggt atgtcttttg gagcatgacc   155220
catttatcct catataatgc ccctcattat ttcctcgccc tgatgtctgt tctctctgaa   155280
agaaatatag cctctccagg tctcttttgg ttggtgttaa aatgacttaa ctttctttat   155340
cccccttact tttagtttat atgtggtttt aaatttaaag tgggtttctt gtagacagca   155400
aatagttcag agttgttttt cgatccactt tgacaatctt tgtcttttaa ttggtatatt   155460
tggactattg atattttaag tgattattga tatagttaga taaacatcta ctatatttat   155520
tactgttttc tgtctgttac actacttgtt ctttgtttat attttattg tctactcttt    155580
ttctttccat tgtggtttta atcgagcatt ttatatgttt ccattttctt ttcttagcat   155640
agtaattctt ctttaaaaaa acattttta gtggttgccc ctagagtttg caatatacat    155700
ttacaactaa tctaagtcca ttttcaaata atactaaata atttcatgtg tagtgcaagt   155760
acctttaat aataaaacac tcccagttcc accttccagt ctcttgtatt atagctataa    155820
tttagttcac ttacatatat gggtatacct aagtatatac attatcatat ttatgattga   155880
atatattgat gaaattattt tgaaaaaact gttatcgtta aatcaattaa gagtaagaaa   155940
aatagttcta atttattat aaaatgaaat accttcattt attcattctc taatacactt    156000
tctttcttta tgtagatcca agtttctgac ctgtataatt ttccttttct ctcttcagct   156060
tctttgaaca tttcttacca gccagaccta ctgacaacaa ttttccccaa tttttgtttg   156120
tctgatagag actttatttc ttcttgactt ttgaagaata attccacagg gcacagaact   156180
ctagattggt gatttcttcc cctcaaaccc ttaaatattt cattccactg ccttcttgct   156240
tgcattgttt ctgagaagtt agatataatt cttatctttg cctttctata ggtaagatgt   156300
tttttcctct ggcttctatc aagatttttt ctttatgaac atgatatgcc tttcttttg    156360
aacatgatat gcctttcttt ttgaacatga tatgcctttg tgtcggattt tttttggcat   156420
tattctgctt ggttttctct gagtttcttg gatatgtggt atggtatctg acactaattt   156480
ggaaaaattc tcagtcatta ttgcttcaaa tatttcttct gttctttttt ttccttat    156540
ctccttctgg tattcccatt acatgtatgt tacagttttt gtagtcatcc cgctgttttg   156600
gatattctgt tttttcagt tttttttttcc ttcgcatttc agtgttggaa gtttctattg   156660
acatattctc aacctcagag attctttctt cagctgtgtt cagtctacca atgagtccat   156720
caaaggcatt ttacattttt attacagaat ttttgaccta tagaatttct tttgattcca   156780
tctttgaatc tccatttctc ttctgctttt catctgttct tgcatgttgc ctactttttc   156840
catgaaaacc tttagctttt ttttttttc tttttgaggt ggagtctcac tgttgcccag    156900
gctggagtgc agtggtgtga tcttggctca ctgcaacctc tgcctcctgg gttcaagtga   156960
ttctcctcct cagcctccca agtagctggg attacaggtg cctgccacca tgcctgagta   157020
attttttgtat tttagtaga gatggggttt tatcatgttg gccaggcggg tcttgaactc    157080
```

```
ctaacctcaa gtgatctgcc caccttagcc tcccaaattg ctgggattat aggtgtgagc   157140
caccatgccc tgcctttagc atgttaatca tagttgtttt aaattcctga tctgttaatt   157200
ccaacatccc tgtcatatct gactgtggtt ctgatgcttg ctctgtgttt tcaaatggtg   157260
tttttttttt tttgccttt agtaagcctt gtaattttt attgaaaggt ggacatgatg    157320
tgctgggtaa aaggaactgt agtaaatagg cctttagtaa tgtactggta ggtgtagcag   157380
agggtgaggg aagtattctg tagtcctatg attaggtttt agtcttttag tgagcctgtg   157440
cgcctgcagc ttggaagcac ttgtgaagtg ttttttcacc ccttttggtg ggacatagtg   157500
actagtgtga gcgggagttg agtatttccc ttccctagg tcagttaggc tctgaaaaaa    157560
ccctgatagg ttaggcatgg taaaatagtc tcttttgagg gcaggcattg ttataagaat   157620
agaatgctct ggggccaggt gcggtggctc acgcctgtaa tccccgcact tgggaggct    157680 aaggcaggtg gatcacctga ggtcaggagt tcgagaccag cctggccaac atggtgaaac   157740
cccgtctcta ctaaaaatac aaaaatcagc caggtgtggt ggcacacacc tataatccca   157800
gctactcagg aggctgaggc aggagaactg cttgaaccca gtaagtggag gttacagtga   157860
cccaagattg tgccactgca gtctagtctg ggtgacagag caagactccg tctcaaaaaa   157920 aaagaatgc tctggcatat ttgaaaatgg ttacttttcc ctttttttct ctgatcttca    157980
ctgtgagaac ctggtaagca tcctataggc aaaattcata aaagtataga agtcggccag   158040
tgacttggac ccacttggaa ttttcttgct ctcacatcat gcacactgaa tctccagcaa   158100 ttttcactt acagtttagg ttttcctacc ctactactgg ttctctcaga ggtttctgct    158160
tattggtttc tgttttgtaa gttgtgattc tctgtaccta actgcctgtc tcccattttg   158220
gggggcagtg gtttgccctg tgacctcact tctctgacag atctaagaaa agttgtttat   158280
ttttcagtgt gctctgcttt ttacttgtta cgatgaagcc aaccactttc agaatttcta   158340
caaaccagat cagaatctgg aagtcctgtt ttttatttt ttttatccct tgtttagca     158400 tgttacctat cttaacacat tttaaataag tgaatgcata gcttatatct acttctaggt   158460
tatatgcttc cttagaatag gaattgattc ttaaaatgtc gttctgctca cgcctgtaat   158520
tccagcactt tgggaggcca aggcaggcgg atcactggg gtcaggagtt caagaccagc    158580
ctggtcaaca tggtaaaacc ctgtgcctgc aaaaaataca aaaattagct gggcatggtg   158640
gtggccatct gtaatcccag ctactaggga agctaaggca tgagaatcac ttgaacctgg   158700
gaggtggagg ttgcagtgag ctgagatcgc gccactgcac tccagcctgg gtgacaagag   158760
caaaactcca tctcataaat aaataaataa ataaatatt aaataataaa aataaaaaaa    158820
taaaataaaa caaaaatttt attctgagca gtctctgaag aatataaatt ctactgcctt   158880
gcctttagaa cttataacag catctcgcaa actatcacaa gatgctccaa acatacttct   158940
tatgtgctga attaagaagt caactcaaat ttagtatact agtaatattt tggatatcc    159000 caaacactg ccagctcagc tttaggctgc ccttcttggg ggggaaaaaa gcagttgaaa    159060
tttaggactt aagtgggcat ctcgtttaat ttttaatgga tttctatgtt gttggttatg   159120
gtgaagaggt gaaagaaata aatattctgt gcagaaaaat tattcagtct tcatgtgaaa   159180
acactttgtc catagcaatt actttatgaa aaagatgtgg tattacttc tttgctctta    159240 actgagacct ttaatttaaa gaacctatac tttacaagtt tttattttca atgcatgaaa   159300
aatgtagcag ctatttcaca acctttactt ttaaaatcca tttttctttt taatctcaaa   159360 tagtttttc ttaaaacctt ttgactttt atctaaattg taatagccag agcaccttcc     159420
```

```
cacaactaga atatctcatc cttttttgtct tttcttttttc ctctcaaaat gcctactggg    159480
aacttaattt ggagtcagat tcttcatgat aaatctggac ttaatcaaaa ttcctcatat    159540
ggtatattgt atatatcaca gtactggata gtcctctgat taaatagata tttgatagta    159600
ctttaaggtc tatacttttg gatgaactta actgctttct ccatttgtag tctcttgaaa    159660
atacagaaat ttcagaaata atttataaga atatcaagga ttcaaatcat atcagcacaa    159720
acacctaaat acttgtttgc tttgttaaac acatatccca ttttctatct tgataaacat    159780
tggtgtaaag tagttgaatc attcagtggg tataagcagc atattctcaa tactatgttt    159840
cattaataat taatagagat atatgaacac ataaaagatt caattataat caccttgtgg    159900
atctaaattt cagttgactt gtcatcttga tttctggaga ccacaaggta atgaaaaata    159960
attacaagag tcttccatct gttgcagtat taaaatggcg agtaagcacac cctgaaagga    160020
aatgttctat tcatggtaca atgcaattac agctagcacc aaattcaaca ctgtttaact    160080
ttcaacatat tattttgatt tatcttgatc caacattctc agggaggagg tgcattgaag    160140
ttattagaaa acactgactt agatttaggg tatgtcttaa aagcttatt gcgggaagta    160200
ctctagcctt attcaacaga tcactgagaa gcctggaaaa acaaatcccg gaaactaatt    160260
attatgtgcc agttatataa acaagaagac tttgttgggt acaaaccagt gattccttgc    160320
ctttgaaaaa tgtgtcagat atcatgcatt accagcagtt caatgatata aggaaaccag    160380
agtaatagct aaaaccttta aagctaaacc aaagatttac aaattgcctc ttcatccagt    160440
ctttcccaac ctaaaaactg agttctctaa aaatttagt attttttttct gaagaaaagg    160500
gaacatggac attatctaa tcctcattag aaatctgact aatgataaca aggatttaga    160560
cctcaagcac ttcttaccaa aattcttgat atgaccttat agcaaattac tttcacctgt    160620
tgaactttcc tttctttttat tccctgtac ctcacctgca ctgggcatat tcaagttgct    160680
tatacaacac tttactattg tgttagaaaa atcatgacac atgatgaatg tgtttgtgca    160740
acatgagctg attcataaat gaaaatgtgc attgaaattc cacaatattt taaaattagg    160800
agtttatcta gcaattgaac aaaattgatt aaatccatta tttgttagat cagctaaatt    160860
acataagttc attcatctgc tcataaatcc atccattctt ccatctggct atcccttagt    160920
caattcaaat aaatatttat ggggcacttt gggtaagcca ggtgctaaga attcaatgca    160980
aaacaagata gactcccctg tccttgttga acttatattt ttggtacaaa caaaagcaat    161040
aatcaagaaa aaataaaaaa agtactgatt gtgattaata atatgaagaa attcaacaga    161100
gtattgtact taacatttga ttgatctgat tttctcagtt gtctgagaac aaacatttgt    161160
gaaaatctca ttgtagagtt cttacgatgg ataggggtc aactgtgtca ttattgctta    161220
tcagcttatc ccaaagacct agtttattac cagattgcaa atagtgttca ataaattatt    161280
cttattaagg gttgttatgt actctaaaac atttattgtg gtcccttcac tggttctggt    161340
ttacaaactt acttttctat gatgacatag tatagaaatt gagagtgaat atttagaagt    161400
tcatttttat tatatatttt tgaagtattg atatgtagtg aattagaaat ttaaaaagaa    161460
aacaaaactg tccttcacta cagattgaaa agcattatac taaaagacca tttgctcagt    161520
tatagtatat aaaggccaaa tgacttaaaa acaaattatg taaggagaag gaaacaacca    161580
tttattcagt gccactaact gtcagccagt tttttcagtg gtcagttaat gactgcagta    161640
gtgttctacc ttgctcaaag caccctcctc aagttctggc atctaagctg acatcagaac    161700
acagagttgg ggctctctgt gggtcacctc tagcacttga tctcctcatg cagtgcatgg    161760
tgctctcacg tctatgctat gttcttatgg tctttaggta acaagaataa ttttctttct    161820
```

-continued

```
tttccttact atacattttg ctttctgaaa ttcccttctc gccaatccag gtgaatgtca 161880
gaatgtgatt tgacaactgt ccaaagtact cattcactga ggagtggtaa ggccttcgcc 161940
caacctgcct tctctgggaa tatactgctg cctgaacata tcattgttta ttgccaggct 162000
tgaacttcac caaattaatt tattagggtc aacatctaaa tattagaact atttcagatt 162060
aatttttaag tcgtatccac tttgggtact agatcaaatt gcaggtctct gcttctggct 162120
tgagcctatg tttagagatg atgtgcatga agacactctt tgcttttcct ttatgcaaaa 162180
tgggcatttt caatcttttt gtcattagta aaggtcagtg ataaaggaag tctgcatcag 162240
gggtccaatt cctatggcc agtttctcta ttctgttcca aggttgtttg tctccatata 162300
tcaacattgg tcaggattga aagtgtgcaa caaggtttga atgaataagt gaaaatcttc 162360
cactggtgac aggataaaat attccaatgg ttttattga agtacaatac tgaattatgt 162420
ttatggcatg gtacctatat gtcacagaag tgatcccatc acttttacct tataggtggg 162480
cctcttggga agaactggat cagggaagag tactttgtta tcagcttttt tgagactact 162540
gaacactgaa ggagaaatcc agatcgatgg tgtgtcttgg gattcaataa ctttgcaaca 162600
gtggaggaaa gcctttggag tgataccaca ggtgagcaaa aggacttagc cagaaaaaag 162660
gcaactaaat tatatttttt actgctattt gatacttgta ctcaagaaat tcatattact 162720
ctgcaaaata tatttgttat gcattgctgt ctttttctc cagtgcagtt ttctcatagg 162780
cagaaaagat gtctctaaaa gtttggaatt ctcaaattct ggttattgaa atgttcatag 162840
ctttgatagt gttttcaga agaccaaatt tacagtggga gccttgggct tttgttttt 162900
aacagctctt ttttgttcct gcttcagtgg cctgacctcc aagttagcaa tcgccaggtt 162960
gagaaatgct ttgcgagaca taacagatgc tcctgaaata acaaacactt ggaatcatga 163020
ggtagtggaa ttgaaaatag aaagtgtagt gattgttttt tgttatttgg atgggatgaa 163080
caatgtcaga ttagtctgta actatttttt tttaatgtca ctctgatttg gtcacaaagg 163140
atctctagtc tcattgcctt agtatcattc tacgaattag aatgtgttac tgtgtaagag 163200
cacttcttgt atatgagaga aatagcaaca gttccagttt aaagtgatat aaatggaaac 163260
caagaaatgt cttactggg accaaatctg gacagcattt actgtatttt tgctggtatt 163320
ttctctagtc tttccgggta tattcacatt taatgatcac ttttctccct ttgtgctaat 163380
ggacactgaa tccattccac taccatagtt cttgctaata ctactctact ttttacacaa 163440
aattaaaatg ccaggagcac ctccaggtag actgactata aatctagact gaaaaaaaag 163500
cttgtatttc ttaacagatt accttgtgga acatttgctc ctttcaacta atgaggcact 163560
aaatattgta actgctcaac tggtgctttt aatttatttg tctagacttt gtcatgttgc 163620
cagaagcttt atcctggttg gagttttgaa aacagtattg tttcttcaga agaaaaaag 163680
ggattgtcag atgatctaaa aataaagaaa cactggaaat acaagtatcc caaggtgata 163740
gcattaggca agataaaaat gttgaaaagc gaaaagaac tggttgatag agaagtgttg 163800
ttattcagta gaacctaagt cttgtggtcc cattttaat gaaaaatggt gaatttttg 163860
gttttttattg ttcttgttca cacaaatctg cccattagaa taagccaagc cctaaaaatt 163920
aatttcagtt tcactgggaa tcctttagtt tatctactat gtagtagaga ggttttgttt 163980
tattgcatgt ttgacgtagg aacgtatata tgcaagacat ggaggaaaac caagtgggcc 164040
agagttttga aaattcttta tcttttcttt ctgccaaagt gagtctccca agtttgtctt 164100
tttttttca tttccactct tctatggttt ctagcattat ataaaccaaa caaaaaaaat 164160
```

```
acgttcagag attccttcag aaatgctgga tgatcttgat atcgatgctt ttcatatatg   164220
tgtttatgat gctggtttct ggggctggct ctcagtatca caaagatgtc tgtaaacaga   164280
atatgctatt tcttctttgt gacaaatttt gaacattatg tgaatgtcca agaaagagca   164340
aaagagggca aacttctcat acatttttga tgtcgaaacc aagagacgct tttatttcc    164400 taacttttct ttgaaagttc aaattaagta attttatcct gtcctaaagt ttaaaaagaa   164460 aaaaaaagg aagaaggaat taaaaatcca agaaaatta tgtttgtttg cttttctgtt     164520 ttttcttcc ttccaactcc gagactttgc aagggcatag ttctgaagat ctctgacact    164580
gagacattag agatctctgt atcaatggat catttgtttt cagacatatg aaacaggaac   164640
tttgaacaag aaatttcccc tcttttctc atagtgatcc tgagacatca gctgtggaat    164700
cacaacacgt cattagtttt ggcaggtcct tgcaggtgtt ttgttttgtt ttattaatgt   164760
tcttccctcc tgtagctaga cagcaatctt ggagaatctg ccagcttgga agactattgt   164820
gtaaatttca aggtggagcc tcctttaatt tgttctgtgt tacctgtgag ctgtgaggtc   164880
atgaagagga gacaatgagg ctaatcatga gagccccatt ggtttaggca attagaacaa   164940
caagatctaa aatggtttat tagccttgaa ttgtgttaag cacataattc ataaaaaaca   165000
gaaaaaatat ttttaaatgt atgtctaaat cttcagttac aagtttgaaa ggtgacaaac   165060
tattctgagg aaatgattag gcctattctt gcaacgagtc tttatgatct gaaagaatcc   165120
tatgtccaca cataactccc acctcaaaga tggggcatct tttgctctgg gagatatcaa   165180
atgcgaccaa aacaagtgtt tgtagatttg aatgatgatt cagcagtgta gcagttctca   165240 ctcatttat aataattaac aacttaataa ttaattatta aactcctaca tgcttaacat    165300
tataagtatg ataacttctg tggttacata aagatatac atagcacttg tccttgatct    165360
gtcacagtga ggtcccaatc caacctatga gcttcaaatg aaaagttcaa aattacactc   165420
attgtcataa gtcagagatc aaaggaagaa aggatttaac caaaatgata aattaaatat   165480
aggtgattaa atatagtcat ggttcaaggc atgggccagt tagggagtgt gatgtgggta   165540
attatgaaag gccagctccc aagccctgtt gttgctactc ccccacatca gtcatccttc   165600 cttttttct acttctactg cagtgccttc ctcatcttt cccttgcatc cctccattat     165660
atgagtcata caaattagac ttttcaaagc aacattaaca ttgtgtgaat ttggggtttt   165720
tgactaatcc caacattcca ccccacatt ccagtcccac atgggatttg gagccttgtt    165780
tataaacctg gcacttctaa tatatcttat cttagagtaa tccttgtatt tgtttaattt   165840
ccacttagca ttgtaaatac ttgcaggtat cctagttaag aaagcaaggt ttaaacacaa   165900
aatcatcacc aattaaagca ggctagataa agaatgtaat agaaatgcta gataaaacag   165960
attttttctt actaagtttt ctgtcccta tagagtgcat aacacaataa cttgcttgat    166020
aagaattcaa tgtacattgt tttgtgctga atcactaaat gcttgattc tgtaacaaga    166080 gattgtggtt ccatcagtat ctggatttta gtctgtgtaa tcttaggcaa gttatttgat   166140
ttctctgtgc ctctgttttc ttgtctgtaa aatgagtata atggtagtaa ctaattcatt   166200 gtgttttgt gaggattaaa tgagttaata actagtactc ctccctggca catagtaagt    166260
acaatatgct gtgctgtggt ggttgttatt attttttata gttccttgag caaaagaaat   166320
aatgtcccca tcttagtata atattggagg tatataccat agaagtgaac aaaagaatat   166380
agtttcacaa agaaagtgat aattaaggcg gttcataaag ggtcataaag cttgtagatt   166440
ttagaaatgt gggggcatga ggatgtggag agggtattcc aggatgccag acagggagat   166500
tatggatgag tactaagatg agaactagaa aaagctgagg ggcaaaaggt cagaggaggc   166560
```

```
cacaagttag ggagtattag gaaaaagaag ttaatacttg acaagtgcca acatggcttc 166620
acgaggaatg ggttgggcct ttttgagtga ggaagaggct ggtgaaaggg tggtggagga 166680
cactgctgct gctgatggca tggggtgtag gtggcaggag aggcagggac atgagctagg 166740
aaactctcca gctatgaagt gatgagtctg gagtaatata aggacagtag gggtggagtg 166800
ctgaacttaa gggaggagag aaaaataatt ggtatggaag taggtacaat gcaattttat 166860
tatttctgag cctaaaaatg tgaaattttt gattatttgg tcagaccagg gaagtatttt 166920
cttttatgct atctctgaaa atgtatacac taaaaagttg tagtataaaa aggttgtaaa 166980
gcattaagta attttagagg aaacaataat ttggatattt tacatgcaat catttatatg 167040
caaatatatg taaatattac aaaattattc tctatttgtt acaaaccttaa aatattttg 167100 actgaggaat attttattca tctaattata gctactttgt tctaactaat agatattctt 167160
gaaaacaaag caacactttt ttggagacag agtcttgcac tgtcacctag acttgagtgt 167220
gttaccttga actccagggc tccagtgatc ctcccacctc agtctcttgg gtaggtggat 167280
tacaggccca cactaccatg cccagctgta ttagtccatc ctttcattgc tataaagaaa 167340
taccggaaac tgggtaattt ataaagaaaa taaatgtaac tggctcacgg ttcttcaggc 167400
tgtacgggaa gcatagcagc atctgcttct gaggaggcct caggaagttt tcaatcatgg 167460
tggaaggcaa ataagaagca ggcatgttac acgacgaatc aggagcaaga caaagtgagg 167520
gaggaggtgc cacacacttt gaaatgagca gatctcatga gaacagcgcc aagaggatgg 167580
tgctataccg ttcatgagaa atccacccccc atgatccagt tacctcccac caggcccgc 167640 ctccaacact gggaattaca attcaacatg agatttgggc agagacacag atccaaacca 167700
taccaccagc taataccaaa aaaaaaaaaa aattttttttt ttaagacatg gtcttactat 167760
gttctacagg ctggtcttaa actcctggcc tcaagtgatc ctcccacctt ggcctcccaa 167820
agcactggga attcagacat gagtaacagt gcctggccaa tacttatttt taaacattct 167880
ctaccataaa cttaggatct tgatttgttc acattgaaca gattttttatt atacagattg 167940 aatttataag aaaatgttgc agacattgtc aaaaagggac gtccaaacca ctgtgatatt 168000
tataagcatt tgggccacat tttgatagaa ctatacacgg agtgtgtgtg tgtgtgtgtg 168060
tgtatatata tatacacaca cacattattt atatatatgt atatatgtat atatatatat 168120
gtatttatat atatatgtgt atatgtatgt acacattatt tacctaccta ctgtgtgagt 168180
gtgtgcatat atacacgcac acacacacac acaaatatat atatttccct tctgagacaa 168240
agccaaacag cactgtatgc ttaaagaaaa acagtcacac ttcccactta tgtaatttat 168300
attacatcca gtcaccacac cagccaaact gctttattgt ttttttgttt acatccaatg 168360
ctaaagcata atgcctgttg cagtgaaata tacatgagca accctgagaa ctcaatatag 168420
cctcacgtgt tgccactgag ttgagttgag gagtcaagct gtagcaaaaa ggtttgtcac 168480
cgggtgagta atggtgctct tatttttctc tgggtctcaa gaagtgctct ttatgacata 168540
tatggcatta ataaatatc agatatttgc acatcctaac tttcctattg gtgaagtttc 168600
ttaaaagaga gataaaggc cattgtgtga ttgatagttt caggtatatt tttgctgcac 168660
agtcagtccg agtgtaccac gtagggcaaa ccacgtaact tctcagggcc ttgactgttt 168720
catttgtaaa ccagagaaaa ggacttgggt gacctccaaa gacctttcaa atttggagat 168780
gagtttgtgg aaagttcaaa cagtttagaa aacagaacta agacacccac tggcaccccct 168840 ggaagcaaga gagtgccagg tactatttgt aatacaggaa tgaaataccc aattgtatga 168900
```

```
aattgaattc taactgaacc agtttgttca gttaaatttt tttttttcaat tagagtgctt 168960
acttcagtat ctaacactag acagtaaact gtagacaaaa gacctacaga atttctgaat 169020
ggtatcaaat tcaccacact taaaactttg ggatgtctaa tttcaaccaa cagctttctt 169080
tcttcataat gttgaatata tgtgtatcta ttttagctaa atttaatata tatcaatata 169140
ctttgataga tattttatat aaactattag actatagtat tatgagtaaa agacccacca 169200
tttcccaagc aattataaag aacgatcaaa attttaatgg gttgttagta ttatttcttt 169260
aaagattgtg atactgataa atatttggcc acattttaat agaattatac atgggatgtg 169320
tgtgtgtgtg tgtgtgtgtg tatatgtgtg tgtgtatata tatatggcag tagagatata 169380
tatatctaca cacatctaga tatatatata catgtatatc tatatataca cacatatatc 169440
tgtgtgtata tatacatatg tatatatacc tacatacata tgtacatata catacatgca 169500
tatatctgta catatatata tagtgtgtgt gtgtgtatat atatatatat atatatattt 169560
tttttttcct gagccaaaac aaaatactag gttgtaatag ctgttctttc agaaggaaga 169620
aaaacaacat gtgctgaact ctgagtttga tgttttttgta ttttacttcc tattttcata 169680
tcagtccatt tatttattca ggaagaattt attgagcata tattatgaac acagcttttg 169740
ctaaggacag ggtatgcagc agttatggcc tagtaggaga tatggatgtt aaaaacaaaa 169800
tgctcacaaa tgcacatata atcttaatac tcattgtaag ctatgaaagc agagtgtgag 169860
tattatgaga ccatatgttg ggagatttta tttggtattg aggatcagga aagataccc 169920
tgaggaagtg atatttaatt tgaaacctaa agaaagcagt tggccatggg aagaaggtag 169980
ggaatgagat tcccaagcaa taggaatcca atgtgtgaag aagctgaggg agtgaaagaa 170040
agctagtgtg gtggcaggaa gaaagagaag agaatggaga agggcactaa atgagtcaga 170100
gaagtaggag gggctaaacc atgtagggtc gtgtaggcca tcttaaaggc ctgagtgtag 170160
tggaaaacct ttgaaggttt gttaaaaggt caatgaaatg ttctaatttc tgttgtagtg 170220
aattgctttg attgctgaat gcgaatggat gggtagagat gcaagagtga aagggaagaa 170280
atcaattagg aggctcttgc cctgctccag ataggactga taattaattt tatttgggaa 170340
gatcagggag aaagataagt catgaatgac tcccaagttt ctggattgaa gaaatgaagg 170400
taccatacac tgagatggga aagcctaggg gtagagtagc tttgagaaga aaggtagcat 170460
ttccccattt cataaaacat ggaagaacaa agaggctgga ttcctgtttg tagacatacc 170520
ttccaggcca gaactgcatt actacaacat cttttgcaagc cacattgcct ttcataactc 170580
tgtgtcagtt tgatgccgt aacatctttg gccttccccc taccatcctc ccgcagtcct 170640
ccatgataat gccattattc cgtttcaaat tgtgtgcttc cattggatgt gtgagtctcc 170700
ttgaaagtta taatgaggct gtagcccata tgaaatgctt caactcaggt cctgcatagg 170760
aagaggaagc taatctctcc aggaactgag cctgtggcta gagggatgga taattgttta 170820
aataaagaat atgctgctga gtactgatgg gctctttatg tacccatttg gctgctgctg 170880
cccaaccttt aatctttcct gagctttaaa taggaaggaa aaaatggtcc acaaaggatt 170940
tgagccatt tgctgtggtg atgaggagca cgggtttaga gacaaacact cctgtgtttg 171000
aattccagct cctactatct cctagctaag tgaccttgga caagtcactt accttctcca 171060
acctgctgtt tcttcatgta cgtaatagga tttacctcat gaggttgaca tgaagattga 171120
aagaggtaac atatagaatg agcctgtccc aggacatggt tcatgataag tctgccataa 171180
atgggagcta tgtgtcccac cctttggag gagataactg ttctgtagca ggtaaatatat 171240
tgtttgatac ttggttaacc cttacaatta tcatttcctg ttcttctcaa taatgctaga 171300
```

```
aaccttttat ttaaagaacc acaatataaa atgaaaaata tataaaaaaa gcaaatggaa   171360
aaattctatt ggcaaggctt tttaacttta tatactaaat aaatccaatt gcttaaataa   171420
tgaactgact caagttctca gcactgcttc ttgtttaatt ctctttagtt tttcagaatt   171480
ctccaataat gaccttttgtc tactctcttc agtttattca gaaattactt ttatttacat   171540
agaagtttgg aagtggatac acaaacatat ccctcacata tcttatgatc ctatgagtca   171600
tatactcatc tcttatattc cctctgtaaa gcaatgtagg tacctttcag gaaggtgatt   171660
tttatgtagg ttgagaaata tcagcatgga ggtcctagct gacctctcta gagagtttct   171720
gagacatttg acaacaactt tttctttaag tcatcagtta tgccccgggg tatgaaattt   171780
ctaacatgat cctcagtaaa cttggctgcc ttgctgagga tactctccat ctgcctgaga   171840
gacacagaca ccattaattg ggaattgact tgacttgtgt ggttccttgt ggaccagatg   171900
gccactaaat attctcattt caaggcaatt ggtaaaaact acacttcaag aaatttcatt   171960
cttaattccc cttagtggat gttattaacc aaaggcaaaa gaaaaaaagg gtaaaaaaaa   172020
tattctaaat gttaatatca aaaatattat tttcaattca ccccaggcac agagaactaa   172080
gtattattat tgctattgca ccggcattcc ccaatgagac agtgattttc ttttaagaca   172140
tttttaaata atataggcag aattaagtag acggtgatct ggtaagtaga tgtttcaggg   172200
taacagctgt gcaatgctcc atgcagggaa ttagattgtc attttattcc ttaccaggaa   172260
catacattca gttaaacaat tatttgactt ctgctcttcc actgatttct aagttgaggc   172320
tctctcttgt gcctgtctga tcagataagt agagttgtgc cttggtttat agatgagata   172380
aatgtgtatt tgaataagca taagttaaag aaatttttaaa atcccttagg aagctaggct   172440
tatcagagaa atccaaggaa atacattaac aaactaggaa tttgttctaa caggttaatt   172500
ataactcata aacttattgg gttttttttac cttttaattt tatattacat ttgcttataa   172560
taaggaatat tgctaggaat aaaatttttt aatattctac aattaacaat tatctcaatt   172620
tctttattct aaagacattg ggattagaaa aatgttcaca agggactcca aatattgctg   172680
tagtatttgt ttcttaaaag aatgatacaa agcagacatg ataaaatatt aaaatttgag   172740
agaacttgat ggtaagtaca tgggtgtttc ttattttaaa ataattttc tacttgaaat   172800 attttacaat acaataaggg aaaaataaaa agttatttaa gttattcata ctttcttctt   172860
cttttctttt ttgctataga aagtatttat tttttctgga acatttagaa aaaacttgga   172920
tccctatgaa cagtggagtg atcaagaaat atggaaagtt gcagatgagg taaggctgct   172980
aactgaaatg attttgaaag gggtaactca taccaacaca aatggctgat atagctgaca   173040
tcattctaca cactttgtgt gcatgtatgt gtgtgcacaa ctttaaaatg gagtacccta   173100
acatacctgg agcaacaggt acttttgact ggacctaccc ctaactgaaa tgattttgaa   173160
agaggtaact cataccaaca caaatggttg atatggctaa gatcattcta cacactttgt   173220
gtgcatgtat ttctgtgcac aacttcaaaa tggagtaccc taaaatacct ggcgcgacaa   173280
gtacttttga ctgagcctac ttctctcctc actggtatgg ctccaaccat caggccctat   173340
cttggtccat ttaggctgct aaaataaaat accaaagact gagctgctta taagcaatct   173400
ttggaggctg agaagtcaaa gatcaaggtg ccagcaggtt tgctgtctcg tgagagcata   173460
cttcctggtt cattgatggt gctttcttgc tgtgtcctca cataatggaa agggcaagac   173520
ctctctggtg tctcttttac aatggcacta atcccatcat gagggctttg ttctcatgac   173580
ctaatcacct cccacatgtc ctacattcta atactatcac cttggggggtt aggattttaa   173640
```

```
catatgaatt tgaggaggtg gcgggggggga cacaaatatt tagaccatag catttcactc   173700
ctgacctcca aagttcatgt cttcttcaca tgcaaaatac attcattcca tcccaatagc   173760
ccccaaagtc ttaacttgtt ccagcatcaa cttacaaggc taaagtccaa ggtttcatct   173820
aaatatcagc taaatcagca caaacagcta aatcaggtag agtgggactt aaggtgtgat   173880
tcctctttag gcagattgct ctccaactat gaaattgtga aatcaaacct attatgtact   173940
ttcaaaataa aatggtgaaa caggcacagg ctagacagtc ccatttcaaa aaagagaaat   174000
agaaaagaaa aaaggagtga caggtctcta taagtctaaa actttaaggc ttgagaataa   174060
tttgctttgc tttgcctcca ggctcactgg ggtggtgtct tacctctgga cacactgggg   174120
tggaggctct atcctcatgg atttgagtgt ctcattcttt gtggcaggtc tgtgctccaa   174180
tcccacacct atggctccct gagtgtgcaa ttgcatgcct ggtggttcta ctggtctggg   174240
attgcatagg tggcccagcc ttcatagctc cactgggcat tgccctaatg tgggctctat   174300
gtggtgacct caccctggg cctctacctg ggccctgtga ctccctgggt tcttgaaatc   174360
taggtggagg cagccatccc cctacagttg tgctgagtgt agtgcatgag tgctgggtc   174420 tgctagagct atacctaggg tggtggagat gtatggcaat ggagtatggg gagctgatat   174480
ggtttgggtg tgtccccacc caaatcttgt cttgaattat aatttccata atctccatgt   174540
gttgagggag ggacctggtg agaggtgact ggatcatggg catggttttc ccatgctgtt   174600
catgtgatag tgagtgagtt ctcacgagat ccaatggttt cataaggcag ttttcctgc   174660 tcttgcaccc tctttcttgc ctgtcaccat gtaagacata actctttccc ttccgccatg   174720
attgtaagtt tcctgaggcc ttcccagcca tgtggaactg tgagtcaatt aaacctcttt   174780 tcttataaa ttacccagtc tctttacagc aatgtgaaaa tgtgctaata caggagcaaa   174840
gactgcagtg tgaggtggca atgtgaagtc tgcaatgtga ggtggcacgg ggcagttgta   174900
gcccctcctt tgaaatcttt cttccctacc ccaggcctct gcactctgaa ctatgatggg   174960
aaaggcagct tggaagatct ccaaatggct ttggagtcat tcttccattg tcttggacta   175020
taaattctgg cttctgttta ggtggctgac taatatcccc actgtctgaa tgcatagcac   175080
ctagtttctg ttgagatggc tagtccatag taatttactt atcaaatttg gccacaccct   175140
ttgtattctc tcctgagcag gctttctcat cttttcacaat atggataggc tgagaatttt   175200
ccaaattttg aagttctgct tccccttttga tcaataattc cattttaaag tcatttctca   175260
tcttgaattt tactatgagc agtcaagagt aactaagctg ctccttcaac tttgcttgga   175320
tatttcctca gtcaaacatt caatttcatt gctttcaagt tctgccttcc acaaaacact   175380
aggacacaaa cagctcagcc aagttctttg acatttttata agaaggatag cttttcctcc   175440
attgtccaat aacatgttcc tcatttccat ctgaaaaccc atcagattgg cctttaccgt   175500
ccatatttct gggaacattc tgctcatgac cacttaggta ttcggtaaga agatagtagc   175560
tttctctata gctctcctcc tctctggagc cctcaccaga atggccttta attgtccatt   175620
cacagcaatg taggctttt ctagcatgta cctgaaaact cttccagcct ctactcatta   175680
ccttgttcca aagctgcttc cacattgagt atttgttaca gcagtaccca gatcccagta   175740
ccaatattct gtcttagtcc attgggcta ctacacgatg tcttataaac aacagtaaaa   175800
tttatttttc acagttgtgg aggctgggaa gttcaaaatc tggtgccagc agattttgtg   175860
tctggtgaag gccttcttcc tcacagatgg ctgtgttctc actgtgttgt tacatggcag   175920
aagagtgggc aggctagctc tctgggatgt ctttttataag ggcagtaatc caaatcatgg   175980
gtttagggta gagccctcat gacctaaatc acctcccaaa ggccccacct cctaatacca   176040
```

```
gcatctttga agttaggatt tcaacatatg actttggcag ggggacagaa gctttcagtt 176100
tatagcaaac cctataggta gcactacttt gtcctttcct aatcaatttg cgtcaatgaa 176160
acatgaatta aagagacct  aggcgactcc actatactgg gattattccc agtataaatt 176220
atcatctctc cacaccttct catctactcc ctatctgagt tctgaagctc tccactacaa 176280
gaaggaggct ttggtttgac ttgatatact tctctgggaa acaggtttag cataaaacag 176340
tgatgctcat tctagaacac ctgcaaatga caatagtttt ctttcgaagt cgccaggaat 176400
cgtctgcctt tgggtatgtg gctgtgagca ctgccgggca aaatgccata tgacctagat 176460
gaggcatatg ccatcctttg aagccattag gacattatat aggaaatata ttaactaaaa 176520
tggaataaaa ttttctaaat aacaccttat gtttatccaa caggtggttc attatacttg 176580
agagcattat acagaggaat ttgatgggga ggagagctgg agaaattctc gaaattctgg 176640
gtttctttaa cagaatactc tagctataaa cttataattt taaaaaataa gcattatatt 176700
aaagaaaagg gaacataaat tattttgttt tattaaactt aagtccaaag gtctggattg 176760
tggcagaata ggatcagggg acctaaaatg ttgagcctca aaggtcttct tagagaacaa 176820
ctgtattcca ctattagcgc ttttggtcct tttagcccaa tttctgttta tcccaaatgt 176880
tcttcccttt tctgccttcc ttcacagtgg accctgccag gagctttgaa atgcctgtga 176940
gtgttaaaca cttacccatt gagtgcccaa ccttaacatg cccctaataa aatgtactta 177000
gattaaccgt tttcattatc aaagtttcct tattacccaa caaacacagg cgctttaaag 177060
aaaacattaa ctaaattgca agtgacacat tttaagatct ttgatatgac ttcagagaat 177120
gcactatagg aacacaatgc aatgggaggg aaacttggga gggaagacat tagcctttat 177180
aaaatctgca agtattgcca aatcaaaata aaatttacag gaaagcagga tcataaatat 177240
aatctaaaat cttagaacct gtggttatga ttttaaatac taatacaatg caaaattttt 177300
acctgtttag gttttattt  catcagttca tatttaggta tatacttta ctgttctcct 177360 ttttttataat ttaccattca caaagatgat gatgttagtc taactttaat gtcatgagtg 177420
ctttgagtag tagtgctaag ttttttgttga gtagtagtgt gcttttttga ttagtagtga 177480
taggtttttg atgagtaagc ctgctagcag catacaaaca aacaagcaag tatcagccta 177540
gagaagcaga aaaggcattt gggtttcaaa gtcacaaggc ctaggcttta gtctaataca 177600
gctgataata caatttgtcc aaacaggaca ttttgggtg  tgtcaaacac taaactggac 177660
aggacattat gacaaagtg  caaagcagga cttccggggg caaaccagga tgtatgtcat 177720
ctcactgagt cctctctttg tccttgccat gactagtatc tctagaggta aatgaacaga 177780
gtaatgacaa atagccagac acctgaatct tatcccaaca gcacctccta cataattccc 177840
cattatccca aatggaaatt aaaaatatat acagtgataa ttccaggcca agaaatgctt 177900
tatttctagc ttggacttgg cttccatgtc cagtgtagaa tcttatcctt gctgatctgg 177960
actgtatctc atgaagccat gacttgtacc tagttactag ctggaaggct tagaacaaaa 178020
gctggtccag agagcctcct ttttccttat ttcctgggtc cacacctta  ccatggcagt 178080 ctgcctatca tttgatggag gaatttaaag caagtccaag ggaagggaag agagtttcta 178140
aaatctagaa cttggatagt ttaatttacc tatcccaaaa cagcttaggc ccagacagct 178200
tctctccaag attggtgcca aactgaaatt accagctgtg tagaccaaag agaatttcaa 178260
aagaaactga atcccaagag aaaaaaaaaa gacttctggc attgtggccc aataaattgg 178320
taggattgtt gtgactttc  aagtttacat gtaaaatggg cccagcgcag tgcctggcaa 178380
```

```
atatgggtac taagtaaaag taactataat catgtttttt taatctggac ttcacttggt  178440
catcctttaa atggtgtctg acagaatcct agttcttgtc tcactttact tagtttccct  178500
gggaaatttc atgtgtcctt ttggctttaa ttaatatctc tattttgatg acctccatta  178560
tctgcctatt cccagagctt tccacctgat atctcagcac atgaaaagca ccttatgtca  178620
ataagtgagt tccttccctg ccccaccaca tacctgtcct gtgttcctaa ttccactgaa  178680
tggcatccca tcctccagtt tcccaaggcc aagacctggg actcatcttt cactctcaag  178740
ttcctccacg ggtacccaca tgtcacatcc tgtcaatgct gtccctgggg agtatctgaa  178800
atatattcac ttttcttcat ttccacctga caccactatt aacacttgca caaatttctg  178860
aggttcctgg ctcatttccc tcattgaccc ccaatagttc attctgctct ttgcagctct  178920
ggtgatcttt ccaaacccca catctgatca cttgtttctt cccttcatat ggctccttaa  178980
tgccttctgg actaagtcca cactgcttaa ggtggcttac caggtccttc atgattttgt  179040
ctttgtttgg ctttctacac tcactgccca acttcccctt acttcccatg attcagttat  179100
actgaatttc tttggttctc taaagcacat gtgcttctg ttctgcagag cttttttgt  179160 tcacttgcta ttctctacct gggaaactcc cccagccctt cactgcctcc ttctaccatc  179220
tttcaggcct ctccttacac atcacttctt tccaaaaatc tgccttgaca ctccaggtct  179280
cggtttccta ggtgtaccct ataactccac ccctttcata gcatttctca ctctggctgg  179340
agatttacct tttaacttgt ccatgtcccc cactggagtg gaagttcctg gaggtcaggg  179400
attatatcct attaattgtt gtatttccag tgcctagagt agtcttgcat acatggatgg  179460
tattcaataa atattggttg aatgaataag gagttctttc atttcatatg taatagatca  179520
tggaaatagc cttgtgattg atacacagca ggtattacca tcctcactt agaatgagga  179580 ctcagagcct tgagatgtct gagggccttg actgggacag ctggcagatg caggagcaga  179640
gctgcatcac ccctgtgggc tatctcaggg ttgtctgtaa tctaagtaca atgtctgttg  179700
attttggact gaaggctttt tgggtaattg tttgcttttt caatacttat aaaatagttt  179760
ccatccttac tcattgatag taaggttagt tattttagaa aacaagctaa atagcagaaa  179820
tagtggcctt ttaagttgaa aatttacccct gaaaaatcta cagagtagca aacagagtat  179880
caaaaggagt tgactgtatc tatttttata actgccactt atggattatt cagtaaaacc  179940
acaattcact tttatgattt ttttttcatgt ttctctgtca caagagcaaa ctcttgctcc  180000
ataataacat tccagaatac agcaatagca aaagtcaaca ttttgaatcc tttacaaact  180060
cttagacatt ttttttttt tagtttaaca tgttacaaaa caaatttct tcttttttca  180120 cagcagtttg ggaagtacat actatttatt agctcatcag catgaagctg gaaaattctt  180180
tttcctaaag ttctttatat ctacaaactg ttgatgtttt catttattta tttttaatgc  180240
tacgttgtaa tgaaaatcat tggaaaactt tagattctag taattttgaa gtcttcttag  180300
tttggacagg actgagctaa agtttgtact tttttttaatt tattgaaaaa tggtttctaa  180360
tgatagtatt aacaagatta tattgggggc aggacgcagt ggctcacact tgtaatccta  180420
gcactttggg aggccgaggc ggttggatca cctgaggtca ggagttcaag accagcctgg  180480
ccaacatgta gaaatcccct ctccactaaa atacaaaaat tagctgggca tggtggcagg  180540
cactgtaatc ccagctactt gggaggctga ggcaggagaa ttgtttgaac ctgggagtcg  180600
gaggttgcag tgagcccaga tcgcaccact gcactccagc ctgggcaata gagcaagatt  180660
ctgtctcaaa aaggaagaaa gaaagattat attggggata tatatgtgtg tgtgtgtgtg  180720
tgtgtgtata tacacacaca tatatatata catatataca tatatataca tatttaaagg  180780
```

```
ataaaggatt ctgctgccac agatcactaa atcagatgat ctctagcaat ttcctgtttg 180840 tttgttttt  gcccatagtg cttatctctt tgaacagtaa ttttccactt actatttttc 180900 tcccttttg  gaccataatt tcctttaagg cagagcctcc tgttactcat ctttgaatct 180960
ggggtctgtc agagtaccta gaatttaata aactctcatt aagagccagt tgaaagaata 181020
tatgactaag cagtcattta catccaaaag atccgtagga gaattcttat cagcacatgt 181080
gattggtaac aataactttg tacttttcaa aaacaattac taatctatct tgcttttccat 181140 tatctcacca aaacctatta gcatgtctgg cagaaaatag atacttaata aatttcttaa 181200
atgtttactg acttcaattt taagttttat taactatgtt gacttttctc taatgaagat 181260
gattctaaaa agcttttac  tatacttcac agtgaataaa acagtgagat aggaatattg 181320
caaaatgtcc cctgtgttgg tcagtcttag tgtcattcat tttaaaaatt ctgttctcta 181380
aatattgaca gttatatata aatttatgta attgtttact tctaataaag aatttcatct 181440
ggggaaaaac atactttgct cagctctttg ccacaagtgc aaagtctaag acagtcaaat 181500
agctttccta gtacggcctt aggaacttag tatatgactg gtgtgaatct agagggagca 181560
tactgcattc tgaccaaaat ctccaccctg ttactatggc catcactaac ttcgcagtat 181620
tgcagtactt cctgctagct tagttcccaa ggcaacttgt gaaggaaaat ttttacaaag 181680
ctgttgtcac acaaaggtag tgtttcagtt cctgagccca tgtccttgga gttgcccagg 181740
ctccaataat actaataatt actgtacatt aggtacttac catgtgccat attctgtggg 181800
agccgctttc cacaaattat ctctggtaat ccttgtaaca ccctttgac  atcaatatta 181860 ttattttctc catttttta  catatgagat aaatgagact taaaataatg tgcctgatat 181920
catcagcaaa tgagctgagg agggcagatt caaagctgat tgtgtttgac tctagagctg 181980
cagtcttaag ccagacctt  tcttgctggt taattttact gaaaaaaaa  aaaaaaaaa  182040 aaaaccctca aatactgctg attgatctaa agtactaaca tttctatcag tgttaggaa  182100 attttaattt tataatttga ttttgtgaga aatttatagc atcttgaata ctcacatgca 182160
aagtgatatg tcttagataa cattttacaa tggcagagct taagccagtg ctcagtcatt 182220
cattcatcct caagttttga ttcatttatc attcatcaaa actctgtttt gtttggccac 182280
ccacattcta ggagctcagt acatatttga taaatgaatg aattgttgag gttgacagtt 182340
acccaggact ggcattagga acacagagct gaagagcacg tttttaccct caagaagctt 182400
acagtctaac gagggaactt gcacaaatac tactatcact aggtgcctgg ttgaatggct 182460
taagagatga tcagggatat tcagaaggat atgtcaggct cagcaatggc atcacttgag 182520
agcatcaagg tgtttaggga actacaagat gtttggttct gctgggaata agagtgaagg 182580
gggctccatt tggatgcctc ataccaccagg tgagagatct tagattttat tccaccagga 182640
ggagaactac cataggatt  aaaacagaaa tgatatggtc aaacctacat cttaggaaga 182700
tccctggggt gtttgtatgg tggacttgca atttgactaa ttgagatttg taggatgatt 182760
cttaagagat gatgatgacc cagactggga tcactataat agagttggta aggaggagaa 182820
tgatttaaaa agtagttgga agaattctag ggatggagat aaacatttga aaattattaa 182880
cttataggtg gtcatcaata ccctgaaaat gactgggatc tcagaggaga gtctggagag 182940
ttggaaatga caaagactaa tattcaaggg ggcaggaaga gggagagttg ttcacacatg 183000
acaataggaa gaaatggcca tagagtgtgt ggtttctctc aagccaagga atagatgttt 183060
taagaaagga aaattcttgt ggtgggaagc agtagagatg acagatacac attaatttct 183120
```

```
tgagatttct agatgactaa atgggcagat gttgaatgat agctaaagga gaacccagaa 183180
acaagggagg gattttgttt ttgtttttta aaaagatag accatagcag cttcatagac 183240
tgaaacaata aaaagttga aggcacaaag aaagacacag gtcctctaac tccctgccca 183300 gtgccctta ttcatattct cagcacttgt atttctaagt tttatgtttg agtcttcggg 183360
gatacatcag agtagtcccc cttgtctaat aaatgtgttt acatttcctg ccataccaga 183420
aacccttctc aaactttaat gaatttctac aaggtgagat tactttaatg agaaaccaac 183480
caaggaaagg agtatcatct gcaatatact ttcaaatgtt ttttgcttgt ttgtttcttg 183540
tccagctaaa aaaaaaaaaa aaaaacaagc cattggtcct aacacaactt tcatattcta 183600
ccccaatatc aaagaggctt aaaatctcct ggtcgtgtga tgggcacaca gttaattttt 183660
tgtgaacaaa cacagtgtta tgggccattt ctgaatttat ctctgaaatc ataagattct 183720
ttctgagcca ttatctcatt ctatattaca gtcaggtgga gcccatctta cctcctcata 183780
ctaaattcta gacttctcaa gggcaggaga caatcatctg tatatctctt tggccttcat 183840
acactcagga gtacttgcca aaaataaaca tttaatgcac atttatttga ataattgata 183900
agatccaata cttcaataac tttgtcatat tttatagaa tgggtttcta tatctcattt 183960
gcattttcaa actttacttt tactgtctag ctttaaaaaa aaagcctttg actctaatac 184020
agccctcata ttctacccca atatctaaga ggctttatat ctcctagtgt tgtaccacta 184080
ttttaactcc agtattttt acttcatagt tttacctatt tgttacagtt agttttatg 184140 aattcaagag atgaatagca atttccata tgtaatttaa aaacccac agttgactat 184200 tttatgctat cttttgtcct cagtcatgac agagtagaag atgggaggta gcaccaagga 184260
tgatgtcata cctccatcct ttatgctaca ttctatcttc tgtctacata agatgtcata 184320
ctagagggca tatctgcaat gtatacatat tatcttttcc agcatgcatt cagttgtgtt 184380
ggaataattt atgtacacct ttataaacgc tgagcctcac aagagccatg tgccacgtat 184440
tgttttctta ctacttttg ggatacctgg cacgtaatag acactcattg aaagtttcct 184500
aatgaatgaa gtacaaagat aaaacaagtt atagactgat tcttttgagc tgtcaaggtt 184560
gtaaatagac ttttgctcaa tcaattcaaa tggtggcagg tagtgggggt agagggattg 184620
gtatgaaaaa cataagcttt cagaactcct gtgttatttt ttagaatgtc aactgcttga 184680 gtgttttaa ctctgtggta tctgaactat cttctctaac tgcaggttgg gctcagatct 184740
gtgatagaac agtttcctgg gaagcttgac tttgtccttg tggatggggg ctgtgtccta 184800
agccatggcc acaagcagtt gatgtgcttg gctagatctg ttctcagtaa ggcgaagatc 184860
ttgctgcttg atgaacccag tgctcatttg gatccagtgt gagtttcaga tgttctgtta 184920
cttaatagca cagtgggaac agaatcatta tgcctgcttc atggtgacac atatttctat 184980
taggctgtca tgtctgcgtg tgggggtctc ccccaagata tgaaataatt gcccagtgga 185040
aatgagcata aatgcatatt tccttgctaa gagtcttgtg ttttcttccg aagatagttt 185100
ttagtttcat acaaactctt cccccttgtc aacacatgat gaagctttta aatacatggg 185160
cctaatctga tccttatgat ttgcctttgt atcccatta taccataagc atgtttatag 185220
ccccaaataa agaagtactg gtgattctac ataatgaaaa atgtactcat ttattaaagt 185280
ttctttgaaa tatttgtcct gtttatttat ggatacttag agtctacccc atggttgaaa 185340
agctgattgt ggctaacgct atatcaacat tatgtgaaaa gaacttaaag aaataagtaa 185400
tttaaagaga taatagaaca atagacatat tatcaaggta aatacagatc attactgttc 185460
tgtgatatta tgtgtggtat tttctttctt ttctagaaca taccaaataa ttagaagaac 185520
```

```
tctaaaacaa gcatttgctg attgcacagt aattctctgt gaacacagga tagaagcaat  185580
gctggaatgc caacaatttt tggtgagtct ttataacttt acttaagatc tcattgccct  185640
tgtaattctt gataacaatc tcacatgtga tagttcctgc aaattgcaac aatgtacaag  185700
ttcttttcaa aaatatgtat catacagcca tccagcttta ctcaaaatag ctgcacaagt  185760
ttttcacttt gatctgagcc atgtggtgag gttgaaatat agtaaatcta aaatggcagc  185820
atattactaa gttatgttta taaataggat atatatactt tttgagccct ttatttgggg  185880
accaagtcat acaaaatact ctactgttta agattttaaa aaggtccct gtgattcttt  185940 caataactaa atgtcccatg gatgtggtct gggacaggcc tagttgtctt acagtctgat  186000
ttatggtatt aatgacaaag ttgagaggca catttcattt ttctagccat gatttgggtt  186060
caggtagtac ctttctcaac caccttctca ctgttcttaa aaaaactgtc acatggccag  186120
gcacagtggc ttacatctgt aatcccaata ctttgggagg ctgaggtggg gggattactt  186180
gaggccagga attcaagacc agcccaggca acatagtgag gccccatctg tctttattaa  186240
aacaaaacaa aactgtcaca gcttctttca agtgatgttt acaaattccc tatggtttag  186300
tcacaaggaa gttctgagga tgatgtatca cgtcatttct gttcaggctt ttgagcctcc  186360
tggaggtaaa tggtttcctt actgaaggct tgttattacc atgattatca ctaagcttga  186420
agtaacaaat taggggggca gactcacaac ctcttgccct gccatggaca agttcaagaa  186480
tctaagtaaa gtcctctatt gtctgatctt ggatttgctc aacctgaaca agccaaggag  186540
gtgtattaaa ctcaggcaca tcctgaccaa tttggaattc ttaagcttca gatcactgtg  186600
gaagaggctc aactctttat ggtgctgtag acttacgctc attttctagg taatttataa  186660
gggacctaat attttgtttt caaagcaact tcagttctac taaacctccc tgaagaatct  186720
tccagctgct gagtagaaaa tcacaactaa tttcacagat ggtagaacct ccttagagca  186780
aaaggacaca gcagttaaat gtgacatacc tgattgttca aaatgcaagg ctctggacat  186840
tgcattcttt gactttatt tccttgag cctgtgccag tttctgtccc tgctctggtc  186900
tgacctgcct tctgtcccag atctcactaa cagccatttc cctaggtcat agaagagaac  186960
aaagtgcggc agtacgattc catccagaaa ctgctgaacg agaggagcct cttccggcaa  187020
gccatcagcc cctccgacag ggtgaagctc tttccccacc ggaactcaag caagtgcaag  187080
tctaagcccc agattgctgc tctgaaagag gagacagaag aagaggtgca agatacaagg  187140
ctttagagag cagcataaat gttgacatgg gacatttgct catggaattg gagctcgtgg  187200
gacagtcacc tcatggaatt ggagctcgtg gaacagttac ctctgcctca gaaaacaagg  187260
atgaattaag ttttttttta aaaagaaac atttggtaag gggaattgag gacactgata  187320
tgggtcttga taaatggctt cctggcaata gtcaaattgt gtgaaaggta cttcaaatcc  187380
ttgaagattt accacttgtg ttttgcaagc cagatttttcc tgaaaaccct gccatgtgc  187440 tagtaattgg aaaggcagct ctaaatgtca atcagcctag ttgatcagct tatttgtctag  187500 tgaaactcgt taatttgtag tgttggagaa gaactgaaat catacttctt agggttatga  187560
ttaagtaatg ataactggaa acttcagcgg tttatataag cttgtattcc tttttctctc  187620
ctctccccat gatgtttaga aacacaacta tattgtttgc taagcattcc aactatctca  187680
tttccaagca agtattagaa taccacagga accacaagac tgcacatcaa atatgcccc   187740 attcaacatc tagtgagcag tcaggaaaga gaacttccag atcctggaaa tcagggttag  187800
tattgtccag gtctaccaaa aatctcaata tttcagataa tcacaataca tcccttacct  187860
```

```
gggaaagggc tgttataatc tttcacaggg gacaggatgg ttcccttgat gaagaagttg   187920
atatgccttt tcccaactcc agaaagtgac aagctcacag acctttgaac tagagtttag   187980
ctggaaaagt atgttagtgc aaattgtcac aggacagccc ttctttccac agaagctcca   188040
ggtagagggt gtgtaagtag ataggccatg ggcactgtgg gtagacacac atgaagtcca   188100
agcatttaga tgtataggtt gatggtggta tgttttcagg ctagatgtat gtacttcatg   188160
ctgtctacac taagagagaa tgagagacac actgaagaag caccaatcat gaattagttt   188220
tatatgcttc tgttttataa ttttgtgaag caaaattttt tctctaggaa atatttattt   188280
taataatgtt tcaaacatat ataacaatgc tgtattttaa aagaatgatt atgaattaca   188340
tttgtataaa ataattttta tatttgaaat attgactttt tatggcacta gtatttctat   188400
gaaatattat gttaaaactg gacaggggga gaacctaggg tgatattaac caggggccat   188460
gaatcacctt ttggtctgga gggaagcctt ggggctgatg cagttgttgc ccacagctgt   188520
atgattccca gccagcacag cctcttagat gcagttctga agaagatggt accaccagtc   188580
tgactgtttc catcaagggt acactgcctt ctcaactcca aactgactct taagaagact   188640
gcattatatt tattactgta agaaaatatc acttgtcaat aaaatccata catttgtgtg   188700
aaa                                                                 188703

<210> SEQ ID NO 2
<211> LENGTH: 6130
<212> TYPE: DNA
<213> ORGANISM: Homo sapiens

<400> SEQUENCE: 2
aattggaagc aaatgacatc acagcaggtc agagaaaaag ggttgagcgg caggcaccca     60
gagtagtagg tctttggcat taggagcttg agcccgacg gccctagcag ggaccccagc    120
gcccgagaga ccatgcagag gtcgcctctg gaaaaggcca gcgttgtctc caaactttt    180
ttcagctgga ccagaccaat tttgaggaaa ggatacagac agcgcctgga attgtcagac    240
atataccaaa tcccttctgt tgattctgct gacaatctat ctgaaaaatt ggaaagagaa    300
tgggatagag agctggcttc aaagaaaaat cctaaactca ttaatgccct tcggcgatgt    360
ttttttctgga gatttatgtt ctatggaatc ttttttatatt taggggaagt caccaaagca    420
gtacagcctc tcttactggg aagaatcata gcttcctatg acccggataa caaggaggaa    480
cgctctatcg cgatttatct aggcataggc ttatgccttc tctttattgt gaggacactg    540
ctcctacacc cagccatttt tggccttcat cacattggaa tgcagatgag aatagctatg    600
tttagtttga tttataagaa gactttaaag ctgtcaagcc gtgttctaga taaaataagt    660
attggacaac ttgttagtct cctttccaac aacctgaaca aatttgatga aggacttgca    720
ttggcacatt tcgtgtggat cgctcctttg caagtggcac tcctcatggg gctaatctgg    780
gagttgttac aggcgtctgc cttctgtgga cttggtttcc tgatagtcct tgcccttttt    840
caggctgggc tagggagaat gatgatgaag tacagagatc agagagctgg gaagatcagt    900
gaaagacttg tgattaccct agaaatgatt gaaaatatcc aatctgttaa ggcatactgc    960
tgggaagaag caatggaaaa aatgattgaa aacttaagac aaacagaact gaaactgact   1020
cggaaggcag cctatgtgag atacttcaat agctcagcct tcttcttctc agggttcttt   1080
gtggtgtttt tatctgtgct tcctatgca ctaatcaaag gaatcatcct ccggaaaata   1140
ttcaccacca tctcattctg cattgttctg cgcatggcgg tcactcggca atttcctgg   1200
gctgtacaaa catggtatga ctctcttgga gcaataaaca aaatacagga tttcttacaa    1260
```

```
aagcaagaat ataagacatt ggaatataac ttaacgacta cagaagtagt gatggagaat   1320
gtaacagcct tctgggagga gggatttggg gaattatttg agaaagcaaa acaaaacaat   1380
aacaatagaa aaacttctaa tggtgatgac agcctcttct tcagtaattt ctcacttctt   1440
ggtactcctg tcctgaaaga tattaatttc aagatagaaa gaggacagtt gttggcggtt   1500
gctggatcca ctggagcagg caagacttca cttctaatga tgattatggg agaactggag   1560
ccttcagagg gtaaaattaa gcacagtgga agaatttcat tctgttctca gttttcctgg   1620
attatgcctg gcaccattaa agaaaatatc atctttggtg tttcctatga tgaatataga   1680
tacagaagcg tcatcaaagc atgccaacta gaagaggaca ctccaagtt tgcagagaaa    1740 gacaatatag ttcttggaga aggtggaatc acactgagtg gaggtcaacg agcaagaatt   1800
tctttagcaa gagcagtata caagatgct gatttgtatt tattagactc tcctttttgga   1860 tacctagatg ttttaacaga aaaagaaata tttgaaagct gtgtctgtaa actgatggct   1920
aacaaaacta ggattttggt cacttctaaa atggaacatt taaagaaagc tgacaaaata   1980
ttaattttgc atgaaggtag cagctatttt tatgggacat tttcagaact ccaaaatcta   2040
cagccagact ttagctcaaa actcatggga tgtgattctt tcgaccaatt tagtgcagaa   2100
agaagaaatt caatcctaac tgagacctta caccgtttct cattagaagg atgctcct    2160 gtctcctgga cagaaacaaa aaacaatct tttaaacaga ctggagagtt tggggaaaaa   2220
aggaagaatt ctattctcaa tccaatcaac tctatacgaa aattttccat tgtgcaaaag   2280 actccttac aaatgaatgg catcgaagag gattctgatg agcctttaga gagaaggctg    2340
tccttagtac cagattctga gcagggagag gcgatactgc ctcgcatcag cgtgatcagc   2400
actggcccca cgcttcaggc acgaaggagg cagtctgtcc tgaacctgat gacacactca   2460
gttaaccaag gtcagaacat tcaccgaaag acaaacagcat ccacacgaaa agtgtcactg   2520
gcccctcagg caaacttgac tgaactggat atatattcaa gaaggttatc tcaagaaact   2580
ggcttggaaa taagtgaaga aattaacgaa gaagacttaa aggagtgctt ttttgatgat   2640
atggagagca taccagcagt gactacatgg aacacatacc ttcgatatat tactgtccac   2700
aagagcttaa ttttttgtgct aatttggtgc ttagtaattt ttctggcaga ggtggctgct   2760
tctttggttg tgctgtggct ccttggaaac actcctcttc aagacaaagg gaatagtact   2820
catagtagaa ataacagcta tgcagtgatt atcaccagca ccagttcgta ttatgtgttt   2880
tacatttacg tgggagtagc cgacactttg cttgctatgg gattcttcag aggtctacca   2940
ctggtgcata ctctaatcac agtgtcgaaa attttacacc acaaaatgtt acattctgtt   3000
cttcaagcac ctatgtcaac cctcaacacg ttgaaagcag gtgggattct taatagattc   3060
tccaaagata tagcaatttt ggatgacctt ctgcctctta ccatatttga cttcatccag   3120
ttgttattaa ttgtgattgg agctatagca gttgtcgcag ttttacaacc ctacatcttt   3180
gttgcaacag tgccagtgat agtggctttt attatgttga gcatattt cctccaaacc    3240 tcacagcaac tcaaacaact ggaatctgaa ggcaggagtc aattttcac tcatcttgtt    3300 acaagcttaa aaggactatg gacacttcgt gccttcggac ggcagcctta ctttgaaact   3360
ctgttccaca aagctctgaa tttacatact gccaactggt tcttgtacct gtcaacactg   3420
cgctggttcc aaatgagaat agaaatgatt tttgtcatct tcttcattgc tgttacctc    3480 atttccattt taacaacagg agaagggaaa ggaagagttg gtattatcct gactttagcc   3540
atgaatatca tgagtacatt gcagtgggct gtaaactcca gcatagatgt ggatagcttg   3600
```

```
atgcgatctg tgagccgagt ctttaagttc attgacatgc aacagaagg taaacctacc    3660
aagtcaacca aaccatacaa gaatggccaa ctctcgaaag ttatgattat tgagaattca    3720
cacgtgaaga aagatgacat ctggccctca gggggccaaa tgactgtcaa agatctcaca    3780
gcaaaataca cagaaggtgg aaatgccata ttagagaaca tttccttctc aataagtcct    3840
ggccagaggg tgggcctctt gggaagaact ggatcaggga agagtacttt gttatcagct    3900
tttttgagac tactgaacac tgaaggagaa atccagatcg atggtgtgtc ttgggattca    3960
ataactttgc aacagtggag gaaagccttt ggagtgatac cacagaaagt atttattttt    4020
tctggaacat ttagaaaaaa cttggatccc tatgaacagt ggagtgatca agaaatatgg    4080
aaagttgcag atgaggttgg gctcagatct gtgatagaac agtttcctgg gaagcttgac    4140
tttgtccttg tggatggggg ctgtgtccta agccatggcc acaagcagtt gatgtgcttg    4200
gctagatctg ttctcagtaa ggcgaagatc ttgctgcttg atgaacccag tgctcatttg    4260
gatccagtaa cataccaaat aattagaaga actctaaaac aagcatttgc tgattgcaca    4320
gtaattctct gtgaacacag gatagaagca atgctggaat gccaacaatt tttggtcata    4380
gaagagaaca aagtgcggca gtacgattcc atccagaaac tgctgaacga gaggagcctc    4440
ttccggcaag ccatcagccc ctccgacagg gtgaagctct tccccaccg gaactcaagc    4500
aagtgcaagt ctaagcccca gattgctgct ctgaaagagg agacagaaga agaggtgcaa    4560
gatacaaggc tttagagagc agcataaatg ttgacatggg acatttgctc atggaattgg    4620
agctcgtggg acagtcacct catggaattg gagctcgtgg aacagttacc tctgcctcag    4680
aaaacaagga tgaattaagt ttttttttaa aaagaaaca tttggtaagg ggaattgagg    4740
acactgatat gggtcttgat aaatggcttc ctggcaatag tcaaattgtg tgaaaggtac    4800
ttcaaatcct tgaagattta ccacttgtgt tttgcaagcc agattttcct gaaaacccctt    4860
gccatgtgct agtaattgga aaggcagctc taaatgtcaa tcagcctagt tgatcagctt    4920
attgtctagt gaaactcgtt aatttgtagt gttgagaag aactgaaatc atacttctta    4980
gggttatgat taagtaatga taactggaaa cttcagcggt ttatataagc ttgtattcct    5040
ttttctctcc tctccccatg atgtttagaa acacaactat attgtttgct aagcattcca    5100
actatctcat ttccaagcaa gtattagaat accacaggaa ccacaagact gcacatcaaa    5160
atatgcccca ttcaacatct agtgagcagt caggaaagag aacttccaga tcctggaaat    5220
cagggttagt attgtccagg tctaccaaaa atctcaatat ttcagataat cacaatacat    5280
cccttacctg ggaaagggct gttataatct ttcacagggg acaggatggt tcccttgatg    5340
aagaagttga tatgcctttt cccaactcca gaaagtgaca agctcacaga cctttgaact    5400
agagtttagc tggaaaagta tgttagtgca aattgtcaca ggacagccct tctttccaca    5460
gaagctccag gtagagggtg tgtaagtaga taggccatgg gcactgtggg tagacacaca    5520
tgaagtccaa gcatttagat gtataggttg atggtggtat gttttcaggc tagatgtatg    5580
tacttcatgc tgtctacact aagagagaat gagagacaca ctgaagaagc accaatcatg    5640
aattagtttt atatgcttct gttttataat tttgtgaagc aaaatttttt ctctaggaaa    5700
tatttatttt aataatgttt caaacatata ttacaatgct gtattttaaa agaatgatta    5760
tgaattacat ttgtataaaa aatttttat atttgaaata ttgactttt atggcactag    5820
tatttttatg aaatattatg ttaaaactgg gacaggggag aacctagggt gatattaacc    5880
aggggccatg aatcaccttt tggtctggag ggaagccttg gggctgatcg agttgttgcc    5940
cacagctgta tgattcccag ccagacacag cctcttagat gcagttctga agaagatggt    6000
```

```
accaccagtc tgactgtttc catcaagggt acactgcctt ctcaactcca aactgactct    6060
taagaagact gcattatatt tattactgta agaaaatatc acttgtcaat aaaatccata    6120
catttgtgta                                                           6130
```

<210> SEQ ID NO 3
<211> LENGTH: 1477
<212> TYPE: PRT
<213> ORGANISM: Homo sapiens

<400> SEQUENCE: 3

```
Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Cys Phe
        115                 120                 125

Ile Val Arg Thr Leu Leu Leu His Pro Ala Ile Phe Gly Leu His His
    130                 135                 140

Ile Gly Met Gln Met Arg Ile Ala Met Phe Ser Leu Ile Tyr Lys Lys
145                 150                 155                 160

Thr Leu Lys Leu Ser Ser Arg Val Leu Asp Lys Ile Ser Ile Gly Gln
                165                 170                 175

Leu Val Ser Leu Leu Ser Asn Asn Leu Asn Lys Phe Asp Glu Gly Leu
            180                 185                 190

Ala Leu Ala His Phe Val Trp Ile Ala Pro Leu Gln Val Ala Leu Leu
        195                 200                 205

Met Gly Leu Ile Trp Glu Leu Leu Gln Ala Ser Ala Phe Cys Gly Leu
    210                 215                 220

Gly Phe Leu Ile Val Leu Ala Leu Phe Gly Ala Gly Leu Gly Arg Met
225                 230                 235                 240

Met Met Lys Tyr Arg Asp Gln Arg Ala Gly Lys Ile Ser Glu Arg Leu
                245                 250                 255

Val Ile Thr Ser Glu Met Ile Glu Asn Ile Gln Ser Val Lys Ala Tyr
            260                 265                 270

Cys Trp Glu Glu Ala Met Glu Lys Met Ile Glu Asn Leu Arg Gln Thr
        275                 280                 285

Glu Leu Lys Leu Thr Arg Lys Ala Ala Tyr Val Arg Tyr Phe Asn Ser
    290                 295                 300

Ser Ala Phe Phe Phe Ser Gly Phe Phe Val Val Phe Leu Ser Val Leu
305                 310                 315                 320

Pro Tyr Ala Leu Ile Lys Gly Ile Ile Leu Arg Lys Ile Phe Thr Thr
                325                 330                 335

Ile Ser Phe Cys Ile Val Leu Arg Met Ala Val Thr Arg Gln Phe Pro
```

-continued

```
                340                 345                 350
Trp Ala Val Gln Thr Trp Tyr Asp Ser Leu Gly Ala Ile Asn Lys Ile
            355                 360                 365
Gln Asp Phe Leu Gln Lys Gln Glu Tyr Lys Thr Leu Glu Tyr Asn Leu
        370                 375                 380
Thr Thr Thr Glu Val Val Met Glu Asn Val Thr Ala Phe Trp Glu Glu
385                 390                 395                 400
Gly Phe Gly Glu Leu Phe Glu Lys Ala Lys Gln Asn Asn Asn Asn Arg
                405                 410                 415
Lys Thr Ser Asn Gly Asp Asp Ser Leu Phe Phe Ser Asn Phe Ser Leu
            420                 425                 430
Leu Gly Thr Pro Val Leu Lys Asp Ile Asn Phe Lys Ile Glu Arg Gly
        435                 440                 445
Gln Leu Leu Ala Val Ala Gly Ser Thr Gly Ala Gly Lys Thr Ser Leu
    450                 455                 460
Leu Met Met Ile Met Gly Glu Leu Glu Pro Ser Glu Gly Lys Ile Lys
465                 470                 475                 480
His Ser Gly Arg Ile Ser Phe Cys Ser Gln Phe Ser Trp Ile Met Pro
                485                 490                 495
Gly Thr Ile Lys Glu Asn Ile Ile Phe Gly Val Ser Tyr Asp Glu Tyr
            500                 505                 510
Arg Tyr Arg Ser Val Ile Lys Ala Cys Gln Leu Glu Glu Asp Ile Ser
        515                 520                 525
Lys Phe Ala Glu Lys Asp Asn Ile Val Leu Gly Glu Gly Gly Ile Thr
    530                 535                 540
Leu Ser Gly Gly Gln Arg Ala Arg Ile Ser Leu Ala Arg Ala Val Tyr
545                 550                 555                 560
Lys Asp Ala Asp Leu Tyr Leu Leu Asp Ser Pro Phe Gly Tyr Leu Asp
                565                 570                 575
Val Leu Thr Glu Lys Glu Ile Phe Glu Ser Cys Val Cys Lys Leu Met
            580                 585                 590
Ala Asn Lys Thr Arg Ile Leu Val Thr Ser Lys Met Glu His Leu Lys
        595                 600                 605
Lys Ala Asp Lys Ile Leu Ile Leu His Glu Gly Ser Ser Tyr Phe Tyr
    610                 615                 620
Gly Thr Phe Ser Glu Leu Gln Asn Leu Gln Pro Asp Phe Ser Ser Lys
625                 630                 635                 640
Leu Met Gly Cys Asp Ser Phe Asp Gln Phe Ser Ala Glu Arg Arg Asn
                645                 650                 655
Ser Ile Leu Thr Glu Thr Leu His Arg Phe Ser Leu Glu Gly Asp Ala
            660                 665                 670
Pro Val Ser Trp Thr Glu Thr Lys Lys Gln Ser Phe Lys Gln Thr Gly
        675                 680                 685
Glu Phe Gly Glu Lys Arg Lys Asn Ser Ile Leu Asn Pro Ile Asn Ser
    690                 695                 700
Ile Arg Lys Phe Ser Ile Val Gln Lys Thr Pro Leu Gln Met Asn Gly
705                 710                 715                 720
Ile Glu Glu Asp Ser Asp Glu Pro Leu Glu Arg Arg Leu Ser Leu Val
                725                 730                 735
Pro Asp Ser Glu Gln Gly Glu Ala Ile Leu Pro Arg Ile Ser Val Ile
            740                 745                 750
Ser Thr Gly Pro Thr Leu Gln Ala Arg Arg Arg Gln Ser Val Leu Asn
        755                 760                 765
```

```
Leu Met Thr His Ser Val Asn Gln Gly Gln Asn Ile His Arg Lys Thr
    770                 775                 780

Thr Ala Ser Thr Arg Lys Val Ser Leu Ala Pro Gln Ala Asn Leu Thr
785                 790                 795                 800

Glu Leu Asp Ile Tyr Ser Arg Arg Leu Ser Gln Glu Thr Gly Leu Glu
                805                 810                 815

Ile Ser Glu Glu Ile Asn Glu Glu Asp Leu Lys Glu Cys Phe Phe Asp
                820                 825                 830

Asp Met Glu Ser Ile Pro Ala Val Thr Thr Trp Asn Thr Tyr Leu Arg
            835                 840                 845

Tyr Ile Thr Val His Lys Ser Leu Ile Phe Val Leu Ile Trp Cys Leu
        850                 855                 860

Val Ile Phe Leu Ala Glu Val Ala Ala Ser Leu Val Val Leu Trp Leu
865                 870                 875                 880

Leu Gly Asn Thr Pro Leu Gln Asp Lys Gly Asn Ser Thr His Ser Arg
                885                 890                 895

Asn Asn Ser Tyr Ala Val Ile Ile Thr Ser Thr Ser Ser Tyr Tyr Val
                900                 905                 910

Phe Tyr Ile Tyr Val Gly Val Ala Asp Thr Leu Leu Ala Met Gly Phe
            915                 920                 925

Phe Arg Gly Leu Pro Leu Val His Thr Leu Ile Thr Val Ser Lys Ile
    930                 935                 940

Leu His His Lys Met Leu His Ser Val Leu Gln Ala Pro Met Ser Thr
945                 950                 955                 960

Leu Asn Thr Leu Lys Ala Gly Gly Ile Leu Asn Arg Phe Ser Lys Asp
                965                 970                 975

Ile Ala Ile Leu Asp Asp Leu Leu Pro Leu Thr Ile Phe Asp Phe Ile
                980                 985                 990

Gln Leu Leu Leu Ile Val Ile Gly Ala Ile Ala Val Val Ala Val Leu
        995                 1000                1005

Gln Pro Tyr Ile Phe Val Ala Thr Val Pro Val Ile Val Ala Phe
    1010                1015                1020

Ile Met Leu Arg Ala Tyr Phe Leu Gln Thr Ser Gln Gln Leu Lys
    1025                1030                1035

Gln Leu Glu Ser Glu Gly Arg Ser Pro Ile Phe Thr His Leu Val
    1040                1045                1050

Thr Ser Leu Lys Gly Leu Trp Thr Leu Arg Ala Phe Gly Arg Gln
    1055                1060                1065

Pro Tyr Phe Glu Thr Leu Phe His Lys Ala Leu Asn Leu His Thr
    1070                1075                1080

Ala Asn Trp Phe Leu Tyr Leu Ser Thr Leu Arg Trp Phe Gln Met
    1085                1090                1095

Arg Ile Glu Met Ile Phe Val Ile Phe Phe Ile Ala Val Thr Phe
    1100                1105                1110

Ile Ser Ile Leu Thr Thr Gly Glu Gly Glu Gly Arg Val Gly Ile
    1115                1120                1125

Ile Leu Thr Leu Ala Met Asn Ile Met Ser Thr Leu Gln Trp Ala
    1130                1135                1140

Val Asn Ser Ser Ile Asp Val Asp Ser Leu Met Arg Ser Val Ser
    1145                1150                1155

Arg Val Phe Lys Phe Ile Asp Met Pro Thr Glu Gly Lys Pro Thr
    1160                1165                1170
```

| | | | | | | | | | | | |
|---|---|---|---|---|---|---|---|---|---|---|---|
|Lys|Ser|Thr|Lys|Pro|Tyr|Lys|Asn|Gly|Gln|Leu|Ser|Lys|Val|Met|
| |1175| | | |1180| | | |1185| | | | | |

```
Lys Ser Thr Lys Pro Tyr Lys Asn Gly Gln Leu Ser Lys Val Met
    1175            1180            1185

Ile Ile Glu Asn Ser His Val Lys Lys Asp Asp Ile Trp Pro Ser
    1190            1195            1200

Gly Gly Gln Met Thr Val Lys Asp Leu Thr Ala Lys Tyr Thr Glu
    1205            1210            1215

Gly Gly Asn Ala Ile Leu Glu Asn Ile Ser Phe Ser Ile Ser Pro
    1220            1225            1230

Gly Gln Arg Val Gly Leu Leu Gly Arg Thr Gly Ser Gly Lys Ser
    1235            1240            1245

Thr Leu Leu Ser Ala Phe Leu Arg Leu Leu Asn Thr Glu Gly Glu
    1250            1255            1260

Ile Gly Ile Asp Gly Val Ser Trp Asp Ser Ile Thr Leu Gln Gln
    1265            1270            1275

Trp Arg Lys Ala Phe Gly Val Ile Pro Gln Lys Val Phe Ile Phe
    1280            1285            1290

Ser Gly Thr Phe Arg Lys Asn Leu Asp Pro Tyr Glu Gln Trp Ser
    1295            1300            1305

Asp Gln Glu Ile Trp Lys Val Ala Asp Glu Val Gly Leu Arg Ser
    1310            1315            1320

Val Ile Glu Gln Phe Pro Gly Lys Leu Asp Phe Val Leu Val Asp
    1325            1330            1335

Gly Gly Cys Val Leu Ser His Gly His Lys Gln Leu Met Cys Leu
    1340            1345            1350

Ala Arg Ser Val Leu Ser Lys Ala Lys Ile Leu Leu Leu Asp Glu
    1355            1360            1365

Pro Ser Ala His Leu Asp Pro Val Thr Tyr Gln Ile Ile Arg Arg
    1370            1375            1380

Thr Leu Lys Gln Ala Phe Ala Asp Cys Thr Val Ile Leu Cys Glu
    1385            1390            1395

His Arg Ile Glu Ala Met Leu Glu Cys Gln Gln Phe Leu Val Ile
    1400            1405            1410

Glu Glu Asn Lys Val Arg Gln Tyr Asp Ser Ile Gln Lys Leu Leu
    1415            1420            1425

Asn Glu Arg Ser Leu Phe Arg Gln Ala Ile Ser Pro Ser Asp Arg
    1430            1435            1440

Val Lys Leu Phe Pro His Arg Asn Ser Ser Lys Cys Lys Ser Lys
    1445            1450            1455

Pro Gln Ile Ala Ala Leu Lys Glu Glu Thr Glu Glu Glu Val Gln
    1460            1465            1470

Asp Thr Arg Leu
    1475
```

<210> SEQ ID NO 4
<211> LENGTH: 4389
<212> TYPE: DNA
<213> ORGANISM: Homo sapiens

<400> SEQUENCE: 4

```
gaattcaaag gaaaacataa gatgcaattc gtgcctccaa ggaggttgta gggaagaggg    60
gttatgaatg tatgtaaata gaagttggtg tgcgtgtgtg tttataaaca gaattgtcag   120
accaaacatt attttggaag cagtaaaagt aaactagaat ctggcctagt catgtcccag   180
gacacctctt tcaagtcctg aaacatcttt gtaagactgt aatgtgtgtt tacatcctag   240
```

```
gtaatcactg tggcccactg ttgaagagct gtggctgttc ttacccttct agttagataa    300
acttataagc acaaccagac tacatatatg aagctgaaga gaccttgtct tttttttaacg   360 agcttttctt cccgatagga gtgactattt cttttcttct tccacatttt caggttttag   420
tgtacttgtg attgctaccc acttatcact attaaagtct actcaggaga gaatctgaga   480
aacactctca aattaagttg aacatgatgg ataagtaaag tattgtgaaa gttcactctc   540
atgatttcta atggtgaaac ctggcagggt gactaatctt tgacgagaag gttatcactt   600
ataatctttc atatattgag atcatttgta agaagcaccc agcacattgc tgaacacaaa   660
gtaggtatta ataaaatgtt ggcttccttt tctcctactc atcctcgctc ttcttttaa    720 tataccttta aaatgatgcc acagaaatgg ccacccaatc ttctatattt aaggtcagtt   780
cttgcattag gaaattctat aggggaagta tgtgaagtat gtgtagtcag tcattaaatg   840
cttgggctct ggccacagat tgtttaggtt taaatcccag tttcctcttt tattattaat   900
tgtgcaactt gcttgggaaa acatgaaact tgttttttcct caggttcatt atctgtaata   960
tatagtgaat gaagaagttt cctgtcccat gaaggtgttg taaagattaa aaaaggcaaa  1020
ttaggctgtg tatttgtcat aataattggc atatatggta agtgaccaac aaccataagg  1080
tattataaaa ttgttataaa atgatatgag ctatcattga gcagcatgaa agaagagctt  1140
cactgtttca cctactatca ccctggccca ttaatctctt tcctgttcct gacatttcag  1200
agatacgttt aggatttcaa tcatgacctt aagcccacatt tgaacaattt tctggtggat  1260
aagtcctcat tcccacatta tgtatgtacc tagatgcaaa tcctgaatat catgtcgcaa  1320
ttagtgcatc tggacatgct tgctaactgt gttaaagctc tgaataatgg taagttttta  1380
tttctaccaa aacaaatttg ggctgtaatg ttttatgata aaaatctgtg gtcttcctat  1440
gtacatgtgt gtgtacatgc ttaaaatgca atgttatagt taaatgtaat tcattaaaag  1500
tatgtaactc cagtggctac ttagtttggc tacttggttt gtagatttct gctttcctgt  1560
ttcattgtta aacaggtcta gaagttatta tttcatgaaa ctaatgtgag gaaaagagact  1620 atgttgatat ataagtgaca ttatataaat acatgaggga tgatttgatt agaagcagta  1680
ttacacagtg ataggagtaa tggtttagaa ctagactcag gtttgaatct tagctctatc  1740
attataggca tttacttaac ttttcttgtt tgcttaactg aaaactgaag ataataacac  1800
ctatttacat ggttgttata agggttatat gaataatgtc tggcaaatag taagaactca  1860
agtaactgtt tcactctttc cagaaggaga ttggctgaaa atatttgga gtctcctcca   1920 gccatattcc ttggtcagct tctatgatcc tctttggagc ttaattctta atcccttat    1980 tttcacttgc ttgttgataa caagaagaa ctaattatta atttatttca aaatgcatgt   2040
attatatttg atgggccaca ctaacagtta taaaccaaac aacagattgg gaatggggaa   2100
gtggatgtgg tgagttcaat cacatgtctg ggaaaagtca atagtgaaga cagagtctca   2160
caattttttg tcataatgga gagatgaaaa cacaggtaga ggatttcaaa caacagagtg   2220
gatggtgagt taaaaatgct gaaattcttt cctggtgtct aacttaatgc aatgtggttt   2280
atctctttgc tcttttctct actattcaaa tttaggataa taaagattaa atgtttctaa   2340
atcttacttt acaatatcaa gaaaaaaagg tatgcttttg cccacggaag ggcaaagcag   2400
agctatgaaa acctgctgaa cacattcttt attttcaaca caggttcttg tctttccatc   2460
atgaaatgca cattttattt gtactgtatt tgggtgacca caagtcaaca acaagataat   2520
tcacaagacc cttgccttag atgtgtcggc aataaagtaa tcaggccaaa attttttactt  2580 tccttttgaat ttttcaattc aaacacaatg tatgcttgct tttacacagt agggttcagg  2640
```

```
gattagaggg ttggctcctt taaaaccgtc agagacacag gcaatcctac acaaaattct   2700
cagaaggaag gcgcctacgc ctgggaatgc ccagatgccc ctcagagagt tgaagatggc   2760
gtttctctga gtcaggtcaa agttaacaca ttaccttcgc ttcaaagact gcttggcttc   2820
ctttcggtgg attagtcaag atgttttgct gactgagact aggaaatcta taggagggcg   2880
ggttagttta cattgttcct tgtcattatc gctaaaacac tccaaagcct tccttaaaaa   2940
tgcgcactgg gctaaaaagg atagacaagg aacacatcct gggccggtaa ttacgcaaag   3000
cattatctcc tcttacctcc ttgcagattt tttttttctct ttcagtacgt gtcctaagat   3060
ttctgtgcca cccttggagt tcactcacct aaacctgaaa ctaataaagc ttggttcttt   3120
tctccgacac gcaaaggaag cgctaaggta aatgcatcag acccacactg ccgcggaact   3180
tttcggctct ctaaggctgt attttgatat acgaaaggca cattttcctt ccctttttcaa   3240
aatgcacctt gcaaacgtaa caggaacccg actaggatca tcgggaaaag gaggaggagg   3300
aggaaggcag gctccgggga agctggtggc agcgggtcct gggtctggcg gaccctgacg   3360
cgaaggaggg tctaggaagc ctccggggga gccggttctc ccgccggtgg cttcttctgt   3420
cctccagcgt tgccaactgg acctaaagag aggccgcgac tgtcgcccac ctgcgggatg   3480
ggcctggtgc tgggcggtca ggacactgac ctggaaggag cgcgcgcgag ggagggaggc   3540
tgggagtcag aatcgggaaa gggaggtgcg gggcggcgag ggagcgaagg aggagaggag   3600
gaaggagcgg gaggggtgct ggcggggggtg cgtagtgggt ggagaaagcc gctagagcaa   3660
atttggggcc ggaccaggca gcactcggct tttaacctgg gcagtgaagg cggggggaaag   3720
agcaaaagga aggggttggtg tgcggagtag gggtgggtgg ggggaattgg aagcaaatga   3780
catcacagca ggtcagagaa aaagggttga gcggcaggca cccagagtag taggtctttg   3840
gcattaggag cttgagccca gacggcccta gcagggaccc cagcgcccga gagaccatgc   3900
agaggtcgcc tctggaaaag gccagcgttg tctccaaact tttttttcagg tgagaaggtg   3960
gccaaccgag cttcggaaag acacgtgccc acgaaagagg agggcgtgtg tatgggttgg   4020
gtttggggta aaggaataag cagttttttaa aaagatgcgc tatcattcat tgttttgaaa   4080
gaaaatgtgg gtattgtaga ataaaacaga aagcattaag aagagatgga agaatgaact   4140
gaagctgatt gaatagagag ccacatctac ttgcaactga aaagttagaa tctcaagact   4200
caagtacgct actatgcact tgttttattt cattttctca agaaactaaa atacttgtt   4260
aataagtacc taagtatggt ttattggttt tccccccttca tgccttggac acttgattgt   4320
cttcttggca catacaggtg ccatgcctgc atatagtaag tgctcagaaa acatttcttg   4380
actgaattc                                                          4389
```

<210> SEQ ID NO 5  
<211> LENGTH: 19  
<212> TYPE: DNA  
<213> ORGANISM: Homo sapiens
<400> SEQUENCE: 5
tttaacctgg gcagtgaag                                                19

<210> SEQ ID NO 6  
<211> LENGTH: 17  
<212> TYPE: DNA  
<213> ORGANISM: Homo sapiens
<400> SEQUENCE: 6
aacccaaccc atacaca                                                                17

<210> SEQ ID NO 7
<211> LENGTH: 22
<212> TYPE: DNA
<213> ORGANISM: Homo sapiens

<400> SEQUENCE: 7
caaatcaagt gaatatctgt tc                                                          22

<210> SEQ ID NO 8
<211> LENGTH: 21
<212> TYPE: DNA
<213> ORGANISM: Homo sapiens

<400> SEQUENCE: 8
agccaccata cttggctcct a                                                           21

<210> SEQ ID NO 9
<211> LENGTH: 22
<212> TYPE: DNA
<213> ORGANISM: Homo sapiens

<400> SEQUENCE: 9
ctaaaatatt tgcacatgca ac                                                          22

<210> SEQ ID NO 10
<211> LENGTH: 21
<212> TYPE: DNA
<213> ORGANISM: Homo sapiens

<400> SEQUENCE: 10
tttcttagtg tttggagttg g                                                           21

<210> SEQ ID NO 11
<211> LENGTH: 22
<212> TYPE: DNA
<213> ORGANISM: Homo sapiens

<400> SEQUENCE: 11
tcattttaag tctcctctaa ag                                                          22

<210> SEQ ID NO 12
<211> LENGTH: 21
<212> TYPE: DNA
<213> ORGANISM: Homo sapiens

<400> SEQUENCE: 12
cgatacagaa tatatgtgcc a                                                           21

<210> SEQ ID NO 13
<211> LENGTH: 20
<212> TYPE: DNA
<213> ORGANISM: Homo sapiens

<400> SEQUENCE: 13
aacaactaga agcatgccag                                                             20

<210> SEQ ID NO 14
<211> LENGTH: 24
<212> TYPE: DNA
<213> ORGANISM: Homo sapiens

<400> SEQUENCE: 14

```
gttgtataat ttataacaat agtg                                          24

<210> SEQ ID NO 15
<211> LENGTH: 20
<212> TYPE: DNA
<213> ORGANISM: Homo sapiens

<400> SEQUENCE: 15
ggaagataca atgacacctg                                               20

<210> SEQ ID NO 16
<211> LENGTH: 21
<212> TYPE: DNA
<213> ORGANISM: Homo sapiens

<400> SEQUENCE: 16
ctgaagatca ctgttctatg c                                             21

<210> SEQ ID NO 17
<211> LENGTH: 22
<212> TYPE: DNA
<213> ORGANISM: Homo sapiens

<400> SEQUENCE: 17
atgacttaaa accttgagca gt                                            22

<210> SEQ ID NO 18
<211> LENGTH: 22
<212> TYPE: DNA
<213> ORGANISM: Homo sapiens

<400> SEQUENCE: 18
ggaagtctac catgataaac at                                            22

<210> SEQ ID NO 19
<211> LENGTH: 21
<212> TYPE: DNA
<213> ORGANISM: Homo sapiens

<400> SEQUENCE: 19
gagaccatgc tcagatcttc c                                             21

<210> SEQ ID NO 20
<211> LENGTH: 23
<212> TYPE: DNA
<213> ORGANISM: Homo sapiens

<400> SEQUENCE: 20
acttttataa cttcctagtg aag                                           23

<210> SEQ ID NO 21
<211> LENGTH: 22
<212> TYPE: DNA
<213> ORGANISM: Homo sapiens

<400> SEQUENCE: 21
aagatgtagc acaatgagag ta                                            22

<210> SEQ ID NO 22
<211> LENGTH: 20
<212> TYPE: DNA
<213> ORGANISM: Homo sapiens
```

```
<400> SEQUENCE: 22
cagttaggtg tttagagcaa                                              20

<210> SEQ ID NO 23
<211> LENGTH: 22
<212> TYPE: DNA
<213> ORGANISM: Homo sapiens

<400> SEQUENCE: 23
gtatacagtg taatggatca tg                                           22

<210> SEQ ID NO 24
<211> LENGTH: 22
<212> TYPE: DNA
<213> ORGANISM: Homo sapiens

<400> SEQUENCE: 24
caccaaatta agttcttaat ag                                           22

<210> SEQ ID NO 25
<211> LENGTH: 22
<212> TYPE: DNA
<213> ORGANISM: Homo sapiens

<400> SEQUENCE: 25
ttctgcttag gatgataatt gg                                           22

<210> SEQ ID NO 26
<211> LENGTH: 22
<212> TYPE: DNA
<213> ORGANISM: Homo sapiens

<400> SEQUENCE: 26
gcataggtca tgtgttttat ta                                           22

<210> SEQ ID NO 27
<211> LENGTH: 22
<212> TYPE: DNA
<213> ORGANISM: Homo sapiens

<400> SEQUENCE: 27
cagattgagc atactaaaag tg                                           22

<210> SEQ ID NO 28
<211> LENGTH: 22
<212> TYPE: DNA
<213> ORGANISM: Homo sapiens

<400> SEQUENCE: 28
tacatgaatg acatttacag ca                                           22

<210> SEQ ID NO 29
<211> LENGTH: 21
<212> TYPE: DNA
<213> ORGANISM: Homo sapiens

<400> SEQUENCE: 29
gctacttctg caccactttt g                                            21

<210> SEQ ID NO 30
<211> LENGTH: 23
<212> TYPE: DNA
<213> ORGANISM: Homo sapiens
```

<400> SEQUENCE: 30
cagtctgtct ttctttttatt tta                                          23

<210> SEQ ID NO 31
<211> LENGTH: 21
<212> TYPE: DNA
<213> ORGANISM: Homo sapiens

<400> SEQUENCE: 31
caaaatgcta aaatacgaga c                                             21

<210> SEQ ID NO 32
<211> LENGTH: 19
<212> TYPE: DNA
<213> ORGANISM: Homo sapiens

<400> SEQUENCE: 32
tccaggagac aggagcatc                                                19

<210> SEQ ID NO 33
<211> LENGTH: 20
<212> TYPE: DNA
<213> ORGANISM: Homo sapiens

<400> SEQUENCE: 33
ctcatgggat gtgattcttt                                               20

<210> SEQ ID NO 34
<211> LENGTH: 22
<212> TYPE: DNA
<213> ORGANISM: Homo sapiens

<400> SEQUENCE: 34
gatacacctt atcctaatcc ta                                            22

<210> SEQ ID NO 35
<211> LENGTH: 18
<212> TYPE: DNA
<213> ORGANISM: Homo sapiens

<400> SEQUENCE: 35
accacaatgg tggcatga                                                 18

<210> SEQ ID NO 36
<211> LENGTH: 21
<212> TYPE: DNA
<213> ORGANISM: Homo sapiens

<400> SEQUENCE: 36
tgtatacatc cccaaactat c                                             21

<210> SEQ ID NO 37
<211> LENGTH: 21
<212> TYPE: DNA
<213> ORGANISM: Homo sapiens

<400> SEQUENCE: 37
tgggcatggg aggaataggt g                                             21

<210> SEQ ID NO 38
<211> LENGTH: 24
<212> TYPE: DNA

```
<213> ORGANISM: Homo sapiens

<400> SEQUENCE: 38
ttacaataca tacaaacata gtgg                                          24

<210> SEQ ID NO 39
<211> LENGTH: 16
<212> TYPE: DNA
<213> ORGANISM: Homo sapiens

<400> SEQUENCE: 39
aagtaacttt ggctgc                                                   16

<210> SEQ ID NO 40
<211> LENGTH: 17
<212> TYPE: DNA
<213> ORGANISM: Homo sapiens

<400> SEQUENCE: 40
ctgccattag aaaacca                                                  17

<210> SEQ ID NO 41
<211> LENGTH: 22
<212> TYPE: DNA
<213> ORGANISM: Homo sapiens

<400> SEQUENCE: 41
aagtctatct gattctattt gc                                            22

<210> SEQ ID NO 42
<211> LENGTH: 25
<212> TYPE: DNA
<213> ORGANISM: Homo sapiens

<400> SEQUENCE: 42 gttttttaa taatacagac atact                                          25

<210> SEQ ID NO 43
<211> LENGTH: 19
<212> TYPE: DNA
<213> ORGANISM: Homo sapiens

<400> SEQUENCE: 43
tgtccacttg caatgtgaa                                                19

<210> SEQ ID NO 44
<211> LENGTH: 24
<212> TYPE: DNA
<213> ORGANISM: Homo sapiens

<400> SEQUENCE: 44
caataaagaa tctcaaatag ctct                                          24

<210> SEQ ID NO 45
<211> LENGTH: 20
<212> TYPE: DNA
<213> ORGANISM: Homo sapiens

<400> SEQUENCE: 45
tagtcttttt caggtacaag                                               20

<210> SEQ ID NO 46
<211> LENGTH: 24
```

```
<212> TYPE: DNA
<213> ORGANISM: Homo sapiens

<400> SEQUENCE: 46
caatggaaat tcaaagaaat cact                                          24

<210> SEQ ID NO 47
<211> LENGTH: 23
<212> TYPE: DNA
<213> ORGANISM: Homo sapiens

<400> SEQUENCE: 47
gaatacttac tatatgcaga gca                                           23

<210> SEQ ID NO 48
<211> LENGTH: 22
<212> TYPE: DNA
<213> ORGANISM: Homo sapiens

<400> SEQUENCE: 48
gttcttcctc atgctattac tc                                            22

<210> SEQ ID NO 49
<211> LENGTH: 21
<212> TYPE: DNA
<213> ORGANISM: Homo sapiens

<400> SEQUENCE: 49
gcccgacaaa taaccaagtg a                                             21

<210> SEQ ID NO 50
<211> LENGTH: 21
<212> TYPE: DNA
<213> ORGANISM: Homo sapiens

<400> SEQUENCE: 50
ctaacacatt gcttcaggct a                                             21

<210> SEQ ID NO 51
<211> LENGTH: 22
<212> TYPE: DNA
<213> ORGANISM: Homo sapiens

<400> SEQUENCE: 51
aaggttgttt gtctccatat at                                            22

<210> SEQ ID NO 52
<211> LENGTH: 20
<212> TYPE: DNA
<213> ORGANISM: Homo sapiens

<400> SEQUENCE: 52
gcctatgaga aaactgcact                                               20

<210> SEQ ID NO 53
<211> LENGTH: 20
<212> TYPE: DNA
<213> ORGANISM: Homo sapiens

<400> SEQUENCE: 53
acatgggtgt ttcttattta                                               20

<210> SEQ ID NO 54
```

```
<210> SEQ ID NO 54
<211> LENGTH: 18
<212> TYPE: DNA
<213> ORGANISM: Homo sapiens

<400> SEQUENCE: 54
gttaggggta ggtccagt                                                   18

<210> SEQ ID NO 55
<211> LENGTH: 23
<212> TYPE: DNA
<213> ORGANISM: Homo sapiens

<400> SEQUENCE: 55
gcttgagtgt ttttaactct gtg                                             23

<210> SEQ ID NO 56
<211> LENGTH: 21
<212> TYPE: DNA
<213> ORGANISM: Homo sapiens

<400> SEQUENCE: 56
atgattctgt tcccactgtg c                                               21

<210> SEQ ID NO 57
<211> LENGTH: 21
<212> TYPE: DNA
<213> ORGANISM: Homo sapiens

<400> SEQUENCE: 57
gttctgtgat attatgtgtg g                                               21

<210> SEQ ID NO 58
<211> LENGTH: 21
<212> TYPE: DNA
<213> ORGANISM: Homo sapiens

<400> SEQUENCE: 58
caagggcaat gagatcttaa g                                               21

<210> SEQ ID NO 59
<211> LENGTH: 18
<212> TYPE: DNA
<213> ORGANISM: Homo sapiens

<400> SEQUENCE: 59
agtttctgtc cctgctct                                                   18

<210> SEQ ID NO 60
<211> LENGTH: 21
<212> TYPE: DNA
<213> ORGANISM: Homo sapiens

<400> SEQUENCE: 60
gagcaaatgt cccatgtcaa c                                               21

<210> SEQ ID NO 61
<211> LENGTH: 24
<212> TYPE: DNA
<213> ORGANISM: Homo sapiens

<400> SEQUENCE: 61
aatggtgttt acctacctag agaa                                            24
```

```
<210> SEQ ID NO 62
<211> LENGTH: 19
<212> TYPE: DNA
<213> ORGANISM: Homo sapiens

<400> SEQUENCE: 62
cctcctctga ttccacaag                                                19

<210> SEQ ID NO 63
<211> LENGTH: 22
<212> TYPE: DNA
<213> ORGANISM: Homo sapiens

<400> SEQUENCE: 63
ctgagattct gttctaggtg tg                                            22

<210> SEQ ID NO 64
<211> LENGTH: 21
<212> TYPE: DNA
<213> ORGANISM: Homo sapiens

<400> SEQUENCE: 64
cctacactca gaacccatca t                                             21

<210> SEQ ID NO 65
<211> LENGTH: 21
<212> TYPE: DNA
<213> ORGANISM: Homo sapiens

<400> SEQUENCE: 65
ttcagttgac ttgtcatctt g                                             21

<210> SEQ ID NO 66
<211> LENGTH: 23
<212> TYPE: DNA
<213> ORGANISM: Homo sapiens

<400> SEQUENCE: 66
aatatgttga agttaaaca gtg                                            23

<210> SEQ ID NO 67
<211> LENGTH: 26
<212> TYPE: DNA
<213> ORGANISM: Homo sapiens

<400> SEQUENCE: 67
gttacactat aaaggttgtt ttagac                                        26

<210> SEQ ID NO 68
<211> LENGTH: 25
<212> TYPE: DNA
<213> ORGANISM: Homo sapiens

<400> SEQUENCE: 68
cacagttccc atattaatag aaatg                                         25

<210> SEQ ID NO 69
<211> LENGTH: 19
<212> TYPE: DNA
<213> ORGANISM: Homo sapiens

<400> SEQUENCE: 69
tttttaacag ggatttggg                                                19
```

```
<210> SEQ ID NO 70
<211> LENGTH: 20
<212> TYPE: DNA
<213> ORGANISM: Homo sapiens

<400> SEQUENCE: 70
gattgattga ttgattgatt                                               20

<210> SEQ ID NO 71
<211> LENGTH: 20
<212> TYPE: DNA
<213> ORGANISM: Homo sapiens

<400> SEQUENCE: 71
gcggtcgcat aagggtcagt                                               20

<210> SEQ ID NO 72
<211> LENGTH: 20
<212> TYPE: DNA
<213> ORGANISM: Homo sapiens

<400> SEQUENCE: 72
cgccagcgta ttcccagtca                                               20
```

MUTATIONS ASSOCIATED WITH CYSTIC FIBROSIS

The present application is a continuation application of pending U.S. patent application Ser. No. 13/053,626, filed Mar. 22, 2011, entitled "Mutations Associated With Cystic Fibrosis," which claimed priority under 35 USC 119(e) from U.S. Provisional Patent Application No. 61/316,321 filed Mar. 22, 2010 and U.S. Provisional Patent Application No. 61/359,029 filed Jun. 28, 2010. The disclosures of U.S. Provisional Patent Application Nos. 61/316,321 and 61/359,029 and U.S. patent application Ser. No. 13/053,626 are incorporated by reference in their entireties herein.

BACKGROUND OF THE INVENTION

Cystic fibrosis (CF) is the most common severe autosomal recessive genetic disorder in the Caucasian population. It affects approximately 1 in 2,500 Caucasian live births in North America (Boat et al, The Metabolic Basis of Inherited Disease, 6th ed, pp 2649-2680, McGraw Hill, N.Y. (1989)). The incidence of disease is lower in African American, Hispanic and Asian individuals. Approximately 1 in 25 Caucasian persons are carriers of the disease. The responsible gene has been localized to a 250,000 base pair genomic sequence present on the long arm of chromosome 7. This sequence encodes a membrane-associated protein called the "cystic fibrosis transmembrane regulator" (or "CFTR"). The CFTR gene contains 27 exons and encodes a protein of 1480 amino acids. Several regions are contemplated to have functional importance in the CFTR protein, including two areas for ATP binding, termed Nucleotide Binding Folds (NBF), a Regulatory (R) region that has multiple potential sites for phosphorylation by protein kinases A and C, and two hydrophobic regions believed to interact with cell membranes.

The major symptoms of classical cystic fibrosis include chronic pulmonary disease, pancreatic exocrine insufficiency, congenital absence of the vas deferens in males and elevated sweat electrolyte levels. The symptoms are consistent with CF being an exocrine disorder. Although recent advances have been made in the analysis of ion transport across the apical membrane of the epithelium of CF patient cells, it is not clear that the abnormal regulation of chloride channels represents the only defect in the disease. Mutations in the CFTR gene are also associated with atypical CF and monosymptomatic diseases such as congenital absence of the vas deferens in males, idiopathic chronic pancreatitis and chronic sinusitis (Noone and Knowles, *Respir. Res., vol.* 2, p. 328 (2001); Southern, *Respiration*, vol. 74, p. 241 (2007)). A variety of CFTR gene mutations are known. One of them leads to the omission of phenylalanine residue 508 within the first putative NBF domain. This mutation, termed ΔF508, accounts for about 70% of the CFTR chromosomes in Caucasian patients and was highly associated with the predominant haplotype found on chromosomes of Caucasian CF patients (Kerem, et al., *Science*, vol. 245, p. 1073 (1989); Lemna, et al., *New Engl. J. Med., vol.* 322, p. 291 (1990)). However, the haplotypes associated with Caucasian CF chromosomes without ΔF508 also exist although less common, confirming that allelic heterogeneity is present in CF and CF related disorders.

Therefore, there is a need for more effective genetic screening for other CFTR mutant alleles which are present in the other 30% of Caucasian CF patients, as well as other alleles found in other racial and ethnic groups. Knowledge of such alleles can be used to design probes for screening and/or testing, as well as to devise other screening and/or testing methods. The more complete the set of probes available for CFTR mutant alleles, the more accurate the diagnoses.

SUMMARY OF THE INVENTION

The present invention provides methods, products and systems relating to novel mutations identified in the CFTR gene that can be used for more accurate diagnosis of CF and CF related disorders.

In one aspect, the present invention provides a method for testing for mutations in the CFTR gene, which comprises testing a sample obtained from a subject to determine the presence of one or more mutations selected from Table 1, 2, 3, or 4 in the CFTR gene or protein, wherein the presence of the one or more mutations indicates that the subject has CF or a CFTR related disorder, is at risk of developing CF or a CF related disorder, or is a carrier of a CFTR mutation. In some embodiments, the one or more mutations are selected from Table 1, 2 or 3. In some embodiments, the one or more mutations are selected from Table 1 or 2. In some embodiments, the one or more mutations are selected from Table 1. In some embodiments, the one or more mutations selected from Table 1, 2, 3, or 4 are part of a panel of CFTR mutations.

Yet other embodiments of the present invention comprise systems for performing the method. For example, the system may comprise a station or device for testing a sample obtained from a subject to determine the presence of one or more mutations selected from Table 1, 2, 3, or 4 in the CFTR gene or protein, wherein the presence of the one or more mutations indicates that the subject has CF or a CFTR related disorder, is at risk of developing CF or a CF related disorder, or is a carrier of a CFTR mutation. In some embodiments, the one or more mutations are selected from Table 1, 2 or 3. In some embodiments, the one or more mutations are selected from Table 1 or 2. In some embodiments, the one or more mutations are selected from Table 1. In some embodiments, the one or more mutations selected from Table 1, 2, 3, or 4 are part of a panel of CFTR mutations. Also, the system may comprise a device for analysis and/or interpretation of the data. For example, a computer having software to analyze the data for the presence of one of the mutations of the invention may be included in the system.

The following embodiments may be used in either the methods or the systems of the invention. In some embodiments, the sample contains an isolated nucleic acid. In some embodiments, the testing step comprises nucleic acid sequencing. In some embodiments, the testing step comprises hybridization. In some embodiments, the hybridization is performed using one or more oligonucleotide probes specific for a region in the CFTR gene (SEQ ID NO:1) (FIG. 1) corresponding to the one or more mutations selected from Table 1, 2, 3 or 4, and under conditions sufficiently stringent to disallow a single nucleotide mismatch. In some embodiments, the hybridization is performed with a microarray. In some embodiments, the testing step comprises restriction enzyme digestion. In some embodiments, the testing step comprises PCR amplification. In some embodiments, the PCR amplification is digital PCR amplification. In some embodiments, the testing step comprises primer extension. In some embodiments, the primer extension is single-base primer extension. In some embodiments, the testing step comprises performing a multiplex allele-specific primer extension (ASPE). In yet other embodiments, the testing step may comprise performing real-time PCR.

In some embodiments, the sample contains purified or partially purified protein. In some embodiments, the testing step comprises amino acid sequencing. For example, in certain embodiments, the system comprises a device for amino acid sequencing. In some embodiments, the testing step comprises performing an immuno assay using one or more antibodies that specifically recognize one or more epitopes corresponding to the one or more mutations selected from Table 1, 2, 3 or 4. In some embodiments, the testing step comprises protease digestion (e.g., trypsin digestion). In some embodiments, the testing step further comprises performing 2D-gel electrophoresis.

In some embodiments, the testing step comprises determining the presence of the one or more mutations using mass spectrometry. In some embodiments, the mass spectrometric format is selected from among Matrix-Assisted Laser Desorption/Ionization, Time-of-Flight (MALDI-TOF), Electrospray (ES), IR-MALDI, Ion Cyclotron Resonance (ICR), Fourier Transform, and combinations thereof.

In some embodiments, the sample is obtained from cells, tissue, whole blood, mouthwash, plasma, serum, urine, stool, saliva, cord blood, chorionic villus sample, chorionic villus sample culture, amniotic fluid, amniotic fluid culture, transcervical lavage fluid, and combination thereof. In further embodiments, the sample is obtained from a pregnant woman, for testing the sample for the presence of one or more CFTR mutations in fetal nucleic acids contained therein. For example, in certain embodiments, the system comprises a station for processing of the samples.

In yet another aspect, the present invention provides a method for screening and/or testing for CFTR mutations, comprising steps of: (a) providing a sample obtained from a subject; (b) testing the sample for the presence of a mutation at a pre-determined position selected from Table 1, 2, 3 or 4, in the CFTR gene or protein; and wherein the presence of the mutation at the pre-determined position indicates that the subject has an increased risk of having CF or a CF related disorder, or being a carrier of a CFTR mutation.

Yet other embodiments of the present invention comprise systems for performing the method. For example, the system may comprise a station or device for testing a sample obtained from a subject to determine the presence of one or more mutations selected from Table 1, 2, 3, or 4 in the CFTR gene or protein, wherein the presence of the one or more mutations indicates that the subject has CF or a CFTR related disorder, is at risk of developing CF or a CF related disorder, or is a carrier of a CFTR mutation. In some embodiments, the one or more mutations are selected from Table 1, 2 or 3. In some embodiments, the one or more mutations are selected from Table 1 or 2. In some embodiments, the one or more mutations are selected from Table 1. In some embodiments, the one or more mutations selected from Table 1, 2, 3, or 4 are part of a panel of CFTR mutations. Also, the system may comprise a device for analysis and/or interpretation of the data. For example, a computer having software to analyze the data for the presence of one of the mutations of the invention may be included in the system.

The following embodiments may be used in either the methods or the systems of the invention. In some embodiments, the testing step comprises determining the identity of the nucleotide and/or amino acid at the pre-determined position selected from Table 1, 2, 3 or 4.

In some embodiments, the presence of the mutation is determined by comparing the identity of the nucleotide and/or amino acid at the pre-determined position to a control.

In some embodiments, the method further comprises a step of determining if the mutation is listed in Table 1, 2, 3 or 4.

In another aspect, the present invention provides products, e.g., reagents, for detecting novel CFTR mutations described herein. Such reagents may be used for detection of the mutations described herein in the protein sequence and/or the nucleic acid sequence.

In some embodiments, the invention provides a nucleic acid probe that specifically binds to a normal CFTR gene but not to a mutant CFTR gene containing one or more mutations selected from Table 1, 2, 3, or 4. In some embodiments, the present invention provides a plurality of probes (e.g., as may be used for real-time PCR or sequencing), or an array containing one or more probes that specifically bind to a normal CFTR gene but not to a mutant CFTR gene containing one or more mutations selected from Table 1, 2, 3, or 4. In some embodiments, the present invention provides a nucleic acid probe that specifically binds to a mutant CFTR gene containing one or more mutations selected from Table 1, 2, 3, or 4 but not to a normal CFTR gene. In some embodiments, the array comprises one or more probes that specifically bind to a mutant CFTR gene containing one or more mutations selected from Table 1, 2, 3, or 4 but not to a normal CFTR gene.

In some embodiments, the present invention provides an antibody that specifically binds to a normal CFTR protein but not to a mutant CFTR protein containing one or more mutations selected from Table 1, 2, 3, or 4. In some embodiments, the present invention provides an antibody that specifically binds to a mutant CFTR protein containing one or more mutations selected from Table 1, 2, 3, or 4 but not to a normal CFTR protein.

In some embodiments, the present invention provides a kit for comprising one or more reagents that differentiate a normal CFTR gene or protein from a mutant CFTR gene or protein containing one or more mutations selected from Table 1, 2, 3, or 4. Such kits may be useful, e.g., for screening and/or testing for CFTR mutations. In some embodiments, the one or more reagents comprises one or more nucleic acid probes. In some embodiments, the one or more reagents comprises one or more antibodies. In some embodiments, the one or more reagents are provided in a form of microarray. In some embodiments, the kit further comprises reagents for primer extension. Or, probes for the detection of mutations may be provided. In some embodiments, the kit further comprises a control indicative of a healthy individual. In some embodiments, the kit further comprises an instruction on how to determine if an individual has CF or a CF related disorder, is at risk of developing CF or a CF related disorder, or is a carrier of a CFTR mutation.

In still another aspect, the present invention provides a computer readable medium encoding information corresponding to one or more mutations shown in Tables 1, 2, 3 and 4. Such computer readable media may be part of the systems as described herein.

Other features, objects, and advantages of the present invention are apparent in the detailed description and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

FIGURES

FIG. 1 is a genomic sequence of the CFTR gene according to an embodiment of the invention.

FIG. 2 is a cDNA sequence of CFTR according to an embodiment of the invention.

FIG. 3 is an amino acid sequence of CFTR according to an embodiment of the invention.

FIG. 4 is a nucleotide sequence of the 5' end of the CFTR gene according to an embodiment of the invention.

DEFINITIONS

Figure 5:
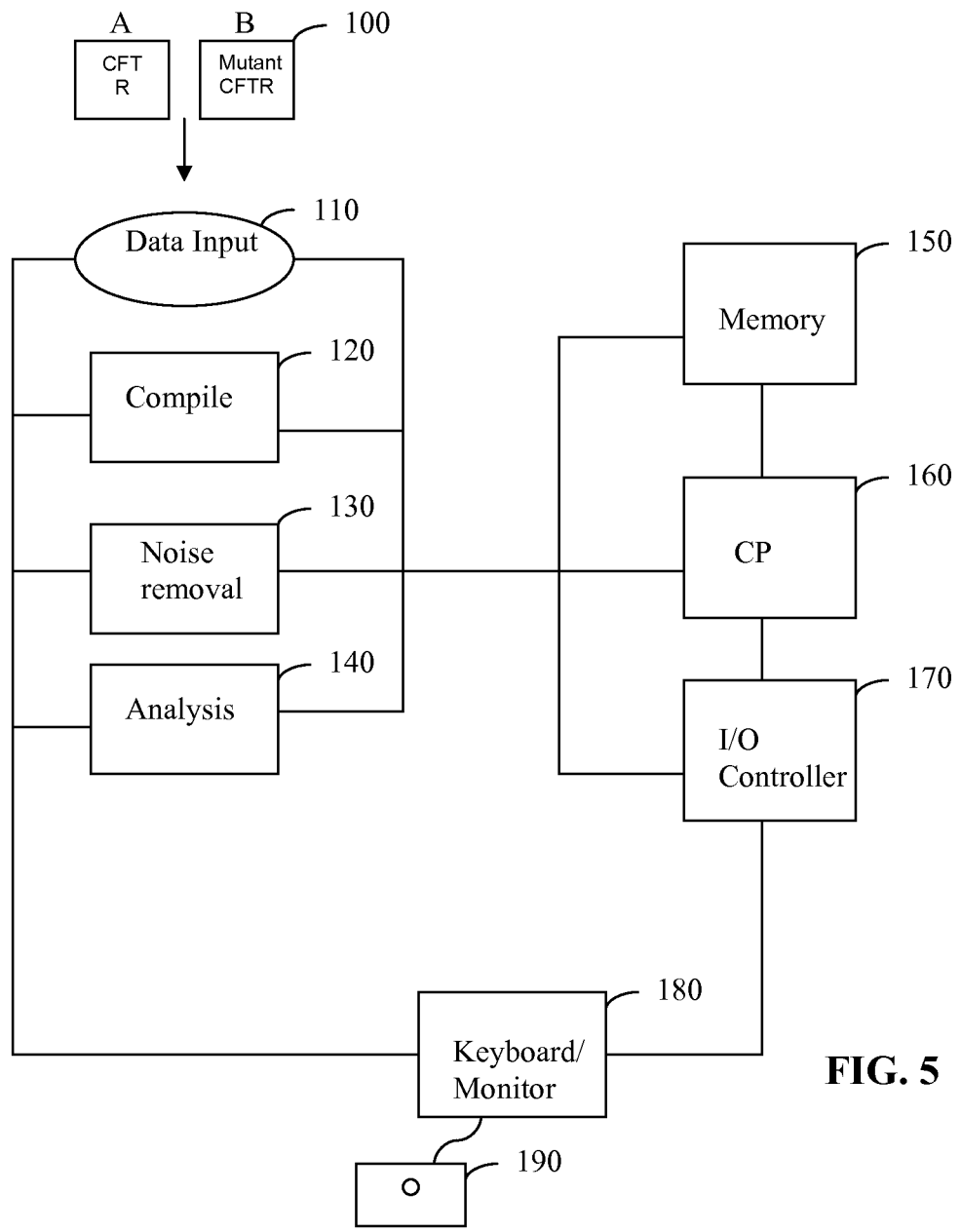
FIG. 5 is a schematic of a system according to an embodiment of the invention.

In order for the present invention to be more readily understood, certain terms are first defined. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Antibody: As used herein, the term "antibody" refers to a polypeptide consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are typically classified as either kappa or lambda. Heavy chains are typically classified as gamma, mu, alpha, delta, or epsilon, which in turn define the immunoglobulin classes, IgG, IgM, IgA, IgD and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain" (VL) and "variable heavy chain" (VH) refer to these light and heavy chains respectively. An antibody can be specific for a particular antigen. The antibody or its antigen can be either an analyte or a binding partner. Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the $(Fab')_2$ dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of ordinary skill in the art will appreciate that such Fab' fragments may be synthesized de novo either chemically or by utilizing recombinant DNA methodology. Thus, the term "antibody," as used herein also includes antibody fragments either produced by the modification of whole antibodies or synthesized de novo using recombinant DNA methodologies. In some embodiments, antibodies are single chain antibodies, such as single chain Fv (scFv) antibodies in which a variable heavy and a variable light chain are joined together (directly or through a peptide linker) to form a continuous polypeptide. A single chain Fv ("scFv") polypeptide is a covalently linked VH::VL heterodimer which may be expressed from a nucleic acid including VH- and VL-encoding sequences either joined directly or joined by a peptide-encoding linker. (See, e.g., Huston, et al. (1988) Proc. Nat. Acad. Sci. USA, 85:5879-5883, the entire contents of which are herein incorporated by reference.) A number of structures exist for converting the naturally aggregated, but chemically separated light and heavy polypeptide chains from an antibody V region into an scFv molecule which will fold into a three dimensional structure substantially similar to the structure of an antigen-binding site. See, e.g. U.S. Pat. Nos. 5,091,513 and 5,132,405 and 4,956,778.

Allele: As used herein, the term "allele" refers to different versions of a nucleotide sequence of a same genetic locus (e.g., a gene).

Allele specific primer extension (ASPE): As used herein, the term "allele specific primer extension (ASPE)" refers to a mutation detection method utilizing primers which hybridize to a corresponding DNA sequence and which are extended depending on the successful hybridization of the 3' terminal nucleotide of such primer. Typically, extension primers that possess a 3' terminal nucleotide which form a perfect match with the target sequence are extended to form extension products. Modified nucleotides can be incorporated into the extension product, such nucleotides effectively labeling the extension products for detection purposes. Alternatively, an extension primer may instead comprise a 3' terminal nucleotide which forms a mismatch with the target sequence. In this instance, primer extension does not occur unless the polymerase used for extension inadvertently possesses exonuclease activity.

Amplification: As used herein, the term "amplification" refers to any methods known in the art for copying a target nucleic acid, thereby increasing the number of copies of a selected nucleic acid sequence. Amplification may be exponential or linear. A target nucleic acid may be either DNA or RNA. Typically, the sequences amplified in this manner form an "amplicon." Amplification may be accomplished with various methods including, but not limited to, the polymerase chain reaction ("PCR"), transcription-based amplification, isothermal amplification, rolling circle amplification, etc. Amplification may be performed with relatively similar amount of each primer of a primer pair to generate a double stranded amplicon. However, asymmetric PCR may be used to amplify predominantly or exclusively a single stranded product as is well known in the art (e.g., Poddar et al. *Molec. And Cell. Probes* 14:25-32 (2000)). This can be achieved using each pair of primers by reducing the concentration of one primer significantly relative to the other primer of the pair (e.g., 100 fold difference). Amplification by asymmetric PCR is generally linear. Additionally, methods such as real-time PCR may be utilized. A skilled artisan will understand that different amplification methods may be used together.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biological sample: As used herein, the term "biological sample" encompasses any sample obtained from a biological source. A biological sample can, by way of non-limiting example, include blood, amniotic fluid, sera, urine, feces, epidermal sample, skin sample, cheek swab, sperm, amniotic fluid, cultured cells, bone marrow sample and/or chorionic villi. Convenient biological samples may be obtained by, for example, scraping cells from the surface of the buccal cavity. The term biological sample encompasses samples which have been processed to release or otherwise make available a nucleic acid or protein for detection as described herein. For example, a biological sample may include a cDNA that has been obtained by reverse transcription of RNA from cells in a biological sample. The biological sample may be obtained from a stage of life such as a fetus, young adult, adult, and the like. Fixed or frozen tissues also may be used.

Carrier: The term "carrier," as used in the context of CF, refers to a person who is symptom-free but carries a CFTR mutation that can be passed to his/her children. Typically, a carrier has one CFTR allele that contains a disease causing mutation and a second allele that is normal or not disease-related. CF and CF related disorders are "autosomal recessive" diseases, meaning that a mutation produces little or no phenotypic effect when present in a heterozygous configuration with a non-disease related allele, but produces a "disease state" when a person is homozygous, i.e., both CFTR alleles are mutant alleles that contain the same disease causing mutation or compound heterozygous, i.e., both CFTR alleles are mutant alleles that contain two different disease-causing mutations. A carrier status is whether or not one is a carrier.

Coding sequence vs. non-coding sequence: As used herein, the term "coding sequence" refers to a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced therefrom. As used herein, the term "non-coding sequence" refers to a sequence of a nucleic acid or its complement, or a part thereof, that is not transcribed into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, etc.

Complement: As used herein, the terms "complement," "complementary" and "complementarity," refer to the pairing of nucleotide sequences according to Watson/Crick pairing rules. For example, a sequence 5'-GCGGTCCCA-3' has the complementary sequence of 5'-TGGGACCGC-3'. A complement sequence can also be a sequence of RNA complementary to the DNA sequence. Certain bases not commonly found in natural nucleic acids may be included in the complementary nucleic acids including, but not limited to, inosine, 7-deazaguanine, Locked Nucleic Acids (LNA), and Peptide Nucleic Acids (PNA). Complementary need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Control: As used herein, the term "control" has its art-understood meaning of being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. In one experiment, the "test" (i.e., the variable being tested) is applied. In the second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control.

Crude: As used herein, the term "crude," when used in connection with a biological sample, refers to a sample which is in a substantially unrefined state. For example, a crude sample can be cell lysates or biopsy tissue sample. A crude sample may exist in solution or as a dry preparation.

Deletion: As used herein, the term "deletion" encompasses a mutation that removes one or more nucleotides from a naturally-occurring nucleic acid.

Epitope: As used herein, the term "epitope" refers to a fragment or portion of a molecule or a molecule compound (e.g., a polypeptide or a protein complex) that makes contact with a particular antibody or antibody like proteins.

Familial history: As used herein, the term "familial history" typically refers to occurrence of events (e.g., CF disease, CF related disorder or CFTR mutation carrier) relating to an individual's immediate family members including parents and siblings. Sometimes, family history also may include grandparents.

Flanking: As used herein, the term "flanking" is meant that a primer hybridizes to a target nucleic acid adjoining a region of interest sought to be amplified on the target. The skilled artisan will understand that preferred primers are pairs of primers that hybridize 3' from a region of interest, one on each strand of a target double stranded DNA molecule, such that nucleotides may be add to the 3' end of the primer by a suitable DNA polymerase. For example, primers that flank mutant CTFR sequences do not actually anneal to the mutant sequence but rather anneal to sequence that adjoins the mutant sequence. In some cases, primers that flank a CFTR exon are generally designed not to anneal to the exon sequence but rather to anneal to sequence that adjoins the exon (e.g. intron sequence). However, in some cases, amplification primer may be designed to anneal to the exon sequence.

Genotype: As used herein, the term "genotype" refers to the genetic constitution of an organism. More specifically, the term refers to the identity of alleles present in an individual. "Genotyping" of an individual or a DNA sample refers to identifying the nature, in terms of nucleotide base, of the two alleles possessed by an individual at a known polymorphic site.

Heterozygous: As used herein, the term "heterozygous" or "HET" refers to an individual possessing two different alleles of the same gene. As used herein, the term "heterozygous" encompasses "compound heterozygous" or "compound heterozygous mutant." As used herein, the term "compound heterozygous" refers to an individual possessing two different alleles. As used herein, the term "compound heterozygous mutant" refers to an individual possessing two different copies of an allele, such alleles are characterized as mutant forms of a gene. The term "mutant" as used herein refers to a mutated, or potentially non-functional form of a gene. (See "mutations of the CFTR gene.")

Homozygous: As used herein, the term "homozygous" refers to an individual possessing two copies of the same allele. As used herein, the term "homozygous mutant" refers to an individual possessing two copies of the same allele, such allele being characterized as the mutant form of a gene. The term "mutant" as used herein refers to a mutated, or potentially non-functional form of a gene.

Hybridize: As used herein, the term "hybridize" or "hybridization" refers to a process where two complementary nucleic acid strands anneal to each other under appropriately stringent conditions. Oligonucleotides or probes suitable for hybridizations typically contain 10-100 nucleotides in length (e.g., 18-50, 12-70, 10-30, 10-24, 18-36 nucleotides in length). Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementary will stably hybridize, while those having lower complementary will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

Insertion or addition: As used herein, the term "insertion" or "addition" refers to a change in an amino acid or nucleotide sequence resulting in the addition of one or more amino acid residues or nucleotides, respectively, as compared to the naturally occurring molecule.

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism such as a non-human animal.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, about 95%, about 98%, about 99%, substantially 100%, or 100% of the other components with which they were initially associated. In some embodiments, isolated agents are more than about 80%, about 85%, about 90%, about 91%, about 92%, about 93%, about 94%, about 95%, about 96%, about 97%, about 98%, about 99%, substantially 100%, or 100% pure. As used herein, a substance is "pure" if it is substantially free of other components. As used herein, the term "isolated cell" refers to a cell not contained in a multi-cellular organism.

Labeled: The terms "labeled" and "labeled with a detectable agent or moiety" are used herein interchangeably to specify that an entity (e.g., a nucleic acid probe, antibody, etc.) can be visualized, for example following binding to another entity (e.g., a nucleic acid, polypeptide, etc.). The detectable agent or moiety may be selected such that it generates a signal which can be measured and whose intensity is related to (e.g., proportional to) the amount of bound entity. A wide variety of systems for labeling and/or detecting proteins and peptides are known in the art. Labeled proteins and peptides can be prepared by incorporation of, or conjugation to, a label that is detectable by spectroscopic, photochemical, biochemical, immunochemical, electrical, optical, chemical or other means. A label or labeling moiety may be directly detectable (i.e., it does not require any further reaction or manipulation to be detectable, e.g., a fluorophore is directly detectable) or it may be indirectly detectable (i.e., it is made detectable through reaction or binding with another entity that is detectable, e.g., a hapten is detectable by immunostaining after reaction with an appropriate antibody comprising a reporter such as a fluorophore). Suitable detectable agents include, but are not limited to, radionucleotides, fluorophores, chemiluminescent agents, microparticles, enzymes, colorimetric labels, magnetic labels, haptens, molecular beacons, aptamer beacons, and the like.

Multiplex PCR: As used herein, the term "multiplex PCR" refers to amplification of two or more regions which are each primed using a distinct primers pair.

Multiplex ASPE: As used herein, the term "multiplex ASPE" refers to an assay combining multiplex PCR and allele specific primer extension for detecting polymorphisms. Typically, multiplex PCR is used to first amplify regions of DNA that will serve as target sequences for ASPE primers. See the definition of allele specific primer extension.

Mutations of the CFTR gene: As used herein, the term "mutations of the CFTR gene" refers to one or more abnormal nucleic acid sequences as compared to a wild-type CFTR gene sequence. The "mutations of the CFTR gene" are also referred to as "mutant CF sequences." Mutations of the CFTR gene encompass substitutions (e.g., single nucleotide polymorphisms (SNP)), deletions, insertions, additions, and/or duplications.

Primer: As used herein, the term "primer" refers to a short single-stranded oligonucleotide capable of hybridizing to a complementary sequence in a nucleic acid sample. Typically, a primer serves as an initiation point for template dependent DNA synthesis. Deoxyribonucleotides can be added to a primer by a DNA polymerase. In some embodiments, such deoxyribonucleotides addition to a primer is also known as primer extension. The term primer, as used herein, includes all forms of primers that may be synthesized including peptide nucleic acid primers, locked nucleic acid primers, phosphorothioate modified primers, labeled primers, and the like. A "primer pair" or "primer set" for a PCR reaction typically refers to a set of primers typically including a "forward primer" and a "reverse primer." As used herein, a "forward primer" refers to a primer that anneals to the anti-sense strand of dsDNA. A "reverse primer" anneals to the sense-strand of dsDNA.

Polymorphism: As used herein, the term "polymorphism" refers to the coexistence of more than one form of a gene or portion thereof.

Pure or substantially pure: As used herein, the term "pure or substantially pure" refers to a compound, e.g., a protein or polypeptide that has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

Real-time PCR: As used herein, the term "real-time PCR" refers to quantitative real time polymerase chain reaction (Q-PCR/qPCR/qrt-PCR) or kinetic polymerase chain reaction (KPCR), is a laboratory technique based on the PCR, which is used to amplify and simultaneously quantify a targeted DNA molecule. It enables both detection and quantification (as absolute number of copies or relative amount when normalized to DNA input or additional normalizing genes) of one or more specific sequences in a DNA sample.

Sense strand vs. anti-sense strand: As used herein, the term "sense strand" refers to the strand of double-stranded DNA (dsDNA) that includes at least a portion of a coding sequence of a functional protein. As used herein, the term "anti-sense strand" refers to the strand of dsDNA that is the reverse complement of the sense strand.

Specific: As used herein, the term "specific," when used in connection with an oligonucleotide primer, refers to an oligonucleotide or primer, under appropriate hybridization or washing conditions, is capable of hybridizing to the target of interest and not substantially hybridizing to nucleic acids which are not of interest. Higher levels of sequence identity are preferred and include at least 60%, 65%, 70%, 75%, 80%, 85%, 90%, 95%, 98%, 99%, or 100% sequence identity. In some embodiments, a specific oligonucleotide or primer contains at least 4, 6, 8, 10, 12, 14, 16, 18, 20, 22, 24, 26, 28, 30, 35, 40, 45, 50, 55, 60, 65, 70, or more bases of sequence identity with a portion of the nucleic acid to be hybridized or amplified when the oligonucleotide and the nucleic acid are aligned.

Subject: As used herein, the term "subject" refers to a human or any non-human animal. A subject can be a patient, which refers to a human presenting to a medical provider for diagnosis or treatment of a disease. A human includes pre and post natal forms. Particularly preferred subjects are humans being tested for the existence of a CFTR carrier state, CF disease or CF related disorder state.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially complementary: As used herein, the term "substantially complementary" refers to two sequences that can hybridize under stringent hybridization conditions. The skilled artisan will understand that substantially complementary sequences need not hybridize along their entire length. In some embodiments, "stringent hybridization conditions" refer to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5× Denhart's solution at 42° C. overnight; washing with 2×SSC, 0.1% SDS at 45° C.; and washing with 0.2×SSC, 0.1% SDS at 45° C. In some embodiments, stringent hybridization conditions should not allow for hybridization of two nucleic acids which differ over a stretch of 20 contiguous nucleotides by more than two bases.

Substitution: As used herein, the term "substitution" refers to the replacement of one or more amino acids or nucleotides by different amino acids or nucleotides, respectively, as compared to the naturally occurring molecule.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Wild-type: As used herein, the term "wild-type" refers to the typical or the most common form existed in nature. For example, a wild-type CFTR gene or protein refers to the typical or the most common form of CFTR gene or protein existed in a natural population. As used herein, "wild-type" is used interchangeably with "naturally-occurring." In some embodiment, a wild-type CFTR gene or a locus thereof, refers to the CFTR gene sequence which is found in NCBI GenBank locus ID M58478 (HUMCFTC) (SEQ ID NO:4) (FIG. 4). The CFTR gene is located on chromosome 7, which may be found in NCBI GenBank locus AC000111 and AC000061, the contents of which are incorporated herein in their entirety by reference. The cDNA for the CFTR gene is found in Audrezet et al., *Hum. Mutat.* (2004) 23 (4), 343-357.

DETAILED DESCRIPTION

The present invention provides, among other things, methods, products and systems that use novel mutations in the cystic fibrosis transmembrane conductance regulator (CFTR) gene in screening and/or testing for CF and CF related diseases, disorders or conditions. For example, the novel mutations provided herein can be used to assist in clinical diagnosis of CF disease, CF related disease, disorder or condition, or carrier status and for genetic counseling (e.g., for evaluation of an individual's risk for developing CF or being a carrier of a CFTR mutation). The novel mutations provided herein can be used alone or in combination with other known CFTR mutations as part of a panel of CFTR mutations.

Various aspects of the invention are described in detail in the following sections. The use of sections is not meant to limit the invention. Each section can apply to any aspect of the invention. In this application, the use of "or" means "and/or" unless stated otherwise.

Novel Mutations in the CFTR Gene

The CFTR gene was mapped to chromosome 7 and described in, for example, U.S. Pat. No. 6,201,107 and U.S. Pat. No. 5,776,677, the disclosures of which are incorporated by reference herein in their entirety. The CFTR genomic sequence is described in GenBank Accession Number NC_000007 (range: 117120016 . . . 117308718; the entire contents of which are herein incorporated by reference) (SEQ ID NO:1) (FIG. 1). The CFTR gene contains 27 exons. The exons are numbered 1, 2, 3, 4, 5, 6a, 6b, 7, 8, 9, 10, 11, 12, 13, 14a, 14b, 15, 16, 17a, 17b, 18, 19, 20, 21, 22, 23, and 24. The CFTR cDNA sequence is described in GenBank Accession Number AR016032.1 (SEQ ID NO:2) (FIG. 2).

The CFTR protein is described in, for example, U.S. Pat. No. 5,543,399, the disclosure of which is incorporated by reference herein in its entirety. The CFTR protein sequence is also described in GenBank Accession Number AAC90840.1 (SEQ ID NO:3) (FIG. 3).

As described in Example 1, the inventors of the present application identified various novel mutations in the CFTR gene (Table 5). These mutations were identified by sequence analysis of the CFTR gene in specimens submitted for clinical testing obtained from individuals who were known to be affected with CF or likely to be a carrier because of familial history, or suspected to be affected with CF based on other CF testing (see Clinical Indication listed in Table 5). The mutations were identified by comparing the CFTR gene sequence from patient samples to the wild-type CFTR gene or protein sequence (see SEQ ID NO:1-3). As shown in Table 5, patients carrying these mutations were from different ethnic groups including Caucasians, African Americans, Hispanics, and Asians. Thus, these mutations may be particularly useful for developing more effective genetic testing for patients from non-Caucasian racial groups.

Novel mutations described herein are located in introns (e.g., intron 3, intron 6a, intron 11, intron 14a, intron 19, intron 20, intron 21, and intron 23) and exons (e.g., exon 2, exon 3, exon 4, exon 5, exon 6a, exon 6b, exon 7, exon 9, exon 10, exon 11, exon 12, exon 13, exon 14a, exon 14b, exon 15, exon 16, exon 17a, exon 17b, exon 19, exon 20, exon 21, exon 22, and exon 24). Some of the novel mutations are nonsense mutations, i.e., mutations that result in a stop codon. Some of the novel mutations are missense mutations, i.e., mutations that result in amino acid substitutions. Some of the novel mutations cause in-frame insertions and/or deletions. Some of the novel mutations delete one or more nucleotides in such a manner as to lead to a shift in the reading frame. Some of the novel mutations alter the sequence at a splice junction, for example, consensus splice site ag/gt or other splice sites. Thus, most of the novel mutations described herein are likely to disrupt CFTR gene or protein expression or function.

The "ACMG recommendations for standards for interpretation and reporting of sequence variations: Revisions 2007" (Richards S C et al. Genetics in Medicine, 10:294-300, which is incorporated herein by reference), provides interpretive categories and definitions of sequence variations which can be used, along with additional test results and clinical information to classify the novel mutations described herein into the following groups.

Group I:
Patient has a novel sequence change that can be classified as category 2 according to the ACMG guidelines (i.e., nonsense, frame shift (FS), consensus splice site ag/gt). Patient has another well established CF disease causing mutation (i.e. F508, W1282X, etc). Patient indication is suspected of having CF, known to be affected with CF or identified through newborn screening. The Group I mutations, which are of particular interest, are shown in Table 1 and these mutations are expected to cause CF or CF related diseases, disorders or conditions.

Group IIA:
Patient has novel sequence change that can be classified as category 3 according to the ACMG guidelines (i.e., missense, in-frame ins/del, other splice site mutations, etc). Patient has another well established CF disease causing mutation (i.e., F508, W1282X, etc.). Patient is suspected of having CF, known to be affected with CF, or identified through positive newborn screening. The Group IIA mutations are shown in Table 2 (under subsection Group IIA).

Group IIB:
Patient has a novel sequence change that can be classified as category 3 according to the ACMG guidelines (i.e., missense, in-frame ins/del, other splice site mutations, etc). Patient is suspected of having CF, known to be affected with CF, or identified through positive newborn screening. The Group IIB mutations are shown in Table 2 (under subsection Group IIB).

Group III:
Patient has novel sequence change that can be classified as category 3 according to the ACMG guidelines (i.e., missense, in-frame insertions/deletions, other splice site mutations, etc). Patient has another well established CF disease causing mutation (i.e. F508, W1282X, etc). Patient indication is suspected of having CF, known to be affected with CF, or identified through newborn screening. Patient has an additional change(s) of unknown clinical significance. The Group III mutations are shown in Table 3.

Group IV:
Mutations other than the Group I, II, and III mutations identified above. The Group IV mutations are shown in Table 4.

Novel CFTR mutations according to the invention however are not limited to the specific nucleotide or amino acid variations identified in Tables 1-4 and should encompass any abnormal nucleotides or amino acid residues, as compared to the wild-type CFTR gene or protein sequences, that may be present at any of the positions identified in Tables 1-4.

TABLE 1

| Sequence Change | Type of mutation | AA Change | Ethnicity | Other Mutations | Clinical Information | Exon |
|---|---|---|---|---|---|---|
| Group I mutations | | | | | | |
| 1824delA | Frameshift (FS) | n/a | Caucasian | F508del | Mutation was identified in a 22 year old patient with a known diagnosis of CF. This patient carried a second mutation known to cause CF (F508del). | e12 |
| 2957delT | FS | n/a | Caucasian | F508del | Mutation was identified in a 1 year old patient with a known diagnosis of CF. The patient carried a second mutation known to cause CF (F508del). | e15 |
| 4089ins4 | FS | n/a | Caucasian | F508del | Mutation was identified in a 7 year old patient with a known diagnosis of CF. The | e21 |

TABLE 1-continued

| Sequence Change | Type of mutation | AA Change | Ethnicity | Other Mutations | Clinical Information | Exon |
|---|---|---|---|---|---|---|
| 4374 + 2T > C | Splice site mutation | n/a | 1. Caucasian | 1. F508del | patient had a positive sweat chloride test. The patient carried a second mutation known to cause CF (F508del). Patient #1: Mutation was identified in a 45 year old patient with a suspected diagnosis of CF. The patient carried a second mutation known to cause CF (F508del). | i23 |
| | | | 2. Caucasian | 2. F508del | Patient #2: Mutation was identified in a 52 year old patient with a suspected diagnosis of CF. The patient carried a second mutation known to cause CF (F508del). | |
| 3064A > T | Nonsense | K978X | African American | Q1042X | Mutation was identified in a 26 year old patient with a known diagnosis of CF. The patient carried a second mutation likely to cause CF Q1042X. | e16 |
| 246C > G | Nonsense | Y38X | Caucasian | F508del | Mutation was identified in a 1 month old patient with a suspected diagnosis of CF. The patient had a positive sweat chloride test. The patient carried a second mutation known to cause CF (F508del). | e2 |
| | | | | Group IIA | | |
| 269C > T | Missense (MS) | A46V | 1) Caucasian | 1) 3849 + 12192G > A | Patient #1: Mutation was identified in a 32 year old patient who was tested due to abnormalities found on fetal ultrasound. The patient carried a second mutation of unknown clinical significance (3849 + 12192G > A). | e2 |
| | | | 2) Black | 2) F508del | Patient #2: Mutation was identified in a 2 month old patient who was tested based on follow-up for a positive newborn screen. The patient carried a second mutation known to cause cystic fibrosis (F508del). | |
| | | | 3) African American | 3) none | Patient #3: Mutation was identified in a 24 year old patient who was tested as a parental follow-up to a positive newborn screen. | |
| 2902G > T | MS | D924Y | Caucasian | F508del | Mutation was identified in a 1 month old patient with a suspected diagnosis of CF. The patient also had a positive sweat chloride test and carried a second mutation known to cause CF (F508del) | e15 |
| 3814G > A | MS | E1228K | Caucasian | F508del | Mutation was identified in a 1 month old patient with a suspected diagnosis of CF. The patient had a borderline sweat chloride test. The patient carried a second mutation known to cause CF (F508del). | e19 |
| 502G > C | MS | G124R | Not Provided | F508del | Mutation was identified in a 2 month old patient with a suspected diagnosis of CF. The patient had a positive sweat chloride test. The patient carried a second mutation known to cause CF (F508del). | e4 |
| 1520G > T | MS | G463V | Caucasian | F508del | Mutation was identified in a 17 year old patient with a known diagnosis of CF. Patient carried a second mutation known to cause CF (F508del). | e9 |
| 511_513dup TTA | In frame duplication | L127dup | Caucasian, Asian | W1282X | Mutation was identified in a newborn with a suspected diagnosis of CF. The patient had clinical symptoms of CF including as a positive sweat chloride test, meconium ileus, echogenic bowel, and pancreatic insufficiency. The patient carried a second mutation known to cause CF (W1282X). | e4 |
| 978A > T | MS | E282D | 1. not provided | 1. 3120 + 1G > A | Patient #1: Mutation was identified in a 10 year old patient with a suspected diagnosis of CF. The patient had a positive sweat chloride test. The patient carried a second mutation known to cause CF (3120 + 1G > A). | e6b |
| | | | 2. not provided | 2) none | Patient #2: Mutation was identified in a 4 year old patient with a suspected diagnosis of CF and a family history of CF. | |
| 843G > C | MS | Q237H | Caucasian | F508del | Mutation was identified in a 2 month old patient with a known diagnosis of CF. The patient carried a second mutation known to cause CF (F508del). | e6a |

TABLE 1-continued

| Sequence Change | Type of mutation | AA Change | Ethnicity | Other Mutations | Clinical Information | Exon |
|---|---|---|---|---|---|---|
| 829C > T | MS | L233F | Caucasian | D1152H | Mutation was identified in a 1 month old patient who was tested following a positive newborn screen. The patient carried a second mutation known to cause CF (D1152H). | e6a |
| 4096 – 6C > T | Splice site mutation | None | Caucasian | F508del | Mutation was identified in a 58 year old patient with a suspected diagnosis of CF. The patient carried a second mutation known to cause CF (F508del). | i21 |
| 4375 – 7delT | Splice site mutation | None | Caucasian | F508del | Mutation was identified in a 6 year old patient with a suspected diagnosis of CF. Patient has a family history, a borderline sweat chloride test and recurrent pneumonia. The patient carried a second mutation known to cause CF (F508del). | i23 |
| 1586G > C | MS | S485T | Caucasian | S1235R | Mutation was identified in a 2 year old patient with a suspected diagnosis of CF. The patient carried a second mutation S1235R (3837T > G) which has been reported in individuals with varying CF phenotypes. | e10 |
| Group IIB | | | | | | |
| 875 + 4G > T | Splice site mutation | n/a | African American | none | Mutation was identified in a 1 month old patient who had a positive newborn screening test. | i6a |
| 4005 + 3G > T | Splice site mutation | n/a | Caucasian | none | Mutation was identified in a 40 year old patient who was tested to determine if they were a carrier, there was no family history of CF. | i20 |

TABLE 3

| Group III Mutations | | | | | | |
|---|---|---|---|---|---|---|
| Sequence Change | Type of mutation | AA Change | Ethnicity | Other Mutations | Clinical Information | Exon |
| 2711T > C | MS | I860T | Caucasian | F508del, E528E | Mutation was identified in a 58 year old woman with a suspected diagnosis of CF. The patient carried a second mutation known to cause CF (F508del) and an additional mutation of unknown clinical significance (E528E).. | e14a |
| 3891G > C | MS | L1253F | Not provided | G85E, L15P | Mutation was identified in a 32 year old patient with a known diagnosis of CF. The patient carried a second mutation known to cause CF (G85E) and an additional mutation of unknown clinical significance (L15P). | e20 |
| 2524C > T | MS | P798S | African American | F508del, R74W, G921E, D1270N | Mutation was identified in a 5 year old patient with a suspected diagnosis of CF. The patient had a positive sweat chloride test. This patient carried a second mutation known to cause CF (F508del) and three additional mutations of unknown clinical significance (R74W, G921E, D1270N). | e13 |
| 2894G > A | MS | G921E | African American | F508del, R74W, P798S, D1270N | Mutation was identified in a 5 year old patient with a suspected diagnosis of CF. The patient had a positive sweat chloride test. This patient carried a second mutation known to cause CF (F508del) and three additional mutations of unknown clinical significance (R74W, P789S, D1270N). | e15 |

TABLE 4

| Group IV Mutations | | | | | | |
|---|---|---|---|---|---|---|
| Sequence Change | Type of mutation | AA Change | Ethnicity | Other Mutations | Clinical Information | Exon |
| 405 + 10247C > T | Possible splice site mutation | n/a | Caucasian | F508del | Mutation was identified in a 35 year old patient who was tested to determine if they were a carrier, there was no family history of CF. This patient carried a second mutation known to cause CF (F508del) | i3 |

TABLE 4-continued

Group IV Mutations

| Sequence Change | Type of mutation | AA Change | Ethnicity | Other Mutations | Clinical Information | Exon |
|---|---|---|---|---|---|---|
| 405 + 10255delC | Possible splice site mutation | n/a | Not Provided | F508del, 124del23bp | Mutation was identified in a 10 year old patient. The patient carries two mutations know to cause CF (F508del and 124del23). | i3 |
| 1811 + 1643G > T | Possible splice site mutation | n/a | 1. Hispanic | 1. F508del | Patient #1: Mutation was identified in a 1 year old patient with a known diagnosis of CF. Patient had a positive sweat chloride test. The patient carried a second mutation known to cause CF (F508del). | i11 |
| | | | 2. Hispanic | 2. F508del | Patient #2: Mutation was identified in a 6 year old patient with a known diagnosis of CF. The patient carried a second mutation know to cause CF (F508del). | |
| | | | 3. Not provided | 3. none | Patient #3: Mutation was identified in an 8 month old patient with a suspected diagnosis of CF. | |
| 1812 − 13A > G | Splice site mutation | n/a | Caucasian | none | Mutation was identified in a 15 year old patient with a suspected diagnosis of CF. The patient has chronic sinusitis. | i11 |
| 2752 − 33insA | Possible splice site mutation | n/a | African American | F693L | Mutation was identified in a 6 year old patient with a known diagnosis of CF. The patient carries a second mutation of unknown clinical significance (F693L). | i14a |
| 3849 + 12192G > A | Possible splice site mutation | n/a | Caucasian | A46V | Mutation was identified in a 32 year old patient who was tested due to abnormalities found on fetal ultrasound. The patient carried an additional mutation of known clinical significance (A46V). | i19 |
| 724G > A | MS | A198T | Hispanic | none | Mutation was identified in a 4 month old patient with a suspected diagnosis of CF. | e6a |
| 3899C > T | MS | A1256V | Guyanese | none | Mutation was identified in a 45 year old patient who was tested to determine if they were a carrier, there was no family history of CF. | e20 |
| 3986C > T | MS | A1285V | Not Provided | none | Mutation was identified in a 23 year old patient who was tested to determine if they were a carrier, there was no family history of CF. | e20 |
| 901G > A | MS | E257K | Hispanic | none | Mutation was identified in a 4 year old patient with a suspected diagnosis of CF. The patient has asthma and recurring pneumonia. | e6b |
| 392T > C | MS | F87S | Not Provided | none | The mutation was identified in a 1 month old patient with a suspected diagnosis of CF. | e3 |
| 3463T > C | MS | F1111L | Hispanic | none | Mutation was identified in a 6 year old patient with a suspected diagnosis of CF. The patient has asthma. | e17b |
| 1757G > A | MS | G542E | Hispanic | none | Mutation was identified in a 25 year old patient who was tested to determine if they were a carrier, there was no family history of CF. The patient carried 2 copies of G542E.. | e11 |
| 4025G > C | MS | G1298A | Asian | G970D, Q1352H | Mutation was identified in a 34 year old patient with congenital absence of the vas deferens. The patient carried two other mutations of unknown clinical significance (G970D and Q1352H). | e21 |
| 4129G > T | MS | G1333W | Not Provided | none | Mutation was identified in an 8 year old patient with a suspected diagnosis of CF. Patient had recurrent respiratory infections and chronic cough. | e22 |
| 663T > G | MS | I177M | Caucasian | none | Mutation was identified in a 34 year old patient who was tested to determine if they were a carrier, there was no family history of CF. | e5 |
| 3200T > C | MS | I1023T | Hispanic | none | Mutation was identified in a 34 year old patient who was tested to determine if they were a carrier, there was no family history of CF. | e17a |
| 4412T > C | MS | I1427T | Asian | S1444S | Mutation was identified in a 34 year old patient who was tested to determine if they were a carrier, there was no family history of CF. The patient carried another mutation that is considered likely to be clinically benign (S144S). | e24 |
| 620A > C | MS | K163T | Caucasian | none | Mutation was identified in a 32 year old patient with a family history of CF. | e4 |
| 1738 A > G | MS | K536E | Hispanic | I488I | Mutation was identified in a 19 year old patient who's son had a positive newborn screening test. The patient carried another mutation that is considered likely to be clinically benign (I488I).. | e11 |
| 3370A > C | MS | K1080Q | Caucasian | none | Mutation was identified in a 9 year old patient with a suspected diagnosis of CF. The patient had asthma and failure to thrive. | e17b |

TABLE 4-continued

Group IV Mutations

| Sequence Change | Type of mutation | AA Change | Ethnicity | Other Mutations | Clinical Information | Exon |
|---|---|---|---|---|---|---|
| 1129 C > T | MS | L333F | Asian | none | Mutation was identified in a 37 year old patient who tested to determine if they were a carrier, there was no family history of CF. | e7 |
| 2383C > T | MS | R751C | Caucasian | 2183delAA > G | Mutation was identified in a 36 year old patient who was being tested due to a partner being a CF carrier. The patient also carried a second mutation known to cause CF (2183delAA > G). | e13 |
| 2761delTCT | In frame deletion | S877del | Caucasian | F508del, D1152H | Mutation was identified in 1 month old patient who had a positive sweat chloride test. The patient carried two additional mutations known to cause CF (F508del and D1152H). | e14b |
| 1106A > G | MS | Y325C | Caucasian | R334W | Mutation was identified in a 35 year old patient who was tested to determine if they were a carrier, there was no family history of CF. Patient carried a second mutation known to cause CF (R334W). | e7 |
| 622A > G | MS | T164A | Caucasian | none | Mutation was identified in a 3 month old patient with a suspected diagnosis of CF. | e5 |

Detection of CFTR Mutations

A variety of methods known in the art can be used to detect CFTR gene mutations disclosed in the present invention. For example, methods that have been used to detect previously identified CFTR gene mutations have been described and are adaptable for use with the present invention. See e.g., Audrezet et al., "Genomic rearrangements in the CFTR gene: extensive allelic heterogeneity and diverse mutational mechanisms" *Hum Mutat.* 2004 April; 23(4):343-57; PCT WO 2004/040013 A1 and corresponding US application No. 20040110138; titled "Method for the detection of multiple genetic targets" by Spiegelman and Lem; US patent application No. 20030235834; titled "Approaches to identify cystic fibrosis" by Dunlop et al.; and US patent application No. 20040126760 titled "Novel compositions and methods for carrying out multiple PCR reactions on a single sample" by N. Broude, the entire contents of each of which are herein incorporated by reference.

Nucleic Acid Analyses

In certain embodiments, CFTR gene mutations disclosed herein are detected at the nucleic acid level. For example, nucleic acid can be analyzed by sequencing, hybridization, PCR amplification, restriction enzyme digestion, primer extension such as single-base primer extension or multiplex allele-specific primer extension (ASPE).

Nucleic acid analyses can be performed on genomic DNA, messenger RNAs, and/or cDNA. In many embodiments, nucleic acids are extracted from a biological sample. In some embodiments, nucleic acids are analyzed without having been amplified. In some embodiments, nucleic acids are amplified using techniques known in the art (such as polymerase chain reaction (PCR)) and amplified nucleic acids are used in subsequent analyses. Multiplex PCR, in which several amplicons (e.g., from different genomic regions) are amplified at once using multiple sets of primer pairs, may be employed. Additionally, methods such as real-time PCR, as are known in the art, may be used to perform nucleic acid analysis.

In some embodiments, nucleic acids are amplified in a manner such that the amplification product for a wild-type allele differs in size from that of a mutant allele. Thus, presence or absence of a particular mutant allele can be determined by detecting size differences in the amplification products, e.g., on an electrophoretic gel. For example, deletions or insertions of CFTR gene regions may be particularly amenable to using size-based approaches.

Certain exemplary nucleic acid analysis methods are described in detail below.

Allele-Specific Amplification

In some embodiments, CFTR gene mutations are detected using an allele-specific amplification assay. This approach is variously referred to as PCR amplification of specific allele (PASA) (Sarkar, et al., 1990 *Anal. Biochem.* 186:64-68), allele-specific amplification (ASA) (Okayama, et al., 1989 *J. Lab. Clin. Med.* 114:105-113), allele-specific PCR (ASPCR) (Wu, et al. 1989 *Proc. Natl. Acad. Sci. USA.* 86:2757-2760), and amplification-refractory mutation system (ARMS) (Newton, et al., 1989 *Nucleic Acids Res.* 17:2503-2516). The entire contents of each of these references is incorporated herein. This method is applicable for single base substitutions as well as micro deletions/insertions.

For example, for PCR-based amplification methods, amplification primers may be designed such that they can distinguish between different alleles (e.g., between a wild-type allele and a mutant allele). Thus, the presence or absence of amplification product can be used to determine whether a CFTR gene mutation is present in a given nucleic acid sample. In some embodiments, allele specific primers can be designed such that the presence of amplification product is indicative of a CFTR gene mutation. In some embodiments, allele specific primers can be designed such that the absence of amplification product is indicative of a CFTR gene mutation.

In some embodiments, two complementary reactions are used. One reaction employs a primer specific for the wild type allele ("wild-type-specific reaction") and the other reaction employs a primer for the mutant allele ("mutant-specific reaction"). The two reactions may employ a common second primer. PCR primers specific for a particular allele (e.g., the wild-type allele or mutant allele) generally perfectly match one allelic variant of the target, but are mismatched to other allelic variant (e.g., the mutant allele or wild-type allele). The mismatch may be located at/near the 3' end of the primer, leading to preferential amplification of the perfectly matched allele. Whether an amplification product can be detected from one or in both reactions indicates the absence or presence of the mutant allele. Detection of an amplification product only from the wild-type-specific reaction indicates presence of the wild-type allele only (e.g., homozygosity of the wild-type allele). Detection of an amplification product in the mutant-specific reaction only indicates presence of the mutant allele only (e.g. homozygosity of the mutant allele). Detection of amplification products from both reactions indicate (e.g., a heterozygote). As used herein, this approach will be referred to as "allele specific amplification (ASA)."

Allele-specific amplification can also be used to detect duplications, insertions, or inversions by using a primer that hybridizes partially across the junction. The extent of junction overlap can be varied to allow specific amplification.

Amplification products can be examined by methods known in the art, including by visualizing (e.g., with one or more dyes) bands of nucleic acids that have been migrated (e.g., by electrophoresis) through a gel to separate nucleic acids by size.

Allele-Specific Primer Extension

In some embodiments, an allele-specific primer extension (ASPE) approach is used to detect CFTR gene mutations. ASPE employs allele-specific primers that can distinguish between alleles (e.g., between a mutant allele and a wild-type allele) in an extension reaction such that an extension product is obtained only in the presence of a particular allele (e.g., mutant allele or wild-type allele). Extension products may be detectable or made detectable, e.g., by employing a labeled deoxynucleotide in the extension reaction. Any of a variety of labels are compatible for use in these methods, including, but not limited to, radioactive labels, fluorescent labels, chemiluminescent labels, enzymatic labels, etc. In some embodiments, a nucleotide is labeled with an entity that can then be bound (directly or indirectly) by a detectable label, e.g., a biotin molecule that can be bound by streptavidin-conjugated fluorescent dyes. In some embodiments, reactions are done in multiplex, e.g., using many allele-specific primers in the same extension reaction.

In some embodiments, extension products are hybridized to a solid or semi-solid support, such as beads, matrix, gel, among others. For example, the extension products may be tagged with a particular nucleic acid sequence (e.g., included as part of the allele-specific primer) and the solid support may be attached to an "anti-tag" (e.g., a nucleic acid sequence complementary to the tag in the extension product). Extension products can be captured and detected on the solid support. For example, beads may be sorted and detected. One such system that can be employed in this manner is the LUMINEX™ MAP system, which can be adapted for cystic fibrosis mutation detection by Luminex Corporation and is sold commercially as a universal bead array (TAG-IT™) (See, e.g., Example 2)

Additional ASPE methods and reagents are described in, e.g., U.S. patent publication number 2008/0138803 A1, the entire contents of which are herein incorporated by reference.

Single Nucleotide Primer Extension

In some embodiments, a single nucleotide primer extension (SNuPE) assay is used, in which the primer is designed to be extended by only one nucleotide. In such methods, the identity of the nucleotide just downstream (e.g., 3') of the 3' end of the primer is known and differs in the mutant allele as compared to the wild-type allele. SNuPE can be performed using an extension reaction in which the only one particular kind of deoxynucleotide is labeled (e.g., labeled dATP, labeled dCTP, labeled dGTP, or labeled dTTP). Thus, the presence of a detectable extension product can be used as an indication of the identity of the nucleotide at the position of interest (e.g., the position just downstream of the 3' end of the primer), and thus as an indication of the presence or absence of a mutation at that position. SNuPE can be performed as described in U.S. Pat. No. 5,888,819; U.S. Pat. No. 5,846,710; U.S. Pat. No. 6,280,947; U.S. Pat. No. 6,482,595; U.S. Pat. No. 6,503,718; U.S. Pat. No. 6,919,174; Piggee, C. et al. *Journal of Chromatography* A 781 (1997), p. 367-375 ("Capillary Electrophoresis for the Detection of Known Point Mutations by Single-Nucleotide Primer Extension and Laser-Induced Fluorescence Detection"); Hoogendoom, B. et al., *Human Genetics* (1999) 104:89-93, ("Genotyping Single Nucleotide Polymorphism by Primer Extension and High Performance Liquid Chromatography"), the entire contents of each of which are herein incorporated by reference.

In some embodiments, primer extension can be combined with mass spectrometry for accurate and fast detection of the presence or absence of a mutation. See, U.S. Pat. No. 5,885,775 to Haff et al. (analysis of single nucleotide polymorphism analysis by mass spectrometry); U.S. Pat. No. 7,501,251 to Koster (DNA diagnosis based on mass spectrometry); the teachings of both of which are incorporated herein by reference. Suitable mass spectrometric format includes, but is not limited to, Matrix-Assisted Laser Desorption/Ionization, Time-of-Flight (MALDI-TOF), Electrospray (ES), IR-MALDI, Ion Cyclotron Resonance (ICR), Fourier Transform, and combinations thereof.

Oligonucleotide Ligation Assay

In some embodiments, an oligonucleotide ligation assay ("OLA" or "OL") is used. OLA employs two oligonucleotides that are designed to be capable of hybridizing to abutting sequences of a single strand of a target molecules. Typically, one of the oligonucleotides is biotinylated, and the other is detectably labeled, e.g., with a streptavidin-conjugated fluorescent moiety. If the precise complementary sequence is found in a target molecule, the oligonucleotides will hybridize such that their termini abut, and create a ligation substrate that can be captured and detected. See e.g., Nickerson et al. (1990) Proc. Natl. Acad. Sci. U.S.A. 87:8923-8927, Landegren, U. et al. (1988) Science 241:1077-1080 and U.S. Pat. No. 4,998,617, the entire contents of which are herein incorporated by reference in their entirety.

Hybridization Approach

In some embodiments, nucleic acids are analyzed by hybridization using one or more oligonucleotide probes specific for a region in the CFTR gene (SEQ ID NO:1) corresponding to the one or more mutations selected from Table 1, 2, 3 or 4, and under conditions sufficiently stringent to disallow a single nucleotide mismatch. In certain embodiments, suitable nucleic acid probes can distinguish between a normal CFTR gene and a mutant CFTR gene containing one or more mutations selected from Table 1, 2, 3, or 4. For example, suitable nucleic acid probes specifically bind to a normal CFTR gene but not to a mutant CFTR gene containing one ore more mutations selected from Table 1, 2, 3, or 4. Alternatively, nucleic acid probes specifically bind to a mutant CFTR gene containing one or more mutations selected from Table 1, 2, 3, or 4 but not to a normal CFTR gene. Probes of the present invention include those that are capable of specifically hybridizing a mutant CFTR allele containing one or more mutations listed in Tables 1, 2, 3, or 4. Probes of the present invention also include those that are capable of specifically hybridizing a normal allele in a particular region of the CFTR gene and therefore capable of distinguishing a normal allele from a mutant CFTR allele containing one or more mutations listed in Tables 1, 2, 3, or 4. Thus, for example, one of ordinary skill in the art could use probes of the invention to determine whether an individual is homozygous or heterozygous for a particular allele.

Nucleic acid hybridization techniques are well known in the art. See, e.g., Sambrook, et al., 1989, Molecular Cloning:

A Laboratory Manual, Second Edition, Cold Spring Harbor Press, Plainview, N.Y. Those skilled in the art understand how to estimate and adjust the stringency of hybridization conditions such that sequences having at least a desired level of complementary will stably hybridize, while those having lower complementary will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

In some embodiments, probe molecules that hybridize to the mutant or wildtype CFTR sequences can be used for detecting such sequences in the amplified product by solution phase or, more preferably, solid phase hybridization. Solid phase hybridization can be achieved, for example, by attaching the CFTR probes to a microchip.

Nucleic acid probes may comprise ribonucleic acids and/or deoxyribonucleic acids. In some embodiments, provided nucleic acid probes are oligonucleotides (i.e., "oligonucleotide probes"). Generally, oligonucleotide probes are long enough to bind specifically to a homologous region of the CFTR gene, but short enough such that a difference of one nucleotide between the probe and the nucleic acid sample being tested disrupts hybridization. Typically, the sizes of oligonucleotide probes vary from approximately 10 to 100 nucleotides. In some embodiments, oligonucleotide probes vary from 15 to 90, 15 to 80, 15 to 70, 15 to 60, 15 to 50, 15 to 40, 15 to 35, 15 to 30, 18 to 30, or 18 to 26 nucleotides in length. As appreciated by those of ordinary skill in the art, the optimal length of an oligonucleotide probe may depend on the particular methods and/or conditions in which the oligonucleotide probe may be employed.

In some embodiments, nucleic acid probes are useful as primers, e.g., for nucleic acid amplification and/or extension reactions.

In some embodiments, nucleic acid probes are labeled with a detectable moiety as described herein.

Arrays

A variety of the methods mentioned herein may be adapted for use with arrays that allow sets of mutations to be analyzed and/or detected in a single experiment. For example, multiple novel CFTR mutations described herein (e.g., Tables 1, 2, 3 or 4) can be analyzed at the same time. Additionally or alternatively, one or more novel CFTR mutations described herein (e.g., Tables 1, 2, 3 or 4) can be analyzed together with other CFTR mutations known in the art at the same time. In particular, methods that involve use of nucleic acid reagents (e.g., probes, primers, oligonucleotides, etc.) are particularly amenable for adaptation to an array-based platform (e.g., microarray). In some embodiments, an array containing one or more probes specific for detecting CFTR mutations described herein (e.g., Tables 1, 2, 3 or 4) can be designed and adapted for various methods described herein. Additionally or alternatively, probes specific for detecting CFTR mutations described herein (e.g., Tables 1, 2, 3 or 4) can be combined with probes specific for CFTR mutations known in the art. In some embodiments, an array containing multiple probes are known as a mutation panel. See, e.g., Wall et al. "A 31-mutation assay for cystic fibrosis testing in the clinical molecular diagnostics laboratory," *Human Mutation,* 1995; 5(4):333-8, the entire contents of which are herein incorporated by reference. Other methods may include the use of real-time PCR with probes for detecting CFTR mutations as described herein.

Protein-Based Analyses

In certain embodiments, CFTR mutations are detected at the protein (or peptide or polypeptide level), that is, a gene product from a CFTR gene mutation is analyzed. For example, CFTR protein or fragment thereof can be analyzed by amino acid sequencing methods, or immuno assays using one or more antibodies that specifically recognize one or more epitopes corresponding to the one or more novel mutations described herein (e.g., Table 1, 2, 3 and 4). CFTR proteins can also be analyzed by protease digestion (e.g., trypsin digestion) and, in some embodiments, the digested protein products can be further analyzed by 2D-gel electrophoresis.

Antibody Detection of Mutant Proteins

For example, specific antibodies that can differentiate between a normal CFTR protein and a mutant CFTR protein can be employed in any of a variety of methods known in the art to detect CFTR mutations. In certain embodiments, suitable antibodies can distinguish between a normal CFTR protein and a mutant CFTR protein containing one or mutations selected from Tables 1, 2, 3, or 4. For example, suitable antibodies specifically bind to a normal CFTR protein but not to a mutant CFTR protein containing one or more mutations selected from Table 1, 2, 3, or 4. Alternatively, suitable antibodies specifically bind to a mutant CFTR protein containing one or more mutations selected from Table 1, 2, 3, or 4 but not to a normal CFTR protein.

Antibodies against particular epitopes, polypeptides, and/or proteins (e.g., mutant or normal CFTR proteins) can be generated using any of a variety of known methods in the art. For example, the epitope, polypeptide, or protein against which an antibody is desired can be produced and injected into an animal, typically a mammal (such as a donkey, mouse, rabbit, horse, chicken, etc.), and antibodies produced by the animal can be collected from the animal. Monoclonal antibodies can also be produced by generating hybridomas that express an antibody of interest with an immortal cell line. For more details on methods of producing, and uses of, antibodies to detect CFTR mutants, see, e.g., U.S. Pat. No. 5,776,677, the entire contents of which are herein incorporated by reference.

In some embodiments, antibodies are labeled with a detectable moiety as described herein.

Antibody detection methods are well known in the art including, but are not limited to, enzyme-linked immunosorbent assays (ELISAs) and Western blots. Some such methods are amenable to being performed in an array format. For example, a variety of different antibodies, each of which is specific for different epitopes within the CFTR protein, could be immobilized in an array and used in an assay such as an ELISA.

Detectable Moieties

In certain embodiments, certain molecules (e.g., nucleic acid probes, antibodies, etc.) used in accordance with and/or provided by the invention comprise one or more detectable entities or moieties, i.e., such molecules are "labeled" with such entities or moieties.

Any of a wide variety of detectable agents can be used in the practice of the present invention. Suitable detectable agents include, but are not limited to: various ligands, radionuclides; fluorescent dyes; chemiluminescent agents (such as, for example, acridinum esters, stabilized dioxetanes, and the like); bioluminescent agents; spectrally resolvable inorganic fluorescent semiconductors nanocrystals (i.e., quantum dots); microparticles; metal nanoparticles (e.g., gold, silver, copper, platinum, etc.); nanoclusters; paramagnetic metal ions; enzymes; colorimetric labels (such as, for example, dyes, colloidal gold, and the like); biotin; dioxigenin; haptens; and proteins for which antisera or monoclonal antibodies are available.

In some embodiments, the detectable moiety is biotin. Biotin can be bound to avidins (such as streptavidin), which are typically conjugated (directly or indirectly) to other moieties (e.g., fluorescent moieties) that are detectable themselves.

Below are described some non-limiting examples of other detectable moieties.

Fluorescent Dyes

In certain embodiments, a detectable moiety is a fluorescent dye. Numerous known fluorescent dyes of a wide variety of chemical structures and physical characteristics are suitable for use in the practice of the present invention. A fluorescent detectable moiety can be stimulated by a laser with the emitted light captured by a detector. The detector can be a charge-coupled device (CCD) or a confocal microscope, which records its intensity.

Suitable fluorescent dyes include, but are not limited to, fluorescein and fluorescein dyes (e.g., fluorescein isothiocyanine or FITC, naphthofluorescein, 4',5'-dichloro-2',7'-dimethoxyfluorescein, 6-carboxyfluorescein or FAM, etc.), carbocyanine, merocyanine, styryl dyes, oxonol dyes, phycoerythrin, erythrosin, eosin, rhodamine dyes (e.g., carboxytetramethylrhodamine or TAMRA, carboxyrhodamine 6G, carboxy-X-rhodamine (ROX), lissamine rhodamine B, rhodamine 6G, rhodamine Green, rhodamine Red, tetramethylrhodamine (TMR), etc.), coumarin and coumarin dyes (e.g., methoxycoumarin, dialkylaminocoumarin, hydroxycoumarin, aminomethylcoumarin (AMCA), etc.), Oregon Green Dyes (e.g., Oregon Green 488, Oregon Green 500, Oregon Green 514, etc.), Texas Red, Texas Red-X, SPECTRUM RED™, SPECTRUM GREEN™, cyanine dyes (e.g., CY-3™ CY-5™ CY-3.5™, CY5.5™, etc.), ALEXA FLUOR™ dyes (e.g., ALEXA FLUOR™ 350, ALEXA FLUOR™ 488, ALEXA FLUOR™ 532, ALEXA FLUOR™ 546, ALEXA FLUOR™ 568, ALEXA FLUOR™ 594, ALEXA FLUOR™ 633, ALEXA FLUOR™ 660, ALEXA FLUOR™ 680, etc.), BODIPY™ dyes (e.g., BODIPY™ FL, BODIPY™ R6G, BODIPY™ TMR, BODIPY™ TR, BODIPY™ 530/550, BODIPY™ 558/568, BODIPY™ 564/570, BODIPY™ 576/589, BODIPY™ 581/591, BODIPY™ 630/650, BODIPY™ 650/665, etc.), IRDyes (e.g., IRD40, IRD 700, IRD 800, etc.), and the like. For more examples of suitable fluorescent dyes and methods for coupling fluorescent dyes to other chemical entities such as proteins and peptides, see, for example, "The Handbook of Fluorescent Probes and Research Products", 9th Ed., Molecular Probes, Inc., Eugene, Oreg. Favorable properties of fluorescent labeling agents include high molar absorption coefficient, high fluorescence quantum yield, and photostability. In some embodiments, labeling fluorophores exhibit absorption and emission wavelengths in the visible (i.e., between 400 and 750 nm) rather than in the ultraviolet range of the spectrum (i.e., lower than 400 nm). For example, a suitable dye for use in real-time PCR procedures may include SYBR Green.

A detectable moiety may include more than one chemical entity such as in fluorescent resonance energy transfer (FRET). Resonance transfer results an overall enhancement of the emission intensity. For instance, see Ju et. al. (1995) Proc. Nat'l Acad. Sci. (USA) 92:4347, the entire contents of which are herein incorporated by reference. To achieve resonance energy transfer, the first fluorescent molecule (the "donor" fluor) absorbs light and transfers it through the resonance of excited electrons to the second fluorescent molecule (the "acceptor" fluor). In one approach, both the donor and acceptor dyes can be linked together and attached to the oligo primer. Methods to link donor and acceptor dyes to a nucleic acid have been described previously, for example, in U.S. Pat. No. 5,945,526 to Lee et al., the entire contents of which are herein incorporated by reference. Donor/acceptor pairs of dyes that can be used include, for example, fluorescein/tetramethylrohdamine, IAEDANS/fluoroescein, EDANS/DABCYL, fluorescein/fluorescein, BODIPY FL/BODIPY FL, and Fluorescein/QSY 7 dye. See, e.g., U.S. Pat. No. 5,945,526 to Lee et al. Many of these dyes also are commercially available, for instance, from Molecular Probes Inc. (Eugene, Oreg.). Suitable donor fluorophores include 6-carboxyfluorescein (FAM), tetrachloro-6-carboxyfluorescein (TET), 2'-chloro-7'-phenyl-1,4-dichloro-6-carboxyfluorescein (VIC), and the like.

Enzymes

In certain embodiments, a detectable moiety is an enzyme. Examples of suitable enzymes include, but are not limited to, those used in an ELISA, e.g., horseradish peroxidase, beta-galactosidase, luciferase, alkaline phosphatase, etc. Other examples include beta-glucuronidase, beta-D-glucosidase, urease, glucose oxidase, etc. An enzyme may be conjugated to a molecule using a linker group such as a carbodiimide, a diisocyanate, a glutaraldehyde, and the like.

Radioactive Isotopes

In certain embodiments, a detectable moiety is a radioactive isotope. For example, a molecule may be isotopically-labeled (i.e., may contain one or more atoms that have been replaced by an atom having an atomic mass or mass number different from the atomic mass or mass number usually found in nature) or an isotope may be attached to the molecule. Non-limiting examples of isotopes that can be incorporated into molecules include isotopes of hydrogen, carbon, fluorine, phosphorous, copper, gallium, yttrium, technetium, indium, iodine, rhenium, thallium, bismuth, astatine, samarium, and lutetium (i.e., $^{3}$H, $^{13}$C, $^{14}$C, $^{18}$F, $^{19}$F, $^{32}$P, $^{35}$S, $^{64}$Cu, $^{67}$Cu, $^{67}$Ga, $^{90}$Y, $^{99m}$Tc, $^{111}$In, $^{125}$I, $^{123}$I, $^{129}$I, $^{131}$I, $^{135}$I, $^{186}$Re, $^{187}$Re, $^{201}$Tl, $^{212}$Bi, $^{213}$Bi, $^{211}$At, $^{153}$Sm, $^{177}$Lu).

In some embodiments, signal amplification is achieved using labeled dendrimers as the detectable moiety (see, e.g., Physiol Genomics 3:93-99, 2000), the entire contents of which are herein incorporated by reference in their entirety. Fluorescently labeled dendrimers are available from Genisphere (Montvale, N.J.). These may be chemically conjugated to the oligonucleotide primers by methods known in the art.

Kits

In certain embodiments, the invention provides kits for use in accordance with the invention. Generally, inventive kits comprise one or more reagents that differentiate a normal CFTR gene or protein from a mutant CFTR gene or protein containing one or more mutations selected from Table 1, 2, 3, or 4. For example, kits may comprise one or more (e.g., any combination of) reagents as described herein, and optionally additional components. For example, a kit according to the present invention may also include reagents that can detect other CFTR mutations well known in the art.

Suitable reagents may include nucleic acid probes and/or antibodies or fragments thereof. In some embodiments, suitable reagents are provided in a form of an array such as a microarray or a CFTR mutation panel.

In some embodiments, provided kits further comprise reagents for carried out various detection methods described herein (e.g., sequencing, hybridization, primer extension, multiplex ASPE, immuno assays, etc.). For example, kits according to the invention may optionally contain buffers, enzymes, and/or reagents for use in methods described herein, e.g., for amplifying nucleic acids via primer-directed amplification, for performing ELISA experiments, etc.

In some embodiments, provided kits further comprise a control indicative of a healthy individual, e.g., a nucleic acid and/or protein sample from an individual who does not carry a CFTR mutation associated with CF or a CF related disorder. In some embodiments, provided kits further comprise a control indicative of known CFTR mutant alleles (such as ΔF508). Kits may also contain instructions on how to determine if an individual has CF or a CF related disorder, is at risk of developing CF or a CF related disorder, or is a carrier of CFTR mutation.

In some embodiments, a computer readable medium encoding information corresponding to one or more mutations shown in Tables 1, 2, 3, and 4 is provided. Such computer readable medium may be included in a kit of the invention.

Systems

In an embodiment, the present invention provides systems for carrying out the analysis of the invention. Thus, in an embodiment, the present invention comprises a computer-readable medium on which is encoded programming code for the methods described herein. Also in an embodiment, present invention may comprise a system comprising a processor in communication with a computer-readable medium, the processor configured to perform the methods described herein. Suitable processors and computer-readable media for various embodiments of the present invention are described in greater detail below and are illustrated in FIG. 5.

Thus, in certain embodiments, the invention comprises a system for predicting the activity of at least one gene comprising: a computer readable medium; and a processor in communication with the computer readable medium, the processor configured to estimate the effects of individual mutations in the at least one gene. The processor may, in certain embodiments, be further in communication with a database comprising data for a plurality of sequences for the portion of the at least one gene, where the processor is configured to compare the nucleic acid and/or amino acid sequence of the portion of the at least one gene to the data of the plurality of sequences for the portion of the at least one gene to determine if there is a mutation in the portion of the at least one gene in the biological sample obtained from the subject.

In other embodiments, the invention comprises a computer readable medium on which is encoded program code for predicting the activity of at least one gene, the program code comprising code for applying a model to estimate the effects of individual mutations in the at least one gene. In certain embodiments, the programming code comprises code configured to compare the amino acid and/or nucleic acid sequence of the portion of the at least one gene to the data for a plurality of sequences for the portion of the at least one gene stored in a database to determine if there is a mutation in the portion of the at least one gene in the biological sample obtained from the subject.

Some embodiments of the systems and computer readable media of the invention may be applied to various genes. In certain embodiments, the at least one gene comprises the CFTR gene.

As noted herein, the sequence of the portion of the at least one gene and the biological activity of interest as assessed for a particular subject may be compared to a database of amino acid and/or nucleic acid sequences and biological activity as assess for a plurality of subjects. Thus, in certain embodiments of the systems and computer readable media, the database comprises data for the biological activity as measured in a plurality of samples from which the sequence of the portion of the at least one gene was determined.

Embodiments in accordance with aspects of the present subject matter can be implemented in digital electronic circuitry, in computer hardware, firmware, software, or in combinations of the preceding. In one embodiment, a computer may comprise a processor or processors. The processor may comprise, or have access to, a computer-readable medium, such as a random access memory coupled to the processor. The processor may execute computer-executable program instructions stored in memory, such as executing one or more computer programs including a sampling routine and suitable programming to produce output to generate the analysis described in detail herein.

Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example tangible computer-readable media that may store instructions that when executed by the processor, can cause the processor to perform the steps described herein as carried out, or assisted, by a processor. Embodiments of computer-readable media may comprise, but are not limited to, all electronic, optical, magnetic, or other storage devices capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. Also, various other devices may include computer-readable media, such as a router, private or public network, or other transmission device. The processor, and the processing may be in one or more structures, and may be dispersed through one or more structures. The processor may comprise code for carrying out one or more of the methods (or parts of methods) described herein.

The system may comprise a data compiling system as well as a means for the user to interact with the system as the analysis proceeds. Thus, in an embodiment, the present invention may comprise a system for collecting and/or compiling data from a plurality of assay measurements and/or sequencing data and transmitting the data to a computer, and a system for transmitting the results of the analysis to a user. The systems of the present invention may be designed for high-throughput analysis of DNA and/or amino acid sequencing data. Thus, in an embodiment, the plurality of measured signals comprise a plurality of known DNA sequences isolated from at least one cell type.

FIG. 5 shows an embodiment of the flow of information in a system comprising the software of the present invention. As discussed above, a computer processor or CPU may include, for example, digital logic processors capable of processing input, executing algorithms, and generating output as necessary in response to the inputs received from the touch-sensitive input device. As detailed herein, such processors may include a microprocessor, such as an ASIC, and state machines, and/or other components. Such processors include, or may be in communication with, media, for example computer-readable media, which stores instructions that, when executed by the processor, cause the processor to perform the steps described herein.

Thus, in an embodiment, the starting point may comprise data (100) that may comprise a normal CFTR gene (100A) and mutant CFTR gene (100B). Once the data has been collected (110), it may be compiled (120) and/or transformed if necessary using any standard spreadsheet software such as Microsoft Excel, FoxPro, Lotus, or the like. In an embodiment, the data are entered into the system for each experiment. Alternatively, data from previous runs are stored in the computer memory (150) and used as required.

At each point in the analysis, the user may input instructions via a keyboard (180), floppy disk, remote access (e.g., via the internet) (190), or other access means. The user may enter instructions including options for the run, how reports should be printed out, and the like. Also, at each step in the analysis, the data may be stored in the computer using a storage device common in the art such as disks, drives or memory (150). As is understood in the art, the processor (160) and I/O controller (170) are required for multiple aspects of computer function. Also, in a embodiment, there may be more than one processor.

The data may also be processed to remove noise (130). In some cases, the user, via the keyboard (180), floppy disk, or remote access (190), may want to input variables or constraints for the analysis, as for example, the threshold for determining noise. The results of the analysis may then be compiled and provided in a form for review by a user (140).

The following examples serve to illustrate the present invention. These examples are in no way intended to limit the scope of the invention.

EXAMPLES

Example 1

Identification of Novel Mutations in the CFTR Gene

Novel mutations in the CFTR gene were identified using the CF full sequencing assay. Typically, samples submitted for CF full sequencing assays were from individuals for whom testing in CF mutation panels has been uninformative, or partially uninformative. These individuals include 1) patients with idiopathic chronic pancreatitis; 2) patients with congenital bilateral absence of the vas deferens (CBAVD); 3) couples who test positive/negative by mutation analysis; 4) CF-affected or suspected patients in whom one or no mutations have been identified; 5) obligate carriers of a rare familial mutation; 6) patients with a family history of CF, for whom mutation analysis by other methodologies is negative; 7) patients with a CF related disease or condition. Sequence changes in the CFTR gene were identified by comparing the patient gene sequence to the wild-type gene sequence. Novel mutations in the CFTR gene that were unreported previously are summarized in Table 5.

As shown in Table 5, patients carrying these novel mutations were from different ethnic groups including Caucasians, African Americans, Hispanics, and Asians. Some of the mutations are located in introns (e.g., intron 3, intron 6a, intron 11, intron 14a, intron 19, intron 20, intron 21, and intron 23). Some of the mutations are located in exons (e.g., exon 2, exon 3, exon 4, exon 5, exon 6a, exon 6b, exon 7, exon 9, exon 10, exon 11, exon 12, exon 13, exon 14a, exon 14b, exon 15, exon 16, exon 17a, exon 17b, exon 19, exon 20, exon 21, exon 22, and exon 24).

As shown in Table 5, most of the novel mutations identified result in codon changes or altered gene splicing sites, which will likely affect the CFTR gene expression and/or protein function. In particular, some of the mutations are nonsense mutations (i.e., mutations predicted to result in the introduction of a stop codon). Some of the mutations affect consensus splice site ag/gt. Some of these mutations are insertion or deletion of at least one nucleotide. These mutations are category 2 mutations according to the ACMG guidelines, and are of the type expected to cause CF or CF related disease, disorder or condition.

Some mutations are missense mutations. Some are predicted to cause in-frame insertions and/or deletions. Some are likely to affect splice sites. These mutations are category 3 mutations according to the ACMG guidelines.

Thus, the novel mutations provided herein can be used, alone or in combination with other known CF mutations, to detect CF or a CF related disorder in CFTR testing assays including carrier testing.

TABLE 5

Novel Mutations in the CFTR gene

| Sequence Change | Type of mutation | AA Change | Ethnicity | Other Mutations | Clinical Information | Exon |
|---|---|---|---|---|---|---|
| 1824delA | Frameshift (FS) | n/a | Caucasian | F508del | Mutation was identified in a 22 year old patient with a known diagnosis of CF. This patient carried a second mutation known to cause CF (F508del). | e12 |
| 2957delT | FS | n/a | Caucasian | F508del | Mutation was identified in a 1 year old patient with a known diagnosis of CF. The patient carried a second mutation known to cause CF (F508del). | e15 |
| 4089ins4 | FS | n/a | Caucasian | F508del | Mutation was identified in a 7 year old patient with a known diagnosis of CF. The patient had a positive sweat chloride test. The patient carried a second mutation known to cause CF (F508del). | e21 |
| 4374 + 2T > C | Splice site mutation | n/a | 1. Caucasian | 1. F508del | Patient #1: Mutation was identified in a 45 year old patient with a suspected diagnosis of CF. The patient carried a second mutation known to cause CF (F508del). | i23 |
|  |  |  | 2. Caucasian | 2. F508del | Patient #2: Mutation was identified in a 52 year old patient with a suspected diagnosis of CF. The patient carried a second mutation known to cause CF (F508del). |  |

TABLE 5-continued

Novel Mutations in the CFTR gene

| Sequence Change | Type of mutation | AA Change | Ethnicity | Other Mutations | Clinical Information | Exon |
|---|---|---|---|---|---|---|
| 3064A > T | Nonsense | K978X | African American | Q1042X | Mutation was identified in a 26 year old patient with a known diagnosis of CF. The patient carried a second mutation likely to cause CF Q1042X. | e16 |
| 246C > G | Nonsense | Y38X | Caucasian | F508del | Mutation was identified in a 1 month old patient with a suspected diagnosis of CF. The patient had a positive sweat chloride test. The patient carried a second mutation known to cause CF (F508del). | e2 |
| 269C > T | Missense (MS) | A46V | 1) Caucasian | 1) 3849 + 12192G > A | Patient #1: Mutation was identified in a 32 year old patient who was tested due to abnormalities found on fetal ultrasound. The patient carried a second mutation of unknown clinical significance (3849 + 12192G > A). | e2 |
|  |  |  | 2) Black | 2) F508del | Patient #2: Mutation was identified in a 2 month old patient who was tested based on follow-up for a positive newborn screen. The patient carried a second mutation known to cause cystic fibrosis (F508del). |  |
|  |  |  | 3) African American | 3) none | Patient #3: Mutation was identified in a 24 year old patient who was tested as a parental follow-up to a positive newborn screen. |  |
| 2902 G > T | MS | D924Y | Caucasian | F508del | Mutation was identified in a 1 month old patient with a suspected diagnosis of CF. The patient also had a positive sweat chloride test and carried a second mutation known to cause CF (F508del). | e15 |
| 3814G > A | MS | E1228K | Caucasian | F508del | Mutation was identified in a 1 month old patient with a suspected diagnosis of CF. The patient had a borderline sweat chloride test. The patient carried a second mutation known to cause CF (F508del). | e19 |
| 502G > C | MS | G124R | Not Provided | F508del | Mutation was identified in a 2 month old patient with a suspected diagnosis of CF. The patient had a positive sweat chloride test. The patient carried a second mutation known to cause CF (F508del). | e4 |
| 1520G > T | MS | G463V | Caucasian | F508del | Mutation was identified in a 17 year old patient with a known diagnosis of CF. Patient carried a second mutation known to cause CF (F508del). | e9 |
| 511_513dupTTA | In frame duplication | L127dup | Caucasian, Asian | W1282X | Mutation was identified in a newborn with a suspected diagnosis of CF. The patient had clinical symptoms of CF including as a positive sweat chloride test, meconium ileus, echogenic bowel, and pancreatic insufficiency. The patient carried a second mutation known to cause CF (W1282X). | e4 |
| 978A > T | MS | E282D | 1. not provided | 1. 3120 + 1G > A | Patient #1: Mutation was identified in a 10 year old patient with a suspected diagnosis of CF. The patient had a positive sweat chloride test. The patient carried a second mutation known to cause CF (3120 + 1G > A). | e6b |
|  |  |  | 2. not provided | 2) none | Patient #2: Mutation was identified in a 4 year old patient with a suspected diagnosis of CF and a family history of CF. |  |
| 843G > C | MS | Q237H | Caucasian | F508del | Mutation was identified in a 2 month old patient with a known diagnosis of CF. The patient carried a second mutation known to cause CF (F508del). | e6a |
| 829C > T | MS | L233F | Caucasian | D1152H | Mutation was identified in a 1 month old patient who was tested following a positive newborn screen. The patient carried a second mutation known to cause CF (D1152H). | e6a |
| 4096 − 6C > T | Splice site mutation | None | Caucasian | F508del | Mutation was identified in a 58 year old patient with a suspected diagnosis of CF. The patient carried a second mutation known to cause CF (F508del). | i21 |
| 4375 − 7delT | Splice site mutation | None | Caucasian | F508del | Mutation was identified in a 6 year old patient with a suspected diagnosis of CF. Patient has a family history, a borderline sweat chloride test and recurrent pneumonia. The patient carried a second mutation known to cause CF (F508del). | i23 |
| 1586G > C | MS | S485T | Caucasian | S1235R | Mutation was identified in a 2 year old patient with a suspected diagnosis of CF. The patient carried a second mutation S1235R (3837T > G) which has been reported in individuals with varying CF phenotypes. | e10 |

TABLE 5-continued

Novel Mutations in the CFTR gene

| Sequence Change | Type of mutation | AA Change | Ethnicity | Other Mutations | Clinical Information | Exon |
|---|---|---|---|---|---|---|
| 875 + 4G > T | Splice site mutation | n/a | African American | none | Mutation was identified in a 1 month old patient who had a positive newborn screening test. | i6a |
| 4005 + 3G > T | Splice site mutation | n/a | Caucasian | none | Mutation was identified in a 40 year old patient who was tested to determine if they were a carrier, there was no family history of CF. | i20 |
| 2711T > C | MS | I860T | Caucasian | F508del, E528E | Mutation was identified in a 58 year old woman with a suspected diagnosis of CF. The patient carried a second mutation known to cause CF (F508del) and an additional mutation of unknown clinical significance (E528E).. | e14a |
| 3891G > C | MS | L1253F | Not provided | G85E, L15P | Mutation was identified in a 32 year old patient with a known diagnosis of CF. The patient carried a second mutation known to cause CF (G85E) and an additional mutation of unknown clinical significance (L15P). | e20 |
| 2524C > T | MS | P798S | African American | F508del, R74W, G921E, D1270N | Mutation was identified in a 5 year old patient with a suspected diagnosis of CF. The patient had a positive sweat chloride test. This patient carried a second mutation known to cause CF (F508del) and three additional mutations of unknown clinical significance (R74W, G921E, D1270N). | e13 |
| 2894G > A | MS | G921E | African American | F508del, R74W, P798S, D1270N | Mutation was identified in a 5 year old patient with a suspected diagnosis of CF. The patient had a positive sweat chloride test. This patient carried a second mutation known to cause CF (F508del) and three additional mutations of unknown clinical significance (R74W, P789S, D1270N). | e15 |
| 405 + 10247C > T | Possible splice site mutation | n/a | Caucasian | F508del | Mutation was identified in a 35 year old patient who was tested to determine if they were a carrier, there was no family history of CF. This patient carried a second mutation known to cause CF (F508del). | i3 |
| 405 + 10255delC | Possible splice site mutation | n/a | Not Provided | F508del, 124del23bp | Mutation was identified in a 10 year old patient. The patient carries two mutations know to cause CF (F508del and 124del23). | i3 |
| 1811 + 1643G > T | Possible splice site mutation | n/a | 1. Hispanic | 1. F508del | Patient #1: Mutation was identified in a 1 year old patient with a known diagnosis of CF. Patient had a positive sweat chloride test. The patient carried a second mutation known to cause CF (F508del). | i11 |
| | | | 2. Hispanic | 2. F508del | Patient #2: Mutation was identified in a 6 year old patient with a known diagnosis of CF. The patient carried a second mutation know to cause CF (F508del). | |
| | | | 3. Not provided | 3. none | Patient #3: Mutation was identified in an 8 month old patient with a suspected diagnosis of CF. | |
| 1812 − 13A > G | Splice site mutation | n/a | Caucasian | none | Mutation was identified in a 15 year old patient with a suspected diagnosis of CF. The patient has chronic sinusitis. | i11 |
| 2752 − 33insA | Possible splice site mutation | n/a | African American | F693L | Mutation was identified in a 6 year old patient with a known diagnosis of CF. The patient carries a second mutation of unknown clinical significance (F693L). | i14a |
| 3849 + 12192G > A | Possible splice site mutation | n/a | Caucasian | A46V | Mutation was identified in a 32 year old patient who was tested due to abnormalities found on fetal ultrasound. The patient carried an additional mutation of known clinical significance (A46V). | i19 |
| 724G > A | MS | A198T | Hispanic | none | Mutation was identified in a 4 month old patient with a suspected diagnosis of CF. | e6a |
| 3899C > T | MS | A1256V | Guyanese | none | Mutation was identified in a 45 year old patient who was tested to determine if they were a carrier, there was no family history of CF. | e20 |
| 3986C > T | MS | A1285V | Not Provided | none | Mutation was identified in a 23 year old patient who was tested to determine if they were a carrier, there was no family history of CF. | e20 |
| 901G > A | MS | E257K | Hispanic | none | Mutation was identified in a 4 year old patient with a suspected diagnosis of CF. The patient has asthma and recurring pneumonia. | e6b |
| 392 T > C | MS | F87S | Not Provided | none | The mutation was identified in a 1 month old patient with a suspected diagnosis of CF. | e3 |
| 3463T > C | MS | F1111L | Hispanic | none | Mutation was identified in a 6 year old patient with a suspected diagnosis of CF. The patient has asthma. | e17b |

TABLE 5-continued

Novel Mutations in the CFTR gene

| Sequence Change | Type of mutation | AA Change | Ethnicity | Other Mutations | Clinical Information | Exon |
|---|---|---|---|---|---|---|
| 1757G > A | MS | G542E | Hispanic | none | Mutation was identified in a 25 year old patient who was tested to determine if they were a carrier, there was no family history of CF. The patient carried 2 copies of G542E.. | e11 |
| 4025G > C | MS | G1298A | Asian | G970D, Q1352H | Mutation was identified in a 34 year old patient with congenital absence of the vas deferens. The patient carried two other mutations of unknown clinical significance (G970D and Q1352H) | e21 |
| 4129G > T | MS | G1333W | Not Provided | none | Mutation was identified in an 8 year old patient with a suspected diagnosis of CF. Patient had recurrent respiratory infections and chronic cough. | e22 |
| 663T > G | MS | I177M | Caucasian | none | Mutation was identified in a 34 year old patient who was tested to determine if they were a carrier, there was no family history of CF. | e5 |
| 3200T > C | MS | I1023T | Hispanic | none | Mutation was identified in a 34 year old patient who was tested to determine if they were a carrier, there was no family history of CF. | e17a |
| 4412 T > C | MS | I1427T | Asian | S1444S | Mutation was identified in a 34 year old patient who was tested to determine if they were a carrier, there was no family history of CF. The patient carried another mutation that is considered likely to be clinically benign (S144S). | e24 |
| 620A > C | MS | K163T | Caucasian | none | Mutation was identified in a 32 year old patient with a family history of CF. | e4 |

Example 2

CFTR Mutation Detection Assay

The present example demonstrates that multiplex ASPE assay can be used to detect novel cystic fibrosis mutations described herein. Multiplex ASPE combines multiplex PCR and allele-specific primer extension. Multiplex PCR is performed to amplify target regions in the CFTR gene containing novel sequence variations described herein from genomic DNA in a sample. Multiplex primer extension reactions are then performed using allele-specific primers, i.e., extension primers that possess a 3' terminal nucleotide, which form a perfect complement with the target sequence, are extended to form extension products and modified nucleotides (e.g., biotinylated dCTP) are incorporated into the extension product for detection purposes. Alternatively, an extension primer may instead contain a 3' terminal nucleotide which forms a mismatch with the target sequence. In this instance, primer extension does not occur. Primer extension products are then hybridized to universal array beads with "anti-tag" sequence (sequences complementary to the tag sequence) for capture and detection purposes.

In some cases, the novel mutations described herein can be detected in combination of other known CF mutations, for example, mutations recommended by the American College of Genetics and American College of Obstetricians and Gynecologists, as well as other common and clinically relevant mutations, such as, for example, ΔF508 (exon 10), G542X (exon 11), G551D (exon 11), R117H (exon 4), W1282X (exon 20), N1303K (exon 21), 3905insT (exon 20), 3849+10 KbC>T (intron 19), G85E (exon 3), R334W (exon 7), A455E (exon 9), 1898+1G>A (exon 12), and/or 2184delA (exon 13).

Various ASPE kits can be used to carry out the detection methods described herein. For example, Luminex's TAG-IT™kit and Data Analysis software can be modified to detect a panel of CF mutations including one or more novel mutations described herein. Mutation detection kit may use non-isotopic fluorescent technology, and a 96-well assay format that is compatible with automation such that result analyses and genotype calling are automated.

Allele Specific Primers

Allele specific primers can be designed based on the sequence variations shown in Table 5 and the CFTR genomic sequences (including exon and intron sequences) using various methods and software known in the art. A universal tag sequence can be added to allele specific primers.

Specimens and Assay Format

Specimens containing genomic DNA to be analyzed can be obtained from, but not limited to, the following sources: Whole blood (e.g., whole blood in EDTA, ACD-A, ACD-B), fresh or frozen tissue, amniotic fluid, CVS (chorionic villus sampling) tissue, cultured cells (e.g., CVS, amniotic fluid, fibroblasts, POC (product of conception)), blood spots, cord blood, mouthwash, genomic DNA extracted by an outside laboratory. Blood and bloodspot DNA samples are typically run undiluted at a 5 μL input volume. An amount of 5 to 200 ng DNA is used as input. For testing prenatal and mouthwash samples, generally between 20 ng and 150 ng is used as input, for example, about 20 ng, 25 ng, 30 ng, 35 ng, 40 ng, 45 ng, 50 ng, 55 ng, 60 ng, 65 ng, 70 ng, 75 ng, 80 ng, 85 ng, 90 ng, 95 ng, 100 ng, 110 ng, 120 ng, 130 ng, 140 ng, or 150 ng.

A 96-well assay plate is used. Two genomic DNA controls are included with each assay plate. The specific controls are rotated sequentially through assay plates. Each assay plate also includes two cocktail blanks and ASPE (Allele-Specific Primer Extension) controls. A calibrating 96-well filter plate is also used during data acquisition.

Single-Well Multiplex PCR

Multiplex PCR are performed to amplify exons containing mutations described herein using consensus flanking intron sequences. Generally, amplicons range in size between about 150 bp and 600 bp (inclusive of endpoints).

Typically, 5 ng-200 ng of DNA is amplified to produce a product containing multiple amplicons using PCR amplification conditions known in the art or optimized/modified using routine experimentation.

Enzymatic Post-PCR Cleanup

PCR products are treated with Exonuclease I and Shrimp Alkaline Phosphatase to remove residual primers that will interfere with allele-specific primer extension reactions. PCR products are incubated with enzyme and then enzyme is heat-deactivated, according to standard protocols or modified protocols readily developed by one of ordinary skill in the art.

Single Well Allele Specific Primer Extension (ASPE) Reactions

Typically up to 100 sequence variations can be distinguished in a single-well reaction; using the Luminex bead set. For example, a set of allele-specific oligonucleotide (ASO) primers (including wildtype control ASOs) with tag sequences are used.

The Exo-SAP-treated PCR product is subjected to an allele-specific primer extension reaction containing tagged primers and biotinylated dCTP using PCR reaction conditions known in the art or modified readily by one of ordinary skill in the art.

Universal Array Sorting and Detection

Each bead is coupled with an anti-tag sequence complementary to the tag sequence ASPE primers. Therefore, any ASPE products, if present, can be captured for genotype analysis. Wild-type control for each amplicon is included. The signals from wildtype alleles serve as a control for each amplicon and provide information for allelic ratio calculation (typically obtained by calculating the ratio of signal for the mutant allele over signal for the wildtype allele), for the detected mutations.

The ASPE product is added to the universal bead array containing anti-tags to the ASPE primers and incubated for hybridization. Hybridization reactions are then washed over a filter that captures the beads and removes any non-hybridized ASPE products containing biotin. Bead hybridization conditions are known in the art and can be adapted readily by one skilled in the art.

Strepatavidin R-Phycoerythrin conjugate is added to the hybridized products on the filter plate and incubated at room temperature, followed by bead sorting and detection. For example, a modified LUMINEX™ 100 IS™ or 200 IS™ can be used. The LUMINEX™ 100 IS™ can upload sample sheets from text files or barcodes. Detection time averages 20-100 seconds per well.

Results

In the LUMINEX™ system, results are generated as a <.csv> file and exported in batches. The batch output file (.csv) is opened in TAG-IT™ Data Analysis Software (TDAS) version 6.0 where results are automatically generated based on pre-determined algorithms for allelic ratios on certain individually tested mutations and the presence or absence of signal on the remaining mutations.

Mutation Confirmation

Samples positive for any of the mutations described herein can be confirmed by a second assay run. Positive samples can also be confirmed by direct DNA sequencing.

Example 3

Cystic Fibrosis Sequencing Assays

The Cystic Fibrosis full sequencing assay and single exon sequence assay can be used to detect mutations in the CFTR gene directly in a patient sample. The Cystic Fibrosis full sequencing assay and single exon sequence assay can also be used to complement CF screening panels, and/or to serve as a confirmatory assay for samples that are positive for multiplex mutations or those without a normal counterpart in the CF mutation detection assay.

The CF full sequencing assay sequences the entire coding region of the CFTR gene plus 15 bp at the 3' end of each intron (30 bp for e17b to cover a known mutation) and 6 bp at the 5' beginning of each intron.

In addition, the assay includes portions of introns 1, 3, 11, and 19 useful in identifying the exon 2, 3 deletion, the A>G mutation at 1811+1.6 kb, and the C>T mutation at 3849+10 kb. Typically, the assay comprises analysis of 31 amplicons: e1, i1, e2, e3, i3, e4, e5, e6a, e6b, e7, e8, e9, e10, e11, e12, e13a, e13b, e14a, e14b, e15, e16, e17a, e17b, e18, e19, i19, e20, e21, e22, e23, and e24. Each amplicon includes the complete coding region of the exon with the exception of 13.1 and 13.2, in which, due to the large size of the exon, the amplicon is divided into two fragments. The CF Single Exon Sequencing assay uses the same primers but on an individual basis as needed.

Samples tested in the CF single exon sequencing assay in this Example include those from individuals that 1) tested positive in a CF mutation detection assay (e.g., multiplex ASPE assay as described in Examples 2) but require confirmation; 2) tested positive in the CF full sequencing assay and require repeat testing; 3) are being tested for a known familial mutation(s); and/or 4) are being tested for a mutation that is not detectable in the CF mutation detection assay of Example 2.

Specimens and Assay Format

Specimens to be analyzed can be extracted genomic DNA from any of, but not limited to, the following sources: Whole blood (e.g., whole blood in EDTA, ACD-A, ACD-B), blood spots, amniotic fluid, chorionic villus samples (CVS) (for single exon sequencing only), cultured cells (e.g., CVS, amniotic fluid, fibroblasts, POC), mouthwash (for single exon sequencing only).

A 96-well format is used. Cocktail blanks are run for all amplicons on each assay.

PCR Amplification

Target regions containing mutations described herein are first amplified by PCR amplification. Typically, 5 ng-200 ng of DNA is amplified in a 25 µL volume reaction. PCR primers include 5' UPS tags—UPS1 for the Forward primers and UPS2 for the Reverse primers. Table 6 presents sequences of exemplary primers used in amplification of certain exemplary target exon or intron regions.

TABLE 6

| Primer sequences | | | | |
|---|---|---|---|---|
| Amplicon | Primer Name | Sequence (5'-3') | Amplicon Length | SEQ ID NO. |
| Primers for exonic sequences | | | | |
| CF exon 1 | UP1CFe1F | TTTAACCTGGGCAGTGAAG | 373 | 5 |
| | UP2CFe1R | AACCCAACCCATACACA | | 6 |

TABLE 6-continued

Primer sequences

| Amplicon | Primer Name | Sequence (5'-3') | Amplicon Length | SEQ ID NO. |
|---|---|---|---|---|
| CF exon 2 | UP1CFe2F | CAAATCAAGTGAATATCTGTTC | 316 | 7 |
|  | UP2CFe2R | AGCCACCATACTTGGCTCCTA |  | 8 |
| CF exon 3 | UP1CFe3F2 | CTAAAATATTTGCACATGCAAC | 333 | 9 |
|  | UP2CFe3R | TTTCTTAGTGTTTGGAGTTGG |  | 10 |
| CF exon 4 | UP1CFe4F2 | TCATTTTAAGTCTCCTCTAAAG | 407 | 11 |
|  | UP2CFe4R | CGATACAGAATATATGTGCCA |  | 12 |
| CF exon 5 | UP1CFe5F2 | AACAACTAGAAGCATGCCAG | 394 | 13 |
|  | UP2CFe5R2 | GTTGTATAATTTATAACAATAGTG |  | 14 |
| CF exon 6a | UP1CFe6aF2 | GGAAGATACAATGACACCTG | 353 | 15 |
|  | UP2CFe6aR3 | CTGAAGATCACTGTTCTATGC |  | 16 |
| CF exon 6b | UP1CFe6bF3 | ATGACTTAAAACCTTGAGCAGT | 336 | 17 |
|  | UP2CFe6bR2 | GGAAGTCTACCATGATAAACAT |  | 18 |
| CF exon 7 | UP1CFe7F2 | GAGACCATGCTCAGATCTTCC | 507 | 19 |
|  | UP2CFe7R | ACTTTTATAACTTCCTAGTGAAG |  | 20 |
| CF exon 8 | UP1CFe8F2 | AAGATGTAGCACAATGAGAGTA | 268 | 21 |
|  | UP2CFe8R | CAGTTAGGTGTTTAGAGCAA |  | 22 |
| CF exon 9 | UP1CFe9F | GTATACAGTGTAATGGATCATG | 402 | 23 |
|  | UP2CFe9R4 | CACCAAATTAAGTTCTTAATAG |  | 24 |
| CF exon 10 | UP1CFe10F | TTCTGCTTAGGATGATAATTGG | 479 | 25 |
|  | UP2CFe10R | GCATAGGTCATGTGTTTTATTA |  | 26 |
| CF exon 11 | UP1CFe11F | CAGATTGAGCATACTAAAAGTG | 240 | 27 |
|  | UTP2CFe11R | TACATGAATGACATTTACAGCA |  | 28 |
| CF exon 12 | UP1CFe12F | GCTACTTCTGCACCACTTTTG | 344 | 29 |
|  | UP2CFe12R | CAGTCTGTCTTTCTTTTATTTTA |  | 30 |
| CF exon 13a | UP1CFe13F3 | CAAAATGCTAAAATACGAGAC | 388 | 31 |
|  | UP2CFe13R5 | TCCAGGAGACAGGAGCATC |  | 32 |
| CF exon 13b | UP1CFe13F4 | CTCATGGGATGTGATTCTTT | 714 | 33 |
|  | UP2CFe13R2 | GATACACCTTATCCTAATCCTA |  | 34 |
| CF exon 14a | UP1CFe14aF3 | ACCACAATGGTGGCATGA | 299 | 35 |
|  | UP2CFe14aR | TGTATACATCCCCAAACTATC |  | 36 |
| CF exon 14b | UP1CFe14bF2 | TGGGCATGGGAGGAATAGGTG | 228 | 37 |
|  | UP2CFe14bR | TTACAATACATACAAACATAGTGG |  | 38 |
| CF exon 15 | UP1CFe15F2 | AAGTAACTTTGGCTGC | 416 | 39 |
|  | UP2CFe15R2 | CTGCCATTAGAAAACCA |  | 40 |
| CF exon 16 | UP1CFe16F2 | AAGTCTATCTGATTCTATTTGC | 307 | 41 |
|  | UP2CFe16R2 | GTTTTTTTAATAATACAGACATACT |  | 42 |
| CF exon 17a | UP1CFe17aF3 | TGTCCACTTTGCAATGTGAA | 317 | 43 |
|  | UP2CFe17aR3 | CAATAAAGAATCTCAAATAGCTCT |  | 44 |
| CF exon 17b | UP1CFe17bF3 | TAGTCTTTTTCAGGTACAAG | 516 | 45 |
|  | UP2CFe17bR6 | CAATGGAAATTCAAAGAAATCACT |  | 46 |
| CF exon 18 | UP1CFe18F6 | GAATACTTACTATATGCAGAGCA | 416 | 47 |
|  | UP2CFe18R3 | GTTCTTCCTCATGCTATTACTC |  | 48 |
| CF exon 19 | UP1CFe19F | GCCCGACAAATAACCAAGTGA | 494 | 49 |
|  | UP2CFe19R2 | CTAACACATTGCTTCAGGCTA |  | 50 |
| CF exon 20 | UP1CFe20F | AAGGTTGTTTGTCTCCATATAT | 544 | 51 |
|  | UP2CFe20R | GCCTATGAGAAAACTGCACT |  | 52 |
| CF exon 21 | UP1CFe21 F | ACATGGGTGTTTCTTATTTA | 428 | 53 |
|  | UP2CFe21 R2 | GTTAGGGGTAGGTCCAGT |  | 54 |
| CF exon 22 | UP1CFe22F | GCTTGAGTGTTTTTAACTCTGTG | 314 | 55 |
|  | UP2CFe22R | ATGATTCTGTTCCCACTGTGC |  | 56 |

TABLE 6-continued

Primer sequences

| Amplicon | Primer Name | Sequence (5'-3') | Amplicon Length | SEQ ID NO. |
|---|---|---|---|---|
| CF exon 23 | UP1CFe23F | GTTCTGTGATATTATGTGTGG | 226 | 57 |
|  | UP2CFe23R | CAAGGGCAATGAGATCTTAAG |  | 58 |
| CF exon 24 | UP1CFe24F2 | AGTTTCTGTCCCTGCTCT | 356 | 59 |
|  | UP2CFe24R | GAGCAAATGTCCCATGTCAAC |  | 60 |
| Primers for intronic sequences | | | | |
| CF intron 1 | UP1CFin1F2 | AATGGTGTTTACCTACCTAGAGAA | 250 | 61 |
|  | UP4CFin1R2 | CCTCCTCTGATTCCACAAG |  | 62 |
| CF intron 3 | UP3CFin3F3 | CTGAGATTCTGTTCTAGGTGTG | 366 | 63 |
|  | UP2CFin3R | CCTACACTCAGAACCCATCAT |  | 64 |
| CF intron 19 | UP1CFin19F | TTCAGTTGACTTGTCATCTTG | 223 | 65 |
|  | UP2CFin19R | AATATGTTGAAAGTTAAACAGTG |  | 66 |
| CF intron 11 | UP1CFin11F | GTTACACTATAAAGGTTGTTTTAGAC | 292 | 67 |
|  | UP2CFin11R | CACAGTTCCCATATTAATAGAAATG |  | 68 |
| (Seq) | CFe9.SEQ.F | TTTTTAACAGGGATTTGGG | N/A | 69 |
| (Seq) | CFe6bF2 | GATTGATTGATTGATTGATT | N/A | 70 |
| (Seq) | UPS1 | GCGGTCGCATAAGGGTCAGT | N/A | 71 |
| (Seq) | UPS2 | CGCCAGCGTATTCCCAGTCA | N/A | 72 |

PCR conditions are as shown in Table 7.

TABLE 7

PCR amplification conditions for CF full sequencing assay

| Cycles | Temperature (° C.) | Time | Function |
|---|---|---|---|
| 1 | 95 | 5 min | Denaturation of enzyme |
| 35 | 95 | 20 sec | Denaturation of dsDNA |
|  | 55 | 20 sec | Annealing |
|  | 72 | 40 sec | Extension |
| 1 | 72 | 7 min | Final extension |
| 1 | 8 | Forever | End |

Enzymatic Post-PCR Clean Up

PCR products are treated with Exonuclease I (Exo) and Shrimp Alkaline Phosphatase (SAP) to remove residual primers that may interfere with sequencing. The following incubation conditions are used:

37° C. for 30 minutes (enzyme digestion)

99° C. for 15 minutes (enzyme deactivation)

Hold at 8° C. until storage

Products can be stored, e.g., at −80° C. or −20° C.

Sequencing

Exo-SAP treated products are diluted 1:2 in water, and 3 μL is added to 7 μL of each forward and reverse sequence cocktail containing Big Dye v3.1 (ABI). In order to obtain bidirectional sequencing results, two sequencing reactions are performed for each amplicon, using both UPS1 and UPS2 primers. An additional forward sequencing reaction using gene specific primers is performed for Exons 6b and 9 to obtain readable sequence beyond the repeat regions. Cycle sequencing is performed in a thermocycler with the conditions shown in Table 8.

TABLE 8

Thermocycler conditions for sequencing reactions for CF full sequencing assay

| Cycles | Temperature (° C.) | Time | Function |
|---|---|---|---|
| 1 | 96 | 1 min | Denaturation of enzyme |
| 25 | 96 | 10 sec | Denaturation of dsDNA |
|  | 53 | 5 sec | Annealing |
|  | 60 | 3 sec | Extension |
| 1 | 8 | Forever | End |

Assay plates can be stored, e.g., at −80° C. for up to 2 weeks until analyzed or further manipulated.

Post-Sequencing Purification

Sequence products are purified using the Performa DTR Ultra 96 Well Plate (Edge Biosystems). Sequencing reactions are diluted 1:2 and 10 μL is purified through the Edge Plate. Sequencing Run: ABI 3730 Genetic Analyzer and Data Analysis A 1 kV/14 second injection is performed on the 3730x1 Genetic Analyzer. POP7 polymer and a 50 cm array are used for optimal resolution. Parameters for a typical sequencing run are shown in Table 9.

TABLE 9

Parameters for typical sequencing runs

| Feature | Parameter for CF full sequencing |
|---|---|
| Run Temp | 60° C. |
| Pre Run Voltage | 15.0 Kvolts |
| Pre Run Time | 180 sec |
| Injection Voltage | 1.0 Kvolts |
| Injection Time | 14 sec |
| Voltage number of steps | 30 |

TABLE 9-continued

Parameters for typical sequencing runs

| Feature | Parameter for CF full sequencing |
|---|---|
| Voltage Step Interval | 15 sec |
| Data Delay Time | 240 sec |
| Run Voltage | 13.4 Kvolts |
| Run Time | 2400 sec |

Sequence data Analysis is performed using SEQSCAPE™ software (ABI).

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. The articles "a", "an", and "the" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses variations, combinations, and permutations in which one or more limitations, elements, clauses, descriptive terms, etc., from one or more of the claims is introduced into another claim dependent on the same base claim (or, as relevant, any other claim) unless otherwise indicated or unless it would be evident to one of ordinary skill in the art that a contradiction or inconsistency would arise. Where elements are presented as lists, e.g., in Markush group or similar format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth herein. It should also be understood that any embodiment of the invention, e.g., any embodiment found within the prior art, can be explicitly excluded from the claims, regardless of whether the specific exclusion is recited in the specification.

It should also be understood that, unless clearly indicated to the contrary, in any methods claimed herein that include more than one act, the order of the acts of the method is not necessarily limited to the order in which the acts of the method are recited, but the invention includes embodiments in which the order is so limited. Furthermore, where the claims recite a composition, the invention encompasses methods of using the composition and methods of making the composition. Where the claims recite a composition, it should be understood that the invention encompasses methods of using the composition and methods of making the composition.

INCORPORATION OF REFERENCES

All publications and patent documents cited in this application are incorporated by reference in their entirety to the same extent as if the contents of each individual publication or patent document were incorporated herein.

What is claimed is:

1. A composition consisting of a plurality of labeled nucleic acid molecules that each consist of a fragment of a cystic fibrosis transmembrane conductance regulator gene and that specifically hybridize to a mutant but not a wild-type cystic fibrosis transmembrane conductance regulator gene, wherein at least one of the labeled nucleic acid molecules contains a cystic fibrosis transmembrane conductance regulator 1824delA mutation, and wherein the label comprises one of a radionucleotide, a fluorophore, a chemiluminescent agent, a microparticle, an enzyme, a colorimetric label, a magnetic label, a hapten, a molecular beacon, or an aptamer beacon.

2. The composition of claim 1, wherein the plurality of labeled nucleic acid molecules that each consist of a fragment of a cystic fibrosis transmembrane conductance regulator gene and that specifically hybridize to a mutant but not a wild-type cystic fibrosis transmembrane conductance regulator gene contains at least one or more of a cystic fibrosis transmembrane conductance regulator 269C>T, 2902G>T, 3814G>A, 502G>C, 1520G>T, 511-513 dup TTA, 978A>T, 843G>C, 82C>T, 4096-6C>T, 4375-7delT, 1586G>C, 875+4G>T, or 4005+3G>T mutation.

3. The composition of claim 1, wherein the plurality of labeled nucleic acid molecules that each consist of a fragment of a cystic fibrosis transmembrane conductance regulator gene and that specifically hybridize to a mutant but not a wild-type cystic fibrosis transmembrane conductance regulator gene contains at least one or more of a cystic fibrosis transmembrane conductance regulator 2711T>C, 3891G>C, 2524C>T or 2894G>A mutation.

4. The composition of claim 1, wherein the plurality of labeled nucleic acid molecules that each consist of a fragment of a cystic fibrosis transmembrane conductance regulator gene and that specifically hybridize to a mutant but not a wild-type cystic fibrosis transmembrane conductance regulator gene contains at least one or more of a 405+10247C>T, 405+10255 del C, 1811+1643 G>T, 1812-13A>G, 2752-33insA, 3849+12192 G>A, 724G>A, 3899C>T, 3986C>T, 901G>A, 392T>C, 3463T>C, 1757G>A, 4025G>C, 4129G>T, 663T>G, 3200T>C, 4412T>C, 620A>C, 1738A>G, 3370A>C, 1129C>T, 2383C>T, 2761delTCT, 1106A>G or 622A>G cystic fibrosis transmembrane conductance regulator mutation.

5. The composition of claim 1, wherein the plurality of labeled nucleic acid molecules that each consist of a fragment of a cystic fibrosis transmembrane conductance regulator gene and that specifically hybridize to a mutant but not a wild-type cystic fibrosis transmembrane conductance regulator gene contains at least one or more of a cystic fibrosis transmembrane conductance regulator 2957delT, 4089insT, 4374+2T>C, 3064A>T, or 246C>G mutation.

6. A kit consisting of a plurality of labeled nucleic acid molecules that each consist of a fragment of a cystic fibrosis transmembrane conductance regulator gene and that specifically hybridize to a mutant but not a wild-type cystic fibrosis transmembrane conductance regulator gene, wherein at least one of the labeled nucleic acid molecules contains a cystic fibrosis transmembrane conductance regulator 1824delA mutation, wherein the label comprises one of a radionucleotide, a fluorophore, a chemiluminescent agent, a microparticle, an enzyme, a colorimetric label, a magnetic label, a hapten, a molecular beacon, or an aptamer beacon; and
   instructions for indicating that a subject has cystic fibrosis, or is at risk of developing cystic fibrosis when the subject is homozygous for the 1824delA mutation, or is a carrier of cystic fibrosis when the subject is heterozygous for the 1824delA mutation.

7. The kit of claim 6, wherein the plurality of labeled nucleic acid molecules that each consist of a fragment of a cystic fibrosis transmembrane conductance regulator gene and that specifically hybridize to a mutant but not a wild-type cystic fibrosis transmembrane conductance regulator gene contains a cystic fibrosis transmembrane conductance regulator 2957delT, 4089insT, 4374+2T>C, 3064A>T, or 246C>G mutation; and
   instructions for indicating that a subject has cystic fibrosis, or is at risk of developing cystic fibrosis when the subject is homozygous for the at least one or more of the 2957delT, 4089insT, 4374+2T>C, 3064A>T, or 246C>G mutation, or is a carrier of cystic fibrosis when the subject is heterozygous for the at least one or more of the 2957delT, 4089insT, 4374+2T>C, 3064A>T, or 246C>G mutation.

8. The kit of claim 6, wherein the plurality of labeled nucleic acid molecules that each consist of a fragment of a cystic fibrosis transmembrane conductance regulator gene and that specifically hybridize to a mutant but not a wild-type cystic fibrosis transmembrane conductance regulator gene contains a cystic fibrosis transmembrane conductance regulator 269C>T, 2902G>T, 3814G>A, 502G>C, 1520G>T, 511-513 dup TTA, 978A>T, 843G>C, 829C>T, 4096-6C>T, 4375-7delT, 1586G>C, 875+4G>T, or 4005+3G>T mutation; and instructions for indicating that a subject has cystic fibrosis, or is at risk of developing cystic fibrosis when the subject is homozygous for the at least one or more of the 269C>T, 2902G>T, 3814G>A, 502G>C, 1520G>T, 511-513 dup TTA, 978A>T, 843G>C, 829C>T, 4096-6C>T, 4375-7delT, 1586G>C, 875+4G>T, or 4005+3G>T mutation, or is a carrier of cystic fibrosis when the subject is heterozygous for the at least one or more of the 269C>T, 2902G>T, 3814G>A, 502G>C, 1520G>T, 511-513 dup TTA, 978A>T, 843G>C, 829C>T, 4096-6C>T, 4375-7delT, 1586G>C, 875+4G>T, or 4005+3G>T mutation.

9. The kit of claim 6, wherein the plurality of labeled nucleic acid molecules that each consist of a fragment of a cystic fibrosis transmembrane conductance regulator gene and that specifically hybridize to a mutant but not a wild-type cystic fibrosis transmembrane conductance regulator gene contains a cystic fibrosis transmembrane conductance regulator 2711T>C, 3891G>C, 2524C>T or 2894G>A mutation; and instructions for indicating that a subject has cystic fibrosis, or is at risk of developing cystic fibrosis when the subject is homozygous for the at least one or more of the 2711T>C, 3891G>C, 2524C>T or 2894G>A mutation, or is a carrier of cystic fibrosis when the subject is heterozygous for the at least one or more of the 2711T>C, 3891G>C, 2524C>T or 2894G>A mutation.

10. The kit of claim 6, wherein the plurality of labeled nucleic acid molecules that each consist of a fragment of a cystic fibrosis transmembrane conductance regulator gene and that specifically hybridize to a mutant but not a wild-type cystic fibrosis transmembrane conductance regulator gene contains a cystic fibrosis transmembrane conductance regulator 405+10247C>T, 405+10255 del C, 1811+1643 G>T, 1812-13A>G, 2752-33insA, 3849+12192 G>A, 724G>A, 3899C>T, 3986C>T, 901G>A, 392T>C, 3463T>C, 1757G>A, 4025G>C, 4129G>T, 663T>G, 3200T>C, 4412T>C, 620A>C, 1738A>G, 3370A>C, 1129C>T, 2383C>T, 2761delTCT, 1106A>G or 622A>G mutation; and instructions for indicating that the subject has cystic fibrosis, or is at risk of developing cystic fibrosis when a subject is homozygous for the at least one or more of the 405+10247C>T, 405+10255 del C, 1811+1643 G>T, 1812-13A>G, 2752-33insA, 3849+12192 G>A, 724G>A, 3899C>T, 3986C>T, 901G>A, 392T>C, 3463T>C, 1757G>A, 4025G>C, 4129G>T, 663T>G, 3200T>C, 4412T>C, 620A>C, 1738A>G, 3370A>C, 1129C>T, 2383C>T, 2761delTCT, 1106A>G or 622A>G mutation, or is a carrier of cystic fibrosis when the subject is heterozygous for the at least one or more of the 405+10247C>T, 405+10255 del C, 1811+1643 G>T, 1812-13A>G, 2752-33insA, 3849+12192 G>A, 724G>A, 3899C>T, 3986C>T, 901G>A, 392T>C, 3463T>C, 1757G>A, 4025G>C, 4129G>T, 663T>G, 3200T>C, 4412T>C, 620A>C, 1738A>G, 3370A>C, 1129C>T, 2383C>T, 2761delTCT, 1106A>G or 622A>G mutation.

\* \* \* \* \*